United States Patent
Corey

(10) Patent No.: US 12,303,551 B2
(45) Date of Patent: *May 20, 2025

(54) CELLULAR IMMUNOTHERAPY COMPOSITIONS AND USES THEREOF

(71) Applicant: CERO THERPEUTICS HOLDINGS, INC., South San Francisco, CA (US)

(72) Inventor: Daniel Mark Corey, Menlo Park, CA (US)

(73) Assignee: Cero Therapeutics Holdings, Inc., South San Francisco, CA (US)

( * ) Notice: Subject to any disclaimer, the term of this patent is extended or adjusted under 35 U.S.C. 154(b) by 1117 days.

This patent is subject to a terminal disclaimer.

(21) Appl. No.: 17/040,472

(22) PCT Filed: Mar. 27, 2019

(86) PCT No.: PCT/US2019/024442
§ 371 (c)(1),
(2) Date: Sep. 22, 2020

(87) PCT Pub. No.: WO2019/191340
PCT Pub. Date: Oct. 3, 2019

(65) Prior Publication Data
US 2021/0023135 A1    Jan. 28, 2021

Related U.S. Application Data

(60) Provisional application No. 62/734,863, filed on Sep. 21, 2018, provisional application No. 62/652,838, (Continued)

(51) Int. Cl.
| | | |
|---|---|---|
| *A61K 38/17* | (2006.01) | |
| *A61K 35/17* | (2025.01) | |
| *A61K 39/00* | (2006.01) | |
| *A61K 40/11* | (2025.01) | |
| *A61K 40/24* | (2025.01) | |
| *A61K 40/32* | (2025.01) | |
| *A61K 40/42* | (2025.01) | |
| *A61K 40/46* | (2025.01) | |
| *A61K 45/06* | (2006.01) | |
| *A61P 35/00* | (2006.01) | |

(Continued)

(52) U.S. Cl.
CPC .......... *A61K 38/1774* (2013.01); *A61K 35/17* (2013.01); *A61K 38/177* (2013.01); *A61K 40/11* (2025.01); *A61K 40/24* (2025.01); *A61K 40/32* (2025.01); *A61K 40/42* (2025.01); *A61K 40/46* (2025.01); *A61K 45/06* (2013.01); *A61P 35/00* (2018.01); *A61P 37/04* (2018.01); *C07K 14/70503* (2013.01); *C07K 14/7051* (2013.01); *C07K 14/70578* (2013.01); *C07K 14/70596* (2013.01); *C07K 16/28* (2013.01); *C12N 5/0636* (2013.01); *C12N 5/0638* (2013.01); *A61K 2039/505* (2013.01); *A61K 2039/545* (2013.01); *C07K 2317/622* (2013.01); *C07K 2317/73* (2013.01); *C07K 2319/02* (2013.01); *C07K 2319/03* (2013.01); *C07K 2319/035* (2013.01); *C07K 2319/30* (2013.01); *C07K 2319/33* (2013.01)

(58) Field of Classification Search
CPC .. A61K 35/17; A61K 38/177; A61K 38/1774; A61K 45/06; A61K 2039/505; A61K 2039/5154; A61K 2039/5158; A61K 2039/545; A61K 39/12; A61K 39/4611; A61K 39/4622; A61K 39/4632; A61K 39/4644; A61K 39/464838; A61P 35/00; A61P 37/04; A61P 31/00; C07K 14/70503; C07K 14/7051; C07K 14/70578; C07K 14/70596; C07K 16/28; C07K 2317/622; C07K 2317/73; C07K 2319/02; C07K 2319/03; C07K 2319/035; C07K 2319/30; C07K 2319/33; C07K 14/705; C12N 2502/99; C12N 5/0636; C12N 5/0638; C12N 2710/20034
See application file for complete search history.

(56) References Cited

U.S. PATENT DOCUMENTS

| | | | |
|---|---|---|---|
| 5,019,368 | A | 5/1991 | Epstein et al. |
| 5,283,173 | A | 2/1994 | Fields et al. |

(Continued)

FOREIGN PATENT DOCUMENTS

| | | | |
|---|---|---|---|
| EP | 0566226 | B1 | 11/1995 |
| EP | 0520722 | B1 | 12/1996 |

(Continued)

OTHER PUBLICATIONS

Wong K et al. Phosphatidylserine receptor Tim-4 is essential for the maintenance of the homeostatic state of resident peritoneal macrophages. Proc Natl Acad Sci U S A. May 11, 2010; 107(19):8712-7. doi: 10.1073/pnas.0910929107. Epub Apr. 26, 2010. PMID: 20421466; PMCID: PMC2889355. (Year: 2010).*

(Continued)

*Primary Examiner* — Hong Sang
*Assistant Examiner* — Carol Ann Chase
(74) *Attorney, Agent, or Firm* — Fox Rothschild LLP

(57) ABSTRACT

The present disclosure relates to cellular immunotherapy compositions comprising a combination of immune cells or cellular subsets modified with chimeric engulfment receptors and chimeric antigen receptors/or T cell receptor binding proteins, and methods of using such cellular immunotherapy compositions.

26 Claims, 81 Drawing Sheets
Specification includes a Sequence Listing.

Related U.S. Application Data filed on Apr. 4, 2018, provisional application No. 62/649,541, filed on Mar. 28, 2018.

(51) Int. Cl.

| | |
|---|---|
| *A61P 37/04* | (2006.01) |
| *C07K 14/705* | (2006.01) |
| *C07K 14/725* | (2006.01) |
| *C07K 16/28* | (2006.01) |
| *C12N 5/0783* | (2010.01) |

(56) References Cited

U.S. PATENT DOCUMENTS

| | | |
|---|---|---|
| 5,468,614 A | 11/1995 | Fields et al. |
| 5,641,863 A | 6/1997 | Schreiber et al. |
| 5,641,875 A | 6/1997 | Schreiber et al. |
| 5,747,498 A | 5/1998 | Schnur et al. |
| 5,776,910 A | 7/1998 | Schreiber et al. |
| 5,821,071 A | 10/1998 | Schreiber et al. |
| 6,068,983 A | 5/2000 | Schreiber et al. |
| 6,475,997 B1 | 11/2002 | Schreiber et al. |
| 6,630,313 B2 | 10/2003 | Fadok et al. |
| 7,195,761 B2 | 3/2007 | Holtzman et al. |
| 7,247,303 B2 | 7/2007 | Thorpe et al. |
| 7,892,544 B2 | 2/2011 | Pfeifer et al. |
| 7,910,333 B2 | 3/2011 | Chilcote et al. |
| 8,025,878 B2 | 9/2011 | Gellerfors et al. |
| 8,119,772 B2 | 2/2012 | Yang et al. |
| 8,496,938 B2 | 7/2013 | Smith et al. |
| 8,940,276 B2 | 1/2015 | Weihofen et al. |
| 8,956,616 B2 | 2/2015 | Thorpe et al. |
| 10,093,717 B2 | 10/2018 | Li et al. |
| 10,125,193 B2 * | 11/2018 | Cooper ............. C07K 14/4748 |
| 10,793,641 B2 | 10/2020 | Wang et al. |
| 10,980,836 B1 | 4/2021 | Getts et al. |
| 11,655,282 B2 | 5/2023 | Corey et al. |
| 11,708,423 B2 | 7/2023 | Corey et al. |
| 2003/0072743 A1 | 4/2003 | Albert et al. |
| 2003/0095962 A1 | 5/2003 | Ueda et al. |
| 2003/0124114 A1 | 7/2003 | McIntire et al. |
| 2003/0130218 A1 | 7/2003 | Schreiber et al. |
| 2006/0002940 A1 | 1/2006 | Stevenson |
| 2006/0257359 A1 | 11/2006 | Francois et al. |
| 2007/0258897 A1 | 11/2007 | Devitt et al. |
| 2008/0213216 A1 | 9/2008 | Schreiber et al. |
| 2011/0165649 A1 | 7/2011 | Tyler et al. |
| 2013/0071414 A1 | 3/2013 | Dotti et al. |
| 2014/0162290 A1 | 6/2014 | Watanabe et al. |
| 2015/0023986 A1 | 1/2015 | Jones et al. |
| 2017/0058024 A1 | 3/2017 | West et al. |
| 2017/0151281 A1 | 6/2017 | Wagner et al. |
| 2017/0166622 A1 | 6/2017 | Baeuerle et al. |
| 2017/0166657 A1 | 6/2017 | O'Neill et al. |
| 2017/0209492 A1 | 7/2017 | June et al. |
| 2018/0186855 A1 | 7/2018 | Rosenthal |
| 2018/0186878 A1 | 7/2018 | Rosenthal |
| 2018/0244748 A1 | 8/2018 | Gill et al. |
| 2018/0291089 A1 | 10/2018 | Epstein et al. |
| 2018/0319862 A1 | 11/2018 | Thompson et al. |
| 2018/0334653 A1 | 11/2018 | O'Neill |
| 2019/0350972 A1 | 11/2019 | Mason et al. |
| 2020/0002402 A1 | 1/2020 | Emtage et al. |
| 2020/0055917 A1 | 2/2020 | Corey |
| 2020/0239592 A1 | 7/2020 | Vale et al. |
| 2020/0308305 A1 | 10/2020 | Corey |
| 2021/0015865 A1 | 1/2021 | Corey |
| 2021/0023135 A1 | 1/2021 | Corey |
| 2021/0024607 A1 | 1/2021 | Corey et al. |
| 2021/0087251 A1 | 3/2021 | Corey |
| 2021/0253696 A1 | 8/2021 | Corey et al. |
| 2022/0098273 A1 | 3/2022 | Corey |

FOREIGN PATENT DOCUMENTS

| | | |
|---|---|---|
| EP | 0787722 A1 | 8/1997 |
| EP | 0837063 A1 | 4/1998 |
| EP | 0564409 B1 | 1/2000 |
| WO | WO 9633980 A1 | 10/1996 |
| WO | WO 9702266 A1 | 1/1997 |
| WO | WO 9709433 A1 | 3/1997 |
| WO | WO 9730034 A1 | 8/1997 |
| WO | WO 9738983 A1 | 10/1997 |
| WO | WO 9749688 A1 | 12/1997 |
| WO | WO 9810767 A2 | 3/1998 |
| WO | WO 9903854 A1 | 1/1999 |
| WO | WO 0168709 A1 | 9/2001 |
| WO | WO 0185207 A2 | 11/2001 |
| WO | WO 02066470 A1 | 8/2002 |
| WO | WO 03064383 A2 | 8/2003 |
| WO | WO 2004067569 A1 | 8/2004 |
| WO | WO 2005019429 A2 | 3/2005 |
| WO | WO 2005090573 A2 | 9/2005 |
| WO | WO 2005097211 A2 | 10/2005 |
| WO | WO 2006122806 A2 | 11/2006 |
| WO | WO 2007084786 A1 | 7/2007 |
| WO | WO 2009036082 A2 | 3/2009 |
| WO | WO 2009055730 A1 | 4/2009 |
| WO | WO 2013074916 A1 | 5/2013 |
| WO | WO 2013192294 A1 | 12/2013 |
| WO | WO 2014031687 A1 | 2/2014 |
| WO | WO 2014059173 A2 | 4/2014 |
| WO | WO 2014153114 A1 | 9/2014 |
| WO | WO 2015066262 A1 | 5/2015 |
| WO | WO 2015123642 A1 | 8/2015 |
| WO | WO 2015184228 A1 | 12/2015 |
| WO | WO 2016019300 A1 | 2/2016 |
| WO | WO 2016044605 A1 | 3/2016 |
| WO | WO 2016126608 A1 | 8/2016 |
| WO | WO 2017019848 A1 | 2/2017 |
| WO | WO 2017025944 A2 | 2/2017 |
| WO | WO 2017083700 A1 | 5/2017 |
| WO | WO 2017205747 A1 | 11/2017 |
| WO | WO 2017219916 A1 | 12/2017 |
| WO | WO 2018031419 A1 | 2/2018 |
| WO | WO 2018064076 A1 | 4/2018 |
| WO | WO 2018132695 A1 | 7/2018 |
| WO | WO 2018212770 A1 | 11/2018 |
| WO | WO 2018220224 A1 | 12/2018 |
| WO | WO 2019067328 A1 | 4/2019 |
| WO | WO 2019079529 A1 | 4/2019 |
| WO | WO 2019086512 A1 | 5/2019 |
| WO | WO 2019091478 A1 | 5/2019 |
| WO | WO 2019157440 A1 | 8/2019 |
| WO | WO 2019191332 A1 | 10/2019 |
| WO | WO 2019191334 A1 | 10/2019 |
| WO | WO 2019191339 A1 | 10/2019 |
| WO | WO 2019191340 A1 | 10/2019 |
| WO | WO 2020114518 A1 | 6/2020 |
| WO | WO 2020223550 A1 | 11/2020 |
| WO | WO 2021003428 A1 | 1/2021 |
| WO | WO 2021067875 A1 | 4/2021 |
| WO | WO 2022036265 A1 | 2/2022 |
| WO | WO 2022036285 A1 | 2/2022 |
| WO | WO 2022036287 A1 | 2/2022 |
| WO | WO 2023010097 A1 | 2/2023 |

OTHER PUBLICATIONS

Moller-Tank S, Maury W. Phosphatidylserine receptors: enhancers of enveloped virus entry and infection. Virology. Nov. 2014;468-470:565-580. doi: 10.1016/j.virol.2014.09.009. Epub Sep. 29, 2014. PMID: 25277499; PMCID: PMC4252826. (Year: 2014).*

Segawa K, Nagata S. An Apoptotic 'Eat Me' Signal: Phosphatidylserine Exposure. Trends Cell Biol. Nov. 2015;25(11):639-650. doi: 10.1016/j.tcb.2015.08.003. Epub Oct. 1, 2015. PMID: 26437594. (Year: 2015).*

Morrissey MA, Williamson AP, Steinbach AM, Roberts EW, Kern N, Headley MB, Vale RD. Chimeric antigen receptors that trigger phagocytosis. Elife. Jun. 4, 2018;7:e36688. doi: 10.7554/eLife.36688. PMID: 29862966; PMCID: PMC6008046. (Year: 2018).*

(56) References Cited

OTHER PUBLICATIONS

Corey D, Haeseleer F, Hou J, Corey L. Novel engineered chimeric engulfment receptors trigger T cell effector functions against SIV-infected CD4+ T cells. Mol Ther Methods Clin Dev. Nov. 15, 2022;28:1-10. doi: 10.1016/j.omtm.2022.11.004. PMID: 36514789; PMCID: PMC9720250. (Year: 2022).*
Sommermeyer D. Chimeric antigen receptor-modified T cells derived from defined CD8+ and CD4+ subsets confer superior antitumor reactivity in vivo. Leukemia. Feb. 2016;30(2):492-500. doi: 10.1038/leu.2015.247. Epub Sep. 15, 2015. PMID: 26369987; PMCID: PMC4746098. (Year: 2016).*
Blackburn et al., "Coregulation of CD8+ T cell exhaustion by multiple inhibitory receptors during chronic viral infection," *Nature Immunology* 10(1):29-37, Jan. 2009.
Aderem, "Phagocytosis and the Inflammatory Response," *JID* 187(Suppl 2):S340-S345, 2003.
Agaugue et al., "224. Development of Safer & Optimized CAR-T Cells Using Lentiviral Vectors," *Mol. Ther.* 23(Suppl. 1):S88, May 2015.
Aggen et al., "Single-chain V(alpha)V(beta) T-cell receptors function without mispairing with endogenous TCR chains," *Gene Therapy* 19:365-374, 2012.
Albert et al., "$\alpha v \beta 5$ integrin recruits the CrkII-Dock180-Rac1 complex for phagocytosis of apoptotic cells," *Nature Cell Biology* 2:899-905, Dec. 2000.
Alder et al., "Antibody responses of variable lymphocyte receptors in the lamprey," *Nature Immunology* 9(3):319-327, Mar. 2008.
Altman et al., "Phenotypic Analysis of Antigen-Specific T Lymphocytes," *Science* 274:94-96, 1996.
Arandjelovic et al., "Phagocytosis of apoptotic cells in homeostasis," *Nat. Immunol.* 16(9):907-917, Sep. 2015.
Baral et al., "Experimental therapy of African trypanosomiasis with a nanobody-conjugated human trypanolytic factor," *Nature Medicine* 12(5):580-584, May 2006.
Barthelemy et al., "Comprehensive Analysis of the Factors Contributing to the Stability and Solubility of Autonomous Human VH Domains*," *J. Biol. Chem.* 283(6):3639-3654, Feb. 8, 2008.
Belzile et al., "Antibody targeting of phosphatidylserine for the detection and immunotherapy of cancer," *ImmunoTargets and Therapy*, (7) pp. 1-14, 2018.
Castellano et al., "Membrane recruitment of Rac1 triggers phagocytosis," *Journal of Cell Science* 113:2955-2961, 2000.
Clackson et al., "Making antibody fragments using phage display libraries," *Nature* 352:624-628, Aug. 1991.
Cortez-Retamozo et al., "Efficient Cancer Therapy with a Nanobody-Based Conjugate," *Cancer Research* 64:2853-2857, Apr. 2004.
Dillon et al., "Annexin V Binds to Viable B Cells and Colocalizes with a Marker of Lipid Rafts upon B Cell Receptor Activation," *The Journal of Immunology* 164:1322-1332, 2000.
Duclos et al., "Rab5 regulates the kiss and run fusion between phagosomes and endosomes and the acquisition of phagosome leishmanicidal properties in RAW 264.7 macrophages," *Journal of Cell Science* 113:3531-3541, 2000.
Engels et al., "Retroviral Vectors for High-Level Transgene Expression in T Lymphocytes," *Human Gene Therapy* 14:1155-1168, Aug. 2003.
Feng et al., "Interleukin-6 increases prostate cancer cells resistance to bicalutamide via TIF2," *Mol. Cancer Ther.* 8(3):665-671, Mar. 2009.
Fesnak et al., "Engineered T Cells: The Promise and Challenges of Cancer Immunotherapy," *Nature Reviews Cancer* 16(9):566-581, Sep. 2016.
Frecha et al., "Advances in the Field of Lentivector-based Transduction of T and B Lymphocytes for Gene Therapy," *Molecular Therapy* 18(10):1748-1757, Oct. 2010.
Gerber et al., "Tumor-specific targeting by Bavituximab, a phosphatidylserine-targeting monoclonal antibody with vascular targeting and immune modulating properties, in lung cancer xenografts," *Am. J. Nucl. Med. Mol. Imaging* 5(5):493-503, 2015.
Ghahroudi et al., "Selection and identification of single domain antibody fragments from camel heavy-chain antibodies," *FEBS Letters* 414:521-526, 1997.
Green et al., "Mitochondria and Apoptosis," *Science* 281(5381):1309-1312, Aug. 1998.
Greenberg et al., "Clustered syk tyrosine kinase domains trigger phagocytosis," *Proc. Natl. Acad. Sci. USA* 93:1103-1107, Feb. 1996.
Greenberg, "Programmed cell death: A way of life for plants," *Proc. Natl. Acad. Sci. USA* 93:12094-12097, Oct. 1996.
Guest et al., "The Role of Extracellular Spacer Regions in the Optimal Design of Chimeric Immune Receptors: Evaluation of Four Different scFvs and Antigens," *Journal of Immunotherapy* 28(3):203-211, May/Jun. 2005.
Hamers-Casterman et al., "Naturally occurring antibodies devoid of light chains," *Nature* 363:446-448, Jun. 1993.
Hanayama et al., "Identification of a factor that links apoptotic cells to phagocytes," *Nature* 417:182-187, May 2002.
Hartt Meyers et al., "TIM-4 is the ligand for TIM-1, and the TIM-1—TIM-4 interaction regulates T cell proliferation," *Nat. Immunol.* 6(5):455-464, May 2005.
Herrin et al., "Structure and specificity of lamprey monoclonal antibodies," *PNAS* 105(6):2040-2045, Feb. 2008.
Hochreiter-Hufford et al., "Clearing the Dead: Apoptotic Cell Sensing, Recognition, Engulfment, and Digestion," *Cold Spring Harb Perspect Biol* 5:a008748, 2013. (21 pages).
Hudecek et al., "Receptor Affinity and Extracellular Domain Modifications Affect Tumor Recognition by ROR1-Specific Chimeric Antigen Receptor T Cells," *Clin. Cancer Res.* 19(12):3153-31564, 2013.
Hudecek et al., "The Nonsignaling Extracellular Spacer Domain of Chimeric Antigen Receptors Is Decisive for In Vivo Antitumor Activity," *Cancer Immunol. Res.* 3(2):125-135, Feb. 2015.
Hull et al., "The Mononuclear Phagocyte System in Homeostasis and Disease: A Role for Heme Oxygenase-1," *Antioxidants & Redox Signaling* 20(11):1770-1788, 2014.
International Search Report and Written Opinion, mailed Aug. 19, 2019, for International Application No. PCT/US2019/024441, 13 pages.
International Search Report and Written Opinion, mailed Feb. 6, 2018, for International Application No. PCT/US17/53553, 13 pages.
International Search Report and Written Opinion, mailed Jun. 28, 2019, for International Application No. PCT/US2019/024442, 12 pages.
International Search Report and Written Opinion, mailed Jun. 7, 2019, for International Application No. PCT/US2019/024433, 13 pages.
International Search Report and Written Opinion, mailed Mar. 25, 2019, for International Application No. PCT/US2018/052297, 10 pages.
International Search Report and Written Opinion, mailed May 29, 2019, for International Application No. PCT/US2019/024435, 12 pages.
Jespers et al., "Aggregation-resistant domain antibodies selected on phage by heat denaturation," *Nature Biotechnology* 22(9):1161-1165, Sep. 2004.
Jolly, "9: Emerging Viral Vectors," *Cold Spring Harbor Monograph Archive* 36:209-240, 1999.
June, "Adoptive T cell therapy for cancer in the clinic," *The Journal of Clinical Investigation* 117(6):1466-1476, Jun. 2007.
Khogeer et al., "Antiphosphatidylserine antibodies as diagnostic indicators of antiphospholipid syndrome," *Lupus* 24:186-190, 2015.
Kitchen et al., "Engineering Antigen-Specific T Cells from Genetically Modified Human Hematopoietic Stem Cells in Immunodeficient Mice," *PLoS One* 4(12):e8208, Dec. 2009.
Kochenderfer et al., "Construction and Pre-clinical Evaluation of an Anti-CD19 Chimeric Antigen Receptor," *J. Immunother.* 32(7):689-702, 2009.
Krisky et al., "Development of herpes simplex virus replication-defective multigene vectors for combination gene therapy applications," *Gene Therapy* 5:1517-1530, 1998.

(56) References Cited

OTHER PUBLICATIONS

Kruskal et al., "Phagocytic Chimeric Receptors Require Both Transmembrane and Cytoplasmic Domains from the Mannose Receptor," *J. Exp. Med.* 176:1673-1680, Dec. 1992.
Luo et al., "Development of genetically engineered $CD4^+$ and $CD8^+$ T cells expressing TCRs specific for a *M. tuberculosis* 38-kDa antigen," *Journal of Molecular Medicine* 89:903-913, 2011.
Miksa et al., "A novel method to determine the engulfment of apoptotic cells by macrophages using pHrodo succinimidyl ester," *J Immunol Methods* 342:71-77, 2009.
Misyurin, "Structure and Functions of Main Apoptosis Receptors and Ligands," *Russian Journal of Biotherapy* 14(2):23-30, 2015.
Miyanishi et al., "Identification of Tim4 as a phosphatidylserine receptor," *Nature* 450:435-439, Nov. 2007.
Morgan et al., "Cancer Regression in Patients After Transfer of Genetically Engineered Lymphocytes," *Science* 314(5796):126-129, Oct. 2006.
Morrissey et al., "Chimeric antigen receptors that trigger phagocytosis," *eLife*, 2018. (21 pages).
Nguyen et al., "Heavy-chain antibodies in *Camelidae*; a case of evolutionary innovation," *Immunogenetics* 54:39-47, 2002.
Nguyen et al., "The Specific Variable Domain of Camel Heavy-chain Antibodies is Encoded in the Germline," *J. Mol. Biol.* 275:413-418, 1998.
Nishi et al., "Systematic characterization of deubiquitylating enzymes for roles in maintaining genome integrity," *Nat Cell Biol.* 16(10):1016-8, Oct. 2014. (27 pages).
Nishi et al., "Tim4- and MerTK-Mediated Engulfment of Apoptotic Cells by Mouse Resident Peritoneal Macrophages," *Molecular and Cellular Biology* 34(8):1512-1520, Apr. 2014.
Penberthy et al., "Apoptotic cell recognition receptors and scavenger receptors," *Immunological Reviews* 269:44-59, 2016.
Pfeifer et al., "Gene Therapy: Promises and Problems," *Annu. Rev. Genomics Hum. Genet.* 2:177-211, 2001.
Portolano et al., "Lack of Promiscuity in Autoantigen-Specific H and L Chain Combinations as Revealed by Human H and L Chain "Roulette"," *J. Immunol.* 150(3):880-887, Feb. 1993.
Ravichandran "Find-me and eat-me signals in apoptotic cell clearance: progress and conundrums," *J. Exp. Med.* 207(9):1807-1817, 2017.
Rossi et al., "Genetic therapies against HIV," *Nat. Biotechnol.* 25(12):1444-1454, Dec. 2007.
Roux et al., "Structural analysis of the nurse shark (new) antigen receptor (NAR): Molecular convergence of NAR and unusual mammalian immunoglobulins," *PNAS* 95:11804-11809, Sep. 1998.
Sandberg et al., "Human T-cell lines with well-defined T-cell receptor gene rearrangements as controls for the BIOMED-2 multiplex polymerase chain reaction tubes," *Leukemia* 21:230-237, 2007.
Sato et al., "Enhancement of Fcγ Receptor-Mediated Phagocytosis by Transforming Mutants of Cbl1," *The Journal of Immunology* 163(11):6123-6131, 1999.
Scatchard et al., "The Attractions of Proteins for Small Molecules and Ions," *Ann. N.Y. Acad. Sci.* 51:660-672, 1949.
Schmitt et al., "T Cell Receptor Gene Therapy for Cancer," *Human Gene Therapy* 20:1240-1248, 2009.
Scholten et al., "Codon modification of T cell receptors allows enhanced functional expression in transgenic human T cells," *Clin. Immunol.* 119:135-145, 2006.
Schutters et al., "Phosphatidylserine targeting for diagnosis and treatment of human diseases," *Apoptosis* 15:1072-1082, 2010.
Stone et al., "A novel T cell receptor single-chain signaling complex mediates antigen-specific T cell activity and tumor control," *Cancer Immunol. Immunother.* 63(11):1163-1176, Nov. 2014. (NIH Public Access, Author Manuscript, available in PMC Nov. 1, 2015) (23 pages).
Verhoeyen et al., "Chapter 8: Lentiviral Vector Gene Transfer into Human T Cells," *Methods Mol. Biol.* 506:97-114, 2009.

Vincke et al., "General Strategy to Humanize a Camelid Single-domain Antibody and Identification of a Universal Humanized Nanobody Scaffold," *J. Biol. Chem.* 284(5):3273-3284, Jan. 2009.
Wälchli et al., "A Practical Approach to T-Cell Receptor Cloning and Expression," *PLoS One* 6(11):e27930, 2011. (11 pages).
Walseng et al., "A TCR-based Chimeric Antigen Receptor," *Scientific Reports* 7: 10713, 2017. (10 pages).
Wang et al., "A transgene-encoded cell surface polypeptide for selection, in vivo tracking, and ablation of engineered cells," *Blood* 118(5):1255-1263, Aug. 2011.
Williamson et al., "Cellular reconstitution of apoptotic cell clearance reveals a multi-step phosphorylation mechanism for Draper receptor triggering," *bioRxiv*:1-48, 2017. (58 pages).
Williamson et al., "Abstract A165: Engineering approaches to uncover the mechanism of apoptotic cell clearance by a conserved signaling system," *CRI-CIMT-EATI-AACR Inaugural International Cancer Immunotherapy Conference*: Translating Science into Survival, New York, New York, Sep. 16-19, 2015. (6 pages).
Williamson et al., "Abstract PR15: Engineering phagocytic signaling," CRI-CIMT-EATI-AACR International Cancer Immunotherapy Conference: Translating Science into Survival, New York, New York, Sep. 25-28, 2016. (4 pages).
Williamson et al., "Spatial control of Draper receptor signaling initiates apoptotic cell engulfment," *J. Cell Biol.* 217(11):3977-3992, 2018.
Wilson, "Analyzing Biomolecular Interactions," *Science* 295(5562):2103-2105, 2002.
Wolff et al., "Monoclonal Antibody Homodimers: Enhanced Antitumor Activity in Nude Mice," *Cancer Res.* 53:2560-2565, Jun. 1993.
Zhang et al., "Transduction of Human T Cells with a Novel T-Cell Receptor Confers Anti-HCV Reactivity," *PLoS Pathogens* 6(7):e1001018, Jul. 2010. (13 pages).
Zhao et al., "Primary Human Lymphocytes Transduced with NY-ESO-1 Antigen-Specific TCR Genes Recognize and Kill Diverse Human Tumor Cell Lines," *J. Immunol.* 174:(7):4415-4423, Apr. 2005. (25 pages).
Zaritskaya et al., "New flow cytometric assays for monitoring cell-mediated cytotoxicity," *Expert Review of Vaccines* 9(6):601-616, Jun. 2010. (26 pages).
Burns et al., "A high molecular weight-melanoma associated antigen-specific chimeric antigen receptor redirects lymphocytes to target human melanomas," *Cancer Res.* 70(8):3027-3033, Apr. 15, 2010.
Chen et al., "Fusion Protein Linkers: Property, Design and Functionality," *Adv. Drug Deliv. Rev.* 65(10): 1357-1369, Oct. 15, 2013.
Colman, "Effects of amino acid sequence changes on antibody-antigen interactions," *Research in Immunology* 145(1):33-36, 1994.
Cordoba et al., "The large ectodomains of CD45 and CD148 regulate their segregation from and inhibition of ligated T-cell receptor," *Blood* 121(21):4295-4302, 2013.
Dolezal et al., "ScFv multimers of the anti-neuraminidase antibody NC10: shortening of the linker in single-chain Fv fragment assembled in V(L) to V(H) orientation drives the formation of dimers, trimers, tetramers and higher molecular mass multimers," *Protein Engineering* 13(8):565-574, 2000.
Jones et al., "Lentiviral Vector Design for Optimal T Cell Receptor Gene Expression in the Transduction of Peripheral Blood Lymphocytes and Tumor-Infiltrating Lymphocytes," *Human Gene Therapy* 20:630-640, Jun. 2009.
Maeda et al., "Engineering of Functional Chimeric Protein G-Vargula Luciferase," *Analytical Biochemistry* 249:147-152, 1997.
Muller et al., "Spliceosomal Peptide P140 for Immunotherapy of Systemic Lupus Erythematosus: Results of an Early Phase II Clinical Trial," *Arthritis & Rheumatism* 58(12):3873-3883, Dec. 2008.
Safdari et al., "Antibody humanization methods—a review and update," *Biotechnology and Genetic Engineering Reviews* 29(2):175-186, 2013.
Srivastava et al., "Engineering CAR-T Cells: Design Concepts," *Trends Immunol.* 36(8):494-502, 2015.
Teplyakov et al., "Antibody modeling assessment II. Structures and models," *Proteins* 82(8):1563-1582, 2014. (20 pages).

(56) References Cited

OTHER PUBLICATIONS

Vallabhapurapu et al., "Variation in human cancer cell external phosphatidylserine is regulated by flippase activity and intracellular calcium," *Oncotarget* 6(33):34375-34388, 2015.

Delgado Tascón et al., "The granulocyte orphan receptor CEACAM4 is able to trigger phagocytosis of bacteria," *Journal of Leukocyte Biology* 97:521-531, Mar. 2015.

Kobayashi et al., "TIM-1 and TIM-4 Glycoproteins Bind Phosphatidylserine and Mediate Uptake of Apoptotic Cells," *Immunity* 27:927-940, Dec. 2007.

Nakaya, "Research on Molecular Mechanisms of Engulfment of Apoptotic Cells", *The Pharmaceutical Society of Japan* 135(8):949-954, 2015.

Moller-Tank et al., "Characterizing Functional Domains for TIM-Mediated Enveloped Virus Entry", J. Virology, Jun. 2014, 88(12): 6702-6713).

Nix, et al., "In Vitro-Selected Nanobody-Based Cellular Therapy Targeting CD72 for Treatement of Refractory B-Cell Malignancies", Blood, American Society of Hematology, vol. 134, Nov. 2019, 4 pages.

Parmar et al., "The CHK1 Inhibitor Prexasertib Exhibits Monotherapy Activity in High-Grade Serous Ovarian Cancer Models and Sensitizes to PARP Inhibition", Translational Cancer Mechanisms and Therapy, Clinical Cancer Research, Aug. 2019, 25(20): 6127-6140.

Takeshi, et al., "Regulation of Immunity by Toll-like Receptor Functions: TheirPhysiological and Pathological Roles," Journal of Gifu Dental Society, 2011?vol. 37?pp. 138-158.

Qin, et al. "Prelinical Development of Bivalent Chimeric Antigen Receptors Targeting Both CD19 and CD22," Molecular Therapy: Oncolytics, vol. 11, Dec. 2018, pp. 127-137.

Ortiz, et al. "The evolutionary history of the CD209 (DC-Sign) family in humans and non-human primates," Genes and Immunity, Jun. 2008, 2008(9), pp. 483-492.

Hayashi et al., "The innate immune response to bacterial flagellin is mediated by Toll-like receptor 5," Nature, 410(6832), Apr. 2001, pp. 1099-1103.

Chen et al., "TIM-2 is expressed on B cells and in liver and kidney and is a receptor for H-ferritin endocytosis," *JEM* 202(7):955-965, Oct. 2005. (11 pages).

Park et al., "The Phosphatidylserine Receptor TIM-4 Does Not Mediate Direct Signaling," *Current Biology* 19:346-351, Feb. 2009. (6 pages).

Blasius et al., "Intracellular Toll-like Receptors," *Immunity* 32:305-315, Mar. 26, 2010. (11 pages).

Kao et al., "Systematic Comparison of the EF-1 Alpha Short (EFS) and Viral Promoters for Gene Modification of Human Primary Cells for Clinical Applications," *Blood* 124(21):3497, Dec. 6, 2014. (3 pages).

Yang et al., "Development of optimal bicistronic lentiviral vectors facilitates high-level TCR gene expression and robust tumor cell recognition," *Gene Therapy* 15:1411-1423, May 22, 2008. (13 pages).

U.S. Appl. No. 18/322,450, filed May 23, 2023.

U.S. Appl. No. 18/527,075, filed Dec. 1, 2023.

Moller-Tank S et al. Phosphatidylserine receptors: enhancers of enveloped virus entry and infection. Virology. Nov. 2014;468-470:565-580. doi: 10.1016/j.virol.2014.09.009. Epub Sep. 29, 2014. PMID: 25277499; PMCID: PMC4252826. (Year: 2014).

Segawa K et al. An Apoptotic 'Eat Me' Signal: Phosphatidylserine Exposure. Trends Cell Biol. Nov. 2015;25(11):639-650. doi: 10.1016/j.tcb.2015.08.003. Epub Oct. 1, 2015. PM ID: 26437594. (Year: 2015).

Sommermeyer D. Chimeric antigen receptor-modified T cells derived from defined CD8+ and CD4+ subsets confer superior antitumor reactivity in vivo. Leukemia. Feb. 2016;30(2):492-500. doi: 10.1038/leu.2015.247. Epub Sep. 15, 2015. PMID: 26369987; PMCID: PMC4746098. (Year: 2016).

Genbank Accession No. NP_612388 (2006) (Year: 2006).

Genbank Accession No. NP_848874 (2009) (Year: 2009).

* cited by examiner

CELLULAR IMMUNOTHERAPY COMPOSITIONS AND USES THEREOF

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200265_407WO_SEQUENCE_LISTING.txt. The text file is 479 KB, was created on Mar. 26, 2019, and is being submitted electronically via EFS-Web.

BACKGROUND

The use of immune cells (e.g., T cells) modified with genetically engineered receptors targeted against cancer antigens has demonstrated clinical successes in hematological malignancies (e.g., CD19 specific chimeric antigen receptor therapy in leukemias). A number of clinical trials are underway for adoptive cellular immunotherapy in the treatment of solid tumors, using engineered receptors targeting CEA, GD2, mesothelin, IL13Rα, HER2, FAP, and L1CAM, to name a few. Engineered receptors include chimeric antigen receptors (CARs) and enhanced affinity T cell receptors (TCRs). However, treatment of solid tumors presents unique challenges including: trafficking to the tumor site, physical barriers to the tumor microenvironment, a stressful metabolic landscape, and immunosuppressive mechanisms (e.g., expression of immune checkpoint molecules, production of inhibitory cytokines). Efforts to augment immune cell persistence and activity in adoptive immunotherapy treatments are ongoing.

BRIEF DESCRIPTION OF THE DRAWINGS

FIG. 22 is time lapse imaging from 96-well co-culture experiments comprising CD8+ T cells transduced with HPV16 E7 TCR+CD4+ T cells transduced with CER21, CER23 or CER26 incubated with SCC152 target cells at a 1:1:1 ratio. SCC152 HPV+ target cells were quantified using automated cell counting software. SCC152 cells are shown to be decreasing in numbers over time in co-culture with CD8+ T cells transduced with HPV E7 TCR+CD4+ T cells transduced with CER21, CER23 or CER26 as compared to control (CD8 T cell HPV E7 TCR+CD4 T cell control).

FIG. 23 is time lapse imaging from 96-well co-culture experiments comprising CD8+ T cells transduced with HPV16 E7 TCR+CD4+ T cells transduced with CER103b, CER104 or CER105 incubated with SCC152 target cells at a 1:1:1 ratio. SCC152 HPV+ target cells were quantified using automated cell counting software. SCC152 cells are shown to be decreasing in numbers over time in co-culture with CD8+ T cells transduced with HPV E7 TCR+CD4+ T cells transduced with CER103b, CER104 or CER105 as compared to control (CD8+ T cell HPV E7 TCR+CD4+ T cell control).

FIG. 24 is time lapse imaging from 96-well co-culture experiments comprising CD8+ T cells transduced with HPV16 E7 TCR+CD4+ T cells transduced with CER106, CER116 or CER27 incubated with SCC152 target cells at a 1:1:1 ratio. SCC152 HPV+ target cells were quantified using automated cell counting software. SCC152 cells are shown to be decreasing in numbers over time in co-culture with CD8+ T cells transduced with HPV E7 TCR+CD4 T cells transduced with CER106, CER116 or CER27 as compared to control (CD8+ T cell HPV E7 TCR+CD4 control).

FIG. 58 are fluorescence micrograph images of the co-culture assay described in FIG. 57, showing clearance of the SCC152 cells (pink) as co-culture with CD8+ T cells transduced with HPV16 E7 TCR and CD4+ T cells transduced with a selected CER (columns from left to right: control, CER29, CER30, CER110, or CER112) progresses (rows from top to bottom: 0 hrs, 12 hrs, 24 hrs, and 36 hrs).

FIG. 59 are fluorescence micrograph images of the co-culture assay described in FIG. 57, showing clearance of the SCC152 cells (pink) as co-culture with CD8+ T cells transduced with HPV16 E7 TCR and CD4+ T cells transduced with a selected CER (columns from left to right: control, CER113, CER114, CER116, or CER117) progresses (rows from top to bottom: 0 hrs, 12 hrs, 24 hrs, and 36 hrs).

FIG. 60A shows a magnitude breadth curve of CD4+ T cell phagocytosis by CER type. FIG. 60B shows fluorescent micrograph images of SCC152 target cells engulfed by CD4+ CER126-transduced T cells. Top image is an enlargement of a cell in the lower left image showing a SCC152 cell engulfed by CER126-transduced CD4+ T cell. Lower left image shows SCC152 cells (stained with pHrodo red) engulfed by CE126R-transduced CD4+ T cells; lower right image is the same micrograph, showing CER126-transduced CD4+ T cells illuminated with CELLTRACE violet. White arrow indicates CD8+ T cell transduced with E7-specific TCR and that is pHrodo Red negative (lower left panel of FIG. 60B). Software rendition of phagocytosis (lower right panel of FIG. 60B).

FIG. 64A: Coloring the plots by a few of the measured markers (GM-CSF, MIP1b, Perforin, TNF, IL-17, Granzyme B, IL-4, IL-2, and IFNγ) shows the phenotype across viSNE 'islands.' Red represents high expression and blue represents low expression for each marker. FIG. 64B: Populations of CD4⁺ T cells were generated using a clustering algorithm from all 32 markers and overlaid onto the viSNE map. Arrows indicate enrichment of islands expressing the intracellular marker IFNγ in samples containing CER104, CER116, and CER117.

FIG. 65A: Populations of CD4+ T cells were generated using a clustering algorithm from all 18 markers and overlaid onto the viSNE map. Arrows indicate enrichment of islands expressing the T cell activation marker CD69 in samples containing CER104 and CER116. FIG. 65B: Color plots show the phenotype across viSNE 'islands.' Red represents high expression and blue represents low expression for each marker. Highlighted region indicates cells expressing T cell activation marker CD69.

FIG. 66A: Populations of CD4+ T cells were generated using a clustering algorithm from all 18 markers and overlaid onto the viSNE map. Arrows indicate loss of islands expressing the naïve T cell marker CD45RA within the CCR7+ population among CER104 and CER116 samples compared to controls. FIG. 66B: Color plots show the phenotype across viSNE 'islands.' Red represents high expression and blue represents low expression for each marker. Highlighted region indicates cells the naïve T cell marker CD45RA. CER104 and CER116-transduced CD4+ T cells were associated with memory formation after antigen encounter.

FIG. 67A shows FACS profiles from phagocytosis assays where hCER104-modified CD4+ and CD8+ T cells were co-cultured with pH rodo-labeled HCC827 NSCLC adenocarcinoma cells overnight and evaluated by FACs for pHrodo-positivity (box indicates % phagocytosis—9.81% for CD8+ T cells and 42.0% for CD4+ T cells). FIG. 67B is a bar graph of frequency of phagocytosis among CER-modified CD4+_T cells vs. CER-modified CD8+ T cells

FIG. 73A is a bar graph showing that CER104-modified T cells phagocytosed TAMRA-SE labeled, osimertinib treated HCC827 NSCLC cells, and bafilomycin (20 nM) blocked uptake of osimertinib treated, TAMRA-SE labeled HCC827 NSCLC cells by CER104-modified T cells. FIG. 73B shows FACS plots from in vitro phagocytosis assays of CER104-modified (left column) or mock transduced T cells (control, right column) co-cultured with untreated HCC827 NSCLC cells or HCC827 cells treated with osimertinib or osimertinib+bafilomycin.

FIG. 74B is a graph of mean values of bioluminescence signal intensities obtained for treatment group.

DETAILED DESCRIPTION

Figure 1:
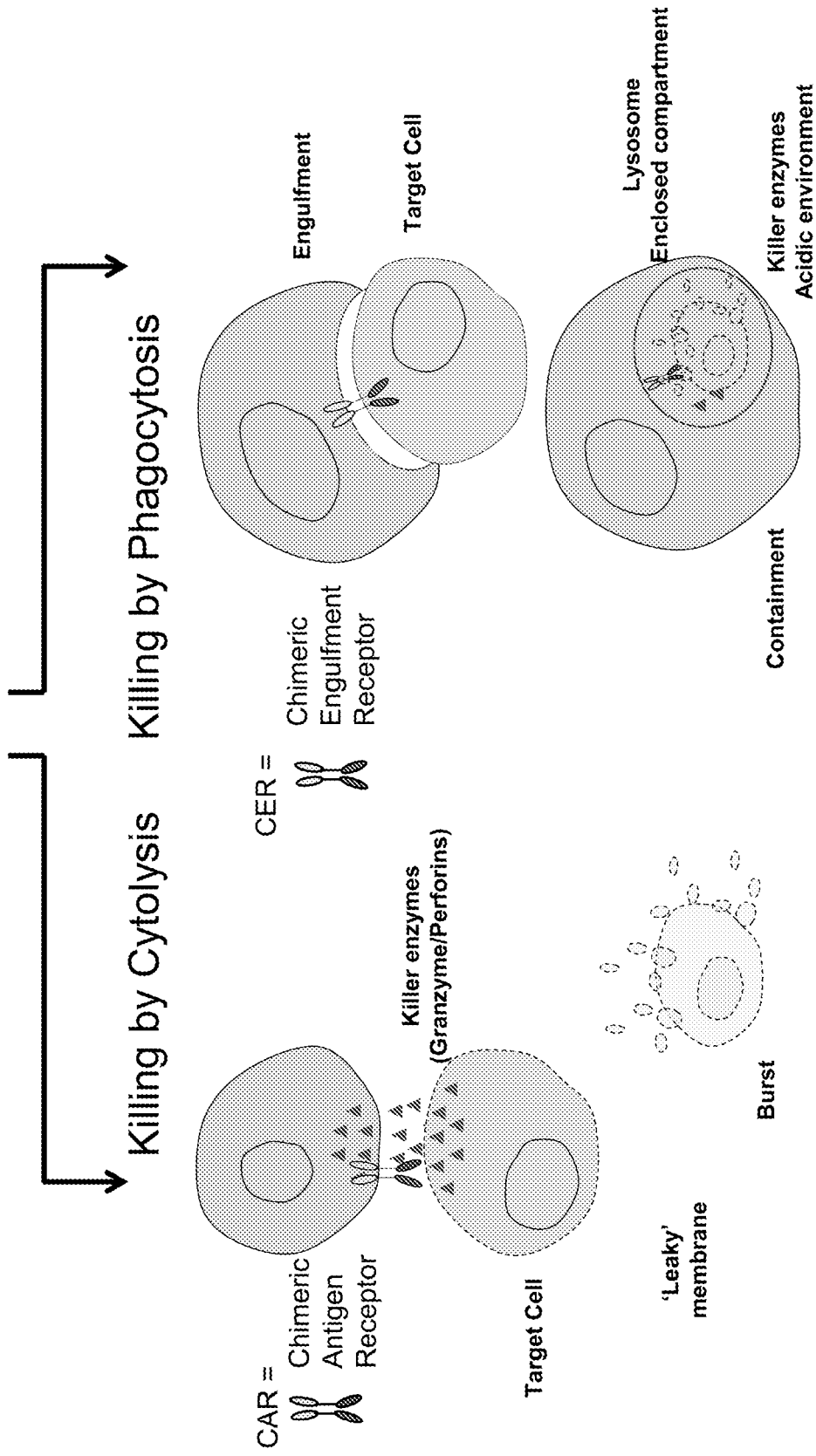
FIG. 1 is a schematic showing distinct mechanisms for cellular elimination by the combination of cellular immunotherapy compositions of the present disclosure. Chimeric Engulfment Receptor (CER)-expressing cells (right) utilize phagocytic machinery to internalize and kill target cells within cellular compartments, while CAR or TCR-expressing cells (left) cytolyse target cells through the release of cytolytic molecules, such as granzymes and perforins, or induction of death ligands (e.g., Fas ligand) to 'pop' cells. Combination of cellular immunotherapy compositions having cytolytic and phagocytic cells can be utilized to enhance adoptive cell therapy (ACT).
Figure 2:
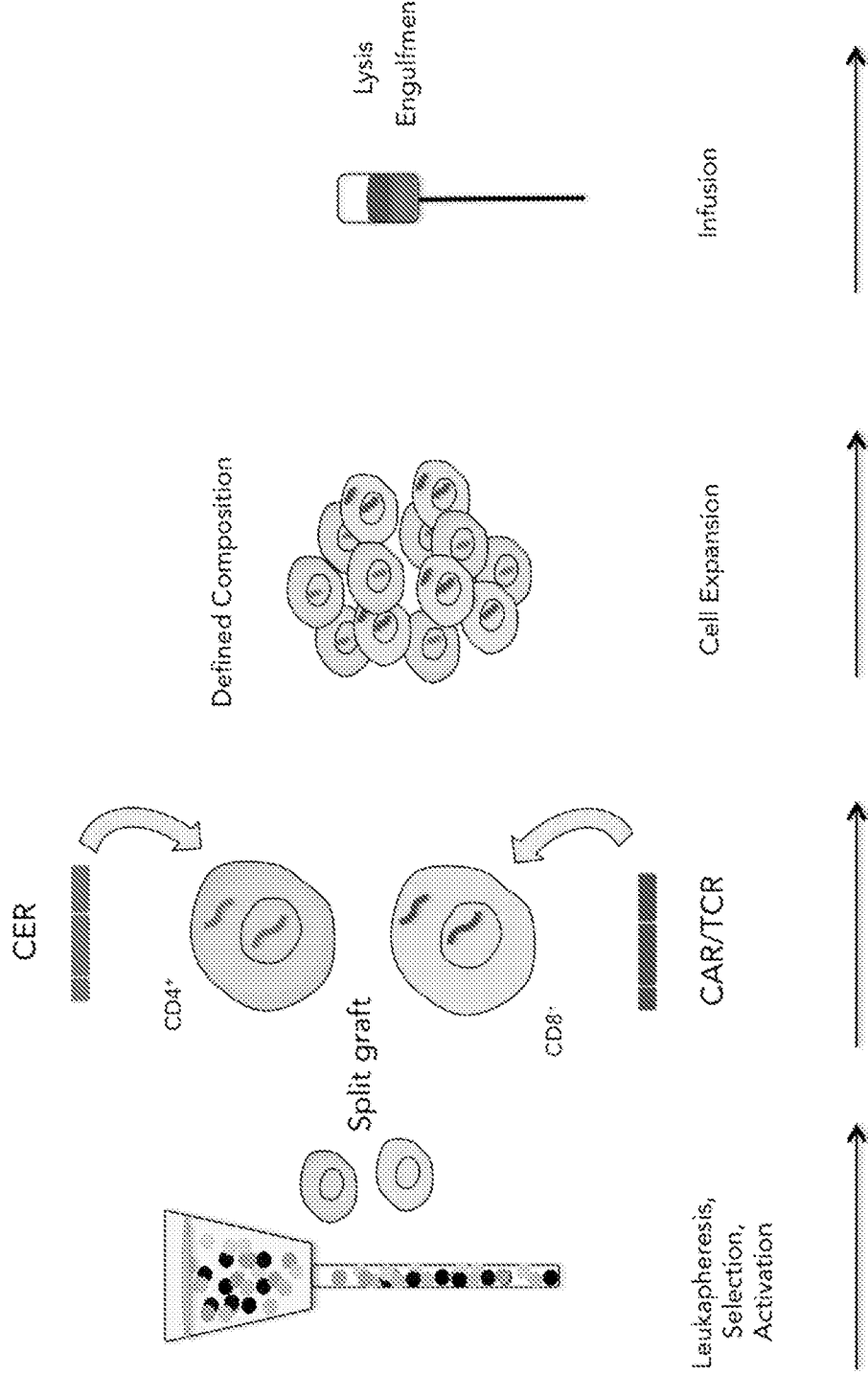
FIG. 2 is a schematic showing an exemplary therapeutic approach of the present disclosure for adoptive cellular immunotherapy utilizing combinations of modified immune cells that eliminate target cells though cytolysis and engulfment. Following leukapharesis, the graft is split into defined cell populations. CD4$^+$ T cells are transduced with a chimeric engulfment receptor (CER) that utilizes phagocytic machinery to specifically engulf target cells. CD8$^+$ T cells are transduced with a chimeric antigen receptor (CAR) or T cell Receptor (TCR) that promotes antigen-specific cytolysis. Cells are then expanded ex vivo and reintroduced into the patient at defined ratios where they target antigen-expressing tumor cells. Autologous cell infusions that utilize both phagocytic and cytolytic modes of cellular elimination work combinatorially.

The present disclosure provides combinations of cellular immunotherapy compositions comprising a combination of immune cells or cellular subsets modified with different recombinant cellular immunotherapy molecules. Embodiments of the present disclosure comprise a first composition comprising an immune cell comprising a CER and a second composition comprising an immune cell comprising a cellular immunotherapy molecule, e.g., a CER, CAR, or TCR binding protein. Exemplary combinations of cellular immunotherapy compositions comprise: a first composition comprising a CD4+ T cell comprising a first chimeric engulfment receptor (CER) and a second composition comprising a CD8+ T cell comprising a second CER; a first composition comprising a CD4+ T cell comprising a CER and a second composition comprising a CD8+ T cell comprising chimeric antigen receptor (CAR) or recombinant T cell receptor (TCR) binding protein; a first composition comprising a CD4+ T cell comprising a CER and a second composition comprising a CD4+ T cell comprising a CAR or recombinant TCR binding protein; a first composition comprising a CD8+ T cell comprising a CER and a second composition comprising a CD8+ T cell comprising a CAR or recombinant TCR binding protein; a first composition comprising a CD8+ T cell comprising a CER and a second composition comprising a CD4+ T cell comprising a CAR or recombinant TCR binding protein; a first composition comprising a B cell comprising a CER and a second composition comprising a CD4+ T cell comprising a CAR or recombinant TCR binding protein; a first composition comprising a B cell comprising a CER and a second composition comprising a CD8+ T cell comprising a CAR or recombinant TCR binding protein; a first composition comprising a NK cell comprising a CER and a second composition comprising a CD4+ T cell comprising a CAR or recombinant TCR binding protein; a first composition comprising a NK cell comprising a CER and a second composition comprising a CD8+ T cell comprising a CAR or recombinant TCR binding protein; a first composition comprising a γδ T cell comprising a CER and a second composition comprising a CD4+ T cell comprising a CAR or recombinant TCR binding protein; a first composition comprising a γδ T cell comprising a CER and a second composition comprising a CD8+ T cell comprising a CAR or recombinant TCR binding protein; a first composition comprising a mucosal-associated invariant T (MAIT) cell comprising a CER and a second composition comprising a CD4+ T cell comprising a CAR or recombinant TCR binding protein; a first composition comprising a mucosal-associated invariant T (MAIT) cell comprising a CER and a second composition comprising a CD8+ T cell comprising a CAR or recombinant TCR binding protein; a first composition comprising a monocyte comprising a CER and a second composition comprising a CD4+ T cell comprising a CAR or recombinant TCR binding protein; a first composition comprising a monocyte comprising a CER and a second composition comprising a CD8+ T cell comprising a CAR or recombinant TCR binding protein; a first composition comprising a macrophage comprising a CER and a second composition comprising a CD4+ T cell comprising a CAR or recombinant TCR binding protein; or a first composition comprising a macrophage comprising a CER and a second composition comprising a CD8+ T cell comprising a CAR or recombinant TCR binding protein. The combinations of cellular immunotherapy compositions provided in the present disclosure may be in the same pharmaceutical composition or in separate pharmaceutical compositions for administration to a subject. Such cellular immunotherapy compositions provided in the present disclosure confer provide multiple, non-redundant modes of target cell killing and enhanced effector function.

Additionally, methods of delivery of such cellular immunotherapy compositions to a subject in need thereof are provided.

Prior to setting forth this disclosure in more detail, it may be helpful to an understanding thereof to provide definitions of certain terms to be used herein.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means±20% of the indicated range, value, or structure, unless otherwise indicated. It should be understood that the terms "a" and "an" as used herein refer to "one or more" of the enumerated components. The use of the alternative (e.g., "or") should be understood to mean either one, both, or any combination thereof of the alternatives. As used herein, the terms "include," "have" and "comprise" are used synonymously, which terms and variants thereof are intended to be construed as non-limiting.

Terms understood by those in the art of antibody technology are each given the meaning acquired in the art, unless expressly defined differently herein. The term "antibody" is used in the broadest sense and includes polyclonal and monoclonal antibodies. An "antibody" may refer to an intact antibody comprising at least two heavy (H) chains and two light (L) chains inter-connected by disulfide bonds, as well as an antigen-binding portion (or antigen-binding domain) of an intact antibody that has or retains the capacity to bind a target molecule. An antibody may be naturally occurring, recombinantly produced, genetically engineered, or modified forms of immunoglobulins, for example intrabodies, peptibodies, nanobodies, single domain antibodies, SMIPs, multispecific antibodies (e.g., bispecific antibodies, diabodies, triabodies, tetrabodies, tandem di-scFV, tandem tri-scFv, ADAPTIR). A monoclonal antibody or antigen-binding portion thereof may be non-human, chimeric, humanized, or human, preferably humanized or human. Immunoglobulin structure and function are reviewed, for example, in Harlow et al., Eds., Antibodies: A Laboratory Manual, Chapter 14 (Cold Spring Harbor Laboratory, Cold Spring Harbor, 1988). "Antigen-binding portion" or "antigen-binding domain" of an intact antibody is meant to encompass an "antibody fragment," which indicates a portion of an intact antibody and refers to the antigenic determining variable regions or complementary determining regions of an intact antibody. Examples of antibody fragments include, but are not limited to, Fab, Fab', F(ab')$_2$, and Fv fragments, Fab'-SH, F(ab')$_2$, diabodies, linear antibodies, scFv antibodies, VH, and multispecific antibodies formed from antibody fragments. A "Fab" (fragment antigen binding) is a portion of an antibody that binds to antigens and includes the variable region and CH1 of the heavy chain linked to the light chain via an inter-chain disulfide bond. An antibody may be of any class or subclass, including IgG and subclasses thereof (IgG$_1$, IgG$_2$, IgG$_3$, IgG$_4$), IgM, IgE, IgA, and IgD.

The term "variable region" or "variable domain" in the context of an antibody refers to the domain of an antibody heavy or light chain that is involved in binding of the antibody to antigen. The variable domains of the heavy chain and light chain (VH and VL, respectively) of a native antibody generally have similar structures, with each domain comprising four conserved framework regions (FRs) and three complementary determining regions (CDRs). (See, e.g., Kindt et al. Kuby Immunology, 6th ed., W.H. Freeman and Co., page 91 (2007)). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., J. Immunol. 150:880-887 (1993); Clarkson et al., Nature 352:624-628 (1991).

The terms "complementarity determining region" and "CDR," which are synonymous with "hypervariable region" or "HVR," are known in the art to refer to non-contiguous sequences of amino acids within antibody variable regions, which confer antigen specificity and/or binding affinity. In general, there are three CDRs in each heavy chain variable region (HCDR1, HCDR2, HCDR3) and three CDRs in each light chain variable region (LCDR1, LCDR2, LCDR3).

As used herein, the terms "binding domain", "binding region", and "binding moiety" refer to a molecule, such as a peptide, oligopeptide, polypeptide, or protein that possesses the ability to specifically and non-covalently bind, associate, unite, recognize, or combine with a target molecule (e.g., tumor antigen). A binding domain includes any naturally occurring, synthetic, semi-synthetic, or recombinantly produced binding partner for a biological molecule or other target of interest. In some embodiments, the binding domain is an antigen-binding domain, such as an antibody or functional binding domain or antigen-binding portion thereof. Exemplary binding domains include single chain antibody variable regions (e.g., domain antibodies, sFv, scFv, Fab), receptor ectodomains (e.g., TNF-α), ligands (e.g., cytokines, chemokines), or synthetic polypeptides selected for the specific ability to bind to a biological molecule.

"T cell receptor" (TCR) refers to a molecule found on the surface of T cells (also referred to as T lymphocytes) that is generally responsible for recognizing antigens bound to major histocompatibility complex (MHC) molecules. The TCR is generally composed of a disulfide-linked heterodimer of the highly variable α and β chains (also known as TCRα and TCRβ, respectively) in most T cells. In a small subset of T cells, the TCR is made up of a heterodimer of γ and δ chains (also known as TCRγ and TCRδ, respectively). Each chain of the TCR is a member of the immunoglobulin superfamily and possesses one N-terminal immunoglobulin variable domain, one immunoglobulin constant domain, a transmembrane region, and a short cytoplasmic tail at the C-terminal end (see Janeway et al., *Immunobiology: The Immune System in Health and Disease*, 3$^{rd}$ Ed., Current Biology Publications, p. 4:33, 1997). TCRs of the present disclosure may be from various animal species, including human, mouse, rat, cat, dog, goat, horse, or other mammals. TCRs may be cell-bound (i.e., have a transmembrane region or domain) or in soluble form. TCRs include recombinantly produced, genetically engineered, fusion, or modified forms of TCRs, including for example, scTCRs, soluble TCRs, TCR fusion constructs (TRuC™; see, U.S. Patent Publication No. 2017/0166622)

The term "variable region" or "variable domain" of a TCR α-chain (Vα) and β-chain (Vβ), or Vγ and Vδ for γδ TCRs, are involved in binding of the TCR to antigen. The V$_α$ and V$_β$ of a native TCR generally have similar structures, with each variable domain comprising four conserved FRs and three CDRs. The V$_α$ domain is encoded by two separate DNA segments, the variable gene segment (V gene) and the joining gene segment (J gene); the V$_β$ domain is encoded by three separate DNA segments, the variable gene segment (V gene), the diversity gene segment (D gene), and the joining gene segment (J gene). A single V$_α$ or V$_β$ domain may be sufficient to confer antigen-binding specificity. "Major histocompatibility complex molecule" (MHC molecule) refers to a glycoprotein that delivers a peptide antigen to a cell surface. MHC class I molecules are heterodimers composed of a membrane spanning α chain (with three α domains) and a non-covalently associated β2 microglobulin. MHC class II molecules are composed of two transmembrane glycoproteins, α and β, both of which span the membrane. Each chain has two domains. MHC class I molecules deliver peptides originating in the cytosol to the cell surface, where peptide: MHC complex is recognized by CD8$^+$ T cells. MHC class II molecules deliver peptides originating in the vesicular system to the cell surface, where they are recognized by CD4$^+$ T cells. An MHC molecule may be from various animal species, including human, mouse, rat, or other mammals.

"Chimeric antigen receptor" (CAR) refers to a chimeric protein comprising two or more distinct domains and can function as a receptor when expressed on the surface of a cell. CARs are generally composed of an extracellular domain comprising a binding domain that binds a target antigen, an optional extracellular spacer domain, a transmembrane domain, and an intracellular signaling domain (e.g., an immunoreceptor tyrosine-based activation motif (ITAM)-containing T cell activating motif, and optionally an intracellular costimulatory domain). In certain embodiments, an intracellular signaling domain of a CAR has an ITAM-containing T cell activating domain (e.g., CD3ζ) and an intracellular costimulatory domain (e.g., CD28). In certain embodiments, a CAR is synthesized as a single polypeptide chain or is encoded by a nucleic acid molecule as a single chain polypeptide.

A variety of assays are known for identifying binding domains of the present disclosure that specifically bind a particular target, as well as determining binding domain affinities, such as Western blot, ELISA, analytical ultracentrifugation, spectroscopy, surface plasmon resonance (BIA-CORE®) analysis, and MHC tetramer analysis (see also, e.g., Scatchard et al., *Ann. N.Y. Acad. Sci.* 51:660, 1949; Wilson, *Science* 295:2103, 2002; Wolff et al., *Cancer Res.* 53:2560, 1993; Altman et al., Science 274:94-96, 1996; and U.S. Pat. Nos. 5,283,173, 5,468,614, or the equivalent). As used herein, "specifically binds" refers to an association or union of a binding domain, or a fusion protein thereof, to a target molecule with an affinity or K$_a$ (i.e., an equilibrium association constant of a particular binding interaction with units of 1/M) equal to or greater than 10$^5$ M$^{-1}$, while not significantly associating or uniting with any other molecules or components in a sample.

The terms "antigen" and "Ag" refer to a molecule that is capable of inducing an immune response. The immune response that is induced may involve antibody production, the activation of specific immunologically-competent cells, or both. Macromolecules, including proteins, glycoproteins, and glycolipids, can serve as an antigen. Antigens can be derived from recombinant or genomic DNA. As contemplated herein, an antigen need not be encoded (i) solely by a full length nucleotide sequence of a gene or (ii) by a "gene" at all. An antigen can be generated or synthesized, or an antigen can be derived from a biological sample. Such a biological sample can include, but is not limited, to a tissue sample, a tumor sample, a cell, or a biological fluid.

The term "epitope" or "antigenic epitope" includes any molecule, structure, amino acid sequence or protein determinant within an antigen that is specifically bound by a cognate immune binding molecule, such as an antibody or fragment thereof (e.g., scFv), T cell receptor (TCR), CAR, chimeric engulfment receptor, or other binding molecule, domain or protein. Epitopic determinants generally contain chemically active surface groupings of molecules, such as amino acids or sugar side chains, and can have specific three dimensional structural characteristics, as well as specific charge characteristics. An epitope may be a linear epitope or a conformational epitope.

As used herein, an "effector domain" is an intracellular portion of a fusion protein or chimeric receptor that can directly or indirectly promote a biological or physiological response in a cell expressing the effector domain when receiving the appropriate signal. In certain embodiments, an effector domain is part of a protein or protein complex that receives a signal when bound. In other embodiments, the effector domain is part of a protein or protein complex that binds directly to a target molecule, which triggers a signal from the effector domain. For example, in response to binding of the CER to a target molecule, the effector domain may transduce a signal to the interior of the host cell, eliciting an effector function, e.g., engulfment, phagolysosome maturation, or secretion of anti-inflammatory, and/or immunosuppressive cytokines. An effector domain may directly promote a cellular response when it contains one or more signaling domains or motifs. In other embodiments, an effector domain will indirectly promote a cellular response by associating with one or more other proteins that directly promote a cellular response.

An "engulfment signaling domain" refers to an intracellular effector domain, which, upon binding of the target molecule (e.g., phosphatidylserine) targeted by the extracellular domain of a CER expressed by a host cell, activates one or more signaling pathways in the host cell resulting in engulfment, including, in specific embodiments, cytoskeletal rearrangement of the host cell and internalization of the target cell or particle associated with the target antigen. In certain embodiments, an engulfment signaling domain activates one or more signaling pathways resulting in phagocytosis of the target cell or particle. In further embodiments, an engulfment signaling domain comprises a primary engulfment signaling domain and a secondary engulfment signaling domain.

"Junction amino acids" or "junction amino acid residues" refer to one or more (e.g., about 2-20) amino acid residues between two adjacent motifs, regions or domains of a polypeptide. Junction amino acids may result from the construct design of a chimeric protein (e.g., amino acid residues resulting from the use of a restriction enzyme site during the construction of a nucleic acid molecule encoding a fusion protein).

A "disease" is a state of health of a subject wherein the subject cannot maintain homeostasis, and wherein, if the disease is not ameliorated, then the subject's health continues to deteriorate. In contrast, a "disorder" or "undesirable condition" in a subject is a state of health in which the subject is able to maintain homeostasis, but in which the subject's state of health is less favorable than it would be in the absence of the disorder or undesirable condition. Left untreated, a disorder or undesirable condition does not necessarily result in a further decrease in the subject's state of health.

"Nucleic acid molecule" and "polynucleotide" can be in the form of RNA or DNA, which includes cDNA, genomic DNA, and synthetic DNA. A nucleic acid molecule may be composed of naturally occurring nucleotides (such as deoxyribonucleotides and ribonucleotides), analogs of naturally occurring nucleotides (e.g., α-enantiomeric forms of naturally occurring nucleotides), or a combination of both. Modified nucleotides can have "modifications in or replacement of sugar moieties, or pyrimidine or purine base moieties. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. A nucleic acid molecule may be double stranded or single stranded, and if single stranded, may be the coding strand or non-coding (anti-sense strand). A coding molecule may have a coding sequence identical to a coding sequence known in the art or may have a different coding sequence, which, as the result of the redundancy or degeneracy of the genetic code, or by splicing, can encode the same polypeptide.

"Encoding" refers to the inherent property of specific polynucleotide sequences, such as DNA, cDNA, and mRNA sequences, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a polynucleotide encodes a protein if transcription and translation of mRNA corresponding to that polynucleotide produces the protein in a cell or other biological system. Both a coding strand and a non-coding strand can be referred to as encoding a protein or other product of the polynucleotide. Unless otherwise specified, a "nucleotide sequence encoding an amino acid sequence" includes all nucleotide sequences that are degenerate versions of each other and that encode the same amino acid sequence.

As used herein, the term "endogenous" or "native" refers to a gene, protein, compound, molecule or activity that is normally present in a host or host cell, including naturally occurring variants of the gene, protein, compound, molecule, or activity.

As used herein, "homologous" or "homolog" refers to a molecule or activity from a host cell that is related by ancestry to a second gene or activity, e.g., from the same host cell, from a different host cell, from a different organism, from a different strain, from a different species. For example, a heterologous molecule or heterologous gene encoding the molecule may be homologous to a native host cell molecule or gene that encodes the molecule, respectively, and may optionally have an altered structure, sequence, expression level or any combination thereof.

As used herein, "heterologous" nucleic acid molecule, construct or sequence refers to a nucleic acid molecule or portion of a nucleic acid molecule that is not native to a host cell, but can be homologous to a nucleic acid molecule or portion of a nucleic acid molecule from the host cell. The source of the heterologous nucleic acid molecule, construct or sequence can be from a different genus or species. In some embodiments, the heterologous nucleic acid molecules are not naturally occurring. In certain embodiments, a heterologous nucleic acid molecule is added (i.e., not endogenous or native) into a host cell or host genome by, for example, conjugation, transformation, transfection, transduction, electroporation, or the like, wherein the added molecule can integrate into the host cell genome or exist as extra-chromosomal genetic material (e.g., as a plasmid or other form of self-replicating vector), and can be present in multiple copies. In addition, "heterologous" refers to a non-native enzyme, protein or other activity encoded by a non-endogenous nucleic acid molecule introduced into the host cell, even if the host cell encodes a homologous protein or activity.

As used herein, the term "engineered," "recombinant," "modified" or "non-natural" refers to an organism, microorganism, cell, nucleic acid molecule, or vector that has been modified by introduction of a heterologous nucleic acid molecule, or refers to a cell or microorganism that has been genetically engineered by human intervention—that is, modified by introduction of a heterologous nucleic acid molecule, or refers to a cell or microorganism that has been altered such that expression of an endogenous nucleic acid molecule or gene is controlled, deregulated or constitutive, where such alterations or modifications can be introduced by genetic engineering. Human-generated genetic alterations can include, for example, modifications introducing nucleic acid molecules (which may include an expression control element, such as a promoter) encoding one or more proteins, chimeric receptors, or enzymes, or other nucleic acid molecule additions, deletions, substitutions, or other functional disruption of or addition to a cell's genetic material. Exemplary modifications include those in coding regions or functional fragments thereof heterologous or homologous polypeptides from a reference or parent molecule. Additional exemplary modifications include, for example, modifications in non-coding regulatory regions in which the modifications alter expression of a gene or operon.

As used herein, the term "transgene" refers to a gene or polynucleotide encoding a protein of interest (e.g., CER, CAR, TCR) whose expression is desired in a host cell and that has been transferred by genetic engineering techniques into a cell. A transgene may encode proteins of therapeutic interest as well as proteins that are reporters, tags, markers, suicide proteins, etc. A transgene may be from a natural source, modification of a natural gene, or a recombinant or synthetic molecule. In certain embodiments, a transgene is a component of a vector.

The term "overexpressed" or "overexpression" of an antigen refers to an abnormally high level of antigen expression in a cell. Overexpressed antigen or overexpression of antigen is often associated with a disease state, such as in hematological malignancies and cells forming a solid tumor within a specific tissue or organ of a subject. Solid tumors or hematological malignancies characterized by overexpression of a tumor antigen can be determined by standard assays known in the art.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

As used herein, the term "mature polypeptide" or "mature protein" refers to a protein or polypeptide that is secreted or localized in the cell membrane or inside certain cell organelles (e.g., the endoplasmic reticulum, golgi, or endosome) and does not include an N-terminal signal peptide.

A "signal peptide", also referred to as "signal sequence", "leader sequence", "leader peptide", "localization signal" or "localization sequence", is a short peptide (usually 15-30 amino acids in length) present at the N-terminus of newly synthesized proteins that are destined for the secretory pathway. A signal peptide typically comprises a short stretch of hydrophilic, positively charged amino acids at the N-terminus, a central hydrophobic domain of 5-15 residues, and a C-terminal region with a cleavage site for a signal peptidase. In eukaryotes, a signal peptide prompts translocation of the newly synthesized protein to the endoplasmic reticulum where it is cleaved by the signal peptidase, creating a mature protein that then proceeds to its appropriate destination.

The "percent identity" between two or more nucleic acid or amino acid sequences is a function of the number of identical positions shared by the sequences (i.e., % identity=number of identical positions/total number of positions×100), taking into account the number of gaps, and the length of each gap that needs to be introduced to optimize alignment of two or more sequences. The comparison of sequences and determination of percent identity between two or more sequences can be accomplished using a mathematical algorithm, such as BLAST and Gapped BLAST programs at their default parameters (e.g., Altschul et al., *J. Mol. Biol.* 215:403, 1990; see also BLASTN at www.ncbi.nlm.nih.gov/BLAST).

A "conservative substitution" is recognized in the art as a substitution of one amino acid for another amino acid that has similar properties. Exemplary conservative substitutions are well known in the art (see, e.g., WO 97/09433, page 10, published Mar. 13, 1997; Lehninger, Biochemistry, Second Edition; Worth Publishers, Inc. NY:NY (1975), pp. 71-77; Lewin, Genes IV, Oxford University Press, NY and Cell Press, Cambridge, MA (1990), p. 8).

The term "chimeric" refers to any nucleic acid molecule or protein that is not endogenous and comprises a combination of sequences joined or linked together that are not naturally found joined or linked together in nature. For example, a chimeric nucleic acid molecule may comprise nucleic acids encoding various domains from multiple different genes. In another example, a chimeric nucleic acid molecule may comprise regulatory sequences and coding sequences that are derived from different sources, or regulatory sequences and coding sequences that are derived from the same source but arranged in a manner different than that found in nature.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

The phrase "under transcriptional control" or "operatively linked" as used herein means that a promoter is in the correct location and orientation in relation to a polynucleotide to control the initiation of transcription by RNA polymerase and expression of the polynucleotide.

A "vector" is a nucleic acid molecule that is capable of transporting another nucleic acid. Vectors may be, for example, plasmids, cosmids, viruses, or phage. The term should also be construed to include non-plasmid and non-viral compounds which facilitate transfer of nucleic acid into cells. An "expression vector" is a vector that is capable of directing the expression of a protein encoded by one or more genes carried by the vector when it is present in the appropriate environment.

In certain embodiments, the vector is a viral vector. Examples of viral vectors include, but are not limited to, adenovirus vectors, adeno-associated virus vectors, retrovirus vectors, gammaretrovirus vectors, and lentivirus vectors. "Retroviruses" are viruses having an RNA genome. "Gammaretrovirus" refers to a genus of the retroviridae family. Examples of gammaretroviruses include mouse stem cell virus, murine leukemia virus, feline leukemia virus, feline sarcoma virus, and avian reticuloendotheliosis viruses. "Lentivirus" refers to a genus of retroviruses that are capable of infecting dividing and non-dividing cells. Examples of lentiviruses include, but are not limited to HIV (human immunodeficiency virus, including HIV type 1 and HIV type 2, equine infectious anemia virus, feline immunodeficiency virus (FIV), bovine immune deficiency virus (BIV), and simian immunodeficiency virus (SIV).

In other embodiments, the vector is a non-viral vector. Examples of non-viral vectors include lipid-based DNA vectors, modified mRNA (modRNA), self-amplifying mRNA, closed-ended linear duplex (CELiD) DNA, and transposon-mediated gene transfer (PiggyBac, Sleeping Beauty). Where a non-viral delivery, system is used, the delivery vehicle can be a liposome. Lipid formulations can be used to introduce nucleic acids into a host cell in vitro, ex vivo, or in vivo. The nucleic acid may be encapsulated in the interior of a liposome, interspersed within the lipid bilayer of a liposome, attached to a liposome via a linking molecule that is associated with both the liposome and the nucleic acid, contained or complexed with a micelle, or otherwise associated with a lipid.

A "particle" refers to a fragment of a cell or a small object of at least 10 nm and up to 50 μm in diameter. A particle may be derived from a living cell or organism, the environment, or synthetic. A particle can be a viral particle, prion particle, protein particle, synthetic particle, small mineral particle, or cellular debris.

As used herein, the term "engulfment" refers to a receptor-mediated process wherein endogenous or exogenous cells or particles greater than 10 nm in diameter are internalized by a phagocyte or host cell of the present disclosure. Engulfment is typically composed of multiple steps: (1) tethering of the target cell or particle via binding of an engulfment receptor to a pro-engulfment marker or antigenic marker directly or indirectly (via a bridging molecule) on a target cell or particle; and (2) internalization or engulfment of the whole target cell or particle, or a portion thereof. In certain embodiments, internalization may occur via cytoskeletal rearrangement of a phagocyte or host cell to form a phagosome, a membrane-bound compartment containing the internalized target. Engulfment may further include maturation of the phagosome, wherein the phagosome becomes increasingly acidic and fuses with lysosomes (to form a phagolysosome), whereupon the engulfed target is degraded (e.g., "phagocytosis"). Alternatively, phagosome-lysosome fusion may not be observed in engulfment. In yet another embodiment, a phagosome may regurgitate or discharge its contents to the extracellular environment before complete degradation. In some embodiments, engulfment refers to phagocytosis. In some embodiments, engulfment includes tethering of the target cell or particle by the phagocyte of host cell of the present disclosure, but not internalization. In some embodiments, engulfment includes tethering of the target cell or particle by the phagocyte of host cell of the present disclosure and internalization of part of the target cell or particle.

As used herein, the term "phagocytosis" refers to an engulfment process of cells or large particles (≥0.5 μm) wherein tethering of a target cell or particle, engulfment of the target cell or particle, and degradation of the internalized target cell or particle occurs. In certain embodiments, phagocytosis comprises formation of a phagosome that encompasses the internalized target cell or particle and phagosome fusion with a lysosome to form a phagolysosome, wherein the contents therein are degraded. In certain embodiments, following binding of a CER expressed on a host cell of the present disclosure to a target antigen expressed by a target cell or particle, a phagocytic synapse is formed; an actin-rich phagocytic cup is generated at the phagocytic synapse; phagocytic arms are extended around the target cell or particle through cytoskeletal rearrangements; and ultimately, the target cell or particle is pulled into the phagocyte or host cell through force generated by motor proteins. As used herein, "phagocytosis" includes the process of "efferocytosis", which specifically refers to the phagocytosis of apoptotic or necrotic cells in a non-inflammatory manner.

The term "immune system cell" or "immune cell" means any cell of the immune system that originates from a hematopoietic stem cell in the bone marrow. Hematopoietic stem cells give rise to two major lineages: myeloid progenitor cells (which give rise to myeloid cells such as monocytes, macrophages, dendritic cells, megakaryocytes and granulocytes) and lymphoid progenitor cells (which give rise to lymphoid cells such as T cells, B cells and natural killer (NK) cells). Exemplary immune system cells include a CD4+ T cell, a CD8+ T cell, a CD4− CD8− double negative T cell, a γδ T cell, a regulatory T cell, a natural killer cell, and a dendritic cell. Macrophages and dendritic cells may also be referred to as "antigen presenting cells" or "APCs," which are specialized cells that can activate T cells when a major histocompatibility complex (MHC) receptor on the surface of the APC complexed with a peptide interacts with a TCR on the surface of a T cell.

The term "T cells" refers to cells of T cell lineage. "Cells of T cell lineage" refer to cells that show at least one phenotypic characteristic of a T cell or a precursor or progenitor thereof that distinguishes the cells from other lymphoid cells, and cells of the erythroid or myeloid lineages. Such phenotypic characteristics can include expression of one or more proteins specific for T cells (e.g., $CD3^+$, $CD4^+$, $CD8^+$), or a physiological, morphological, functional, or immunological feature specific for a T cell. For example, cells of the T cell lineage may be progenitor or precursor cells committed to the T cell lineage; $CD25^+$ immature and inactivated T cells; cells that have undergone CD4 or CD8 lineage commitment; thymocyte progenitor cells that are $CD4^+$ $CD8^+$ double positive; single positive $CD4^+$ or $CD8^+$; TCRαβ or TCR γδ; or mature and functional or activated T cells. The term "T cells" encompasses naïve T cells (CD45 RA+, CCR7+, CD62L+, CD27+, CD45RO−), central memory T cells ($CD45RO^+$, $CD62L^+$, $CD8^+$), effector memory T cells (CD45RA+, CD45RO−, CCR7−, CD62L−, CD27−), mucosal-associated invariant T (MAIT) cells, Tregs, natural killer T cells, and tissue resident T cells.

The term "B cells" refers to cells of the B cell lineage. "Cells of B cell lineage" refer to cells that show at least one phenotypic characteristic of a B cell or a precursor or progenitor thereof that distinguishes the cells from other lymphoid cells, and cells of the erythroid or myeloid lineages. Such phenotypic characteristics can include expression of one or more proteins specific for B cells (e.g., $CD19^+$, CD72+, CD24+, $CD20^+$), or a physiological, morphological, functional, or immunological feature specific for a B cell. For example, cells of the B cell lineage may be progenitor or precursor cells committed to the B cell lineage (e.g., pre-pro-B cells, pro-B cells, and pre-B cells); immature and inactivated B cells or mature and functional or activated B cells. Thus, "B cells" encompass naïve B cells, plasma cells, regulatory B cells, marginal zone B cells, follicular B cells, lymphoplasmacytoid cells, plasmablast cells, and memory B cells (e.g., $CD27^+$, $IgD^-$).

The term "cytotoxic activity," also referred to as "cytolytic activity," with respect to an immune cell (e.g., NK cell or T cell) that expresses an immune receptor (e.g., TCR) on its surface, means that upon antigen-specific signaling (e.g., via the TCR) the cell induces a target cell to undergo apoptosis. In some embodiments, a cytotoxic cell may induce apoptosis in a target cell via the release of cytotoxins, such as perforin, granzyme, and granulysin, from granules. Perforins insert into the target cell membrane and form pores that allow water and salts to rapidly enter the target cell. Granzymes are serine proteases that induce apoptosis in the target cell. Granulysin is also capable of forming pores in the target cell membrane and is a proinflammatory molecule. In some embodiments, a cytotoxic cell may induce apoptosis in a target cell via interaction of Fas ligand, which is upregulated on T cell following antigen-specific signaling, with Fas molecules expressed on the target cell. Fas is an apoptosis-signaling receptor molecule on the surface of a number of different cells. Cytotoxic activity on a target cell may expose pro-engulfment markers, e.g., phosphatidylserine on the surface of the target cell.

A "disease" is a state of health of a subject wherein the subject cannot maintain homeostasis, and wherein, if the disease is not ameliorated, then the subject's health continues to deteriorate. In contrast, a "disorder" or "undesirable condition" in a subject is a state of health in which the subject is able to maintain homeostasis, but in which the subject's state of health is less favorable than it would be in the absence of the disorder or undesirable condition. Left untreated, a disorder or undesirable condition does not necessarily result in a further decrease in the subject's state of health.

The term "cancer" as used herein is defined as disease characterized by the rapid and uncontrolled growth of aberrant cells. The aberrant cells may form solid tumors or constitute a hematological malignancy. Cancer cells can spread locally or through the bloodstream and lymphatic system to other parts of the body. Examples of various cancers include, but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

The term "subject," "patient" and "individual" are used interchangeably, herein and are intended to include living organisms in which an immune response can be elicited (e.g., mammals). Examples of subjects include humans, primates, cows, horses, sheep, dogs, cats, mice, rats, rabbits, guinea pigs, pigs, and transgenic species thereof "Adoptive cellular immunotherapy" or "adoptive immunotherapy" or "cellular immunotherapy" refers to the administration of naturally occurring or genetically engineered, disease antigen-specific immune cells (e.g., T cells). Adoptive cellular immunotherapy may be autologous (immune cells are from the recipient), allogeneic (immune cells are from a donor of the same species) or syngeneic (immune cells are from a donor genetically identical to the recipient).

"Autologous" refers to a graft (e.g., organ, tissue, cells) derived from the same subject to which it is later to be re-introduced.

"Allogeneic" refers to a graft derived from a different subject of the same species.

A "therapeutically effective amount" or "effective amount" of a chimeric protein or cell expressing a chimeric protein of this disclosure (e.g., a chimeric engulfment receptor or a cell expressing a chimeric engulfment receptor) refers to that amount of protein or cells sufficient to result in amelioration of one or more symptoms of the disease, disorder, or undesired condition being treated. When referring to an individual active ingredient or a cell expressing a single active ingredient, administered alone, a therapeutically effective dose refers to the effects of that ingredient or cell expressing that ingredient alone. When referring to a combination, a therapeutically effective dose refers to the combined amounts of active ingredients or combined adjunctive active ingredient with a cell expressing an active ingredient that results in a therapeutic effect, whether administered serially or simultaneously.

"Treat" or "treatment" or "ameliorate" refers to medical management of a disease, disorder, or undesired condition of a subject. In general, an appropriate dose or treatment regimen comprising a host cell expressing a chimeric protein of this disclosure is administered in an amount sufficient to elicit a therapeutic or prophylactic benefit. Therapeutic or prophylactic/preventive benefit includes improved clinical outcome; lessening or alleviation of symptoms associated with a disease, disorder, or undesired condition; decreased occurrence of symptoms; improved quality of life; longer disease-free status; diminishment of extent of disease, disorder, or undesired condition; stabilization of disease state; delay of disease progression; remission; survival; prolonged survival; or any combination thereof.

The term "anti-tumor effect" refers to a biological effect which can be manifested by a decrease in tumor volume, a decrease in the number of tumor cells, a decrease in the number of metastases, an increase in life expectancy, or amelioration of various physiological symptoms associated with a cancerous condition. An "anti-tumor effect" can also be manifested by prevention of a hematological malignancy or tumor formation.

Additional definitions are provided throughout the present disclosure.

Transgenes

Combinations of cellular immunotherapy compositions of the present disclosure are composed of immune cells modified to comprise a transgene encoding a cellular immunotherapy molecule, e.g., a chimeric engulfment receptor (CER), a chimeric antigen receptor, and T cell receptor (TCR) binding protein. Cellular immunotherapy composition combinations of the present disclosure are composed of specific combinations of immune cell types or subtypes, modified with specific cellular immunotherapy molecules, that exhibit distinct mechanisms for target cell elimination in a host, i.e., cytolysis and phagocystosis (see, FIG. 1).

I. Chimeric Engulfment Receptors

Compositions of the present disclosure comprise in part immune cells comprising a transgene encoding a chimeric engulfment receptor (CER). Chimeric engulfment receptors generally comprise: (a) an extracellular domain comprising a binding domain that binds to a target antigen, (b) an engulfment signaling domain; and (c) a transmembrane domain positioned between and connecting the extracellular domain and the engulfment signaling domain. In certain embodiments, the extracellular domain of the chimeric engulfment receptors described herein optionally includes an extracellular spacer domain positioned between and connecting the binding domain and transmembrane domain.

Chimeric engulfment receptors described herein are capable of conferring an engulfment phenotype that is specific for a target antigen to a host cell that is modified to express said chimeric engulfment receptor. In certain embodiments, expression of a CER as described herein confers an engulfment phenotype to a host cell that does not naturally exhibit an engulfment phenotype. In certain embodiments, the engulfment activity is phagocytic activity. CERs of the present disclosure may be used to redirect engulfment specificity to target cells that express the target antigen.

Extracellular Domain

As described herein, a CER comprises an extracellular domain specific to a target antigen. In certain embodiments, the extracellular domain comprises a binding domain that specifically binds a target antigen (e.g., phosphatidylserine). Binding of a target molecule by the binding domain may block the interaction between the target molecule (e.g., a receptor or a ligand) and another molecule and, for example, interfere with, reduce or eliminate certain functions of the target molecule (e.g., signal transduction). In some embodiments, the binding of a target molecule may induce certain biological pathways or identify the target molecule or cell expressing the target molecule for elimination.

A binding domain suitable for use in a CER of the present disclosure may be any polypeptide or peptide that specifically binds a target molecule of interest, e.g., phosphatidylserine. Sources of binding domains include extracellular domains of receptors, ligands for cell surface receptors or molecules, and antibodies or antigen binding portions, such as antibody variable regions from various species. For example a binding domain may comprise a, sFv, scFv, Fab, scFv-based grababody, VH domain, VL domain, single domain camelid antibody (VHH), or domain antibody. A binding domain may be derived from a human, primate, rodent, avian, or ovine. Additional sources of binding domains include variable regions of antibodies from other species, such as camelid (from camels, dromedaries, or llamas; Ghahroudi et al., *FEBS Lett.* 414:521, 1997; Vincke et al., *J. Biol. Chem.* 284:3273, 2009; Hamers-Casterman et al., *Nature* 363:446, 1993 and Nguyen et al., *J. Mol. Biol.* 275:413, 1998), nurse sharks (Roux et al., *Proc. Nat'l. Acad. Sci.* (*USA*) 95:11804, 1998), spotted ratfish (Nguyen et al., *Immunogen.* 54:39, 2002), or lamprey (Herrin et al., *Proc. Nat'l. Acad. Sci.* (*USA*) 105:2040, 2008 and Alder et al. *Nat. Immunol.* 9:319, 2008). These antibodies can form antigen-binding regions using only a heavy chain variable region, i.e., these functional antibodies are homodimers of heavy chains only (referred to as "heavy chain antibodies") (Jespers et al., *Nat. Biotechnol.* 22:1161, 2004; Cortez-Retamozo et al., *Cancer Res.* 64:2853, 2004; Baral et al., *Nature Med.* 12:580, 2006; and Barthelemy et al., *J. Biol. Chem.* 283:3639, 2008). In certain embodiments, a binding domain is murine, chimeric, human, or humanized.

In certain embodiments, the CER binding domain comprises an antibody or antigen binding fragment thereof, such as a single chain Fv fragment (scFv) that comprises VH and VL regions, specific for a target disease antigen. In certain embodiments, the antibody or antigen binding fragment is chimeric, human, or humanized. In further embodiments, the $V_H$ and $V_L$ regions are human or humanized.

A target molecule that is bound by an extracellular domain of a CER of the present disclosure, may be found on or in association with a cell of interest ("target cell"). Exemplary target cells include a cancer cell, a cell associated with an autoimmune disease or disorder, a neurodegenerative disease, or with an inflammatory disease or disorder, an infectious microbe (e.g., bacteria, virus, or fungi), and an infected cell (e.g., virus-infected cell). A cell of an infectious organism, such as a mammalian parasite, is also contemplated as a target cell.

In certain embodiments, the extracellular domain binds to a pro-engulfment marker. As used herein, a pro-engulfment marker is a moiety (e.g., protein, lipid, or polysaccharide) that an apoptotic, necrotic, pyroptotic, or infected cell exhibits on its surface that distinguishes it from a non-apoptotic, non-necrotic, non-pyroptotic, oncotic, or uninfected cell, respectively. A pro-engulfment marker can be an intracellular moiety that is surface exposed on an apoptotic or necrotic cell, a moiety that has altered glycosylation or altered surface charge on an apoptotic or necrotic cell, or a serum moiety that is bound to an apoptotic, necrotic, pyroptotic, or oncotic cell. Examples of pro-engulfment markers for apoptotic cells include phosphatidylserine (PtdSer), ICAM-3, oxidized low density lipoprotein, calreticulin, annexin I, complement C1q, and thrombospondin. Necrotic, oncotic, and pyroptotic cells also expose PtdSer pro-engulfment markers on the cell surface. Engulfment receptors can detect (or bind) a pro-engulfment marker on a target cell (e.g., a damaged, infected, apoptotic, necrotic, pyroptotic, or oncotic cell) directly or indirectly using soluble bridging molecules as intermediaries that bind to the pro-engulfment marker. In certain such embodiments, the pro-engulfment marker targeted by the extracellular domain is phosphatidylserine (PtdSer), ICAM-3, oxidized low density lipoprotein, calreticulin, annexin I, complement C1q, or thrombospondin. Embodiments of binding domains for use in CERs of the present disclosure include a PtdSer binding domain from Tim1, Tim4, Tim3, stabilin-2, receptor for advanced glycation endproducts (RAGE), brain-specific angiogenesis inhibitor 1 (BAI1), Milk Fat Globule-EGF Factor 8 Protein (MFG-E8) (e.g., a FA58C2 domain that mediates high affinity binding to PtdSer), Growth Arrest Specific 6 (GAS6), protein S, protein C, Factor II, Factor VII, Factor IX, Factor X, Beta 2-glycoprotein I, α5β3 integrin and other integrins, CR3 complement receptor, CR4 complement receptor, CD14, CD93, annexin V, phosphatidylserine receptor (PSr), prothrombin, or scavenger receptors such as scavenger receptor B (SRB) (e.g., SRB1 (CD36)), scavenger receptor C (SRC) (e.g., LOX-1, SRCL), scavenger receptor D (SRD) (e.g., CD68, macrosialin), and PSOX. An exemplary human Tim4 binding domain comprises an amino acid sequence that has at least about 75%, 80%, 85%, 90%, 91%, 92%, 93%, 94%, 95%, 96%, 97%, 98%, 99%, 99.5%, or 100% identity to SEQ ID NO:90 or amino acids 25-314 of SEQ ID NO:90. In certain embodiments, a Tim4 binding domain comprises or consists of an amino acid sequence of SEQ ID NO:90, SEQ ID NO:85, amino acids 25-314 of SEQ ID NO:90, or amino acids 23-279 of SEQ ID NO:85.

In certain embodiments, the extracellular domain binds to a tumor antigen, viral antigen, bacterial antigen, fungal antigen, parasitic antigen, neurodegenerative disease antigen, or autoimmune disease antigen. Exemplary tumor antigens include CD138, CD38, CD33, CD123, CD72, CD79a, CD79b, mesothelin, PSMA, BCMA, ROR1, MUC-16, L1CAM, CD22, CD19, CD20, CD23, CD24, CD37, CD30, CA125, CD56, c-Met, EGFR, GD-3, HPV E6, HPV E7, MUC-1, HER2, folate receptor α, CD97, CD171, CD179a, CD44v6, WT1, VEGF-α, VEGFR1, IL-13Rα1, IL-13Rα2, IL-11Rα, PSA, FcRH5, NKG2D ligand, NY-ESO-1, TAG-72, CEA, ephrin A2, ephrin B2, Lewis A antigen, Lewis Y antigen, MAGE, MAGE-A1, RAGE-1, folate receptor β, EGFRviii, VEGFR-2, LGR5, SSX2, AKAP-4, FLT3, fucosyl GM1, GM3, o-acetyl-GD2, and GD2.

In certain embodiments, the extracellular domain binds to a viral antigen, bacterial antigen, fungal antigen, protozoan antigen, or parasitic antigen.

In certain embodiments, the extracellular domain optionally comprises an extracellular, non-signaling spacer or linker domain. Where included, such a spacer or linker domain may position the binding domain away from the host cell surface to further enable proper cell to cell contact, binding, and activation. An extracellular spacer domain is generally located between the extracellular binding domain and the transmembrane domain of the CER. The length of the extracellular spacer may be varied to optimize target molecule binding based on the selected target molecule, selected binding epitope, binding domain size and affinity (see, e.g., Guest et al., *J. Immunother.* 28:203-11, 2005; PCT Publication No. WO 2014/031687). In certain embodiments, an extracellular spacer domain is an immunoglobulin hinge region (e.g., IgG1, IgG2, IgG3, IgG4, IgA, IgD). An immunoglobulin hinge region may be a wild type immunoglobulin hinge region or an altered wild type immunoglobulin hinge region. An altered IgG$_4$ hinge region is described in PCT Publication No. WO 2014/031687, which hinge region is incorporated herein by reference in its entirety. In a particular embodiment, an extracellular spacer domain comprises a modified IgG$_4$ hinge region having an amino acid sequence of ESKYGPPCPPCP (SEQ ID NO:1).

Other examples of hinge regions that may be used in the CERs described herein include the hinge region from the extracellular regions of type 1 membrane proteins, such as CD8a, CD4, CD28 and CD7, which may be wild-type or variants thereof. In further embodiments, an extracellular spacer domain comprises all or a portion of an immunoglobulin Fc domain selected from: a CH1 domain, a CH2 domain, a CH3 domain, or combinations thereof (see, e.g., PCT Publication WO2014/031687, which spacers are incorporated herein by reference in their entirety). In yet further embodiments, an extracellular spacer domain may comprise a stalk region of a type II C-lectin (the extracellular domain located between the C-type lectin domain and the transmembrane domain). Type II C-lectins include CD23, CD69, CD72, CD94, NKG2A, and NKG2D. In yet further embodiments, an extracellular spacer domain may be derived from a toll-like receptor (TLR) juxtamembrane domain. A TLR juxtamembrane domain comprises acidic amino acids lying between the leucine rich repeats (LRRs) and the transmembrane domain of a TLR. In certain embodiments, a TLR juxtamembrane domain is a TLR1, TLR2, TLR3, TLR4, TLR5, TLR6, TLR7, TLR8, or TLR9 juxtamembrane domain. An exemplary TLR juxtamembrane domain is a TLR4 juxtamembrane domain comprising an amino acid sequence of SEQ ID NO:2.

Extracellular domains may be derived from any mammalian species, including humans, primates, cows, horses, goats, sheep, dogs, cats, mice, rats, rabbits, guinea pigs, pigs, and transgenic species thereof. In certain embodiments, an extracellular domain is murine, chimeric, human, or humanized.

Engulfment Signaling Domain

The engulfment signaling domain of a CER is an intracellular effector domain and is capable of transmitting functional signals to a cell in response to binding of the extracellular domain of the CER to a target molecule. The engulfment signaling domain may be any portion of an engulfment signaling molecule that retains sufficient signaling activity. In some embodiments, a full length or full length intracellular component of an engulfment signaling molecule is used. In some embodiments, a truncated portion of an engulfment signaling molecule or intracellular component of an engulfment signaling molecule is used, provided that the truncated portion retains sufficient signal transduction activity. In further embodiments, an engulfment signaling domain is a variant of an entire or truncated portion of an engulfment signaling molecule, provided that the variant retains sufficient signal transduction activity (i.e., is a functional variant).

Exemplary engulfment signaling domains that may be used in a CER include a MRC1 signaling domain, a MERTK signaling domain, a Tyro3 signaling domain, an Axl signaling domain, an ELMO signaling domain, a Traf6 signaling domain, a Syk signaling domain, a MyD88 signaling domain, a PI3K signaling domain, a FcR signaling domain (e.g., FcγR1, FcγR2A, FcγR2C, FcγR2B2, FcγR3A, FcγR2C, FcγR3A, FcεR1, or FcαR1 signaling domain), a B-cell activating factor receptor (BAFF-R) signaling domain, a DAP12 (also referred to as TYRO Protein Tyrosine Kinase Binding Protein (TYROBP)) signaling domain, an NFAT Activating Protein With ITAM Motif 1 (NFAM1) signaling domain, a CD79b signaling domain, a TLR signaling domain (e.g., TLR1, TLR2, TLR3, TLR4, TLR5, TLR6, TLR7, TLR8, or TLR9 signaling domain), a Traf2 signaling domain, or a Traf 3 signaling domain.

In certain embodiments, the engulfment signaling domain comprises a sequence that has at least about 75%, 80%, 85%, 90%, 91%, 92%, 93%, 94%, 95%, 96%, 97%, 98%, 99%, 99.5%, or 100% identity to a MRC1 signaling domain comprising an amino acid sequence of SEQ ID NO:3, a MERTK signaling domain comprising an amino acid sequence of SEQ ID NO:4, a Tyro3 signaling domain comprising an amino acid sequence of SEQ ID NO:6, an Axl signaling domain comprising an amino acid sequence of SEQ ID NO:7, an ELMO signaling domain comprising an amino acid sequence of SEQ ID NO:8, a Traf6 signaling domain comprising an amino acid sequence of SEQ ID NO:9, a Syk signaling domain comprising an amino acid sequence of SEQ ID NO:10, a MyD88 signaling domain comprising an amino acid sequence of SEQ ID NO:11, a FcεRIγ signaling domain comprising an amino acid sequence of SEQ ID NO:13, a FcγR1 signaling domain comprising an amino acid sequence of SEQ ID NO:14, a FcγR2A signaling domain comprising an amino acid sequence of SEQ ID NO:15, a FcγR2C signaling domain comprising an amino acid sequence of SEQ ID NO:16, a FcγR3A signaling domain comprising an amino acid sequence of SEQ ID NO:17, a BAFF-R signaling domain comprising an amino acid sequence of SEQ ID NO:18, a DAP12 signaling domain comprising an amino acid sequence of SEQ ID NO:19, a NFAM1 signaling domain comprising an amino acid sequence of SEQ ID NO:20, a CD79b signaling domain comprising an amino acid sequence of SEQ ID NO:22, a TLR1 signaling domain comprising an amino acid sequence of SEQ ID NO:23, a TLR2 signaling domain comprising an amino acid sequence of SEQ ID NO:24, a TLR3 signaling domain comprising an amino acid sequence of SEQ ID NO:25, a TLR4 signaling domain comprising an amino acid sequence of SEQ ID NO:26, a TLR5 signaling domain comprising an amino acid sequence of SEQ ID NO:27, a TLR6 signaling domain comprising an amino acid sequence of SEQ ID NO:28, a TLR7 signaling domain comprising an amino acid sequence of SEQ ID NO:29, a TLR8 signaling domain comprising an amino acid sequence of SEQ ID NO:30, a TLR9 signaling domain comprising an amino acid sequence of SEQ ID NO:31, a Traf2 signaling domain comprising an amino acid sequence of SEQ ID NO:32, or a Traf3 signaling domain comprising an amino acid sequence of SEQ ID NO:33.

In some embodiments, the engulfment signaling domain is an MRC1 signaling domain comprising or consisting of an amino acid sequence of SEQ ID NO:3, a MERTK signaling domain comprising or consisting of an amino acid sequence of SEQ ID NO:4, a Tyro3 signaling domain comprising or consisting of an amino acid sequence of SEQ ID NO:6, an Axl signaling domain comprising or consisting of an amino acid sequence of SEQ ID NO:7, or an ELMO signaling domain comprising or consisting of an amino acid sequence of SEQ ID NO:8, a Traf6 signaling domain comprising or consisting of an amino acid sequence of SEQ ID NO:9, a Syk signaling domain comprising or consisting of an amino acid sequence of SEQ ID NO:10, a MyD88 signaling domain comprising or consisting of an amino acid sequence of SEQ ID NO:11, a FcεRIγ signaling domain comprising or consisting of an amino acid sequence of SEQ ID NO:13, a FcγR1 signaling domain comprising or consisting of an amino acid sequence of SEQ ID NO:14, a FcγR2A signaling domain comprising or consisting of an amino acid sequence of SEQ ID NO:15, a FcγR2C signaling domain comprising or consisting of an amino acid sequence of SEQ ID NO:16, a FcγR3A signaling domain comprising or consisting of an amino acid sequence of SEQ ID NO:17, a BAFF-R signaling domain comprising or consisting of an amino acid sequence of SEQ ID NO:18, a DAP-12 signaling domain comprising or consisting of an amino acid sequence of SEQ ID NO:19, a NFAM1 signaling domain comprising or consisting of an amino acid sequence of SEQ ID NO:20, a CD79b signaling domain comprising or consisting of an amino acid sequence of SEQ ID NO:22, a TLR1 signaling domain comprising or consisting of an amino acid sequence of SEQ ID NO:23, a TLR2 signaling domain comprising or consisting of an amino acid sequence of SEQ ID NO:24, a TLR3 signaling domain comprising or consisting of an amino acid sequence of SEQ ID NO:25, a TLR4 signaling domain comprising or consisting of an amino acid sequence of SEQ ID NO:26, a TLR5 signaling domain comprising or consisting of an amino acid sequence of SEQ ID NO:27, a TLR6, signaling domain comprising or consisting of an amino acid sequence of SEQ ID NO:28, a TLR7 signaling domain comprising or consisting of an amino acid sequence of SEQ ID NO:29, a TLR8, signaling domain comprising or consisting of an amino acid sequence of SEQ ID NO:30, a TLR9 signaling domain comprising or consisting of an amino acid sequence of SEQ ID NO:31, a Traf2 signaling domain comprising or consisting of an amino acid sequence of SEQ ID NO:32, or a Traf3 signaling domain comprising or consisting of an amino acid sequence of SEQ ID NO:33.

A truncated engulfment signaling domain may be truncated at its N-terminus, its C-terminus, at both the N-terminus and C-terminus. In certain embodiments, the MRC1 engulfment signaling domain is truncated 1, 2, 3, 4, 5, or more amino acids at its N-terminus corresponding to the amino acid sequence of SEQ ID NO:3; the MERTK engulfment signaling domain is truncated 1, 2, 3, 4, 5, or more amino acids at its N-terminus corresponding to the amino acid sequence of SEQ ID NO:4; the Tyro3 engulfment signaling domain is truncated 1, 2, 3, 4, 5, or more amino acids at its N-terminus corresponding to the amino acid sequence of SEQ ID NO:6; the Axl engulfment signaling domain is truncated 1, 2, 3, 4, 5, or more amino acids at its N-terminus corresponding to the amino acid sequence of SEQ ID NO:7; the ELMO engulfment signaling domain is truncated 1, 2, 3, 4, 5, or more amino acids at its N-terminus corresponding to the amino acid sequence of SEQ ID NO:8; the Traf6 engulfment signaling domain is truncated 1, 2, 3, 4, 5, or more amino acids at its N-terminus corresponding to the amino acid sequence of SEQ ID NO:9; the Syk engulfment signaling domain is truncated 1, 2, 3, 4, 5, or more amino acids at its N-terminus corresponding to the amino acid sequence of SEQ ID NO:10; the MyD88 engulfment signaling domain is truncated 1, 2, 3, 4, 5, or more amino acids at its N-terminus corresponding to the amino acid sequence of SEQ ID NO:11; the FcεRIγ engulfment signaling domain is truncated 1, 2, 3, 4, 5, or more amino acids at its N-terminus corresponding to the amino acid sequence of SEQ ID NO:13; the FcγR1 engulfment signaling domain is truncated 1, 2, 3, 4, 5, or more amino acids at its N-terminus corresponding to the amino acid sequence of SEQ ID NO:14; the FcγR2A engulfment signaling domain is truncated 1, 2, 3, 4, 5, or more amino acids at its N-terminus corresponding to the amino acid sequence of SEQ ID NO:15; the FcγR2C engulfment signaling domain is truncated 1, 2, 3, 4, 5, or more amino acids at its N-terminus corresponding to the amino acid sequence of SEQ ID NO:16; the FcγR3A engulfment signaling domain is truncated 1, 2, 3, 4, 5, or more amino acids at its N-terminus corresponding to the amino acid sequence of SEQ ID NO:17; the BAFF-R engulfment signaling domain is truncated 1, 2, 3, 4, 5, or more amino acids at its N-terminus corresponding to the amino acid sequence of SEQ ID NO:18; the DAP-12 engulfment signaling domain is truncated 1, 2, 3, 4, 5, or more amino acids at its N-terminus corresponding to the amino acid sequence of SEQ ID NO:19; the NFAM1 engulfment signaling domain is truncated 1, 2, 3, 4, 5, or more amino acids at its N-terminus corresponding to the amino acid sequence of SEQ ID NO:20; the CD79b engulfment signaling domain is truncated 1, 2, 3, 4, 5, or more amino acids at its N-terminus corresponding to the amino acid sequence of SEQ ID NO:22; the TLR1 engulfment signaling domain is truncated 1, 2, 3, 4, 5, or more amino acids at its N-terminus corresponding to the amino acid sequence of SEQ ID NO:23; the TLR2 engulfment signaling domain is truncated 1, 2, 3, 4, 5, or more amino acids at its N-terminus corresponding to the amino acid sequence of SEQ ID NO:24; the TLR3 engulfment signaling domain is truncated 1, 2, 3, 4, 5, or more amino acids at its N-terminus corresponding to the amino acid sequence of SEQ ID NO:25; the TLR4 engulfment signaling domain is truncated 1, 2, 3, 4, 5, or more amino acids at its N-terminus corresponding to the amino acid sequence of SEQ ID NO:26; the TLR5 engulfment signaling domain is truncated 1, 2, 3, 4, 5, or more amino acids at its N-terminus corresponding to the amino acid sequence of SEQ ID NO:27; the TLR6 engulfment signaling domain is truncated 1, 2, 3, 4, 5, or more amino acids at its N-terminus corresponding to the amino acid sequence of SEQ ID NO:28; the TLR7 engulfment signaling domain is truncated 1, 2, 3, 4, 5, or more amino acids at its N-terminus corresponding to the amino acid sequence of SEQ ID NO:29; the TLR8 engulfment signaling domain is truncated 1, 2, 3, 4, 5, or more amino acids at its N-terminus corresponding to the amino acid sequence of SEQ ID NO:30; the TLR9 engulfment signaling domain is truncated 1, 2, 3, 4, 5, or more amino acids at its N-terminus corresponding to the amino acid sequence of SEQ ID NO:31; the Traf2 engulfment signaling domain is truncated 1, 2, 3, 4, 5, or more amino acids at its N-terminus corresponding to the amino acid sequence of SEQ ID NO:32; or the Traf3 engulfment signaling domain is truncated 1, 2, 3, 4, 5, or more amino acids at its N-terminus corresponding to the amino acid sequence of SEQ ID NO:33.

In certain embodiments, the MRC1 engulfment signaling domain is truncated 1, 2, 3, 4, 5, or more amino acids at its C-terminus corresponding to the amino acid sequence of SEQ ID NO:3; the MERTK engulfment signaling domain is truncated 1, 2, 3, 4, 5, or more amino acids at its C-terminus corresponding to the amino acid sequence of SEQ ID NO:4; the Tyro3 engulfment signaling domain is truncated 1, 2, 3, 4, 5, or more amino acids at its C-terminus corresponding to the amino acid sequence of SEQ ID NO:6; the Axl engulfment signaling domain is truncated 1, 2, 3, 4, 5, or more amino acids at its C-terminus corresponding to the amino acid sequence of SEQ ID NO:7; the ELMO engulfment signaling domain is truncated 1, 2, 3, 4, 5, or more amino acids at its C-terminus corresponding to the amino acid sequence of SEQ ID NO:8; the Traf6 engulfment signaling domain is truncated 1, 2, 3, 4, 5, or more amino acids at its C-terminus corresponding to the amino acid sequence of SEQ ID NO:9; the Syk engulfment signaling domain is truncated 1, 2, 3, 4, 5, or more amino acids at its C-terminus corresponding to the amino acid sequence of SEQ ID NO:10; the MyD88 engulfment signaling domain is truncated 1, 2, 3, 4, 5, or more amino acids at its C-terminus corresponding to the amino acid sequence of SEQ ID NO:11; the FcεRIγ engulfment signaling domain is truncated 1, 2, 3, 4, 5, or more amino acids at its C-terminus corresponding to the amino acid sequence of SEQ ID NO:13; the FcγR1 engulfment signaling domain is truncated 1, 2, 3, 4, 5, or more amino acids at its C-terminus corresponding to the amino acid sequence of SEQ ID NO:14; the FcγR2A engulfment signaling domain is truncated 1, 2, 3, 4, 5, or more amino acids at its C-terminus corresponding to the amino acid sequence of SEQ ID NO:15; the FcγR2C engulfment signaling domain is truncated 1, 2, 3, 4, 5, or more amino acids at its C-terminus corresponding to the amino acid sequence of SEQ ID NO:16; the FcγR3A engulfment signaling domain is truncated 1, 2, 3, 4, 5, or more amino acids at its C-terminus corresponding to the amino acid sequence of SEQ ID NO:17; the BAFF-R engulfment signaling domain is truncated 1, 2, 3, 4, 5, or more amino acids at its C-terminus corresponding to the amino acid sequence of SEQ ID NO:18; the DAP-12 engulfment signaling domain is truncated 1, 2, 3, 4, 5, or more amino acids at its C-terminus corresponding to the amino acid sequence of SEQ ID NO:19; the NFAM1 engulfment signaling domain is truncated 1, 2, 3, 4, 5, or more amino acids at its C-terminus corresponding to the amino acid sequence of SEQ ID NO:20; the CD79b engulfment signaling domain is truncated 1, 2, 3, 4, 5, or more amino acids at its C-terminus corresponding to the amino acid sequence of SEQ ID NO:22; the TLR1 engulfment signaling domain is truncated 1, 2, 3, 4, 5, or more amino acids at its C-terminus corresponding to the amino acid sequence of SEQ ID NO:23; the TLR2 engulfment signaling domain is truncated 1, 2, 3, 4, 5, or more amino acids at its C-terminus corresponding to the amino acid sequence of SEQ ID NO:24; the TLR3 engulfment signaling domain is truncated 1, 2, 3, 4, 5, or more amino acids at its C-terminus corresponding to the amino acid sequence of SEQ ID NO:25; the TLR4 engulfment signaling domain is truncated 1, 2, 3, 4, 5, or more amino acids at its C-terminus corresponding to the amino acid sequence of SEQ ID NO:26; the TLR5 engulfment signaling domain is truncated 1, 2, 3, 4, 5, or more amino acids at its C-terminus corresponding to the amino acid sequence of SEQ ID NO:27; the TLR6 engulfment signaling domain is truncated 1, 2, 3, 4, 5, or more amino acids at its C-terminus corresponding to the amino acid sequence of SEQ ID NO:28; the TLR7 engulfment signaling domain is truncated 1, 2, 3, 4, 5, or more amino acids at its C-terminus corresponding to the amino acid sequence of SEQ ID NO:29; the TLR8 engulfment signaling domain is truncated 1, 2, 3, 4, 5, or more amino acids at its C-terminus corresponding to the amino acid sequence of SEQ ID NO:30; the TLR9 engulfment signaling domain is truncated 1, 2, 3, 4, 5, or more amino acids at its C-terminus corresponding to the amino acid sequence of SEQ ID NO:31; the Traf2 engulfment signaling domain is truncated 1, 2, 3, 4, 5, or more amino acids at its C-terminus corresponding to the amino acid sequence of SEQ ID NO:32; or the Traf3 engulfment signaling domain is truncated 1, 2, 3, 4, 5, or more amino acids at its C-terminus corresponding to the amino acid sequence of SEQ ID NO:33.

In certain embodiments, a truncated MyD88 engulfment signaling domain comprises a death domain but lacks a Toll/interleukin-1 receptor (TIR) homology domain. An example of such a truncated MyD88 engulfment signaling domain comprises an amino acid sequence of SEQ ID NO:34. In certain embodiments, a truncated MyD88 engulfment signaling domain comprises a TIR domain. An example of a truncated MyD88 engulfment signaling domain comprising a TIR domain comprises an amino acid sequence of SEQ ID NO:91. An exemplary truncated Traf6 signaling domain comprises an amino acid sequence of SEQ ID NO:35. An exemplary truncated NFAM1 signaling domain comprises an amino acid sequence of SEQ ID NO:36. An exemplary truncated CD79b signaling domain comprises an amino acid sequence of SEQ ID NO:21.

In certain embodiments, a CER comprises a first engulfment signaling domain (or primary engulfment signaling domain) and a second engulfment signaling domain (or secondary engulfment signaling domain) selected from any of the engulfment signaling domains provided herein. An exemplary first engulfment signaling domain is selected from a MRC1 signaling domain, a MERTK signaling domain, a Tyro3 signaling domain, an Axl signaling domain, an ELMO signaling domain, a Traf6 signaling domain, a Syk signaling domain, a MyD88 signaling domain, a PI3K signaling domain, a FcR signaling domain (e.g., FcγR1, FcγR2A, FcγR2C, FcγR2B2, FcγR3A, FcγR2C, FcγR3A, FcεR1, or FcαR1 signaling domain), a B-cell activating factor receptor (BAFF-R) signaling domain, a DAP12 (also referred to as TYRO Protein Tyrosine Kinase Binding Protein (TYROBP)) signaling domain, an NFAT Activating Protein With ITAM Motif 1 (NFAM1) signaling domain, a CD79b signaling domain, a TLR signaling domain (e.g., TLR1, TLR2, TLR3, TLR4, TLR5, TLR6, TLR7, TLR8, or TLR9 signaling domain), a Traf2 signaling domain, and a Traf 3 signaling domain; an exemplary second engulfment signaling domain is selected from a MRC1 signaling domain, a MERTK signaling domain, a Tyro3 signaling domain, an Axl signaling domain, an ELMO signaling domain, a Traf6 signaling domain, a Syk signaling domain, a MyD88 signaling domain, a PI3K signaling domain, a FcR signaling domain (e.g., FcγR1, FcγR2A, FcγR2C, FcγR2B2, FcγR3A, FcγR2C, FcγR3A, FcεR1, or FcαR1 signaling domain), a B-cell activating factor receptor (BAFF-R) signaling domain, a DAP12 (also referred to as TYRO Protein Tyrosine Kinase Binding Protein (TYROBP)) signaling domain, an NFAT Activating Protein With ITAM Motif 1 (NFAM1) signaling domain, a CD79b signaling domain, a TLR signaling domain (e.g., TLR1, TLR2, TLR3, TLR4, TLR5, TLR6, TLR7, TLR8, or TLR9 signaling domain), a Traf2 signaling domain, and a Traf 3 signaling domain.

It is understood that the positions of the first engulfment signaling domain and second engulfment signaling domain are interchangeable in the CER. Thus, in one example, a first engulfment signaling domain may be positioned N-terminal to a second engulfment signaling domain in a CER. In another example, a first engulfment signaling domain may be positioned C-terminal to a second engulfment signaling domain in a CER. In some embodiments, a CER comprises a first engulfment signaling domain and a second engulfment signaling domain that are from the same molecule. In other embodiments, the first engulfment signaling domain and the second engulfment signaling domain are from different molecules.

Engulfment signaling domains may be derived from a mammalian species, including humans, primates, cows, horses, goats, sheep, dogs, cats, mice, rats, rabbits, guinea pigs, pigs, and transgenic species thereof.

Transmembrane Domain

CERs of the present disclosure comprise a transmembrane domain that connects and is positioned between the extracellular domain and the engulfment signaling domain. The transmembrane domain is a hydrophobic alpha helix that transverses the host cell membrane and anchors the CER in the host cell membrane. The transmembrane domain may be directly fused to the binding domain or to the extracellular spacer domain if present. In certain embodiments, the transmembrane domain is derived from an integral membrane protein (e.g., receptor, cluster of differentiation (CD) molecule, enzyme, transporter, cell adhesion molecule, or the like). The transmembrane domain can be selected from the same molecule as the extracellular domain or the engulfment signaling domain (e.g., a CER comprising a TLR4 engulfment signaling domain and a TLR4 transmembrane domain or a CER comprising a Tim4 binding domain and a Tim4 transmembrane domain). In certain embodiments, the transmembrane domain and the extracellular domain are each selected from different molecules. In other embodiments, the transmembrane domain and the engulfment signaling domain are each selected from different molecules. In yet other embodiments, the transmembrane domain, the extracellular domain, and the engulfment signaling domain are each selected from different molecules.

In certain embodiments, the transmembrane domain comprises a Tim1, Tim4, Tim3, FcR (e.g., FcγR1, FcγR2A, FcγR2B2, FcγR2C, FcγR3A, FcεR1, or FcαR1), CD8a, CD28, MERTK, Axl, Tyro3, CD4, DAP12, MRC1, TLR1, TLR2, TLR3, TLR4, TLR5, TLR6, TLR7, TLR8, or TLR9 transmembrane domain.

In certain embodiments, the transmembrane domain comprises a sequence that has at least about 75%, 80%, 85%, 90%, 91%, 92%, 93%, 94%, 95%, 96%, 97%, 98%, 99%, 99.5%, or 100% identity to a Tim1 transmembrane domain comprising an amino acid sequence of SEQ ID NO:37, Tim4 transmembrane domain comprising an amino acid sequence of SEQ ID NO:38 or 39, Tim3 transmembrane domain comprising an amino acid sequence of SEQ ID NO:40, FcγR1 transmembrane domain comprising an amino acid sequence of SEQ ID NO:41, FcγR2A transmembrane domain comprising an amino acid sequence of SEQ ID NO:42, FcγR2B2 transmembrane domain comprising an amino acid sequence of SEQ ID NO:43, FcγR2C transmembrane domain comprising an amino acid sequence of SEQ ID NO:44, FcγR3A transmembrane domain comprising an amino acid sequence of SEQ ID NO:45, FcεR1 transmembrane domain comprising an amino acid sequence of SEQ ID NO:46, FcαR1 transmembrane domain comprising an amino acid sequence of SEQ ID NO:47, CD8a transmembrane domain comprising an amino acid sequence of SEQ ID NO:48, CD28 transmembrane domain comprising an amino acid sequence of SEQ ID NO:49, MERTK transmembrane domain comprising an amino acid sequence of SEQ ID NO:50, Axl transmembrane domain comprising an amino acid sequence of SEQ ID NO:51, Tyro3 transmembrane domain comprising an amino acid sequence of SEQ ID NO:52, CD4 transmembrane domain comprising an amino acid sequence of SEQ ID NO:53, DAP12 transmembrane domain comprising an amino acid sequence of SEQ ID NO:54, MRC1 transmembrane domain comprising an amino acid sequence of SEQ ID NO:55, TLR1 transmembrane domain comprising an amino acid sequence of SEQ ID NO:56, TLR2 transmembrane domain comprising an amino acid sequence of SEQ ID NO:57, TLR3 transmembrane domain comprising an amino acid sequence of SEQ ID NO:58, TLR4 transmembrane domain comprising an amino acid sequence of SEQ ID NO:59, TLR5 transmembrane domain comprising an amino acid sequence of SEQ ID NO:60, TLR6 transmembrane domain comprising an amino acid sequence of SEQ ID NO:61, TLR7 transmembrane domain comprising an amino acid sequence of SEQ ID NO:62, TLR8 transmembrane domain comprising an amino acid sequence of SEQ ID NO:63, or TLR9 transmembrane domain comprising an amino acid sequence of SEQ ID NO:64.

In certain embodiments, the transmembrane domain is a Tim1 transmembrane domain comprising or consisting of an amino acid sequence of SEQ ID NO:37, Tim4 transmembrane domain comprising or consisting of an amino acid sequence of SEQ ID NO:38 or 39, Tim3 transmembrane domain comprising or consisting of an amino acid sequence of SEQ ID NO:40, FcγR1 transmembrane domain comprising or consisting of an amino acid sequence of SEQ ID NO:41, FcγR2A transmembrane domain comprising or consisting of an amino acid sequence of SEQ ID NO:42, FcγR2B2 transmembrane domain comprising or consisting of an amino acid sequence of SEQ ID NO:43, FcγR2C transmembrane domain comprising or consisting of an amino acid sequence of SEQ ID NO:44, FcγR3A transmembrane domain comprising or consisting of an amino acid sequence of SEQ ID NO:45, FcεR1 transmembrane domain comprising or consisting of an amino acid sequence of SEQ ID NO:46, FcαR1 transmembrane domain comprising or consisting of an amino acid sequence of SEQ ID NO:47, CD8a transmembrane domain comprising or consisting of an amino acid sequence of SEQ ID NO:48, CD28 transmembrane domain comprising or consisting of an amino acid sequence of SEQ ID NO:49, MERTK transmembrane domain comprising or consisting of an amino acid sequence of SEQ ID NO:50, Axl transmembrane domain comprising or consisting of an amino acid sequence of SEQ ID NO:51, Tyro3 transmembrane domain comprising or consisting of an amino acid sequence of SEQ ID NO:52, CD4 transmembrane domain comprising or consisting of an amino acid sequence of SEQ ID NO:53, DAP12 transmembrane domain comprising or consisting of an amino acid sequence of SEQ ID NO:54, MRC1 transmembrane domain comprising or consisting of an amino acid sequence of SEQ ID NO:55, TLR1 transmembrane domain comprising or consisting of an amino acid sequence of SEQ ID NO:56, TLR2 transmembrane domain comprising or consisting of an amino acid sequence of SEQ ID NO:57, TLR3 transmembrane domain comprising or consisting of an amino acid sequence of SEQ ID NO:58, TLR4 transmembrane domain comprising or consisting of an amino acid sequence of SEQ ID NO:59, TLR5 transmembrane domain comprising or consisting of an amino acid sequence of SEQ ID NO:60, TLR6 transmembrane domain comprising or consisting of an amino acid sequence of SEQ ID NO:61, TLR7 transmembrane domain comprising or consisting of an amino acid sequence of SEQ ID NO:62, TLR8 transmembrane domain comprising or consisting of an amino acid sequence of SEQ ID NO:63, or TLR9 transmembrane domain comprising or consisting of an amino acid sequence of SEQ ID NO:64.

Transmembrane domains may derived from any mammalian species, including humans, primates, cows, horses, goats, sheep, dogs, cats, mice, rats, rabbits, guinea pigs, pigs, and transgenic species thereof.

It is understood that direct fusion of one domain to another domain of a CER described herein does not preclude the presence of intervening junction amino acids. Junction amino acids may be natural or non-natural (e.g., resulting from the construct design of a chimeric protein).

In certain embodiments, a chimeric engulfment receptor comprises polynucleotide sequences derived from any mammalian species, including humans, primates, cows, horses, goats, sheep, dogs, cats, mice, rats, rabbits, guinea pigs, pigs, transgenic species thereof, or any combination thereof. In certain embodiments, a chimeric engulfment receptor is murine, chimeric, human, or humanized.

Embodiments of CERs for use in cellular immunotherapy composition combinations of the present disclosure are provided in the Examples, Table 1, Sequence Listing, and disclosed in PCT Application No. PCT/US2017/053553, PCT/US/2018/52297, U.S. Provisional Application Nos. 62/563,615 and 62/649,529, which are incorporated by reference in their entirety.

TABLE 1

Exemplary Chimeric Engulfment Receptors

| CER Name | Binding Domain | Transmembrane Domain | First Engulfment Signaling Domain | Second Engulfment Signaling Domain | Exemplary Amino Acid Sequences |
|---|---|---|---|---|---|
| CER1 | Tim4 | Tim4 | MERTK | | SEQ ID NO: 101 |
| CER5 | Tim4 | Tim4 | TLR4 | | SEQ ID NO: 94 |
| CER6 | Tim4 | TLR4 | TLR4 | | SEQ ID NO: 102 |
| CER7 | Tim 4 + TLR juxtamembrane domain | TLR4 | TLR4 | | SEQ ID NO: 103 |
| CER8 | Tim4 | Tim4 | Tyro3 | | SEQ ID NO: 104 |
| CER9 | Tim4 | Tim4 | DAP12 | | SEQ ID NO: 105 |
| CER10 | Tim4 | DAP12 | DAP12 | | SEQ ID NO: 106 |
| CER11 | Tim4 | Tim4 | Axl | | SEQ ID NO: 107 |
| CER12 | Tim4 | Tim4 | FcRg | | SEQ ID NO: 108 |
| CER13 | Tim4 | FcεR1 | FcRg | | SEQ ID NO: 109 |
| CER15 | Tim4 | Tim4 | MyD88 | | SEQ ID NO: 110 |
| CER16 | Tim4 | Tim4 | MyD88_TIR | | SEQ ID NO: 111 |
| CER17 | Tim4 | Tim4 | TLR_3 | | SEQ ID NO: 112 |
| CER18 | Tim4 | TLR_3 | TLR_3 | | SEQ ID NO: 113 |
| CER19 | Tim4 | Tim4 | TLR_5 | | SEQ ID NO: 95 |
| CER20 | Tim4 | TLR_5 | TLR_5 | | SEQ ID NO: 114 |
| CER21 | Tim4 | Tim4 | TLR_8 | | SEQ ID NO: 96 |
| CER22 | Tim4 | TLR_8 | TLR_8 | | SEQ ID NO: 115 |
| CER23 | Tim4 | Tim4 | TLR_9 | | SEQ ID NO: 116 |
| CER24 | Tim4 | TLR_9 | TLR_9 | | SEQ ID NO: 117 |
| CER25 | Tim4 | Tim4 | NFAM | | SEQ ID NO: 97 |
| CER26 | Tim4 | Tim4 | TLR_1 | | SEQ ID NO: 118 |
| CER27 | Tim4 | Tim4 | TLR_2 | | SEQ ID NO: 98 |
| CER28 | Tim4 | Tim4 | TLR_7 | | SEQ ID NO: 119 |

TABLE 1-continued

Exemplary Chimeric Engulfment Receptors

| CER Name | Binding Domain | Transmembrane Domain | First Engulfment Signaling Domain | Second Engulfment Signaling Domain | Exemplary Amino Acid Sequences |
|---|---|---|---|---|---|
| CER29 | Tim4 | Tim4 | TRAF6 | | SEQ ID NO: 99 |
| CER30 | Tim4 | Tim4 | TRAF2 | | SEQ ID NO: 120 |
| CER31 | Tim4 | Tim4 | TRAF3 | | SEQ ID NO: 100 |
| CER85 | Tim4 | Tim4 | MyD88 | Baff-R | SEQ ID NO: 121 |
| CER86 | Tim4 | Tim4 | MyD88 | DAP12 | SEQ ID NO: 122 |
| CER87 | Tim4 | Tim4 | Baff-R | MyD88 | SEQ ID NO: 123 |
| CER88 | Tim4 | Tim4 | DAP12 | MyD88 | SEQ ID NO: 124 |
| CER89 | Tim4 | Tim4 | MyD88 | CD79b (185-229) | SEQ ID NO: 125 |
| CER90 | Tim4 | Tim4 | MyD88 | NFAM1 | SEQ ID NO: 126 |
| CER91 | Tim4 | Tim4 | MyD88 | P2A-Rab | SEQ ID NO: 127 |
| CER92 | Tim4 | Tim4 | MERTK | MyD88 | SEQ ID NO: 128 |
| CER93 | Tim4 | Tim4 | MERTK | Baff-R | SEQ ID NO: 129 |
| CER94 | Tim4 | Tim4 | MERTK | DAP12 | SEQ ID NO: 130 |
| CER95 | Tim4 | Tim4 | MERTK | CD79b (185-229) | SEQ ID NO: 131 |
| CER96 | Tim4 | Tim4 | MERTK | NFAM1 | SEQ ID NO: 132 |
| CER97 | Tim4 | Tim4 | AXL | Dap12 | SEQ ID NO: 133 |
| CER98 | Tim4 | Tim4 | AXL | CD79b | SEQ ID NO: 134 |
| CER99 | Tim4 | Tim4 | AXL | NFAM1 | SEQ ID NO: 135 |
| CER102 | Tim4 | Tim4 | TLR8 | NFAM1 | SEQ ID NO: 136 |
| CER103A | Tim4 | Tim4 | TLR8 | CD79b (185-229) | SEQ ID NO: 137 |
| CER103B | Tim4 | Tim4 | TLR8 | CD79b (185-213) | SEQ ID NO: 138 |
| CER104 | Tim4 | Tim4 | TLR8 | DAP12 | SEQ ID NO: 139 |
| CER105 | Tim4 | Tim4 | TLR8 | Baff-R | SEQ ID NO: 140 |
| CER106 | Tim4 | Tim4 | NFAM1 | TLR8 | SEQ ID NO: 141 |
| CER107 | Tim4 | Tim4 | CD79b (185-213) | TLR8 | SEQ ID NO: 142 |
| CER108 | Tim4 | Tim4 | DAP12 | TLR8 | SEQ ID NO: 143 |
| CER109 | Tim4 | Tim4 | Baff-R | TLR8 | SEQ ID NO: 144 |
| CER110 | Tim4 | Tim4 | TRAF6 | DAP12 | SEQ ID NO: 145 |
| CER111A | Tim4 | Tim4 | TRAF6 | CD79b (185-229) | SEQ ID NO: 146 |
| CER111B | Tim4 | Tim4 | TRAF6 | CD79b (185-213) | SEQ ID NO: 147 |
| CER112 | Tim4 | Tim4 | TRAF6 | NFAM1 | SEQ ID NO: 148 |
| CER113 | Tim4 | Tim4 | TRAF6 | Baff-R | SEQ ID NO: 149 |
| CER114 | Tim4 | Tim4 | TRAF6 | MERTK | SEQ ID NO: 150 |
| CER115 | Tim4 | Tim4 | MERTK | TRAF6 | SEQ ID NO: 151 |
| CER116 | Tim4 | Tim4 | TRAF6 | TLR8 | SEQ ID NO: 152 |
| CER117 | Tim4 | Tim4 | TLR8 | TRAF6 | SEQ ID NO: 153 |

TABLE 1-continued

Exemplary Chimeric Engulfment Receptors

| CER Name | Binding Domain | Transmembrane Domain | First Engulfment Signaling Domain | Second Engulfment Signaling Domain | Exemplary Amino Acid Sequences |
|---|---|---|---|---|---|
| CER118 | Tim4 | Tim4 | TLR1 | NFAM1 | SEQ ID NO: 154 |
| CER119B | Tim4 | Tim4 | TLR1 | CD79b (185-213) | SEQ ID NO: 155 |
| CER119A | Tim4 | Tim4 | TLR1 | CD79b (185-229) | SEQ ID NO: 173 |
| CER120 | Tim4 | Tim4 | TLR1 | DAP12 | SEQ ID NO: 156 |
| CER121 | Tim4 | Tim4 | TLR1 | TRAF6 | SEQ ID NO: 157 |
| CER122 | Tim4 | Tim4 | TLR2 | DAP12 | SEQ ID NO: 163 |
| CER123 | Tim4 | Tim4 | TLR2 | TRAF6 | SEQ ID NO: 164 |
| CER124 | Tim4 | Tim4 | TLR2 | NFAM1 | SEQ ID NO: 165 |
| CER125A | Tim4 | Tim4 | TLR2 | CD79b (185-229) | SEQ ID NO: 166 |
| CER125B | Tim4 | Tim4 | TLR2 | CD79b (185-213) | SEQ ID NO: 167 |
| CER126 | Tim4 | Tim4 | TLR2 | TRAF2 | SEQ ID NO: 169 |
| CER127 | Tim4 | Tim4 | TRAF2 | TLR2 | SEQ ID NO: 170 |
| CER128 | Tim4 | Tim4 | TRAF2 | TLR8 | SEQ ID NO: 171 |
| CER129 | Tim4 | Tim4 | TLR8 | TRAF2 | SEQ ID NO: 172 |
| hCER21 | Tim4 | Tim4 | TLR8 | | SEQ ID NO: 174 |
| hCER29 | Tim4 | Tim4 | TRAF6 | | SEQ ID NO: 175 |
| hCER104 | Tim4 | Tim4 | TLR8 | Dap12 | SEQ ID NO: 176 |
| hCER116 | Tim4 | Tim4 | TRAF6 | TLR8 | SEQ ID NO: 177 |
| hCER117 | Tim4 | Tim4 | TLR8 | TRAF6 | SEQ ID NO: 178 |
| hCER122 | Tim4 | Tim4 | TLR2 | Dap12 | SEQ ID NO: 179 |
| hCER123 | Tim4 | Tim4 | TLR2 | TRAF6 | SEQ ID NO: 180 |
| hCER126 | Tim4 | Tim4 | TLR2 | TRAF2 | SEQ ID NO: 181 |

Additional embodiments of CERs of the present disclosure comprise an extracellular domain that binds to a pro-engulfment marker or target antigen, an optional extracellular spacer domain, a transmembrane domain, and an engulfment signaling domain comprising a primary engulfment signaling domain selected from a TLR signaling domain and a secondary engulfment signaling domain selected from a TRAF2 signaling domain, a TRAF3 signaling domain, or a TRAF6 signaling domain. Further embodiments of CERs comprise an extracellular domain that binds to a pro-engulfment marker or target antigen, an optional extracellular spacer domain, a transmembrane domain, and an engulfment signaling domain comprising a primary engulfment signaling domain selected from a TLR2 signaling domain or a TLR8 signaling domain and a secondary engulfment signaling domain selected from a TRAF2 signaling domain, a TRAF6 signaling domain, or a DAP12 signaling domain. In certain embodiments, the extracellular domain comprises an scFv. In some embodiments, the extracellular domain comprises a Tim4 binding domain. An exemplary Tim4 binding domain comprises an amino acid sequence of SEQ ID NO:90 or amino acids 25-314 of SEQ ID NO:90. In certain embodiments, the transmembrane domain comprises a Tim4 transmembrane domain. An exemplary Tim4 transmembrane domain comprises an amino acid sequence of SEQ ID NO:38. Exemplary TLR2 and TLR8 signaling domains that may be used include amino acid sequences comprising SEQ ID NO:24 and SEQ ID NO:30, respectively. An exemplary TRAF2 signaling domain comprises an amino acid sequence of SEQ ID NO:32. An exemplary DAP12 signaling domain comprises an amino acid sequence of SEQ ID NO:19. Exemplary TRAF6 signaling domains comprise an amino acid sequence of SEQ ID NO:9 or 35.

II. Chimeric Antigen Receptors

In certain embodiments, compositions of the present disclosure comprise in part immune cells comprising a transgene encoding a chimeric antigen receptor (CAR). Chimeric antigen receptors are recombinant receptors that generally comprise: an extracellular domain comprising a binding domain that binds to a target antigen; an intracellular signaling domain, and a transmembrane domain positioned between and connecting the extracellular domain and the intracellular signaling domain. Chimeric antigen receptors generally confer antigen specific cytotoxic activity to the host cell in which they are expressed.

Binding domains suitable for use in CARs of the present disclosure include any antigen-binding polypeptide. A binding domain may comprise an antibody or antigen binding fragment thereof, including for example, a full length heavy chain, Fab fragment, Fab', F(ab')$_2$, sFv, VH domain, VL domain, dAb, VHH, CDR, and scFv. In certain embodiments, a CAR binding domain is murine, chimeric, human, or humanized.

In certain embodiments, the extracellular domain of CARs provided in the present disclosure optionally comprises an extracellular, non-signaling spacer or linker domain. Where included, such a spacer or linker domain may position the binding domain away from the host cell surface to further enable proper cell to cell contact, binding, and activation. An extracellular spacer domain is generally located between the extracellular binding domain and the transmembrane domain of the CAR. The length of the extracellular spacer may be varied to optimize target molecule binding based on the selected target molecule, selected binding epitope, binding domain size and affinity (see, e.g., Guest et al., *J. Immunother.* 28:203-11, 2005; PCT Publication No. WO 2014/031687). In certain embodiments, an extracellular spacer domain is an immunoglobulin hinge region (e.g., IgG1, IgG2, IgG3, IgG4, IgA, IgD). An immunoglobulin hinge region may be a wild type immunoglobulin hinge region or an altered wild type immunoglobulin hinge region. An altered IgG$_4$ hinge region is described in PCT Publication No. WO 2014/031687, which hinge region is incorporated herein by reference in its entirety. In a particular embodiment, an extracellular spacer domain comprises a modified IgG$_4$ hinge region having an amino acid sequence of ESKYGPPCPPCP (SEQ ID NO:1).

Other examples of hinge regions that may be used in the CARs described herein include the hinge region from the extracellular regions of type 1 membrane proteins, such as CD8a, CD4, CD28 and CD7, which may be wild-type or variants thereof. In further embodiments, an extracellular spacer domain comprises all or a portion of an immunoglobulin Fc domain selected from: a CH1 domain, a CH2 domain, a CH3 domain, or combinations thereof (see, e.g., PCT Publication WO2014/031687, which spacers are incorporated herein by reference in their entirety). In yet further embodiments, an extracellular spacer domain may comprise a stalk region of a type II C-lectin (the extracellular domain located between the C-type lectin domain and the transmembrane domain). Type II C-lectins include CD23, CD69, CD72, CD94, NKG2A, and NKG2D.

CARs of the present disclosure comprise a transmembrane domain that connects and is positioned between the extracellular domain and the intracellular signaling domain. The transmembrane domain is a hydrophobic alpha helix that transverses the host cell membrane and anchors the CAR in the host cell membrane. The transmembrane domain may be directly fused to the binding domain or to the extracellular spacer domain if present. In certain embodiments, the transmembrane domain is derived from an integral membrane protein (e.g., receptor, cluster of differentiation (CD) molecule, enzyme, transporter, cell adhesion molecule, or the like). The transmembrane domain can be selected from the same molecule as the extracellular domain or the intracellular signaling domain (e.g., a CAR comprising a CD28 costimulatory signaling domain and a CD28 transmembrane domain). In certain embodiments, the transmembrane domain and the extracellular domain are each selected from different molecules. In other embodiments, the transmembrane domain and the intracellular signaling domain are each selected from different molecules. In yet other embodiments, the transmembrane domain, the extracellular domain, and the intracellular signaling domain are each selected from different molecules.

Exemplary transmembrane domains for use in CARs of the present disclosure include CD28, CD2, CD3ε, CD3δ, CD3ζ, CD25, CD27, CD40, CD79A, CD79B, CD80, CD86, CD95 (Fas), CD134 (OX40), CD137 (4-1BB), CD150 (SLAMF1), CD152 (CTLA4), CD200R, CD223 (LAG3), CD270 (HVEM), CD272 (BTLA), CD273 (PD-L2), CD274 (PD-L1), CD278 (ICOS), CD279 (PD-1), CD300, CD357 (GITR), A2aR, DAP10, FcRα, FcRβ, FcRγ, Fyn, GAL9, KIR, Lck, LAT, LRP, NKG2D, NOTCH1, NOTCH2, NOTCH3, NOTCH4, PTCH2, ROR2, Ryk, Slp76, SIRPα, pTα, TCRα, TCRβ, TIM3, TRIM, LPA5, and Zap70. An exemplary CD28 transmembrane domain comprises an amino acid sequence of SEQ ID NO:49.

The intracellular signaling domain of a CAR is an intracellular effector domain and is capable of transmitting functional signals to a cell in response to binding of the extracellular domain of the CAR to a target molecule. The intracellular signaling domain may be any portion of an intracellular signaling molecule that retains sufficient signaling activity. In some embodiments, a full length or full length intracellular component of an intracellular signaling molecule is used. In some embodiments, a truncated portion of an intracellular signaling molecule or intracellular component of an intracellular signaling molecule is used, provided that the truncated portion retains sufficient signal transduction activity. In further embodiments, an intracellular signaling domain is a variant of an entire or truncated portion of an intracellular signaling molecule, provided that the variant retains sufficient signal transduction activity (i.e., is a functional variant).

In certain embodiments, the intracellular signaling domain of a CAR comprises an immunoreceptor tyrosine-based activation motif (ITAM) containing signaling domain. An ITAM containing signaling domain generally contains at least one (one, two, three, four, or more) ITAMs, which refer to a conserved motif of YXXL/I-X$_{6-8}$-YXXL/I. An ITAM containing signaling domain may initiate T cell activation signaling following antigen binding or ligand engagement. ITAM-signaling domains include, for example, intracellular signaling domains of CD3γ, CD3δ, CD3ε, CD3ζ, CD5, CD22, CD79a, CD278 (ICOS), DAP10, DAP12, and CD66d. Exemplary CD3 signaling domains that may be used in CARs of the present disclosure comprise an amino acid sequence of SEQ ID NO:158 or 159.

CAR intracellular signaling domains optionally comprise a costimulatory signaling domain, which, when activated in conjunction with a primary or classic (e.g., ITAM-driven) activation signal, promotes or enhances T cell response, such as T cell activation, cytokine production, proliferation, differentiation, survival, effector function, or combinations thereof. Costimulatory signaling domains for use in CARs include, for example, CD27, CD28, CD40L, GITR, NKG2C, CARD1, CD2, CD7, CD27, CD30, CD40, CD54 (ICAM), CD83, CD134 (OX-40), CD137 (4-1BB), CD150 (SLAMF1), CD152 (CTLA4), CD223 (LAG3), CD226, CD270 (HVEM), CD273 (PD-L2), CD274 (PD-L1), CD278 (ICOS), DAP10, LAT, LFA-1, LIGHT, NKG2C, SLP76, TRIM, ZAP70, or any combination thereof. In particular embodiments, the costimulatory signaling domain comprises a OX40, CD2, CD27, CD28, ICAM-1, LFA-1 (CD11a/CD18), ICOS (CD278), or 4-1BB (CD137) signaling domain. Exemplary CD28 costimulatory signaling domains that may be used in CARs of the present disclosure comprise an amino acid sequence of SEQ ID NO:161 or 162. An exemplary 4-1BB costimulatory signaling domain comprises an amino acid sequence of SEQ ID NO:160.

In certain embodiments, a chimeric antigen receptor comprises polynucleotide sequences derived from any mammalian species, including humans, primates, cows, horses, goats, sheep, dogs, cats, mice, rats, rabbits, guinea pigs, pigs, transgenic species thereof, or any combination thereof. In certain embodiments, the chimeric antigen receptor is murine, chimeric, human, or humanized.

In certain embodiments, a CAR is a first generation CAR, a second generation CAR, or a third generation CAR. A first generation CAR generally has an intracellular signaling domain comprising an intracellular signaling domain of CD3ζ, FcγRI, or other ITAM-containing activating domain to provide a T cell activation signal. Second generation CARs further comprise a costimulatory signaling domain (e.g., a costimulatory signaling domain from an endogenous T cell costimulatory receptor, such as CD28, 4-1BB, or ICOS). Third generation CARs comprise an ITAM-containing activating domain, a first costimulatory signaling domain and a second costimulatory signaling domain.

In certain embodiments, a CAR is a T cell receptor-based chimeric antigen receptor (TCR-CAR). A TCR-CAR is a heterodimeric fusion protein generally comprising a soluble TCR (a polypeptide chain comprising a Vα domain and Cα domain and a polypeptide chain comprising a Vβ domain and a Cβ domain), wherein the VβCβ polypeptide chain is linked to a transmembrane domain and an intracellular signaling component (e.g., an ITAM-containing activating domain and optionally a costimulatory signaling domain) (see, e.g., Walseng et al., 2017 Scientific Reports 7:10713).

CARs of the present disclosure may target a variety of antigens, including a viral antigen, bacterial antigen, fungal antigen, parasitic antigen, tumor antigen, neurodegenerative disease antigen, or autoimmune disease antigen. Exemplary tumor antigens that a CAR may target include CD138, CD38, CD33, CD123, CD72, CD79a, CD79b, mesothelin, PSMA, BCMA, ROR1, MUC-16, L1CAM, CD22, CD19, CD20, CD23, CD24, CD37, CD30, CA125, CD56, c-Met, EGFR, GD-3, HPV E6, HPV E7, MUC-1, HER2, folate receptor α, CD97, CD171, CD179a, CD44v6, WT1, VEGF-α, VEGFR1, IL-13Rα1, IL-13Rα2, IL-11Rα, PSA, FcRH5, NKG2D ligand, NY-ESO-1, TAG-72, CEA, ephrin A2, ephrin B2, Lewis A antigen, Lewis Y antigen, MAGE, MAGE-A1, RAGE-1, folate receptor β, EGFRviii, VEGFR-2, LGR5, SSX2, AKAP-4, FLT3, fucosyl GM1, GM3, o-acetyl-GD2, and GD2.

III. T Cell Receptor Binding Proteins

In certain embodiments, compositions of the present disclosure comprise in part immune cells comprising a transgene encoding a recombinant TCR binding protein. Recombinant TCR binding proteins include "traditional" TCRs composed of a heterodimer of an α chain polypeptide and β chain polypeptide (αβ TCR) or a heterodimer of a γ chain polypeptide and a δ chain polypeptide (γδ TCR), binding fragments and fusion proteins thereof, including for example, single chain TCRs, single domain TCRs, soluble TCR fusion TCR proteins, and TCR fusion constructs (TRuC™). In certain embodiments, a recombinant TCR is an enhanced affinity TCR.

In certain embodiments, a recombinant TCR binding protein is a single chain TCR (scTCR) comprising a Vα joined to a Vβ by a flexible linker. In some embodiments, a scTCR comprises a Vα-linker-Vβ polypeptide. In other embodiments, a scTCR comprises a Vβ-linker-Vα polypeptide.

In certain embodiments, a recombinant TCR binding protein is a single domain TCR (e.g., Vβ).

In certain embodiments, a recombinant TCR binding protein is a single chain TCR (scTCR) fusion protein. A scTCR fusion protein comprises a binding domain comprising a scTCR (a TCR Vα domain linked to a TCR Vβ domain), an optional extracellular spacer, a transmembrane domain, and an intracellular signaling domain comprising a CD3ζ ITAM-containing activating domain and optionally a costimulatory signaling domain (see, Aggen et al., 2012, Gene Ther. 19:365-374; Stone et al., Cancer Immunol. Immunother. 2014, 63:1163-76).

In certain embodiments, a recombinant TCR binding protein is a TCR fusion construct (TRuC™ construct) (see, U.S. Patent Publication No. 2017/0166622). TRuC™ constructs comprise an antigen-specific binding domain (e.g., scFv) fused at least one component of a TCR complex (CD3γ, CD3ε, or CD3δ) to form a TCR complex component fusion protein. A human TCR complex contains the CD3ε polypeptide, the CD3γ polypeptide, the CD3δ polypeptide, the CD3ζ polypeptide, the TCR α chain polypeptide, and the TCR β chain polypeptide. The TCR complex component fusion protein is capable of associating with the other components of the TCR complex to form a functional, complete TCR fusion complex. Unlike TCRs, TRuC™ constructs are capable of binding a target antigen in a MHC independent manner.

In certain embodiments, a TCR binding protein comprises polynucleotide sequences derived from any mammalian species, including humans, primates, cows, horses, goats, sheep, dogs, cats, mice, rats, rabbits, guinea pigs, pigs, transgenic species thereof, or any combination thereof. In certain embodiments, the TCR binding protein is murine, chimeric, human, or humanized.

TCR binding proteins of the present disclosure may bind to a variety of antigens, including tumor antigens, viral antigens, bacterial antigens, fungal antigens, parasitic antigens, neurodegenerative disease antigen, and autoimmune disease antigens. Exemplary tumor antigens that a recombinant TCR binding protein may target include WT-1, mesothelin, MART-1, NY-ESO-1, MAGE-A3, HPV E7, survivin, α Fetoprotein, and a tumor-specific neoantigen. Exemplary HPV16 E7 protein-specific TCRs that may be used in combination of cellular immunotherapy compositions of the present disclosure are provided in PCT Published Application No. WO2015/184228 (incorporated by reference in its entirety). In certain embodiments, a HPV16 E7 TCR comprises an amino acid sequence of SEQ ID NO:84. The amino acid sequence of SEQ ID NO:84 contains a P2A self-cleaving peptide between the TCRβ chain sequence and the TCRα chain sequence, which would be cleaved in the host cell to form two polypeptide chains. Thus, in certain embodiments, the TCR represented by SEQ ID NO:84 comprises separate TCRβ and TCRα polypeptide chains that are capable of dimerizing to form a αβTCR. In certain embodiments, a HPV16 E7 TCR comprises a Vβ comprising an amino acid sequence of SEQ ID NO:86. In certain embodiments, a HPV16 E7 TCR comprises a Vα comprising an amino acid sequence of SEQ ID NO:88. In further embodiments, a HPV16 E7 TCR comprises a Vβ comprising an amino acid sequence of SEQ ID NO:86 and a Vα comprising an amino acid sequence of SEQ ID NO:88.

In certain embodiments, a TCR Cα domain, a Cβ domain, or both comprises a cysteine substitution to create an inter-chain disulfide bond between the two constant domain cysteine residues, which is not present in unmodified TCRs. Such modified TCRs may form more stable heterodimers. In particular embodiments, the Cα domain comprises a Thr→Cys substitution at position 48 of the wildtype protein sequence, and the Cβ domain comprises a Ser→Cys substitution at position 56 of the wild type protein sequence (see, PCT Published Application No. WO2015/184228). An exemplary cysteine modified TCR Cβ constant region comprises an amino acid sequence of SEQ ID NO:87.

In certain embodiments, a TCR comprises substitutions of one, two, or three amino acids in the transmembrane domain of the constant region of one or both of the α and β chains with a hydrophobic amino acid to increase the hydrophobicity of the transmembrane domain. In certain embodiments, one, two, or three of the residues selected from Ser112, Met114, and Gly115 of the TCRα chain are substituted with Gly, Ala, Val, Leu, Ile, Pro, Phe, Met, or Trp. An exemplary cysteine modified, "LVL" substituted TCR Cα region comprises an amino acid sequence of SEQ ID NO:89.

In certain embodiments, the CER and the CAR, or the CER and TCR binding protein in a combination cellular immunotherapy composition target the same antigen. In other embodiments, the CER and the CAR, or the CER and TCR binding protein in a combination cellular immunotherapy composition target different antigens.

Polynucleotides, Vectors, Host Cells

In certain aspects, the present disclosure provides nucleic acid molecules that encode any one or more of the cellular immunotherapy molecules (e.g., CERs, CARs, and TCR binding proteins) described herein. A nucleic acid may refer to a single- or double-stranded DNA, cDNA, or RNA, and may include a positive and a negative strand of the nucleic acid which complement one another, including antisense DNA, cDNA, and RNA. A nucleic acid may be naturally occurring or synthetic forms of DNA or RNA. The nucleic acid sequences encoding a desired receptor can be obtained or produced using recombinant methods known in the art using standard techniques, such as by screening libraries from cells expressing the desired sequence or a portion thereof, by deriving the sequence from a vector known to include the same, or by isolating the sequence or a portion thereof directly from cells or tissues containing the same as described in, for example, Sambrook et al. (1989 and 2001 editions; *Molecular Cloning: A Laboratory Manual*, Cold Spring Harbor Laboratory Press, NY) and Ausubel et al. (Current Protocols in Molecular Biology, 2003). Alternatively, the sequence of interest can be produced synthetically, rather than being cloned.

Polynucleotides encoding the cellular immunotherapy molecules provided herein may be derived from any animal, such as humans, primates, cows, horses, sheep, dogs, cats, mice, rats, rabbits, guinea pigs, pigs, or a combination thereof. In certain embodiments, a polynucleotide encoding cellular immunotherapy molecule is from the same animal species as the host cell into which the polynucleotide is inserted.

In certain embodiments, a polynucleotide encoding a cellular immunotherapy molecule comprises a sequence encoding a signal peptide (also referred to as leader peptide or signal sequence) at the 5'-end for targeting of the precursor protein to the secretory pathway. The signal peptide is optionally cleaved from the N-terminus of the extracellular domain during cellular processing and localization of the receptor to the host cell membrane. A polypeptide from which a signal peptide sequence has been cleaved or removed may also be called a mature polypeptide. Examples of signal peptides that may be used in the receptors of the present disclosure include signal peptides derived from endogenous secreted proteins, including, e.g., GM-CSF (amino acid sequence of SEQ ID NO:67) or Tim4 (amino acid sequence of SEQ ID NO:68). As used herein, reference to a polynucleotide or polypeptide sequence of a cellular immunotherapy molecule, e.g., CER, CAR, or TCR binding protein, provided herein may include or exclude the signal sequence. It is understood by persons of skill in the art that for sequences disclosed herein that include a signal peptide sequence, the signal peptide sequence may be replaced with another signal peptide that is capable of trafficking the encoded protein to the extracellular membrane.

In certain embodiments, a cellular immunotherapy molecule encoding polynucleotide of the present disclosure is codon optimized for efficient expression in a target host cell comprising the polynucleotide (see, e.g, Scholten et al., *Clin. Immunol.* 119:135-145 (2006)). As used herein, a "codon optimized" polynucleotide comprises a heterologous polynucleotide having codons modified with silent mutations corresponding to the abundances of tRNA in a host cell of interest.

The polynucleotides encoding cellular immunotherapy molecules of the present disclosure may be operatively linked to expression control sequences. Expression control sequences may include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequences); sequences that enhance protein stability; and possibly sequences that enhance protein secretion.

In certain embodiments, polynucleotides encoding cellular immunotherapy molecules of the present disclosure can be constructed to optimize spatial and temporal control. For example, a polynucleotide encoding a cellular immunotherapy molecule can include promoter elements to optimize spatial and temporal control. In some embodiments, a polynucleotide encoding a cellular immunotherapy molecule includes tissue specific promoters or enhancers that enable specific induction of the polynucleotide encoding a cellular immunotherapy molecule to an organ, a cell type (e.g., immune cell), or a pathologic microenvironment, such as a tumor or infected tissue. An "enhancer" is an additional promoter element that can function either cooperatively or independently to activate transcription. In certain embodiments, a polynucleotide encoding a cellular immunotherapy molecule includes a constitutive promoter. An exemplary constitutive promoter for use in expressing the polynucleotides of the present disclosure is an EF-1α promoter. In certain embodiments, a polynucleotide encoding a cellular immunotherapy molecule includes an inducible promoter. In certain embodiments, a polynucleotide encoding a cellular immunotherapy molecule includes a tissue specific promoter.

A polynucleotide encoding a cellular immunotherapy molecule of the present disclosure can be inserted into an appropriate vector, e.g., a viral vector, non-viral plasmid vector, and non-viral vectors, such as lipid-based DNA vectors, modified mRNA (modRNA), self-amplifying mRNA, CELiD, and transposon-mediated gene transfer (PiggyBac, Sleeping Beauty), for introduction into a host cell of interest (e.g., an immune cell). Polynucleotides encoding a polynucleotide encoding a cellular immunotherapy molecule of the present disclosure can be cloned into any suitable vector, such as an expression vector, a replication vector, a probe generation vector, or a sequencing vector. In certain embodiments, a polynucleotide encoding the extracellular domain, a polynucleotide encoding the transmembrane domain, and a polynucleotide encoding the engulfment signaling domain are joined together into a single polynucleotide encoding a CER and then inserted into a vector. In other embodiments, a polynucleotide encoding the extracellular domain, a polynucleotide encoding the transmembrane domain, and a polynucleotide encoding the engulfment signaling domain may be inserted separately into a vector such that the expressed amino acid sequence produces a functional CER. Similarly, the components of a polynucleotide encoding a CAR or TCR binding protein may be assembled prior to insertion into a vector or separately inserted into the vector and assembled. A vector that encodes a CER is referred to herein as a "CER vector." A vector that encodes a CAR is referred to herein as a "CAR vector." A vector that encodes a TCR binding protein is referred to herein as a "TCR binding protein vector." Collectively, these vectors are referred to herein as "cellular immunotherapy molecule vectors"

In certain embodiments, vectors that allow long-term integration of a cellular immunotherapy molecule polynucleotide and propagation to daughter cells are utilized. Examples include viral vectors such as, adenovirus, adeno-associated virus, vaccinia virus, herpes viruses, cytomegalovirus, pox virus, or retroviral vectors, such as lentiviral vectors. Vectors derived from lentivirus can be used to achieve long-term gene transfer and have added advantages over vectors including the ability to transduce non-proliferating cells, such as hepatocytes, and low immunogenicity.

In certain embodiments, non-integrating vectors that that remain episomal are used for the polynucleotides encoding cellular immunotherapy molecules of the present disclosure. Examples of non-integrating viral vectors include adenoviral vectors and integrating viral vectors that have been mutated to be non-integrating, such as non-integrating lentiviral vectors and non-integrating foamy virus vectors.

A vector that encodes a core virus is referred to herein as a "viral vector." There are a large number of available viral vectors suitable for use with the compositions of the instant disclosure, including those identified for human gene therapy applications (see Pfeifer and Verma, *Ann. Rev. Genomics Hum. Genet.* 2:177, 2001). Suitable viral vectors include vectors based on RNA viruses, such as retrovirus-derived vectors, e.g., Moloney murine leukemia virus (MLV)-derived vectors, and include more complex retrovirus-derived vectors, e.g., lentivirus-derived vectors. HIV-1-derived vectors belong to this category. Other examples include lentivirus vectors derived from HIV-2, FIV, equine infectious anemia virus, SIV, and Maedi-Visna virus (ovine lentivirus). Methods of using retroviral and lentiviral viral vectors and packaging cells for transducing mammalian host cells with viral particles containing chimeric receptor transgenes are known in the art and have been previous described, for example, in U.S. Pat. No. 8,119,772; Walchli et al., *PLoS One* 6:327930, 2011; Zhao et al., *J. Immunol.* 174:4415, 2005; Engels et al., *Hum. Gene Ther.* 14:1155, 2003; Frecha et al., *Mol. Ther.* 18:1748, 2010; Verhoeyen et al., *Methods Mol. Biol.* 506:97, 2009. Retroviral and lentiviral vector constructs and expression systems are also commercially available.

In certain embodiments, a viral vector is used to introduce a non-endogenous polynucleotide encoding a cellular immunotherapy molecule to a host cell. A viral vector may be a retroviral vector or a lentiviral vector. A viral vector may also include a nucleic acid sequence encoding a marker for transduction. Transduction markers for viral vectors are known in the art and include selection markers, which may confer drug resistance, or detectable markers, such as fluorescent markers or cell surface proteins that can be detected by methods such as flow cytometry. In particular embodiments, a viral vector further comprises a gene marker for transduction comprising a fluorescent protein (e.g., green, yellow), an extracellular domain of human CD2, or a truncated human EGFR (EGFRt or tEGFR; see Wang et al., *Blood* 118:1255, 2011). An exemplary tEGFR sequence comprises an amino acid sequence of SEQ ID NO:70.

Other viral vectors also can be used for polynucleotide delivery including DNA viral vectors, including, for example adenovirus-based vectors and adeno-associated virus (AAV)-based vectors; vectors derived from herpes simplex viruses (HSVs), including amplicon vectors, replication-defective HSV and attenuated HSV (Krisky et al., *Gene Ther.* 5: 1517, 1998).

Other viral vectors recently developed for gene therapy uses can also be used with the compositions and methods of this disclosure. Such vectors include those derived from baculoviruses and α-viruses. (Jolly, D J. 1999. Emerging Viral Vectors. pp 209-40 in Friedmann T. ed. The Development of Human Gene Therapy. New York: Cold Spring Harbor Lab), or plasmid vectors (such as sleeping beauty or other transposon vectors).

Where temporal control is desired, a cellular immunotherapy molecule vector may include an element that allows for inducible depletion of transduced cells. For example, such a vector may include an inducible suicide gene. A suicide gene may be an apoptotic gene or a gene that confers sensitivity to an agent (e.g., a drug). Exemplary suicide genes include chemically inducible caspase 9 (iCASP9) (U.S. Patent Publication No. 2013/0071414), chemically inducible Fas, or Herpes simplex virus thymidine kinase (HSV-TK), which confers sensitivity to ganciclovir. In further embodiments, a cellular immunotherapy molecule vector can be designed to express a known cell surface antigen that, upon infusion of an associated antibody, enables depletion of transduced cells. Examples of cell surface antigens and their associated antibodies that may be used for depletion of transduced cells include CD20 and Rituximab, RQR8 (combined CD34 and CD20 epitopes, allowing CD34 selection and anti-CD20 deletion) and Rituximab, and EGFR and Cetuximab.

Inducible vector systems, such as the tetracycline (Tet)-On vector system which activates transgene expression with doxycycline (Heinz et al., Hum. Gene Ther. 2011, 22:166-76) may also be used for inducible expression of a cellular immunotherapy molecule. Small molecule responsive transcription factors may also be used to regulate expression. Inducible expression of a cellular immunotherapy molecule may be also accomplished via retention using a selective hook (RUSH) system based on streptavidin anchored to the membrane of the endoplasmic reticulum through a hook and a streptavidin binding protein introduced into the cellular immunotherapy molecule structure, where addition of biotin to the system leads to the release of the cellular immunotherapy molecular from the endoplasmic reticulum (Agague et al., 2015, Mol. Ther. 23(Suppl. 1):588).

In certain embodiments, a CER modified host cell may also be modified to co-express one or more small GTPases. Rho GTPases, a family of small (~21 k Da) signaling G proteins and also a subfamily of the Ras superfamily, regulate actin cytoskeleton organization in various cell types and promote pseudopod extension and phagosome closure during phagocytosis (see, e.g., Castellano et al., 2000, J. Cell Sci. 113:2955-2961). Engulfment requires F-actin recruitment beneath tethered cells or particles, and F-actin rearrangement to allow membrane extension resulting in cell or particle internalization. RhoGTPases include RhoA, Rac1, Rac2, RhoG, and CDC42. Other small GTPases, such as Rap1, is involved in regulation of complement mediated phagocytosis. Co-expression of a small GTPase with the CER may promote or enhance target cell or particle internalization and/or phagosome formation by the host cell. In some embodiments, a recombinant nucleic acid molecule encoding a GTPase is encoded on a separate vector than the CER-containing vector. In other embodiments, a recombinant nucleic acid molecule encoding a GTPase is encoded on the same vector as the CER. The GTPase and CER may be expressed under the regulation of different promoters on the same vector (e.g., at different multiple cloning sites). Alternatively, the CER and GTPase may be expressed under the regulation of one promoter in a multicistronic vector.

Examples of GTPases that may be co-expressed with a CER include Rac1, Rac2, Rab5 (also referred to as Rab5a), Rab7, Rap1, RhoA, RhoG, CDC42, or any combination thereof. In specific embodiments, the GTPase comprises or is a sequence that is at least 90%, at least 91%, at least 92%, at least 93%, at least 94%, at least 95%, at least 96%, at least 97%, at least 98%, at least 99%, at least 99.5%, or 100% identical to a Rac1 amino acid sequence of SEQ ID NO:71, a Rab5 amino acid sequence of SEQ ID NO:72, a Rab7 amino acid sequence of SEQ ID NO:73, a Rap1 amino acid sequence of SEQ ID NO:74, a RhoA amino acid sequence of SEQ ID NO:75, a CDC42 amino acid sequence of SEQ ID NO:76, or any combination thereof. In certain embodiments, expression of the GTPase is induced or regulated in a host cell such that following a sufficient amount of time for the CER to have bound its target antigen, the expression of GTPase is switched on. In further embodiments, expression of the GTPase may be switched off following a sufficient amount of time for CER mediated engulfment of the cells expressing the target antigen.

In certain embodiments, polynucleotides or vectors of the present disclosure may comprise an internal ribosome entry site (IRES), furin cleavage site, or viral 2A peptide disposed between multiple genes encoded therein to allow for coexpression of multiple proteins from a single mRNA. For example, an IRES, furin cleavage site, or viral 2A peptide may be disposed between a polynucleotide encoding a TCRα chain polypeptide and a polynucleotide encoding a TCRβ chain polypeptide. In another example, an IRES, furin cleavage site, or viral 2A peptide may be disposed between a polynucleotide encoding a CER and a polynucleotide encoding a transduction marker (e.g., truncated EGFR). In certain embodiments, a viral 2A peptide is a porcine teschovirus-1 (P2A), *Thosea asigna* virus (T2A), equine rhinitis A virus (E2A), foot-and-mouth disease virus (F2A), or a variant thereof. An exemplary T2A peptide comprises an amino acid sequence of any one of SEQ ID NOs:77, 78, 79, and 168. An exemplary P2A peptide comprises an amino acid sequence of SEQ ID NO:80 or 81. An exemplary E2A peptide sequence comprises an amino acid sequence of SEQ ID NO:82. An exemplary F2A peptide sequence comprises an amino acid sequence of SEQ ID NO:83.

In certain embodiments, a cell, such as an immune cell, obtained from a subject may be genetically modified into a non-natural or recombinant cell (e.g., a non-natural or recombinant immune cell) by introducing a polynucleotide encoding a cellular immunotherapy molecule as described herein and whereby the cell expresses a cell surface localized cellular immunotherapy molecule (e.g., CER, CAR, or TCR binding protein). In certain embodiments, a host cell is an immune cell, such as a myeloid progenitor cell or a lymphoid progenitor cell. Exemplary immune cells that may be modified to comprise a cellular immunotherapy molecule or a vector comprising a cellular immunotherapy molecule include a T cell, a natural killer cell, a B cell, a lymphoid precursor cell, an antigen presenting cell, a dendritic cell, a Langerhans cell, a myeloid precursor cell, a mature myeloid cell, a monocyte, or a macrophage.

In certain embodiments, a B cell is genetically modified to express a CER of the present disclosure. B cells possess certain properties that may be advantageous as host cells, including: trafficking to sites of inflammation, capable of internalizing and presenting antigen, capable of costimulating T cells, highly proliferative, and self-renewing (persist for life). In certain embodiments, a CER modified B cell is capable of digesting an engulfed target cell or engulfed target particle into smaller peptides and presenting them to T cells via an MHC molecule. Antigen presentation by a CER modified B cell may contribute to antigen spreading of the immune response to non-targeted antigens. B cells include progenitor or precursor cells committed to the B cell lineage (e.g., pre-pro-B cells, pro-B cells, and pre-B cells); immature and inactivated B cells; or mature and functional or activated B cells. In certain embodiments, B cells may be naïve B cells, plasma cells, regulatory B cells, marginal zone B cells, follicular B cells, lymphoplasmacytoid cell, plasmablast cell, memory B cells, or any combination thereof. Memory B cells may be distinguished from naïve B cells by expression of CD27, which is absent on naïve B cells. In certain embodiments, the B cells can be primary cells or cell lines derived from human, mouse, rat, or other mammals. B cell lines are well known in the art. If obtained from a mammal, a B cell can be obtained from numerous sources, including blood, bone marrow, spleen, lymph node, or other tissues or fluids. A B cell composition may be enriched or purified.

In certain embodiments, a T cell is genetically modified to express a cellular immunotherapy molecule (e.g., CER, CAR, and TCR binding protein) of the present disclosure. Exemplary T cells include $CD4^+$ helper, $CD8^+$ effector (cytotoxic), naïve (CD45 RA+, CCR7+, CD62L+, CD27+, CD45RO−), central memory ($CD45RO^+$, $CD62L^+$, $CD8^+$), effector memory (CD45RA+, CD45RO−, CCR7−, CD62L−, CD27−), T memory stem, regulatory, mucosal-associated invariant (MAIT), γδ (gd), tissue resident T cells, natural killer T cells, or any combination thereof. In certain embodiments, the T cells can be primary cells or cell lines derived from human, mouse, rat, or other mammals. If obtained from a mammal, a T cell can be obtained from numerous sources, including blood, bone marrow, lymph node, thymus, or other tissues or fluids. A T cell composition may be enriched or purified. T cell lines are well known in the art, some of which are described in Sandberg et al., *Leukemia* 21:230, 2000. In certain embodiments, the T cells lack endogenous expression of a TCRα gene, TCRβ gene, or both. Such T cells may naturally lack endogenous expression of TCRα and β chains, or may have been modified to block expression (e.g., T cells from a transgenic mouse that does not express TCR α and β chains or cells that have been manipulated to inhibit expression of TCR α and β chains) or to knockout a TCRα chain, a TCRβ chain, or both genes.

In certain embodiments, host cells expressing a cellular immunotherapy molecule of the present disclosure are not T cells or cells of a T cell lineage, but cells that are progenitor cells, stem cells or cells that have been modified to express cell surface anti-CD3.

In certain embodiments, gene editing methods are used to modify the host cell genome to comprise a cellular immunotherapy molecule of the present disclosure. Gene editing, or genome editing, is a method of genetic engineering wherein DNA is inserted, replaced, or removed from a host cell's genome using genetically engineered endonucleases. The nucleases create specific double-stranded breaks at targeted loci in the genome. The host cell's endogenous DNA repair pathways then repair the induced break(s), e.g., by non-homologous ending joining (NHEJ) and homologous recombination. Exemplary endonucleases useful for gene editing include a zinc finger nuclease (ZFN), a transcription activator-like effector (TALE) nuclease, a clustered regularly interspaced short palindromic repeats (CRISPR)/Cas nuclease system (e.g., CRISPR-Cas9), a meganuclease, or combinations thereof. Methods of disrupting genes or gene expression in immune cells including B cells and T cells, using gene editing endonucleases are known in the art and described, for example, in PCT Publication Nos. WO 2015/066262; WO 2013/074916; WO 2014/059173; Cheong et al., Nat. Comm. 2016 7:10934; Chu et al., Proc. Natl. Acad. Sci. USA 2016 113:12514-12519; methods from each of which are incorporated herein by reference in their entirety.

In certain embodiments, expression of an endogenous gene of the host cell is inhibited, knocked down, or knocked out. Examples of endogenous genes that may be inhibited, knocked down, or knocked out in a B cell include IGH, IGκ, IGλ, or any combination thereof. Examples of endogenous genes that may be inhibited, knocked down, or knocked out in a T cell include a TCR gene (TRA or TRB), an HLA gene (HLA class I gene or HLA class II gene), an immune checkpoint molecule (PD-L1, PD-L2, CD80, CD86, B7-H3, B7-H4, HVEM, adenosine, GALS, VISTA, CEACAM-1, CEACAM-3, CEACAM-5, PVRL2, PD-1, CTLA-4, BTLA, KIR, LAG3, TIM3, A2aR, CD244/2B4, CD160, TIGIT, LAIR-1, or PVRIG/CD112R), or any combination thereof. Expression of an endogenous gene may be inhibited, knocked down, or knocked out at the gene level, transcriptional level, translational level, or a combination thereof. Methods of inhibiting, knocking down, or knocking out an endogenous gene may be accomplished, for example, by an RNA interference agent (e.g., siRNA, shRNA, miRNA, etc.) or an engineered endonuclease (e.g., CRISPR/Cas nuclease system, a zinc finger nuclease (ZFN), a Transcription Activator Like Effector nuclease (TALEN), a meganuclease), or any combination thereof. In certain embodiments, an endogenous B cell gene (e.g., IGH, IGκ, or IGλ) is knocked out by insertion of a polynucleotide encoding a CER of the present disclosure into the locus of the endogenous B cell gene, such as via an engineered endonuclease. In certain embodiments, an endogenous T cell gene (e.g., a TCR gene, an HLA gene, or an immune checkpoint molecule gene) is knocked out by insertion of a polynucleotide encoding a CER, CAR, or TCR binding protein of the present disclosure into the locus of the endogenous T cell gene, such as via an engineered endonuclease.

The present disclosure also provides a composition comprising a population of cellular immunotherapy molecule modified host cells. In certain embodiments, the population of cellular immunotherapy molecule modified host cells may be a population of B cells, a population of T cells, a population of natural killer cells, a population of lymphoid precursor cells, a population of antigen presenting cells, a population of dendritic cells, a population of Langerhans cells, a population of myeloid precursor cells, a population of mature myeloid cells, or any combination thereof. Furthermore, a population of cellular immunotherapy molecule modified host cells of a particular cell type may be composed of one or more subtypes. For example, a population of B cells may be composed of CER modified naïve B cells, plasma cells, regulatory B cells, marginal zone B cells, follicular B cells, lymphoplasmacytoid cell, plasmablast cell, memory B cells, or any combination thereof. In another example, a population of T cells may be composed of CAR modified $CD4^+$ helper T cells, $CD8^+$ effector (cytotoxic) T cells, naïve (CD45 RA+, CCR7+, CD62L+, CD27+, CD45RO-) T cells, central memory ($CD45RO^+$, $CD62L^+$, $CD8^+$) T cells, effector memory (CD45RA+, CD45RO-, CCR7-, CD62L-, CD27-) T cells, T memory stem cells, regulatory T cells, mucosal-associated invariant T cells (MAIT), γδ (gd), tissue resident T cells, natural killer T cells, or any combination thereof.

In certain embodiments, when preparing cellular immunotherapy molecule modified host cells, e.g., B cells or T cells, one or more growth factor cytokines that promote proliferation of the host cells, e.g., B cells or T cells, may be added to the cell culture. The cytokines may be human or non-human. Exemplary growth factor cytokines that may be used to promote T cell proliferation include IL-2, IL-15, or the like. Exemplary growth factor cytokines that may be used to promote B cell proliferation include CD40L, IL-2, IL-4, IL-15, IL-21, BAFF, or the like.

Prior to genetic modification of the host cells with a polynucleotide encoding a cellular immunotherapy molecule, a source of host cells (e.g., T cells, B cells, natural killer cells, etc.) is obtained from a subject (e.g., whole blood, peripheral blood mononuclear cells, bone marrow, lymph node tissue, cord blood, thymus tissue, tissue from a site of infection, ascites, pleural effusion, spleen tissue), from which host cells are isolated using methods known in the art. Specific host cell subsets can be collected in accordance with known techniques and enriched or depleted by known techniques, such as affinity binding to antibodies, flow cytometry and/or immunomagnetic selection. After enrichment and/or depletion steps and introduction of a polynucleotide encoding a cellular immunotherapy molecule, in vitro expansion of the desired modified host cells can be carried out in accordance with known techniques, or variations thereof that will be apparent those skilled in the art.

The expression of a cellular immunotherapy molecule on host cells may be functionally characterized according to any of a large number of art-accepted methodologies for assaying host cell (e.g., T cell) activity, including determination of T cell binding, activation or induction and also including determination of T cell responses that are antigen-specific. Examples include determination of T cell proliferation, T cell cytokine release, antigen-specific T cell stimulation, CTL activity (e.g., by detecting $^{51}Cr$ or Europium release from pre-loaded target cells, induction of caspase activity in target cells, extracellular release of lactate dehydrogenase by target cells), changes in T cell phenotypic marker expression, and other measures of T cell functions. Procedures for performing these and similar assays are may be found, for example, in Lefkovits (*Immunology Methods Manual: The Comprehensive Sourcebook of Techniques*, 1998). See, also, *Current Protocols in Immunology*; Weir, *Handbook of Experimental Immunology*, Blackwell Scientific, Boston, MA (1986); Mishell and Shigii (eds.) *Selected Methods in Cellular Immunology*, Freeman Publishing, San Francisco, CA (1979); Green and Reed, *Science* 281:1309 (1998) and references cited therein. Cytokine levels may be determined according to methods known in the art, including for example, ELISA, ELISPOT, intracellular cytokine staining, flow cytometry, and any combination thereof (e.g., intracellular cytokine staining and flow cytometry). Immune cell proliferation and clonal expansion resulting from an antigen-specific elicitation or stimulation of an immune response may be determined by isolating lymphocytes, such as circulating lymphocytes in samples of peripheral blood cells or cells from lymph nodes, stimulating the cells with antigen, and measuring cytokine production, cell proliferation and/or cell viability, such as by incorporation of tritiated thymidine or non-radioactive assays, such as MTT assays and the like.

In certain embodiments, a CER modified host cell has a phagocytic index of about 20 to about 1,500 for a target cell. A "phagocytic index" is a measure of phagocytic activity of the transduced host cell as determined by counting the number of target cells or particles ingested per CER modified host cell during a set period of incubation of a suspension of target cells or particles and CER modified host cells in media. Phagocytic index may be calculated by multiplying [total number of engulfed target cells/total number of counted CER modified cells (e.g., phagocytic frequency)]× [average area of target cell or particle staining per $CER^+$ host cell×100 (e.g., hybrid capture)] or [total number of engulfed particles/total number of counted CER modified host cells]× [number of CER modified host cells containing engulfed particles/total number of counted $CER^+$ cells]×100. In certain embodiments, a CER modified cell has a phagocytic index of about 30 to about 1,500; about 40 to about 1,500; about 50 to about 1,500; about 75 to about 1,500; about 100 to about 1,500; about 200 to about 1,500; about 300 to about 1,500; about 400 to about 1,500; about 500 to about 1,500; about 20 to about 1,400; about 30 to about 1,400; about 40 to about 1,400; about 50 to about 1,400; about 100 to about 1,400; about 200 to about 1,400; about 300 to about 1,400; about 400 to about 1,400; about 500 to about 1,400; about 20 to about 1,300; about 30 to about 1,300; about 40 to about 1,300; about 50 to about 1,300; about 100 to about 1,300; about 200 to about 1,300; about 300 to about 1,300; about 400 to about 1,300; about 500 to about 1,300; about 20 to about 1,200; about 30 to about 1,200; about 40 to about 1,200; about 50 to about 1,200; about 100 to about 1,200; about 200 to about 1,200; about 300 to about 1,200; about 400 to about 1,200; about 500 to about 1,200; about 20 to about 1,100; about 30 to about 1,100; about 40 to about 1,100; about 50 to about 1,100; about 100 to about 1,100; about 200 to about 1,100; about 300 to about 1,100; about 400 to about 1,100; or about 500 to about 1,100; about 20 to about 1,000; about 30 to about 1,000; about 40 to about 1,000; about 50 to about 1,000; about 100 to about 1,000; about 200 to about 1,000; about 300 to about 1,000; about 400 to about 1,000; or about 500 to about 1,000; about 20 to about 750; about 30 to about 750; about 40 to about 750; about 50 to about 750; about 100 to about 750; about 200 to about 750; about 300 to about 750; about 400 to about 750; or about 500 to about 750; about 20 to about 500; about 30 to about 500; about 40 to about 500; about 50 to about 500; about 100 to about 500; about 200 to about 500; or about 300 to about 500. In further embodiments, the incubation time is from about 2 hours to about 4 hours, e.g., about 2 hours, about 3 hours, or about 4 hours. In yet further embodiments, a CER modified cell exhibits phagocytic index that is statistically significantly higher than a cell transduced with truncated EGFR control. Phagocytic index may be calculated using methods known in the art and as further described in the Examples and PCT Application No. PCT/ US2017/053553 (incorporated herein by reference in its entirety), including quantification by flow cytometry or fluorescence microscopy.

Host cells may be from an animal, such as a human, primate, cow, horse, sheep, dog, cat, mouse, rat, rabbit, guinea pig, pig, or a combination thereof. In a preferred embodiment, the animal is a human. Host cells may be obtained from a healthy subject or a subject having a disease associated with expression of an antigen.

Cellular Immunotherapy Compositions

The present disclosure provides combinations of cellular immunotherapy compositions. The combination of cellular immunotherapy compositions comprise a first composition comprising an immune cell comprising a CER (also referred to as "Composition #1) and a second composition comprising an immune cell comprising a cellular immunotherapy molecule, e.g., a CER, CAR, or TCR (also referred to as "Composition #2). The CER present in the immune cell of the first composition can be selected from any one or more of the CER binding proteins described herein. The CER, CAR or TCR present in the immune call of the second composition can be selected from any one or more of the CER, CAR, or TCR binding proteins described herein. In particular embodiments, the immune cell comprising a CER in the first composition is a CER modified host cell as described herein, and the immune cell comprising a cellular immunotherapy molecule of the second composition is a host cell modified with a CER, CAR or TCR as described herein. Exemplary embodiments of combinations of host immune cells and cellular immunotherapy molecules are shown in Table 2 and Table 3.

In certain embodiments, the CER of the first composition and the cellular immunotherapy molecule, e.g., CER, CAR, or TCR binding protein, of the second composition bind to target antigens associated with the same disease or disorder, e.g., cancer. The CER of the first composition and the cellular immunotherapy molecule, e.g., CER, CAR, or TCR binding protein, of the second composition may bind to the same target antigen or bind to different target antigens. In certain embodiments, the CER of the first composition binds to a pro-engulfment marker (e.g., phosphatidylserine) and the cellular immunotherapy molecule, e.g., CER, CAR, or TCR binding protein, of the second composition binds to a target antigen associated with a disease (e.g., cancer). Other embodiments provide that the CER of the first composition binds to a first tumor antigen and the cellular immunotherapy molecule, e.g., CER, CAR, or TCR binding protein, of the second composition binds to the first tumor antigen. Yet other embodiments provide that the CER of the first composition binds to a first tumor antigen and the cellular immunotherapy molecule, e.g., CER, CAR, or TCR binding protein, of the second composition binds to a second tumor antigen.

In one embodiment of the compositions shown in Table 2, the specified immune cell of the first composition comprises a CER that targets a pro-engulfment marker, while the CER, CAR or TCR of the specified immune cell of the second composition targets a tumor antigen. In another embodiment of the compositions shown in Table 2, the specified immune cell of the first composition comprises a CER that targets a pro-engulfment marker, while the CER, CAR or TCR of the specified immune cell of the second composition targets a bacterial, viral or parasitic antigen. In another embodiment of the compositions shown in Table 2, the specified immune cell of the first composition comprises a CER that targets a pro-engulfment marker, while the CER, CAR or TCR of the specified immune cell of the second composition targets an autoimmune disease antigen. In still another embodiment of the compositions shown in Table 2, the specified immune cell of the first composition comprises a CER that targets a tumor antigen, and the CER, CAR or TCR of the specified immune cell of the second composition targets a tumor antigen.

TABLE 2

Exemplary Cellular Immunotherapy Composition Combinations

| Composition #1 | Composition #2 |
|---|---|
| B cell/CER | CD4 T cell/CAR |
| B cell/CER | CD8 T cell/CAR |
| B cell/CER | CD4 T cell/TCR binding protein |
| B cell/CER | CD8 T cell/TCR binding protein |
| CD4 T cell/CER | CD8 T cell/CER |
| CD4 T cell/CER | CD4 T cell/CAR |
| CD4 T cell/CER | CD8 T cell/CAR |
| CD4 T cell/CER | CD4 T cell/TCR binding protein |
| CD4 T cell/CER | CD8 T cell/TCR binding protein |
| CD8 T cell/CER | CD4 T cell/CAR |
| CD8 T cell/CER | CD8 T cell/CAR |
| CD8 T cell/CER | CD4 T cell/TCR binding protein |
| CD8 T cell/CER | CD8 T cell/TCR binding protein |
| NK cell/CER | CD4 T cell/CAR |
| NK cell/CER | CD8 T cell/CAR |
| NK cell/CER | CD4 T cell/TCR binding protein |
| NK cell/CER | CD8 T cell/TCR binding protein |
| γδ T cell/CER | CD4 T cell/CAR |
| γδ T cell/CER | CD8 T cell/CAR |
| γδ T cell/CER | CD4 T cell/TCR binding protein |
| γδ T cell/CER | CD8 T cell/TCR binding protein |
| MAIT T cell/CER | CD4 T cell/CAR |
| MAIT T cell/CER | CD8 T cell/CAR |
| MAIT T cell/CER | CD4 T cell/TCR binding protein |
| MAIT T cell/CER | CD8 T cell/TCR binding protein |
| Monocyte/CER | CD4 T cell/CAR |
| Monocyte/CER | CD8 T cell/CAR |
| Monocyte/CER | CD4 T cell/TCR binding protein |
| Monocyte/CER | CD8 T cell/TCR binding protein |
| Macrophage/CER | CD4 T cell/CAR |
| Macrophage/CER | CD8 T cell/CAR |
| Macrophage/CER | CD4 T cell/TCR binding protein |
| Macrophage/CER | CD8 T cell/TCR binding protein |

| Antigenic Target of Composition #1 | Antigenic Target of Composition #2 |
|---|---|
| Targets Pro-engulfment marker | Targets Tumor antigen |
| Targets Pro-engulfment marker | Targets bacterial, viral, parasitic antigen |
| Targets Pro-engulfment marker | Targets autoimmune disease antigen |
| Targets Tumor antigen | Targets Tumor antigen (may be same tumor antigen target or different tumor antigen target as Composition #1) |

TABLE 3

Specific Cellular Immunotherapy Composition Combinations

| Composition #1 | Composition #2 |
|---|---|
| CD4 T cell/CER5 (SEQ ID NO: 94) | CD8 T cell/HPV E7 TCR (SEQ ID NO: 84) |
| CD4 T cell/CER17 (SEQ ID NO: 112) | CD8 T cell/HPV E7 TCR (SEQ ID NO: 84) |
| CD4 T cell/CER19 (SEQ ID NO: 95) | CD8 T cell/HPV E7 TCR (SEQ ID NO: 84) |
| CD4 T cell/CER21 (SEQ ID NO: 96) | CD8 T cell/HPV E7 TCR (SEQ ID NO: 84) |
| CD4 T cell/CER23 (SEQ ID NO: 116) | CD8 T cell/HPV E7 TCR (SEQ ID NO: 84) |

TABLE 3-continued

Specific Cellular Immunotherapy Composition Combinations

| Composition #1 | Composition #2 |
|---|---|
| CD4 T cell/CER26 (SEQ ID NO: 118) | CD8 T cell/HPV E7 TCR (SEQ ID NO: 84) |
| CD4 T cell/CER27 (SEQ ID NO: 98) | CD8 T cell/HPV E7 TCR (SEQ ID NO: 84) |
| CD4 T cell/CER103B (SEQ ID NO: 138) | CD8 T cell/HPV E7 TCR (SEQ ID NO: 84) |
| CD4 T cell/CER104 (SEQ ID NO: 139) | CD8 T cell/HPV E7 TCR (SEQ ID NO: 84) |
| CD4 T cell/CER105 (SEQ ID NO: 140) | CD8 T cell/HPV E7 TCR (SEQ ID NO: 84) |
| CD4 T cell/CER106 (SEQ ID NO: 141) | CD8 T cell/HPV E7 TCR (SEQ ID NO: 84) |
| CD4 T cell/CER116 (SEQ ID NO: 152) | CD8 T cell/HPV E7 TCR (SEQ ID NO: 84) |

In certain embodiments, reference to an immune cell type in a cellular immunotherapy composition may include any one or more specific cellular subtypes as provided herein. In one example, a cellular immunotherapy composition comprising a CD4+ T cell includes a naïve CD4+ T cell, an effector memory CD4+ T cell, a central memory CD4+ T cell, or any combination thereof. In another example, a cellular immunotherapy composition comprising a CD8+ T cell includes a naive CD8 T cell, an effector memory CD8+ T cell, a central memory CD8+ T cell, or any combination thereof. In yet another example, a cellular immunotherapy composition comprising a B cell includes a naïve B cell, a memory B cell, or both.

In certain embodiments, the combination of cellular immunotherapy compositions further comprise a third composition comprising an immune cell comprising a cellular immunotherapy molecule, e.g., a CER, CAR, or TCR binding protein according to any of the embodiments provided herein.

The cellular immunotherapy composition combinations provided in the present disclosure may be formulated as a single pharmaceutical composition comprising both the first composition and the second composition. Alternatively, cellular immunotherapy composition combinations provided in the present disclosure may be formulated in separate pharmaceutical compositions, with the first composition being formulated in a first pharmaceutical composition and the second composition being formulated in a second pharmaceutical composition distinct from the first pharmaceutical composition. Embodiments of the cellular immunotherapy composition combinations provided in the present disclosure provide multiple, non-redundant modes of target cell killing and enhanced effector function. Examples of enhanced effector function include: cytolytic activity towards a target cell; enhanced activation (e.g., enhanced cytokine production, such as IFNγ); enhanced cell proliferation; enhanced cell expansion; enhanced persistence; enhanced memory formation; antigen presentation activity; induction of antigen-specific phagocytic signaling or enhanced antigen-specific phagocytic signaling; degradation of an engulfed target cell; or any combination thereof. In certain embodiments, such cellular immunotherapy compositions confer a synergistic effect on effector function.

The relative amounts of the first composition and the second composition (whether included in the same or separate formulations) utilized in a cellular immunotherapy composition combinations according to the present description can be adjusted to achieve a defined cellular ratio to be administered to a subject. As used herein, the term "cellular ratio" refers to a ratio of the number of immune cells included in the first composition to the number of immune cells included in the second composition. For example, where a cellular immunotherapy composition combination according to the present description includes a first composition having 100 immune cells comprising a CER and a second composition having 100 immune cells comprising a CER, CAR or TCR, the ratio of the first composition to the second composition would be 1:1. In another example, where a cellular immunotherapy composition combination according to the present description includes a first composition having 50 immune cells comprising a CER and a second composition having 100 immune cells comprising a CER, CAR or TCR, the ratio of the first composition to the second composition would be 1:2. In still another example, where a cellular immunotherapy composition combination according to the present description includes a first composition having 100 immune cells comprising a CER and a second composition having 50 immune cells comprising a CER, CAR or TCR, the ratio of the first composition to the second composition would be 2:1. In certain embodiments, the cellular immunotherapy composition combination according to the present description includes the first composition and the second composition at a ratio selected from about 0.1:1, about 0.25:1, about 0.5:1, about 0.75:1, about 1:1, about 1.25:1, about 1.5:1, about 1.75:1, about 2:1, about 3:1, about 4:1, about 5:1, about 6:1, about 7:1, about 8:1, about 9:1, about 10:1, about 15:1, about 20:1, about 25:1, about 30:1, about 35:1, about 40:1, about 45:1, about 50:1, about 1:1.1, about 1:1.25, about 1:1.5, about 1:1.75, about 1:2, about 1:3, about 1:4, about 1:5, about 1:6, about 1:7, about 1:8, about 1:9, about 1:10, about 1:15, about 1:20, 1:25, about 1:30, about 1:35, about 1:40, about 1:45, and about 1:50. In another embodiment, the cellular immunotherapy composition according to the present description includes the first composition and the second composition at a ratio selected from ratios ranging from about 1:1 to about 1:2, from about 1:1 to about 1:5, from about 1:1 to about 1:7.5, from about 1:1 to about 1:10, from about 1:1 to about 1:15, from about 1:1 to about 1:20, from about 1:1 to about 1:30, from about 1:1 to about 1:40, and from about 1:1 to about 1:50. In another embodiment, the cellular immunotherapy composition according to the present description includes the first composition and the second composition at a ratio selected from ratios ranging from about 50:1 to about 1:1, from about 40:1 to about 1:1, from about 30:1 to about 1:1, from about 20:1 to about 1:1, from about 15:1 to about 1:1, from about 10:1 to about 1:1, from about 7.5:1 to about 1:1, from about 5:1 to about 1:1, and from about 2:1 to about 1:1. In each such embodiment, the cellular immunotherapy composition can include a first composition (i.e., Composition #1) and a second composition (i.e., Composition #2) according to any of the combinations described herein.

Embodiments of the combinations of specific cellular immunotherapy molecules and defined populations of immune cells used in the cellular immunotherapy compositions provided in the present disclosure provide multiple, non-redundant modes of target cell killing and enhanced effector function. By way of example, a combination of cellular immunotherapy compositions may comprise: a first composition comprising a CD4+ T cell comprising a CER and a second composition comprising a CD8+ T cell comprising a CAR or TCR binding protein. Upon antigen binding by an expressed CAR or TCR, the CAR or TCR modified CD8+ T cell is capable of inducing apoptosis (cytolysis) in a target cell by releasing contents of cytotoxic granules (e.g., granzymes, granulysins, perforins). CER modified CD4+ T cells are also capable of inducing apoptosis in target cells upon antigen binding, and also secrete Th1 cytokines (e.g., IFN-γ, IL-2) that support cytotoxic CD8+ T cell response. Furthermore, CER modified CD4+ T cells are capable of engulfing target cells that are bound by the CER. In another example, a combination of cellular immunotherapy compositions comprising: a first composition comprising a B cell comprising a CER and a second composition comprising a CD8+ T cell comprising a CAR or TCR binding protein. Upon antigen binding by an expressed CAR or TCR, the CAR/or TCR modified CD8+ T cell is capable of inducing apoptosis (cytolysis) in a target cell by releasing contents of cytotoxic granules (e.g., granzymes, granulysins, perforins). CER modified B cells are capable of engulfing target cells that are bound by the CER. Moreover, B cells can present internalized antigens to T cells and costimulate T cells. Thus, the combinations of cellular immunotherapy compositions provided herein possess unique specificity and functionality conferred by the particular cellular immunotherapy molecules expressed by the host immune cells.

In certain embodiments, the cytotoxic activity of the combination of cellular immunotherapy compositions is increased at least about 10%, 15%, 20%, 25%, 30%, 35%, 40%, 50%, 55%, 60%, 65%, 70%, 75%, 80%, 85%, 90%, 95%, 100%, 110%, 120%, 130%, 140%, 150%, 160%, 170%, 180%, 190%, 200% or more as compared to the first cellular immunotherapy composition or the second cellular immunotherapy composition contained therein alone. In further embodiments, a synergistic cytotoxic response is exhibited. In some embodiments, the host cell is a T cell or an NK cell. Methods of measuring cytotoxic activity of host cells, particularly immune cells such as T cells and NK cells, include a chromium ($^{51}$Cr)-release assay, a β-gal or firefly luciferase release assay, flow cytometric methods of measuring target cell death and effector cell activity (see, e.g., Expert Rev. Vaccines, 2010, 9:601-616). In certain embodiments, cytotoxic activity of host cells may be measured by detecting target cell apoptosis following exposure to the host cell, e.g., caspase 3/7 activity, lactate dehydrogenase release.

Methods of Use

In one aspect, combinations of cellular immunotherapy compositions according to any of the embodiments provided herein may be used in a method of treating a subject suffering from a disease, disorder or undesired condition. Embodiments of these methods include administering to a subject a therapeutically effective amount of a pharmaceutical composition(s) including a combination of cellular immunotherapy compositions according to the present description.

Diseases that may be treated with combinations of cellular immunotherapy compositions provided in the present disclosure include cancer, autoimmune diseases, neurodegenerative diseases, and infectious diseases (viral, bacterial, fungal, protozoan infections). Adoptive immune and gene therapies are promising treatments for various types of cancer (Morgan et al., *Science* 314:126, 2006; Schmitt et al., *Hum. Gene Ther.* 20:1240, 2009; June, *J. Clin. Invest.* 117:1466, 2007) and infectious disease (Kitchen et al., *PLoS One* 4:38208, 2009; Rossi et al., *Nat. Biotechnol.* 25:1444, 2007; Zhang et al., *PLoS Pathog.* 6:e1001018, 2010; Luo et al., *J. Mol. Med.* 89:903, 2011).

A wide variety of cancers, including solid tumors and leukemias are amenable to treatment using the combinations of cellular immunotherapy compositions provided herein. Exemplary cancers that may be treated using the combinations of cellular immunotherapy compositions described herein include adenocarcinoma of the breast, prostate, and colon; all forms of bronchogenic carcinoma of the lung; myeloid leukemia; melanoma; hepatoma; neuroblastoma; papilloma; apudoma; choristoma; branchioma; malignant carcinoid syndrome; carcinoid heart disease; and carcinoma (e.g., Walker, basal cell, basosquamous, Brown-Pearce, ductal, Ehrlich tumor, Krebs 2, Merkel cell, mucinous, non-small cell lung, oat cell, papillary, scirrhous, bronchiolar, bronchogenic, squamous cell, and transitional cell). Additional types of cancers that may be treated using the receptors, modified host cells, and composition described herein include histiocytic disorders; malignant histiocytosis; leukemia; Hodgkin's disease; immunoproliferative small; non-Hodgkin's lymphoma; plasmacytoma; multiple myeloma; plasmacytoma; reticuloendotheliosis; melanoma; chondroblastoma; chondroma; chondrosarcoma; fibroma; fibrosarcoma; giant cell tumors; histiocytoma; lipoma; liposarcoma; mesothelioma; myxoma; myxosarcoma; osteoma; osteosarcoma; chordoma; craniopharyngioma; dysgerminoma; hamartoma; mesenchymoma; mesonephroma; myosarcoma; ameloblastoma; cementoma; odontoma; teratoma; thymoma; trophoblastic tumor. Further, the following types of cancers are also contemplated as amenable to treatment using the receptors, modified host cells, and composition described herein: adenoma; cholangioma; cholesteatoma; cyclindroma; cystadenocarcinoma; cystadenoma; granulosa cell tumor; gynandroblastoma; hepatoma; hidradenoma; islet cell tumor; Leydig cell tumor; papilloma; sertoli cell tumor; theca cell tumor; leimyoma; leiomyosarcoma; myoblastoma; myomma; myosarcoma; rhabdomyoma; rhabdomyosarcoma; ependymoma; ganglioneuroma; glioma; medulloblastoma; meningioma; neurilemmoma; neuroblastoma; neuroepithelioma; neurofibroma; neuroma; paraganglioma; paraganglioma nonchromaffin. The types of cancers that may be treated also include angiokeratoma; angiolymphoid hyperplasia with eosinophilia; angioma sclerosing; angiomatosis; glomangioma; hemangioendothelioma; hemangioma; hemangiopericytoma; hemangiosarcoma; lymphangioma; lymphangiomyoma; lymphangiosarcoma; pinealoma; carcinosarcoma; chondrosarcoma; cystosarcoma phyllodes; fibrosarcoma; hemangiosarcoma; leiomyosarcoma; leukosarcoma; liposarcoma; lymphangiosarcoma; myosarcoma; myxosarcoma; ovarian carcinoma; rhabdomyosarcoma; sarcoma; neoplasms; neurofibromatosis; and cervical dysplasia.

Examples of hyperproliferative disorders amenable to therapy using the combinations of cellular immunotherapy compositions described herein include B-cell cancers, including B-cell lymphomas (such as various forms of Hodgkin's disease, non-Hodgkins lymphoma (NHL) or central nervous system lymphomas), leukemias (such as acute lymphoblastic leukemia (ALL), chronic lymphocytic leukemia (CLL), Hairy cell leukemia, B cell blast transformation of chronic myeloid leukemia) and myelomas (such as multiple myeloma). Additional B cell cancers that may be treated using the combinations of cellular immunotherapy compositions described herein include small lymphocytic lymphoma, B-cell prolymphocytic leukemia, lymphoplasmacytic lymphoma, splenic marginal zone lymphoma, plasma cell myeloma, solitary plasmacytoma of bone, extraosseous plasmacytoma, extra-nodal marginal zone B-cell lymphoma of mucosa-associated (MALT) lymphoid tissue, nodal marginal zone B-cell lymphoma, follicular lymphoma, mantle cell lymphoma, diffuse large B-cell lymphoma, mediastinal (thymic) large B-cell lymphoma, intravascular large B-cell lymphoma, primary effusion lymphoma, Burkitt's lymphoma/leukemia, B-cell proliferations of uncertain malignant potential, lymphomatoid granulomatosis, and post-transplant lymphoproliferative disorder.

Infectious diseases include those associated with infectious agents and include any of a variety of bacteria (e.g., pathogenic *E. coli, S. typhimurium, P. aeruginosa, B. anthracis, C. botulinum, C. difficile, C. perfringens, H. pylori, V. cholerae, Listeria* spp., *Rickettsia* spp., *Chlamydia* spp., and the like), mycobacteria, and parasites (including any known parasitic member of the Protozoa). Infectious viruses include eukaryotic viruses, such as adenovirus, bunyavirus, herpesvirus, papovavirus, papillomavirus (e.g., HPV), paramyxovirus, picornavirus, rhabdovirus (e.g., Rabies), orthomyxovirus (e.g., influenza), poxvirus (e.g., Vaccinia), reovirus, retrovirus, lentivirus (e.g., HIV), flavivirus (e.g., HCV, HBV) or the like. In certain embodiments, a combination of cellular immunotherapy compositions according to the present disclosure is used for treating infection with a microbe capable of establishing a persistent infection in a subject.

Methods of treating a subject comprise administering an effective amount of a combination of cellular immunotherapy compositions of the present disclosure. The combinations of cellular immunotherapy compositions may be xenogeneic, syngeneic, allogeneic, or autologous to the subject. Moreover, each of the individual cellular immunotherapy compositions within the cellular immunotherapy composition combination may independently be xenogeneic, syngeneic, allogeneic, or autologous to the subject.

Pharmaceutical compositions comprising cellular immunotherapy compositions may be administered in a manner appropriate to the disease or condition to be treated (or prevented) as determined by persons skilled in the medical art. An appropriate dose, suitable duration, and frequency of administration of the compositions will be determined by such factors as the condition of the patient, size, weight, body surface area, age, sex, type and severity of the disease, particular therapy to be administered, particular form of the active ingredient, time and the method of administration, and other drugs being administered concurrently. The present disclosure provides pharmaceutical compositions comprising cellular immunotherapy compositions and a pharmaceutically acceptable carrier, diluent, or excipient. Suitable excipients include water, saline, dextrose, glycerol, or the like and combinations thereof. Other suitable infusion medium can be any isotonic medium formulation, including saline, Normosol R (Abbott), Plasma-Lyte A (Baxter), 5% dextrose in water, or Ringer's lactate. In certain embodiments, the cellular immunotherapy compositions within a combination are formulated together in the same pharmaceutical composition. In other embodiments, each cellular immunotherapy composition within a combination are formulated separate pharmaceutical compositions.

A treatment effective amount of cells in a pharmaceutical composition is at least one cell (for example, one CER modified T cell) or is more typically greater than $10^2$ cells, for example, up to $10^6$, up to $10^7$, up to $10^8$ cells, up to $10^9$ cells, up to $10^{10}$ cells, or up to $10^{11}$ cells or more. In certain embodiments, the cells are administered in a range from about $10^6$ to about $10^{10}$ cells/m$^2$, preferably in a range of about $10^7$ to about $10^9$ cells/m$^2$. In a specific embodiment, the CER modified cells are administered in an amount of at least about $1 \times 10^6$ cells, $2 \times 10^6$ cells, $3 \times 10^6$ cells, $4 \times 10^6$ cells, $5 \times 10^6$ cells, $6 \times 10^6$ cells, $7 \times 10^6$ cells, $8 \times 10^6$ cells, $9 \times 10^6$ cells, $1 \times 10^7$ cells, $2 \times 10^7$ cells, $3 \times 10^7$ cells, $4 \times 10^7$ cells, $5 \times 10^7$ cells, $6 \times 10^7$ cells, $7 \times 10^7$ cells, $8 \times 10^7$ cells, $9 \times 10^7$ cells, $1 \times 10^8$ cells, $2 \times 10^8$ cells, $3 \times 10^8$ cells, $4 \times 10^8$ cells, $5 \times 10^8$ cells, $6 \times 10^8$ cells, $7 \times 10^8$ cells, $8 \times 10^8$ cells, $9 \times 10^8$ cells, $1 \times 10^9$ cells, $2 \times 10^9$ cells, $3 \times 10^9$ cells, $4 \times 10^9$ cells, $5 \times 10^9$ cells, $6 \times 10^9$ cells, $7 \times 10^9$ cells, $8 \times 10^9$ cells, $9 \times 10^9$ cells, $1 \times 10^{10}$ cells, $2 \times 10^{10}$ cells, $3 \times 10^{10}$ cells, $4 \times 10^{10}$ cells, $5 \times 10^{10}$ cells, $6 \times 10^{10}$ cells, $7 \times 10^{10}$ cells, $8 \times 10^{10}$ cells, $9 \times 10^{10}$ cells, $1 \times 10^{11}$ cells, $2 \times 10^{11}$ cells, $3 \times 10^{11}$ cells, $4 \times 10^{11}$ cells, $5 \times 10^{11}$ cells, $6 \times 10^{11}$ cells $7 \times 10^{11}$ cells, $8 \times 10^{11}$ cells, or $9 \times 10^{11}$ cells. The number of cells will depend upon the ultimate use for which the composition is intended as well the type of cells included therein. For example, a composition comprising cells modified to contain a CER will comprise a cell population containing from about 5% to about 95% or more of such cells. In certain embodiments, a composition comprising CER modified cells comprises a cell population comprising at least 5%, 10%, 15%, 20%, 25%, 30%, 35%, 40%, 45%, 50%, 55%, 60%, 65%, 70%, 75%, 80%, 85%, 90%, 95% or more of such cells. For uses provided herein, the cells are generally in a volume of a liter or less, 500 mls or less, 250 mls or less, or 100 mls or less. Hence the density of the desired cells is typically greater than $10^4$ cells/ml and generally is greater than $10^7$ cells/ml, generally $10^8$ cells/ml or greater. The cells may be administered as a single infusion or in multiple infusions over a range of time. Repeated infusions of cellular immunotherapy molecule modified cells may be separated by days, weeks, months, or even years if relapses of disease or disease activity are present. A clinically relevant number of immune cells can be apportioned into multiple infusions that cumulatively equal or exceed $10^6$, $10^7$, $10^8$, $10^9$, $10^{10}$, or $10^{11}$ cells. A preferred dose for administration of a host cell comprising a recombinant expression vector as described herein is about $10^7$ cells/m$^2$, about $5 \times 10^7$ cells/m$^2$, about $10^8$ cells/m$^2$, about $5 \times 10^8$ cells/m$^2$, about $10^9$ cells/m$^2$, about $5 \times 10^9$ cells/m$^2$, about $10^{10}$ cells/m$^2$, about $5 \times 10^{10}$ cells/m$^2$, or about $10^{11}$ cells/m$^2$.

In certain embodiments, the first composition comprising an immune cell comprising a CER, the second composition comprising an immune cell comprising a cellular immunotherapy molecule, e.g., a CER, CAR, or TCR binding protein, or both are administered at a dose that might otherwise be considered subtherapeutic if administered as a monotherapy. In such embodiments, the combination of the first composition and second composition may provide an additive or synergistic effect such that the first composition, the second composition, or both can be administered at a lower dose The cellular immunotherapy compositions as described herein may be administered intravenously, intraperitoneally, intranasally, intratumorally, into the bone marrow, into the lymph node, and/or into cerebrospinal fluid.

Where the cellular immunotherapy compositions in a combination therapy are formulated in separated pharmaceutical compositions, the treatment methods include administration of a first composition comprising an immune cell expressing a CER as described herein before the second composition comprising an immune cell expressing a CER, CAR, or TCR binding protein as described herein (e.g., 1 day to 7 days, 1 day to 10 days, 1 day to 14 days, 1 day to 30 days or more before the second composition), concurrently with the second composition (on the same day), or after the second composition (e.g., 1 day to 7 days, 1 day to 10 days, 1 day to 14 days, 1 day to 30 days or more after the second composition). In certain embodiments, the first composition comprising an immune cell expressing a CER is administered after administration of the second composition comprising an immune expressing a CER, CAR, or TCR. In further embodiments, the first composition is administered 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days after administration of the second composition. In still further embodiments, the first composition is administered within 4 weeks, within 3 weeks, within 2 weeks, or within 1 week after administration of the second composition. Where the second composition involves multiple doses, the first composition may be administered after the initial dose of the second composition, after the final dose of the second composition, or in between multiple doses of the second composition.

Combinations of cellular immunotherapy compositions may be administered to a subject in combination with one or more additional therapeutic agents. Examples of therapeutic agents that may be administered in combinations with a combination of cellular immunotherapy compositions according to the present description include radiation therapy, antibody therapy, immune checkpoint molecule inhibitor therapy, UV light therapy, electric pulse therapy, high intensity focused ultrasound therapy, oncolytic virus therapy, or a pharmaceutical therapy, such as a chemotherapeutic agent, a therapeutic peptide, hormone therapy, an aptamer, antibiotic, anti-viral agent, anti-fungal agent, anti-inflammatory agent, a small molecule therapy.

Radiation therapy includes external beam radiation therapy (e.g., conventional external beam radiation therapy, stereotactic radiation, 3-dimensional conformal radiation therapy, intensity-modulated radiation therapy, volumetric modulated arc therapy, particle therapy, proton therapy, and auger therapy), brachytherapy, systemic radioisotope therapy, intraoperative radiotherapy, or any combination thereof. In certain embodiments, a lower dose of radiation therapy than the typical dose is used in combination with CER therapy. Low dose radiation therapy may be sufficient to cause sub-lytic membrane damage to the cells but not necessarily be cytolytic. The sub-lytic membrane damage is sufficient to expose pro-engulfment markers (e.g., phosphatidylserine) that can be targeted by CER therapy.

Exemplary antibodies for use in conjunction with the combinations of cellular immunotherapy compositions described herein include rituxmab, pertuzumab, trastuzumab, alemtuzumab, Ibritumomab tiuxetan, Brentuximab vedotin, cetuximab, bevacizumab, abciximab, adalimumab, alefacept, basilizimab, belimumab, bezlotoxumab, canakinumab, certolizumab pegol, daclizumab, denosumab, efalizumab, golimumab, olaratumab, palivizumab, panitumumab, and tocilizumab.

Exemplary inhibitors of immune checkpoint molecules that may be for use in conjunction with the combinations of cellular immunotherapy compositions described herein include checkpoint inhibitors targeting PD-L1, PD-L2, CD80, CD86, B7-H3, B7-H4, HVEM, adenosine, GALS, VISTA, CEACAM-1, CEACAM-3, CEACAM-5, PVRL2, PD-1, CTLA-4, BTLA, KIR, LAG3, TIM3, A2aR, CD244/2B4, CD160, TIGIT, LAIR-1, PVRIG/CD112R, or any combination thereof. In certain embodiments, an immune checkpoint inhibitor may be an antibody, a peptide, an RNAi agent, or a small molecule. An antibody specific for CTLA-4 may be ipilimumab or tremelimumab. An antibody specific for PD-1 may be pidilizumab, nivolumab, or pembrolizumab. An antibody specific for PD-L1 may be durvalumab, atezolizumab, or avelumab.

A chemotherapeutic includes non-specific cytotoxic agents that inhibit mitosis or cell division, as well as molecularly targeted therapy that blocks the growth and spread of cancer cells by targeting specific molecules that are involved in tumor growth, progression, and metastasis (e.g., oncogenes). Exemplary non-specific chemotherapeutics for use in conjuction with the combinations of cellular immunotherapy compositions described herein may include an alkylating agent, a platinum based agent, a cytotoxic agent, an inhibitor of chromatin function, a topoisomerase inhibitor, a microtubule inhibiting drug, a DNA damaging agent, an antimetabolite (such as folate antagonists, pyrimidine analogs, purine analogs, and sugar-modified analogs), a DNA synthesis inhibitor, a DNA interactive agent (such as an intercalating agent), and a DNA repair inhibitor.

Exemplary molecularly targeted inhibitors for use in conjunction with the combinations of cellular immunotherapy compositions described herein include inhibitors that target molecules involved in cancer cell growth and survival, including for example, hormones, signal transduction inhibitors, gene expression inhibitors (e.g., translation inhibitors), apoptosis inducers, angiogenesis inhibitors (e.g., a VEGF pathway inhibitor), GTPase inhibitors, receptor tyrosine kinase inhibitors, growth factor inhibitors, serine/threonine kinase inhibitors, transcription factor inhibitors, and tyrosine kinase inhibitors (e.g., an EGF/EGFR pathway inhibitor). Additional exemplary molecularly targeted inhibitors include B-Raf inhibitors, MEK inhibitors, mTOR inhibitors, adenosine pathway inhibitors, EGFR inhibitors, ALK inhibitors, VEGFR inhibitors, MET inhibitors, MYC inhibitors, ABS inhibitors, HER2 inhibitors, H-RAS inhibitors, K-RAS inhibitors, PDGFR inhibitors, PI3K inhibitors, BCR-ABL inhibitors, ALK/ROS1 inhibitor, and BTK inhibitors. In certain embodiments, use of molecularly targeted therapy comprises administering a molecularly targeted therapy specific for the molecular target to a subject identified as having a tumor that possesses the molecular target (e.g., driver oncogene). In certain embodiments, the molecular target has an activating mutation. In certain embodiments, use of CER modified cells in combination with a molecularly targeted inhibitor increases the magnitude of anti-tumor response, the durability of anti-tumor response, or both. In certain embodiments, a lower than typical dose or sub-therapeutic dose of molecularly targeted therapy is used in combination with CER modified cells.

Examples of chemotherapeutic agents considered for use in combination therapies contemplated herein include vemurafenib, dabrafenib, trametinib, cobimetinib, anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), fdabra tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), ibrutinib, venetoclax, crizotinib, alectinib, brigatinib, ceritinib, and vinorelbine (Navelbine®).

Exemplary alkylating agents for use in combination therapies contemplated herein include nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents for use in combination therapies contemplated herein include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®).

Exemplary platinum based agents for use in combination therapies contemplated herein include carboplatin, cisplatin, oxaliplatin, nedaplatin, picoplatin, satraplatin, phenanthriplatin, and triplatin tetranitrate.

Exemplary angiogenesis inhibitors for use in conjunction with combinations of cellular immunotherapy compositions described herein may include, without limitation A6 (Angstrom Pharmaceuticals), ABT-510 (Abbott Laboratories), ABT-627 (Atrasentan) (Abbott Laboratories/Xinlay), ABT-869 (Abbott Laboratories), Actimid (CC4047, Pomalidomide) (Celgene Corporation), AdGVPEDF.11D (GenVec), ADH-1 (Exherin) (Adherex Technologies), AEE788 (Novartis), AG-013736 (Axitinib) (Pfizer), AG3340 (Prinomastat) (Agouron Pharmaceuticals), AGX1053 (AngioGenex), AGX51 (AngioGenex), ALN-VSP (ALN-VSP O2) (Alnylam Pharmaceuticals), AMG 386 (Amgen), AMG706 (Amgen), Apatinib (YN968D1) (Jiangsu Hengrui Medicine), AP23573 (Ridaforolimus/MK8669) (Ariad Pharmaceuticals), AQ4N (Novavea), ARQ 197 (ArQule), ASA404 (Novartis/Antisoma), Atiprimod (Callisto Pharmaceuticals), ATN-161 (Attenuon), AV-412 (Aveo Pharmaceuticals), AV-951 (Aveo Pharmaceuticals), Avastin (Bevacizumab) (Genentech), AZD2171 (Cediranib/Recentin) (AstraZeneca), BAY 57-9352 (Telatinib) (Bayer), BEZ235 (Novartis), BIBF1120 (Boehringer Ingelheim Pharmaceuticals), BIBW 2992 (Boehringer Ingelheim Pharmaceuticals), BMS-275291 (Bristol-Myers Squibb), BMS-582664 (Brivanib) (Bristol-Myers Squibb), BMS-690514 (Bristol-Myers Squibb), Calcitriol, CCI-779 (Torisel) (Wyeth), CDP-791 (ImClone Systems), Ceflatonin (Homoharringtonine/HHT) (ChemGenex Therapeutics), Celebrex (Celecoxib) (Pfizer), CEP-7055 (Cephalon/Sanofi), CHIR-265 (Chiron Corporation), NGR-TNF, COL-3 (Metastat) (Collagenex Pharmaceuticals), Combretastatin (Oxigene), CP-751,871 (Figitumumab) (Pfizer), CP-547,632 (Pfizer), CS-7017 (Daiichi Sankyo Pharma), CT-322 (Angiocept) (Adnexus), Curcumin, Dalteparin (Fragmin) (Pfizer), Disulfiram (Antabuse), E7820 (Eisai Limited), E7080 (Eisai Limited), EMD 121974 (Cilengitide) (EMD Pharmaceuticals), ENMD-1198 (EntreMed), ENMD-2076 (EntreMed), Endostar (Simcere), Erbitux (ImClone/Bristol-Myers Squibb), EZN-2208 (Enzon Pharmaceuticals), EZN-2968 (Enzon Pharmaceuticals), GC1008 (Genzyme), Genistein, GSK1363089 (Foretinib) (GlaxoSmithKline), GW786034 (Pazopanib) (GlaxoSmithKline), GT-111 (Vascular Biogenics Ltd.), IMC-1121B (Ramucirumab) (ImClone Systems), IMC-18F1 (ImClone Systems), IMC-3G3 (ImClone LLC), INCB007839 (Incyte Corporation), INGN 241 (Introgen Therapeutics), Iressa (ZD1839/Gefitinib), LBH589 (Faridak/Panobinostst) (Novartis), Lucentis (Ranibizumab) (Genentech/Novartis), LY317615 (Enzastaurin) (Eli Lilly and Company), Macugen (Pegaptanib) (Pfizer), MEDI522 (Abegrin) (MedImmune), MLN518 (Tandutinib) (Millennium), Neovastat (AE941/Benefin) (Aeterna Zentaris), Nexavar (Bayer/Onyx), NM-3 (Genzyme Corporation), Noscapine (Cougar Biotechnology), NPI-2358 (Nereus Pharmaceuticals), OSI-930 (OSI), Palomid 529 (Paloma Pharmaceuticals, Inc.), Panzem Capsules (2ME2) (EntreMed), Panzem NCD (2ME2) (EntreMed), PF-02341066 (Pfizer), PF-04554878 (Pfizer), PI-88 (Progen Industries/Medigen Biotechnology), PKC412 (Novartis), Polyphenon E (Green Tea Extract) (Polypheno E International, Inc), PPI-2458 (Praecis Pharmaceuticals), PTC299 (PTC Therapeutics), PTK787 (Vatalanib) (Novartis), PXD101 (Belinostat) (CuraGen Corporation), RAD001 (Everolimus) (Novartis), RAF265 (Novartis), Regorafenib (BAY73-4506) (Bayer), Revlimid (Celgene), Retaane (Alcon Research), SN38 (Liposomal) (Neopharm), SNS-032 (BMS-387032) (Sunesis), SOM230 (Pasireotide) (Novartis), Squalamine (Genaera), Suramin, Sutent (Pfizer), Tarceva (Genentech), TB-403 (Thrombogenics), Tempostatin (Collard Biopharmaceuticals), Tetrathiomolybdate (Sigma-Aldrich), TG100801 (TargeGen), Thalidomide (Celgene Corporation), Tinzaparin Sodium, TKI258 (Novartis), TRC093 (Tracon Pharmaceuticals Inc.), VEGF Trap (Aflibercept) (Regeneron Pharmaceuticals), VEGF Trap-Eye (Regeneron Pharmaceuticals), Veglin (VasGene Therapeutics), Bortezomib (Millennium), XL184 (Exelixis), XL647 (Exelixis), XL784 (Exelixis), XL820 (Exelixis), XL999 (Exelixis), ZD6474 (AstraZeneca), Vorinostat (Merck), and ZSTK474.

Exemplary Vascular Endothelial Growth Factor (VEGF) receptor inhibitors for use in conjunction with the combinations of cellular immunotherapy compositions described herein may include, but are not limited to, Bevacizumab (Avastin®), axitinib (Inlyta®); Brivanib alaninate (BMS-582664, (S)—((R)-1-(4-(4-Fluoro-2-methyl-1H-indol-5-yloxy)-5-methylpyrrolo[2,1-f][1,2,4]triazin-6-yloxy)propan-2-yl)2-aminopropanoate); Sorafenib (Nexavar®); Pazopanib (Votrient®); Sunitinib malate (Sutent®); Cediranib (AZD2171, CAS 288383-20-1); Vargatef (BIBF1120, CAS 928326-83-4); Foretinib (GSK1363089); Telatinib (BAY57-9352, CAS 332012-40-5); Apatinib (YN968D1, CAS 811803-05-1); Imatinib (Gleevec®); Ponatinib (AP24534, CAS 943319-70-8); Tivozanib (AV951, CAS 475108-18-0); Regorafenib (BAY73-4506, CAS 755037-03-7); Vatalanib dihydrochloride (PTK787, CAS 212141-51-0); Brivanib (BMS-540215, CAS 649735-46-6); Vandetanib (Caprelsa® or AZD6474); Motesanib diphosphate (AMG706, CAS 857876-30-3, N-(2,3-dihydro-3,3-dimethyl-1H-indol-6-yl)-2-[(4-pyridinylmethyl)amino]-3-pyridinecarboxamide, described in PCT Publication No. WO 02/066470); Dovitinib dilactic acid (TKI258, CAS 852433-84-2); Linfanib (ABT869, CAS 796967-16-3); Cabozantinib (XL184, CAS 849217-68-1); Lestaurtinib (CAS 111358-88-4); N-[5-[[[5-(1,1-Dimethylethyl)-2-oxazolyl] methyl]thio]-2-thiazolyl]-4-piperidinecarboxamide (BMS38703, CAS 345627-80-7); (3R,4R)-4-Amino-1-((4-((3-methoxyphenyl)amino)pyrrolo[2,1-f][1,2,4]triazin-5-yl) methyl)piperidin-3-ol (BMS690514); N-(3,4-Dichloro-2-fluorophenyl)-6-methoxy-7-[[(3aα,5β,6aα)-octahydro-2-methylcyclopenta[c]pyrrol-5-yl]methoxy]-4-quinazolinamine (XL647, CAS 781613-23-8); 4-Methyl-3-[[1-methyl-6-(3-pyridinyl)-1H-pyrazolo[3,4-d]pyrimidin-4-yl]amino]-N-[3-(trifluoromethyl)phenyl]-benzamide (BHG712, CAS 940310-85-0); and Aflibercept (Eylea®).

Exemplary EGF pathway inhibitors for use in conjunction with the combinations of cellular immunotherapy compositions described herein may include, without limitation tyrphostin 46, EKB-569, erlotinib (Tarceva®), gefitinib (Iressa®), erbitux, nimotuzumab, lapatinib (Tykerb®), cetuximab (anti-EGFR mAb), $^{188}$Re-labeled nimotuzumab (anti-EGFR mAb), and those compounds that are generically and specifically disclosed in WO 97/02266, EP 0 564 409, WO 99/03854, EP 0 520 722, EP 0 566 226, EP 0 787 722, EP 0 837 063, U.S. Pat. No. 5,747,498, WO 98/10767, WO 97/30034, WO 97/49688, WO 97/38983 and WO 96/33980. Exemplary EGFR antibodies include, but are not limited to, Cetuximab (Erbitux®); Panitumumab (Vectibix®); Matuzumab (EMD-72000); Trastuzumab (Herceptin®); Nimotuzumab (hR3); Zalutumumab; TheraCIM h-R3; MDX0447 (CAS 339151-96-1); and ch806 (mAb-806, CAS 946414-09-1). Exemplary Epidermal growth factor receptor (EGFR) inhibitors include, but not limited to, Osimertinib (Tagrisso®), Erlotinib hydrochloride (Tarceva®); brigatinib; osimeritinib; icotinib; Gefitnib (Iressa®); N-[4-[(3-Chloro-4-fluorophenyl)amino]-7-[[(3"S")-tetrahydro-3-furanyl]oxy]-6-quinazolinyl]-4-(dimethylamino)-2-butenamide, Tovok®); Vandetanib (Caprelsa®); Lapatinib (Tykerb®); (3R,4R)-4-Amino-1-((4-((3-methoxyphenyl)amino)pyrrolo[2,1-f][1,2,4]triazin-5-yl)methyl)piperidin-3-ol (BMS690514); Canertinib dihydrochloride (CI-1033); 6-[4-[(4-Ethyl-1-piperazinyl) methyl]phenyl]-N-[(1R)-1-phenylethyl]-7H-Pyrrolo[2,3-d] pyrimidin-4-amine (AEE788, CAS 497839-62-0); Mubritinib (TAK165); Pelitinib (EKB569); Afatinib (BIBW2992); Neratinib (HKI-272); N-[4-[[1-[(3-Fluorophenyl)methyl]-1H-indazol-5-yl]amino]-5-methylpyrrolo [2,1-f][1,2,4]triazin-6-yl]-carbamic acid, (3S)-3-morpholinylmethyl ester (BMS599626); N-(3,4-Dichloro-2-fluorophenyl)-6-methoxy-7-[[(3aα,5β,6aα)-octahydro-2-methylcyclopenta[c]pyrrol-5-yl]methoxy]-4-quinazolinamine (XL647, CAS 781613-23-8); and 4-[4-[[(1R)-1-Phenylethyl]amino]-7H-pyrrolo[2,3-d]pyrimidin-6-yl]-phenol (PKI166, CAS 187724-61-4).

Exemplary mTOR inhibitors for use in conjunction with the combinations of cellular immunotherapy compositions described herein may include, without limitation, rapamycin (Rapamune®), and analogs and derivatives thereof; SDZ-RAD; Temsirolimus (Torisel®; also known as CCI-779);

Ridaforolimus (formally known as deferolimus, (1R,2R, 4S)-4-[(2R)-2[(1R,9S,12S,15R,16E,18R,19R,21R,23S,24E, 26E,28Z,30S,32S,35R)-1,18-dihydroxy-19,30-dimethoxy-15,17,21,23,29,35-hexamethyl-2,3,10,14,20-pentaoxo-11, 36-dioxa-4-azatricyclo[30.3.1.0$^{4,9}$]hexatriaconta-16,24,26, 28-tetraen-12-yl]propyl]-2-methoxycyclohexyl dimethylphosphinate, also known as AP23573 and MK8669, and described in PCT Publication No. WO 03/064383); Everolimus (Afinitor® or RAD001); Rapamycin (AY22989, Sirolimus®); Simapimod (CAS 164301-51-3); (5-{2,4-Bis[(3 S)-3-methylmorpholin-4-yl]pyrido[2,3-d]pyrimidin-7-yl}-2-methoxyphenyl)methanol (AZD8055); 2-Amino-8-[trans-4-(2-hydroxyethoxy)cyclohexyl]-6-(6-methoxy-3-pyridinyl)-4-methyl-pyrido[2,3-d]pyrimidin-7 (8H)-one (PF04691502, CAS 1013101-36-4); and N$^2$-[1,4-dioxo-[[4-(4-oxo-8-phenyl-4H-1-benzopyran-2-yl) morpholinium-4-yl]methoxy]butyl]-L-arginylglycyl-L-α-aspartylL-serine-, inner salt (SF1126, CAS 936487-67-1).

In certain embodiments, a tyrosine kinase inhibitor used in conjunction with the combinations of cellular immunotherapy compositions described herein is an anaplastic lymphoma kinase (ALK) inhibitor. Exemplary ALK inhibitors include crizotinib, ceritinib, alectinib, brigatinib, dalantercept, entrectinib, and lorlatinib.

Exemplary Phosphoinositide 3-kinase (PI3K) inhibitors for use in conjunction with the combinations of cellular immunotherapy compositions described herein may include, but are not limited to, 4-[2-(1H-Indazol-4-yl)-6-[[4-(methylsulfonyl)piperazin-1-yl]methyl]thieno[3,2-d]pyrimidin-4-yl]morpholine (also known as GDC 0941 and described in PCT Publication Nos. WO 09/036082 and WO 09/055730); 2-Methyl-2-[4-[3-methyl-2-oxo-8-(quinolin-3-yl)-2,3-dihydroimidazo[4,5-c]quinolin-1-yl]phenyl]propionitrile (also known as BEZ 235 or NVP-BEZ 235, and described in PCT Publication No. WO 06/122806); 4-(trifluoromethyl)-5-(2, 6-dimorpholinopyrimidin-4-yl)pyridin-2-amine (also known as BKM120 or NVP-BKM120, and described in PCT Publication No. WO2007/084786); Tozasertib (VX680 or MK-0457, CAS 639089-54-6); (5Z)-5-[[4-(4-Pyridinyl)-6-quinolinyl]methylene]-2,4-thiazolidinedione (GSK1059615, CAS 958852-01-2); (1E,4S,4aR,5R,6aS, 9aR)-5-(Acetyloxy)-1-[(di-2-propenylamino)methylene]-4, 4a,5,6,6a,8,9,9a-octahydro-11-hydroxy-4-(methoxymethyl)-4a,6a-dimethyl-cyclopenta[5,6]naphtho[1,2-c]pyran-2,7,10(1H)-trione (PX866, CAS 502632-66-8); and 8-Phenyl-2-(morpholin-4-yl)-chromen-4-one (LY294002, CAS 154447-36-6). Exemplary Protein Kinase B (PKB) or AKT inhibitors include, but are not limited to. 8-[4-(1-Aminocyclobutyl)phenyl]-9-phenyl-1,2,4-triazolo[3,4-f][1, 6]naphthyridin-3(2H)-one (MK-2206, CAS 1032349-93-1); Perifosine (KRX0401); 4-Dodecyl-N-1,3,4-thiadiazol-2-yl-benzenesulfonamide (PHT-427, CAS 1191951-57-1); 4-[2-(4-Amino-1,2,5-oxadiazol-3-yl)-1-ethyl-7-[(3S)-3-piperidinylmethoxy]-1H-imidazo[4,5-c]pyridin-4-yl]-2-methyl-3-butyn-2-ol (GSK690693, CAS 937174-76-0); 8-(1-Hydroxyethyl)-2-methoxy-3-[(4-methoxyphenyl)methoxy]-6H-dibenzo[b,d]pyran-6-one (palomid 529, P529, or SG-00529); Triciribine (6-Amino-4-methyl-8-(β-D-ribofuranosyl)-4H,8H-pyrrolo[4,3,2-de]pyrimido[4,5-c]pyridazine); (αS)-α-[[[5-(3-Methyl-1H-indazol-5-yl)-3-pyridinyl]oxy] methyl]-benzeneethanamine (A674563, CAS 552325-73-2); 4-[(4-Chlorophenyl)methyl]-1-(7H-pyrrolo[2,3-d]pyrimidin-4-yl)-4-piperidinamine (CCT128930, CAS 885499-61-6); 4-(4-Chlorophenyl)-4-[4-(1H pyrazol-4-yl)phenyl]-piperidine (AT7867, CAS 857531-00-1); and Archexin (RX-0201, CAS 663232-27-7).

In certain embodiments where a combination of cellular immunotherapy compositions is administered in combination with one or more additional therapies, the one or more additional therapies may be administered at a dose that might otherwise be considered subtherapeutic if administered as a monotherapy. In such embodiments, the combination of cellular immunotherapy compositions may provide an additive or synergistic effect such that the one or more additional therapies can be administered at a lower dose. Combination therapy includes administration of a combination of cellular immunotherapy compositions as described herein before an additional therapy (e.g., 1 day to 30 days or more before the additional therapy), concurrently with an additional therapy (on the same day), or after an additional therapy (e.g., 1 day-30 days or more after the additional therapy). In certain embodiments, the combination of cellular immunotherapy compositions is administered after administration of the one or more additional therapies. In further embodiments, the cellular immunotherapy molecule modified cells are administered 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days after administration of the one or more additional therapies. In still further embodiments, the combination of cellular immunotherapy compositions are administered within 4 weeks, within 3 weeks, within 2 weeks, or within 1 week after administration of the one or more additional therapies. Where the one or more additional therapies involves multiple doses, the combination of cellular immunotherapy compositions may be administered after the initial dose of the one or more additional therapies, after the final dose of the one or more additional therapies, or in between multiple doses of the one or more additional therapies.

In certain embodiments, methods of the present disclosure include a depletion step. A depletion step to remove cellular immunotherapy molecule modified cells from the subject may occur after a sufficient amount of time for therapeutic benefit in order to mitigate toxicity to a subject. In such embodiments, a vector comprising the cellular immunotherapy molecule (e.g., CER, CAR, or TCR binding protein) may include an inducible suicide gene, such as iCASP9, inducible Fas, or HSV-TK. Similarly, the vector may be designed for expression of a known cell surface antigen such as CD20 or truncated EGFR (SEQ ID NO:70) that facilitates depletion of transduced cells through infusion of an associated monoclonal antibody (mAb), for example, Rituximab for CD20 or Cetuximab for EGFR. Alemtuzumab, which targets CD52 present on the surface of mature lymphocytes, may also be used to deplete transduced B cells, T cells, or natural killer cells.

Subjects that can be treated by the compositions and methods of the present disclosure include animals, such as humans, primates, cows, horses, sheep, dogs, cats, mice, rats, rabbits, guinea pigs, or pigs. The subject may be male or female, and can be any suitable age, including infant, juvenile, adolescent, adult, and geriatric subjects.

EXAMPLES

Example 1: Construction of CERs, TCRs, and Modified T Cells

A polynucleotide comprising the extracellular domain of the phosphatidylserine binding protein Tim4 and Tim4 transmembrane domain was fused to the engulfment signaling domain of TLR4 to create chimeric engulfment receptor "CER5" encoding an amino acid sequence of SEQ ID NO:94.

A polynucleotide comprising the extracellular domain of the phosphatidylserine binding protein Tim4 and Tim4 transmembrane domain was fused to the engulfment signaling domain of TLR3 to create chimeric engulfment receptor "CER17" encoding an amino acid sequence of SEQ ID NO:112.

A polynucleotide comprising the extracellular domain of the phosphatidylserine binding protein Tim4 and Tim4 transmembrane domain was fused to the engulfment signaling domain of TLR5 to create chimeric engulfment receptor "CER19" encoding an amino acid sequence of SEQ ID NO:95.

A polynucleotide comprising the extracellular domain of the phosphatidylserine binding protein Tim4 and Tim4 transmembrane domain was fused to the TLR8 engulfment signaling domain to create chimeric engulfment receptor "CER21" encoding an amino acid sequence of SEQ ID NO:96.

A polynucleotide comprising the extracellular domain of the phosphatidylserine binding protein Tim4 and Tim4 transmembrane domain was fused to the engulfment signaling domain of TLR9 to create chimeric engulfment receptor "CER23" encoding an amino acid sequence of SEQ ID NO:116.

A polynucleotide comprising the extracellular domain of the phosphatidylserine binding protein Tim4 and Tim4 transmembrane domain was fused to the engulfment signaling domain of TLR1 to create chimeric engulfment receptor "CER26" encoding an amino acid sequence of SEQ ID NO:118.

A polynucleotide comprising the extracellular domain of the phosphatidylserine binding protein Tim4 and Tim4 transmembrane domain was fused to the engulfment signaling domain of TLR2 to create chimeric engulfment receptor "CER27" encoding an amino acid sequence of SEQ ID NO:98.

A polynucleotide comprising the extracellular domain of the phosphatidylserine binding protein Tim4 and Tim4 transmembrane domain was fused to the engulfment signaling domain of TRAF6 to create chimeric engulfment receptor "CER29" encoding an amino acid sequence of SEQ ID NO:99.

A polynucleotide comprising the extracellular domain of the phosphatidylserine binding protein Tim4 and Tim4 transmembrane domain was fused to the engulfment signaling domain of TRAF2 to create chimeric engulfment receptor "CER30" encoding an amino acid sequence of SEQ ID NO:120.

A polynucleotide comprising the extracellular domain of the phosphatidylserine binding protein Tim4 and Tim4 transmembrane domain was fused to the engulfment signaling domain of TLR8 and a truncated engulfment signaling domain of CD79b to create chimeric engulfment receptor "CER103B" encoding an amino acid sequence of SEQ ID NO:138.

A polynucleotide comprising the extracellular domain of the phosphatidylserine binding protein Tim4 and Tim4 transmembrane domain was fused to the engulfment signaling domain of TLR8 and the engulfment signaling domain of DAP12 to create chimeric engulfment receptor "CER104" encoding an amino acid sequence of SEQ ID NO:139.

A polynucleotide comprising the extracellular domain of the phosphatidylserine binding protein Tim4 and Tim4 transmembrane domain was fused to the engulfment signaling domain of TLR8 and the engulfment signaling domain of BAFF-R to create chimeric engulfment receptor "CER105" encoding an amino acid sequence of SEQ ID NO:140.

A polynucleotide comprising the extracellular domain of the phosphatidylserine binding protein Tim4 and Tim4 transmembrane domain was fused to the engulfment signaling domain of NFAM1 and the engulfment signaling domain of TLR8 to create chimeric engulfment receptor "CER106" encoding an amino acid sequence of SEQ ID NO:141.

A polynucleotide comprising the extracellular domain of the phosphatidylserine binding protein Tim4 and Tim4 transmembrane domain was fused to the engulfment signaling domain of TRAF6 and the engulfment signaling domain of DAP12 to create chimeric engulfment receptor "CER110" encoding an amino acid sequence of SEQ ID NO:145.

A polynucleotide comprising the extracellular domain of the phosphatidylserine binding protein Tim4 and Tim4 transmembrane domain was fused to the engulfment signaling domain of TRAF6 and the engulfment signaling domain of NFAM1 to create chimeric engulfment receptor "CER112" encoding an amino acid sequence of SEQ ID NO:148.

A polynucleotide comprising the extracellular domain of the phosphatidylserine binding protein Tim4 and Tim4 transmembrane domain was fused to the engulfment signaling domain of TRAF6 and the engulfment signaling domain of BAFF-R to create chimeric engulfment receptor "CER113" encoding an amino acid sequence of SEQ ID NO:149.

A polynucleotide comprising the extracellular domain of the phosphatidylserine binding protein Tim4 and Tim4 transmembrane domain was fused to the engulfment signaling domain of TRAF6 and engulfment signaling domain of MERTK to create chimeric engulfment receptor "CER114" encoding an amino acid sequence of SEQ ID NO:150.

A polynucleotide comprising the extracellular domain of the phosphatidylserine binding protein Tim4 and Tim4 transmembrane domain was fused to the engulfment signaling domain of MERTK and engulfment signaling domain of TRAF6 to create chimeric engulfment receptor "CER115" encoding an amino acid sequence of SEQ ID NO:151.

A polynucleotide comprising the extracellular domain of the phosphatidylserine binding protein Tim4 and Tim4 transmembrane domain was fused to the engulfment signaling domain of Traf6 and the engulfment signaling domain of TLR8 to create chimeric engulfment receptor "CER116" encoding an amino acid sequence of SEQ ID NO:152.

A polynucleotide comprising the extracellular domain of the phosphatidylserine binding protein Tim4 and Tim4 transmembrane domain was fused to the engulfment signaling domain of TLR8 and engulfment signaling domain of TRAF6 to create chimeric engulfment receptor "CER117" encoding an amino acid sequence of SEQ ID NO:153.

A polynucleotide encoding a TCRβ chain and a polynucleotide encoding a TCRα of a HPV16 E7 specific TCR (see, PCT Publication No. WO2015/184228) were fused using a sequence encoding a P2A self cleaving peptide therebetween. The TCR Vα domain comprises an amino acid sequence of SEQ ID NO:88, and the TCR Vβ region comprises an amino acid sequence of SEQ ID NO:86. The Cα domain comprises a cysteine substitution and LVL substitutions at positions 12, 14, and 15 and comprises an amino acid sequence of SEQ ID NO:89. The Cβ also comprises a cysteine substitution and comprises an amino acid sequence of SEQ ID NO:87. The encoded HPV16 E7 specific TCR comprises an amino acid sequence of SEQ ID NO:84.

A selected CER polynucleotide and the HPV16 E7 TCR polynucleotide were each inserted into a pLenti lentiviral vector. Peripheral blood was collected by venipuncture from a human donor, and human peripheral blood mononuclear cells (PBMCs) were isolated by density gradient centrifugation using lymphocyte separation media. CD8+ or CD4+ T cells were enriched from PBMCs using a commerically available isolation kit and activated with anti-CD3 and anti-CD28 in Complete Cell Growth Media. 50 µl of viral vector expressing the HPV16 E7 TCR were diluted in 0.5 ml Complete Cell Growth Media and added to the CD8+ T cells. 50 µl of viral vector expressing the a selected CER were diluted in 0.5 ml Complete Cell Growth Media and added to the CD4+ T cells. The transduced T cells were then centrifuged at 270×g rpm for 1 hour in a 32° C. pre-warmed centrifuge. The T cells were incubated for 24 hours at 37° C. T cells were expanded for another 72 hours in Complete Cell Growth Media, de-beaded, and allowed to expand×5 days prior to being utilized for functional assays. Transduced CD4+ and CD8+ T cells were combined at a 1:1 ratio for functional assays.

Figure 3:
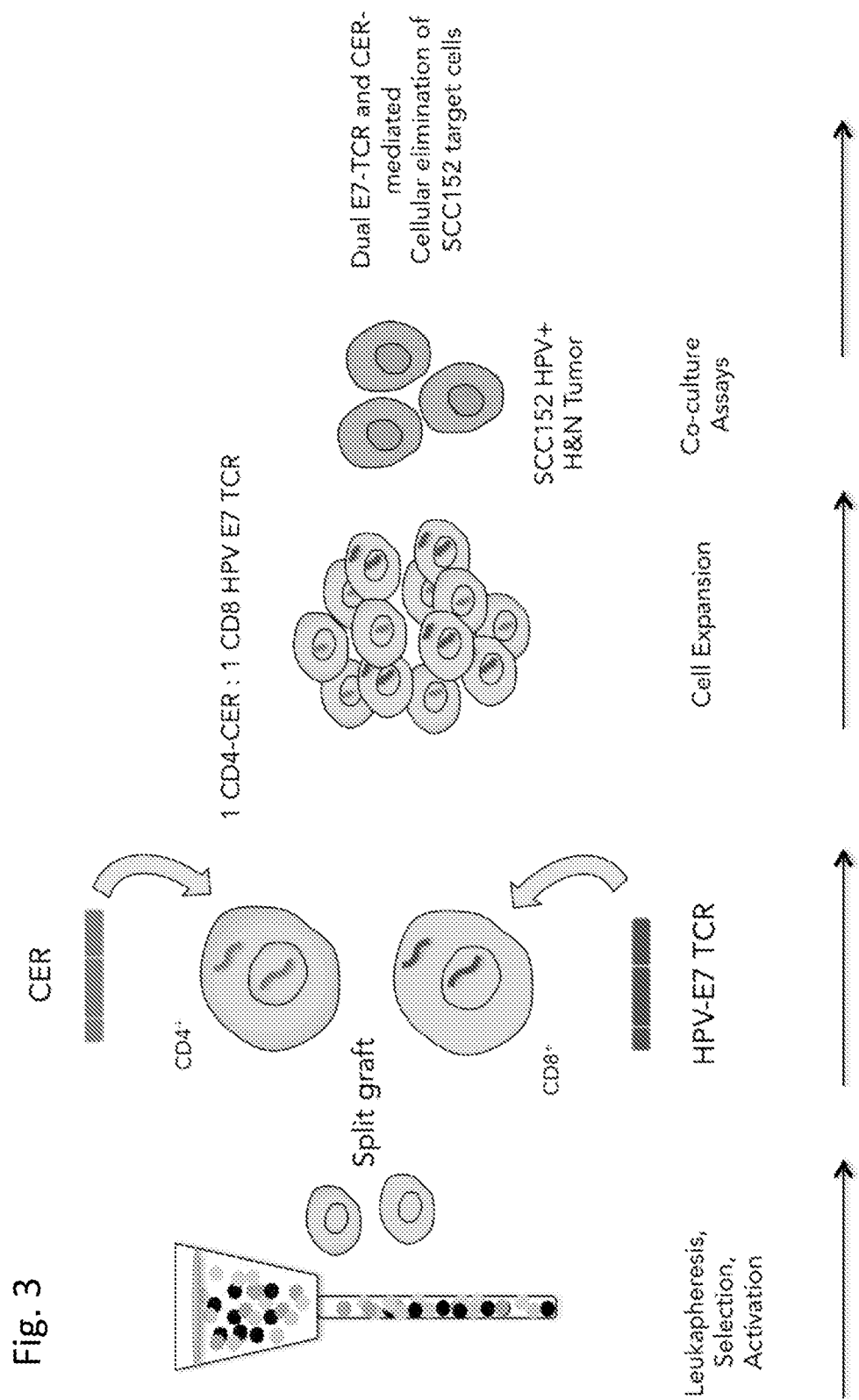
FIG. 3 is a schematic for exemplary in vitro co-culture experiments. CD8+ T cells were activated and transduced with a lentivirus cassette encoding a human papilloma virus 16 (HPV16) E7 protein-specific TCR, while CD4+ T cells from the same graft were activated and transduced with a lentivirus encoding a CER. Both sets of cells were expanded ex vivo and combined at a 1:1 ratio and co-cultured with HPV16 E7+ head and neck squamous cell carcinoma cells (SCC152).
Figure 4:
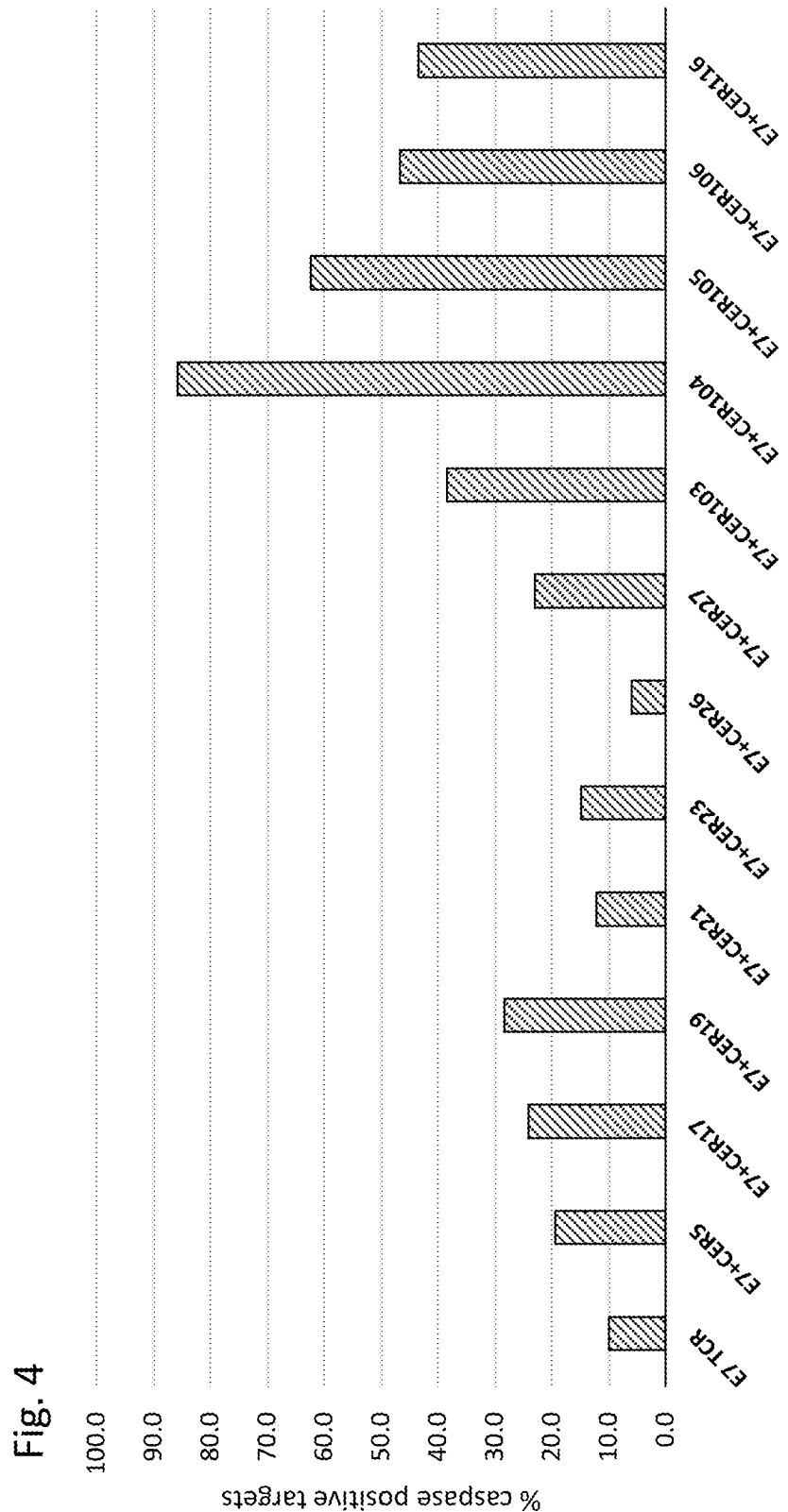
FIG. 4 is a bar graph showing the number of caspase positive SCC152 target cells in a co-culture assay with CD8+ T cells transduced with HPV16 E7 TCR and CD4+ T cells transduced with either control or a selected CER as indicated in the x-axis. The intensity of caspase was measured by quantifying the intensity of red fluorescence from a caspase 3/7 apoptosis reagent that couples the activated caspase 3/7 recognition motif with a red reagent that fluoresces upon cleavage. The caspase 3/7 apoptosis reagent was added to the co-culture assay after 6 hours, and fluorescence was detected using BZ-X710 Keyence microscope and using hybrid capture software. The target SCC152 cells (transduced with green fluorescent protein (GFP)) were determined similarly. The Y-axis represents % caspase positive targets (# of caspase events/# of GFP target cells)*100.
Figure 5:
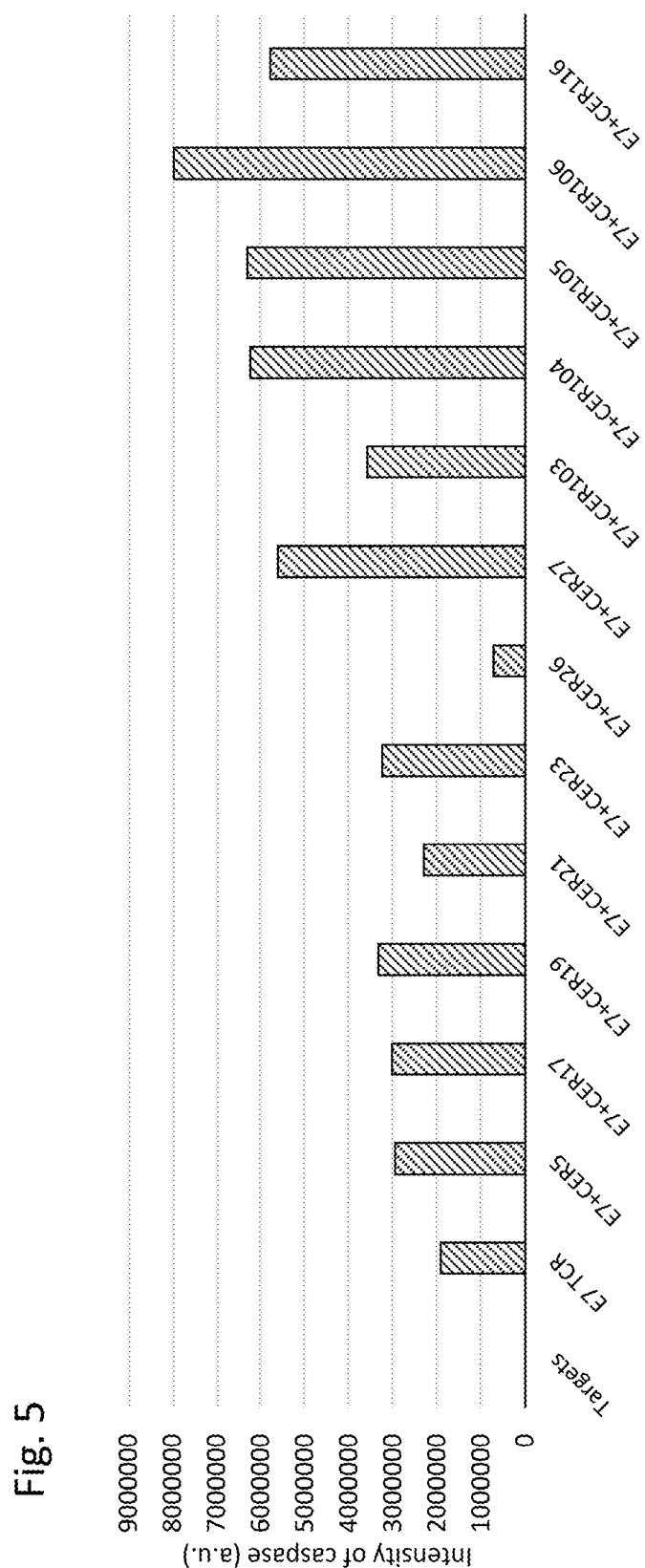
FIG. 5 is a bar graph showing the intensity of caspase in target SCC152 cells quantified from a co-culture assay containing CD8+ T cells transduced with HPV16 E7 TCR and CD4+ T cells transduced with either control or a selected CER as indicated in the x-axis. The intensity of caspase was measured by quantifying the intensity of red fluorescence from a caspase 3/7 apoptosis reagent that couples the activated caspase 3/7 recognition motif with a red reagent that fluoresces upon cleavage. The caspase 3/7 apoptosis reagent was added to the co-culture assay after 6 hours, and fluorescence was detected using BZ-X710 Keyence microscope and using hybrid capture software. The Y-axis represent the intensity of caspase reagent in arbitrary units (a.u.).
Figure 6:
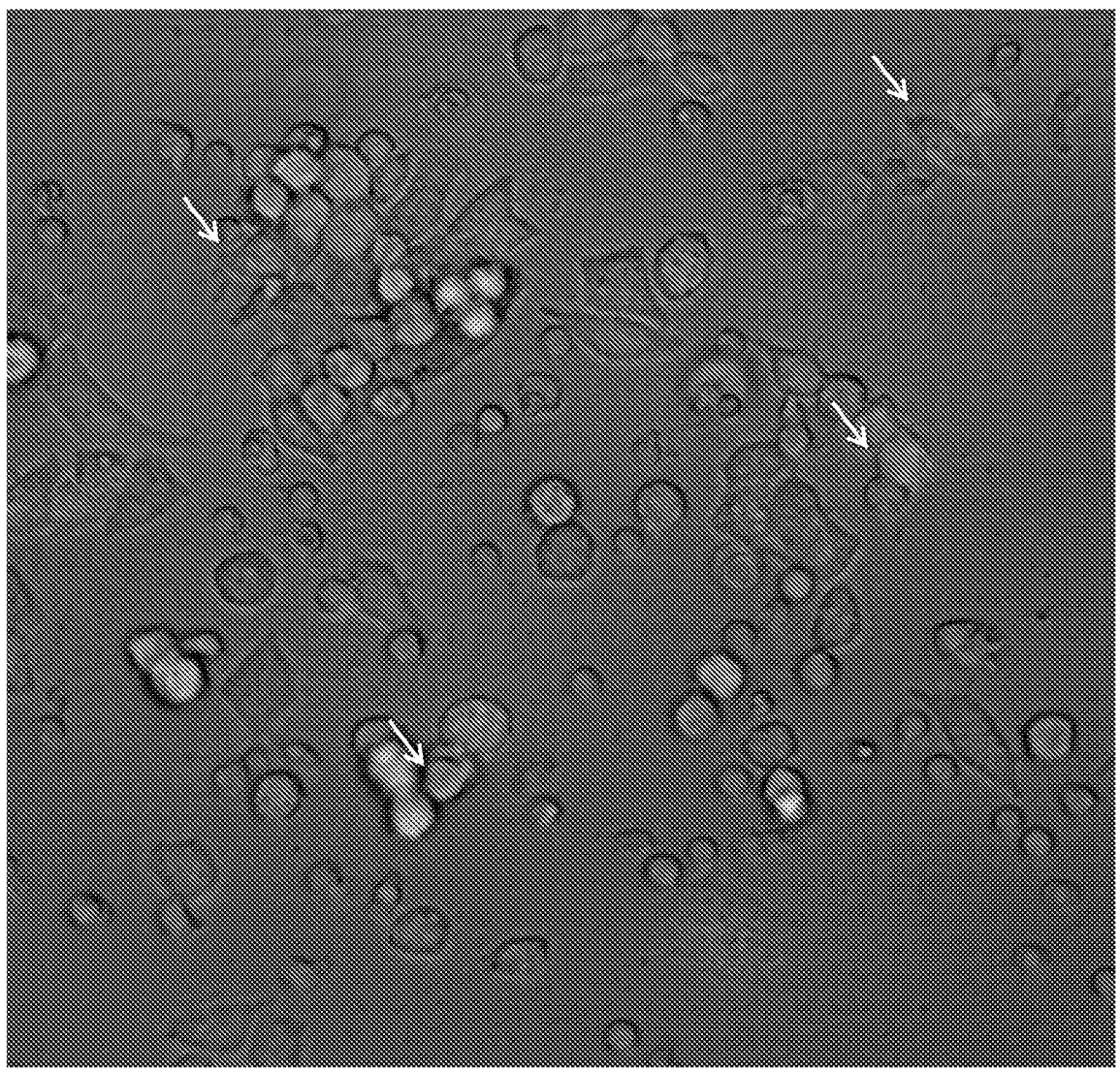
FIG. 6 is a fluorescent micrograph of a co-culture assay containing CD8+ T cells transduced with a HPV16 E7 TCR and CD4+ T cells transduced with control (blue) at a 1:1 ratio with SCC152 cells (green). The red signals (representative red signals indicated with white arrows) are fluorescent signals from a caspase reagent that was added to the co-culture assay after 6 hours.
Figure 7:
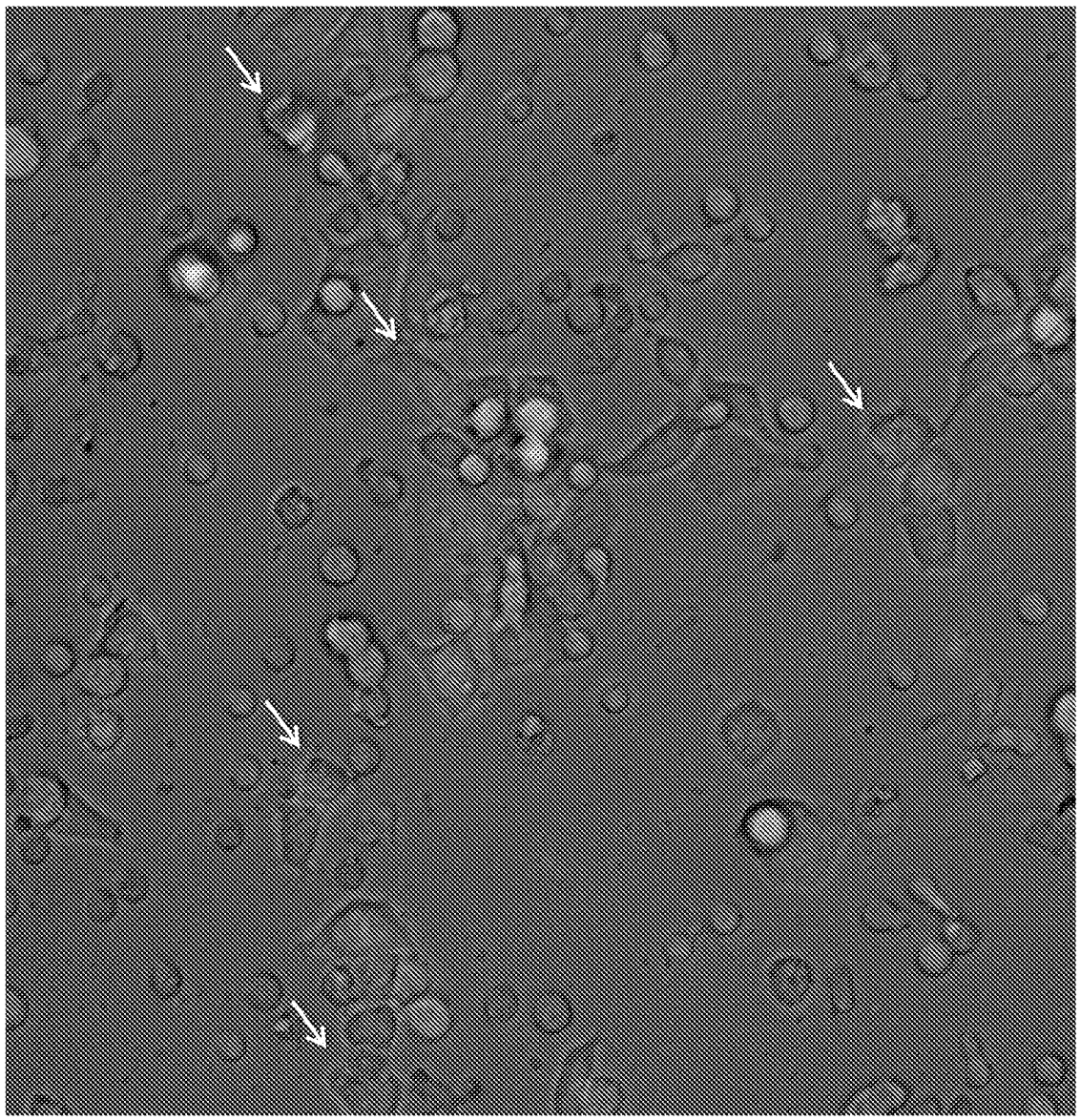
FIG. 7 is a fluorescent micrograph of a co-culture assay containing CD8+ T cells transduced with a HPV16 E7 TCR and CD4+ T cells transduced with CER5 (blue) at a 1:1 ratio with SCC152 cells (green). The red signals (representative red signals indicated with white arrows) are fluorescent signals from a caspase reagent that was added to the co-culture assay after 6 hours.
Figure 8:
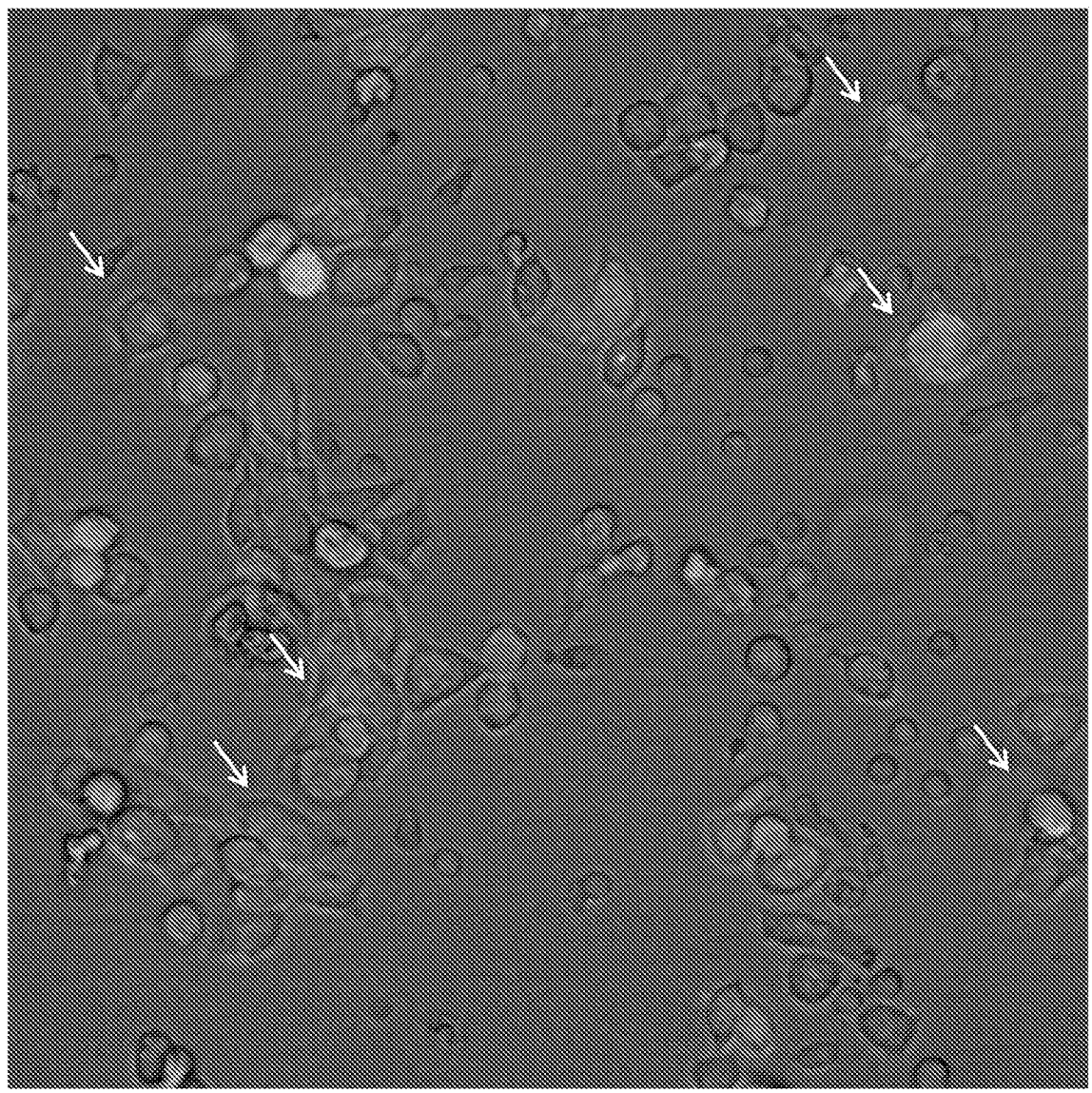
FIG. 8 is a fluorescent micrograph of a co-culture assay containing CD8+ T cells transduced with a HPV16 E7 TCR and CD4+ T cells transduced with CER17 (blue) at a 1:1 ratio with SCC152 cells (green). The red signals (representative red signals indicated with white arrows) are fluorescent signals from a caspase reagent that was added to the co-culture assay after 6 hours.
Figure 9:
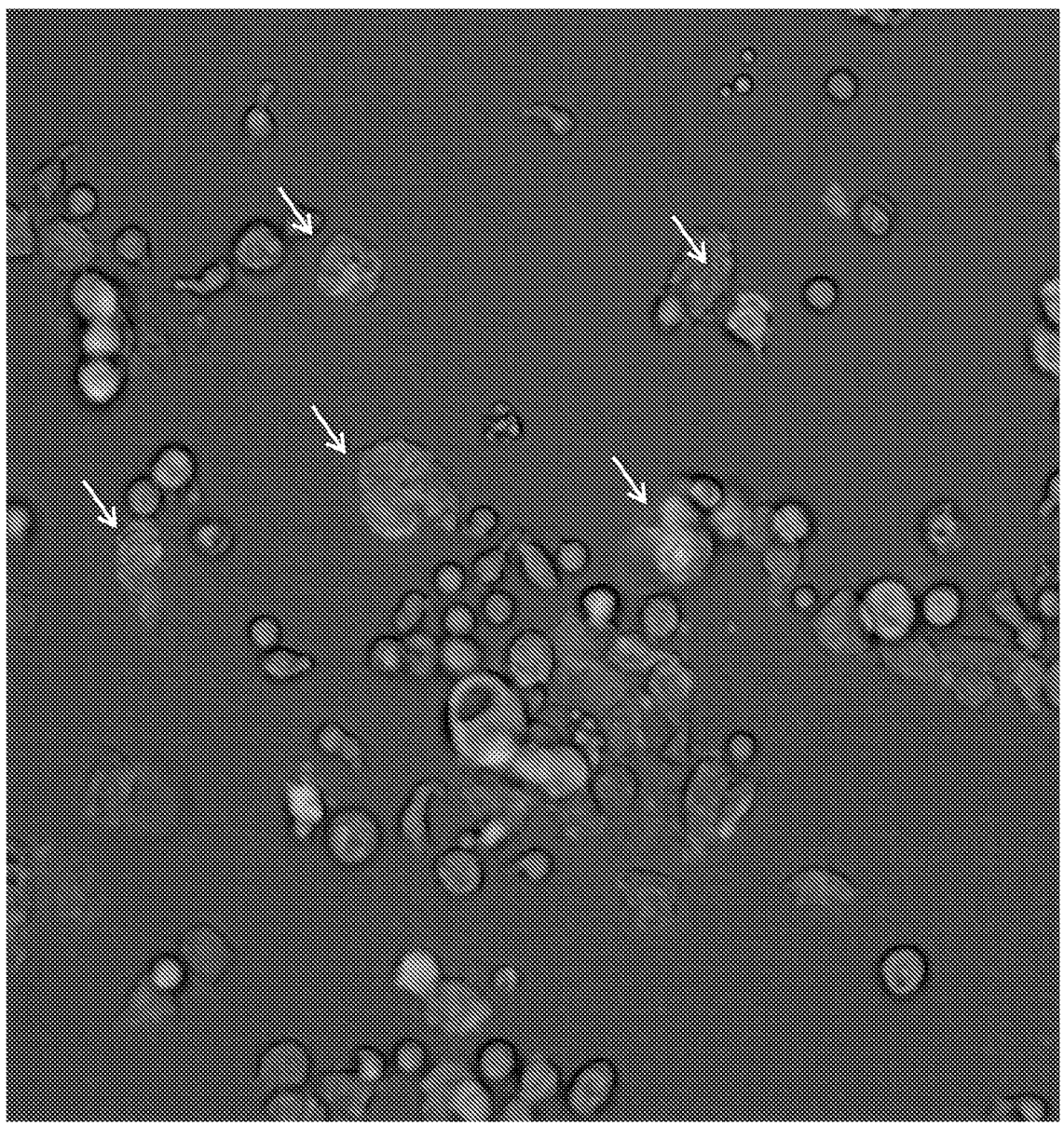
FIG. 9 is a fluorescent micrograph of a co-culture assay containing CD8+ T cells transduced with a HPV16 E7 TCR and CD4+ T cells transduced with CER19 (blue) at a 1:1 ratio with SCC152 cells (green). The red signals (representative red signals indicated with white arrows) are fluorescent signals from a caspase reagent that was added to the co-culture assay after 6 hours.
Figure 10:
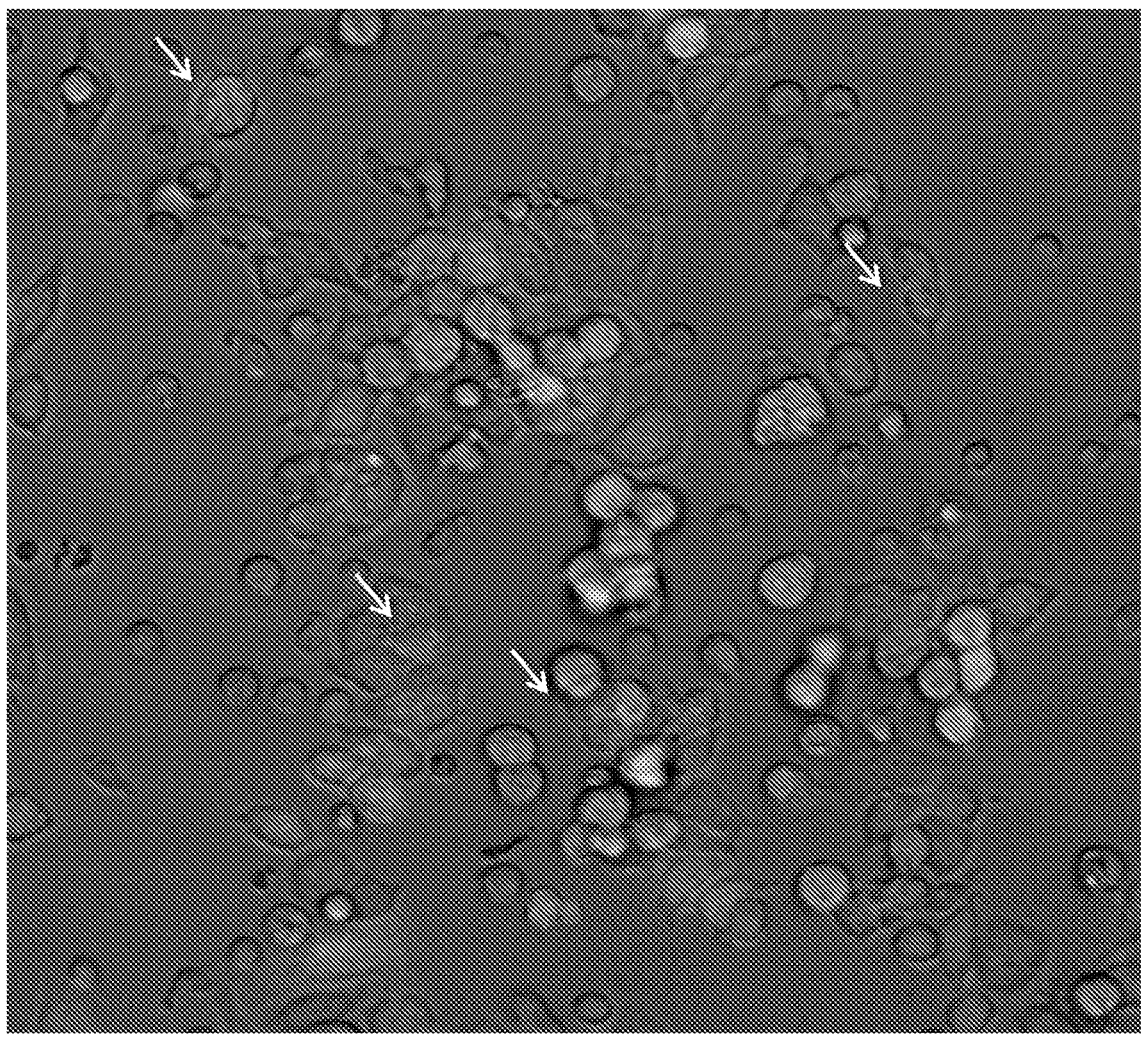
FIG. 10 is a fluorescent micrograph of a co-culture assay containing CD8+ T cells transduced with a HPV16 E7 TCR and CD4+ T cells transduced with CER21 (blue) at a 1:1 ratio with SCC152 cells (green). The red signals (representative red signals indicated with white arrows) are fluorescent signals from a caspase reagent that was added to the co-culture assay after 6 hours.
Figure 11:
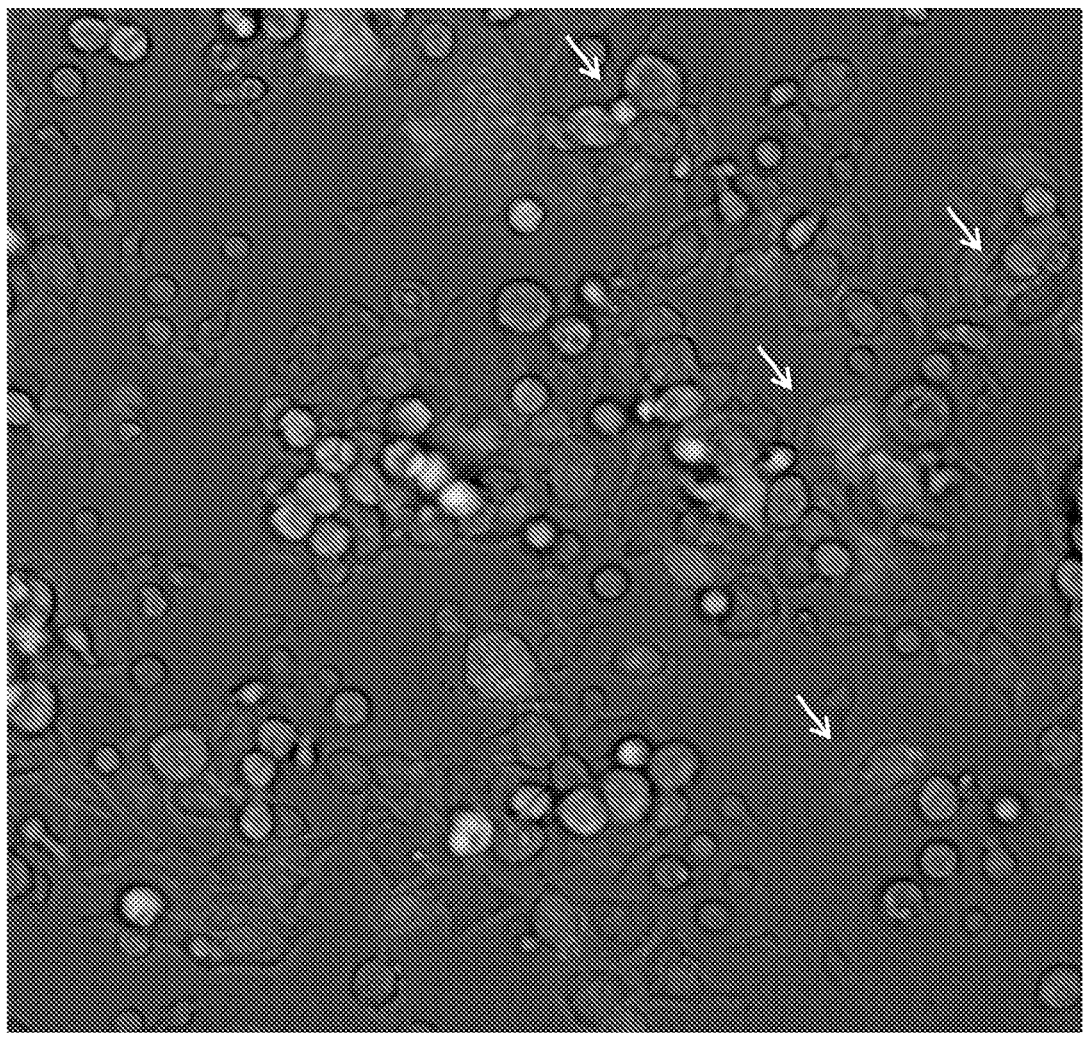
FIG. 11 is a fluorescent micrograph of a co-culture assay containing CD8+ T cells transduced with a HPV16 E7 TCR and CD4+ T cells transduced with CER23 (blue) at a 1:1 ratio with SCC152 cells (green). The red signals (representative red signals indicated with white arrows) are fluorescent signals from a caspase reagent that was added to the co-culture assay after 6 hours.
Figure 12:
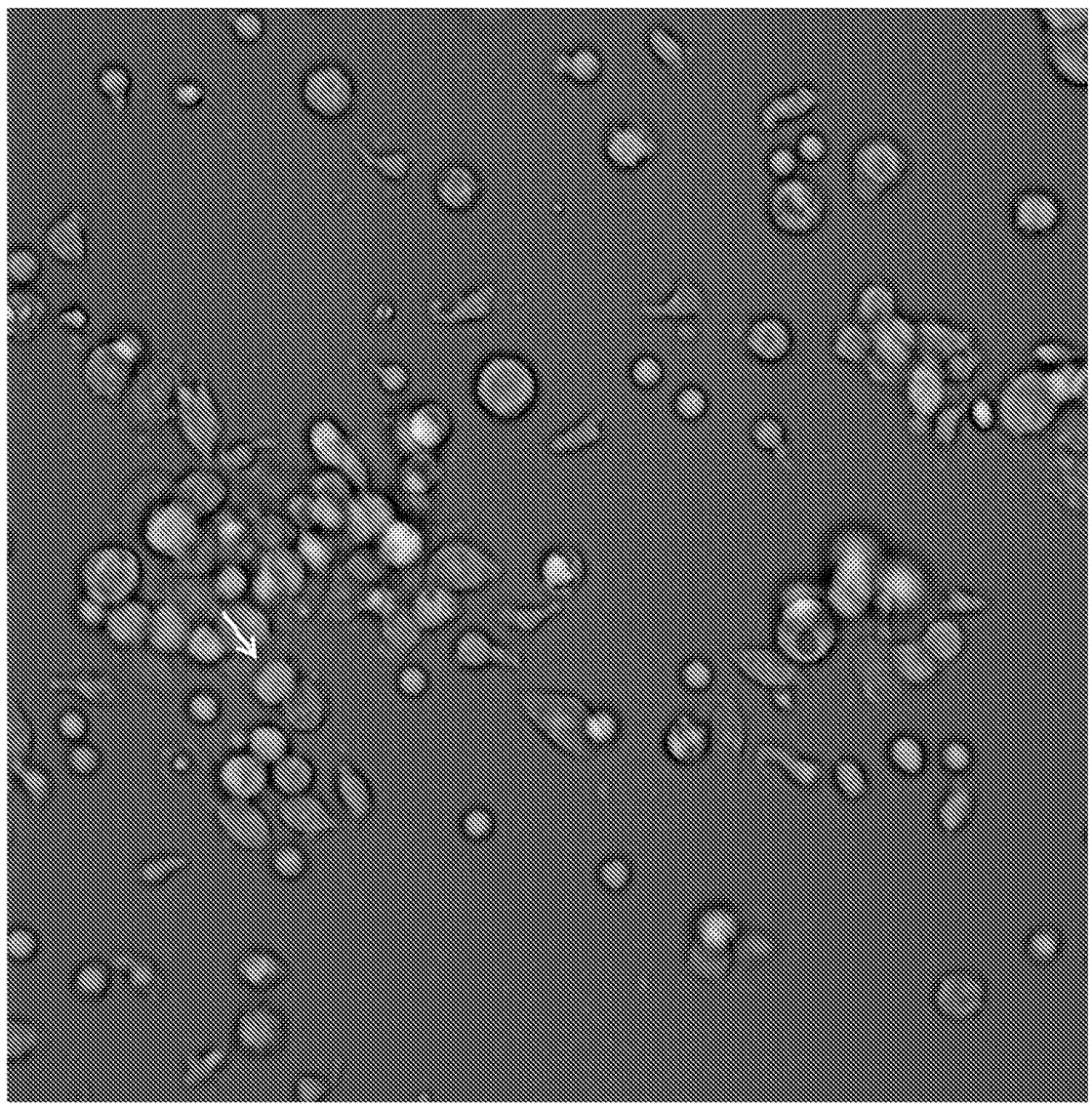
FIG. 12 is a fluorescent micrograph of a co-culture assay containing CD8+ T cells transduced with a HPV16 E7 TCR and CD4+ T cells transduced with CER26 (blue) at a 1:1 ratio with SCC152 cells (green). The red signals (representative red signals indicated with white arrows) are fluorescent signals from a caspase reagent that was added to the co-culture assay after 6 hours.
Figure 13:
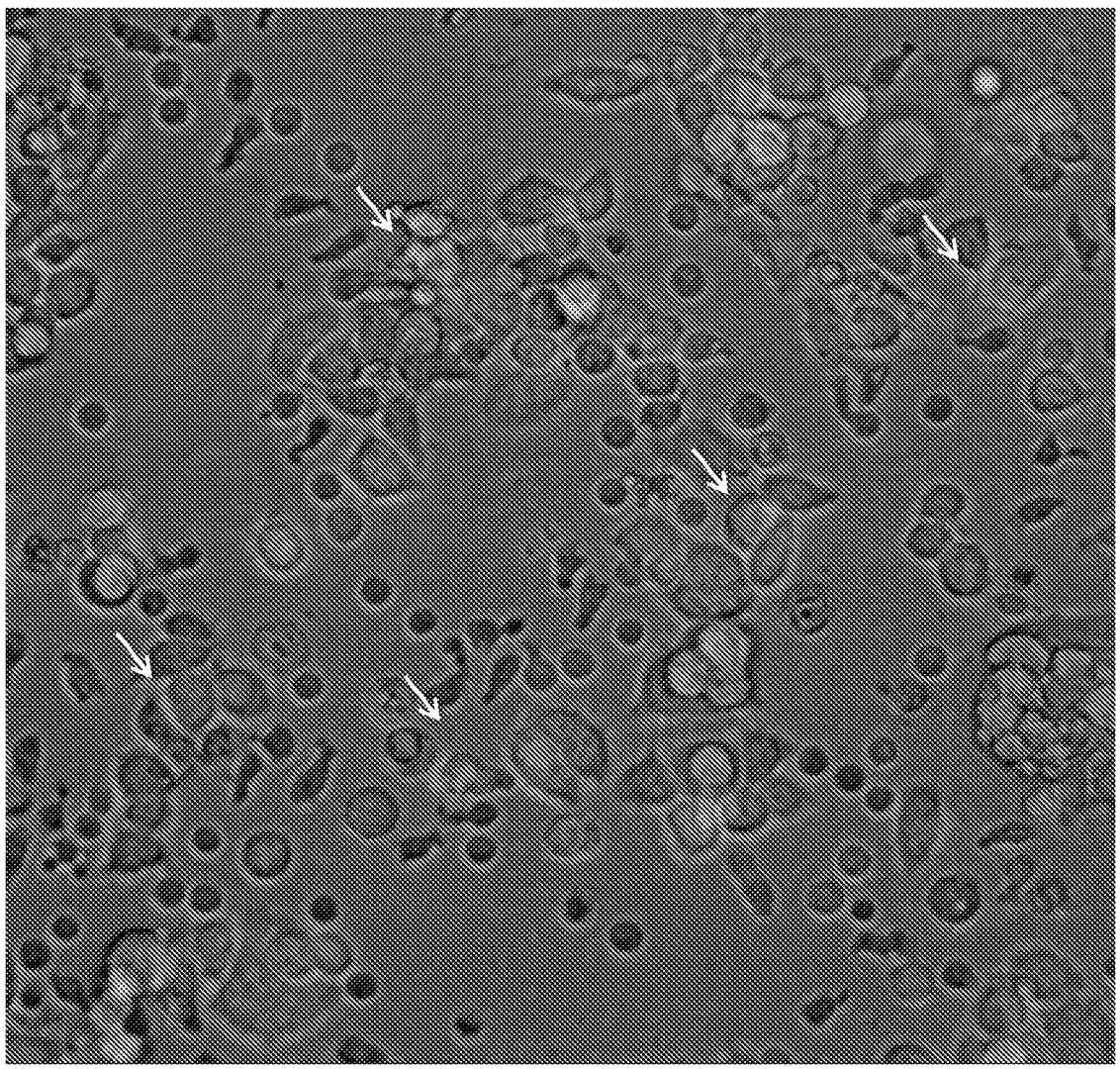
FIG. 13 is a fluorescent micrograph of a co-culture assay containing CD8+ T cells transduced with a HPV16 E7 TCR and CD4+ T cells transduced with CER27 (blue) at a 1:1 ratio with SCC152 cells (green). The red signals (representative red signals indicated with white arrows) are fluorescent signals from a caspase reagent that was added to the co-culture assay after 6 hours.
Figure 14:
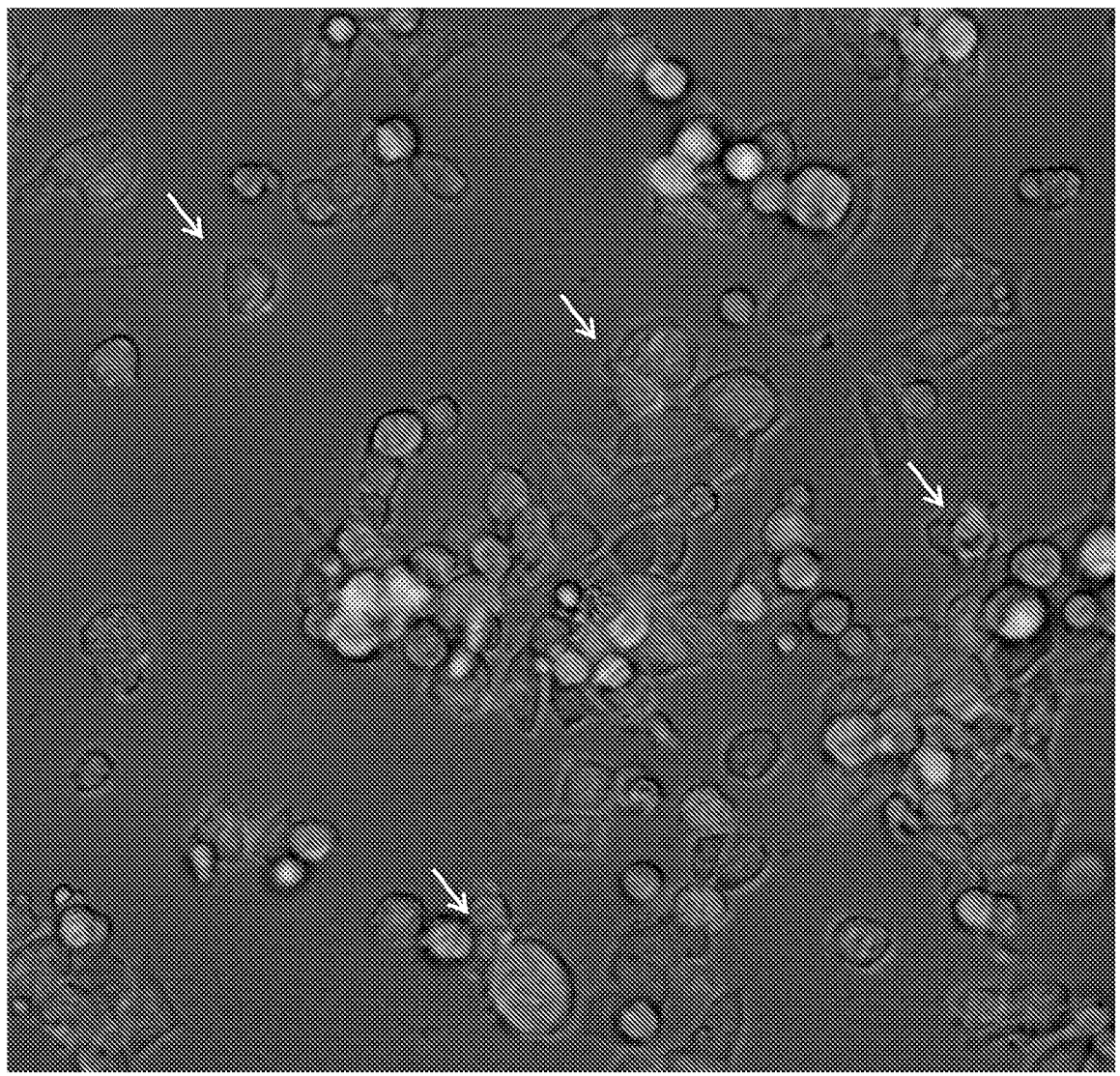
FIG. 14 is a fluorescent micrograph of a co-culture assay containing CD8+ T cells transduced with a HPV16 E7 TCR and CD4+ T cells transduced with CER103B (blue) at a 1:1 ratio with SCC152 cells (green). The red signals (representative red signals indicated with white arrows) are fluorescent signals from a caspase reagent that was added to the co-culture assay after 6 hours.
Figure 15:
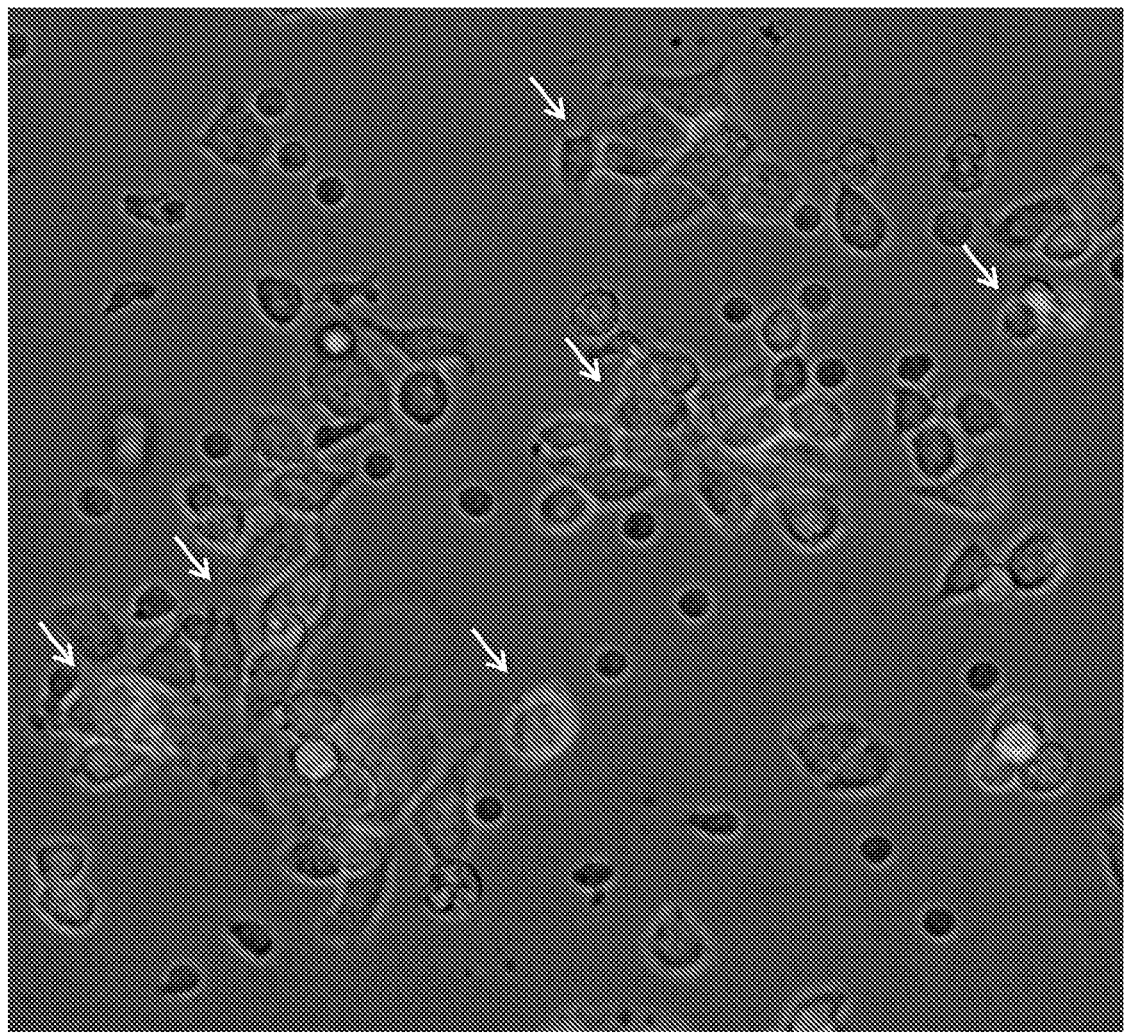
FIG. 15 is a fluorescent micrograph of a co-culture assay containing CD8+ T cells transduced with a HPV16 E7 TCR and CD4+ T cells transduced with CER104 (blue) at a 1:1 ratio with SCC152 cells (green). The red signals (representative red signals indicated with white arrows) are fluorescent signals from a caspase reagent that was added to the co-culture assay after 6 hours.
Figure 16:
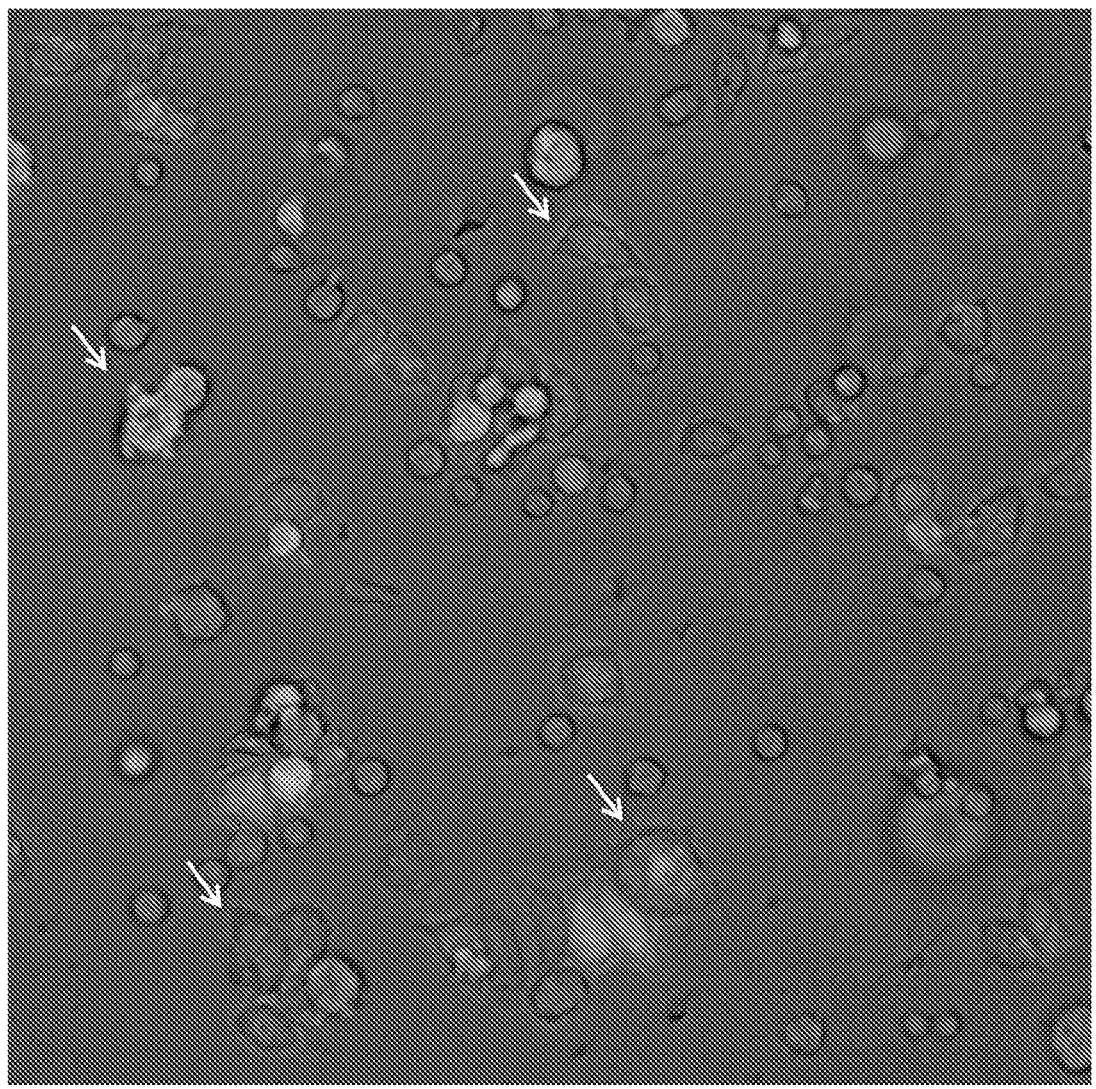
FIG. 16 is a fluorescent micrograph of a co-culture assay containing CD8+ T cells transduced with a HPV16 E7 TCR and CD4+ T cells transduced with CER105 (blue) at a 1:1 ratio with SCC152 cells (green). The red signals (representative red signals indicated with white arrows) are fluorescent signals from a caspase reagent that was added to the co-culture assay after 6 hours.
Figure 17:
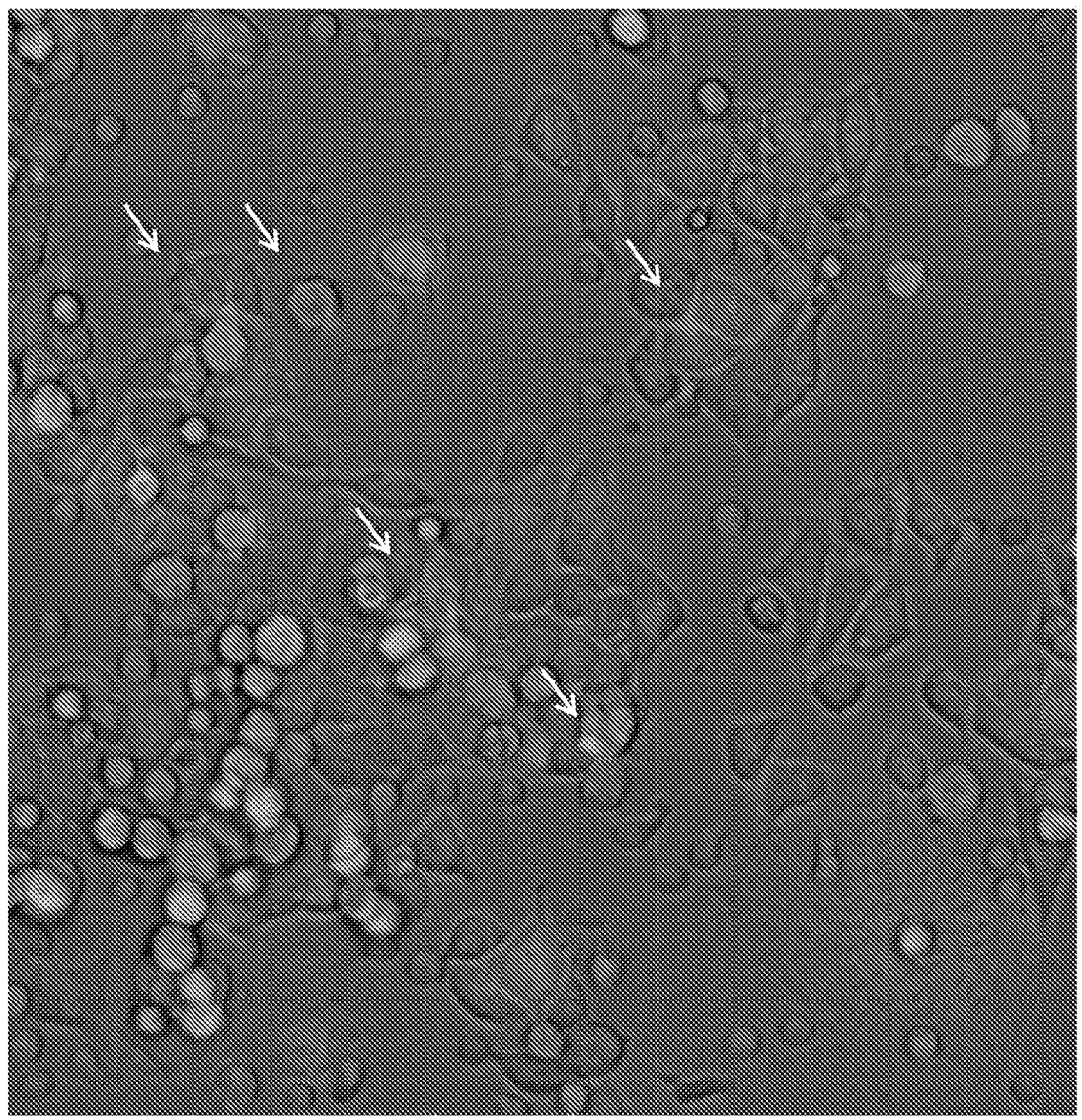
FIG. 17 is a fluorescent micrograph of a co-culture assay containing CD8+ T cells transduced with a HPV16 E7 TCR and CD4+ T cells transduced with CER106 (blue) at a 1:1 ratio with SCC152 cells (green). The red signals (representative red signals indicated with white arrows) are fluorescent signals from a caspase reagent that was added to the co-culture assay after 6 hours.
Figure 18:
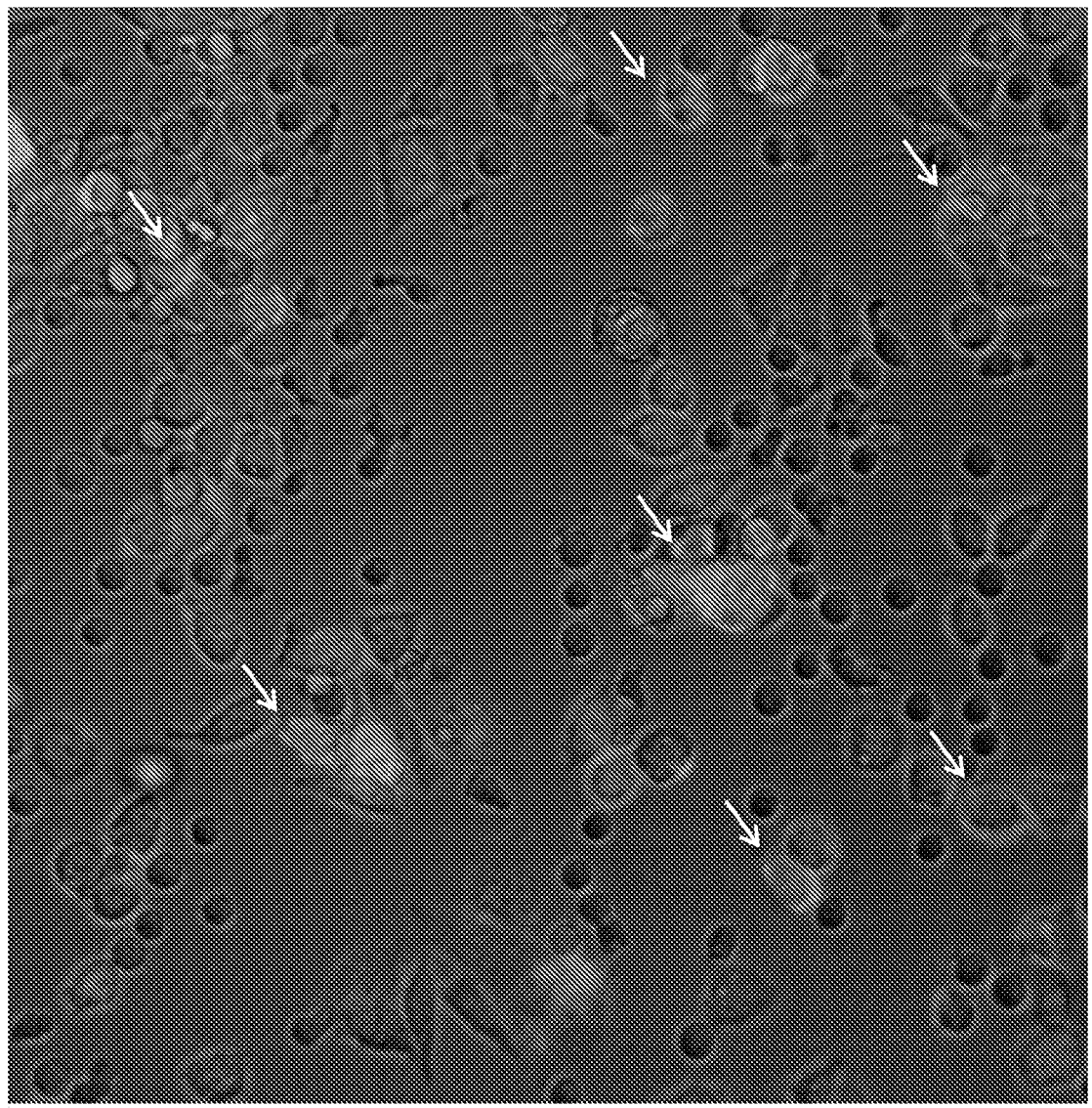
FIG. 18 is a fluorescent micrograph of a co-culture assay containing CD8+ T cells transduced with a HPV16 E7 TCR and CD4+ T cells transduced with CER116 (blue) at a 1:1 ratio with SCC152 cells (green). The red signals (representative red signals indicated with white arrows) are fluorescent signals from a caspase reagent that was added to the co-culture assay after 6 hours.
Figure 26:
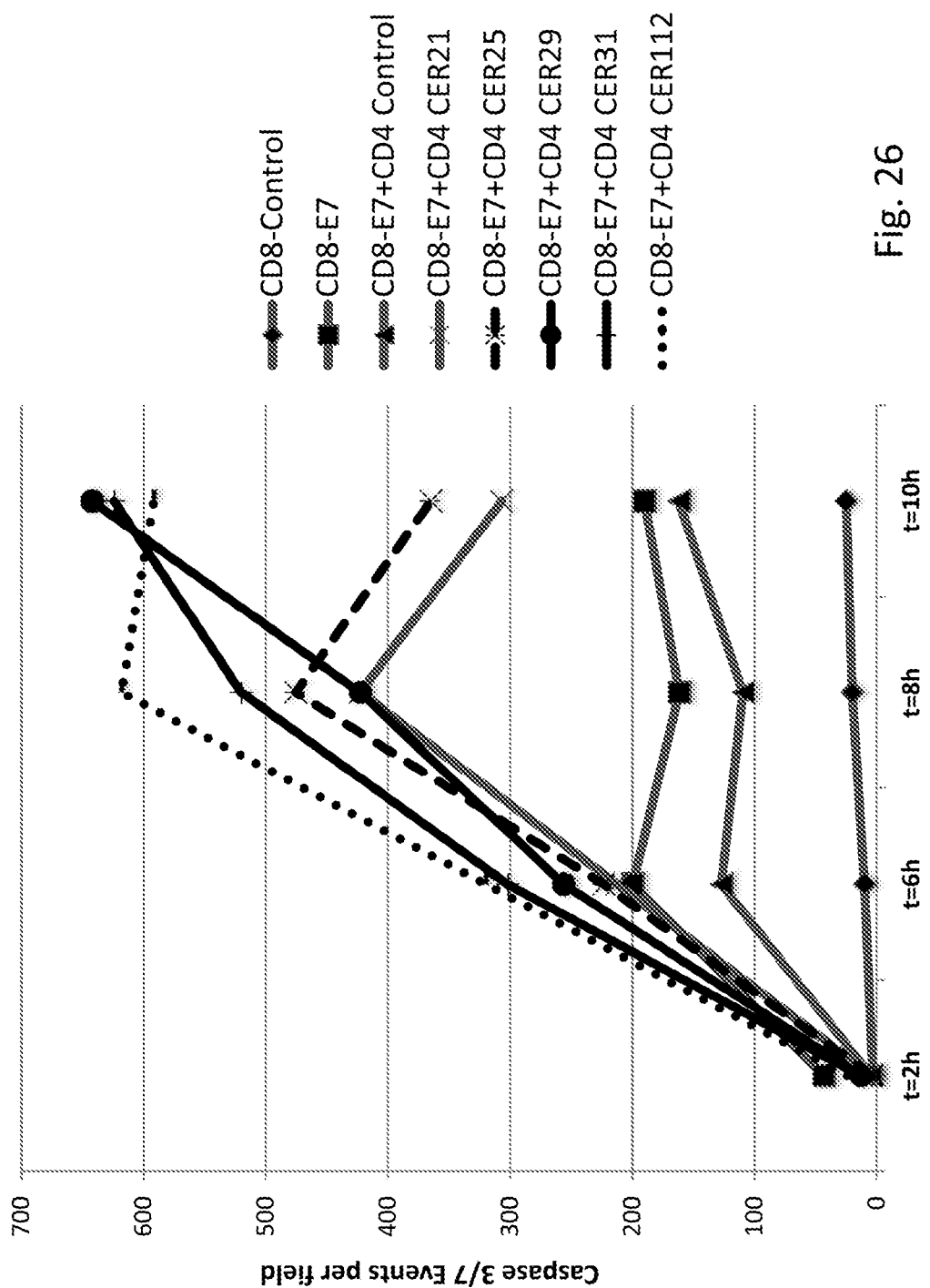
FIG. 26 is a line graph showing caspase 3/7 induction over time in co-culture experiments. The graph shows the number of caspase positive SCC152 target cells in a co-culture assay containing CD8+ T cells transduced with HPV16 E7 TCR and CD4+ T cells transduced with either control or a selected CER. The intensity of caspase was measured by quantifying the intensity of red fluorescence from a caspase 3/7 apoptosis reagent that couples the activated caspase 3/7 recognition motif with a red reagent that fluoresces upon cleavage. Measurements were taken at 2, 6, 8, and 10 hours of the co-culture assay.

Example 2: Combinations of CD8+ T Cell-TCR+CD4+ T Cell-CER Exhibit Enhanced Antigen Specific Cytolytic Activity and Phagocytic Activity Dual HPV16 E7 TCR and CER-mediated elimination of target SCC152 cells was detected using cytotoxicty and and phagocytosis assays (see, FIG. 3). SCC152 cells are HPV16+ cells from a squamous cell carcinoma of the hypopharynx. Cytotoxic activity of CD8+ T cells transduced with HPV16 E7 specific TCR was detected using a caspase 3/7 apoptosis reagent (IncuCyte®) that couples the activated caspase 3/7 recognition motif with a red reagent that fluoresces upon cleavage. The fluorescent signal was measured using fluorescent microscopy. HPV16 E7 TCR transduced CD8+ T cells and selected CER transduced CD4+ T cells were mixed at a 1:1 ratio and co-cultured with HPV16 E7+ head and neck squamous cell carcinoma cells (SCC152) at a 1:1 ratio, and caspase 3/7 apoptosis reagent was added to the co-culture. Cytotoxic activity was measured over time by measuring fluorescence. Control samples were CD8+ T cells transduced with HPV16 E7 TCR alone. As shown in the graphs of FIGS. 4, 5, and 26, and the fluorescent micrographs of FIGS. 6-18, addition of CD4+ T cells transduced with most of the CERs tested to CD8+ T cells transduced with the HPV16 E7 TCR enhanced cytolytic activity over monotreatment with CD8 T cells transduced with HPV16 E7 TCR.

Figure 19:
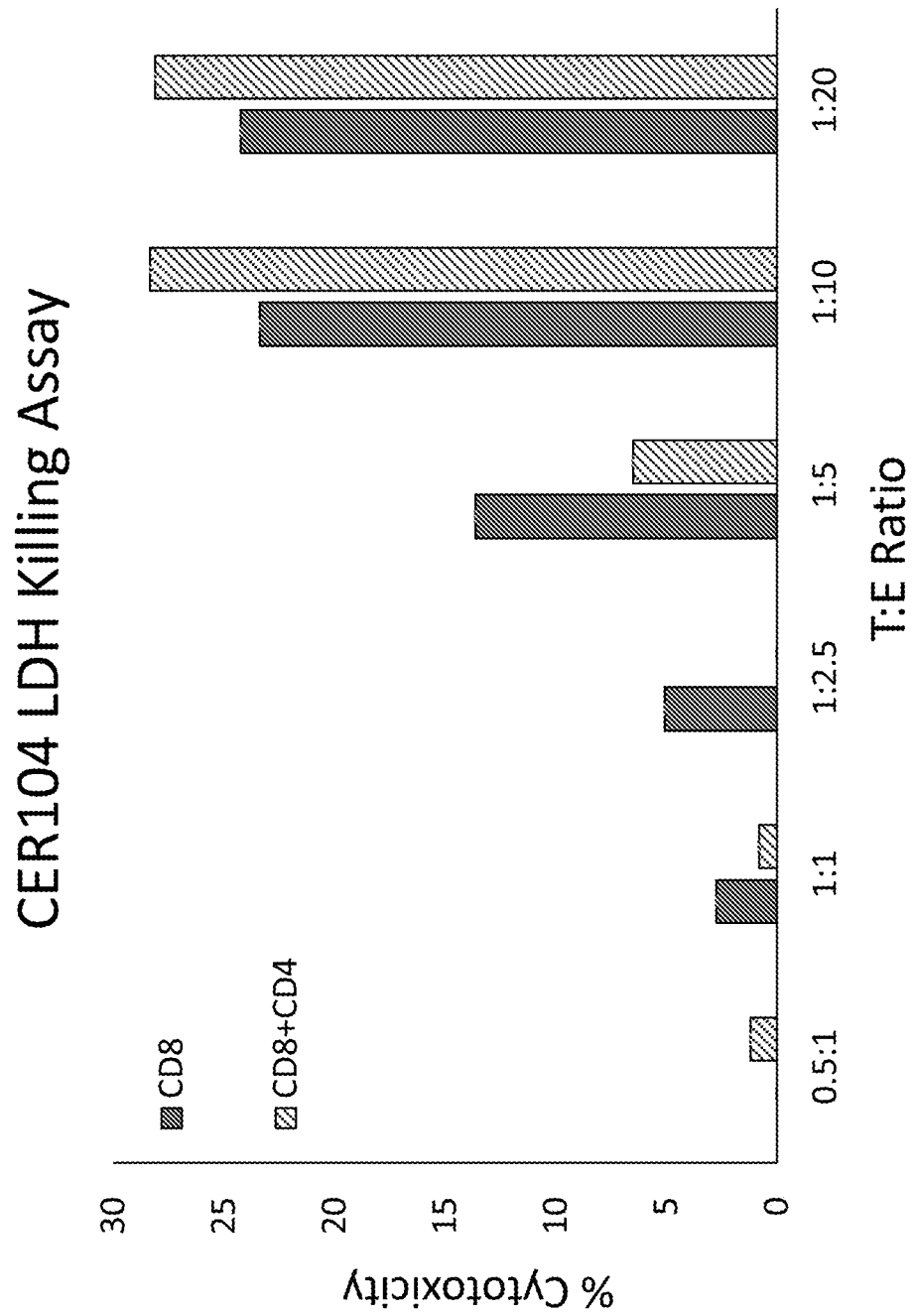
FIG. 19 is a bar graph showing a lactate dehydrogenase (LDH) cytotoxicity assay performed 4 hours after co-culture of CD8+ T cells transduced with a HPV16 E7 TCR and CD4+ T cells transduced with CER104 at a 1:1 ratio with SCC152 target cells at varying target cell:effector cell ratios (0.5:1, 1:1, 1:2.5, 1:5, 1:10, 1:20).

The enhanced cytolytic activity of CD4+ T cell transduced with CER104+CD8+ T cells transduced with HPV16 E7 TCR was observed when measured using a lactate dehydrogenase (LDH) cytoxicity assay (see, FIG. 19). LDH is a cytosolic enzyme that is released by a cell into cell culture media when the plasma membrane is damaged. Thus, LDH's presence in culture medium is a marker for cell death. LDH assays are capable of detecting low level damage to cell membrane which cannot be detected using other methods. LDH may be detected using colorimetric or fluorometric methods.

Figure 20:
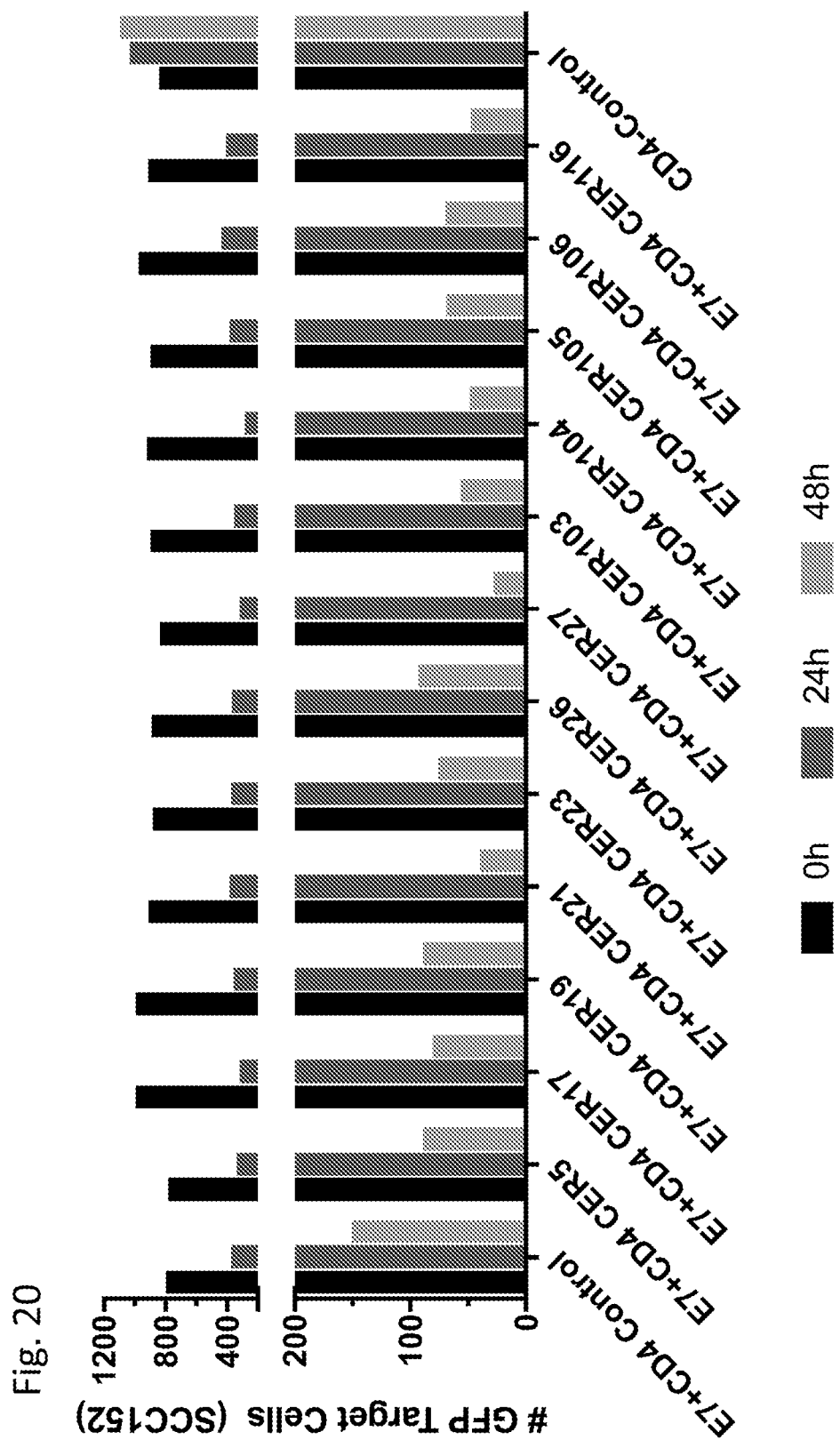
FIG. 20 shows a bar graph of the quantification of SCC152 HPV+ head and neck squamous carcinoma cells over time. Target SCC152 cells were co-cultured with CD8+ T cells transduced with HPV E7 TCR+CD4+ T cells transduced with a selected CER, or controls (CD8+ T cell transduced with HPV E7 TCR+CD4+ transduced control) at a 1:1:1 ratio. The number of target cells were quantified using imaging software. 0 hours, 24 hours, and 48 hours are shown from left to right.
Figure 21:
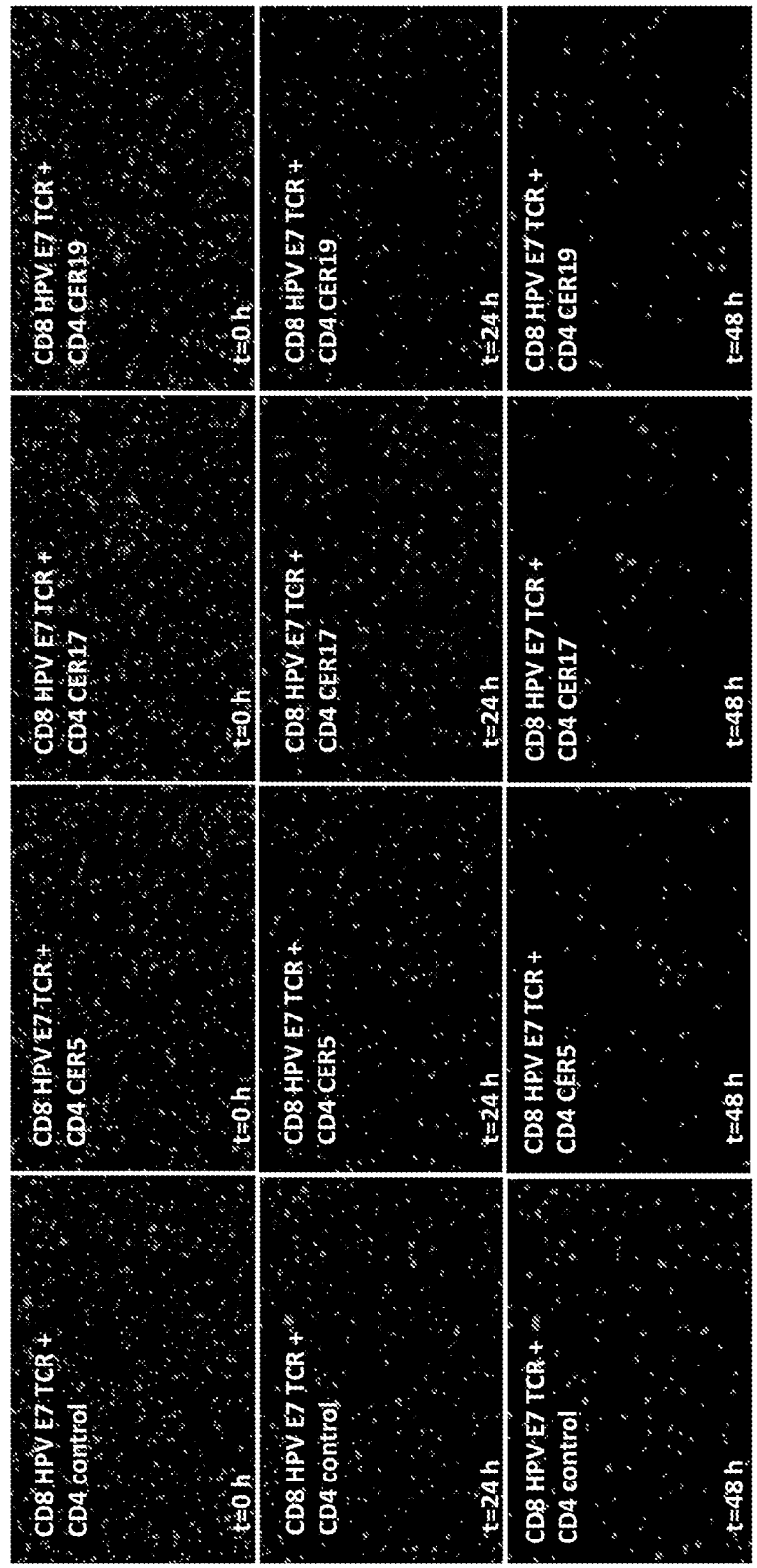
FIG. 21 is time lapse imaging from 96-well co-culture experiments comprising CD8+ T cells transduced with HPV16 E7 TCR+CD4+ T cells transduced with CER5, CER17 or CER19 incubated with SCC152 target cells at a 1:1:1 ratio. SCC152 HPV+ target cells were quantified using automated cell counting software. SCC152 cells are shown to be decreasing in numbers over time in co-culture with CD8+ T cells transduced with HPV E7 TCR+CD4+ T cells transduced with CER5, CER17 or CER19 as compared to control (CD8+ T cell HPV16 E7 TCR+CD4+ T cell control).
Figure 22:
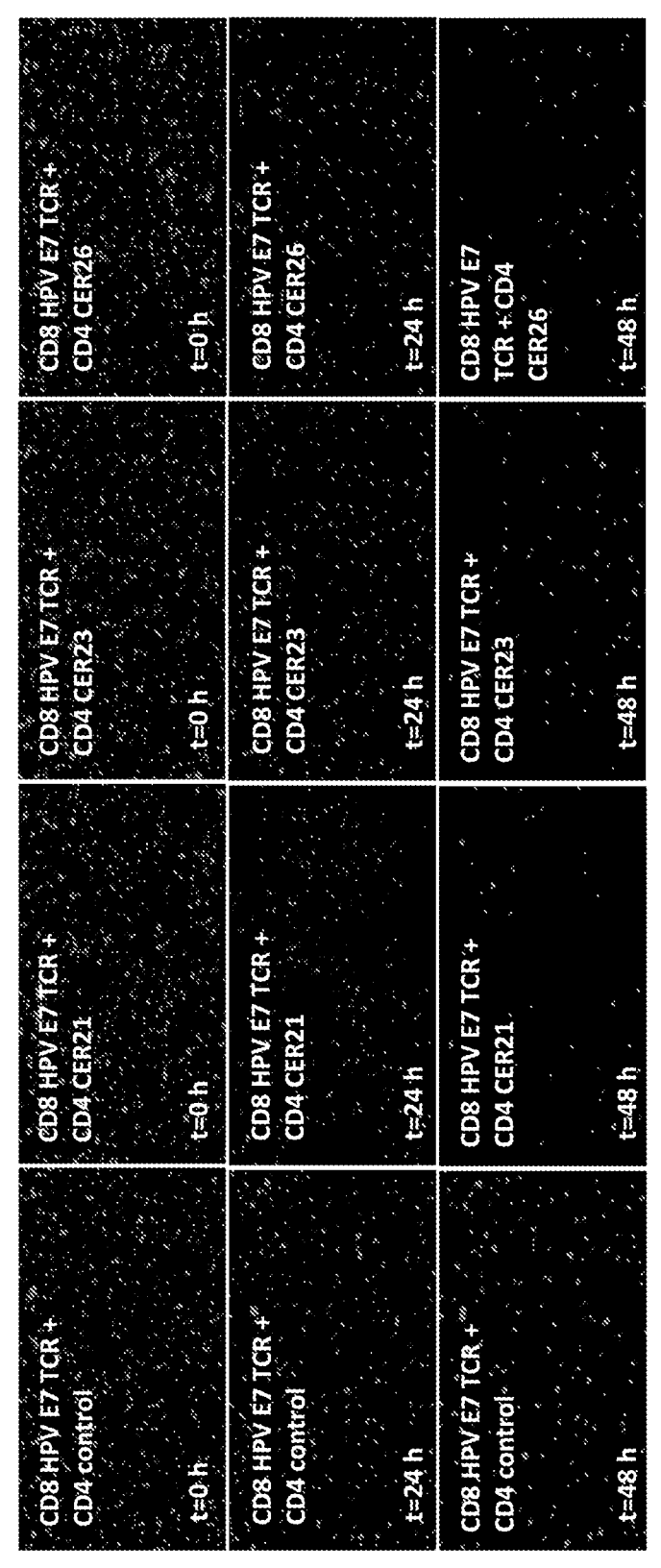
Figure 23:
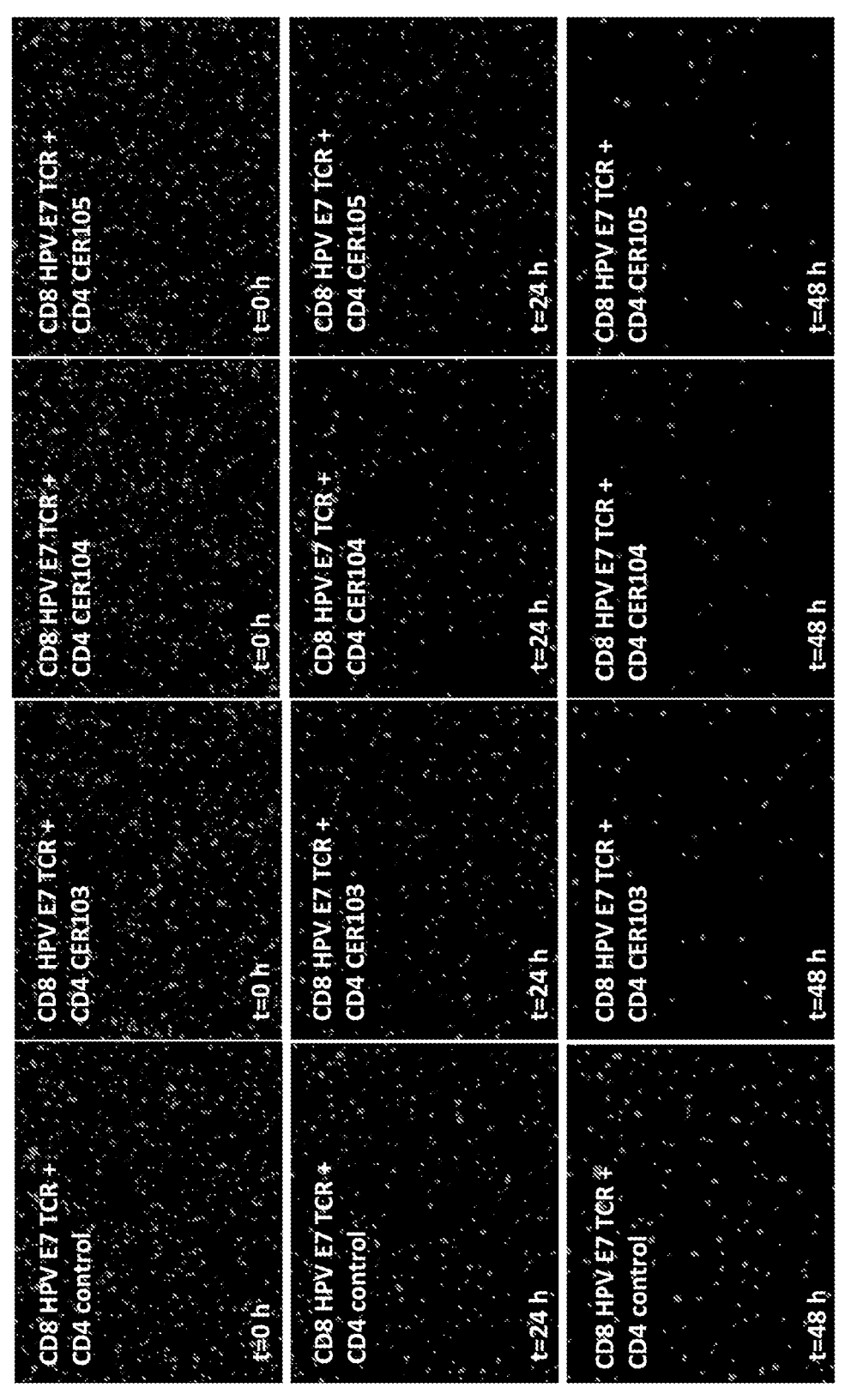
Figure 24:
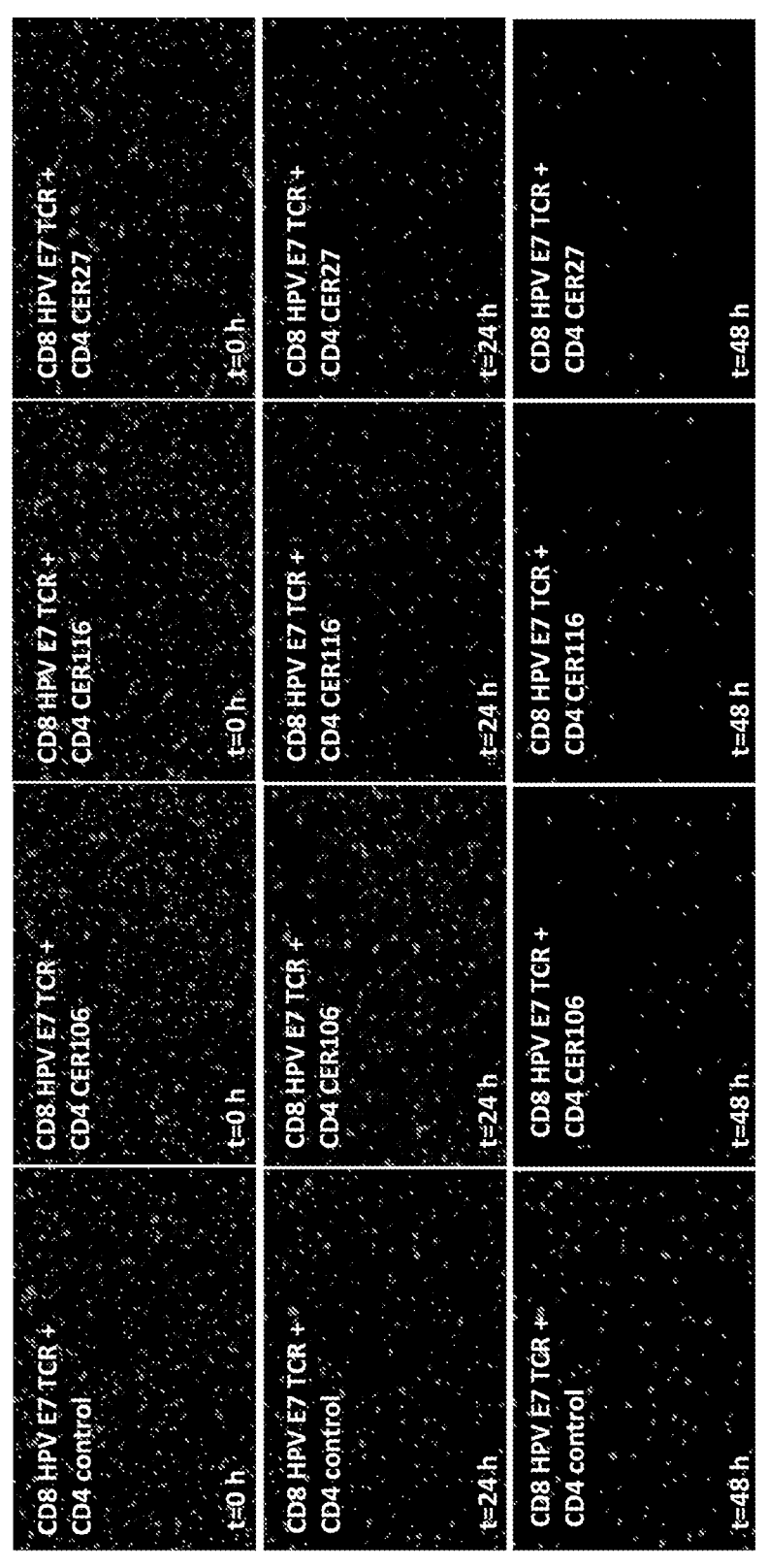
Figure 25:
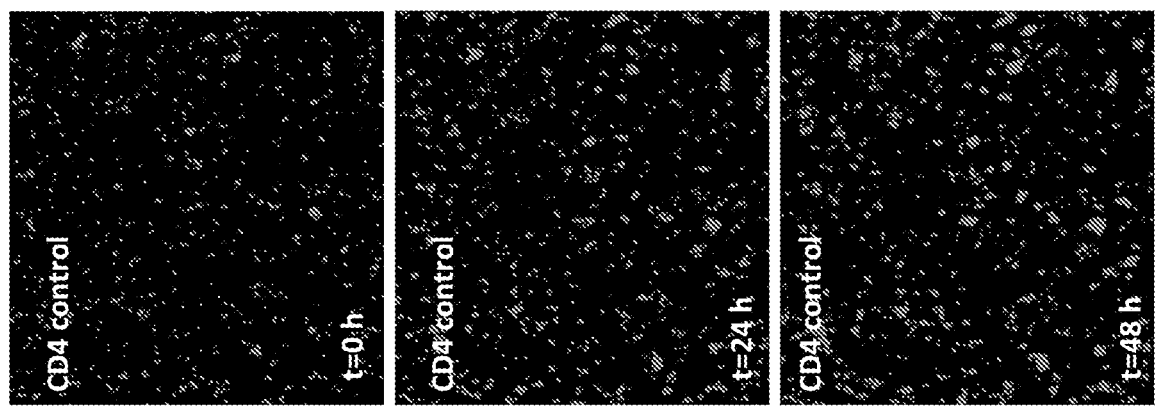
FIG. 25 is time lapse imaging from 96-well co-culture experiments. SCC152 target cells were incubated with CD4+ T cells (control) and quantified using automated cell counting software. SCC152 cells in co-culture with control CD4+ T cells do not decrease in number over time.

Elimination of target SCC152 cells was also detected by quantifying green fluorescent protein expression by SCC152 cells over time (0 hr, 24 hr, 48 hr) during co-incubation with CD8+ T cells transduced with HPV16 E7 specific TCR+ CD4 T cells transduced with selected CER (see, FIG. 20). By 48 hrs, all of the CD4+ T cell/CER+CD8+ T cell/HPV16 E7 TCR combination co-cultures showed enhanced elimination of SCC152 cells compared to controls. Time lapse imaging of co-culture experiments similarly showed showed enhanced elimination of SCC152 cells by CD4+ T cell/CER+CD8+ T cell/HPV16 E7 TCR combination co-cultures compared to controls (see, FIGS. 21-25).

Figure 27:
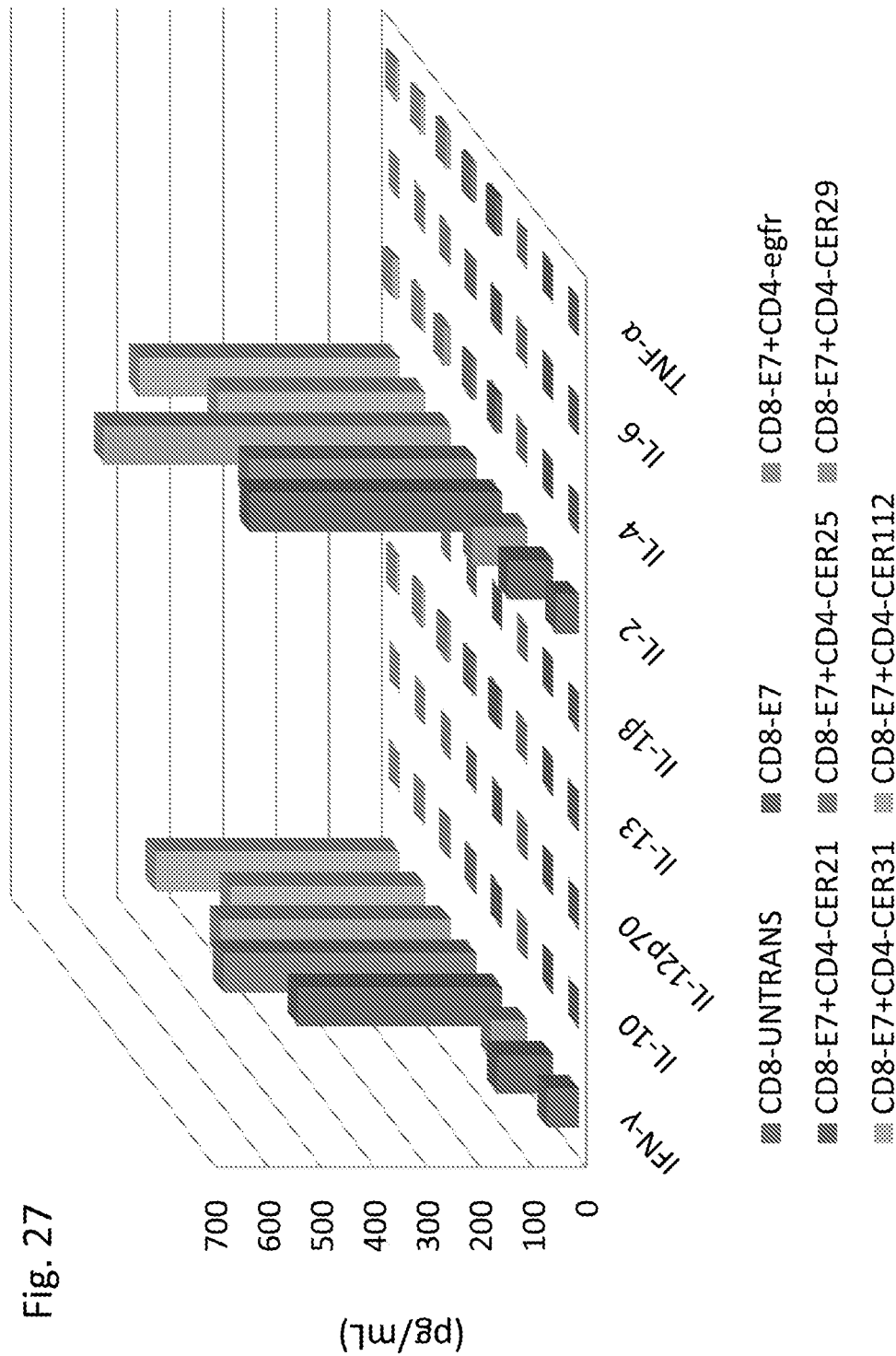
FIG. 27 is a 3D bar graph showing enhanced effector cytokine profile elicited upon co-culture of SCC152 cells with CD8+ T cells transduced with HPV16 E7 TCR+CD4+ T cells transduced with selected CERs. CD8+ T cells transduced with HPV16 E7 TCRs were co-administered with CD4+ T cells transduced selected CERs at a 1:1 ratio to SCC152 target cells for an effector:target cell ratio of 1:1. Antigen-specific cytokine secretion was determined by measuring cytokine concentrations in the cell supernatants from each co-culture experiment using a mesoscale multi-array cytokine plate. The combination of a CD8+ T cell/HPV16 E7 TCR+CD4+ T cell/CER enhanced IFN-γ, IL-2, TNFα, and IL-13 responses over CD8+ T cell/HPV E7 TCR alone or combined with CD4+ T cell transduced with truncated EGFR. The following cytokines were measured in the assay: IFN-γ, IL-2, TNFα, IL-4, IL-6, IL-12b, IL-13, IL-1b, and IL-10. Bars shown from front to back: CD8+ T cells untransduced; CD8+ T cells transduced with HPV E7 TCR; CD8+ T cells transduced with HPV E7 TCR+CD4+ T cells transduced with EGFR; CD8+ transduced with HPV E7 TCR+CD4+ T cells transduced with CER21; CD8+ transduced with HPV E7 TCR+CD4+ T cells transduced with CER25; CD8+ transduced with HPV E7 TCR+CD4+ T cells transduced with CER29; CD8+ transduced with HPV E7 TCR+CD4+ T cells transduced with CER31; and CD8+ transduced with HPV E7 TCR+CD4+ T cells transduced with CER112.
Figure 28:
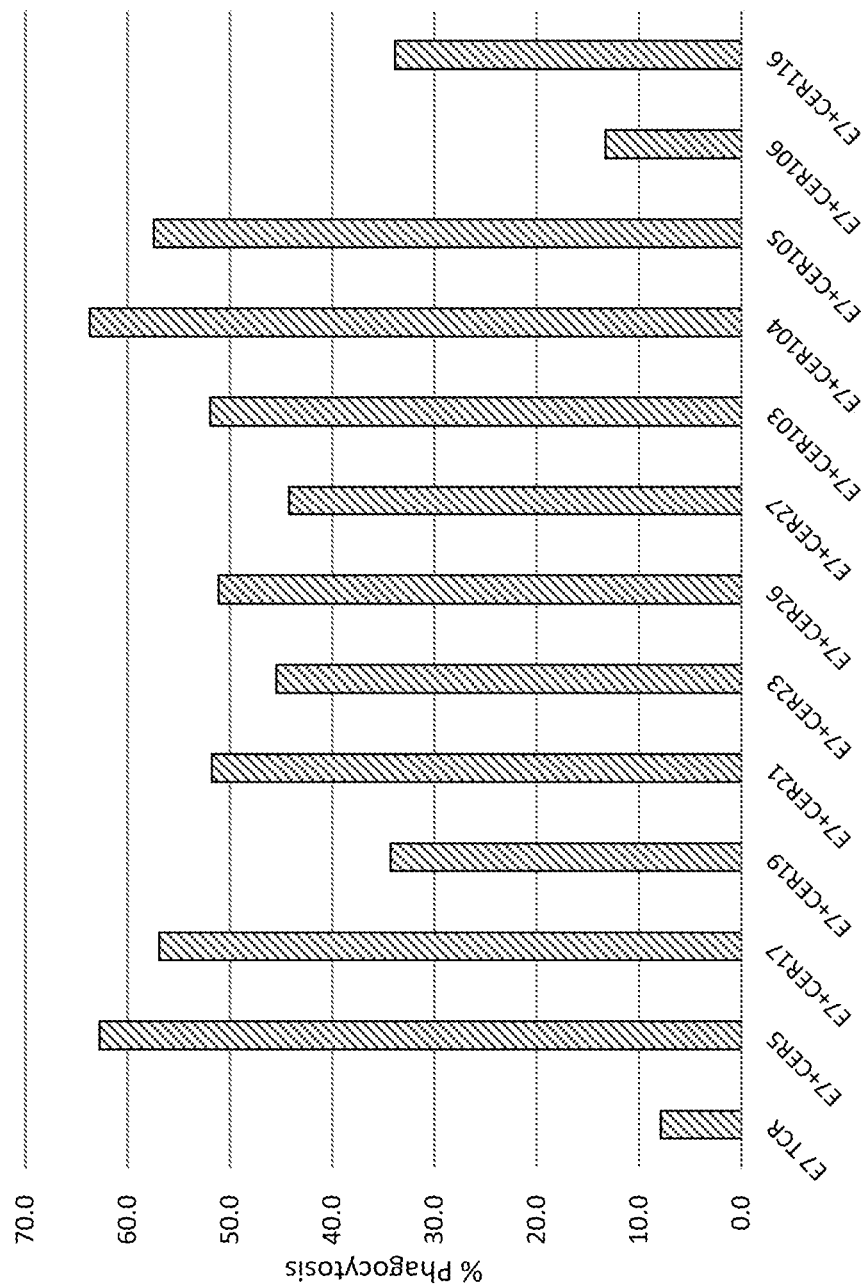
FIG. 28 is a bar graph representing quantification of CD4+ T cell-CER mediated phagocytosis of SCC152 target cells. Results calculated as ((number of phagocytic target events)/(total number of effectors))*100 from 3×3 40× images, 4 hours after initiation of co-culture assay. CD8+ T cells transduced with HPV16 E7 TCR and CD4+ T cells transduced with selected CERs (CER5, CER17, CER19, CER21, CER23, CER26, CER27, CER103b, CER104, CER105, CER106, or CER116) were co-cultured with SCC152 squamous head and neck carcinoma target cells at a 1:1:0.5 ratio for 4 hours and imaged.
Figure 29:
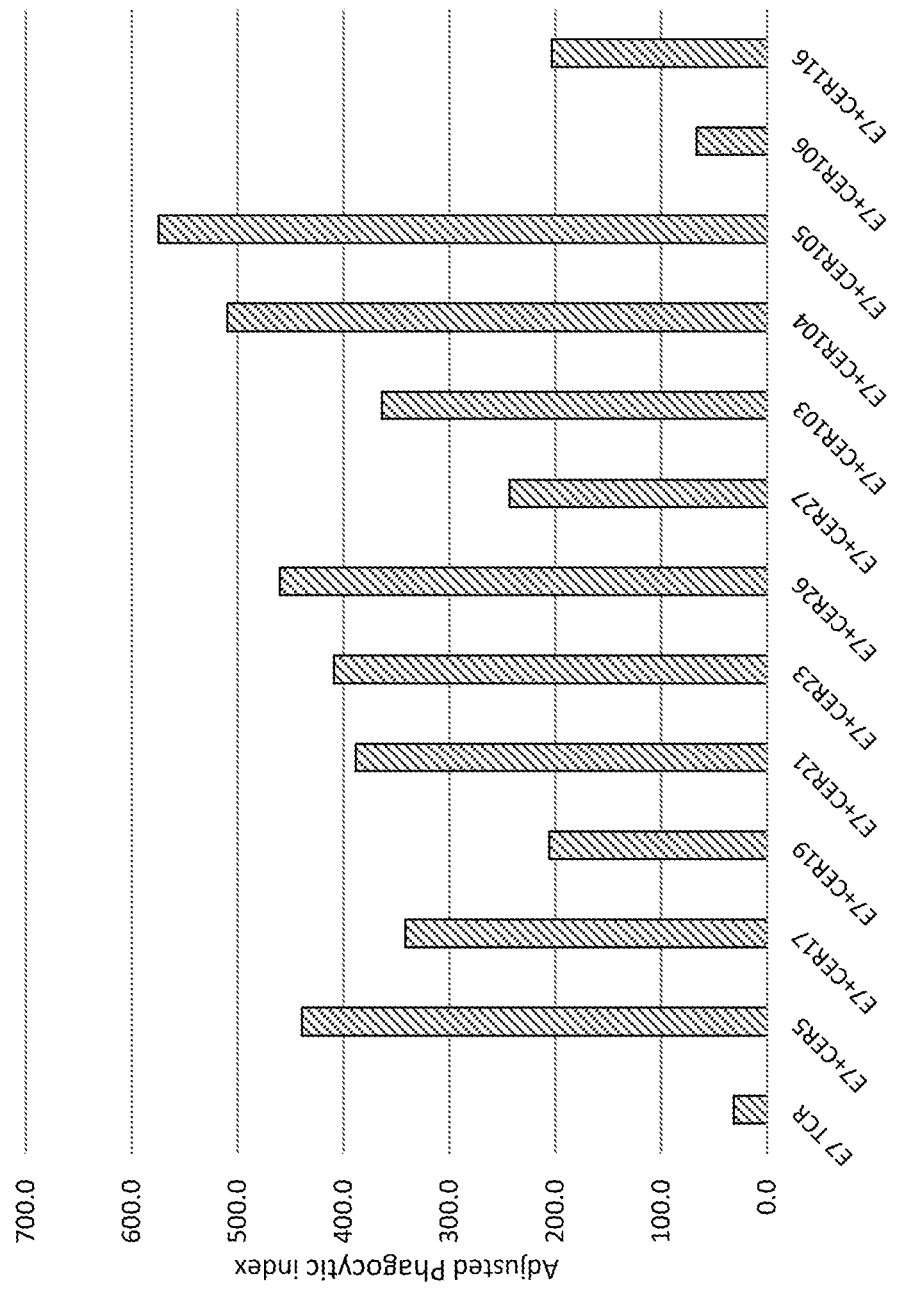
FIG. 29 is a bar graph representing quantification of CD4+ T cell-CER mediated phagocytosis of SCC152 target cells. Results calculated as (median area ratio of target events in effector cells*% phagocytosis) from 3×3 40× images, 4 hours after initiation of co-culture assay. CD8+ T cells transduced with HPV16 E7 TCR and CD4+ T cells transduced with selected CERs (CER5, CER17, CER19, CER21, CER23, CER26, CER27, CER103b, CER104, CER105, CER106, or CER116) were co-cultured with SCC152 squamous head and neck carcinoma target cells at a 1:1:0.5 ratio for 4 hours and imaged.
Figure 30:
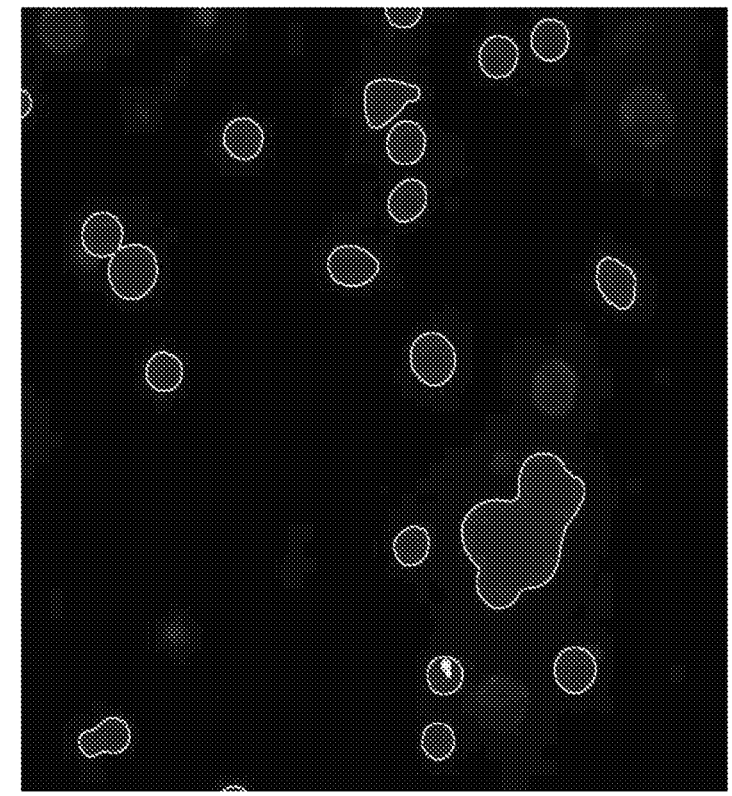
FIG. 30 is a fluorescent micrograph of CD8+ T cells transduced with HPV16 E7 TCR and a truncated EGFR tag (unstained), CD4+ T cells transduced control (blue), and SCC152 target cells (red) in a 4 h co-culture assay at 40× (left panel). Phagocytosis events were identified by marking for red target events inside blue effector cells. These events were quantified by the hybrid capture software (Keyence BZ-X710) to provide number of phagocytosed targets, total number of effector cells, and area occupied by the phagocytosed target cells in the effector cells (right panel).
Figure 30:
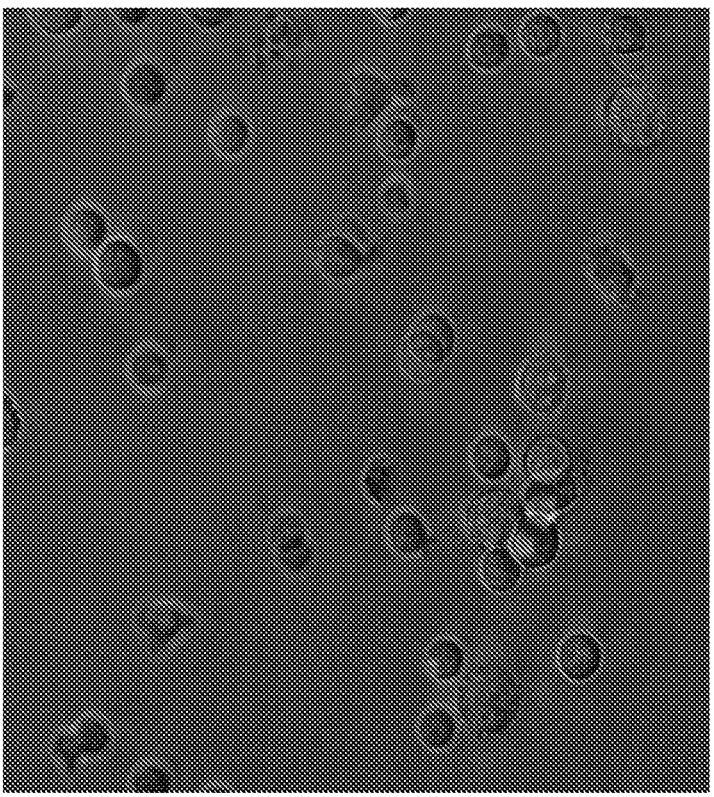
Figure 31:
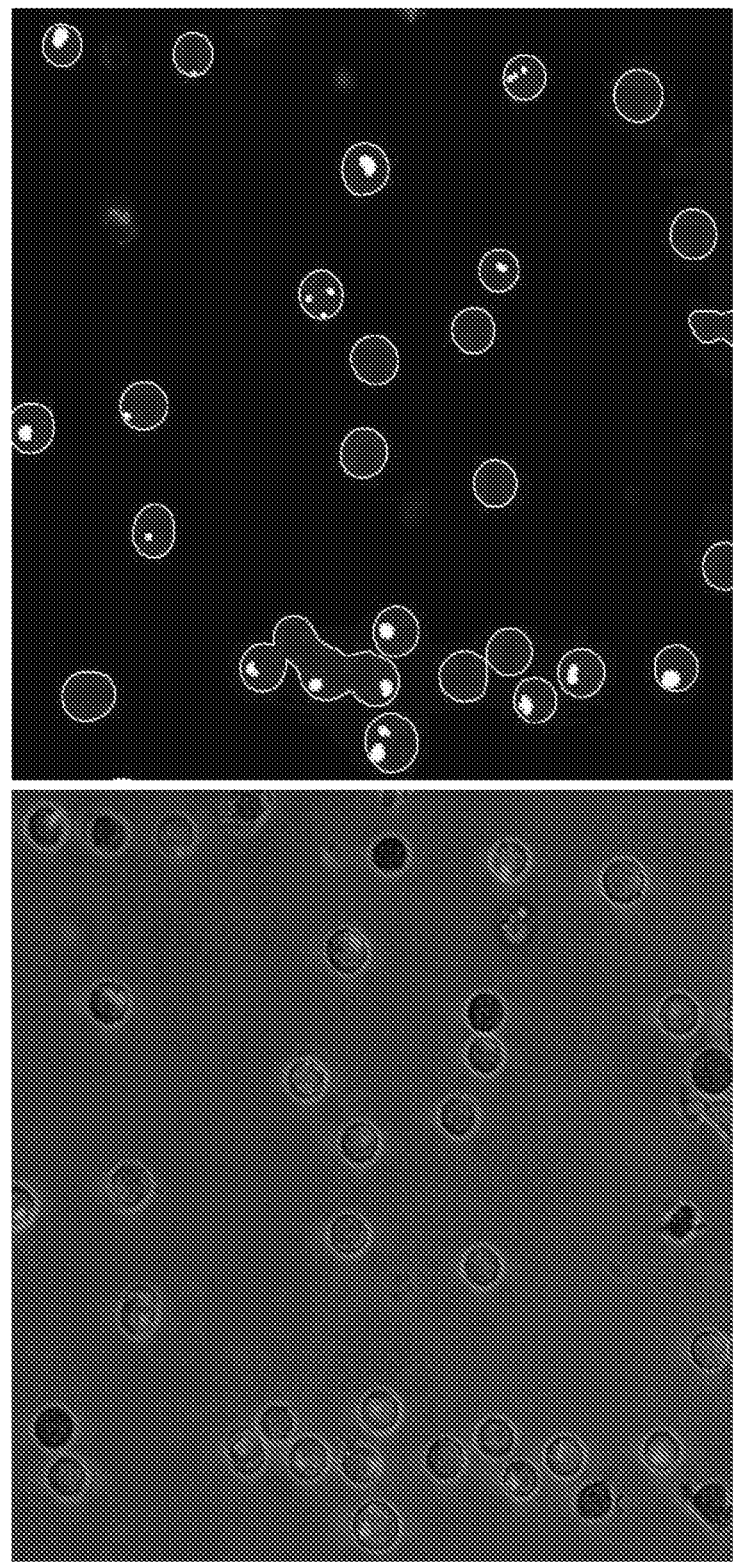
FIG. 31 is a fluorescent micrograph of CD8+ T cells transduced with HPV16 E7 TCR and a truncated EGFR tag (unstained), CD4+ T cells transduced with CER5 (blue), and SCC152 target cells (red) in a 4 h co-culture assay at 40× (left panel). Phagocytosis events were identified by marking for red target events inside blue effector cells. These events were quantified by the hybrid capture software (Keyence BZ-X710) to provide number of phagocytosed targets, total number of effector cells, and area occupied by the phagocytosed target cells in the effector cells (right panel).
Figure 32:
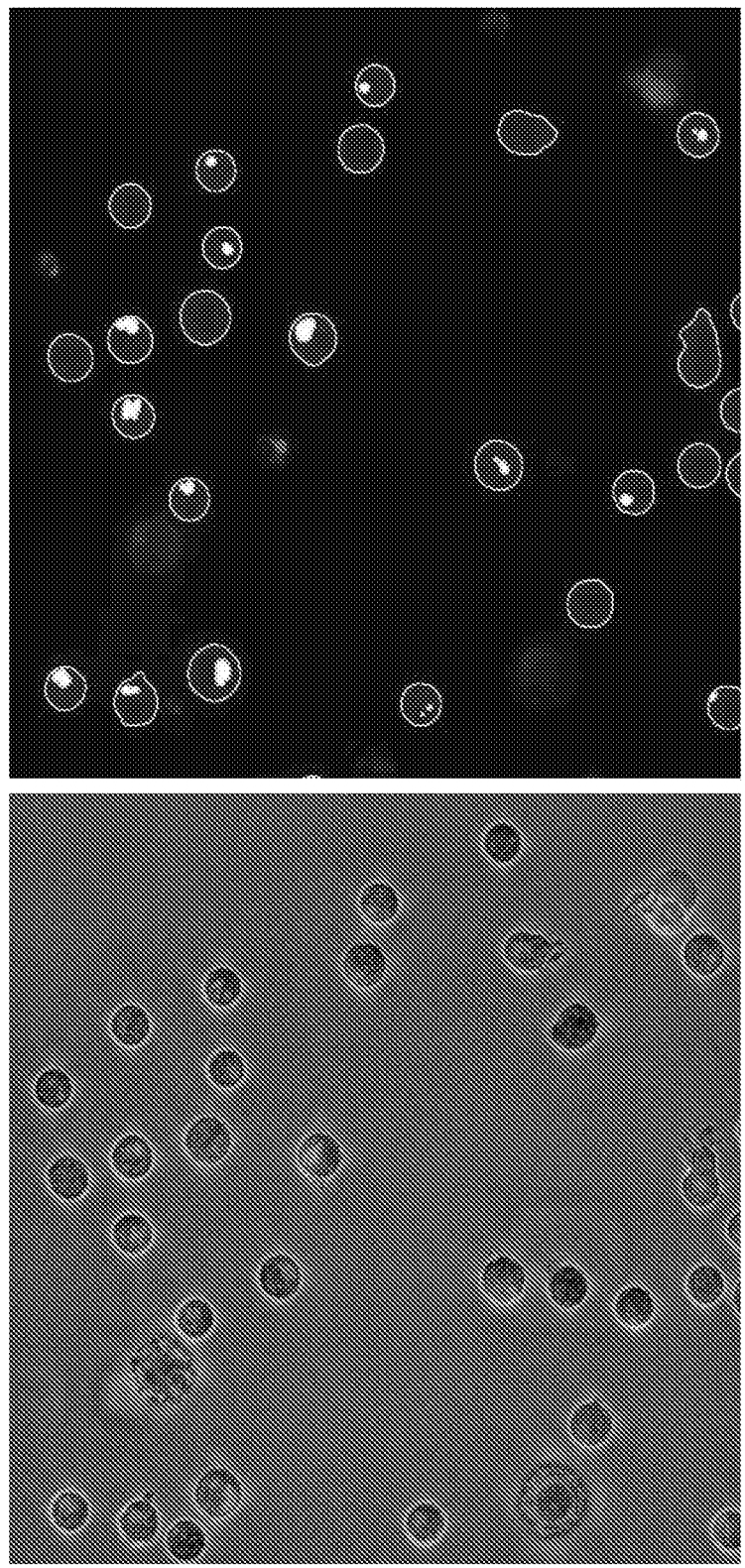
FIG. 32 is a fluorescent micrograph of CD8+ T cells transduced with HPV16 E7 TCR and a truncated EGFR tag (unstained), CD4+ T cells transduced with CER17 (blue), and SCC152 target cells (red) in a 4 h co-culture assay at 40× (left panel). Phagocytosis events were identified by marking for red target events inside blue effector cells. These events were quantified by the hybrid capture software (Keyence BZ-X710) to provide number of phagocytosed targets, total number of effector cells, and area occupied by the phagocytosed target cells in the effector cells (right panel).
Figure 33:
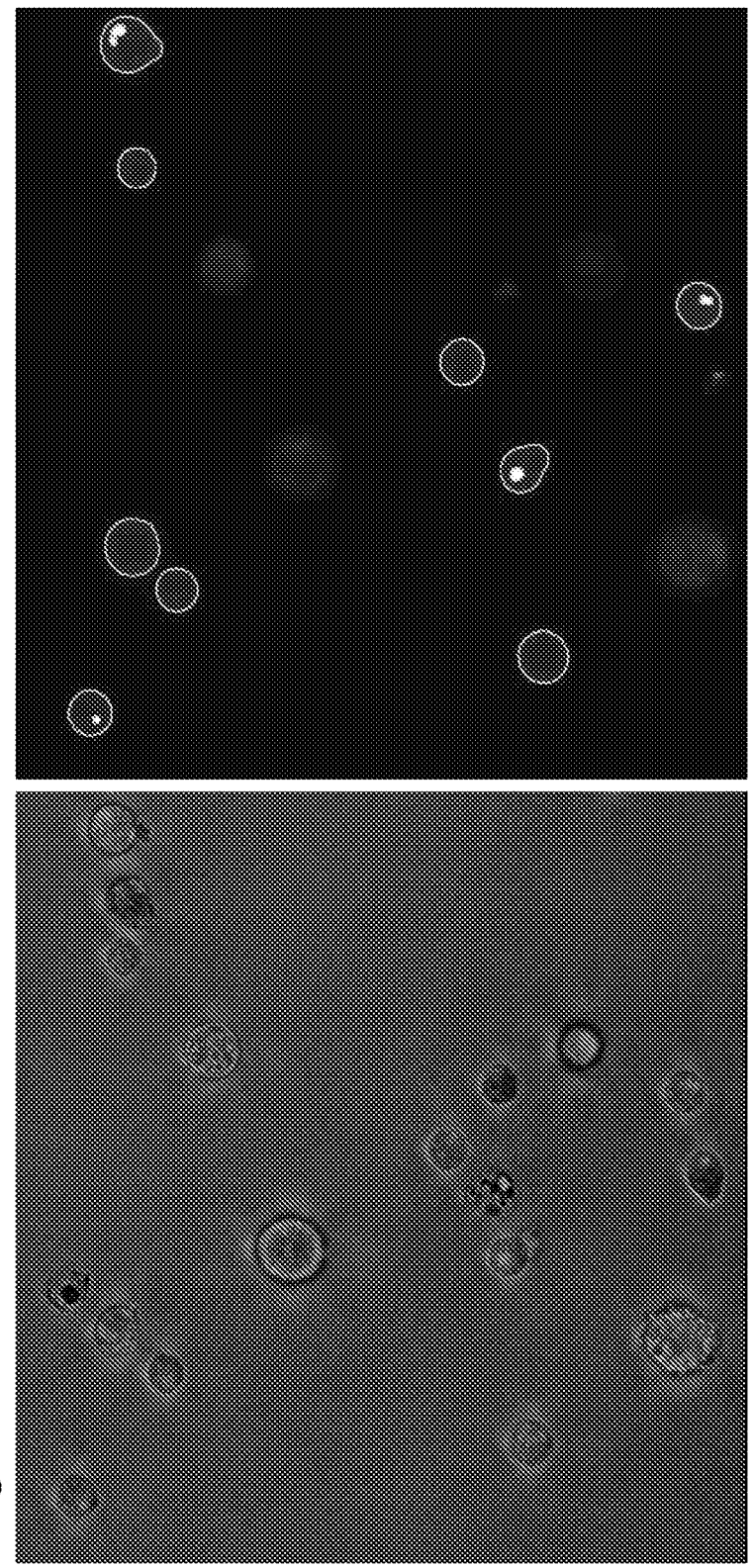
FIG. 33 is a fluorescent micrograph of CD8+ T cells transduced with HPV16 E7 TCR and a truncated EGFR tag (unstained), CD4+ T cells transduced with CER19 (blue), and SCC152 target cells (red) in a 4 h co-culture assay at 40× (left panel). Phagocytosis events were identified by marking for red target events inside blue effector cells. These events were quantified by the hybrid capture software (Keyence BZ-X710) to provide number of phagocytosed targets, total number of effector cells, and area occupied by the phagocytosed target cells in the effector cells (right panel).
Figure 34:
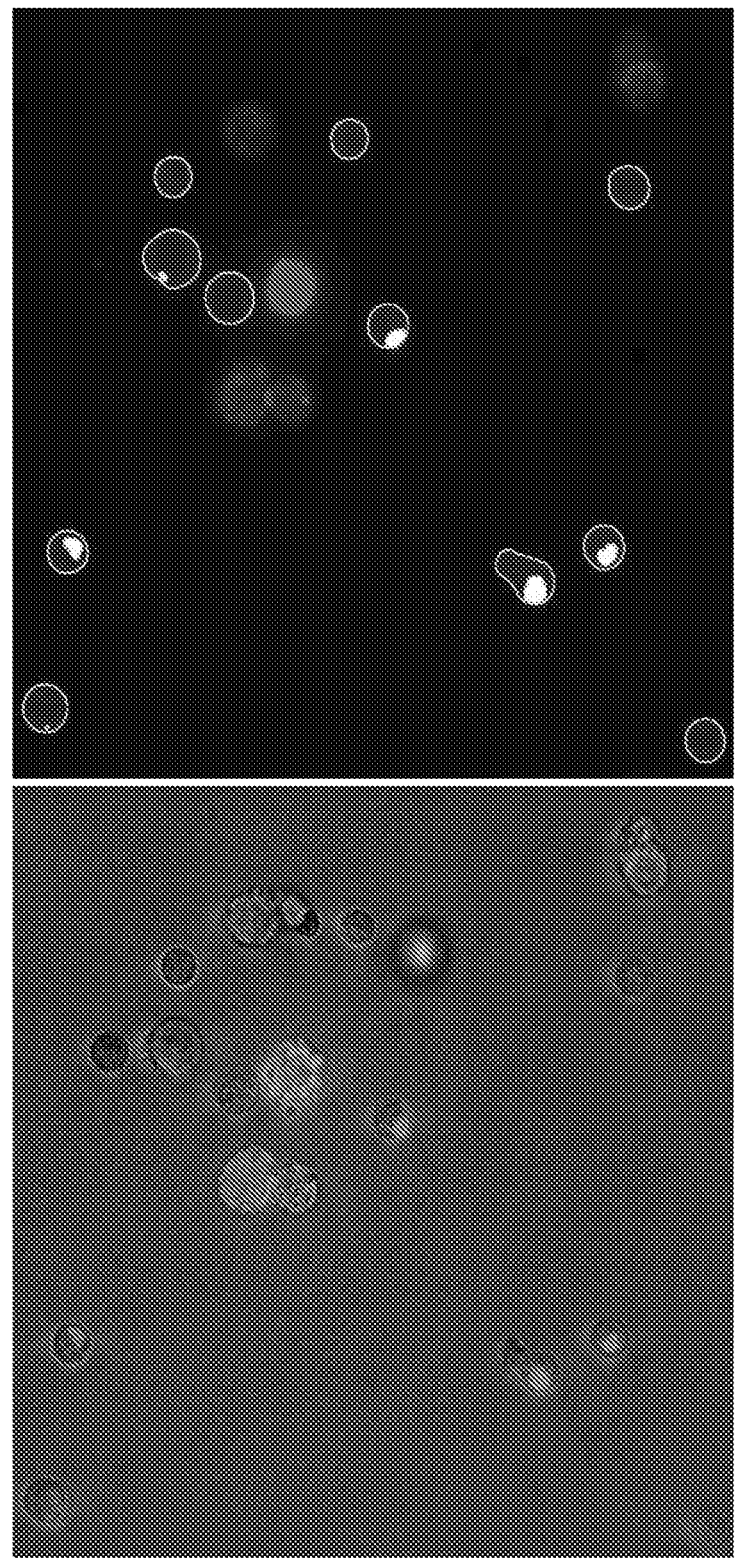
FIG. 34 is a fluorescent micrograph of CD8+ T cells transduced with HPV16 E7 TCR and a truncated EGFR tag (unstained), CD4+ T cells transduced with CER21 (blue), and SCC152 target cells (red) in a 4 h co-culture assay at 40× (left panel). Phagocytosis events were identified by marking for red target events inside blue effector cells. These events were quantified by the hybrid capture software (Keyence BZ-X710) to provide number of phagocytosed targets, total number of effector cells, and area occupied by the phagocytosed target cells in the effector cells (right panel).
Figure 35:
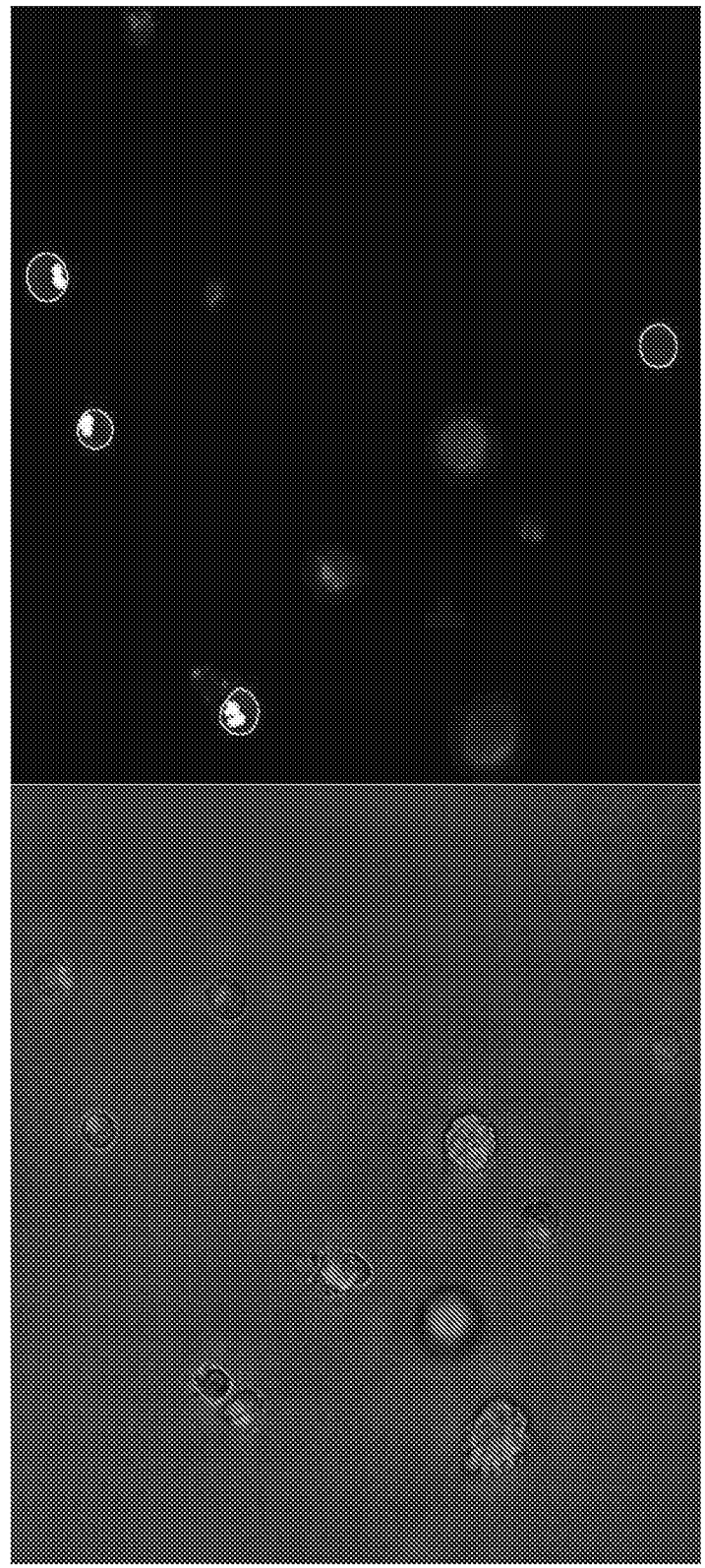
FIG. 35 is a fluorescent micrograph of CD8+ T cells transduced with HPV16 E7 TCR and a truncated EGFR tag (unstained), CD4+ T cells transduced with CER23 (blue), and SCC152 target cells (red) in a 4 h co-culture assay at 40× (left panel). Phagocytosis events were identified by marking for red target events inside blue effector cells. These events were quantified by the hybrid capture software (Keyence BZ-X710) to provide number of phagocytosed targets, total number of effector cells, and area occupied by the phagocytosed target cells in the effector cells (right panel).
Figure 36:
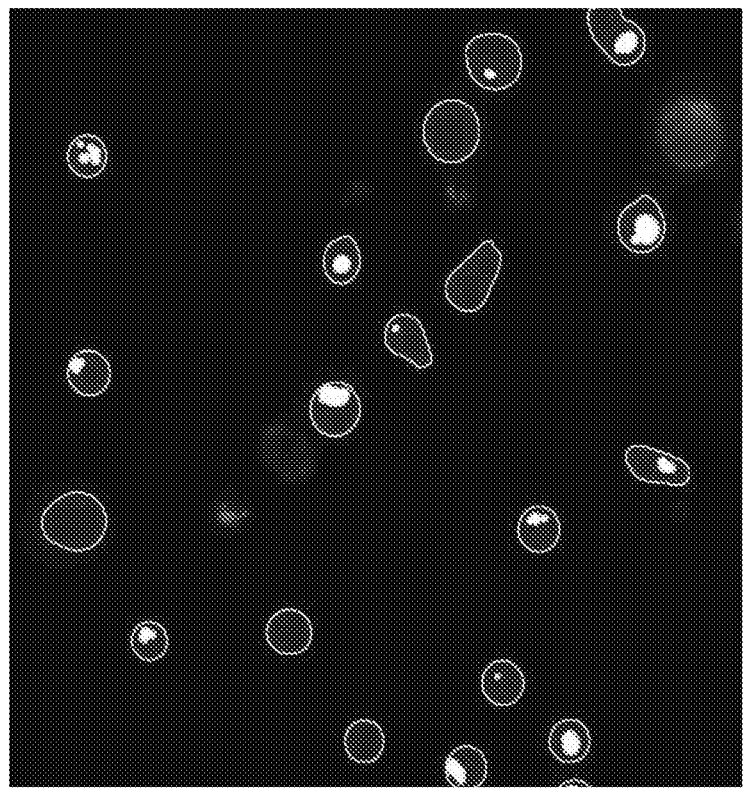
FIG. 36 is a fluorescent micrograph of CD8+ T cells transduced with HPV16 E7 TCR and a truncated EGFR tag (unstained), CD4+ T cells transduced with CER26 (blue), and SCC152 target cells (red) in a 4 h co-culture assay at 40× (left panel). Phagocytosis events were identified by marking for red target events inside blue effector cells. These events were quantified by the hybrid capture software (Keyence BZ-X710) to provide number of phagocytosed targets, total number of effector cells, and area occupied by the phagocytosed target cells in the effector cells (right panel).
Figure 36:
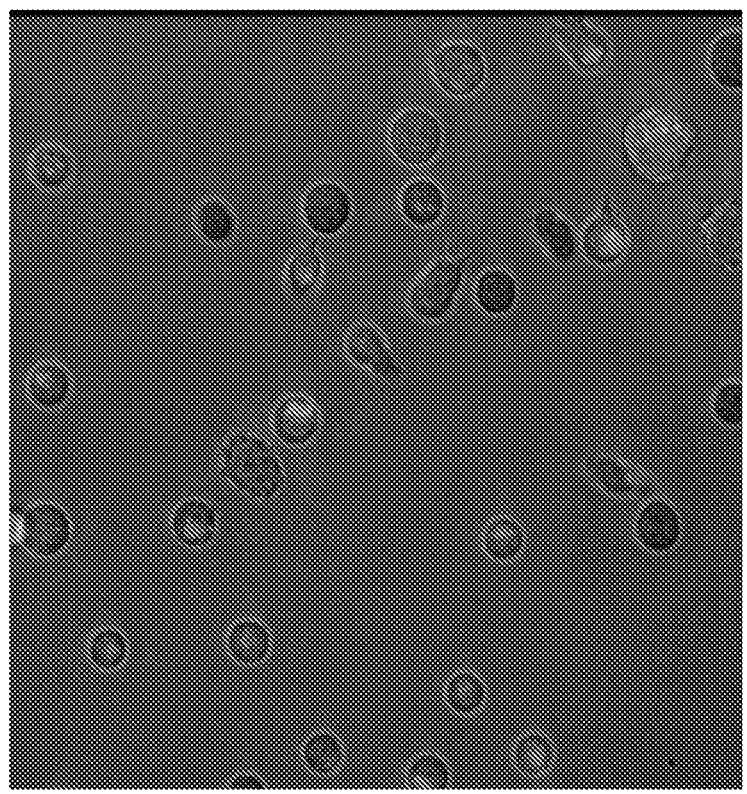
Figure 37:
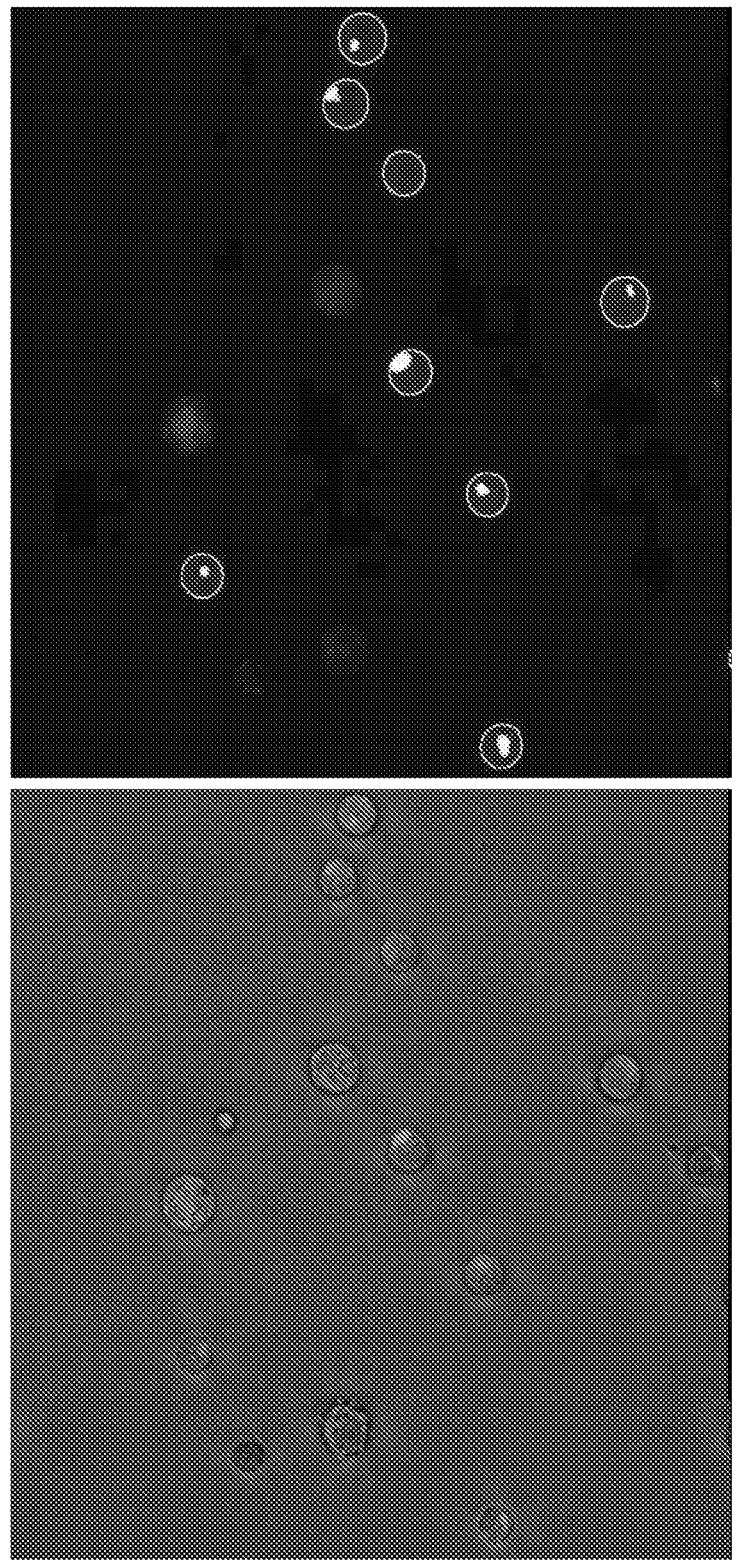
FIG. 37 is a fluorescent micrograph of CD8+ T cells transduced with HPV16 E7 TCR and a truncated EGFR tag (unstained), CD4+ T cells transduced with CER27 (blue), and SCC152 target cells (red) in a 4 h co-culture assay at 40× (left panel). Phagocytosis events were identified by marking for red target events inside blue effector cells. These events were quantified by the hybrid capture software (Keyence BZ-X710) to provide number of phagocytosed targets, total number of effector cells, and area occupied by the phagocytosed target cells in the effector cells (right panel).
Figure 38:
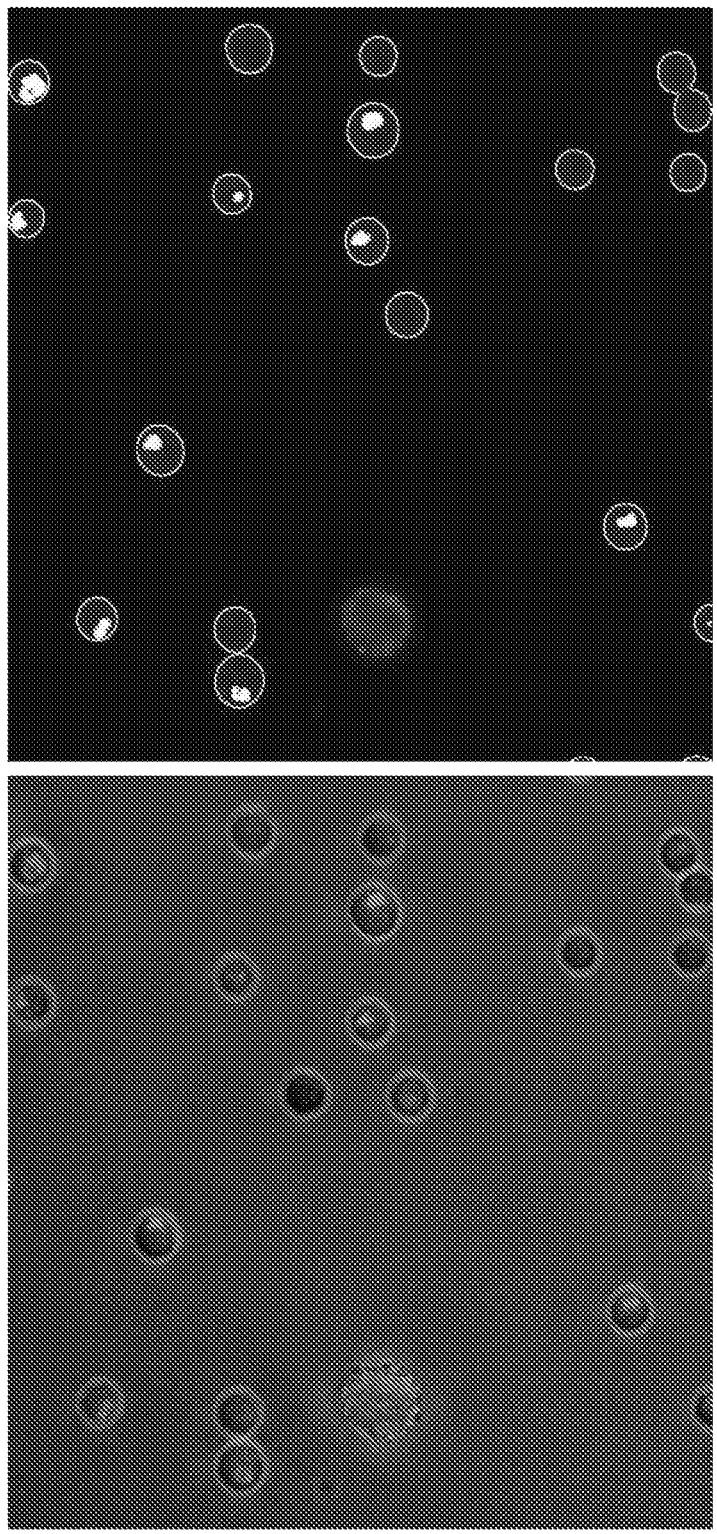
FIG. 38 is a fluorescent micrograph of CD8+ T cells transduced with HPV16 E7 TCR and a truncated EGFR tag (unstained), CD4+ T cells transduced with CER103b (blue), and SCC152 target cells (red) in a 4 h co-culture assay at 40× (left panel). Phagocytosis events were identified by marking for red target events inside blue effector cells. These events were quantified by the hybrid capture software (Keyence BZ-X710) to provide number of phagocytosed targets, total number of effector cells, and area occupied by the phagocytosed target cells in the effector cells (right panel).
Figure 39:
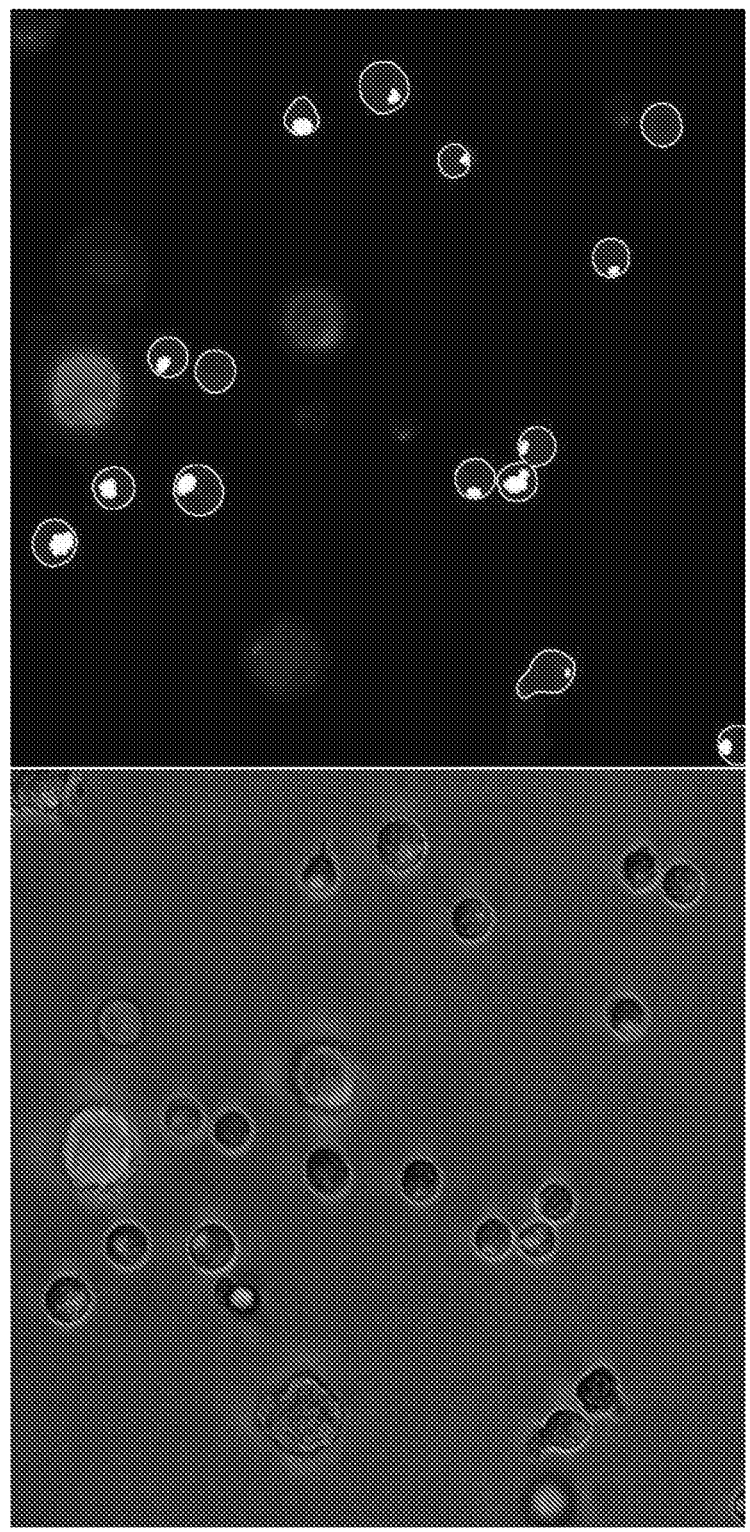
FIG. 39 is a fluorescent micrograph of CD8+ T cells transduced with HPV16 E7 TCR and a truncated EGFR tag (unstained), CD4+ T cells transduced with CER104 (blue), and SCC152 target cells (red) in a 4 h co-culture assay at 40× (left panel). Phagocytosis events were identified by marking for red target events inside blue effector cells. These events were quantified by the hybrid capture software (Keyence BZ-X710) to provide number of phagocytosed targets, total number of effector cells, and area occupied by the phagocytosed target cells in the effector cells (right panel).
Figure 40:
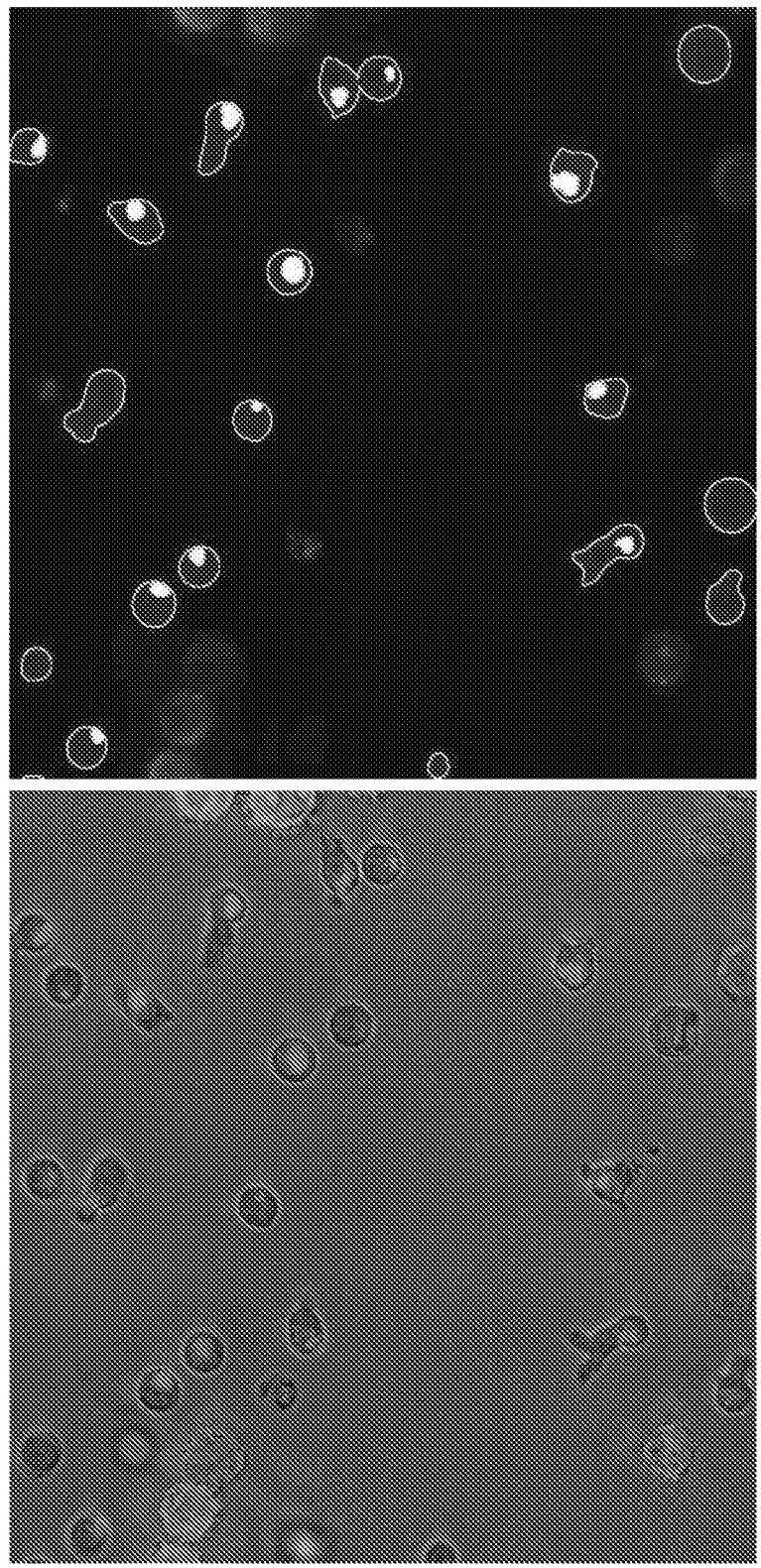
FIG. 40 is a fluorescent micrograph of CD8+ T cells transduced with HPV16 E7 TCR and a truncated EGFR tag (unstained), CD4+ T cells transduced with CER105 (blue), and SCC152 target cells (red) in a 4 h co-culture assay at 40× (left panel). Phagocytosis events were identified by marking for red target events inside blue effector cells. These events were quantified by the hybrid capture software (Keyence BZ-X710) to provide number of phagocytosed targets, total number of effector cells, and area occupied by the phagocytosed target cells in the effector cells (right panel).
Figure 41:
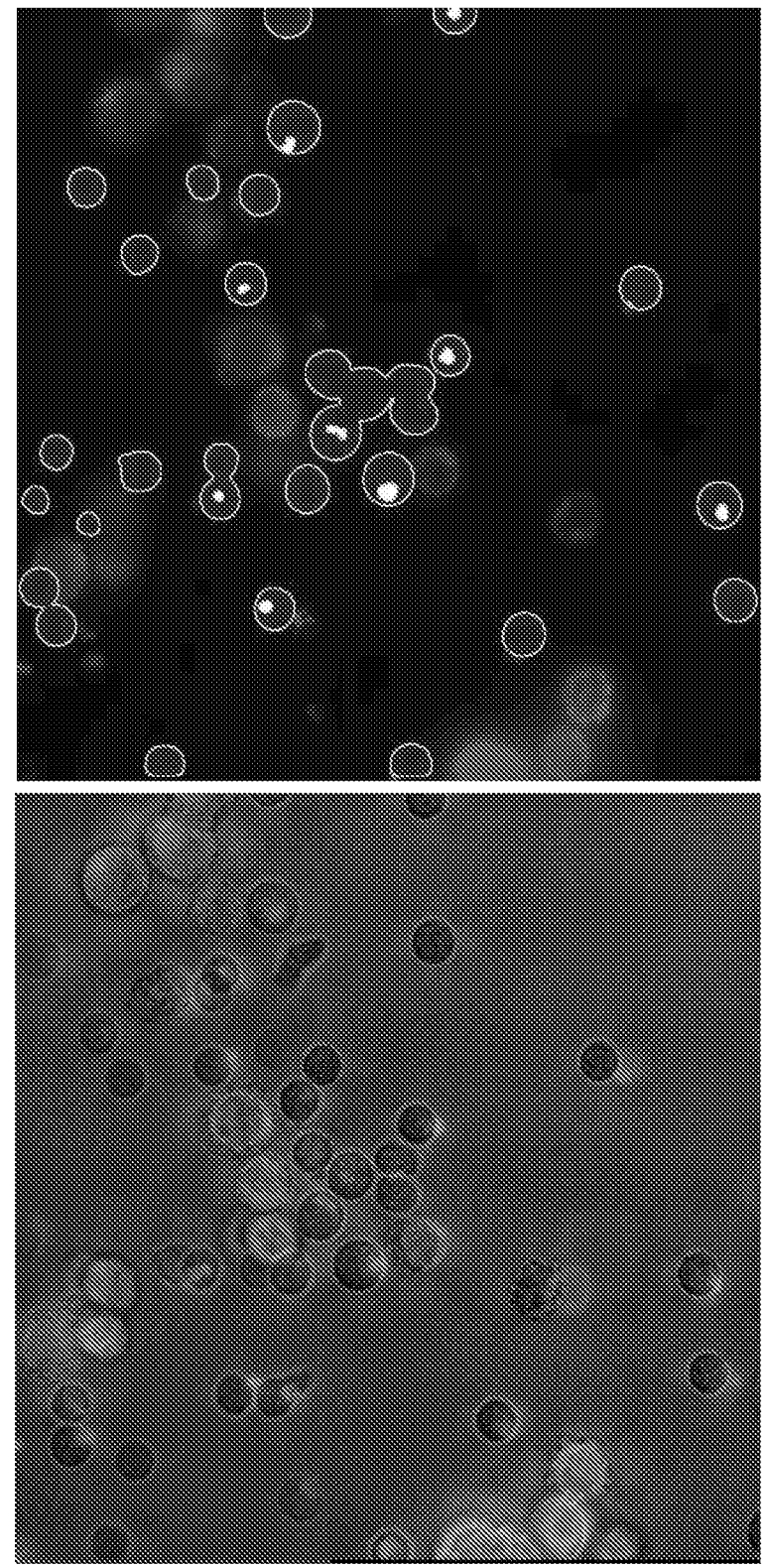
FIG. 41 is a fluorescent micrograph of CD8+ T cells transduced with HPV16 E7 TCR and a truncated EGFR tag (unstained), CD4+ T cells transduced with CER106 (blue), and SCC152 target cells (red) in a 4 h co-culture assay at 40× (left panel). Phagocytosis events were identified by marking for red target events inside blue effector cells. These events were quantified by the hybrid capture software (Keyence BZ-X710) to provide number of phagocytosed targets, total number of effector cells, and area occupied by the phagocytosed target cells in the effector cells (right panel).
Figure 42:
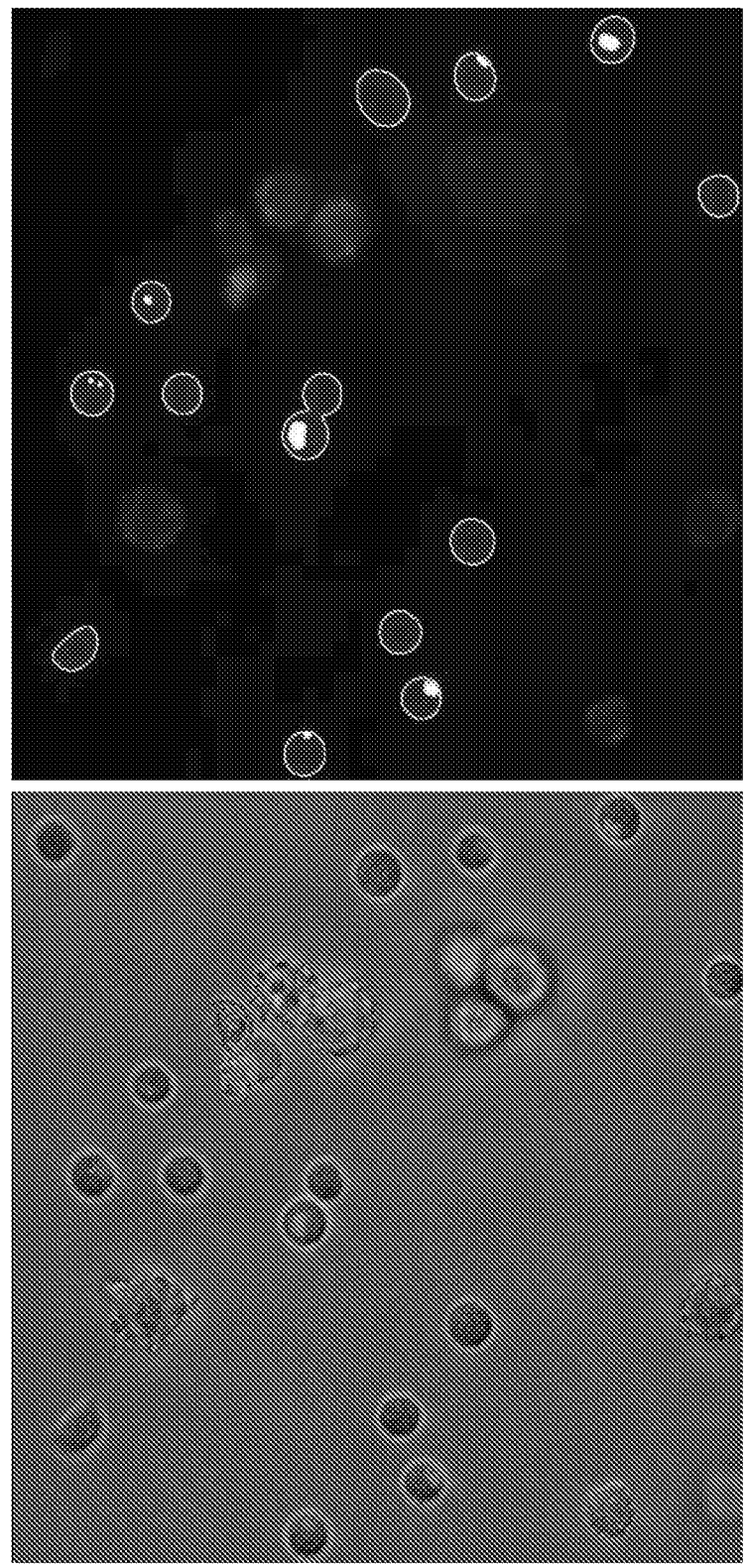
FIG. 42 is a fluorescent micrograph of CD8+ T cells transduced with HPV16 E7 TCR and a truncated EGFR tag (unstained), CD4+ T cells transduced with CER116 (blue), and SCC152 target cells (red) in a 4 h co-culture assay at 40× (left panel). Phagocytosis events were identified by marking for red target events inside blue effector cells. These events were quantified by the hybrid capture software (Keyence BZ-X710) to provide number of phagocytosed targets, total number of effector cells, and area occupied by the phagocytosed target cells in the effector cells (right panel).

Cytokine response of co-culture experiments was measured by sampling the cellular supernatants using a mesoscale multi-array cytokine plate. The following cytokines were measured: IFNγ, IL-2, TNFα, IL-4, IL-6, IL-12b, IL-13, IL-1b, and IL-10. Enhanced cytokine production indicative of activated profile (e.g., IFNγ, IL-2) were elicited in co-cultures with CD4+ T cell/CER+CD8+ T cell/HPV16 E7 TCR combinations compared to controls (see, FIG. 27).

Phagocytic activity of CD4+ T cell/CER+CD8+ T cell/HPV16 E7 TCR combinations co-cultured with SCC152 cells was visualized and quantified using KEYENCE BZ-X710 fluorescence microscope, 20× objective and hybrid capture software. FIGS. 28-42 show that CD4+ T cells transduced with various CERs used in co-culture with CD8+ T cells/HPV E7 TCR exhibited enhanced engulfment of SCC152 target cells over co-culture with control CD8+ T cell/HPV16 E7 TCR alone.

Figure 43:
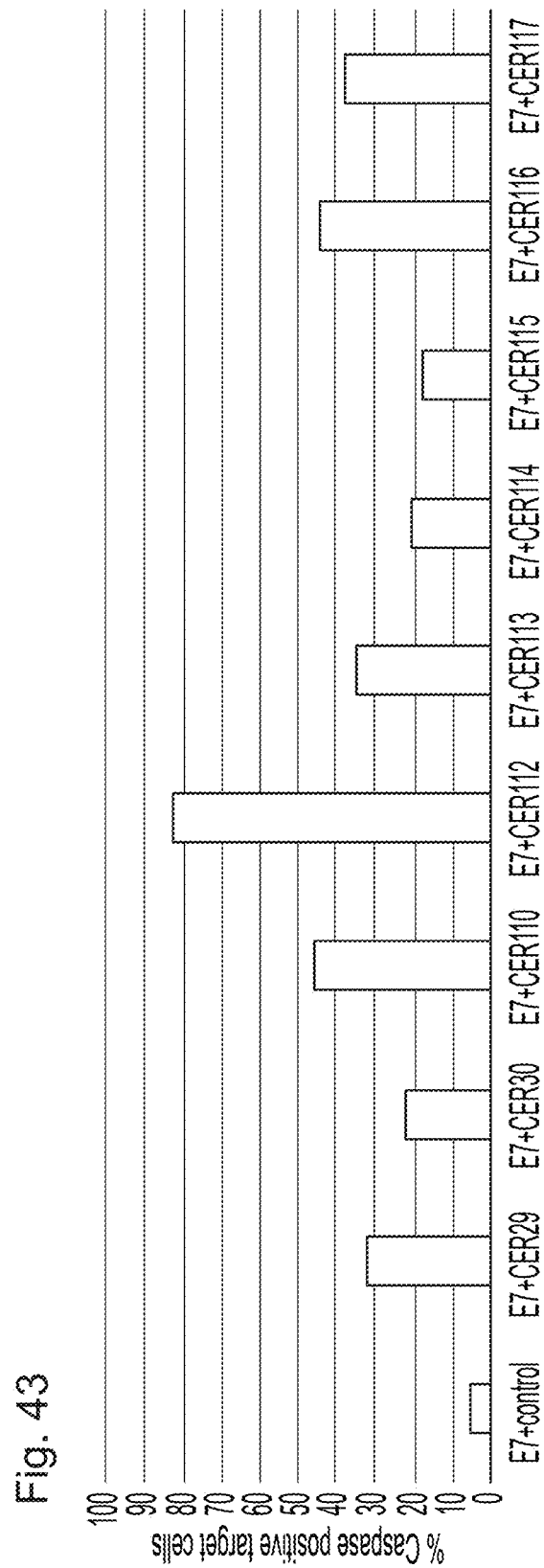
FIG. 43 is a bar graph showing that combination of CD4+ T cells transduced with various CERs containing TRAF signaling domains with CD8+ T cells transduced with HPV16 E7 TCR enhances cytolysis of target SCC152 cells as measured by caspase induction compared to administration of the HPV16 E7 TCR alone. Human primary CD8+ cells transduced with a HPV16 E7 TCR were co-cultured alone with SCC152 cells or in combination with CD4+ T cells transduced with a selected CER of the present disclosure (from left to right: control, CER29, CER30, CER110, CER112, CER113, CER114, CER115, CER116, or CER117) at a 1:1 ratio (CD4:CD8). The number of caspase positive SCC152 target cells in the co-culture assay was measured by quantifying the intensity of red fluorescence from a caspase 3/7 apoptosis reagent that couples the activated caspase 3/7 recognition motif with a red reagent that fluoresces upon cleavage. The caspase 3/7 apoptosis reagent was added to the co-culture assay after 6 hours, and fluorescence was detected using BZ-X710 Keyence microscope and using hybrid capture software. Target SCC152 cells were transduced with green fluorescent protein (GFP) for visualization. The Y-axis represents (# of caspase events/# of GFP target SCC152 cells)*100.
Figure 44:
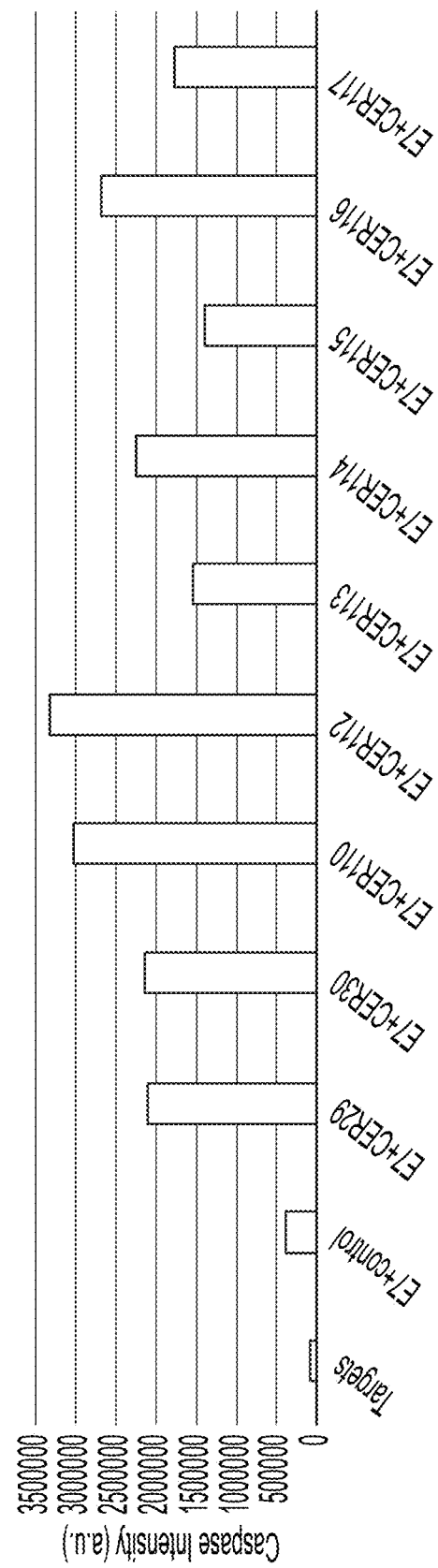
FIG. 44 is a bar graph showing that combination of CD4+ T cells transduced with various CERs containing TRAF signaling domains with CD8+ T cells transduced with HPV16 E7 TCR enhances cytolysis of target SCC152 cells as measured by caspase induction compared to administration of the HPV16 E7 TCR alone. Human primary CD8+ cells transduced with a HPV16 E7 TCR were co-cultured alone with SCC152 cells or in combination with CD4+ T cells transduced with various CERs of the present disclosure (from left to right: control, CER29, CER30, CER110, CER112, CER113, CER114, CER115, CER116, or CER117) at a 1:1 ratio (CD4:CD8). The number of caspase positive SCC152 target cells in the co-culture assay was measured by quantifying the intensity of red fluorescence from a caspase 3/7 apoptosis reagent that couples the activated caspase 3/7 recognition motif with a red reagent that fluoresces upon cleavage. The caspase 3/7 apoptosis reagent was added to the co-culture assay after 6 hours, and fluorescence was detected using BZ-X710 Keyence microscope and using hybrid capture software. The Y-axis represents the intensity of caspase reagent in arbitrary units (a.u.).
Figure 45:
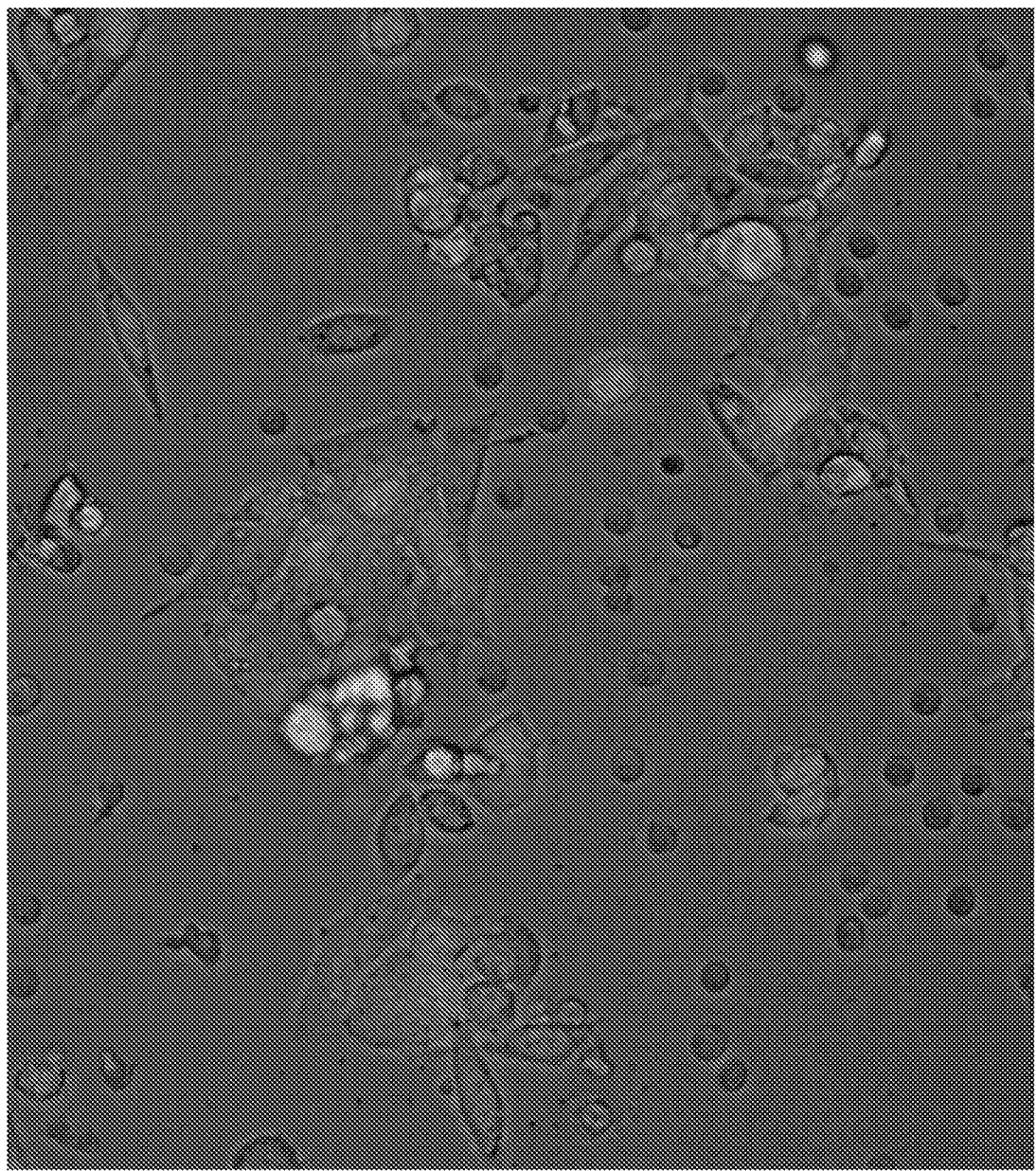
FIG. 45 is a fluorescence micrograph of a co-culture assay containing CD8+ T cells transduced with HPV16 E7 TCR and CD4+ T cells transduced control (blue) at a 1:1 ratio (CD8:CD4) with head and neck squamous cancer SCC152 cells (green). The red signals are fluorescent signals from a caspase reagent that was added to the co-culture assay after 6 hours.
Figure 46:
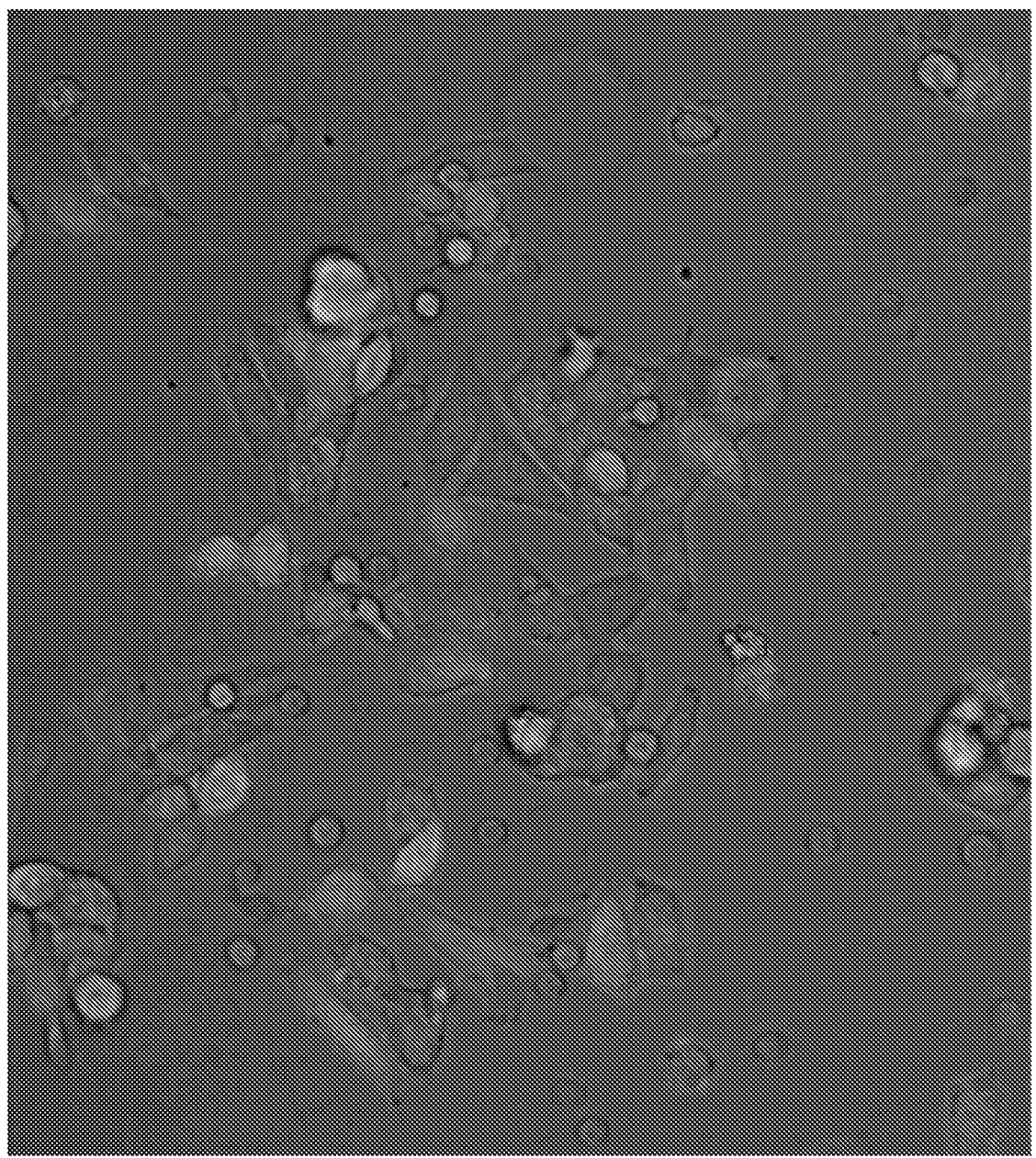
FIG. 46 is a fluorescence micrograph of a co-culture assay containing CD8+ T cells transduced with HPV16 E7 TCR and CD4+ T cells transduced with CER29 (blue) at a 1:1 ratio with head and neck squamous cancer SCC152 cells (green). The red signals are fluorescent signals from a caspase reagent that was added to the co-culture assay after 6 hours.
Figure 47:
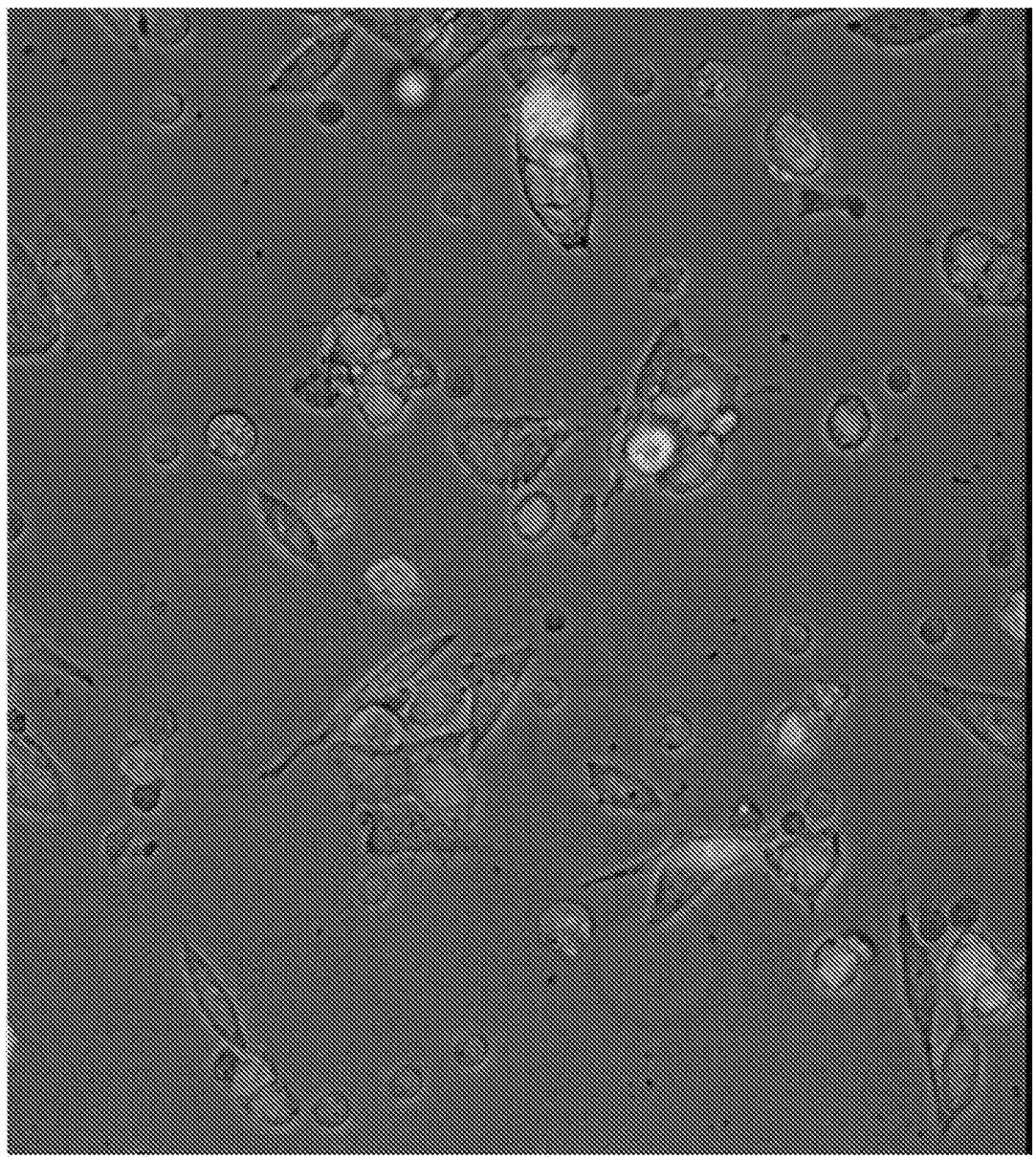
FIG. 47 is a fluorescence micrograph of a co-culture assay containing CD8+ T cells transduced with HPV16 E7 TCR and CD4+ T cells transduced with CER30 (blue) at a 1:1 ratio with head and neck squamous cancer SCC152 cells (green). The red signals are fluorescent signals from a caspase reagent that was added to the co-culture assay after 6 hours.
Figure 48:
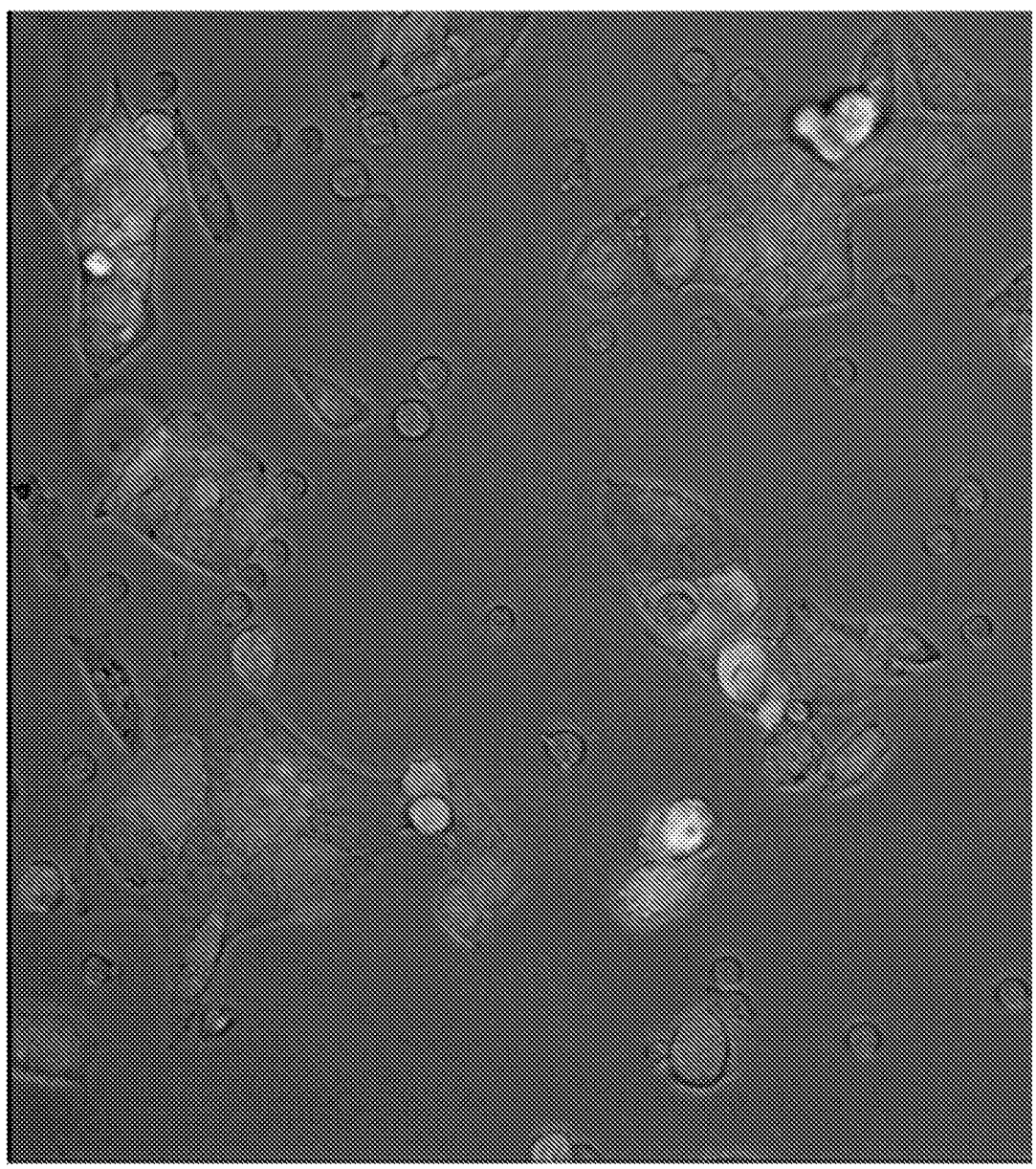
FIG. 48 is a fluorescence micrograph of a co-culture assay containing CD8+ T cells transduced with HPV16 E7 TCR and CD4+ T cells transduced with CER110 (blue) at a 1:1 ratio with head and neck squamous cancer SCC152 cells (green). The red signals are fluorescent signals from a caspase reagent that was added to the co-culture assay after 6 hours.
Figure 49:
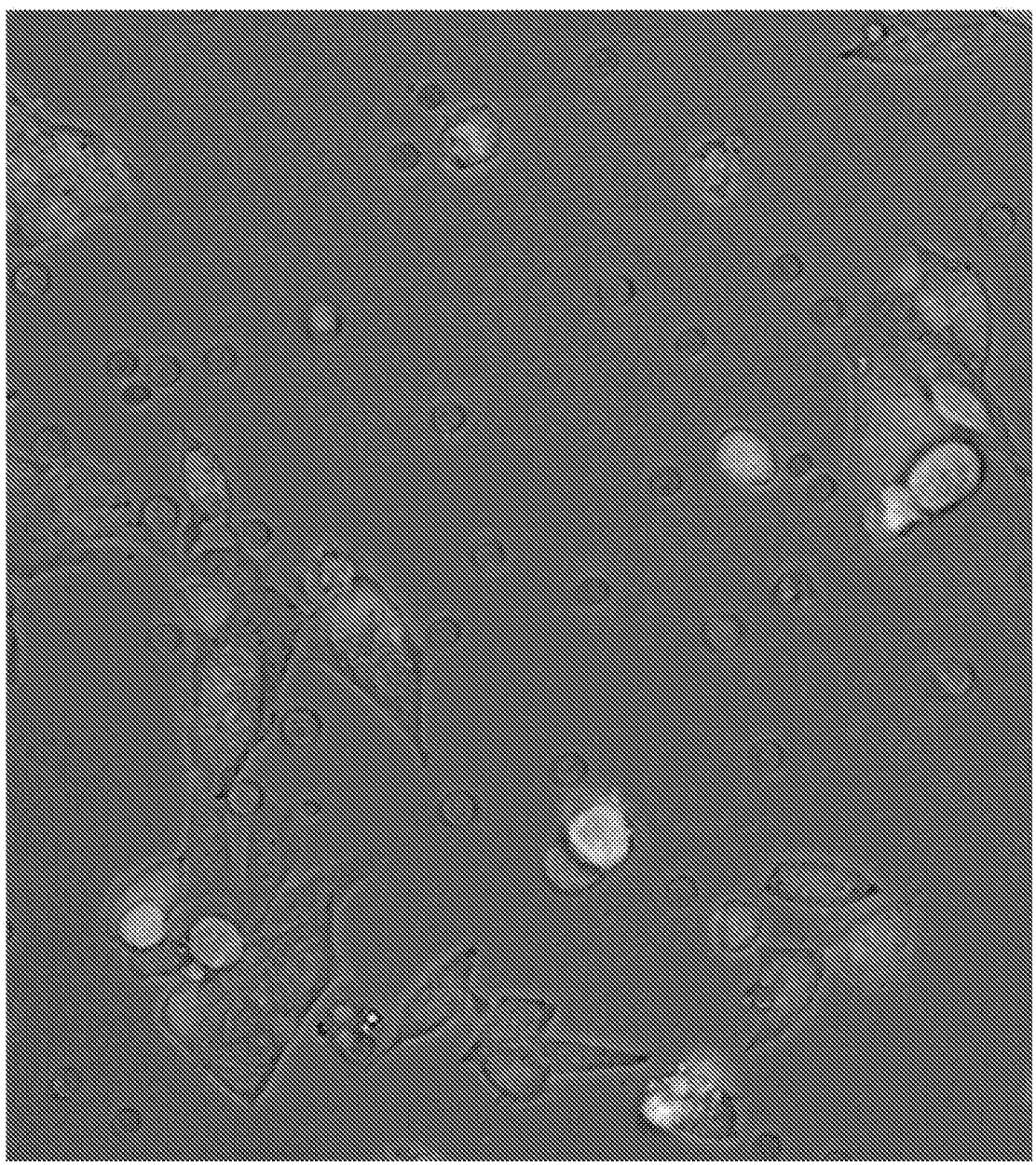
FIG. 49 is a fluorescence micrograph of a co-culture assay containing CD8+ T cells transduced with HPV16 E7 TCR and CD4+ T cells transduced with CER112 (blue) at a 1:1 ratio with head and neck squamous cancer SCC152 cells (green). The red signals are fluorescent signals from a caspase reagent that was added to the co-culture assay after 6 hours.
Figure 50:
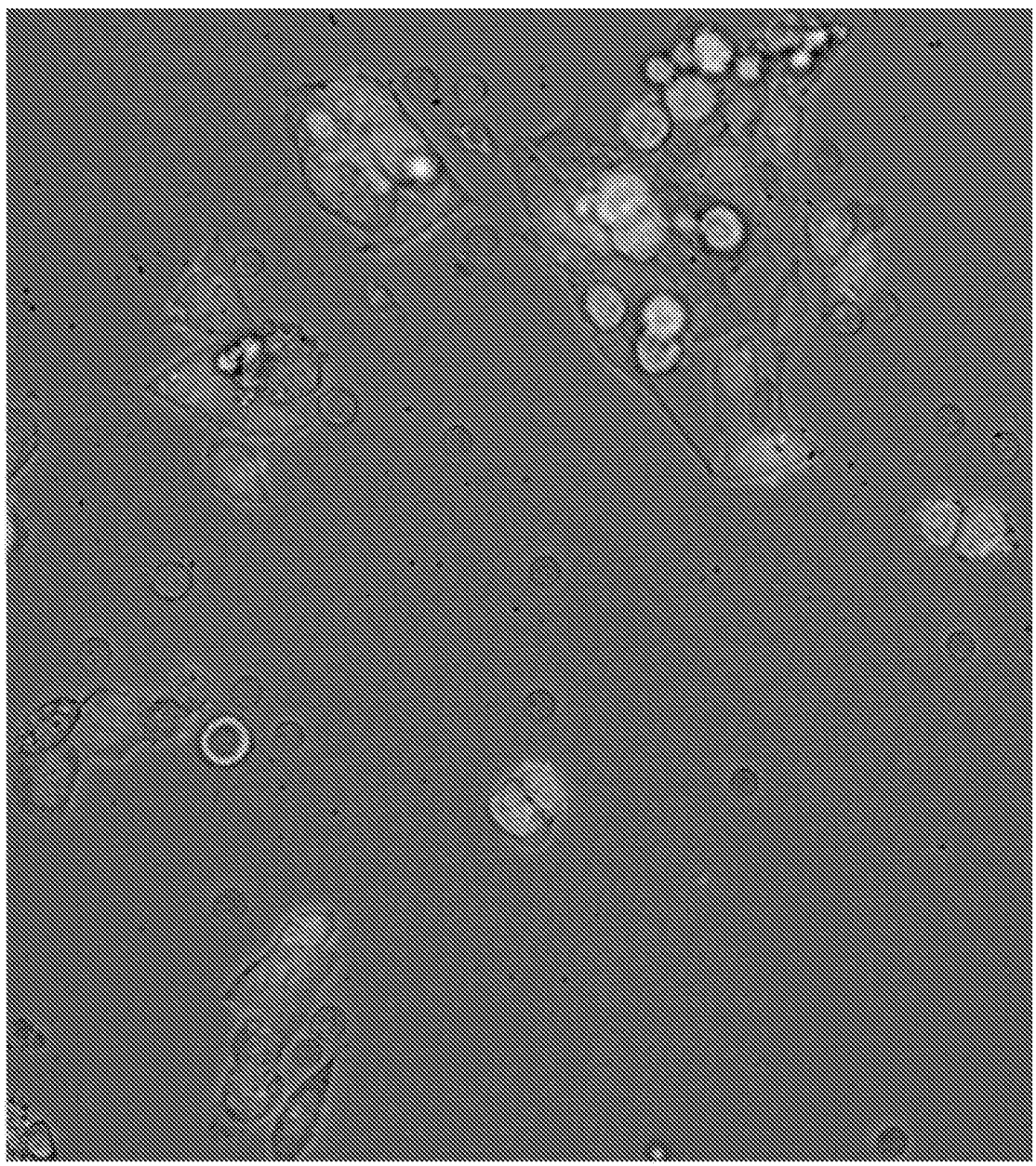
FIG. 50 is a fluorescence micrograph of a co-culture assay containing CD8+ T cells transduced with HPV16 E7 TCR and CD4+ T cells transduced with CER113 (blue) at a 1:1 ratio with head and neck squamous cancer SCC152 cells (green). The red signals are fluorescent signals from a caspase reagent that was added to the co-culture assay after 6 hours.
Figure 51:
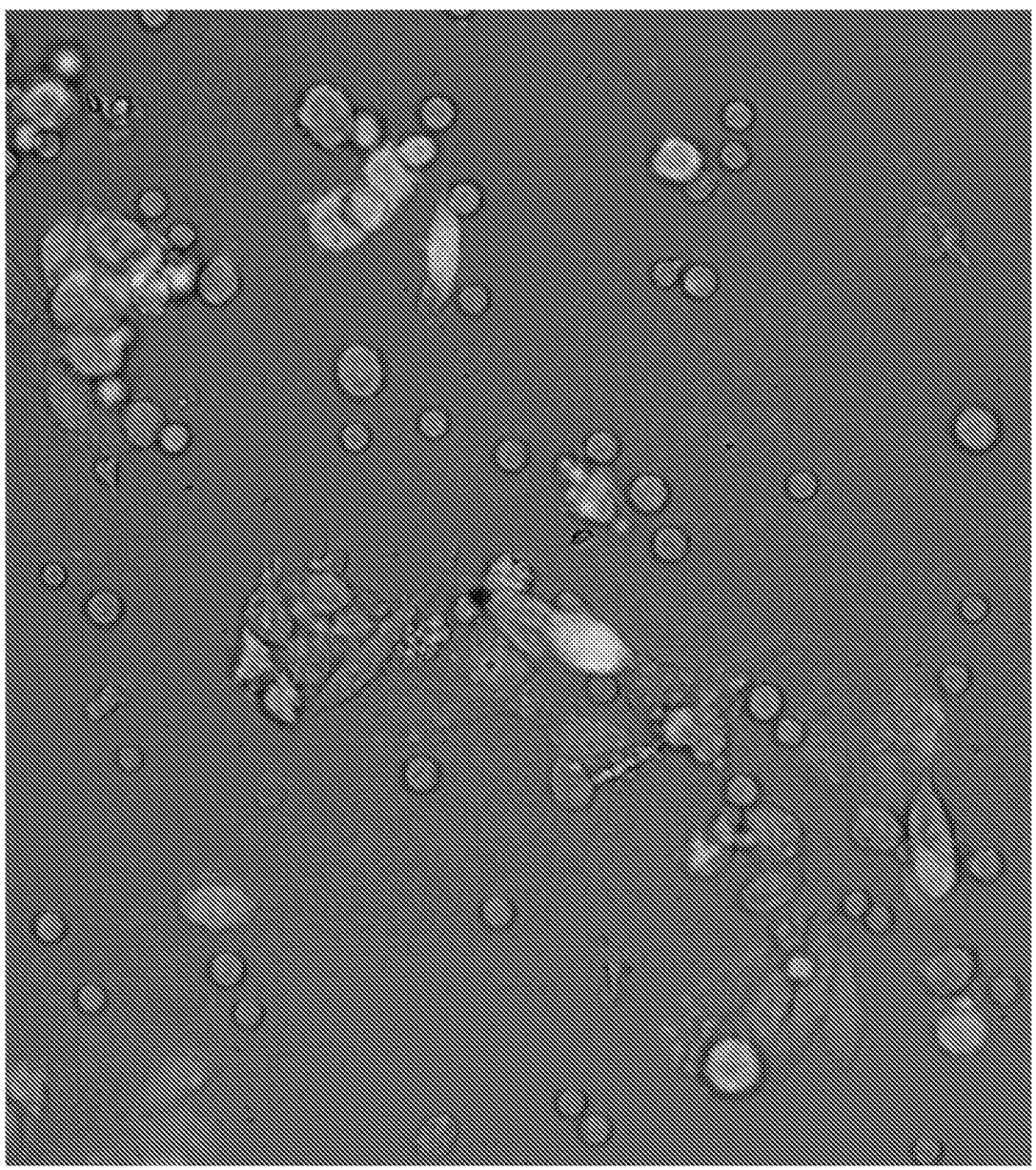
FIG. 51 is a fluorescence micrograph of a co-culture assay containing CD8+ T cells transduced with HPV16 E7 TCR and CD4+ T cells transduced with CER114 (blue) at a 1:1 ratio with head and neck squamous cancer SCC152 cells (green). The red signals are fluorescent signals from a caspase reagent that was added to the co-culture assay after 6 hours.
Figure 52:
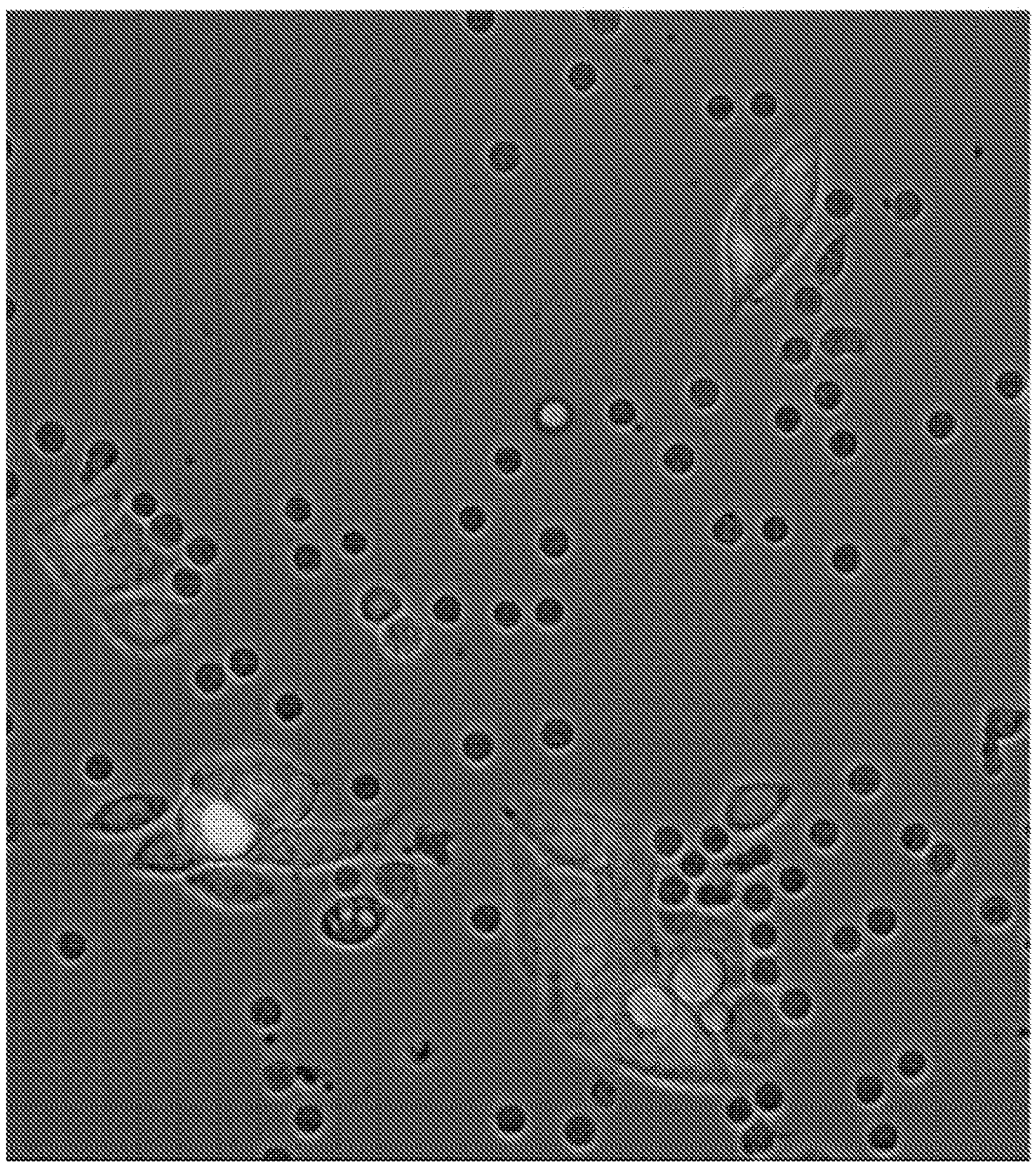
FIG. 52 is a fluorescence micrograph of a co-culture assay containing CD8+ T cells transduced with HPV16 E7 TCR and CD4+ T cells transduced with CER115 (blue) at a 1:1 ratio with head and neck squamous cancer SCC152 cells (green). The red signals are fluorescent signals from a caspase reagent that was added to the co-culture assay after 6 hours.
Figure 53:
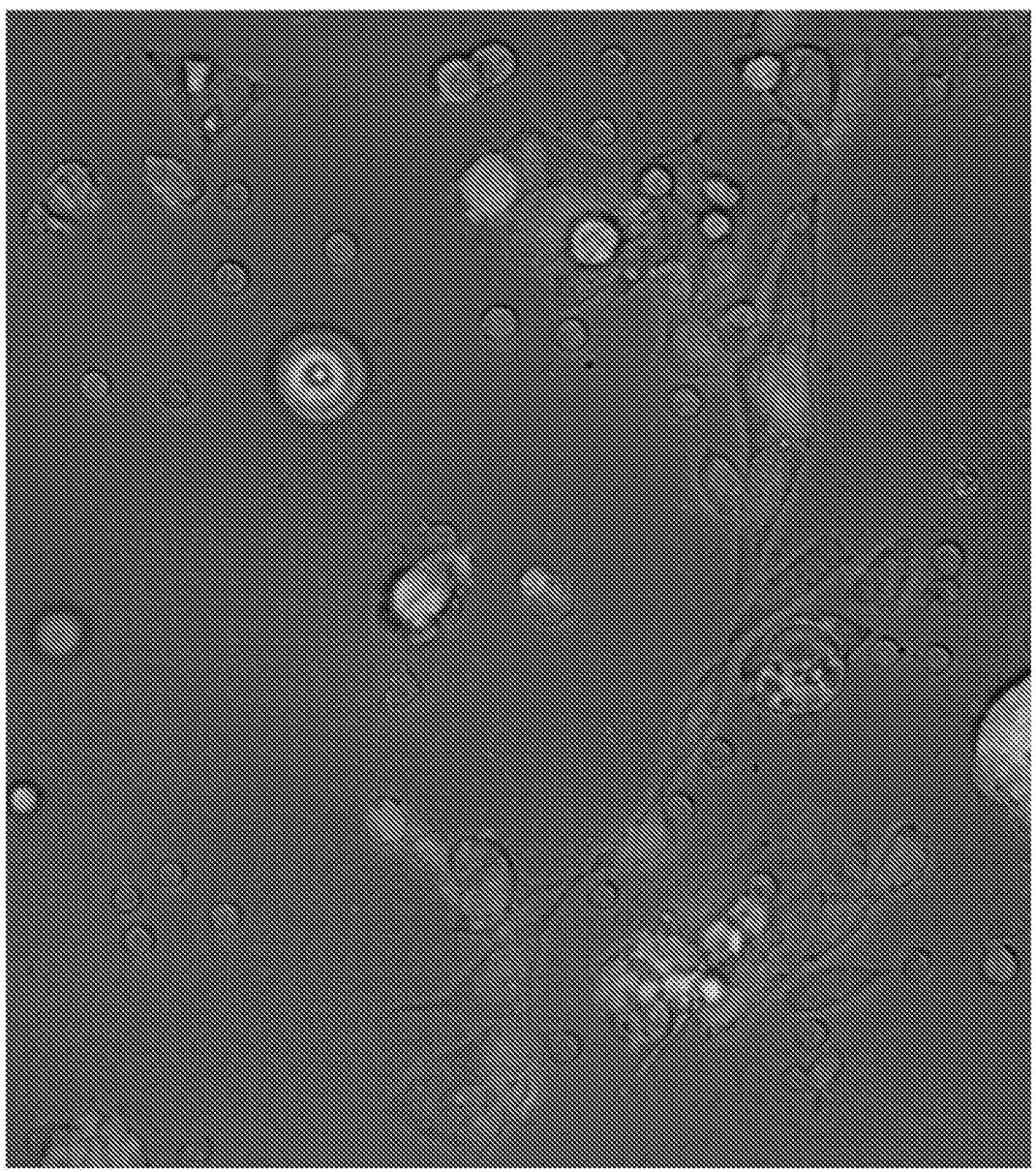
FIG. 53 is a fluorescence micrograph of a co-culture assay containing CD8+ T cells transduced with HPV16 E7 TCR and CD4+ T cells transduced with CER116 (blue) at a 1:1 ratio with head and neck squamous cancer SCC152 cells (green). The red signals are fluorescent signals from a caspase reagent that was added to the co-culture assay after 6 hours.
Figure 54:
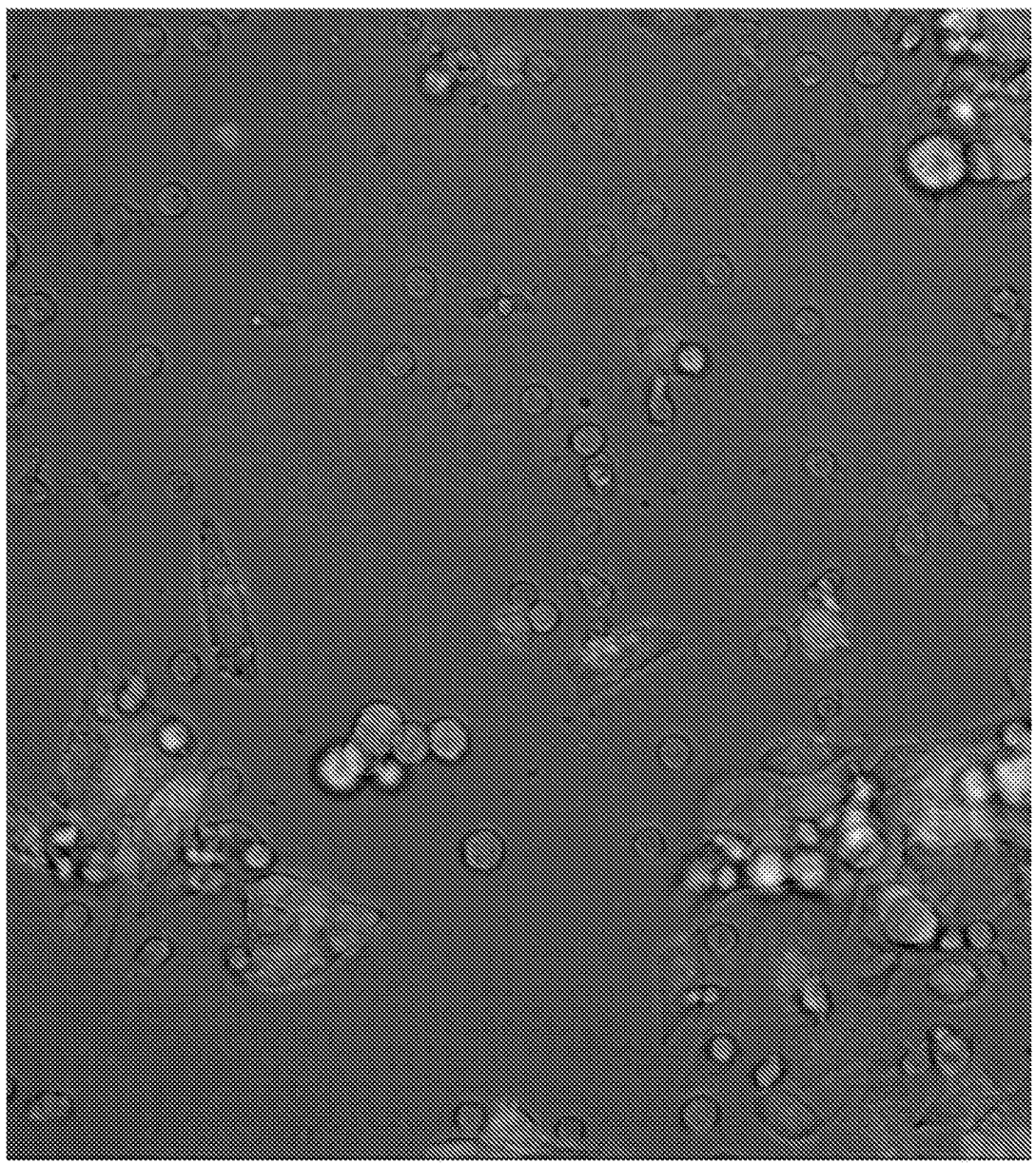
FIG. 54 is a fluorescence micrograph of a co-culture assay containing CD8+ T cells transduced with HPV16 E7 TCR and CD4+ T cells transduced with CER117 (blue) at a 1:1 ratio with head and neck squamous cancer SCC152 cells (green). The red signals are fluorescent signals from a caspase reagent that was added to the co-culture assay after 6 hours.

Compositions comprising CD8+ T cells transduced with HPV E7 TCR and CD4+ T cells transduced with a selected CER containing a TRAF signaling domain were also tested for cytolytic and phagocytic activity. HPV16 E7 TCR transduced CD8+ T cells and selected CER (CER29, CER30, CER110, CER112, CER113, CER114, CER115, CER116, or CER117) transduced CD4+ T cells were mixed at a 1:1 ratio and co-cultured with HPV16 E7+ head and neck squamous cell carcinoma cells (SCC152) at a 1:1 ratio, and caspase 3/7 apoptosis reagent was added to the co-culture after 6 hours. Cytotoxic activity was measured over time by measuring fluorescence. Control samples were CD8+ T cells transduced with HPV16 E7 TCR+CD4+ T cells transduced with control. As shown in the bar graphs of FIGS. 43 and 44 and fluorescent micrographs of FIGS. 45-54, addition of CD4+ T cells transduced with all of the CERs tested to CD8+ T cells transduced with the HPV16 E7 TCR enhanced cytolytic activity.

Figure 55:
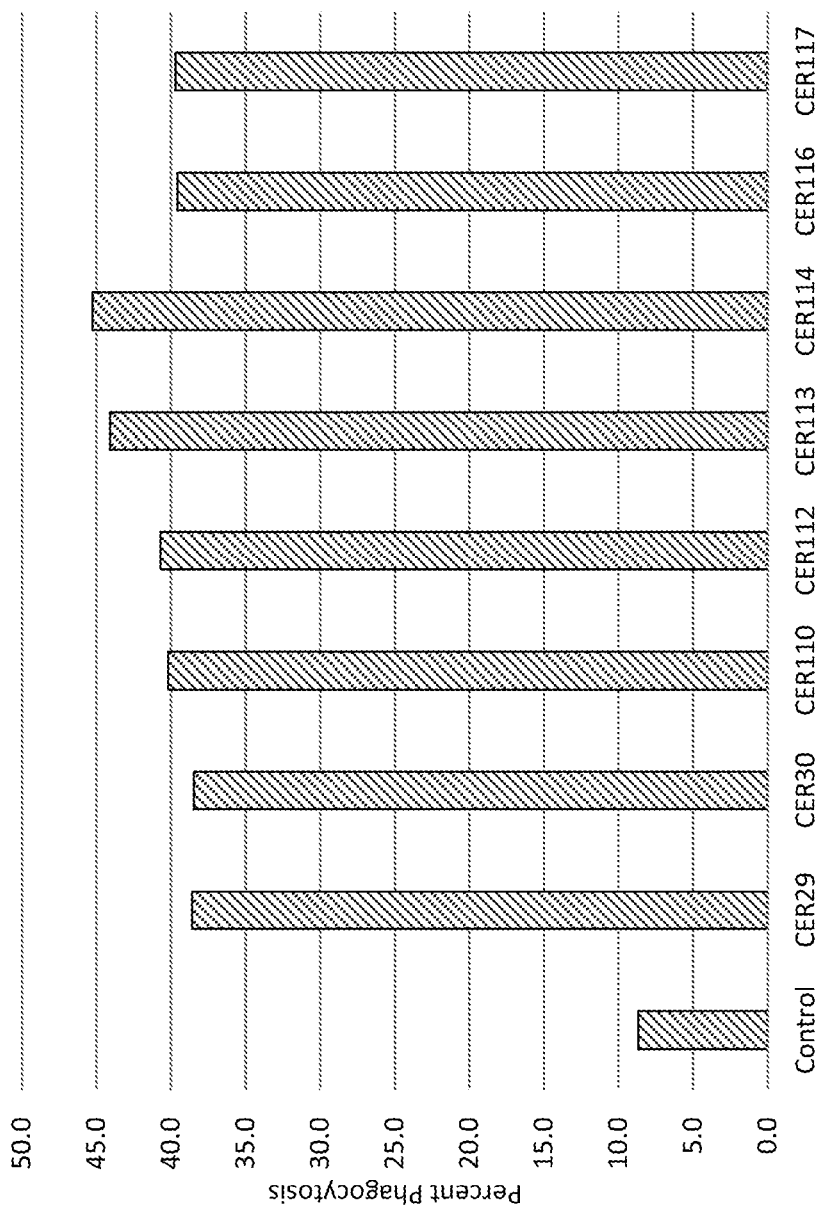
FIG. 55 is a bar graph representing quantification of CD4+ T cell-CER mediated phagocytosis of SCC152 target cells. Percent phagocytosis was calculated as ((number of phagocytic target events)/(total number of effector cells))*100. These numbers were calculated from 3×3 images captured by Keyence BZ-X710 fluorescence microscope at 40× resolution, 4 hours after initiation of co-culture assay. CD8+ T cells transduced with HPV16 E7 TCR and CD4+ T cells transduced with a selected CER (CER29, CER30, CER110, CER112, CER113, CER114, CER116, or CER117) were co-cultured with SCC152 target cells at a 1:1:0.5 ratio (CD8:CD4:target cell) for 4 hours and imaged.
Figure 56:
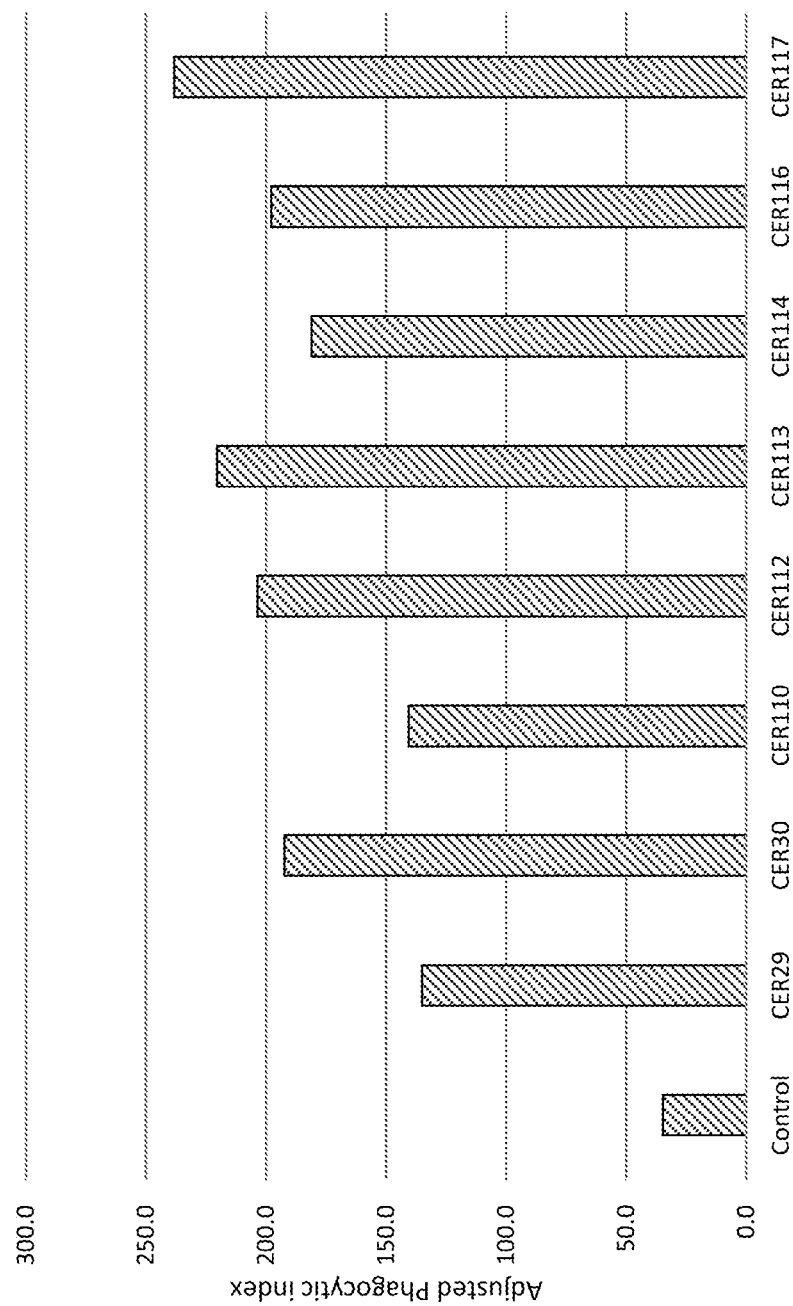
FIG. 56 is a bar graph representing quantification of CD4+ T cell-CER mediated phagocytosis of SCC152 target cells. Adjusted phagocytic index was calculated as (median area ratio of target events in effector cells*% phagocytosis). These numbers were calculated from 3×3 images captured by Keyence BZ-X710 fluorescence microscope at 40× resolution, 4 hours after initiation of co-culture assay. CD8+ T cells transduced with HPV16 E7 TCR and CD4+ T cells transduced with a selected CER (CER29, CER30, CER110, CER112, CER113, CER114, CER116, or CER117) were co-cultured with SCC152 target cells at a 1:1:0.5 ratio (CD8:CD4:target cell) for 4 hours and imaged.

Phagocytic activity of CD4+ T cell/CER+CD8+ T cell/HPV16 E7 TCR combinations co-cultured with SCC152 cells was visualized and quantified using KEYENCE BZ-X710 fluorescence microscope, 20× objective and hybrid capture software. CD4+ T cell/control+CD8+ T cell/HPV16 E7 TCR was used a control The bar graphs of FIGS. 55 and 56 show that CD4+ T cells transduced with all of the CERs tested (CER29, CER30, CER110, CER112, CER113, CER114, CER116, or CER117) used in co-culture with CD8 T cells/HPV E7 TCR enhanced engulfment of SCC152 target cells over the control.

Figure 57:
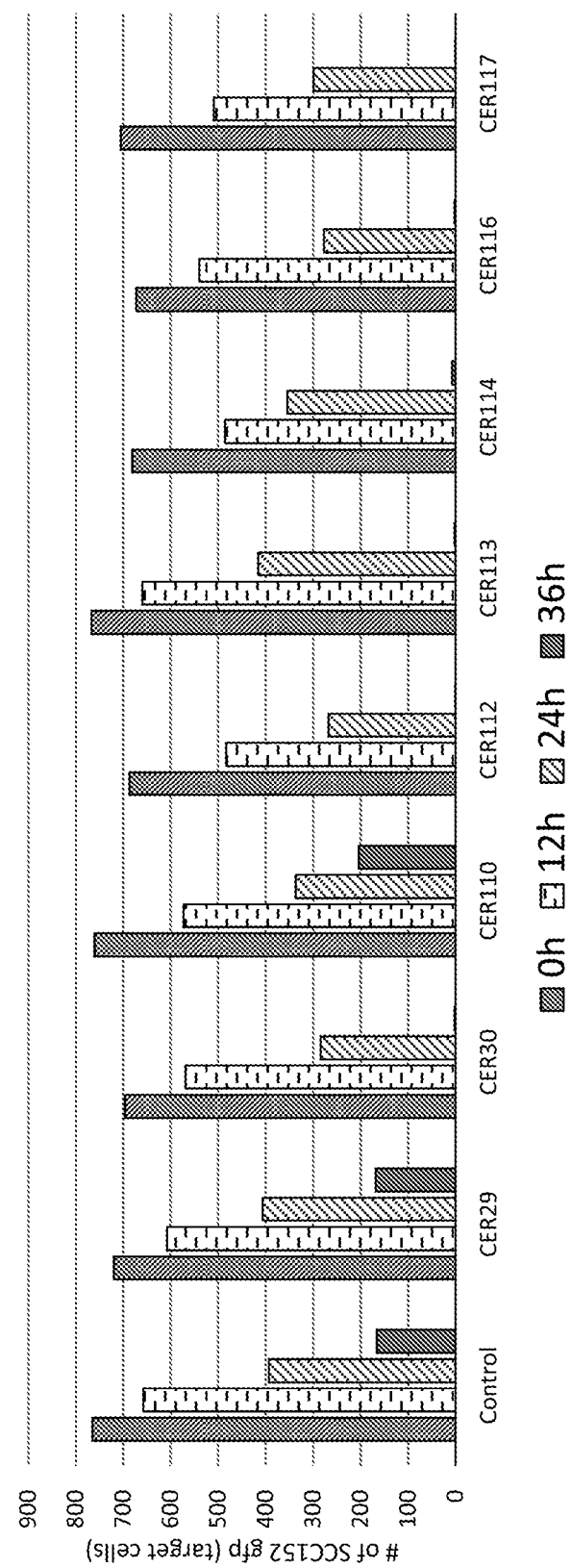
FIG. 57 is a bar graph showing quantification of loss of SCC152 HPV16+ target cells over time during co-culture assays. SCC152 cells were transduced with green fluorescent protein (GFP) and co-cultured with CD8+ T cells transduced with HPV16 E7 TCR and CD4+ T cells transduced with a selected CER (CER29, CER30, CER110, CER112, CER113, CER114, CER116, or CER117) or a CD4+ T cell control at a 1:1:1 ratio (CD8:CD4:target cell). The number of target cells was quantified at various time points during co-culture (0 hrs, 12 hrs, 24 hrs, and 36 hrs) using fluorescence microscopy and imaging software. A number of CERs (CER30, CER112, CER113, CER114, CER116, and CER117) showed nearly complete clearance of target SCC152 cells at 36 hours.
Figure 58:
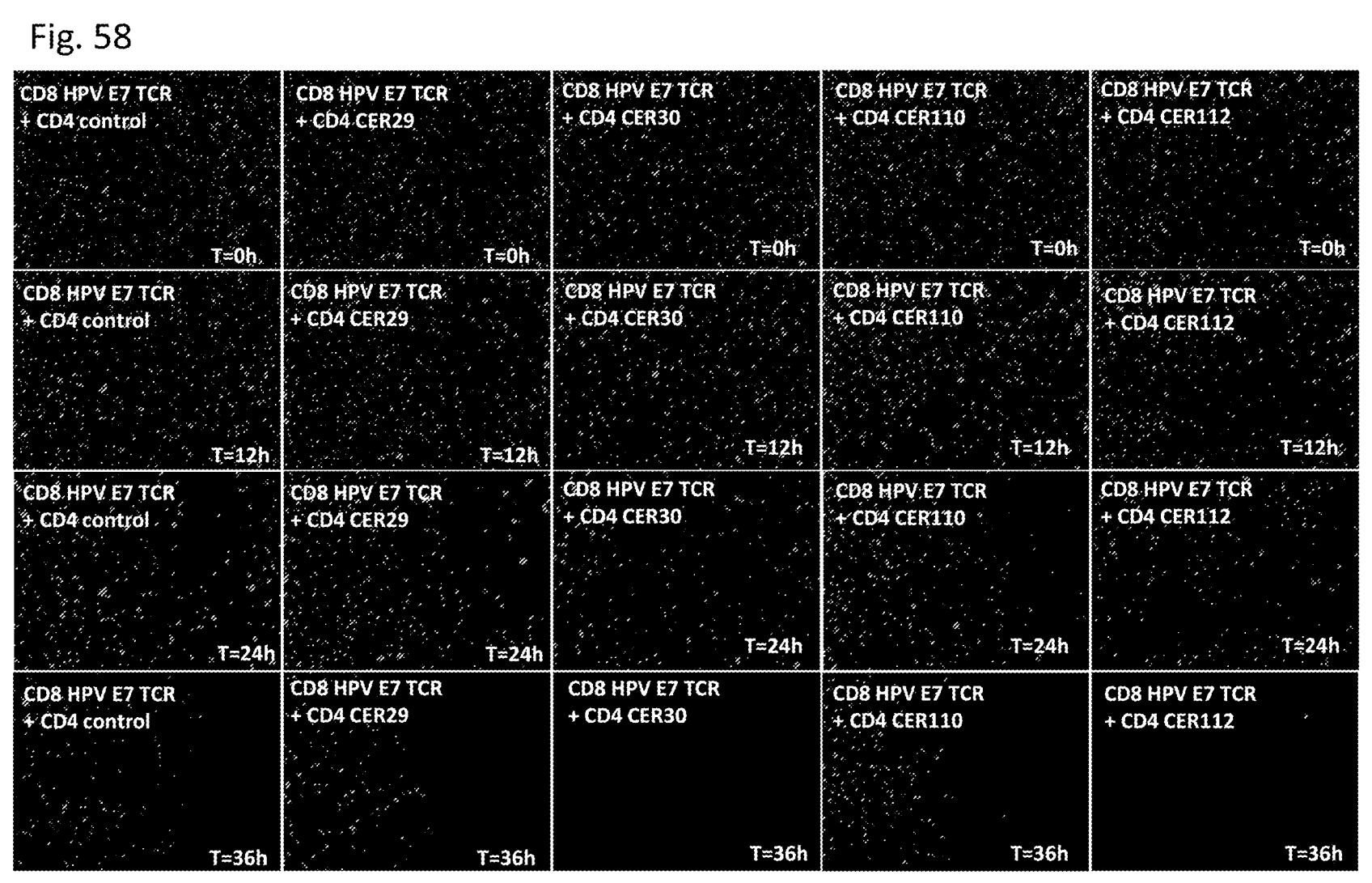
Figure 59:
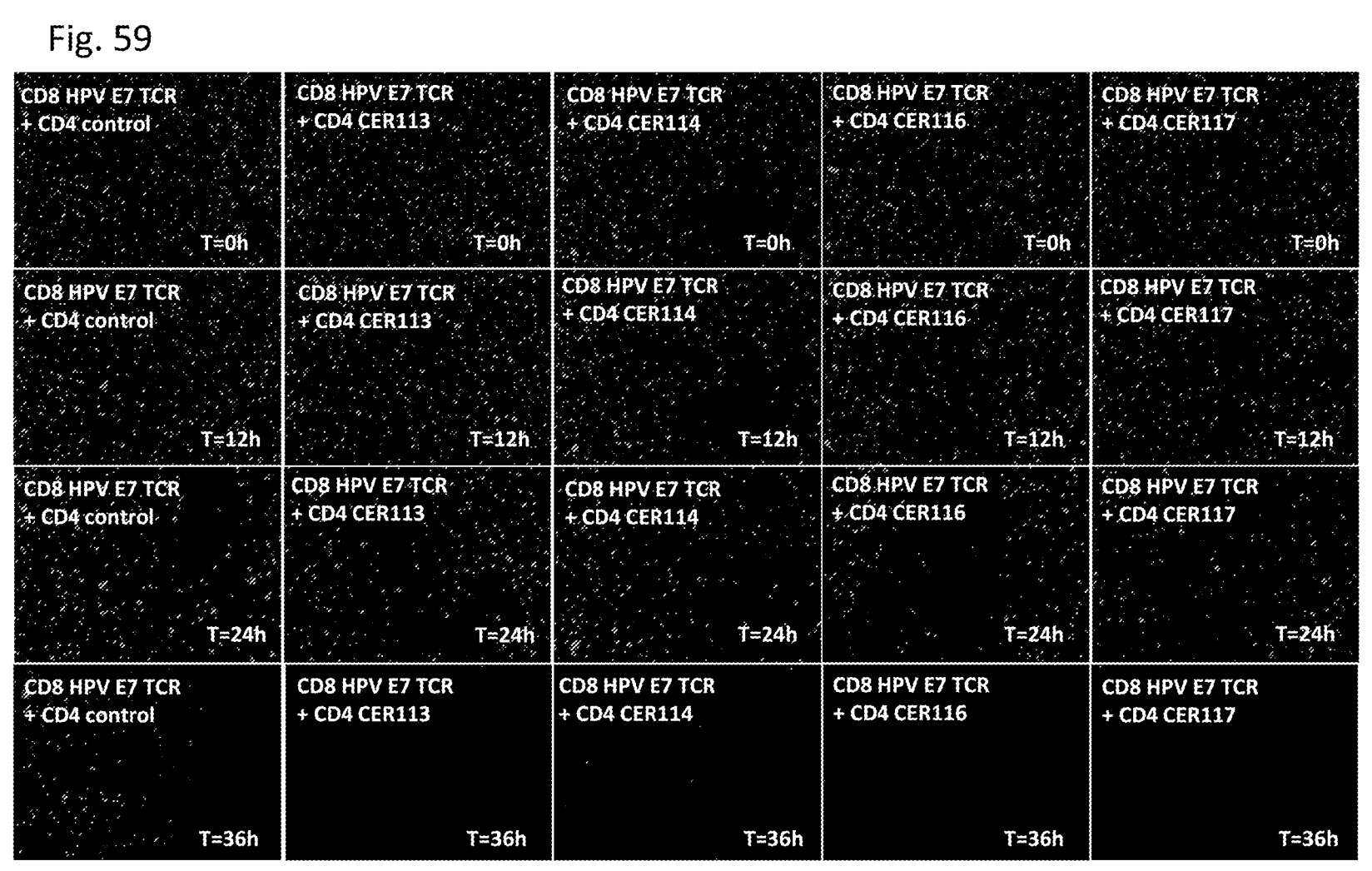

Elimination of target SCC152 cells was also detected by quantifying green fluorescent protein expression by SCC152 cells over time (0 hr, 12 hr, 24 hr, 36 hr) during co-incubation with CD8+ T cells transduced with HPV16 E7 specific TCR+ CD4+ T cells transduced with selected CER (CER29, CER30, CER110, CER112, CER113, CER114, CER116, or CER117) (see, FIG. 57). By 36 hrs, co-cultures treated with compositions comprising CD4+ T cells transduced with CER30, CER112, CER113, CER114, CER116, or CER117 showed nearly complete elimination of SCC152 cells compared to control (see, FIG. 57). Time lapse imaging of co-culture experiments similarly showed enhanced elimination of SCC152 cells in co-cultures treated with CD4+ T cells transduced with CER30, CER112, CER113, CER114, CER116, or CER117 compared to the control (FIGS. 58 and 59).

Example 3: Characterization of CER Modified CD4 T Cells

Figure 60A:
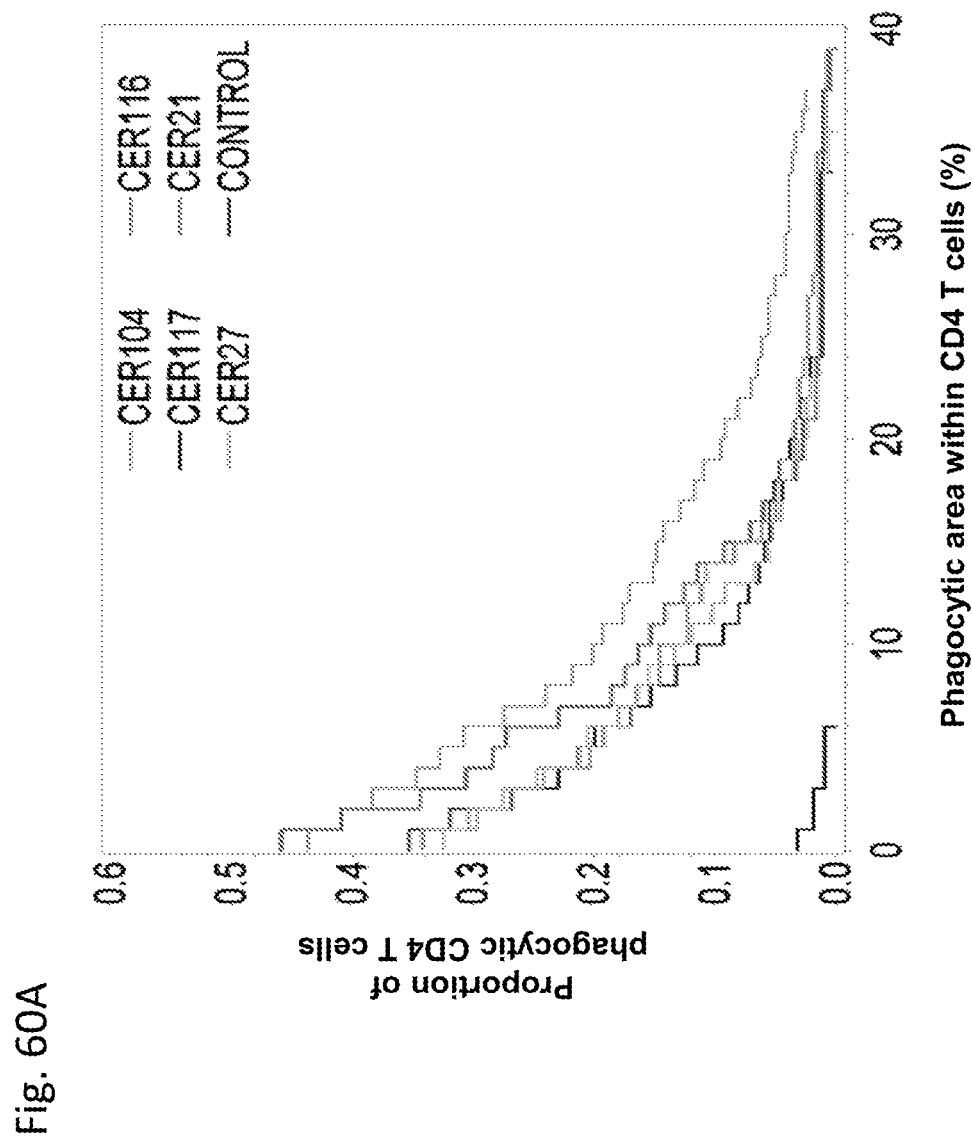
FIGS. 60A-60B shows analysis of phagocytosis of HPV+ SCC152 cells by CER-expressing CD4+ T cells.
Figure 60B:
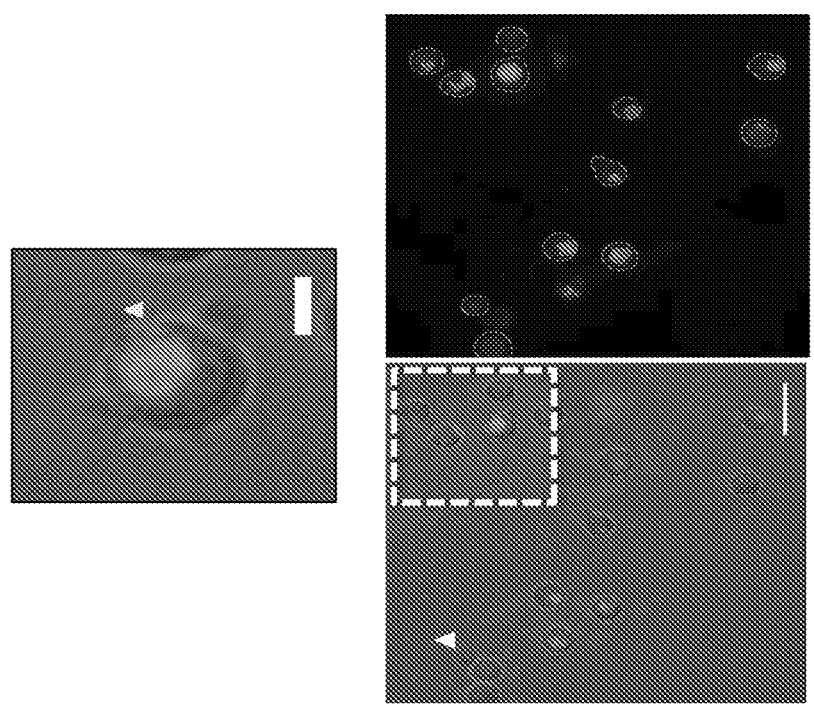

Various CER-modified CD4+ T cells were also evaluated for breadth of response to determine whether a particular CER confers a broad phagocytic response of low magnitude (e.g., 10% engulfment in 90% of cells) or a less frequent but strong phagocytic response (e.g., 90% engulfment in 10% of cells) in the host cells. CD8+ T cells were transduced with HPV16 E7 specific TCR as described in Example 1. CD4+ T cells were transduced with lentiviral vectors comprising a CER21, CER27, CER104, CER116, or CER117 nucleic acid. Mock-transduced (vector alone) CD4+ T cell were used as control. CD4+/CER+ and CD8+/E7 TCR+ T cells were stained with CELLTRACE violet. HPV16 E7+ head and neck squamous cell carcinoma cells (SCC152) were stained with pHrodo red. HPV16 E7 TCR transduced CD8+ T cells and selected CER transduced CD4+ T cells were mixed at a 1:1 ratio and co-cultured with SCC152 cells at a 1:1 ratio for 8 hours. Phagocytosis of target SCC152 cells by CER-transduced CD4+ T cells was analyzed by fluorescence microscopy. FIG. 60A shows a magnitude breadth curve for phagocytosis by CER type. The horizontal axis represents the % area of CER-transduced CD4+ T cells having engulfment or % area of the CER-transduced CD4+ T cells taken up by target SCC152 cells. This measure was rarely above 40% across CER types tested. The vertical axis represents the proportion of CER-transduced CD4+ T cells that were phagocytic. For CER104, about 20% of CER104-transduced CD4+ T cells have more than 10% engulfment. For CER117-transduced CD4+ T cells, less than 10% have more than 10% engulfment. FIG. 60B shows fluorescent micrograph images of SCC152 target cells engulfed by CER126-transduced CD4+ T cells.

Figure 61:
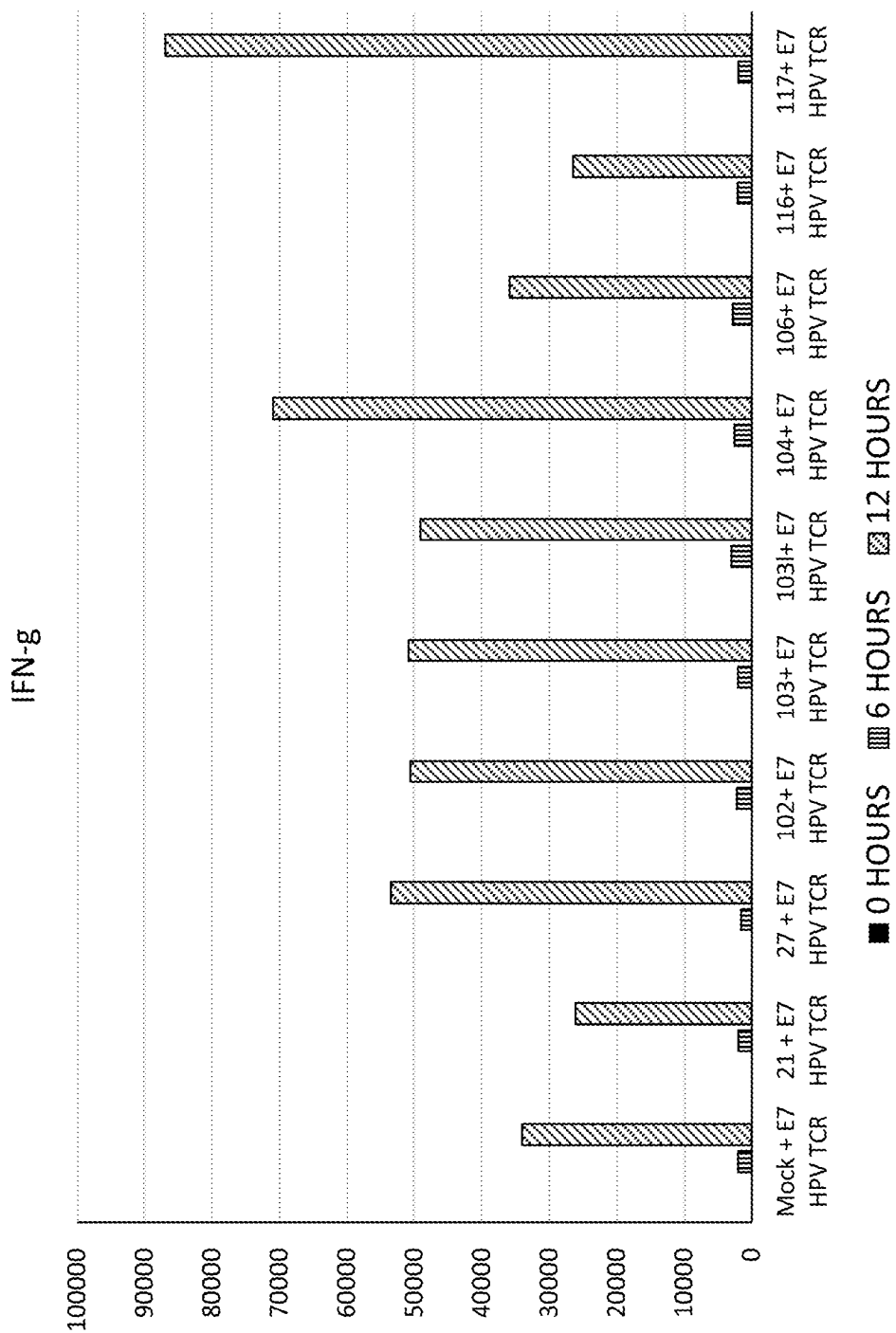
FIG. 61 shows cytokine secretion from CER-expressing CD4+ T cell+E7-specific TCR CD8+ T cell co-culture experiments. The addition of a CER-expressing CD4+ T cell to E7-specific TCR expressing CD8+ T cell enhanced levels of IFNγ secretion.

CD4+ T cells were transduced with lentiviral vectors comprising a CER21, CER27, CER102, CER103A, CER103B, CER104, CER106, CER116, or CER117 nucleic acid. Mock-transduced (vector alone) CD4+ T cell were used as control. CD8+ T cells were transduced with HPV16 E7 specific TCR. HPV16 E7 TCR transduced CD8+ T cells and selected CER transduced CD4+ T cells were mixed at a 1:1 ratio and co-cultured with SCC152 cells at a 1:1 ratio for 10 hours. Supernatants were then collected and analyzed for bulk cytokine secretion. As shown in FIG. 61, addition of a CER-expressing CD4+ T cell to E7 TCR-transduced CD8+ T cells enhanced levels of IFNγ secretion.

Example 4: Antigen Presentation by CER Modified T Cells

One strategy to enhance tumor cell killing by cytotoxic CD8+ T cells (CTLs) is to utilize antigen presenting cells (APCs), which have the unique capacity to "cross-present" exogenous antigen on MHC I molecules. Broadening tumor-specific CTL responses has the potential to induce effective immune responses against tumors. In this example the viral HPV E6 and E7 oncoproteins were used as model antigens to characterize the antigen processing and presenting capacity of chimeric engulfment receptor (CER)-expressing cells.

CD4+ and CD8+ CER-expressing T cell lines were established from human PBMCs. Purified T cells were transduced with lentivirus encoding CER123 (SEQ ID NO:164) and truncated EGFR (transduction marker), after activation with CD3 & CD28 microbeads, and then expanded in medium containing IL-7, IL-15, and IL-2 for 5 days. The percentage of tEGFR+ T cells ranged between 40-60%.

A Jurkat cell line with a stable integration of an NFAT-inducible Luciferase reporter construct was utilized to study T cell responses. Human E6- and E7-specific engineered TCRs were transduced into Jurkat NFAT reporter cell lines to characterize NFAT activation upon co-culture with engineered CERs.

Figure 62:
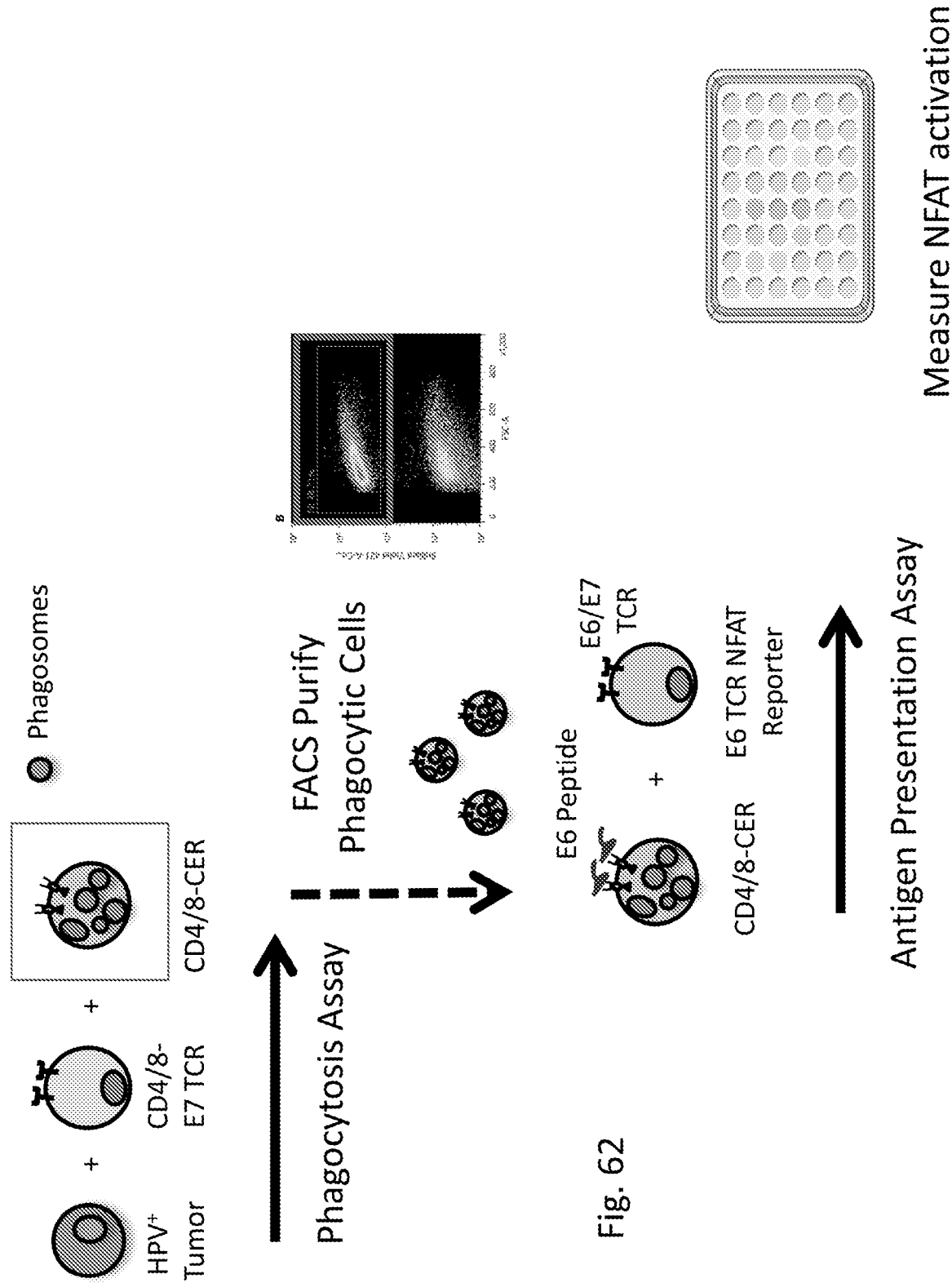
FIG. 62 shows a schematic of an exemplary antigen presentation assay. In a phagocytic assay step, CD4+ and CD8+ T cell lines expressing CERs were co-cultured with the CD4+ and CD8+ T cells expressing HPV E7 specific TCR and SCC152 (HPV+) cells overnight. The following day CER+ T cells were subsequently FACS-sorted. FACS plot depicts CT violet⁺ CERs. Following FACS purification, antigen presentation of HPV oncoproteins was evaluated. CER-expressing cells were co-cultured at a 1:2 ratio with E6 & E7-specific TCR/NFAT reporter cell lines, and NFAT activation measured over time using a plate reader.
Figure 63:
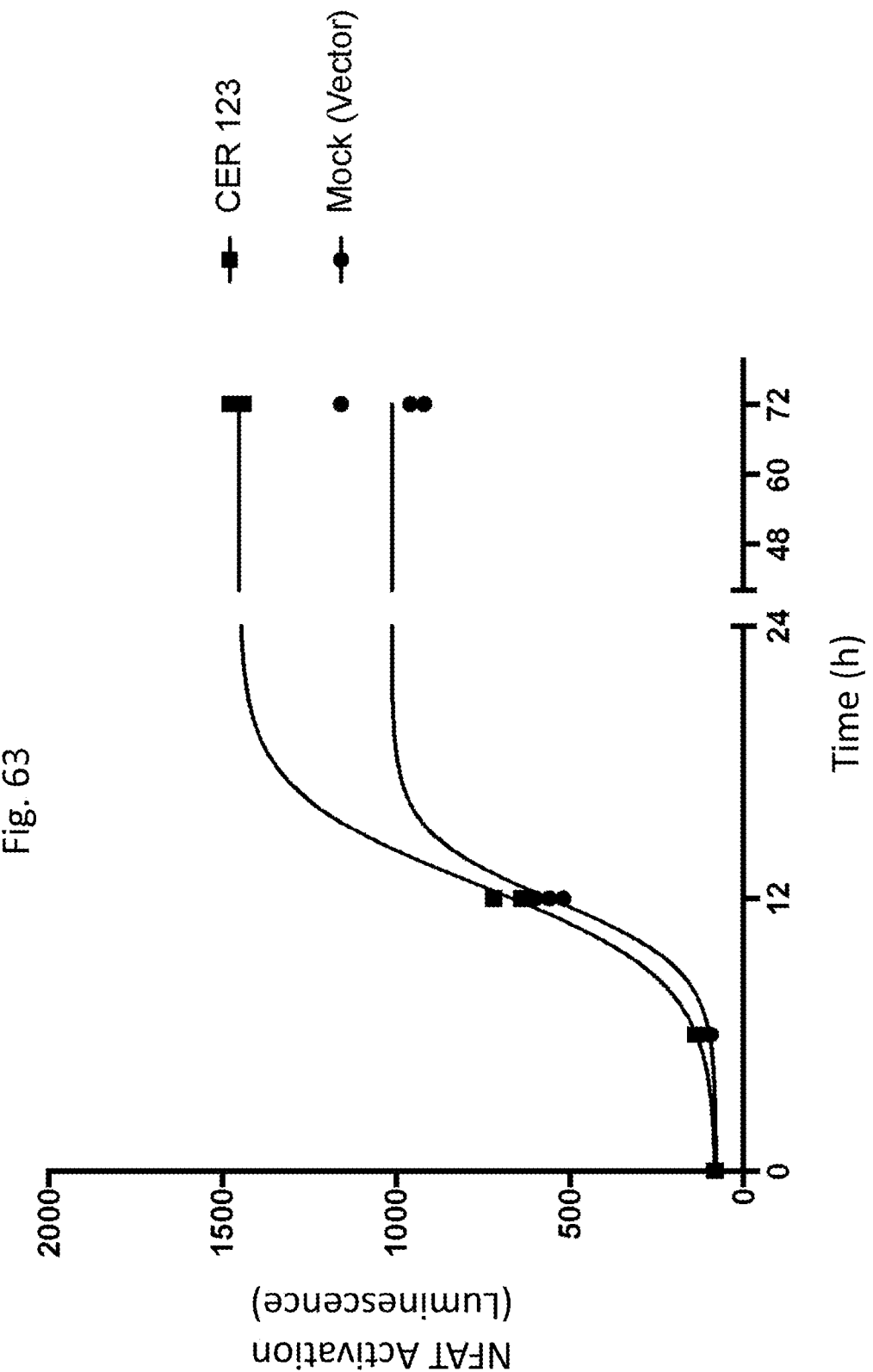
FIG. 63 shows a line graph of NFAT activation in E6/E7 TCR-transduced T cells comprising an NFAT reporter gene following co-culture with CD4+ and CD8+ CER123-transduced T cells that have been co-cultured with HPV+ tumor cells and CD4+/CD8+ E7 TCR transduced T cells as shown in the schematic in FIG. 62. CER-expressing CD4⁺ and CD8⁺ T cell lines, after phagocytosing HPV⁺ tumor cells, are capable of cross-presentation of E7 HPV oncoproteins to E7 TCR/NFAT reporter-expressing T cells as measured by NFAT activation.

For assessing MHC-I cross-presentation, SCC152 HPV+ cells were co-cultured overnight with CER123-expressing CD4+ and CD8+ T cells or mock-transduced (vector only) T cells in the presence of T cells expressing an E7-specific TCR. Following overnight co-culture, CER123-expressing T cells or Mock-transduced T cells were purified using FACS, washed, and subsequently cultured with E6/E7-specific human TCR/NFAT reporter cell line at a 1:1 ratio. NFAT activation was assessed at serial time points (0, 6, 12, 24, and 72 hrs) by measuring luciferase activity in cell culture supernatants. A schematic of this assay is provided in FIG. 62. Cells were cultured in RPMI/10% FCS in 96-well round-bottom plates. CER123-expressing CD4+ and CD8+ T cell lines, after phagocytosing HPV+ tumors, were co-cultured overnight with Jurkat T cells expressing a $E7_{11\text{-}19}$-specific TCR and an NFAT reporter. Induction of $E7_{11\text{-}19}$-specific Jurkat T cells were quantified by luminescence of NFAT signaling at indicated time points and compared to Mock (vector-alone) transduced T cells (FIG. 63). CER123-expressing T cells demonstrated enhanced cross-presentation efficiency of HPV E7 oncoproteins following phagocytosis of HPV+ tumor cells.

Example 5: Marker Analysis of CER Modified CD4 T Cells

Figure 64A:
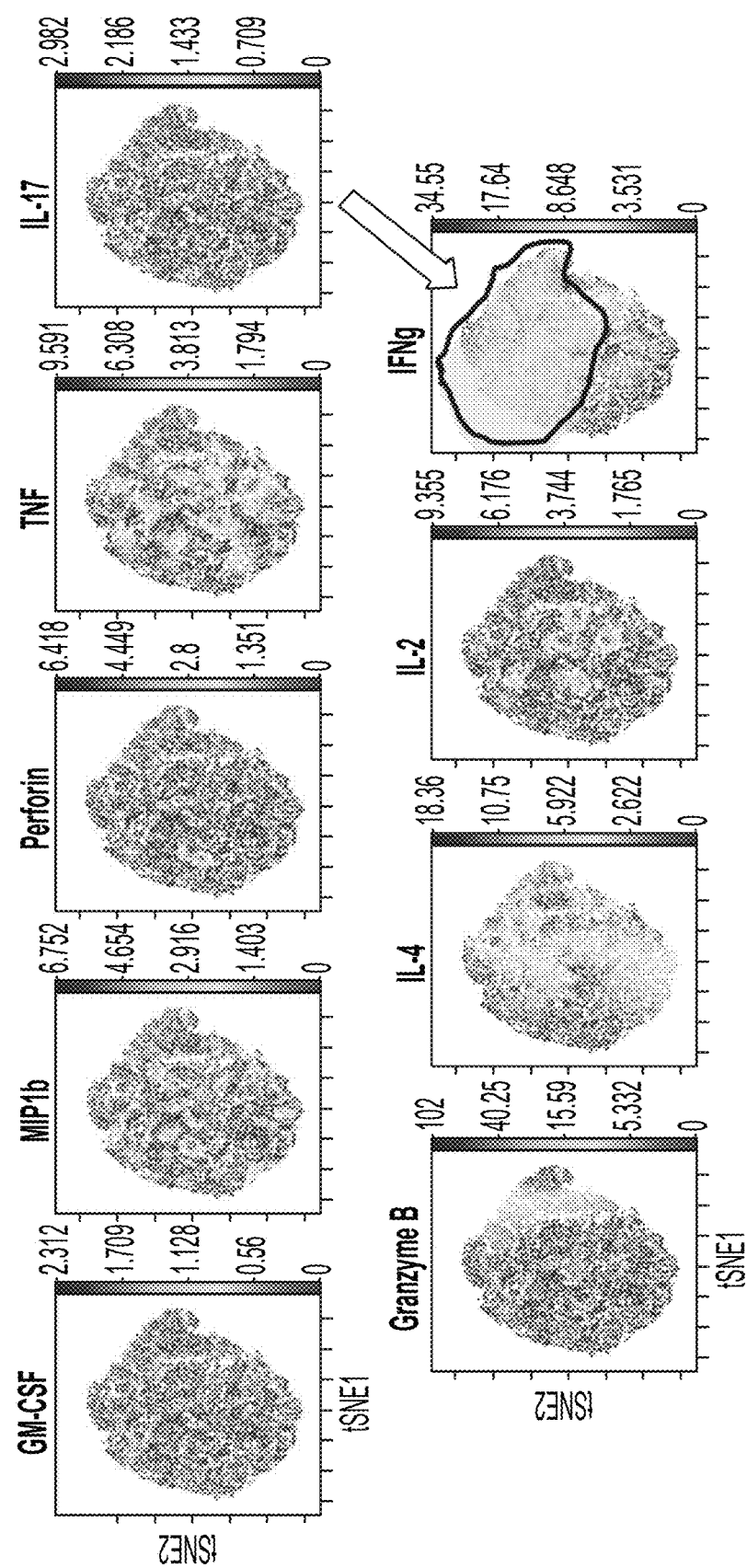
FIG. 64A-64B show viSNE maps of mass cytometry data of CER-transduced CD4+ T cells upon antigen encounter. CER-transduced CD4+ T cells were co-cultured with E7-specific TCR-transduced CD8+ T cells and HPV+ SCC152 target cells and then interrogated by mass cytometry (CyTof). Intact CER-CD4+ T cells are shown in plots displaying tSNE1 and tSNE2 axes. Nine intracellular markers were used for the viSNE analysis. Each dot represents a single cell.
Figure 64B:
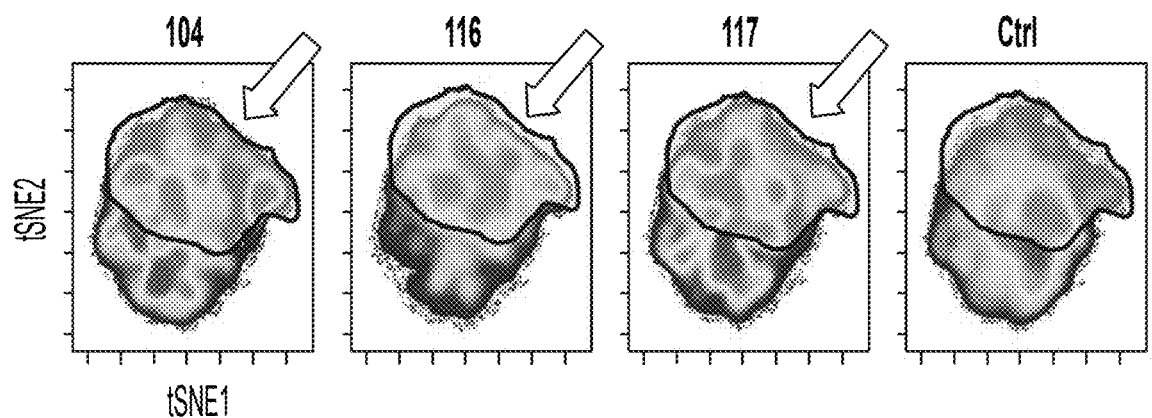
Figure 65A:
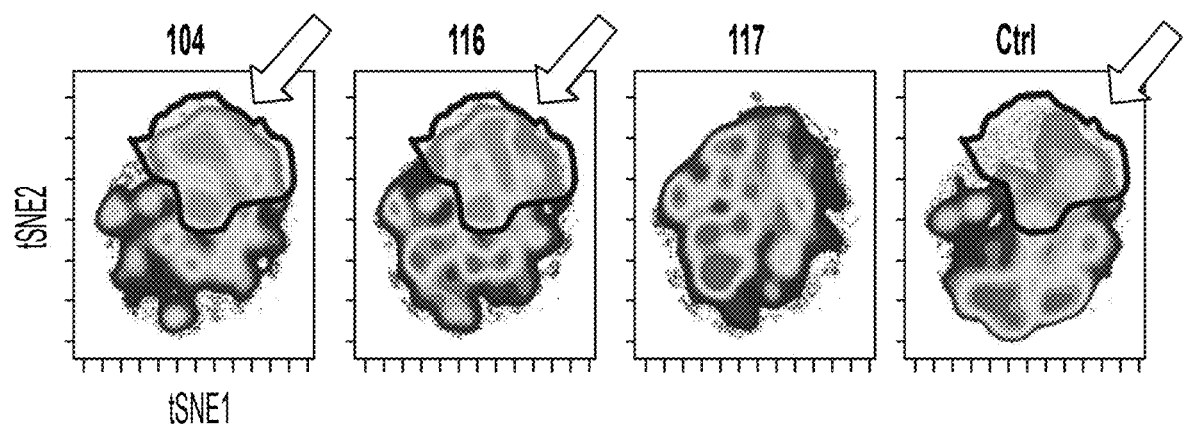
FIGS. 65A-65B show viSNE maps of mass cytometry data of CER-expressing CD4+ T cells upon antigen encounter. CER-transduced CD4+ T cells were co-cultured with E7-specific TCR-transduced CD8+ T cells and HPV+ SCC152 target cells and then interrogated by mass cytometry (CyTof). Intact CER-CD4+ T cells are shown in plots displaying tSNE1 and tSNE2 axes. Eighteen cell surface markers were used for the viSNE analysis. Each dot represents a single cell.
Figure 65B:
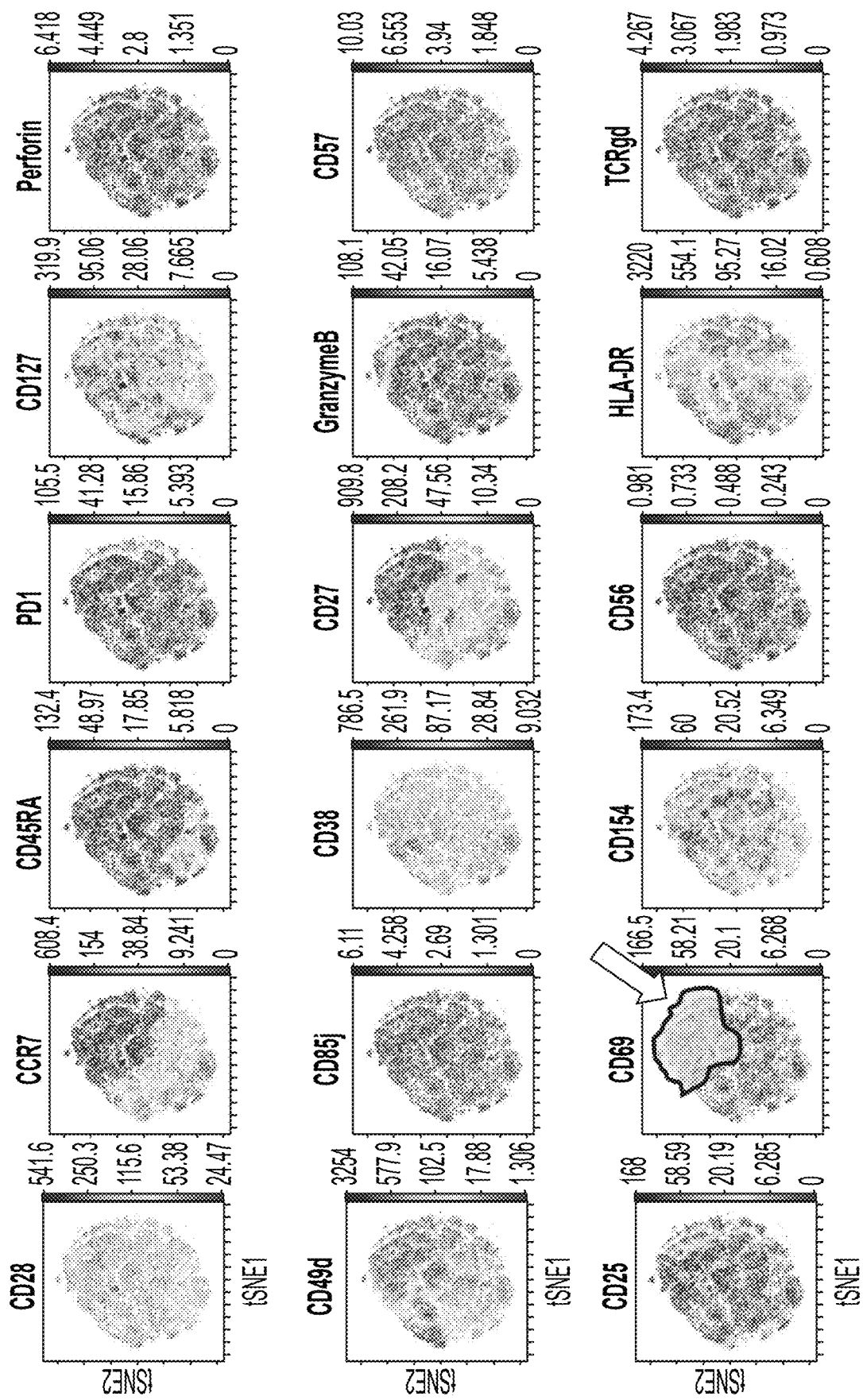
Figure 66A:
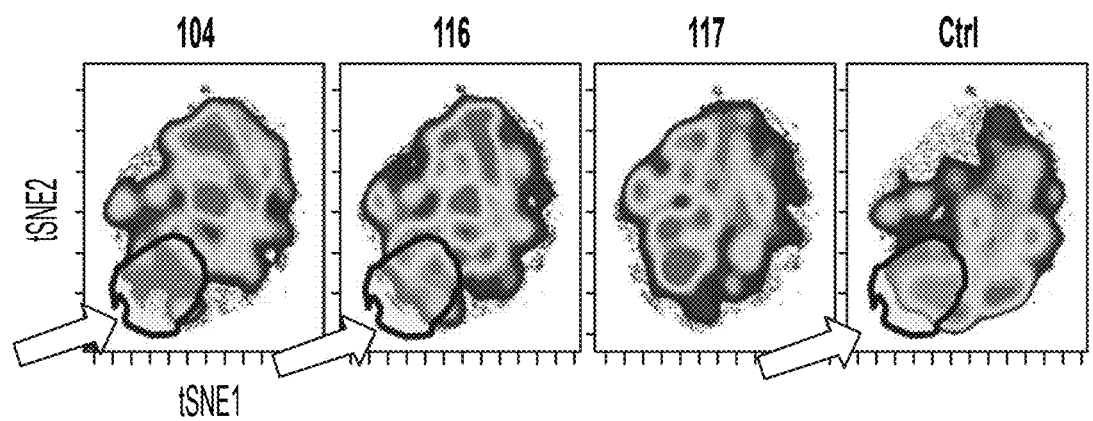
FIGS. 66A-66B show viSNE maps of mass cytometry data of CER-expressing CD4+ T cells upon antigen encounter. CER-transduced CD4+ T cells were co-cultured with E7-specific TCR-transduced CD8+ T cells and HPV+ SCC152 target cells and then interrogated by mass cytometry (CyTof). Intact CER-CD4+ T cells are shown in plots displaying tSNE1 and tSNE2 axes. Eighteen cell surface markers were used for the viSNE analysis. Each dot represents a single cell.
Figure 66B:
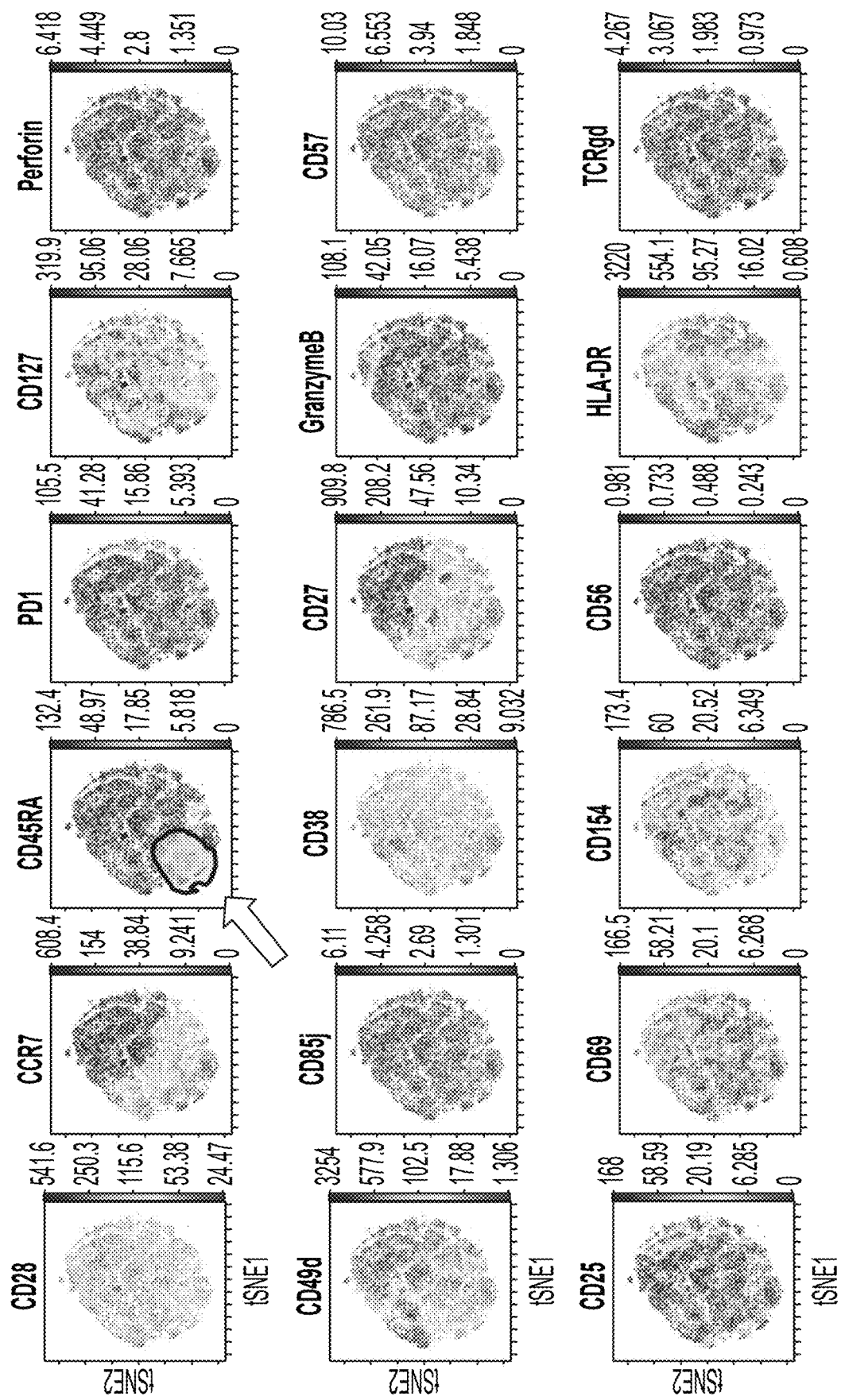

CD4+ T cells were transduced with lentiviral vector comprising CER104, CER116, or CER117 nucleic acid. CER104 (SEQ ID NO:139) comprises a Tim4 binding domain, Tim4 transmembrane domain, and an engulfment signaling domain comprising a primary engulfment signaling domain comprising a TLR8 signaling domain and a secondary engulfment signaling domain comprising a DAP12 signaling domain. CER116 (SEQ ID NO:152) comprises a Tim4 binding domain, Tim4 transmembrane domain, and an engulfment signaling domain comprising a primary engulfment signaling domain comprising a TRAF6 signaling domain and a secondary engulfment signaling domain comprising a TLR8 signaling domain. CER117 (SEQ ID NO:153) comprises a Tim4 binding domain, Tim4 transmembrane domain, and an engulfment signaling domain comprising a primary engulfment signaling domain comprising a TLR8 signaling domain and a secondary engulfment signaling domain comprising a TRAF6 signaling domain. CER-transduced CD4+ T cells were co-cultured with E7 TCR-transduced CD8+ T cells and HPV+ SCC152 target cells and interrogated by mass cytometry (CyTOF) with viSNE for visualization of high dimensional single cell data (FIGS. 64-66). Intact CER-transduced CD4+ T cells are shown in plots displaying tSNE1 (horizontal) and tSNE2 (vertical) axes. 27 intracellular markers were used for the viSNE analysis. Each dot represents a single cell. Coloring the plots by a few of the measured markers (GM-CSF, MIP1b, Perforin, TNF, IL-17, Granzyme B, IL-4, IL-2, and IFNγ) shows the phenotype across viSNE 'islands' (FIG. 64A). Red represents high expression and blue represents low expression for each marker. Populations of CD4+ T cells were generated using a clustering algorithm from all 27 markers and overlaid onto the viSNE map. Arrows indicate enrichment of islands expressing the intracellular marker IFNγ in samples containing CER104, CER116, and CER117 (FIG. 64B). Populations of CD4+ T cells were generated using a clustering algorithm from all 18 markers and overlaid onto the viSNE map (FIG. 65A). Arrows indicate enrichment of islands expressing the T cell activation marker CD69 in samples containing CER104- and CER116-transduced CD4+ T cells. Color plots by 18 intracellular markers (CD28, CCR7, CD45RA, PD1, CD127, Perforin, CD49d, CD85j, CD38, CD27, Granzyme B, CD57, CD25, CD69, CD154, CD56, HLA-DR, and TCRγδ) show the phenotype across viSNE 'islands' (FIG. 65B). Red represents high expression and blue represents low expression for each marker. Highlighted region with arrow indicates cells expressing T cell activation marker CD69. Populations of CD4+ T cells were generated using a clustering algorithm from 18 intracellular markers (CD28, CCR7, CD45RA, PD1, CD127, Perforin, CD49d, CD85j, CD38, CD27, Granzyme B, CD57, CD25, CD69, CD154, CD56, HLA-DR, and TCRγδ) and overlaid onto the viSNE map. Arrows indicate loss of islands expressing the naïve T cell marker CD45RA within the CCR7+ population among CER104 and CER116 samples compared to controls (FIG. 66A). Color plots by the 18 intracellular markers show the phenotype across viSNE 'islands' (FIG. 66B). Red represents high expression and blue represents low expression for each marker. Highlighted region with arrow indicates cells expressing the naïve T cell marker CD45RA. Thus, this data show that CER104 and CER116-transduced CD4+ T cells are associated with memory formation after antigen encounter.

Figure 67A:
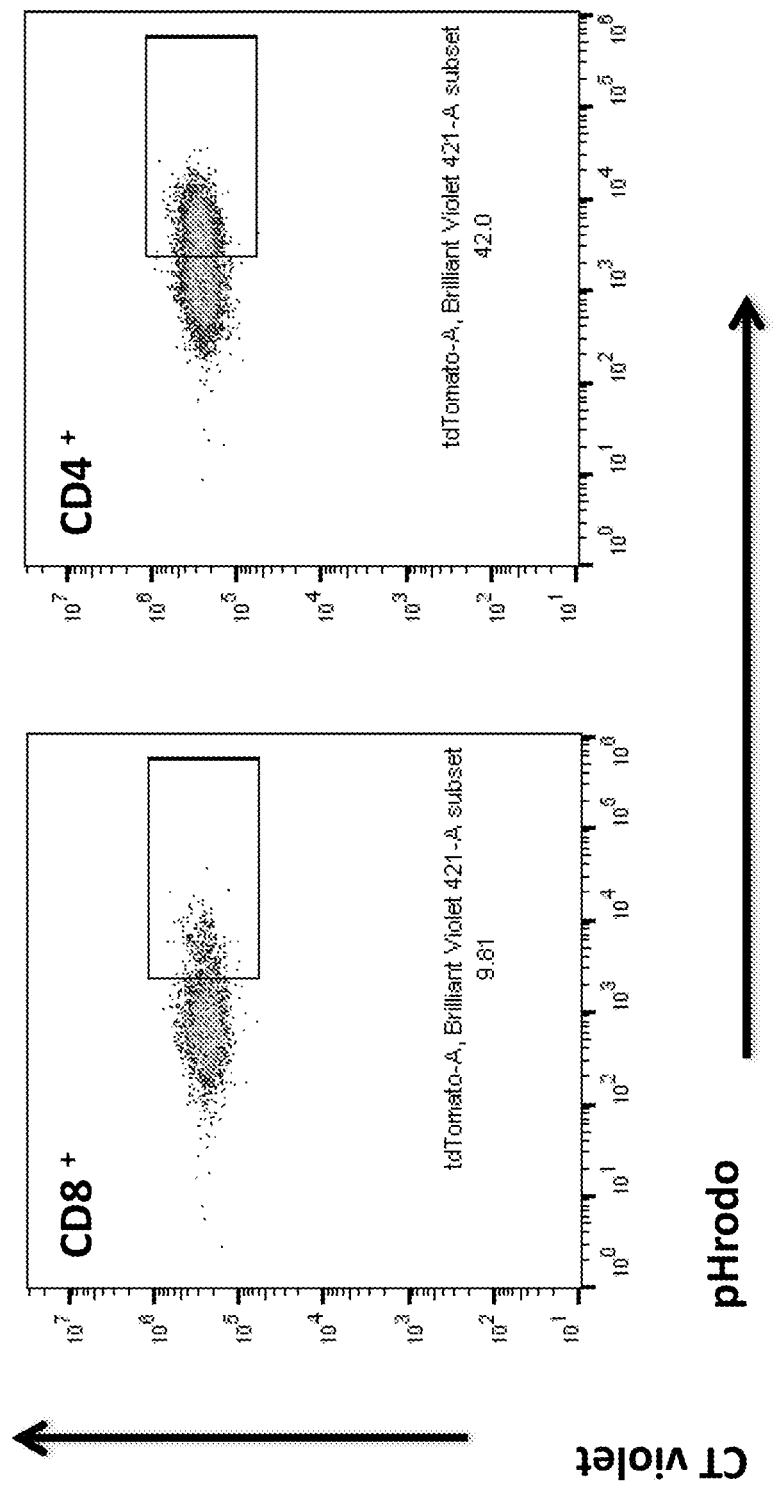
FIGS. 67A-67B show that of CD4+ and CD8+ T cell subtypes, CER-modified CD4+ T cells harbor the majority of engulfment activity.
Figure 67B:
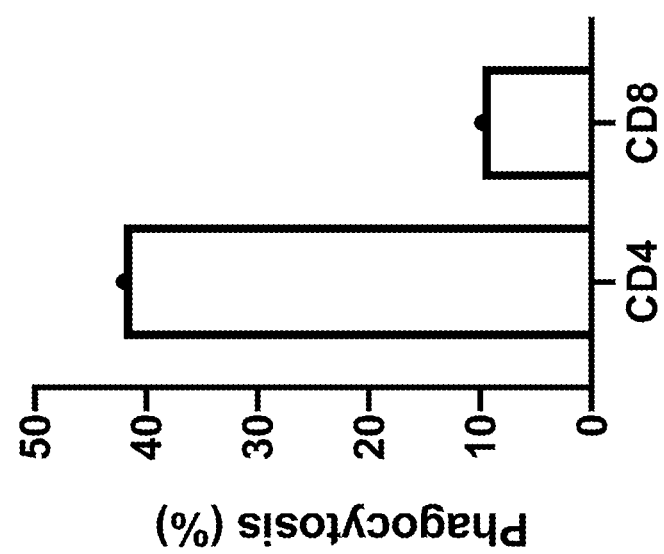
Figure 68:
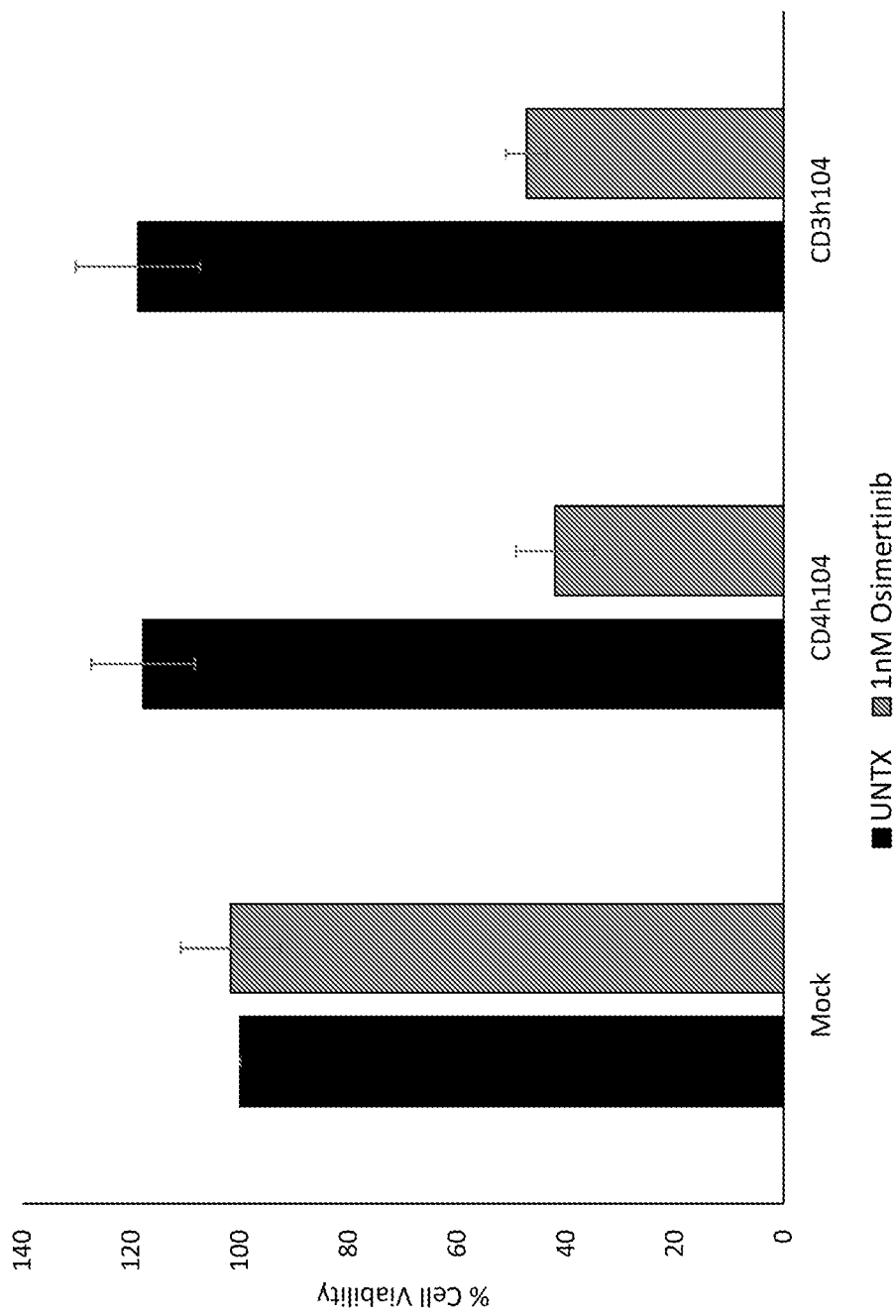
FIG. 68 shows viability of HCC827 NSCLC adenocarcinoma cells co-cultured with hCER104 modified T cells. Assays were performed at an effector to target cell ratio of 5:1 in the presence or absence of an EGFR small molecular inhibitor (1 nM osimertinib). Co-culture of hCER104 modified CD3+ T cells was compared with co-culture of purified hCER104 modified CD4+ T cells. Cell viability was quantified using 3-(4,5-dimethylthiazol-2-yl)-2,5-diphenyltetrazolium bromide (MTT) assay.
Figure 69:
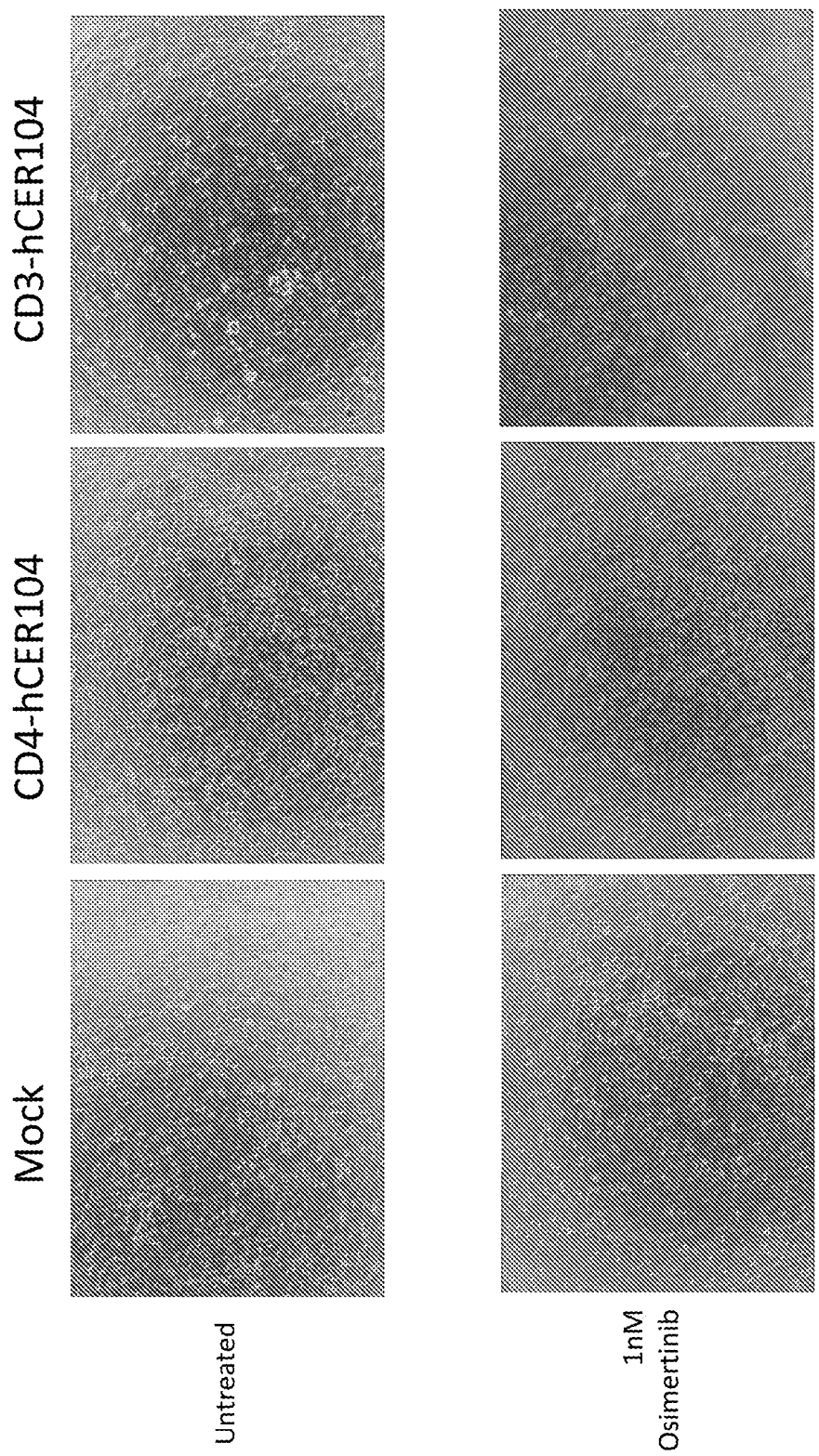
FIG. 69 shows phase contrast microscope images of hCER104 modified CD3+ T cells or hCER104 modified, purified CD4+ T cells following 48 hours co-culture with HCC827 cells and 1 nM osimertinib. Specific target cell killing of HCC827 observed in hCER104 modified T cells in the presence of osimertinib.

Example 6: CD4+ CER-Modified T Cells Harbor Majority of Engulfment Activity and Enhance Tumor Killing In Vivo CD4+ or CD3+ T cells were purified from PBMCs, activated, and transduced with lentiviral vector comprising hCER104 nucleic acid. hCER104 is a human CER104 construct comprising a Tim4 binding domain, a Tim4 transmembrane domain, TLR8 engulfment signaling domain, and Dap12 engulfment signaling domain and comprises an amino acid sequence of SEQ ID NO:176. HCC827 cells harbor an EGFR mutation and treatment with EGFR inhibitor osimertinib induces exposure of phosphatidylserine on the cell surface. Transduced T cells were expanded. CER-modified T cells were co-cultured with pHrodo-red labeled HCC827 NSCLC adenocarcinoma cells overnight and evaluated by FACs for pHrodo-positive signals to detect phagocytosis of HCC827 target cells (see, FIG. 67A, box inside FACs plot indicates % phagocytosis). T cell subsets were analyzed for their capacity to phagocytosis using antibody staining. Frequency of in vitro phagocytosis among CD4+ CER-modified T cells was much higher than CD8+ CER-modified T cells (see, FIG. 67B).

hCER104 modified CD3+ T cells and hCER104 modified CD4+ T cells were co-cultured with HCC827 NSCLC adenocarcinoma cells treated for 48 hours with or without 1 nM osimertinib at an effector to target cell ratio of 5:1. Mock transduced T cells were used as control. Viability of HCC827 cells following co-culture was measured by MTT assay and shown in FIG. 68. HCC827 cells exhibited lower cell viability when co-cultured with hCER104 CD4+ T cells than hCER104 modified CD3+ T cells, which represent a mixture of CD4+ and CD8+ T cell subsets. Phase contrast microscopy at 48 hours co-culture show specific cell killing of HCC827 cells by hCER104 modified CD4+ T cells and CD3+ T cells in the presence of osimertinib (FIG. 69).

Figure 70:
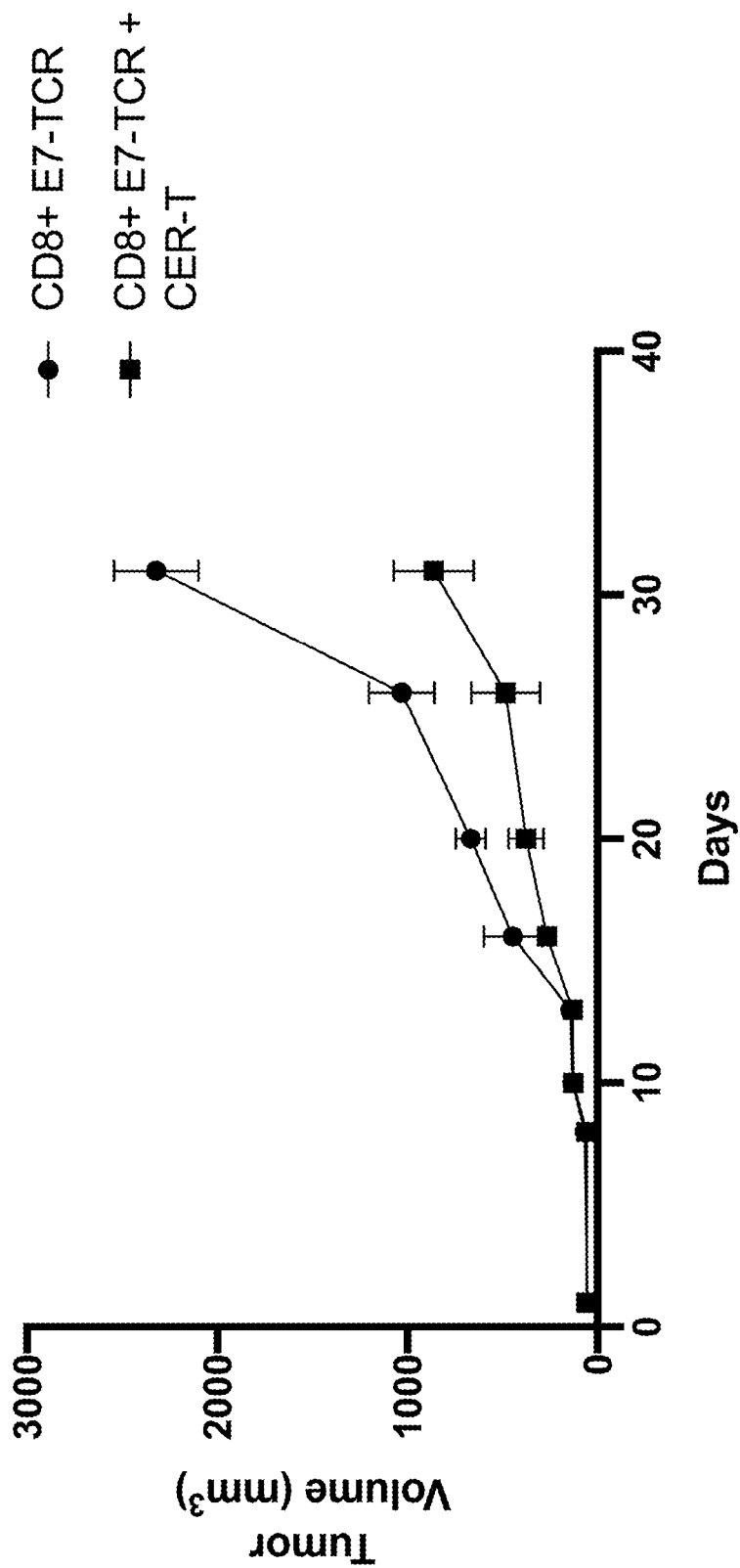
FIG. 70 shows tumor growth of SCC152 HPV+ Head & Neck Squamous Carcinoma in NSG mice. $1\times10^6$ CD8+ T cells engineered with a HPV E7 specific TCR were infused with or without $3\times10^6$ CD4+ T cells engineered with CER104. Data represents mean value of tumor caliper measurements (n=5 mice per group).

Cellular immunotherapy composition combination comprising HPV E7 specific TCR modified CD8+ T cells ($1\times10^6$) (as described in Example 1) and hCER104 modified CD4+ T cells ($3\times10^6$) were infused into head neck squamous cell cancer mouse model generated by injecting HPV+ SCC152 cells into NSG mice and compared with SCC152 xenograft mice treated with HPV E7 specific TCR modified CD8+ T cells alone (n=5 mice/treatment group). Tumor volume was measured over time via caliper measurements and shown in FIG. 70. The addition of CER104 modified CD4+ T cells to the E7 specific TCR modified CD8+ T cells enhanced tumor killing in vivo.

Figure 71:
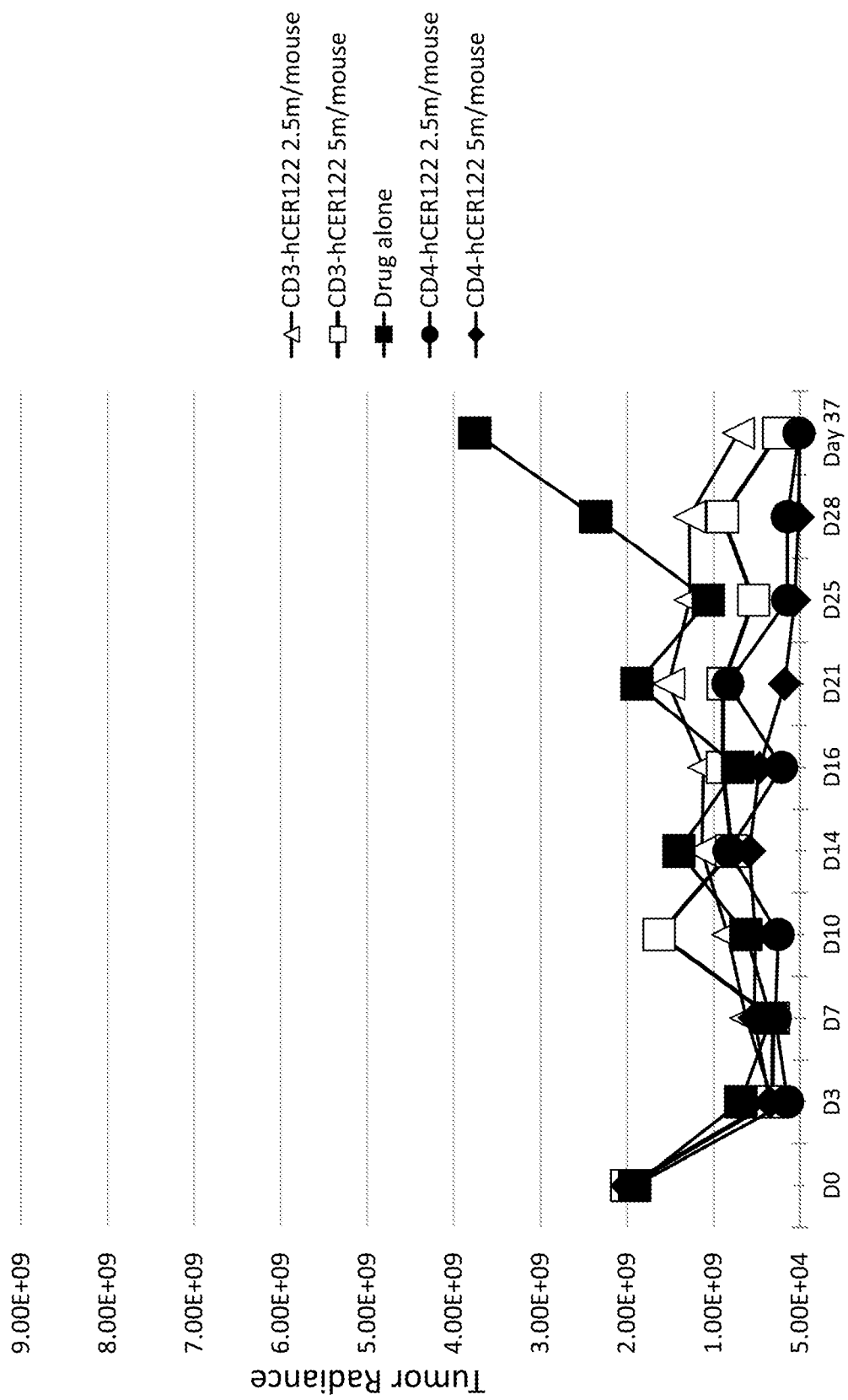
FIG. 71 shows HCC827 xenograft studies. Growth of HCC827/luceriferase+ cells in NSG mice upon adoptive transfer of purified hCER122 modified CD4+ T cells or hCER122 modified CD+ T cells with concomitant targeted inhibitor therapy was measured by bioluminescence imaging. Data represents mean values (n=5 mice/treatment group).
Figure 72:
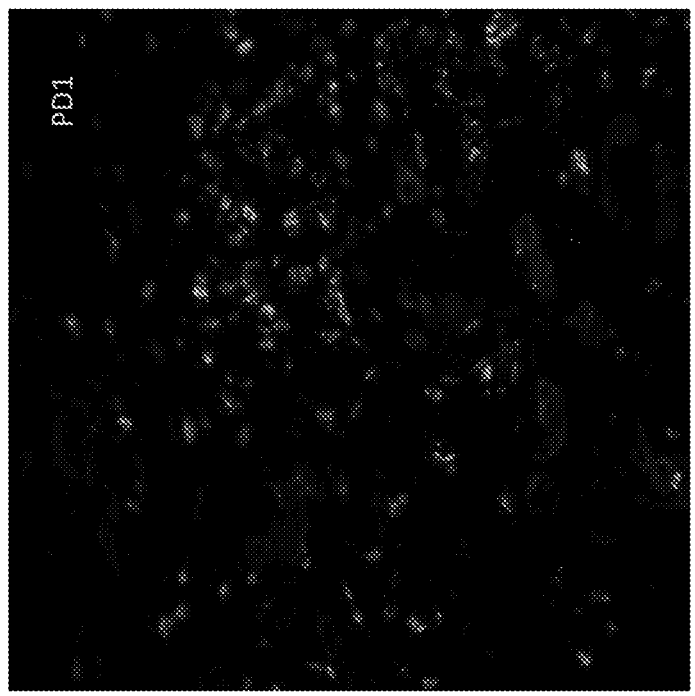
FIG. 72 shows immunofluorescence staining from HCC827 xenograft studies at day 16. Tumor staining shows infiltration of PD1+ CD4+ T cells (functionally active) into tumor stroma. Tumor specimens were stained with anti-EGFR (tumor antigen), anti-CD4, anti-PD1, and DAPI counter-stain (left image).
Figure 72:
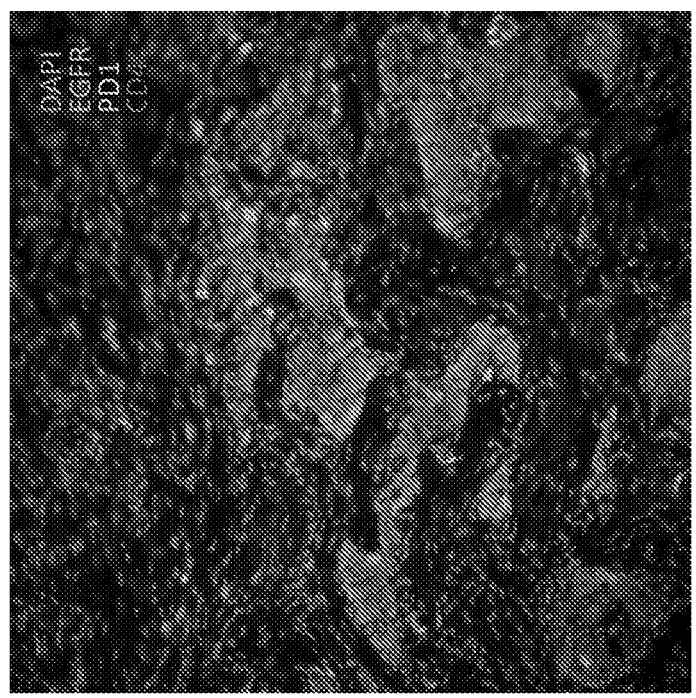

CD3+ or CD4+ T cells were purified from PBMCs, activated, and transduced with lentiviral vector comprising hCER122 nucleic acid. hCER122 is a human CER122 construct comprising a Tim4 binding domain, a Tim4 transmembrane domain, TLR2 engulfment signaling domain, and Dap12 engulfment signaling domain and comprises an amino acid sequence of SEQ ID NO:179. Transduced T cells were expanded. hCER122 modified CD3+ T cells ($2.5\times10^6$ or $5\times10^6$) or hCER122 modified CD4+ T cells ($2.5\times10^6$ or $5\times10^6$) were infused into NSG mice engrafted with HCC827 adenocarcinoma cells (2 million/mouse). HCC827 xenograft mice also received 1 mg/kg osimertinib post-engraftment. Both hCER122 modified CD3+ and CD4+ T cells exhibited enhanced anti-tumor responses in vov compared to osimertinib treatment alone (FIG. 71). hCER122 modified CD4+ T cells eliminated tumors xenograft model (FIG. 71). Microscopy images of immunofluorescence stained tumor cells from HCC827 xenograft model at day 16. Tumor specimens were stained with anti-EGFR (tumor antigen), anti-CD4, anti-PD1, and DAPI counter-stain. Tumor staining shows infiltration of PD1+CD4+ T cells (functionally active) into tumor stroma (FIG. 72, left image). FIG. 72, right image, shows anti-PD1 stained T cells.

Figure 73A:
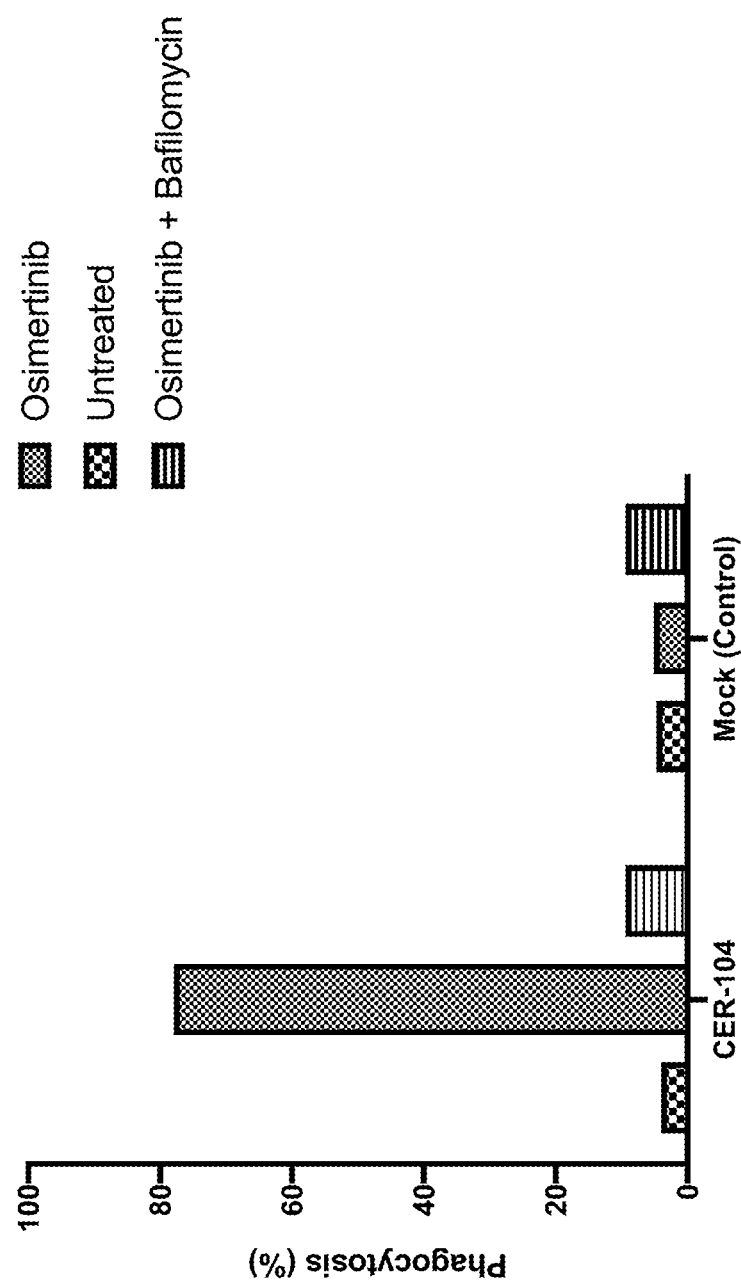
FIGS. 73A-73B show ablation of CER-induced phagocytosis by bafilomycin, an inhibitor of phagolysosome V-ATPase. CER104-modified CD4+ T cells and mock transduced CD4+ T cells (control) were co-cultured with HCC827 cells that were labeled with TAMRA-SE fluorescent dye and treated with osimertinib. Phagocytosis was quantified by FACs.
Figure 73B:
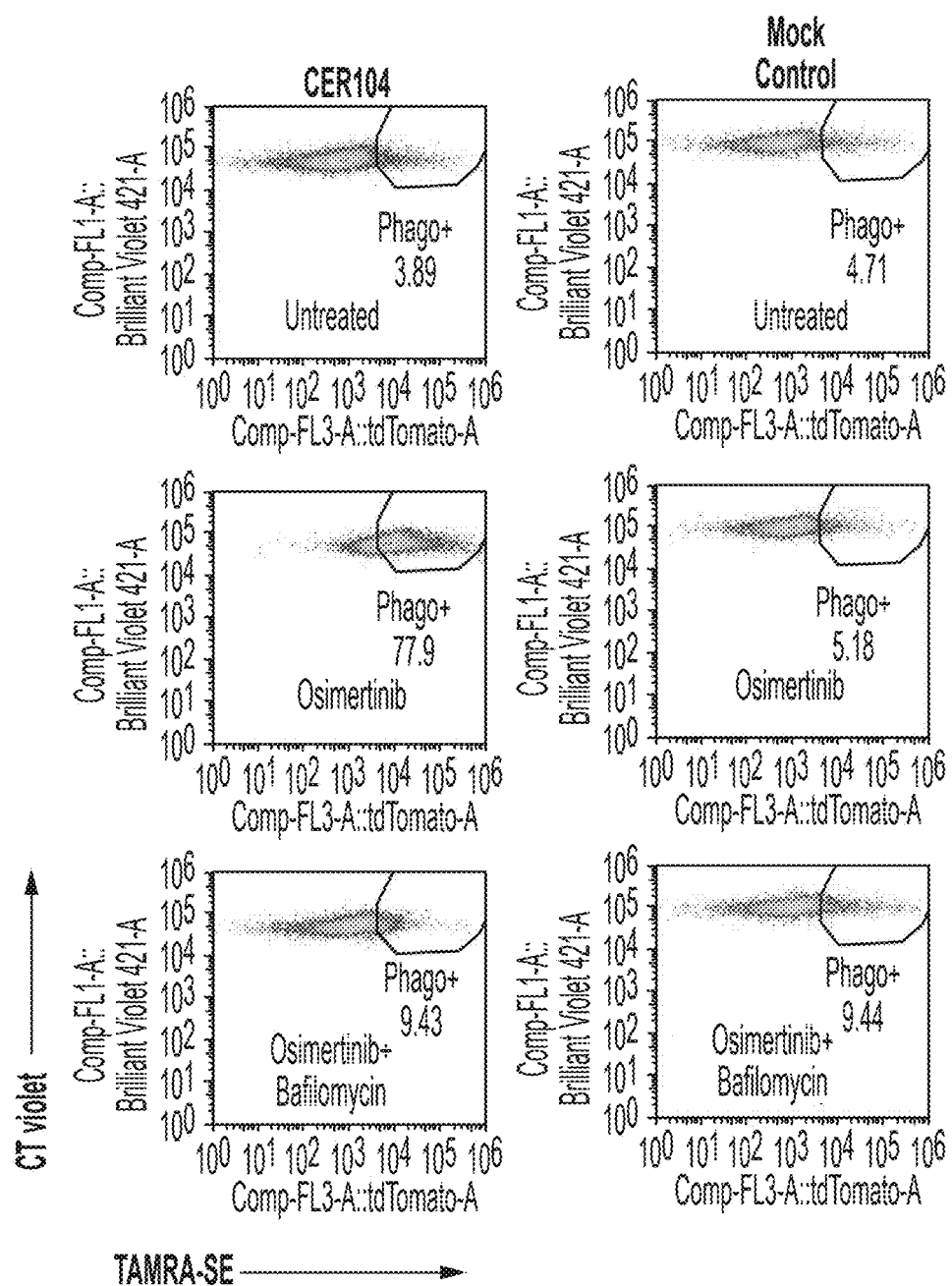

Example 7: Inhibition of Phagolysosome V-ATPase Ablates CER-Induced Phagocytosis T cells were transduced with lentiviral vector comprising hCER104 nucleic acid as described in Example 6. hCER104 modified T cells were co-cultured with HCC827 adenocarcinoma cells with or without osimertinib. Bafilomycin is an inhibitor of V-ATPase and disrupts phagosome acidification. hCER104 modified T cells exhibited phagocytosis of TAN/IRA-SE fluorescent dye-labeled HCC827 cells (FIG. 73A). Addition of bafilomycin (20 nM) to co-culture blocked uptake of labeled HCC827 cells by hCER104 modified T cells (FIG. 73A). FACs plots from in vitro phagocytosis assays in hCER104 modified T cells or mock transduced control T cells are shown in FIG. 73B.

Figure 74A:
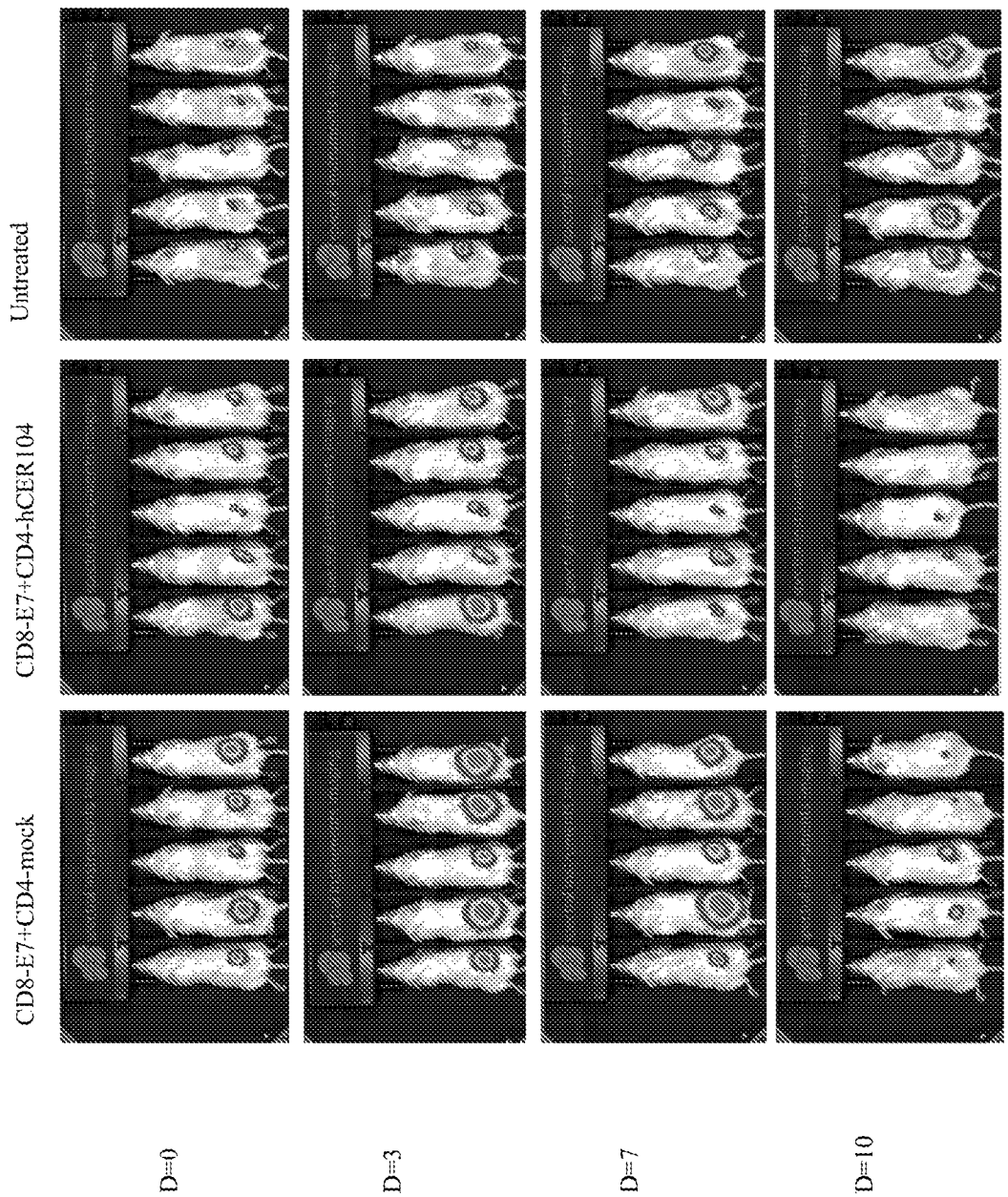
FIGS. 74A-74B show that addition of hCER104-modified CD4+ T cells to HPV E7 TCR modified CD8+ T cells enhanced tumor killing in vivo. HPV+ SCC152 engrafted NSG mice were treated with HPV E7 TCR modified CD8+ T cells+CD4+ T cells (mock transduced), HPV E7 TCR modified CD8+ T cells+hCER104 modified CD4+ T cells, or untreated. Tumor volume was measured by serial bioluminescence imaging and shown in FIG. 74A.
Figure 74B:
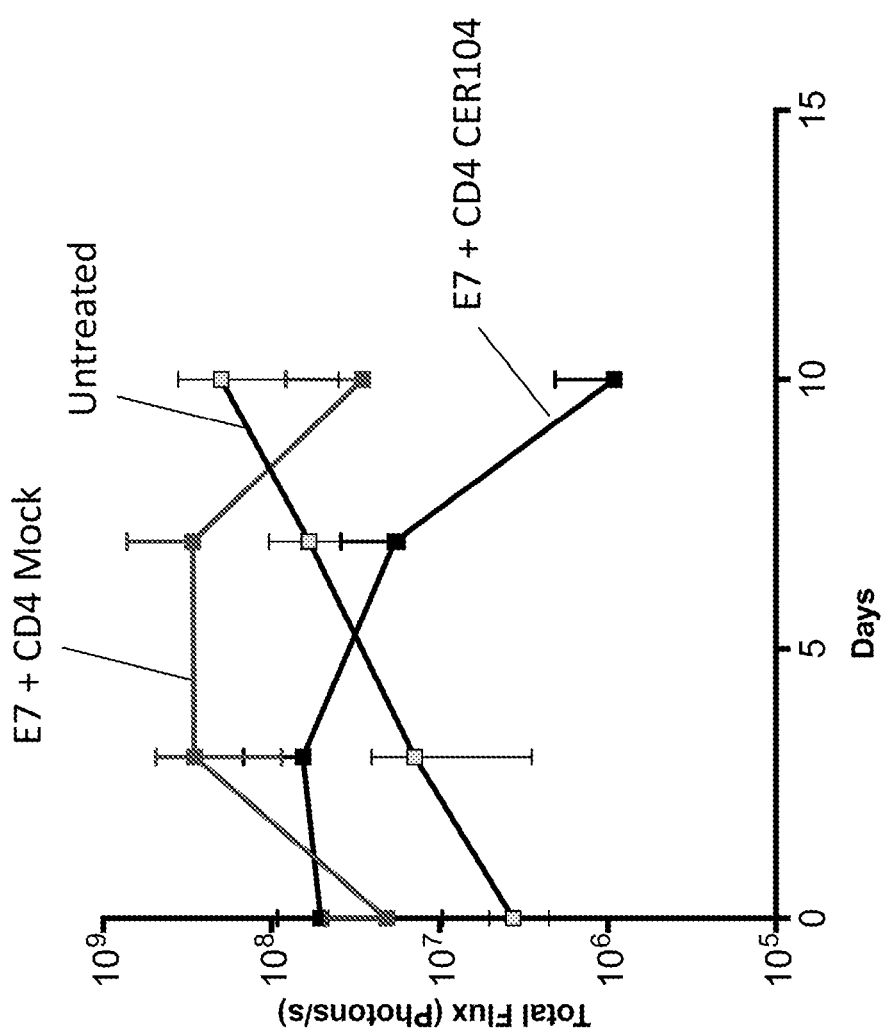

Example 8: HCER104 Modified CD4+ T Cells Enhanced E7 Specific TCR Modified CD8+ T Cells Tumor Killing In Vivo HPV+ SCC152/luceriferase+ cells were engrafted in NSG mice. Once tumors were established, mice were treated with HPV E7 specific TCR (SEQ ID NO:84) modified CD8+ T cells+mock transduced CD4+ T cells, HPV E7 specific TCR modified CD8+ T cells+hCER104 (SEQ ID NO:176) modified CD4+ T cells, or untreated (n=5 per treatment group). HPV E7 CD8+ T cells and hCER104 CD4+ T cells were administered at a 1:1 ratio. Tumor volume was measured over time by bioluminescence imaging (see, FIGS. 74A-

74B). HPV E7 CD8+ T cells exhibited anti-tumor response as compared to untreated controls in xenograft model. Addition of hCER104 CD4+ T cells to HPV E7 CD8+ T cells enhanced tumor killing in vivo.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including but not limited to U.S. Provisional Patent Application No. 62/649,541, filed Mar. 28, 2018, U.S. Provisional Patent Application No. 62/652,838, filed Apr. 4, 2018, and U.S. Provisional Patent Application No. 62/734,863, filed Sep. 21, 2018, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A combination cellular immunotherapy composition comprising:
   (a) a first composition comprising a CD4+ T cell comprising a chimeric engulfment receptor (CER) comprising:
      an extracellular domain comprising a Tim4 extracellular domain that binds to phosphatidylserine,
      an engulfment signaling domain, wherein the engulfment signaling domain comprises a TLR signaling domain, a TRAF2 signaling domain, a TRAF6 signaling domain, a DAP12 signaling domain, a NFAM1 signaling domain, a Baff-R signaling domain, or a CD79b signaling domain, and
      a transmembrane domain positioned between and connecting the extracellular domain and the engulfment signaling domain; and
   (b) a second composition comprising a CD8+ T cell comprising:
      (i) a chimeric antigen receptor (CAR) comprising:
      an extracellular domain comprising an antibody binding domain that binds to a target antigen,
      an intracellular signaling domain, and
      a transmembrane domain positioned between and connecting the extracellular domain and the intracellular signaling domain; or
      (ii) a recombinant T cell receptor (TCR) that binds to a target antigen.

2. The combination cellular immunotherapy composition of claim 1, wherein:
   (a) the CAR antibody binding domain comprises a scFv; and/or
   (b) the CAR extracellular domain further comprises a spacer domain between the antibody binding domain and the transmembrane domain.

3. The combination cellular immunotherapy composition of claim 1, wherein:
   (a) the CAR transmembrane domain comprises a CD28, CD2, CD4, CD8, CD3ε, CD3δ, CD3ζ, CD25, CD27, CD40, CD79A, CD79B, CD80, CD86, CD95 (Fas), CD134 (OX40), CD137 (4-1BB), CD150 (SLAMF1), CD152 (CTLA4), CD200R, CD223 (LAG3), CD270 (HVEM), CD272 (BTLA), CD273 (PD-L2), CD274 (PD-L1), CD278 (ICOS), CD279 (PD-1), CD300, CD357 (GITR), A2aR, DAP10, FcRα, FcRβ, FcRγ, Fyn, GAL9, KIR, Lck, LAT, LRP, NKG2D, NOTCH1, NOTCH2, NOTCH3, NOTCH4, PTCH2, ROR2, Ryk, Slp76, SIRPα, pTα, TCRα, TCRβ, TIM3, TRIM, LPA5, or Zap70 transmembrane domain;
   (b) the CAR intracellular signaling domain comprises an ITAM-containing activating signaling domain selected from CD3ζ, CD3γ, CD3δ, CD3ε, CD5, CD22, CD79a, CD278 (ICOS), DAP10, DAP12, and CD66d signaling domain;
   (c) the CAR intracellular signaling domain comprises a first costimulatory signaling domain selected from CD27, CD28, 4-1BB, OX40, CD30, CD40, PD-1, ICOS, lymphocyte function-associated antigen-1 (LFA-1), CD2, CD7, LIGHT, NKG2C, and B7-H3 signaling domain;
   or any combination of (a)-(c).

4. The combination cellular immunotherapy composition of claim 3, wherein the CAR intracellular signaling domain comprises a second costimulatory signaling domain selected from CD27, CD28, 4-1BB, OX40, CD30, CD40, PD-1, ICOS, lymphocyte function-associated antigen-1 (LFA-1), CD2, CD7, LIGHT, NKG2C, and B7-H3 signaling domain.

5. The combination cellular immunotherapy composition of claim 1, wherein the CAR is a first generation CAR, second generation CAR, third generation CAR, or TCR-CAR.

6. The combination cellular immunotherapy composition of claim 1, wherein the target antigen of the CAR is a tumor antigen.

7. The combination cellular immunotherapy composition of claim 6, wherein the target antigen of the CAR is a tumor antigen selected from the group consisting of CD138, CD38, CD33, CD123, CD72, CD79a, CD79b, mesothelin, PSMA, BCMA, ROR1, MUC-16, L1CAM, CD22, CD19, CD20, CD23, CD24, CD37, CD30, CA125, CD56, c-Met, EGFR, GD-3, HPV E6, HPV E7, MUC-1, HER2, folate receptor α, CD97, CD171, CD179a, CD44v6, WT1, VEGF-α, VEGFR1, IL-13Rα1, IL-13Rα2, IL-11Rα, PSA, FcRH5, NKG2D ligand, NY-ESO-1, TAG-72, CEA, ephrin A2, ephrin B2, Lewis A antigen, Lewis Y antigen, MAGE, MAGE-A1, RAGE-1, folate receptor β, EGFRviii, VEGFR-2, LGR5, SSX2, AKAP-4, FLT3, fucosyl GM1, GM3, o-acetyl-GD2, and GD2.

8. The combination cellular immunotherapy composition of claim 1, wherein the recombinant TCR is an αβTCR, γδTCR, enhanced affinity TCR, soluble TCR, or single chain TCR.

9. The combination cellular immunotherapy composition of claim 1, wherein the target antigen of the recombinant TCR is WT-1, mesothelin, MART-1, NY-ESO-1, MAGE-A3, HPV E7, survivin, a Fetoprotein, or a tumor neoantigen.

10. The combination cellular immunotherapy composition of claim 1, wherein:
(a) the CER extracellular domain further comprises a spacer domain between the Tim4 extracellular domain and the transmembrane domain.

11. The combination cellular immunotherapy composition of claim 1, wherein:
the CER transmembrane domain comprises a Tim1, Tim4, Tim3, FcR, CD8, CD28, MERTK, Axl, Tyro3, BAI1, CD4, DAP12, MRC1, FcR, TLR1, TLR2, TLR3, TLR4, TLR5, TLR6, TLR7, TLR8, or TLR9 transmembrane domain.

12. The combination cellular immunotherapy composition of claim 1, wherein the CER engulfment signaling domain comprises a primary engulfment signaling domain and a secondary engulfment signaling domain.

13. The combination cellular immunotherapy composition of claim 12, wherein the CER primary engulfment signaling domain and secondary engulfment signaling domain are each independently selected from MERTK, Tyro3, ItgB5, MRC1, ELMO, Axl, Syk, MyD88, FcγR1, FcγR2A, FcγR2B2, FcγR2C, FcγR3A, FcεR1, FcαR1, BAFF-R, DAP12, NFAM1, CD79b, TLR1, TLR2, TLR3, TLR4, TLR5, TLR6, TLR7, TLR8, TLR9, Traf6, Traf2, and Traf3 signaling domain.

14. The combination cellular immunotherapy composition of claim 1, wherein the CER comprises the amino acid sequence of any one of SEQ ID NOS: 94, 102 103, 105, 106, 112, 113, 95, 114, 96, 115, 116, 117, 97, 118, 98, 119, 99, 120, 121, 122, 123, 124, 125, 126, 129, 130, 131, 132, 133, 134, 135, 136, 137, 138, 139, 140, 141, 142, 143, 144, 145, 146, 147, 148, 149, 150, 151, 152, 153, 154, 155, 173, 156, 157, 163, 164, 165, 166, 167, 169, 170, 171, 172, 174, 175, 176, 177, 178, 179, 180, and 181.

15. The combination cellular immunotherapy composition of claim 1, wherein:
(a) the CD4+ T cell is a naïve CD4+ T cell, an effector memory CD4+ T cell, or a central memory CD4+ T cell; and/or
(b) the CD8+ T cell is a naïve CD8+ T cell, an effector memory CD8+ T cell, or a central memory CD8+ T cell.

16. The combination cellular immunotherapy composition of claim 1, wherein the CD4+ T cell, CD8+ T cell, or both are human.

17. The combination cellular immunotherapy composition of claim 1, wherein the ratio of CD4+ T cells to CD8+ T cells in the composition is about 1:1, 1:2, 1:4, 1:8, 1:10, or 1:20.

18. The combination cellular immunotherapy composition of claim 1, wherein the first composition and second composition each further comprises a pharmaceutically acceptable carrier.

19. The combination cellular immunotherapy composition of claim 1, wherein the Tim4 extracellular domain comprises SEQ ID NO:90 or amino acids 25-314 of SEQ ID NO:90.

20. The combination cellular immunotherapy composition of claim 1, wherein the TLR signaling domain comprises a TLR1, TLR2, TLR3, TLR4, TLR5, TLR6, TLR7, TLR8, or TLR9 signaling domain.

21. A method of treating a subject having cancer comprising administering an effective amount of a combination cellular immunotherapy composition of claim 1 to the subject.

22. The method of claim 21, wherein the cancer is a solid tumor, melanoma, non-small cell lung cancer, renal cell carcinoma, renal cancer, a hematological cancer, prostate cancer, castration-resistant prostate cancer, colon cancer, rectal cancer, gastric cancer, esophageal cancer, bladder cancer, head and neck cancer, thyroid cancer, breast cancer, triple-negative breast cancer, ovarian cancer, cervical cancer, lung cancer, urothelial cancer, pancreatic cancer, glioblastoma, hepatocellular cancer, myeloma, multiple myeloma, leukemia, Hodgkin's lymphoma, non-Hodgkin's lymphoma, myelodysplastic syndrome, brain cancer, CNS cancer, or malignant glioma.

23. The method of claim 21, wherein the CD4+ T cell is autologous or allogeneic to the subject, the CD8+ T cell is autologous or allogeneic to the subject, or both.

24. The method of claim 21, wherein the combination cellular immunotherapy composition is administered in combination with an additional therapeutic agent.

25. The method of claim 24, wherein the additional therapeutic agent is an antibody, radiation therapy, chemotherapeutic agent, immune checkpoint molecule inhibitor therapy, small molecule therapy, cellular immunotherapy, oncolytic virus, electropulse therapy, UV light therapy high intensity focused ultrasound therapy, oncolytic virus, peptide, hormone, aptamer, anti-inflammatory agent, antibiotic, anti-fungal agent, or anti-viral agent.

26. The method of claim 21, wherein the first composition and second composition are administered concurrently or sequentially to the subject.

* * * * *

```
                      SEQUENCE LISTING

<160> NUMBER OF SEQ ID NOS: 181

<210> SEQ ID NO 1
    <211> LENGTH: 12
    <212> TYPE: PRT
    <213> ORGANISM: Artificial Sequence
    <220> FEATURE:
    <223> OTHER INFORMATION: modified IgG4 hinge

<400> SEQUENCE: 1

Glu Ser Lys Tyr Gly Pro Pro Cys Pro Pro Cys Pro
    1               5                   10

<210> SEQ ID NO 2
    <211> LENGTH: 13
    <212> TYPE: PRT
    <213> ORGANISM: Homo sapiens
    <220> FEATURE:
    <223> OTHER INFORMATION: TLR4 juxtamembrane domain

<400> SEQUENCE: 2

Pro Val Leu Ser Leu Asn Ile Thr Cys Gln Met Asn Lys
    1               5                   10

<210> SEQ ID NO 3
    <211> LENGTH: 46
    <212> TYPE: PRT
    <213> ORGANISM: Homo sapiens
    <220> FEATURE:
    <223> OTHER INFORMATION: MRC1 signaling domain

<400> SEQUENCE: 3

Tyr Lys Lys Arg Arg Val His Leu Pro Gln Glu Gly Ala Phe Glu Asn
    1               5                   10                  15

Thr Leu Tyr Phe Asn Ser Gln Ser Ser Pro Gly Thr Ser Asp Met Lys
                20                  25                  30

Asp Leu Val Gly Asn Ile Glu Gln Asn Glu His Ser Val Ile
            35                  40                  45

<210> SEQ ID NO 4
    <211> LENGTH: 473
    <212> TYPE: PRT
    <213> ORGANISM: Homo sapiens
    <220> FEATURE:
    <223> OTHER INFORMATION: MERTK signaling domain

<400> SEQUENCE: 4

Lys Arg Val Gln Glu Thr Lys Phe Gly Asn Ala Phe Thr Glu Asp
    1               5                   10                  15

Ser Glu Leu Val Val Asn Tyr Ile Ala Lys Ser Phe Cys Arg Arg
                20                  25                  30
```

```
Ala Ile Glu Leu Thr Leu His Ser Leu Gly Val Ser Glu Glu Leu Gln
         35                  40                  45

Asn Lys Leu Glu Asp Val Val Ile Asp Arg Asn Leu Leu Ile Leu Gly
     50                  55                  60

Lys Ile Leu Gly Glu Gly Glu Phe Gly Ser Val Met Glu Gly Asn Leu
 65                  70                  75                  80

Lys Gln Glu Asp Gly Thr Ser Leu Lys Val Ala Val Lys Thr Met Lys
                 85                  90                  95

Leu Asp Asn Ser Ser Gln Arg Glu Ile Glu Glu Phe Leu Ser Glu Ala
                100                 105                 110

Ala Cys Met Lys Asp Phe Ser His Pro Asn Val Ile Arg Leu Leu Gly
            115                 120                 125

Val Cys Ile Glu Met Ser Ser Gln Gly Ile Pro Lys Pro Met Val Ile
        130                 135                 140

Leu Pro Phe Met Lys Tyr Gly Asp Leu His Thr Tyr Leu Leu Tyr Ser
145                 150                 155                 160

Arg Leu Glu Thr Gly Pro Lys His Ile Pro Leu Gln Thr Leu Leu Lys
                165                 170                 175

Phe Met Val Asp Ile Ala Leu Gly Met Glu Tyr Leu Ser Asn Arg Asn
            180                 185                 190

Phe Leu His Arg Asp Leu Ala Ala Arg Asn Cys Met Leu Arg Asp Asp
        195                 200                 205

Met Thr Val Cys Val Ala Asp Phe Gly Leu Ser Lys Lys Ile Tyr Ser
    210                 215                 220

Gly Asp Tyr Tyr Arg Gln Gly Arg Ile Ala Lys Met Pro Val Lys Trp
225                 230                 235                 240

Ile Ala Ile Glu Ser Leu Ala Asp Arg Val Tyr Thr Ser Lys Ser Asp
                245                 250                 255

Val Trp Ala Phe Gly Val Thr Met Trp Glu Ile Ala Thr Arg Gly Met
            260                 265                 270

Thr Pro Tyr Pro Gly Val Gln Asn His Glu Met Tyr Asp Tyr Leu Leu
        275                 280                 285

His Gly His Arg Leu Lys Gln Pro Glu Asp Cys Leu Asp Glu Leu Tyr
    290                 295                 300

Glu Ile Met Tyr Ser Cys Trp Arg Thr Asp Pro Leu Asp Arg Pro Thr
305                 310                 315                 320

Phe Ser Val Leu Arg Leu Gln Leu Glu Lys Leu Leu Glu Ser Leu Pro
                325                 330                 335

Asp Val Arg Asn Gln Ala Asp Val Ile Tyr Val Asn Thr Gln Leu Leu
            340                 345                 350

Glu Ser Ser Glu Gly Leu Ala Gln Gly Ser Thr Leu Ala Pro Leu Asp
        355                 360                 365

Leu Asn Ile Asp Pro Asp Ser Ile Ile Ala Ser Cys Thr Pro Arg Ala
    370                 375                 380

Ala Ile Ser Val Val Thr Ala Glu Val His Asp Ser Lys Pro His Glu
385                 390                 395                 400

Gly Arg Tyr Ile Leu Asn Gly Gly Ser Glu Glu Trp Glu Asp Leu Thr
                405                 410                 415

Ser Ala Pro Ser Ala Ala Val Thr Ala Glu Lys Asn Ser Val Leu Pro
            420                 425                 430

Gly Glu Arg Leu Val Arg Asn Gly Val Ser Trp Ser His Ser Ser Met
        435                 440                 445
```

```
Leu Pro Leu Gly Ser Ser Leu Pro Asp Glu Leu Leu Phe Ala Asp Asp
    450             455                 460
Ser Ser Glu Gly Ser Glu Val Leu Met
465             470

<210> SEQ ID NO 5
<211> LENGTH: 476
<212> TYPE: PRT
<213> ORGANISM: Mus musculus
<220> FEATURE:
<223> OTHER INFORMATION: MERTK signaling domain

<400> SEQUENCE: 5

Ala Leu Arg Arg Val Gln Glu Thr Lys Phe Gly Gly Ala Phe Ser
1               5                   10                  15
Glu Glu Asp Ser Gln Leu Val Val Asn Tyr Arg Ala Lys Lys Ser Phe
                20                  25                  30
Cys Arg Arg Ala Ile Glu Leu Thr Leu Gln Ser Leu Gly Val Ser Glu
            35                  40                  45
Glu Leu Gln Asn Lys Leu Glu Asp Val Val Ile Asp Arg Asn Leu Leu
        50                  55                  60
Val Leu Gly Lys Val Leu Gly Glu Gly Glu Phe Gly Ser Val Met Glu
65                  70                  75                  80
Gly Asn Leu Lys Gln Glu Asp Gly Thr Ser Gln Lys Val Ala Val Lys
                85                  90                  95
Thr Met Lys Leu Asp Asn Phe Ser Gln Arg Glu Ile Glu Glu Phe Leu
            100                 105                 110
Ser Glu Ala Ala Cys Met Lys Asp Phe Asn His Pro Asn Val Ile Arg
        115                 120                 125
Leu Leu Gly Val Cys Ile Glu Leu Ser Ser Gln Gly Ile Pro Lys Pro
130                 135                 140
Met Val Ile Leu Pro Phe Met Lys Tyr Gly Asp Leu His Thr Phe Leu
145                 150                 155                 160
Leu Tyr Ser Arg Leu Asn Thr Gly Pro Lys Tyr Ile His Leu Gln Thr
                165                 170                 175
Leu Leu Lys Phe Met Met Asp Ile Ala Gln Gly Met Glu Tyr Leu Ser
            180                 185                 190
Asn Arg Asn Phe Leu His Arg Asp Leu Ala Ala Arg Asn Cys Met Leu
        195                 200                 205
Arg Asp Asp Met Thr Val Cys Val Ala Asp Phe Gly Leu Ser Lys Lys
210                 215                 220
Ile Tyr Ser Gly Asp Tyr Tyr Arg Gln Gly Arg Ile Ala Lys Met Pro
225                 230                 235                 240
Val Lys Trp Ile Ala Ile Glu Ser Leu Ala Asp Arg Val Tyr Thr Ser
                245                 250                 255
Lys Ser Asp Val Trp Ala Phe Gly Val Thr Met Trp Glu Ile Thr Thr
            260                 265                 270
Arg Gly Met Thr Pro Tyr Pro Gly Val Gln Asn His Glu Met Tyr Asp
        275                 280                 285
Tyr Leu Leu His Gly His Arg Leu Lys Gln Pro Glu Asp Cys Leu Asp
        290                 295                 300
Glu Leu Tyr Asp Ile Met Tyr Ser Cys Trp Ser Ala Asp Pro Leu Asp
305                 310                 315                 320
Arg Pro Thr Phe Ser Val Leu Arg Leu Gln Leu Glu Lys Leu Ser Glu
                325                 330                 335
```

```
Ser Leu Pro Asp Ala Gln Asp Lys Glu Ser Ile Ile Tyr Ile Asn Thr
            340                 345                 350

Gln Leu Leu Glu Ser Cys Glu Gly Ile Ala Asn Gly Pro Ser Leu Thr
            355                 360                 365

Gly Leu Asp Met Asn Ile Asp Pro Asp Ser Ile Ile Ala Ser Cys Thr
        370                 375                 380

Pro Gly Ala Ala Val Ser Val Val Thr Ala Glu Val His Glu Asn Asn
385                 390                 395                 400

Leu Arg Glu Glu Arg Tyr Ile Leu Asn Gly Gly Asn Glu Glu Trp Glu
                405                 410                 415

Asp Val Ser Ser Thr Pro Phe Ala Ala Val Thr Pro Glu Lys Asp Gly
            420                 425                 430

Val Leu Pro Glu Asp Arg Leu Thr Lys Asn Gly Val Ser Trp Ser His
            435                 440                 445

His Ser Thr Leu Pro Leu Gly Ser Pro Ser Pro Asp Glu Leu Leu Phe
        450                 455                 460

Val Asp Asp Ser Leu Glu Asp Ser Glu Val Leu Met
465                 470                 475

<210> SEQ ID NO 6
<211> LENGTH: 440
<212> TYPE: PRT
<213> ORGANISM: Homo sapiens
<220> FEATURE:
<223> OTHER INFORMATION: Tyro3 signaling domain

<400> SEQUENCE: 6

Leu Arg Lys Arg Arg Lys Glu Thr Arg Phe Gly Gln Ala Phe Asp Ser
1               5                   10                  15

Val Met Ala Arg Gly Glu Pro Ala Val His Phe Arg Ala Ala Arg Ser
            20                  25                  30

Phe Asn Arg Glu Arg Pro Glu Arg Ile Glu Ala Thr Leu Asp Ser Leu
        35                  40                  45

Gly Ile Ser Asp Glu Leu Lys Glu Lys Leu Glu Asp Val Leu Ile Pro
    50                  55                  60

Glu Gln Gln Phe Thr Leu Gly Arg Met Leu Gly Lys Gly Glu Phe Gly
65                  70                  75                  80

Ser Val Arg Glu Ala Gln Leu Lys Gln Glu Asp Gly Ser Phe Val Lys
                85                  90                  95

Val Ala Val Lys Met Leu Lys Ala Asp Ile Ile Ala Ser Ser Asp Ile
            100                 105                 110

Glu Glu Phe Leu Arg Glu Ala Ala Cys Met Lys Glu Phe Asp His Pro
        115                 120                 125

His Val Ala Lys Leu Val Gly Val Ser Leu Arg Ser Arg Ala Lys Gly
    130                 135                 140

Arg Leu Pro Ile Pro Met Val Ile Leu Pro Phe Met Lys His Gly Asp
145                 150                 155                 160

Leu His Ala Phe Leu Leu Ala Ser Arg Ile Gly Glu Asn Pro Phe Asn
                165                 170                 175

Leu Pro Leu Gln Thr Leu Ile Arg Phe Met Val Asp Ile Ala Cys Gly
            180                 185                 190

Met Glu Tyr Leu Ser Ser Arg Asn Phe Ile His Arg Asp Leu Ala Ala
        195                 200                 205

Arg Asn Cys Met Leu Ala Glu Asp Met Thr Val Cys Val Ala Asp Phe
    210                 215                 220
```

```
Gly Leu Ser Arg Lys Ile Tyr Ser Gly Asp Tyr Arg Gln Gly Cys
225                 230                 235                 240

Ala Ser Lys Leu Pro Val Lys Trp Leu Ala Leu Glu Ser Leu Ala Asp
            245                 250                 255

Asn Leu Tyr Thr Val Gln Ser Asp Val Trp Ala Phe Gly Val Thr Met
                260                 265                 270

Trp Glu Ile Met Thr Arg Gly Gln Thr Pro Tyr Ala Gly Ile Glu Asn
            275                 280                 285

Ala Glu Ile Tyr Asn Tyr Leu Ile Gly Gly Asn Arg Leu Lys Gln Pro
        290                 295                 300

Pro Glu Cys Met Glu Asp Val Tyr Asp Leu Met Tyr Gln Cys Trp Ser
305                 310                 315                 320

Ala Asp Pro Lys Gln Arg Pro Ser Phe Thr Cys Leu Arg Met Glu Leu
            325                 330                 335

Glu Asn Ile Leu Gly Gln Leu Ser Val Leu Ser Ala Ser Gln Asp Pro
            340                 345                 350

Leu Tyr Ile Asn Ile Glu Arg Ala Glu Pro Thr Ala Gly Gly Ser
        355                 360                 365

Leu Glu Leu Pro Gly Arg Asp Gln Pro Tyr Ser Gly Ala Gly Asp Gly
370                 375                 380

Ser Gly Met Gly Ala Val Gly Gly Thr Pro Ser Asp Cys Arg Tyr Ile
385                 390                 395                 400

Leu Thr Pro Gly Gly Leu Ala Glu Gln Pro Gly Gln Ala Glu His Gln
                405                 410                 415

Pro Glu Ser Pro Leu Asn Glu Thr Gln Arg Leu Leu Leu Leu Gln Gln
            420                 425                 430

Gly Leu Leu Pro His Ser Ser Cys
        435                 440

<210> SEQ ID NO 7
<211> LENGTH: 422
<212> TYPE: PRT
<213> ORGANISM: Homo sapiens
<220> FEATURE:
<223> OTHER INFORMATION: Axl signaling domain

<400> SEQUENCE: 7

His Arg Arg Lys Lys Glu Thr Arg Tyr Gly Glu Val Phe Glu Pro Thr
1               5                   10                  15

Val Glu Arg Gly Glu Leu Val Val Arg Tyr Arg Val Arg Lys Ser Tyr
            20                  25                  30

Ser Arg Arg Thr Thr Glu Ala Thr Leu Asn Ser Leu Gly Ile Ser Glu
        35                  40                  45

Glu Leu Lys Glu Lys Leu Arg Asp Val Met Val Asp Arg His Lys Val
    50                  55                  60

Ala Leu Gly Lys Thr Leu Gly Glu Gly Glu Phe Gly Ala Val Met Glu
65                  70                  75                  80

Gly Gln Leu Asn Gln Asp Asp Ser Ile Leu Lys Val Ala Val Lys Thr
                85                  90                  95

Met Lys Ile Ala Ile Cys Thr Arg Ser Glu Leu Glu Asp Phe Leu Ser
            100                 105                 110

Glu Ala Val Cys Met Lys Glu Phe Asp His Pro Asn Val Met Arg Leu
        115                 120                 125

Ile Gly Val Cys Phe Gln Gly Ser Glu Arg Glu Ser Phe Pro Ala Pro
    130                 135                 140
```

```
Val Val Ile Leu Pro Phe Met Lys His Gly Asp Leu His Ser Phe Leu
145                 150                 155                 160

Leu Tyr Ser Arg Leu Gly Asp Gln Pro Val Tyr Leu Pro Thr Gln Met
                165                 170                 175

Leu Val Lys Phe Met Ala Asp Ile Ala Ser Gly Met Glu Tyr Leu Ser
            180                 185                 190

Thr Lys Arg Phe Ile His Arg Asp Leu Ala Ala Arg Asn Cys Met Leu
        195                 200                 205

Asn Glu Asn Met Ser Val Cys Val Ala Asp Phe Gly Leu Ser Lys Lys
    210                 215                 220

Ile Tyr Asn Gly Asp Tyr Tyr Arg Gln Gly Arg Ile Ala Lys Met Pro
225                 230                 235                 240

Val Lys Trp Ile Ala Ile Glu Ser Leu Ala Asp Arg Val Tyr Thr Ser
                245                 250                 255

Lys Ser Asp Val Trp Ser Phe Gly Val Thr Met Trp Glu Ile Ala Thr
            260                 265                 270

Arg Gly Gln Thr Pro Tyr Pro Gly Val Glu Asn Ser Glu Ile Tyr Asp
        275                 280                 285

Tyr Leu Arg Gln Gly Asn Arg Leu Lys Gln Pro Ala Asp Cys Leu Asp
    290                 295                 300

Gly Leu Tyr Ala Leu Met Ser Arg Cys Trp Glu Leu Asn Pro Gln Asp
305                 310                 315                 320

Arg Pro Ser Phe Thr Glu Leu Arg Glu Asp Leu Glu Asn Thr Leu Lys
                325                 330                 335

Ala Leu Pro Pro Ala Gln Glu Pro Asp Glu Ile Leu Tyr Val Asn Met
            340                 345                 350

Asp Glu Gly Gly Gly Tyr Pro Glu Pro Pro Gly Ala Ala Gly Gly Ala
        355                 360                 365

Asp Pro Pro Thr Gln Pro Asp Pro Lys Asp Ser Cys Ser Cys Leu Thr
    370                 375                 380

Ala Ala Glu Val His Pro Ala Gly Arg Tyr Val Leu Cys Pro Ser Thr
385                 390                 395                 400

Thr Pro Ser Pro Ala Gln Pro Ala Asp Arg Gly Ser Pro Ala Ala Pro
                405                 410                 415

Gly Gln Glu Asp Gly Ala
            420

<210> SEQ ID NO 8
<211> LENGTH: 727
<212> TYPE: PRT
<213> ORGANISM: Homo sapiens
<220> FEATURE:
<223> OTHER INFORMATION: ELMO signaling domain

<400> SEQUENCE: 8

Met Pro Pro Pro Ala Asp Ile Val Lys Val Ala Ile Glu Trp Pro Gly
1               5                   10                  15

Ala Tyr Pro Lys Leu Met Glu Ile Asp Gln Lys Lys Pro Leu Ser Ala
                20                  25                  30

Ile Ile Lys Glu Val Cys Asp Gly Trp Ser Leu Ala Asn His Glu Tyr
            35                  40                  45

Phe Ala Leu Gln His Ala Asp Ser Ser Asn Phe Tyr Ile Thr Glu Lys
        50                  55                  60

Asn Arg Asn Glu Ile Lys Asn Gly Thr Ile Leu Arg Leu Thr Thr Ser
65                  70                  75                  80
```

-continued

```
Pro Ala Gln Asn Ala Gln Gln Leu His Glu Arg Ile Gln Ser Ser Ser
                85                  90                  95
Met Asp Ala Lys Leu Glu Ala Leu Lys Asp Leu Ala Ser Leu Ser Arg
            100                 105                 110
Asp Val Thr Phe Ala Gln Glu Phe Ile Asn Leu Asp Gly Ile Ser Leu
        115                 120                 125
Leu Thr Gln Met Val Glu Ser Gly Thr Glu Arg Tyr Gln Lys Leu Gln
    130                 135                 140
Lys Ile Met Lys Pro Cys Phe Gly Asp Met Leu Ser Phe Thr Leu Thr
145                 150                 155                 160
Ala Phe Val Glu Leu Met Asp His Gly Ile Val Ser Trp Asp Thr Phe
                165                 170                 175
Ser Val Ala Phe Ile Lys Lys Ile Ala Ser Phe Val Asn Lys Ser Ala
            180                 185                 190
Ile Asp Ile Ser Ile Leu Gln Arg Ser Leu Ala Ile Leu Glu Ser Met
        195                 200                 205
Val Leu Asn Ser His Asp Leu Tyr Gln Lys Val Ala Gln Glu Ile Thr
    210                 215                 220
Ile Gly Gln Leu Ile Pro His Leu Gln Gly Ser Asp Gln Glu Ile Gln
225                 230                 235                 240
Thr Tyr Thr Ile Ala Val Ile Asn Ala Leu Phe Leu Lys Ala Pro Asp
                245                 250                 255
Glu Arg Arg Gln Glu Met Ala Asn Ile Leu Ala Gln Lys Gln Leu Arg
            260                 265                 270
Ser Ile Ile Leu Thr His Val Ile Arg Ala Gln Arg Ala Ile Asn Asn
        275                 280                 285
Glu Met Ala His Gln Leu Tyr Val Leu Gln Val Leu Thr Phe Asn Leu
    290                 295                 300
Leu Glu Asp Arg Met Met Thr Lys Met Asp Pro Gln Asp Gln Ala Gln
305                 310                 315                 320
Arg Asp Ile Ile Phe Glu Leu Arg Arg Ile Ala Phe Asp Ala Glu Ser
                325                 330                 335
Glu Pro Asn Asn Ser Ser Gly Ser Met Glu Lys Arg Lys Ser Met Tyr
            340                 345                 350
Thr Arg Asp Tyr Lys Lys Leu Gly Phe Ile Asn His Val Asn Pro Ala
        355                 360                 365
Met Asp Phe Thr Gln Thr Pro Pro Gly Met Leu Ala Leu Asp Asn Met
    370                 375                 380
Leu Tyr Phe Ala Lys His His Gln Asp Ala Tyr Ile Arg Ile Val Leu
385                 390                 395                 400
Glu Asn Ser Ser Arg Glu Asp Lys His Glu Cys Pro Phe Gly Arg Ser
                405                 410                 415
Ser Ile Glu Leu Thr Lys Met Leu Cys Glu Ile Leu Lys Val Gly Glu
            420                 425                 430
Leu Pro Ser Glu Thr Cys Asn Asp Phe His Pro Met Phe Phe Thr His
        435                 440                 445
Asp Arg Ser Phe Glu Glu Phe Phe Cys Ile Cys Ile Gln Leu Leu Asn
    450                 455                 460
Lys Thr Trp Lys Glu Met Arg Ala Thr Ser Glu Asp Phe Asn Lys Val
465                 470                 475                 480
Met Gln Val Val Lys Glu Gln Val Met Arg Ala Leu Thr Thr Lys Pro
                485                 490                 495
Ser Ser Leu Asp Gln Phe Lys Ser Lys Leu Gln Asn Leu Ser Tyr Thr
```

```
                500                 505                 510
Glu Ile Leu Lys Ile Arg Gln Ser Glu Arg Met Asn Gln Glu Asp Phe
            515                 520                 525

Gln Ser Arg Pro Ile Leu Glu Leu Lys Glu Lys Ile Gln Pro Glu Ile
530                 535                 540

Leu Glu Leu Ile Lys Gln Gln Arg Leu Asn Arg Leu Val Glu Gly Thr
545                 550                 555                 560

Cys Phe Arg Lys Leu Asn Ala Arg Arg Gln Asp Lys Phe Trp Tyr
            565                 570                 575

Cys Arg Leu Ser Pro Asn His Lys Val Leu His Tyr Gly Asp Leu Glu
            580                 585                 590

Glu Ser Pro Gln Gly Glu Val Pro His Asp Ser Leu Gln Asp Lys Leu
            595                 600                 605

Pro Val Ala Asp Ile Lys Ala Val Val Thr Gly Lys Asp Cys Pro His
            610                 615                 620

Met Lys Glu Lys Gly Ala Leu Lys Gln Asn Lys Glu Val Leu Glu Leu
625                 630                 635                 640

Ala Phe Ser Ile Leu Tyr Asp Ser Asn Cys Gln Leu Asn Phe Ile Ala
            645                 650                 655

Pro Asp Lys His Glu Tyr Cys Ile Trp Thr Asp Gly Leu Asn Ala Leu
            660                 665                 670

Leu Gly Lys Asp Met Met Ser Asp Leu Thr Arg Asn Asp Leu Asp Thr
            675                 680                 685

Leu Leu Ser Met Glu Ile Lys Leu Arg Leu Asp Leu Glu Asn Ile
            690                 695                 700

Gln Ile Pro Asp Ala Pro Pro Ile Pro Lys Glu Pro Ser Asn Tyr
705                 710                 715                 720

Asp Phe Val Tyr Asp Cys Asn
            725

<210> SEQ ID NO 9
<211> LENGTH: 522
<212> TYPE: PRT
<213> ORGANISM: Homo sapiens
<220> FEATURE:
<223> OTHER INFORMATION: Traf6 signaling domain - full length

<400> SEQUENCE: 9

Met Ser Leu Leu Asn Cys Glu Asn Ser Cys Gly Ser Ser Gln Ser Glu
1               5                   10                  15

Ser Asp Cys Cys Val Ala Met Ala Ser Ser Cys Ser Ala Val Thr Lys
            20                  25                  30

Asp Asp Ser Val Gly Gly Thr Ala Ser Thr Gly Asn Leu Ser Ser Ser
            35                  40                  45

Phe Met Glu Glu Ile Gln Gly Tyr Asp Val Glu Phe Asp Pro Pro Leu
50                  55                  60

Glu Ser Lys Tyr Glu Cys Pro Ile Cys Leu Met Ala Leu Arg Glu Ala
65                  70                  75                  80

Val Gln Thr Pro Cys Gly His Arg Phe Cys Lys Ala Cys Ile Ile Lys
            85                  90                  95

Ser Ile Arg Asp Ala Gly His Lys Cys Pro Val Asp Asn Glu Ile Leu
            100                 105                 110

Leu Glu Asn Gln Leu Phe Pro Asp Asn Phe Ala Lys Arg Glu Ile Leu
            115                 120                 125

Ser Leu Met Val Lys Cys Pro Asn Glu Gly Cys Leu His Lys Met Glu
```

```
            130                 135                 140
Leu Arg His Leu Glu Asp His Gln Ala His Cys Glu Phe Ala Leu Met
145                 150                 155                 160

Asp Cys Pro Gln Cys Gln Arg Pro Phe Gln Lys Phe His Ile Asn Ile
                165                 170                 175

His Ile Leu Lys Asp Cys Pro Arg Arg Gln Val Ser Cys Asp Asn Cys
            180                 185                 190

Ala Ala Ser Met Ala Phe Glu Asp Lys Glu Ile His Asp Gln Asn Cys
        195                 200                 205

Pro Leu Ala Asn Val Ile Cys Glu Tyr Cys Asn Thr Ile Leu Ile Arg
210                 215                 220

Glu Gln Met Pro Asn His Tyr Asp Leu Asp Cys Pro Thr Ala Pro Ile
225                 230                 235                 240

Pro Cys Thr Phe Ser Thr Phe Gly Cys His Glu Lys Met Gln Arg Asn
                245                 250                 255

His Leu Ala Arg His Leu Gln Glu Asn Thr Gln Ser His Met Arg Met
            260                 265                 270

Leu Ala Gln Ala Val His Ser Leu Ser Val Ile Pro Asp Ser Gly Tyr
        275                 280                 285

Ile Ser Glu Val Arg Asn Phe Gln Glu Thr Ile His Gln Leu Glu Gly
290                 295                 300

Arg Leu Val Arg Gln Asp His Gln Ile Arg Glu Leu Thr Ala Lys Met
305                 310                 315                 320

Glu Thr Gln Ser Met Tyr Val Ser Glu Leu Lys Arg Thr Ile Arg Thr
                325                 330                 335

Leu Glu Asp Lys Val Ala Glu Ile Glu Ala Gln Gln Cys Asn Gly Ile
            340                 345                 350

Tyr Ile Trp Lys Ile Gly Asn Phe Gly Met His Leu Lys Cys Gln Glu
        355                 360                 365

Glu Glu Lys Pro Val Val Ile His Ser Pro Gly Phe Tyr Thr Gly Lys
370                 375                 380

Pro Gly Tyr Lys Leu Cys Met Arg Leu His Leu Gln Leu Pro Thr Ala
385                 390                 395                 400

Gln Arg Cys Ala Asn Tyr Ile Ser Leu Phe Val His Thr Met Gln Gly
                405                 410                 415

Glu Tyr Asp Ser His Leu Pro Trp Pro Phe Gln Gly Thr Ile Arg Leu
            420                 425                 430

Thr Ile Leu Asp Gln Ser Glu Ala Pro Val Arg Gln Asn His Glu Glu
        435                 440                 445

Ile Met Asp Ala Lys Pro Glu Leu Leu Ala Phe Gln Arg Pro Thr Ile
450                 455                 460

Pro Arg Asn Pro Lys Gly Phe Gly Tyr Val Thr Phe Met His Leu Glu
465                 470                 475                 480

Ala Leu Arg Gln Arg Thr Phe Ile Lys Asp Asp Thr Leu Leu Val Arg
                485                 490                 495

Cys Glu Val Ser Thr Arg Phe Asp Met Gly Ser Leu Arg Arg Glu Gly
            500                 505                 510

Phe Gln Pro Arg Ser Thr Asp Ala Gly Val
        515                 520

<210> SEQ ID NO 10
<211> LENGTH: 261
<212> TYPE: PRT
<213> ORGANISM: Homo sapiens
```

<220> FEATURE:
<223> OTHER INFORMATION: Syk signaling domain

<400> SEQUENCE: 10

Thr Leu Glu Asp Lys Glu Leu Gly Ser Gly Asn Phe Gly Thr Val Lys
1               5                   10                  15

Lys Gly Tyr Tyr Gln Met Lys Lys Val Val Lys Thr Val Ala Val Lys
            20                  25                  30

Ile Leu Lys Asn Glu Ala Asn Asp Pro Ala Leu Lys Asp Glu Leu Leu
        35                  40                  45

Ala Glu Ala Asn Val Met Gln Gln Leu Asp Asn Pro Tyr Ile Val Arg
    50                  55                  60

Met Ile Gly Ile Cys Glu Ala Glu Ser Trp Met Leu Val Met Glu Met
65                  70                  75                  80

Ala Glu Leu Gly Pro Leu Asn Lys Tyr Leu Gln Gln Asn Arg His Val
                85                  90                  95

Lys Asp Lys Asn Ile Ile Glu Leu Val His Gln Val Ser Met Gly Met
            100                 105                 110

Lys Tyr Leu Glu Glu Ser Asn Phe Val His Arg Asp Leu Ala Ala Arg
        115                 120                 125

Asn Val Leu Leu Val Thr Gln His Tyr Ala Lys Ile Ser Asp Phe Gly
    130                 135                 140

Leu Ser Lys Ala Leu Arg Ala Asp Glu Asn Tyr Tyr Lys Ala Gln Thr
145                 150                 155                 160

His Gly Lys Trp Pro Val Lys Trp Tyr Ala Pro Glu Cys Ile Asn Tyr
                165                 170                 175

Tyr Lys Phe Ser Ser Lys Ser Asp Val Trp Ser Phe Gly Val Leu Met
            180                 185                 190

Trp Glu Ala Phe Ser Tyr Gly Gln Lys Pro Tyr Arg Gly Met Lys Gly
        195                 200                 205

Ser Glu Val Thr Ala Met Leu Glu Lys Gly Glu Arg Met Gly Cys Pro
    210                 215                 220

Ala Gly Cys Pro Arg Glu Met Tyr Asp Leu Met Asn Leu Cys Trp Thr
225                 230                 235                 240

Tyr Asp Val Glu Asn Arg Pro Gly Phe Ala Ala Val Glu Leu Arg Leu
                245                 250                 255

Arg Asn Tyr Tyr Tyr
            260

<210> SEQ ID NO 11
<211> LENGTH: 296
<212> TYPE: PRT
<213> ORGANISM: Homo sapiens
<220> FEATURE:
<223> OTHER INFORMATION: MyD88 signaling domain

<400> SEQUENCE: 11

Met Ala Ala Gly Gly Pro Gly Ala Gly Ser Ala Ala Pro Val Ser Ser
1               5                   10                  15

Thr Ser Ser Leu Pro Leu Ala Ala Leu Asn Met Arg Val Arg Arg Arg
            20                  25                  30

Leu Ser Leu Phe Leu Asn Val Arg Thr Gln Val Ala Ala Asp Trp Thr
        35                  40                  45

Ala Leu Ala Glu Glu Met Asp Phe Glu Tyr Leu Glu Ile Arg Gln Leu
    50                  55                  60

Glu Thr Gln Ala Asp Pro Thr Gly Arg Leu Leu Asp Ala Trp Gln Gly

```
                65                  70                  75                  80
Arg Pro Gly Ala Ser Val Gly Arg Leu Leu Glu Leu Leu Thr Lys Leu
                    85                  90                  95

Gly Arg Asp Asp Val Leu Leu Glu Leu Gly Pro Ser Ile Glu Glu Asp
                100                 105                 110

Cys Gln Lys Tyr Ile Leu Lys Gln Gln Gln Glu Glu Ala Glu Lys Pro
                115                 120                 125

Leu Gln Val Ala Ala Val Asp Ser Ser Val Pro Arg Thr Ala Glu Leu
            130                 135                 140

Ala Gly Ile Thr Thr Leu Asp Asp Pro Leu Gly His Met Pro Glu Arg
145                 150                 155                 160

Phe Asp Ala Phe Ile Cys Tyr Cys Pro Ser Asp Ile Gln Phe Val Gln
                    165                 170                 175

Glu Met Ile Arg Gln Leu Glu Gln Thr Asn Tyr Arg Leu Lys Leu Cys
                180                 185                 190

Val Ser Asp Arg Asp Val Leu Pro Gly Thr Cys Val Trp Ser Ile Ala
                195                 200                 205

Ser Glu Leu Ile Glu Lys Arg Cys Arg Arg Met Val Val Val Val Ser
    210                 215                 220

Asp Asp Tyr Leu Gln Ser Lys Glu Cys Asp Phe Gln Thr Lys Phe Ala
225                 230                 235                 240

Leu Ser Leu Ser Pro Gly Ala His Gln Lys Arg Leu Ile Pro Ile Lys
                    245                 250                 255

Tyr Lys Ala Met Lys Lys Glu Phe Pro Ser Ile Leu Arg Phe Ile Thr
                260                 265                 270

Val Cys Asp Tyr Thr Asn Pro Cys Thr Lys Ser Trp Phe Trp Thr Arg
                275                 280                 285

Leu Ala Lys Ala Leu Ser Leu Pro
            290                 295

<210> SEQ ID NO 12

<400> SEQUENCE: 12

000

<210> SEQ ID NO 13
<211> LENGTH: 42
<212> TYPE: PRT
<213> ORGANISM: Homo sapiens
<220> FEATURE:
<223> OTHER INFORMATION: FcepsilonR1gamma signaling domain

<400> SEQUENCE: 13

Arg Leu Lys Ile Gln Val Arg Lys Ala Ala Ile Thr Ser Tyr Glu Lys
1               5                   10                  15

Ser Asp Gly Val Tyr Thr Gly Leu Ser Thr Arg Asn Gln Glu Thr Tyr
                20                  25                  30

Glu Thr Leu Lys His Glu Lys Pro Pro Gln
            35                  40

<210> SEQ ID NO 14
<211> LENGTH: 61
<212> TYPE: PRT
<213> ORGANISM: Homo sapiens
<220> FEATURE:
<223> OTHER INFORMATION: FcgammaR1 signaling domain

<400> SEQUENCE: 14
```

Arg Lys Glu Leu Lys Arg Lys Lys Trp Asp Leu Glu Ile Ser Leu
1               5                   10                  15

Asp Ser Gly His Glu Lys Lys Val Ile Ser Ser Leu Gln Glu Asp Arg
            20                  25                  30

His Leu Glu Glu Glu Leu Lys Cys Gln Glu Gln Lys Glu Glu Gln Leu
                35                  40                  45

Gln Glu Gly Val His Arg Lys Glu Pro Gln Gly Ala Thr
    50                  55                  60

<210> SEQ ID NO 15
<211> LENGTH: 77
<212> TYPE: PRT
<213> ORGANISM: Homo sapiens
<220> FEATURE:
<223> OTHER INFORMATION: FcgammaR2A signaling domain

<400> SEQUENCE: 15

Cys Arg Lys Lys Arg Ile Ser Ala Asn Ser Thr Asp Pro Val Lys Ala
1               5                   10                  15

Ala Gln Phe Glu Pro Pro Gly Arg Gln Met Ile Ala Ile Arg Lys Arg
            20                  25                  30

Gln Leu Glu Glu Thr Asn Asn Asp Tyr Glu Thr Ala Asp Gly Gly Tyr
        35                  40                  45

Met Thr Leu Asn Pro Arg Ala Pro Thr Asp Asp Asp Lys Asn Ile Tyr
    50                  55                  60

Leu Thr Leu Pro Pro Asn Asp His Val Asn Ser Asn Asn
65                  70                  75

<210> SEQ ID NO 16
<211> LENGTH: 77
<212> TYPE: PRT
<213> ORGANISM: Homo sapiens
<220> FEATURE:
<223> OTHER INFORMATION: FcgammaR2c signaling domain

<400> SEQUENCE: 16

Cys Arg Lys Lys Arg Ile Ser Ala Asn Ser Thr Asp Pro Val Lys Ala
1               5                   10                  15

Ala Gln Phe Glu Pro Pro Gly Arg Gln Met Ile Ala Ile Arg Lys Arg
            20                  25                  30

Gln Pro Glu Glu Thr Asn Asn Asp Tyr Glu Thr Ala Asp Gly Gly Tyr
        35                  40                  45

Met Thr Leu Asn Pro Arg Ala Pro Thr Asp Asp Asp Lys Asn Ile Tyr
    50                  55                  60

Leu Thr Leu Pro Pro Asn Asp His Val Asn Ser Asn Asn
65                  70                  75

<210> SEQ ID NO 17
<211> LENGTH: 25
<212> TYPE: PRT
<213> ORGANISM: Homo sapiens
<220> FEATURE:
<223> OTHER INFORMATION: FcgammaR3A signaling domain

<400> SEQUENCE: 17

Lys Thr Asn Ile Arg Ser Ser Thr Arg Asp Trp Lys Asp His Lys Phe
1               5                   10                  15

Lys Trp Arg Lys Asp Pro Gln Asp Lys
            20                  25

```
<210> SEQ ID NO 18
<211> LENGTH: 85
<212> TYPE: PRT
<213> ORGANISM: Homo sapiens
<220> FEATURE:
<223> OTHER INFORMATION: BAFF-R signaling domain

<400> SEQUENCE: 18

Ser Trp Arg Arg Arg Gln Arg Arg Leu Arg Gly Ala Ser Ser Ala Glu
1               5                   10                  15

Ala Pro Asp Gly Asp Lys Asp Ala Pro Glu Pro Leu Asp Lys Val Ile
                20                  25                  30

Ile Leu Ser Pro Gly Ile Ser Asp Ala Thr Ala Pro Ala Trp Pro Pro
            35                  40                  45

Pro Gly Glu Asp Pro Gly Thr Thr Pro Pro Gly His Ser Val Pro Val
    50                  55                  60

Pro Ala Thr Glu Leu Gly Ser Thr Glu Leu Val Thr Thr Lys Thr Ala
65                  70                  75                  80

Gly Pro Glu Gln Gln
                85

<210> SEQ ID NO 19
<211> LENGTH: 52
<212> TYPE: PRT
<213> ORGANISM: Homo sapiens
<220> FEATURE:
<223> OTHER INFORMATION: DAP12 signaling domain

<400> SEQUENCE: 19

Tyr Phe Leu Gly Arg Leu Val Pro Arg Gly Arg Gly Ala Ala Glu Ala
1               5                   10                  15

Ala Thr Arg Lys Gln Arg Ile Thr Glu Thr Glu Ser Pro Tyr Gln Glu
                20                  25                  30

Leu Gln Gly Gln Arg Ser Asp Val Tyr Ser Asp Leu Asn Thr Gln Arg
            35                  40                  45

Pro Tyr Tyr Lys
    50

<210> SEQ ID NO 20
<211> LENGTH: 86
<212> TYPE: PRT
<213> ORGANISM: Homo sapiens
<220> FEATURE:
<223> OTHER INFORMATION: NFAM1 signaling domain

<400> SEQUENCE: 20

Leu Trp Asn Lys Lys Arg Met Arg Gly Pro Gly Lys Asp Pro Thr Arg
1               5                   10                  15

Lys Cys Pro Asp Pro Arg Ser Ala Ser Ser Pro Lys Gln His Pro Ser
                20                  25                  30

Glu Ser Val Tyr Thr Ala Leu Gln Arg Arg Glu Thr Glu Val Tyr Ala
            35                  40                  45

Cys Ile Glu Asn Glu Asp Gly Ser Ser Pro Thr Ala Lys Gln Ser Pro
    50                  55                  60

Leu Ser Gln Glu Arg Pro His Arg Phe Glu Asp Asp Gly Glu Leu Asn
65                  70                  75                  80

Leu Val Tyr Glu Asn Leu
                85
```

```
<210> SEQ ID NO 21
<211> LENGTH: 29
<212> TYPE: PRT
<213> ORGANISM: Homo sapiens
<220> FEATURE:
<223> OTHER INFORMATION: CD79b signaling domain 185-213

<400> SEQUENCE: 21

Asp Ser Lys Ala Gly Met Glu Glu Asp His Thr Tyr Glu Gly Leu Asp
1               5                   10                  15

Ile Asp Gln Thr Ala Thr Tyr Glu Asp Ile Val Thr Leu
            20                  25

<210> SEQ ID NO 22
<211> LENGTH: 45
<212> TYPE: PRT
<213> ORGANISM: Homo sapiens
<220> FEATURE:
<223> OTHER INFORMATION: CD79b signaling domain 185-229

<400> SEQUENCE: 22

Asp Ser Lys Ala Gly Met Glu Glu Asp His Thr Tyr Glu Gly Leu Asp
1               5                   10                  15

Ile Asp Gln Thr Ala Thr Tyr Glu Asp Ile Val Thr Leu Arg Thr Gly
            20                  25                  30

Glu Val Lys Trp Ser Val Gly Glu His Pro Gly Gln Glu
        35                  40                  45

<210> SEQ ID NO 23
<211> LENGTH: 185
<212> TYPE: PRT
<213> ORGANISM: Homo sapiens
<220> FEATURE:
<223> OTHER INFORMATION: TLR1 signaling domain

<400> SEQUENCE: 23

Ser Tyr Leu Asp Leu Pro Trp Tyr Leu Arg Met Val Cys Gln Trp Thr
1               5                   10                  15

Gln Thr Arg Arg Arg Ala Arg Asn Ile Pro Leu Glu Glu Leu Gln Arg
            20                  25                  30

Asn Leu Gln Phe His Ala Phe Ile Ser Tyr Ser Gly His Asp Ser Phe
        35                  40                  45

Trp Val Lys Asn Glu Leu Leu Pro Asn Leu Glu Lys Glu Gly Met Gln
    50                  55                  60

Ile Cys Leu His Glu Arg Asn Phe Val Pro Gly Lys Ser Ile Val Glu
65                  70                  75                  80

Asn Ile Ile Thr Cys Ile Glu Lys Ser Tyr Lys Ser Ile Phe Val Leu
                85                  90                  95

Ser Pro Asn Phe Val Gln Ser Glu Trp Cys His Tyr Glu Leu Tyr Phe
            100                 105                 110

Ala His His Asn Leu Phe His Glu Gly Ser Asn Ser Leu Ile Leu Ile
        115                 120                 125

Leu Leu Glu Pro Ile Pro Gln Tyr Ser Ile Pro Ser Ser Tyr His Lys
    130                 135                 140

Leu Lys Ser Leu Met Ala Arg Arg Thr Tyr Leu Glu Trp Pro Lys Glu
145                 150                 155                 160

Lys Ser Lys Arg Gly Leu Phe Trp Ala Asn Leu Arg Ala Ala Ile Asn
                165                 170                 175

Ile Lys Leu Thr Glu Gln Ala Lys Lys
            180                 185
```

```
<210> SEQ ID NO 24
<211> LENGTH: 175
<212> TYPE: PRT
<213> ORGANISM: Homo sapiens
<220> FEATURE:
<223> OTHER INFORMATION: TLR2 signaling domain

<400> SEQUENCE: 24

His Arg Phe His Gly Leu Trp Tyr Met Lys Met Met Trp Ala Trp Leu
1               5                   10                  15

Gln Ala Lys Arg Lys Pro Arg Lys Ala Pro Ser Arg Asn Ile Cys Tyr
            20                  25                  30

Asp Ala Phe Val Ser Tyr Ser Glu Arg Asp Ala Tyr Trp Val Glu Asn
        35                  40                  45

Leu Met Val Gln Glu Leu Glu Asn Phe Asn Pro Pro Phe Lys Leu Cys
    50                  55                  60

Leu His Lys Arg Asp Phe Ile Pro Gly Lys Trp Ile Ile Asp Asn Ile
65                  70                  75                  80

Ile Asp Ser Ile Glu Lys Ser His Lys Thr Val Phe Val Leu Ser Glu
                85                  90                  95

Asn Phe Val Lys Ser Glu Trp Cys Lys Tyr Glu Leu Asp Phe Ser His
            100                 105                 110

Phe Arg Leu Phe Asp Glu Asn Asn Asp Ala Ala Ile Leu Ile Leu Leu
        115                 120                 125

Glu Pro Ile Glu Lys Lys Ala Ile Pro Gln Arg Phe Cys Lys Leu Arg
    130                 135                 140

Lys Ile Met Asn Thr Lys Thr Tyr Leu Glu Trp Pro Met Asp Glu Ala
145                 150                 155                 160

Gln Arg Glu Gly Phe Trp Val Asn Leu Arg Ala Ala Ile Lys Ser
                165                 170                 175

<210> SEQ ID NO 25
<211> LENGTH: 179
<212> TYPE: PRT
<213> ORGANISM: Homo sapiens
<220> FEATURE:
<223> OTHER INFORMATION: TLR3 signaling domain

<400> SEQUENCE: 25

Glu Gly Trp Arg Ile Ser Phe Tyr Trp Asn Val Ser Val His Arg Val
1               5                   10                  15

Leu Gly Phe Lys Glu Ile Asp Arg Gln Thr Glu Gln Phe Glu Tyr Ala
            20                  25                  30

Ala Tyr Ile Ile His Ala Tyr Lys Asp Lys Asp Trp Val Trp Glu His
        35                  40                  45

Phe Ser Ser Met Glu Lys Glu Asp Gln Ser Leu Lys Phe Cys Leu Glu
    50                  55                  60

Glu Arg Asp Phe Glu Ala Gly Val Phe Glu Leu Glu Ala Ile Val Asn
65                  70                  75                  80

Ser Ile Lys Arg Ser Arg Lys Ile Ile Phe Val Ile Thr His His Leu
                85                  90                  95

Leu Lys Asp Pro Leu Cys Lys Arg Phe Lys Val His His Ala Val Gln
            100                 105                 110

Gln Ala Ile Glu Gln Asn Leu Asp Ser Ile Ile Leu Val Phe Leu Glu
        115                 120                 125

Glu Ile Pro Asp Tyr Lys Leu Asn His Ala Leu Cys Leu Arg Arg Gly
```

```
                130           135           140
Met Phe Lys Ser His Cys Ile Leu Asn Trp Pro Val Gln Lys Glu Arg
145                 150                 155                 160

Ile Gly Ala Phe Arg His Lys Leu Gln Val Ala Leu Gly Ser Lys Asn
                165                 170                 175

Ser Val His

<210> SEQ ID NO 26
<211> LENGTH: 187
<212> TYPE: PRT
<213> ORGANISM: Homo sapiens
<220> FEATURE:
<223> OTHER INFORMATION: TLR4 signaling domain

<400> SEQUENCE: 26

Lys Phe Tyr Phe His Leu Met Leu Leu Ala Gly Cys Ile Lys Tyr Gly
1               5                   10                  15

Arg Gly Glu Asn Ile Tyr Asp Ala Phe Val Ile Tyr Ser Ser Gln Asp
                20                  25                  30

Glu Asp Trp Val Arg Asn Glu Leu Val Lys Asn Leu Glu Glu Gly Val
            35                  40                  45

Pro Pro Phe Gln Leu Cys Leu His Tyr Arg Asp Phe Ile Pro Gly Val
50                  55                  60

Ala Ile Ala Ala Asn Ile Ile His Glu Gly Phe His Lys Ser Arg Lys
65                  70                  75                  80

Val Ile Val Val Ser Gln His Phe Ile Gln Ser Arg Trp Cys Ile
                85                  90                  95

Phe Glu Tyr Glu Ile Ala Gln Thr Trp Gln Phe Leu Ser Ser Arg Ala
                100                 105                 110

Gly Ile Ile Phe Ile Val Leu Gln Lys Val Glu Lys Thr Leu Leu Arg
            115                 120                 125

Gln Gln Val Glu Leu Tyr Arg Leu Leu Ser Arg Asn Thr Tyr Leu Glu
        130                 135                 140

Trp Glu Asp Ser Val Leu Gly Arg His Ile Phe Trp Arg Arg Leu Arg
145                 150                 155                 160

Lys Ala Leu Leu Asp Gly Lys Ser Trp Asn Pro Glu Gly Thr Val Gly
                165                 170                 175

Thr Gly Cys Asn Trp Gln Glu Ala Thr Ser Ile
            180                 185

<210> SEQ ID NO 27
<211> LENGTH: 198
<212> TYPE: PRT
<213> ORGANISM: Homo sapiens
<220> FEATURE:
<223> OTHER INFORMATION: TLR5 signaling domain

<400> SEQUENCE: 27

Thr Lys Phe Arg Gly Phe Cys Phe Ile Cys Tyr Lys Thr Ala Gln Arg
1               5                   10                  15

Leu Val Phe Lys Asp His Pro Gln Gly Thr Glu Pro Asp Met Tyr Lys
                20                  25                  30

Tyr Asp Ala Tyr Leu Cys Phe Ser Ser Lys Asp Phe Thr Trp Val Gln
                35                  40                  45

Asn Ala Leu Leu Lys His Leu Asp Thr Gln Tyr Ser Asp Gln Asn Arg
50                  55                  60

Phe Asn Leu Cys Phe Glu Glu Arg Asp Phe Val Pro Gly Glu Asn Arg
```

```
                65                  70                  75                  80
Ile Ala Asn Ile Gln Asp Ala Ile Trp Asn Ser Arg Lys Ile Val Cys
                    85                  90                  95
Leu Val Ser Arg His Phe Leu Arg Asp Gly Trp Cys Leu Glu Ala Phe
                   100                 105                 110
Ser Tyr Ala Gln Gly Arg Cys Leu Ser Asp Leu Asn Ser Ala Leu Ile
                   115                 120                 125
Met Val Val Gly Ser Leu Ser Gln Tyr Gln Leu Met Lys His Gln
    130                 135                 140
Ser Ile Arg Gly Phe Val Gln Lys Gln Tyr Leu Arg Trp Pro Glu
145                 150                 155                 160
Asp Phe Gln Asp Val Gly Trp Phe Leu His Lys Leu Ser Gln Gln Ile
                    165                 170                 175
Leu Lys Lys Glu Lys Glu Lys Lys Asp Asn Asn Ile Pro Leu Gln
                180                 185                 190
Thr Val Ala Thr Ile Ser
                195
```

<210> SEQ ID NO 28
<211> LENGTH: 189
<212> TYPE: PRT
<213> ORGANISM: Homo sapiens
<220> FEATURE:
<223> OTHER INFORMATION: TLR6 signaling domain

<400> SEQUENCE: 28

```
Tyr Leu Asp Leu Pro Trp Tyr Leu Arg Met Val Cys Gln Trp Thr Gln
1               5                   10                  15
Thr Arg Arg Arg Ala Arg Asn Ile Pro Leu Glu Glu Leu Gln Arg Asn
                20                  25                  30
Leu Gln Phe His Ala Phe Ile Ser Tyr Ser Glu His Asp Ser Ala Trp
                35                  40                  45
Val Lys Ser Glu Leu Val Pro Tyr Leu Glu Lys Glu Asp Ile Gln Ile
            50                  55                  60
Cys Leu His Glu Arg Asn Phe Val Pro Gly Lys Ser Ile Val Glu Asn
65                  70                  75                  80
Ile Ile Asn Cys Ile Glu Lys Ser Tyr Lys Ser Ile Phe Val Leu Ser
                85                  90                  95
Pro Asn Phe Val Gln Ser Glu Trp Cys His Tyr Glu Leu Tyr Phe Ala
                100                 105                 110
His His Asn Leu Phe His Glu Gly Ser Asn Asn Leu Ile Leu Ile Leu
                115                 120                 125
Leu Glu Pro Ile Pro Gln Asn Ser Ile Pro Asn Lys Tyr His Lys Leu
                130                 135                 140
Lys Ala Leu Met Thr Gln Arg Thr Tyr Leu Gln Trp Pro Lys Glu Lys
145                 150                 155                 160
Ser Lys Arg Gly Leu Phe Trp Ala Asn Ile Arg Ala Ala Phe Asn Met
                165                 170                 175
Lys Leu Thr Leu Val Thr Glu Asn Asn Asp Val Lys Ser
                180                 185
```

<210> SEQ ID NO 29
<211> LENGTH: 189
<212> TYPE: PRT
<213> ORGANISM: Homo sapiens
<220> FEATURE:
<223> OTHER INFORMATION: TLR7 signaling domain

<400> SEQUENCE: 29

```
His Leu Tyr Phe Trp Asp Val Trp Tyr Ile Tyr His Phe Cys Lys Ala
1               5                   10                  15

Lys Ile Lys Gly Tyr Gln Arg Leu Ile Ser Pro Asp Cys Cys Tyr Asp
            20                  25                  30

Ala Phe Ile Val Tyr Asp Thr Lys Asp Pro Ala Val Thr Glu Trp Val
            35                  40                  45

Leu Ala Glu Leu Val Ala Lys Leu Glu Asp Pro Arg Glu Lys His Phe
50                  55                  60

Asn Leu Cys Leu Glu Glu Arg Asp Trp Leu Pro Gly Gln Pro Val Leu
65                  70                  75                  80

Glu Asn Leu Ser Gln Ser Ile Gln Leu Ser Lys Lys Thr Val Phe Val
                85                  90                  95

Met Thr Asp Lys Tyr Ala Lys Thr Glu Asn Phe Lys Ile Ala Phe Tyr
            100                 105                 110

Leu Ser His Gln Arg Leu Met Asp Glu Lys Val Asp Val Ile Ile Leu
            115                 120                 125

Ile Phe Leu Glu Lys Pro Phe Gln Lys Ser Lys Phe Leu Gln Leu Arg
130                 135                 140

Lys Arg Leu Cys Gly Ser Ser Val Leu Glu Trp Pro Thr Asn Pro Gln
145                 150                 155                 160

Ala His Pro Tyr Phe Trp Gln Cys Leu Lys Asn Ala Leu Ala Thr Asp
                165                 170                 175

Asn His Val Ala Tyr Ser Gln Val Phe Lys Glu Thr Val
            180                 185
```

<210> SEQ ID NO 30
<211> LENGTH: 193
<212> TYPE: PRT
<213> ORGANISM: Homo sapiens
<220> FEATURE:
<223> OTHER INFORMATION: TLR8 signaling domain

<400> SEQUENCE: 30

```
His His Leu Phe Tyr Trp Asp Val Trp Phe Ile Tyr Asn Val Cys Leu
1               5                   10                  15

Ala Lys Val Lys Gly Tyr Arg Ser Leu Ser Thr Ser Gln Thr Phe Tyr
            20                  25                  30

Asp Ala Tyr Ile Ser Tyr Asp Thr Lys Asp Ala Ser Val Thr Asp Trp
            35                  40                  45

Val Ile Asn Glu Leu Arg Tyr His Leu Glu Glu Ser Arg Asp Lys Asn
50                  55                  60

Val Leu Leu Cys Leu Glu Glu Arg Asp Trp Asp Pro Gly Leu Ala Ile
65                  70                  75                  80

Ile Asp Asn Leu Met Gln Ser Ile Asn Gln Ser Lys Lys Thr Val Phe
                85                  90                  95

Val Leu Thr Lys Lys Tyr Ala Lys Ser Trp Asn Phe Lys Thr Ala Phe
            100                 105                 110

Tyr Leu Ala Leu Gln Arg Leu Met Asp Glu Asn Met Asp Val Ile Ile
            115                 120                 125

Phe Ile Leu Leu Glu Pro Val Leu Gln His Ser Gln Tyr Leu Arg Leu
130                 135                 140

Arg Gln Arg Ile Cys Lys Ser Ser Ile Leu Gln Trp Pro Asp Asn Pro
145                 150                 155                 160
```

```
Lys Ala Glu Gly Leu Phe Trp Gln Thr Leu Arg Asn Val Val Leu Thr
                165                 170                 175

Glu Asn Asp Ser Arg Tyr Asn Asn Met Tyr Val Asp Ser Ile Lys Gln
            180                 185                 190

Tyr

<210> SEQ ID NO 31
<211> LENGTH: 193
<212> TYPE: PRT
<213> ORGANISM: Homo sapiens
<220> FEATURE:
<223> OTHER INFORMATION: TLR9 signaling domain

<400> SEQUENCE: 31

Gly Trp Asp Leu Trp Tyr Cys Phe His Leu Cys Leu Ala Trp Leu Pro
1               5                   10                  15

Trp Arg Gly Arg Gln Ser Gly Arg Asp Glu Ala Leu Pro Tyr Asp
            20                  25                  30

Ala Phe Val Val Phe Asp Lys Thr Gln Ser Ala Val Ala Asp Trp Val
        35                  40                  45

Tyr Asn Glu Leu Arg Gly Gln Leu Glu Glu Cys Arg Gly Arg Trp Ala
50                  55                  60

Leu Arg Leu Cys Leu Glu Glu Arg Asp Trp Leu Pro Gly Lys Thr Leu
65                  70                  75                  80

Phe Glu Asn Leu Trp Ala Ser Val Tyr Gly Ser Arg Lys Thr Leu Phe
                85                  90                  95

Val Leu Ala His Thr Asp Arg Val Ser Gly Leu Leu Arg Ala Ser Phe
            100                 105                 110

Leu Leu Ala Gln Gln Arg Leu Leu Glu Asp Arg Lys Asp Val Val Val
        115                 120                 125

Leu Val Ile Leu Ser Pro Asp Gly Arg Arg Ser Arg Tyr Val Arg Leu
130                 135                 140

Arg Gln Arg Leu Cys Arg Gln Ser Val Leu Leu Trp Pro His Gln Pro
145                 150                 155                 160

Ser Gly Gln Arg Ser Phe Trp Ala Gln Leu Gly Met Ala Leu Thr Arg
                165                 170                 175

Asp Asn His His Phe Tyr Asn Arg Asn Phe Cys Gln Gly Pro Thr Ala
            180                 185                 190

Glu

<210> SEQ ID NO 32
<211> LENGTH: 303
<212> TYPE: PRT
<213> ORGANISM: Homo sapiens
<220> FEATURE:
<223> OTHER INFORMATION: TRAF2 signaling domain

<400> SEQUENCE: 32

Met Ala Ala Ala Ser Val Thr Pro Pro Gly Ser Leu Glu Leu Leu Gln
1               5                   10                  15

Pro Gly Phe Ser Lys Thr Leu Leu Gly Thr Lys Leu Glu Ala Lys Tyr
            20                  25                  30

Leu Cys Ser Ala Cys Arg Asn Val Leu Arg Arg Pro Phe Gln Ala Gln
        35                  40                  45

Cys Gly His Arg Tyr Cys Ser Phe Cys Leu Ala Ser Ile Leu Ser Ser
    50                  55                  60

Gly Pro Gln Asn Cys Ala Ala Cys Val His Glu Gly Ile Tyr Glu Glu
```

```
                65                  70                  75                  80
Gly Ile Ser Ile Leu Glu Ser Ser Ala Phe Pro Asp Asn Ala Ala
                    85                  90                  95

Arg Arg Glu Val Glu Ser Leu Pro Ala Val Cys Pro Ser Asp Gly Cys
                100                 105                 110

Thr Trp Lys Gly Thr Leu Lys Glu Tyr Glu Ser Cys His Glu Gly Arg
                115                 120                 125

Cys Pro Leu Met Leu Thr Glu Cys Pro Ala Cys Lys Gly Leu Val Arg
            130                 135                 140

Leu Gly Glu Lys Glu Arg His Leu Glu His Glu Cys Pro Glu Arg Ser
145                 150                 155                 160

Leu Ser Cys Arg His Cys Arg Ala Pro Cys Cys Gly Ala Asp Val Lys
                165                 170                 175

Ala His His Glu Val Cys Pro Lys Phe Pro Leu Thr Cys Asp Gly Cys
                180                 185                 190

Gly Lys Lys Lys Ile Pro Arg Glu Lys Phe Gln Asp His Val Lys Thr
            195                 200                 205

Cys Gly Lys Cys Arg Val Pro Cys Arg Phe His Ala Ile Gly Cys Leu
            210                 215                 220

Glu Thr Val Glu Gly Glu Lys Gln Gln Glu His Glu Val Gln Trp Leu
225                 230                 235                 240

Arg Glu His Leu Ala Met Leu Leu Ser Ser Val Leu Glu Ala Lys Pro
                245                 250                 255

Leu Leu Gly Asp Gln Ser His Ala Gly Ser Glu Leu Leu Gln Arg Cys
            260                 265                 270

Glu Ser Leu Glu Lys Lys Thr Ala Thr Phe Glu Asn Ile Val Cys Val
            275                 280                 285

Leu Asn Arg Glu Val Glu Arg Val Ala Met Thr Ala Glu Ala Cys
            290                 295                 300

<210> SEQ ID NO 33
<211> LENGTH: 274
<212> TYPE: PRT
<213> ORGANISM: Homo sapiens
<220> FEATURE:
<223> OTHER INFORMATION: TRAF3 signaling domain

<400> SEQUENCE: 33

Met Glu Ser Ser Lys Lys Met Asp Ser Pro Gly Ala Leu Gln Thr Asn
1               5                   10                  15

Pro Pro Leu Lys Leu His Thr Asp Arg Ser Ala Gly Thr Pro Val Phe
                20                  25                  30

Val Pro Glu Gln Gly Gly Tyr Lys Glu Lys Phe Val Lys Thr Val Glu
            35                  40                  45

Asp Lys Tyr Lys Cys Glu Lys Cys His Leu Val Leu Cys Ser Pro Lys
    50                  55                  60

Gln Thr Glu Cys Gly His Arg Phe Cys Glu Ser Cys Met Ala Ala Leu
65                  70                  75                  80

Leu Ser Ser Ser Pro Lys Cys Thr Ala Cys Gln Glu Ser Ile Val
                85                  90                  95

Lys Asp Lys Val Phe Lys Asp Asn Cys Cys Lys Arg Glu Ile Leu Ala
                100                 105                 110

Leu Gln Ile Tyr Cys Arg Asn Glu Ser Arg Gly Cys Ala Glu Gln Leu
            115                 120                 125

Met Leu Gly His Leu Leu Val His Leu Lys Asn Asp Cys His Phe Glu
```

```
                130                 135                 140
Glu Leu Pro Cys Val Arg Pro Asp Cys Lys Glu Lys Val Leu Arg Lys
145                 150                 155                 160

Asp Leu Arg Asp His Val Glu Lys Ala Cys Lys Tyr Arg Glu Ala Thr
                165                 170                 175

Cys Ser His Cys Lys Ser Gln Val Pro Met Ile Ala Leu Gln Lys His
                180                 185                 190

Glu Asp Thr Asp Cys Pro Cys Val Val Val Ser Cys Pro His Lys Cys
                195                 200                 205

Ser Val Gln Thr Leu Leu Arg Ser Glu Leu Ser Ala His Leu Ser Glu
                210                 215                 220

Cys Val Asn Ala Pro Ser Thr Cys Ser Phe Lys Arg Tyr Gly Cys Val
225                 230                 235                 240

Phe Gln Gly Thr Asn Gln Gln Ile Lys Ala His Glu Ala Ser Ser Ala
                245                 250                 255

Val Gln His Val Asn Leu Leu Lys Glu Trp Ser Asn Ser Leu Glu Lys
                260                 265                 270

Lys Val

<210> SEQ ID NO 34
<211> LENGTH: 155
<212> TYPE: PRT
<213> ORGANISM: Homo sapiens
<220> FEATURE:
<223> OTHER INFORMATION: truncated MyD88 signaling domain without TIR
      domain

<400> SEQUENCE: 34

Met Ala Ala Gly Gly Pro Gly Ala Gly Ser Ala Ala Pro Val Ser Ser
1               5                   10                  15

Thr Ser Ser Leu Pro Leu Ala Ala Leu Asn Met Arg Val Arg Arg Arg
                20                  25                  30

Leu Ser Leu Phe Leu Asn Val Arg Thr Gln Val Ala Ala Asp Trp Thr
                35                  40                  45

Ala Leu Ala Glu Glu Met Asp Phe Glu Tyr Leu Glu Ile Arg Gln Leu
50                  55                  60

Glu Thr Gln Ala Asp Pro Thr Gly Arg Leu Leu Asp Ala Trp Gln Gly
65                  70                  75                  80

Arg Pro Gly Ala Ser Val Gly Arg Leu Leu Glu Leu Leu Thr Lys Leu
                85                  90                  95

Gly Arg Asp Asp Val Leu Leu Glu Leu Gly Pro Ser Ile Glu Glu Asp
                100                 105                 110

Cys Gln Lys Tyr Ile Leu Lys Gln Gln Gln Glu Glu Ala Glu Lys Pro
                115                 120                 125

Leu Gln Val Ala Ala Val Asp Ser Ser Val Pro Arg Thr Ala Glu Leu
                130                 135                 140

Ala Gly Ile Thr Thr Leu Asp Asp Pro Leu Gly
145                 150                 155

<210> SEQ ID NO 35
<211> LENGTH: 274
<212> TYPE: PRT
<213> ORGANISM: Homo sapiens
<220> FEATURE:
<223> OTHER INFORMATION: truncated TRAF6 signaling domain

<400> SEQUENCE: 35
```

```
Met Ser Leu Leu Asn Cys Glu Asn Ser Cys Gly Ser Gln Ser Glu
1               5                   10                  15

Ser Asp Cys Cys Val Ala Met Ala Ser Cys Ser Ala Val Thr Lys
            20                  25                  30

Asp Asp Ser Val Gly Gly Thr Ala Ser Thr Gly Asn Leu Ser Ser Ser
        35                  40                  45

Phe Met Glu Glu Ile Gln Gly Tyr Asp Val Glu Phe Asp Pro Pro Leu
    50                  55                  60

Glu Ser Lys Tyr Glu Cys Pro Ile Cys Leu Met Ala Leu Arg Glu Ala
65                  70                  75                  80

Val Gln Thr Pro Cys Gly His Arg Phe Cys Lys Ala Cys Ile Ile Lys
                85                  90                  95

Ser Ile Arg Asp Ala Gly His Lys Cys Pro Val Asp Asn Glu Ile Leu
            100                 105                 110

Leu Glu Asn Gln Leu Phe Pro Asp Asn Phe Ala Lys Arg Glu Ile Leu
            115                 120                 125

Ser Leu Met Val Lys Cys Pro Asn Glu Gly Cys Leu His Lys Met Glu
            130                 135                 140

Leu Arg His Leu Glu Asp His Gln Ala His Cys Glu Phe Ala Leu Met
145                 150                 155                 160

Asp Cys Pro Gln Cys Gln Arg Pro Phe Gln Lys Phe His Ile Asn Ile
                165                 170                 175

His Ile Leu Lys Asp Cys Pro Arg Arg Gln Val Ser Cys Asp Asn Cys
            180                 185                 190

Ala Ala Ser Met Ala Phe Glu Asp Lys Glu Ile His Asp Gln Asn Cys
            195                 200                 205

Pro Leu Ala Asn Val Ile Cys Glu Tyr Cys Asn Thr Ile Leu Ile Arg
    210                 215                 220

Glu Gln Met Pro Asn His Tyr Asp Leu Asp Cys Pro Thr Ala Pro Ile
225                 230                 235                 240

Pro Cys Thr Phe Ser Thr Phe Gly Cys His Glu Lys Met Gln Arg Asn
                245                 250                 255

His Leu Ala Arg His Leu Gln Glu Asn Thr Gln Ser His Met Arg Met
            260                 265                 270

Leu Ala

<210> SEQ ID NO 36
<211> LENGTH: 29
<212> TYPE: PRT
<213> ORGANISM: Homo sapiens
<220> FEATURE:
<223> OTHER INFORMATION: truncated NFAM1 signaling domain

<400> SEQUENCE: 36

Ser Ser Pro Lys Gln His Pro Ser Glu Ser Val Tyr Thr Ala Leu Gln
1               5                   10                  15

Arg Arg Glu Thr Glu Val Tyr Ala Cys Ile Glu Asn Glu
            20                  25

<210> SEQ ID NO 37
<211> LENGTH: 21
<212> TYPE: PRT
<213> ORGANISM: Homo sapiens
<220> FEATURE:
<223> OTHER INFORMATION: Tim1 transmembrane domain

<400> SEQUENCE: 37
```

-continued

Ile Tyr Ala Gly Val Cys Ile Ser Val Leu Val Leu Leu Ala Leu Leu
1               5                   10                  15

Gly Val Ile Ile Ala
            20

<210> SEQ ID NO 38
<211> LENGTH: 21
<212> TYPE: PRT
<213> ORGANISM: Homo sapiens
<220> FEATURE:
<223> OTHER INFORMATION: Tim4 transmembrane domain

<400> SEQUENCE: 38

Leu Leu Met Ile Ile Ala Pro Ser Leu Gly Phe Val Leu Phe Ala Leu
1               5                   10                  15

Phe Val Ala Phe Leu
            20

<210> SEQ ID NO 39
<211> LENGTH: 21
<212> TYPE: PRT
<213> ORGANISM: Mus musculus
<220> FEATURE:
<223> OTHER INFORMATION: Tim4 transmembrane domain

<400> SEQUENCE: 39

Ile Leu Ile Ile Ala Cys Cys Val Gly Phe Val Leu Met Val Leu Leu
1               5                   10                  15

Phe Leu Ala Phe Leu
            20

<210> SEQ ID NO 40
<211> LENGTH: 21
<212> TYPE: PRT
<213> ORGANISM: Homo sapiens
<220> FEATURE:
<223> OTHER INFORMATION: Tim3 transmembrane domain

<400> SEQUENCE: 40

Ile Tyr Ile Gly Ala Gly Ile Cys Ala Gly Leu Ala Leu Ala Leu Ile
1               5                   10                  15

Phe Gly Ala Leu Ile
            20

<210> SEQ ID NO 41
<211> LENGTH: 21
<212> TYPE: PRT
<213> ORGANISM: Homo sapiens
<220> FEATURE:
<223> OTHER INFORMATION: FcgammaR1 transmembrane domain

<400> SEQUENCE: 41

Val Leu Phe Tyr Leu Ala Val Gly Ile Met Phe Leu Val Asn Thr Val
1               5                   10                  15

Leu Trp Val Thr Ile
            20

<210> SEQ ID NO 42
<211> LENGTH: 23
<212> TYPE: PRT
<213> ORGANISM: Homo sapiens
<220> FEATURE:
<223> OTHER INFORMATION: FcgammaR2A transmembrane domain

<400> SEQUENCE: 42

```
Ile Ile Val Ala Val Val Ile Ala Thr Ala Val Ala Ala Ile Val Ala
1               5                   10                  15

Ala Val Val Ala Leu Ile Tyr
            20

<210> SEQ ID NO 43
<211> LENGTH: 23
<212> TYPE: PRT
<213> ORGANISM: Homo sapiens
<220> FEATURE:
<223> OTHER INFORMATION: FcgammaR2B2 transmembrane domain

<400> SEQUENCE: 43

Ser Ser Ser Pro Met Gly Ile Ile Val Ala Val Val Thr Gly Ile Ala
1               5                   10                  15

Val Ala Ala Ile Val Ala Ala
            20

<210> SEQ ID NO 44
<211> LENGTH: 23
<212> TYPE: PRT
<213> ORGANISM: Homo sapiens
<220> FEATURE:
<223> OTHER INFORMATION: FcgammaR2C transmembrane domain

<400> SEQUENCE: 44

Ile Ile Val Ala Val Val Thr Gly Ile Ala Val Ala Ala Ile Val Ala
1               5                   10                  15

Ala Val Val Ala Leu Ile Tyr
            20

<210> SEQ ID NO 45
<211> LENGTH: 21
<212> TYPE: PRT
<213> ORGANISM: Homo sapiens
<220> FEATURE:
<223> OTHER INFORMATION: FcgammaR3A transmembrane domain

<400> SEQUENCE: 45

Val Ser Phe Cys Leu Val Met Val Leu Leu Phe Ala Val Asp Thr Gly
1               5                   10                  15

Leu Tyr Phe Ser Val
            20

<210> SEQ ID NO 46
<211> LENGTH: 21
<212> TYPE: PRT
<213> ORGANISM: Homo sapiens
<220> FEATURE:
<223> OTHER INFORMATION: FcepsilonR1 transmembrane domain

<400> SEQUENCE: 46

Leu Cys Tyr Ile Leu Asp Ala Ile Leu Phe Leu Tyr Gly Ile Val Leu
1               5                   10                  15

Thr Leu Leu Tyr Cys
            20

<210> SEQ ID NO 47
<211> LENGTH: 19
<212> TYPE: PRT
<213> ORGANISM: Homo sapiens
<220> FEATURE:
<223> OTHER INFORMATION: FcalphaR1 transmembrane domain
```

```
<400> SEQUENCE: 47

Leu Ile Arg Met Ala Val Ala Gly Leu Val Leu Val Ala Leu Ala
1               5                   10                  15

Ile Leu Val

<210> SEQ ID NO 48
<211> LENGTH: 21
<212> TYPE: PRT
<213> ORGANISM: Homo sapiens
<220> FEATURE:
<223> OTHER INFORMATION: CD8 transmembrane domain

<400> SEQUENCE: 48

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 49
<211> LENGTH: 27
<212> TYPE: PRT
<213> ORGANISM: Homo sapiens
<220> FEATURE:
<223> OTHER INFORMATION: CD28 transmembrane domain

<400> SEQUENCE: 49

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 50
<211> LENGTH: 21
<212> TYPE: PRT
<213> ORGANISM: Homo sapiens
<220> FEATURE:
<223> OTHER INFORMATION: MERTK transmembrane domain

<400> SEQUENCE: 50

Phe Gly Cys Phe Cys Gly Phe Ile Leu Ile Gly Leu Ile Leu Tyr Ile
1               5                   10                  15

Ser Leu Ala Ile Arg
            20

<210> SEQ ID NO 51
<211> LENGTH: 21
<212> TYPE: PRT
<213> ORGANISM: Homo sapiens
<220> FEATURE:
<223> OTHER INFORMATION: Axl transmembrane domain

<400> SEQUENCE: 51

Tyr Val Leu Leu Gly Ala Val Val Ala Ala Ala Cys Val Leu Ile Leu
1               5                   10                  15

Ala Leu Phe Leu Val
            20

<210> SEQ ID NO 52
<211> LENGTH: 21
<212> TYPE: PRT
<213> ORGANISM: Homo sapiens
<220> FEATURE:
<223> OTHER INFORMATION: Tyro3 transmembrane domain
```

```
<400> SEQUENCE: 52

Val Pro Val Val Leu Gly Val Leu Thr Ala Leu Val Thr Ala Ala Ala
1               5                   10                  15

Leu Ala Leu Ile Leu
            20

<210> SEQ ID NO 53
<211> LENGTH: 22
<212> TYPE: PRT
<213> ORGANISM: Homo sapiens
<220> FEATURE:
<223> OTHER INFORMATION: CD4 transmembrane domain

<400> SEQUENCE: 53

Met Ala Leu Ile Val Leu Gly Gly Val Ala Gly Leu Leu Leu Phe Ile
1               5                   10                  15

Gly Leu Gly Ile Phe Phe
            20

<210> SEQ ID NO 54
<211> LENGTH: 21
<212> TYPE: PRT
<213> ORGANISM: Homo sapiens
<220> FEATURE:
<223> OTHER INFORMATION: DAP12 transmembrane domain

<400> SEQUENCE: 54

Gly Val Leu Ala Gly Ile Val Met Gly Asp Leu Val Leu Thr Val Leu
1               5                   10                  15

Ile Ala Leu Ala Val
            20

<210> SEQ ID NO 55
<211> LENGTH: 21
<212> TYPE: PRT
<213> ORGANISM: Homo sapiens
<220> FEATURE:
<223> OTHER INFORMATION: MRC1 transmembrane domain

<400> SEQUENCE: 55

Gly Val Val Ile Ile Val Ile Leu Leu Ile Leu Thr Gly Ala Gly Leu
1               5                   10                  15

Ala Ala Tyr Phe Phe
            20

<210> SEQ ID NO 56
<211> LENGTH: 21
<212> TYPE: PRT
<213> ORGANISM: Homo sapiens
<220> FEATURE:
<223> OTHER INFORMATION: TLR1 transmembrane domain

<400> SEQUENCE: 56

Leu Leu Ile Val Thr Ile Val Ala Thr Met Leu Val Leu Ala Val Thr
1               5                   10                  15

Val Thr Ser Leu Cys
            20

<210> SEQ ID NO 57
<211> LENGTH: 21
<212> TYPE: PRT
<213> ORGANISM: Homo sapiens
<220> FEATURE:
<223> OTHER INFORMATION: TLR2 transmembrane domain
```

<400> SEQUENCE: 57

Ala Leu Val Ser Gly Met Cys Cys Ala Leu Phe Leu Leu Ile Leu Leu
1               5                   10                  15

Thr Gly Val Leu Cys
            20

<210> SEQ ID NO 58
<211> LENGTH: 21
<212> TYPE: PRT
<213> ORGANISM: Homo sapiens
<220> FEATURE:
<223> OTHER INFORMATION: TLR3 Transmembrane domain

<400> SEQUENCE: 58

Phe Phe Met Ile Asn Thr Ser Ile Leu Leu Ile Phe Ile Phe Ile Val
1               5                   10                  15

Leu Leu Ile His Phe
            20

<210> SEQ ID NO 59
<211> LENGTH: 21
<212> TYPE: PRT
<213> ORGANISM: Homo sapiens
<220> FEATURE:
<223> OTHER INFORMATION: TLR4 transmembrane domain

<400> SEQUENCE: 59

Thr Ile Ile Gly Val Ser Val Leu Ser Val Leu Val Val Ser Val Val
1               5                   10                  15

Ala Val Leu Val Tyr
            20

<210> SEQ ID NO 60
<211> LENGTH: 21
<212> TYPE: PRT
<213> ORGANISM: Homo sapiens
<220> FEATURE:
<223> OTHER INFORMATION: TLR5 transmembrane domain

<400> SEQUENCE: 60

Phe Ser Leu Phe Ile Val Cys Thr Val Thr Leu Thr Leu Phe Leu Met
1               5                   10                  15

Thr Ile Leu Thr Val
            20

<210> SEQ ID NO 61
<211> LENGTH: 21
<212> TYPE: PRT
<213> ORGANISM: Homo sapiens
<220> FEATURE:
<223> OTHER INFORMATION: TLR6 transmembrane domain

<400> SEQUENCE: 61

Ala Leu Val Ser Gly Met Cys Cys Ala Leu Phe Leu Leu Ile Leu Leu
1               5                   10                  15

Thr Gly Val Leu Cys
            20

<210> SEQ ID NO 62
<211> LENGTH: 21
<212> TYPE: PRT
<213> ORGANISM: Homo sapiens
<220> FEATURE:

```
<223> OTHER INFORMATION: TLR7 transmembrane domain

<400> SEQUENCE: 62

Leu Ile Leu Phe Ser Leu Ser Ile Ser Val Ser Leu Phe Leu Met Val
1               5                   10                  15

Met Met Thr Ala Ser
            20

<210> SEQ ID NO 63
<211> LENGTH: 21
<212> TYPE: PRT
<213> ORGANISM: Homo sapiens
<220> FEATURE:
<223> OTHER INFORMATION: TLR8 transmembrane domain

<400> SEQUENCE: 63

Ala Val Ile Leu Phe Phe Phe Thr Phe Phe Ile Thr Thr Met Val Met
1               5                   10                  15

Leu Ala Ala Leu Ala
            20

<210> SEQ ID NO 64
<211> LENGTH: 21
<212> TYPE: PRT
<213> ORGANISM: Homo sapiens
<220> FEATURE:
<223> OTHER INFORMATION: TLR9 transmembrane domain

<400> SEQUENCE: 64

Phe Ala Leu Ser Leu Leu Ala Val Ala Leu Gly Leu Gly Val Pro Met
1               5                   10                  15

Leu His His Leu Cys
            20

<210> SEQ ID NO 65

<400> SEQUENCE: 65

000

<210> SEQ ID NO 66

<400> SEQUENCE: 66

000

<210> SEQ ID NO 67
<211> LENGTH: 22
<212> TYPE: PRT
<213> ORGANISM: Homo sapiens
<220> FEATURE:
<223> OTHER INFORMATION: GM-CSF signal peptide

<400> SEQUENCE: 67

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 68
<211> LENGTH: 24
<212> TYPE: PRT
<213> ORGANISM: Homo sapiens
<220> FEATURE:
<223> OTHER INFORMATION: Tim4 signal peptide
```

<400> SEQUENCE: 68

Met Ser Lys Glu Pro Leu Ile Leu Trp Leu Met Ile Glu Phe Trp Trp
1               5                   10                  15

Leu Tyr Leu Thr Pro Val Thr Ser
            20

<210> SEQ ID NO 69
<211> LENGTH: 22
<212> TYPE: PRT
<213> ORGANISM: Mus musculus
<220> FEATURE:
<223> OTHER INFORMATION: Tim4 signal peptide

<400> SEQUENCE: 69

Met Ser Lys Gly Leu Leu Leu Trp Leu Val Thr Glu Leu Trp Trp
1               5                   10                  15

Leu Tyr Leu Thr Pro Ala
            20

<210> SEQ ID NO 70
<211> LENGTH: 285
<212> TYPE: PRT
<213> ORGANISM: Homo sapiens
<220> FEATURE:
<223> OTHER INFORMATION: truncated EGFR

<400> SEQUENCE: 70

Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
                20                  25                  30

Ser Gly Asp Leu His Ile Leu Pro Val Ala Phe Arg Gly Asp Ser Phe
            35                  40                  45

Thr His Thr Pro Pro Leu Asp Pro Gln Glu Leu Asp Ile Leu Lys Thr
        50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Cys Arg Asn Val Ser Arg Gly Arg Glu Cys Val Asp Lys Cys Asn Leu
        195                 200                 205

Leu Glu Gly Glu Pro Arg Glu Phe Val Glu Asn Ser Glu Cys Ile Gln
    210                 215                 220

Cys His Pro Glu Cys Leu Pro Gln Ala Met Asn Ile Thr Cys Thr Gly
225                 230                 235                 240

Arg Gly Pro Asp Asn Cys Ile Gln Cys Ala His Tyr Ile Asp Gly Pro
            245                 250                 255

His Cys Val Lys Thr Cys Pro Ala Gly Val Met Gly Glu Asn Asn Thr
        260                 265                 270

Leu Val Trp Lys Tyr Ala Asp Ala Gly His Val Cys His
        275                 280                 285

<210> SEQ ID NO 71
<211> LENGTH: 192
<212> TYPE: PRT
<213> ORGANISM: Homo sapiens
<220> FEATURE:
<223> OTHER INFORMATION: Rac1

<400> SEQUENCE: 71

Met Gln Ala Ile Lys Cys Val Val Val Gly Asp Gly Ala Val Gly Lys
1               5                   10                  15

Thr Cys Leu Leu Ile Ser Tyr Thr Thr Asn Ala Phe Pro Gly Glu Tyr
            20                  25                  30

Ile Pro Thr Val Phe Asp Asn Tyr Ser Ala Asn Val Met Val Asp Gly
        35                  40                  45

Lys Pro Val Asn Leu Gly Leu Trp Asp Thr Ala Gly Gln Glu Asp Tyr
    50                  55                  60

Asp Arg Leu Arg Pro Leu Ser Tyr Pro Gln Thr Asp Val Phe Leu Ile
65                  70                  75                  80

Cys Phe Ser Leu Val Ser Pro Ala Ser Phe Glu Asn Val Arg Ala Lys
                85                  90                  95

Trp Tyr Pro Glu Val Arg His His Cys Pro Asn Thr Pro Ile Ile Leu
            100                 105                 110

Val Gly Thr Lys Leu Asp Leu Arg Asp Asp Lys Asp Thr Ile Glu Lys
        115                 120                 125

Leu Lys Glu Lys Lys Leu Thr Pro Ile Thr Tyr Pro Gln Gly Leu Ala
    130                 135                 140

Met Ala Lys Glu Ile Gly Ala Val Lys Tyr Leu Glu Cys Ser Ala Leu
145                 150                 155                 160

Thr Gln Arg Gly Leu Lys Thr Val Phe Asp Glu Ala Ile Arg Ala Val
                165                 170                 175

Leu Cys Pro Pro Pro Val Lys Lys Arg Lys Arg Lys Cys Leu Leu Leu
            180                 185                 190

<210> SEQ ID NO 72
<211> LENGTH: 215
<212> TYPE: PRT
<213> ORGANISM: Homo sapiens
<220> FEATURE:
<223> OTHER INFORMATION: Rab5

<400> SEQUENCE: 72

Met Ala Ser Arg Gly Ala Thr Arg Pro Asn Gly Pro Asn Thr Gly Asn
1               5                   10                  15

Lys Ile Cys Gln Phe Lys Leu Val Leu Leu Gly Glu Ser Ala Val Gly
            20                  25                  30

Lys Ser Ser Leu Val Leu Arg Phe Val Lys Gly Gln Phe His Glu Phe
        35                  40                  45

Gln Glu Ser Thr Ile Gly Ala Ala Phe Leu Thr Gln Thr Val Cys Leu
    50                  55                  60

Asp Asp Thr Thr Val Lys Phe Glu Ile Trp Asp Thr Ala Gly Gln Glu

```
                65                  70                  75                  80
Arg Tyr His Ser Leu Ala Pro Met Tyr Tyr Arg Gly Ala Gln Ala Ala
                85                  90                  95

Ile Val Val Tyr Asp Ile Thr Asn Glu Glu Ser Phe Ala Arg Ala Lys
                100                 105                 110

Asn Trp Val Lys Glu Leu Gln Arg Gln Ala Ser Pro Asn Ile Val Ile
                115                 120                 125

Ala Leu Ser Gly Asn Lys Ala Asp Leu Ala Asn Lys Arg Ala Val Asp
130                 135                 140

Phe Gln Glu Ala Gln Ser Tyr Ala Asp Asp Asn Ser Leu Leu Phe Met
145                 150                 155                 160

Glu Thr Ser Ala Lys Thr Ser Met Asn Val Asn Glu Ile Phe Met Ala
                165                 170                 175

Ile Ala Lys Lys Leu Pro Lys Asn Glu Pro Gln Asn Pro Gly Ala Asn
                180                 185                 190

Ser Ala Arg Gly Arg Gly Val Asp Leu Thr Glu Pro Thr Gln Pro Thr
                195                 200                 205

Arg Asn Gln Cys Cys Ser Asn
                210                 215

<210> SEQ ID NO 73
<211> LENGTH: 207
<212> TYPE: PRT
<213> ORGANISM: Homo sapiens
<220> FEATURE:
<223> OTHER INFORMATION: Rab7

<400> SEQUENCE: 73

Met Thr Ser Arg Lys Lys Val Leu Leu Lys Val Ile Ile Leu Gly Asp
1               5                   10                  15

Ser Gly Val Gly Lys Thr Ser Leu Met Asn Gln Tyr Val Asn Lys Lys
                20                  25                  30

Phe Ser Asn Gln Tyr Lys Ala Thr Ile Gly Ala Asp Phe Leu Thr Lys
            35                  40                  45

Glu Val Met Val Asp Asp Arg Leu Val Thr Met Gln Ile Trp Asp Thr
50                  55                  60

Ala Gly Gln Glu Arg Phe Gln Ser Leu Gly Val Ala Phe Tyr Arg Gly
65                  70                  75                  80

Ala Asp Cys Cys Val Leu Val Phe Asp Val Thr Ala Pro Asn Thr Phe
                85                  90                  95

Lys Thr Leu Asp Ser Trp Arg Asp Glu Phe Leu Ile Gln Ala Ser Pro
                100                 105                 110

Arg Asp Pro Glu Asn Phe Pro Phe Val Val Leu Gly Asn Lys Ile Asp
                115                 120                 125

Leu Glu Asn Arg Gln Val Ala Thr Lys Arg Ala Gln Ala Trp Cys Tyr
130                 135                 140

Ser Lys Asn Asn Ile Pro Tyr Phe Glu Thr Ser Ala Lys Glu Ala Ile
145                 150                 155                 160

Asn Val Glu Gln Ala Phe Gln Thr Ile Ala Arg Asn Ala Leu Lys Gln
                165                 170                 175

Glu Thr Glu Val Glu Leu Tyr Asn Glu Phe Pro Glu Pro Ile Lys Leu
                180                 185                 190

Asp Lys Asn Asp Arg Ala Lys Ala Ser Ala Glu Ser Cys Ser Cys
                195                 200                 205
```

<210> SEQ ID NO 74
<211> LENGTH: 184
<212> TYPE: PRT
<213> ORGANISM: Homo sapiens
<220> FEATURE:
<223> OTHER INFORMATION: Rap1

<400> SEQUENCE: 74

Met Arg Glu Tyr Lys Leu Val Val Leu Gly Ser Gly Gly Val Gly Lys
1               5                   10                  15

Ser Ala Leu Thr Val Gln Phe Val Gln Gly Ile Phe Val Glu Lys Tyr
                20                  25                  30

Asp Pro Thr Ile Glu Asp Ser Tyr Arg Lys Gln Val Glu Val Asp Cys
            35                  40                  45

Gln Gln Cys Met Leu Glu Ile Leu Asp Thr Ala Gly Thr Glu Gln Phe
    50                  55                  60

Thr Ala Met Arg Asp Leu Tyr Met Lys Asn Gly Gln Gly Phe Ala Leu
65                  70                  75                  80

Val Tyr Ser Ile Thr Ala Gln Ser Thr Phe Asn Asp Leu Gln Asp Leu
                85                  90                  95

Arg Glu Gln Ile Leu Arg Val Lys Asp Thr Glu Asp Val Pro Met Ile
            100                 105                 110

Leu Val Gly Asn Lys Cys Asp Leu Glu Asp Glu Arg Val Val Gly Lys
        115                 120                 125

Glu Gln Gly Gln Asn Leu Ala Arg Gln Trp Cys Asn Cys Ala Phe Leu
    130                 135                 140

Glu Ser Ser Ala Lys Ser Lys Ile Asn Val Asn Glu Ile Phe Tyr Asp
145                 150                 155                 160

Leu Val Arg Gln Ile Asn Arg Lys Thr Pro Val Glu Lys Lys Lys Pro
                165                 170                 175

Lys Lys Lys Ser Cys Leu Leu Leu
            180

<210> SEQ ID NO 75
<211> LENGTH: 193
<212> TYPE: PRT
<213> ORGANISM: Homo sapiens
<220> FEATURE:
<223> OTHER INFORMATION: RhoA

<400> SEQUENCE: 75

Met Ala Ala Ile Arg Lys Lys Leu Val Ile Val Gly Asp Gly Ala Cys
1               5                   10                  15

Gly Lys Thr Cys Leu Leu Ile Val Phe Ser Lys Asp Gln Phe Pro Glu
                20                  25                  30

Val Tyr Val Pro Thr Val Phe Glu Asn Tyr Val Ala Asp Ile Glu Val
            35                  40                  45

Asp Gly Lys Gln Val Glu Leu Ala Leu Trp Asp Thr Ala Gly Gln Glu
    50                  55                  60

Asp Tyr Asp Arg Leu Arg Pro Leu Ser Tyr Pro Asp Thr Asp Val Ile
65                  70                  75                  80

Leu Met Cys Phe Ser Ile Asp Ser Pro Asp Ser Leu Glu Asn Ile Pro
                85                  90                  95

Glu Lys Trp Thr Pro Glu Val Lys His Phe Cys Pro Asn Val Pro Ile
            100                 105                 110

Ile Leu Val Gly Asn Lys Lys Asp Leu Arg Asn Asp Glu His Thr Arg
        115                 120                 125

```
Arg Glu Leu Ala Lys Met Lys Gln Glu Pro Val Lys Pro Glu Glu Gly
    130                 135                 140

Arg Asp Met Ala Asn Arg Ile Gly Ala Phe Gly Tyr Met Glu Cys Ser
145                 150                 155                 160

Ala Lys Thr Lys Asp Gly Val Arg Glu Val Phe Glu Met Ala Thr Arg
                165                 170                 175

Ala Ala Leu Gln Ala Arg Arg Gly Lys Lys Lys Ser Gly Cys Leu Val
            180                 185                 190

Leu
```

<210> SEQ ID NO 76
<211> LENGTH: 191
<212> TYPE: PRT
<213> ORGANISM: Homo sapiens
<220> FEATURE:
<223> OTHER INFORMATION: CDC42

<400> SEQUENCE: 76

```
Met Gln Thr Ile Lys Cys Val Val Val Gly Asp Gly Ala Val Gly Lys
1               5                   10                  15

Thr Cys Leu Leu Ile Ser Tyr Thr Thr Asn Lys Phe Pro Ser Glu Tyr
            20                  25                  30

Val Pro Thr Val Phe Asp Asn Tyr Ala Val Thr Val Met Ile Gly Gly
        35                  40                  45

Glu Pro Tyr Thr Leu Gly Leu Phe Asp Thr Ala Gly Gln Glu Asp Tyr
    50                  55                  60

Asp Arg Leu Arg Pro Leu Ser Tyr Pro Gln Thr Asp Val Phe Leu Val
65                  70                  75                  80

Cys Phe Ser Val Val Ser Pro Ser Ser Phe Glu Asn Val Lys Glu Lys
                85                  90                  95

Trp Val Pro Glu Ile Thr His His Cys Pro Lys Thr Pro Phe Leu Leu
            100                 105                 110

Val Gly Thr Gln Ile Asp Leu Arg Asp Asp Pro Ser Thr Ile Glu Lys
        115                 120                 125

Leu Ala Lys Asn Lys Gln Lys Pro Ile Thr Pro Glu Thr Ala Glu Lys
130                 135                 140

Leu Ala Arg Asp Leu Lys Ala Val Lys Tyr Val Glu Cys Ser Ala Leu
145                 150                 155                 160

Thr Gln Lys Gly Leu Lys Asn Val Phe Asp Glu Ala Ile Leu Ala Ala
                165                 170                 175

Leu Glu Pro Pro Glu Pro Lys Lys Ser Arg Arg Cys Val Leu Leu
            180                 185                 190
```

<210> SEQ ID NO 77
<211> LENGTH: 18
<212> TYPE: PRT
<213> ORGANISM: Artificial Sequence
<220> FEATURE:
<223> OTHER INFORMATION: T2A self-cleaving peptide

<400> SEQUENCE: 77

```
Glu Gly Arg Gly Ser Leu Leu Thr Cys Gly Asp Val Glu Glu Asn Pro
1               5                   10                  15

Gly Pro
```

<210> SEQ ID NO 78
<211> LENGTH: 23
<212> TYPE: PRT

```
<213> ORGANISM: Artificial Sequence
<220> FEATURE:
<223> OTHER INFORMATION: T2A self-cleaving peptide variant

<400> SEQUENCE: 78

Leu Glu Gly Gly Gly Glu Gly Arg Gly Ser Leu Leu Thr Cys Gly Asp
1               5                   10                  15

Val Glu Glu Asn Pro Gly Pro
            20

<210> SEQ ID NO 79
<211> LENGTH: 19
<212> TYPE: PRT
<213> ORGANISM: Artificial Sequence
<220> FEATURE:
<223> OTHER INFORMATION: T2A self-cleaving peptide variant

<400> SEQUENCE: 79

Glu Gly Arg Gly Ser Leu Leu Thr Cys Gly Asp Val Glu Glu Asn Pro
1               5                   10                  15

Gly Pro Arg

<210> SEQ ID NO 80
<211> LENGTH: 19
<212> TYPE: PRT
<213> ORGANISM: Artificial Sequence
<220> FEATURE:
<223> OTHER INFORMATION: P2A self-cleaving peptide

<400> SEQUENCE: 80

Ala Thr Asn Phe Ser Leu Leu Lys Gln Ala Gly Asp Val Glu Glu Asn
1               5                   10                  15

Pro Gly Pro

<210> SEQ ID NO 81
<211> LENGTH: 27
<212> TYPE: PRT
<213> ORGANISM: Artificial Sequence
<220> FEATURE:
<223> OTHER INFORMATION: P2A self-cleaving peptide variant

<400> SEQUENCE: 81

Arg Ala Lys Arg Ser Gly Ser Gly Ala Thr Asn Phe Ser Leu Leu Lys
1               5                   10                  15

Gln Ala Gly Asp Val Glu Glu Asn Pro Gly Pro
            20                  25

<210> SEQ ID NO 82
<211> LENGTH: 20
<212> TYPE: PRT
<213> ORGANISM: Artificial Sequence
<220> FEATURE:
<223> OTHER INFORMATION: E2A self-cleaving peptide

<400> SEQUENCE: 82

Gln Cys Thr Asn Tyr Ala Leu Leu Lys Leu Ala Gly Asp Val Glu Ser
1               5                   10                  15

Asn Pro Gly Pro
            20

<210> SEQ ID NO 83
<211> LENGTH: 22
<212> TYPE: PRT
<213> ORGANISM: Artificial Sequence
```

<220> FEATURE:
<223> OTHER INFORMATION: F2A self-cleaving peptide

<400> SEQUENCE: 83

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 84
<211> LENGTH: 598
<212> TYPE: PRT
<213> ORGANISM: Artificial Sequence
<220> FEATURE:
<223> OTHER INFORMATION: HPV16 E7 TCRbeta chain-P2A-TCRalpha chain

<400> SEQUENCE: 84

Met Ala Pro Gly Leu Leu Cys Trp Ala Leu Leu Cys Leu Leu Gly Ala
1               5                   10                  15

Gly Leu Val Asp Ala Gly Val Thr Gln Ser Pro Thr His Leu Ile Lys
            20                  25                  30

Thr Arg Gly Gln Gln Val Thr Leu Arg Cys Ser Pro Lys Ser Gly His
        35                  40                  45

Asp Thr Val Ser Trp Tyr Gln Gln Ala Leu Gly Gln Gly Pro Gln Phe
    50                  55                  60

Ile Phe Gln Tyr Tyr Glu Glu Glu Arg Gln Arg Gly Asn Phe Pro
65                  70                  75                  80

Asp Arg Phe Ser Gly His Gln Phe Pro Asn Tyr Ser Ser Glu Leu Asn
                85                  90                  95

Val Asn Ala Leu Leu Leu Gly Asp Ser Ala Leu Tyr Leu Cys Ala Ser
            100                 105                 110

Ser Leu Gly Trp Arg Gly Gly Arg Tyr Asn Glu Gln Phe Phe Gly Pro
        115                 120                 125

Gly Thr Arg Leu Thr Val Leu Glu Asp Leu Arg Asn Val Thr Pro Pro
    130                 135                 140

Lys Val Ser Leu Phe Glu Pro Ser Lys Ala Glu Ile Ala Asn Lys Gln
145                 150                 155                 160

Lys Ala Thr Leu Val Cys Leu Ala Arg Gly Phe Phe Pro Asp His Val
                165                 170                 175

Glu Leu Ser Trp Trp Val Asn Gly Lys Glu Val His Ser Gly Val Cys
            180                 185                 190

Thr Asp Pro Gln Ala Tyr Lys Glu Ser Asn Tyr Ser Tyr Cys Leu Ser
        195                 200                 205

Ser Arg Leu Arg Val Ser Ala Thr Phe Trp His Asn Pro Arg Asn His
    210                 215                 220

Phe Arg Cys Gln Val Gln Phe His Gly Leu Ser Glu Glu Asp Lys Trp
225                 230                 235                 240

Pro Glu Gly Ser Pro Lys Pro Val Thr Gln Asn Ile Ser Ala Glu Ala
                245                 250                 255

Trp Gly Arg Ala Asp Cys Gly Ile Thr Ser Ala Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Thr Leu Val Val Met Ala Met Val Lys
    290                 295                 300

Arg Lys Asn Ser Arg Ala Lys Arg Ser Gly Ser Gly Ala Thr Asn Phe

```
              305                 310                 315                 320
        Ser Leu Leu Lys Gln Ala Gly Asp Val Glu Glu Asn Pro Gly Pro Met
                        325                 330                 335

Trp Gly Val Phe Leu Leu Tyr Val Ser Met Lys Met Gly Gly Thr Thr
                        340                 345                 350

Gly Gln Asn Ile Asp Gln Pro Thr Glu Met Thr Ala Thr Glu Gly Ala
                        355                 360                 365

Ile Val Gln Ile Asn Cys Thr Tyr Gln Thr Ser Gly Phe Asn Gly Leu
            370                 375                 380

Phe Trp Tyr Gln Gln His Ala Gly Glu Ala Pro Thr Phe Leu Ser Tyr
        385                 390                 395                 400

Asn Val Leu Asp Gly Leu Glu Glu Lys Gly Arg Phe Ser Ser Phe Leu
                        405                 410                 415

Ser Arg Ser Lys Gly Tyr Ser Tyr Leu Leu Leu Lys Glu Leu Gln Met
                        420                 425                 430

Lys Asp Ser Ala Ser Tyr Leu Cys Ala Ser Val Asp Gly Asn Asn Arg
                        435                 440                 445

Leu Ala Phe Gly Lys Gly Asn Gln Val Val Ile Pro Asn Ile Gln
            450                 455                 460

Asn Pro Glu Pro Ala Val Tyr Gln Leu Lys Asp Pro Arg Ser Gln Asp
        465                 470                 475                 480

Ser Thr Leu Cys Leu Phe Thr Asp Phe Asp Ser Gln Ile Asn Val Pro
                        485                 490                 495

Lys Thr Met Glu Ser Gly Thr Phe Ile Thr Asp Lys Cys Val Leu Asp
                        500                 505                 510

Met Lys Ala Met Asp Ser Lys Ser Asn Gly Ala Ile Ala Trp Ser Asn
                        515                 520                 525

Gln Thr Ser Phe Thr Cys Gln Asp Ile Phe Lys Glu Thr Asn Ala Thr
                        530                 535                 540

Tyr Pro Ser Ser Asp Val Pro Cys Asp Ala Thr Leu Thr Glu Lys Ser
        545                 550                 555                 560

Phe Glu Thr Asp Met Asn Leu Asn Phe Gln Asn Leu Leu Val Ile Val
                        565                 570                 575

Leu Arg Ile Leu Leu Leu Lys Val Ala Gly Phe Asn Leu Leu Met Thr
                        580                 585                 590

Leu Arg Leu Trp Ser Ser
                        595

<210> SEQ ID NO 85
<211> LENGTH: 279
<212> TYPE: PRT
<213> ORGANISM: Mus musculus
<220> FEATURE:
<223> OTHER INFORMATION: Tim4 binding domain, amino acids 1-22 are
      signal peptide

<400> SEQUENCE: 85

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
                20                  25                  30

Gly Gln Pro Val Thr Leu Pro Cys His Tyr Leu Ser Trp Ser Gln Ser
                35                  40                  45

Arg Asn Ser Met Cys Trp Gly Lys Gly Ser Cys Pro Asn Ser Lys Cys
            50                  55                  60
```

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
            85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
            115                 120                 125

Leu Glu Leu Arg Arg Ala Thr Thr Lys Lys Pro Thr Thr Thr Thr Thr
        130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Pro Pro
            165                 170                 175

Gln Thr Leu Ala Thr Thr Ala Phe Ser Thr Ala Val Thr Cys Pro
            180                 185                 190

Ser Thr Thr Pro Gly Ser Phe Ser Gln Glu Thr Thr Lys Gly Ser Ala
            195                 200                 205

Phe Thr Thr Glu Ser Glu Thr Leu Pro Ala Ser Asn His Ser Gln Arg
            210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
                260                 265                 270

Gln Ile Asn Ser Arg Gln Thr
        275

<210> SEQ ID NO 86
<211> LENGTH: 135
<212> TYPE: PRT
<213> ORGANISM: Artificial Sequence
<220> FEATURE:
<223> OTHER INFORMATION: TCR Vbeta region

<400> SEQUENCE: 86

Met Ala Pro Gly Leu Leu Cys Trp Ala Leu Leu Cys Leu Leu Gly Ala
1               5                   10                  15

Gly Leu Val Asp Ala Gly Val Thr Gln Ser Pro Thr His Leu Ile Lys
            20                  25                  30

Thr Arg Gly Gln Gln Val Thr Leu Arg Cys Ser Pro Lys Ser Gly His
        35                  40                  45

Asp Thr Val Ser Trp Tyr Gln Gln Ala Leu Gly Gln Gly Pro Gln Phe
    50                  55                  60

Ile Phe Gln Tyr Tyr Glu Glu Glu Arg Gln Arg Gly Asn Phe Pro
65                  70                  75                  80

Asp Arg Phe Ser Gly His Gln Phe Pro Asn Tyr Ser Ser Glu Leu Asn
            85                  90                  95

Val Asn Ala Leu Leu Leu Gly Asp Ser Ala Leu Tyr Leu Cys Ala Ser
            100                 105                 110

Ser Leu Gly Trp Arg Gly Arg Tyr Asn Glu Gln Phe Phe Gly Pro
        115                 120                 125

Gly Thr Arg Leu Thr Val Leu
        130                 135

<210> SEQ ID NO 87
<211> LENGTH: 173
<212> TYPE: PRT
<213> ORGANISM: Artificial Sequence
<220> FEATURE:
<223> OTHER INFORMATION: TCR Cbeta region, Cys-substituted

<400> SEQUENCE: 87

```
Glu Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
            20                  25                  30

Ala Arg Gly Phe Phe Pro Asp His Val Glu Leu Ser Trp Trp Val Asn
        35                  40                  45

Gly Lys Glu Val His Ser Gly Val Cys Thr Asp Pro Gln Ala Tyr Lys
    50                  55                  60

Glu Ser Asn Tyr Ser Tyr Cys Leu Ser Ser Arg Leu Arg Val Ser Ala
65                  70                  75                  80

Thr Phe Trp His Asn Pro Arg Asn His Phe Arg Cys Gln Val Gln Phe
                85                  90                  95

His Gly Leu Ser Glu Glu Asp Lys Trp Pro Glu Gly Ser Pro Lys Pro
            100                 105                 110

Val Thr Gln Asn Ile Ser Ala Glu Ala Trp Gly Arg Ala Asp Cys Gly
        115                 120                 125

Ile Thr Ser Ala Ser Tyr Gln Gln Gly Val Leu Ser Ala Thr Ile Leu
    130                 135                 140

Tyr Glu Ile Leu Leu Gly Lys Ala Thr Leu Tyr Ala Val Leu Val Ser
145                 150                 155                 160

Thr Leu Val Val Met Ala Met Val Lys Arg Lys Asn Ser
                165                 170
```

<210> SEQ ID NO 88
<211> LENGTH: 126
<212> TYPE: PRT
<213> ORGANISM: Artificial Sequence
<220> FEATURE:
<223> OTHER INFORMATION: TCR Valpha region

<400> SEQUENCE: 88

```
Met Trp Gly Val Phe Leu Leu Tyr Val Ser Met Lys Met Gly Gly Thr
1               5                   10                  15

Thr Gly Gln Asn Ile Asp Gln Pro Thr Glu Met Thr Ala Thr Glu Gly
            20                  25                  30

Ala Ile Val Gln Ile Asn Cys Thr Tyr Gln Thr Ser Gly Phe Asn Gly
        35                  40                  45

Leu Phe Trp Tyr Gln Gln His Ala Gly Glu Ala Pro Thr Phe Leu Ser
    50                  55                  60

Tyr Asn Val Leu Asp Gly Leu Glu Glu Lys Gly Arg Phe Ser Ser Phe
65                  70                  75                  80

Leu Ser Arg Ser Lys Gly Tyr Ser Tyr Leu Leu Leu Lys Glu Leu Gln
                85                  90                  95

Met Lys Asp Ser Ala Ser Tyr Leu Cys Ala Ser Val Asp Gly Asn Asn
            100                 105                 110

Arg Leu Ala Phe Gly Lys Gly Asn Gln Val Val Val Ile Pro
        115                 120                 125
```

<210> SEQ ID NO 89

```
<211> LENGTH: 137
<212> TYPE: PRT
<213> ORGANISM: Artificial Sequence
<220> FEATURE:
<223> OTHER INFORMATION: TCR Calpha region, Cys-substituted, LVL
      substituted

<400> SEQUENCE: 89

Asn Ile Gln Asn Pro Glu Pro Ala Val Tyr Gln Leu Lys Asp Pro Arg
1               5                   10                  15

Ser Gln Asp Ser Thr Leu Cys Leu Phe Thr Asp Phe Asp Ser Gln Ile
                20                  25                  30

Asn Val Pro Lys Thr Met Glu Ser Gly Thr Phe Ile Thr Asp Lys Cys
            35                  40                  45

Val Leu Asp Met Lys Ala Met Asp Ser Lys Ser Asn Gly Ala Ile Ala
    50                  55                  60

Trp Ser Asn Gln Thr Ser Phe Thr Cys Gln Asp Ile Phe Lys Glu Thr
65                  70                  75                  80

Asn Ala Thr Tyr Pro Ser Ser Asp Val Pro Cys Asp Ala Thr Leu Thr
                85                  90                  95

Glu Lys Ser Phe Glu Thr Asp Met Asn Leu Asn Phe Gln Asn Leu Leu
                100                 105                 110

Val Ile Val Leu Arg Ile Leu Leu Leu Lys Val Ala Gly Phe Asn Leu
            115                 120                 125

Leu Met Thr Leu Arg Leu Trp Ser Ser
            130                 135

<210> SEQ ID NO 90
<211> LENGTH: 314
<212> TYPE: PRT
<213> ORGANISM: Homo sapiens
<220> FEATURE:
<223> OTHER INFORMATION: Tim4 binding domain, amino acids 1-24 signal
      peptide

<400> SEQUENCE: 90

Met Ser Lys Glu Pro Leu Ile Leu Trp Leu Met Ile Glu Phe Trp Trp
1               5                   10                  15

Leu Tyr Leu Thr Pro Val Thr Ser Glu Thr Val Val Thr Glu Val Leu
                20                  25                  30

Gly His Arg Val Thr Leu Pro Cys Leu Tyr Ser Ser Trp Ser His Asn
            35                  40                  45

Ser Asn Ser Met Cys Trp Gly Lys Asp Gln Cys Pro Tyr Ser Gly Cys
    50                  55                  60

Lys Glu Ala Leu Ile Arg Thr Asp Gly Met Arg Val Thr Ser Arg Lys
65                  70                  75                  80

Ser Ala Lys Tyr Arg Leu Gln Gly Thr Ile Pro Arg Gly Asp Val Ser
                85                  90                  95

Leu Thr Ile Leu Asn Pro Ser Glu Ser Asp Ser Gly Val Tyr Cys Cys
                100                 105                 110

Arg Ile Glu Val Pro Gly Trp Phe Asn Asp Val Lys Ile Asn Val Arg
            115                 120                 125

Leu Asn Leu Gln Arg Ala Ser Thr Thr Thr His Arg Thr Ala Thr Thr
            130                 135                 140

Thr Thr Arg Arg Thr Thr Thr Thr Ser Pro Thr Thr Thr Arg Gln Met
145                 150                 155                 160

Thr Thr Thr Pro Ala Ala Leu Pro Thr Thr Val Val Thr Thr Pro Asp
                165                 170                 175
```

```
Leu Thr Thr Gly Thr Pro Leu Gln Met Thr Thr Ile Ala Val Phe Thr
            180                 185                 190

Thr Ala Asn Thr Cys Leu Ser Leu Thr Pro Ser Thr Leu Pro Glu Glu
            195                 200                 205

Ala Thr Gly Leu Leu Thr Pro Glu Pro Ser Lys Glu Gly Pro Ile Leu
            210                 215                 220

Thr Ala Glu Ser Glu Thr Val Leu Pro Ser Asp Ser Trp Ser Ser Val
225                 230                 235                 240

Glu Ser Thr Ser Ala Asp Thr Val Leu Leu Thr Ser Lys Glu Ser Lys
                245                 250                 255

Val Trp Asp Leu Pro Ser Thr Ser His Val Ser Met Trp Lys Thr Ser
            260                 265                 270

Asp Ser Val Ser Ser Pro Gln Pro Gly Ala Ser Asp Thr Ala Val Pro
            275                 280                 285

Glu Gln Asn Lys Thr Thr Lys Thr Gly Gln Met Asp Gly Ile Pro Met
            290                 295                 300

Ser Met Lys Asn Glu Met Pro Ile Ser Gln
305                 310

<210> SEQ ID NO 91
<211> LENGTH: 141
<212> TYPE: PRT
<213> ORGANISM: Homo sapiens
<220> FEATURE:
<223> OTHER INFORMATION: MyD88 TIR domain

<400> SEQUENCE: 91

His Met Pro Glu Arg Phe Asp Ala Phe Ile Cys Tyr Cys Pro Ser Asp
1               5                   10                  15

Ile Gln Phe Val Gln Glu Met Ile Arg Gln Leu Glu Gln Thr Asn Tyr
            20                  25                  30

Arg Leu Lys Leu Cys Val Ser Asp Arg Asp Val Leu Pro Gly Thr Cys
        35                  40                  45

Val Trp Ser Ile Ala Ser Glu Leu Ile Glu Lys Arg Cys Arg Arg Met
    50                  55                  60

Val Val Val Val Ser Asp Asp Tyr Leu Gln Ser Lys Glu Cys Asp Phe
65                  70                  75                  80

Gln Thr Lys Phe Ala Leu Ser Leu Ser Pro Gly Ala His Gln Lys Arg
                85                  90                  95

Leu Ile Pro Ile Lys Tyr Lys Ala Met Lys Lys Glu Phe Pro Ser Ile
            100                 105                 110

Leu Arg Phe Ile Thr Val Cys Asp Tyr Thr Asn Pro Cys Thr Lys Ser
        115                 120                 125

Trp Phe Trp Thr Arg Leu Ala Lys Ala Leu Ser Leu Pro
    130                 135                 140

<210> SEQ ID NO 92
<211> LENGTH: 70
<212> TYPE: PRT
<213> ORGANISM: Homo sapiens
<220> FEATURE:
<223> OTHER INFORMATION: FcgammaR2B2 signaling domain

<400> SEQUENCE: 92

Val Val Ala Leu Ile Tyr Cys Arg Lys Lys Arg Ile Ser Ala Leu Pro
1               5                   10                  15

Gly Tyr Pro Glu Cys Arg Glu Met Gly Glu Thr Leu Pro Glu Lys Pro
```

```
                    20                  25                  30

Ala Asn Pro Thr Asn Pro Asp Glu Ala Asp Lys Val Gly Ala Glu Asn
                35                  40                  45

Thr Ile Thr Tyr Ser Leu Leu Met His Pro Asp Ala Leu Glu Glu Pro
            50                  55                  60

Asp Asp Gln Asn Arg Ile
65                  70

<210> SEQ ID NO 93
<211> LENGTH: 41
<212> TYPE: PRT
<213> ORGANISM: Homo sapiens
<220> FEATURE:
<223> OTHER INFORMATION: FcalphaR1 signaling domain

<400> SEQUENCE: 93

Glu Asn Trp His Ser His Thr Ala Leu Asn Lys Glu Ala Ser Ala Asp
1               5                   10                  15

Val Ala Glu Pro Ser Trp Ser Gln Gln Met Cys Gln Pro Gly Leu Thr
            20                  25                  30

Phe Ala Arg Thr Pro Ser Val Cys Lys
        35                  40

<210> SEQ ID NO 94
<211> LENGTH: 487
<212> TYPE: PRT
<213> ORGANISM: Artificial Sequence
<220> FEATURE:
<223> OTHER INFORMATION: CER5, amino acids 1-22 are signal peptide

<400> SEQUENCE: 94

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
        35                  40                  45

Arg Asn Ser Met Cys Trp Gly Lys Gly Ser Cys Pro Asn Ser Lys Cys
    50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Thr Lys Lys Pro Thr Thr Thr Thr
    130                 135                 140

Arg Pro Thr Thr Thr Pro Tyr Val Thr Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Ala Phe Ser Thr Ala Val Thr Thr Cys Pro
            180                 185                 190

Ser Thr Thr Pro Gly Ser Phe Ser Gln Glu Thr Lys Gly Ser Ala
        195                 200                 205
```

Phe Thr Thr Glu Ser Glu Thr Leu Pro Ala Ser Asn His Ser Gln Arg
210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
            245                 250                 255

Thr Thr Leu Thr Thr Ser Glu Ser Leu Gln Lys Thr Thr Lys Ser His
            260                 265                 270

Gln Ile Asn Ser Arg Gln Thr Leu Ile Ile Ala Cys Cys Val Gly
            275                 280                 285

Phe Val Leu Met Val Leu Leu Phe Leu Ala Phe Leu Lys Phe Tyr Phe
290                 295                 300

His Leu Met Leu Leu Ala Gly Cys Ile Lys Tyr Gly Arg Gly Glu Asn
305                 310                 315                 320

Ile Tyr Asp Ala Phe Val Ile Tyr Ser Ser Gln Asp Glu Asp Trp Val
            325                 330                 335

Arg Asn Glu Leu Val Lys Asn Leu Glu Glu Gly Val Pro Pro Phe Gln
            340                 345                 350

Leu Cys Leu His Tyr Arg Asp Phe Ile Pro Gly Val Ala Ile Ala Ala
            355                 360                 365

Asn Ile Ile His Glu Gly Phe His Lys Ser Arg Lys Val Ile Val Val
370                 375                 380

Val Ser Gln His Phe Ile Gln Ser Arg Trp Cys Ile Phe Glu Tyr Glu
385                 390                 395                 400

Ile Ala Gln Thr Trp Gln Phe Leu Ser Ser Arg Ala Gly Ile Ile Phe
            405                 410                 415

Ile Val Leu Gln Lys Val Glu Lys Thr Leu Leu Arg Gln Gln Val Glu
            420                 425                 430

Leu Tyr Arg Leu Leu Ser Arg Asn Thr Tyr Leu Glu Trp Glu Asp Ser
            435                 440                 445

Val Leu Gly Arg His Ile Phe Trp Arg Arg Leu Arg Lys Ala Leu Leu
            450                 455                 460

Asp Gly Lys Ser Trp Asn Pro Glu Gly Thr Val Gly Thr Gly Cys Asn
465                 470                 475                 480

Trp Gln Glu Ala Thr Ser Ile
                485

<210> SEQ ID NO 95
<211> LENGTH: 498
<212> TYPE: PRT
<213> ORGANISM: Artificial Sequence
<220> FEATURE:
<223> OTHER INFORMATION: CER19, amino acids 1-22 are signal peptide

<400> SEQUENCE: 95

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
                20                  25                  30

Gly Gln Pro Val Thr Leu Pro Cys His Tyr Leu Ser Trp Ser Gln Ser
            35                  40                  45

Arg Asn Ser Met Cys Trp Gly Lys Gly Ser Cys Pro Asn Ser Lys Cys
        50                  55                  60

Asn Ala Glu Leu Leu Arg Thr Asp Gly Thr Arg Ile Ile Ser Arg Lys
65                  70                  75                  80

```
Ser Thr Lys Tyr Thr Leu Leu Gly Lys Val Gln Phe Gly Glu Val Ser
                 85                  90                  95
Leu Thr Ile Ser Asn Thr Asn Arg Gly Asp Ser Gly Val Tyr Cys Cys
            100                 105                 110
Arg Ile Glu Val Pro Gly Trp Phe Asn Asp Val Lys Lys Asn Val Arg
        115                 120                 125
Leu Glu Leu Arg Arg Ala Thr Thr Lys Lys Pro Thr Thr Thr
    130                 135                 140
Arg Pro Thr Thr Thr Pro Tyr Val Thr Thr Thr Pro Glu Leu Leu
145                 150                 155                 160
Pro Thr Thr Val Met Thr Thr Ser Val Leu Pro Thr Thr Thr Pro Pro
                165                 170                 175
Gln Thr Leu Ala Thr Thr Ala Phe Ser Thr Ala Val Thr Thr Cys Pro
            180                 185                 190
Ser Thr Thr Pro Gly Ser Phe Ser Gln Glu Thr Thr Lys Gly Ser Ala
        195                 200                 205
Phe Thr Thr Glu Ser Glu Thr Leu Pro Ala Ser Asn His Ser Gln Arg
    210                 215                 220
Ser Met Met Thr Ile Ser Thr Asp Ile Ala Val Leu Arg Pro Thr Gly
225                 230                 235                 240
Ser Asn Pro Gly Ile Leu Pro Ser Thr Ser Gln Leu Thr Thr Gln Lys
                245                 250                 255
Thr Thr Leu Thr Thr Ser Glu Ser Leu Gln Lys Thr Thr Lys Ser His
            260                 265                 270
Gln Ile Asn Ser Arg Gln Thr Ile Leu Ile Ala Cys Cys Val Gly
        275                 280                 285
Phe Val Leu Met Val Leu Leu Phe Leu Ala Phe Leu Thr Lys Phe Arg
    290                 295                 300
Gly Phe Cys Phe Ile Cys Tyr Lys Thr Ala Gln Arg Leu Val Phe Lys
305                 310                 315                 320
Asp His Pro Gln Gly Thr Glu Pro Asp Met Tyr Lys Tyr Asp Ala Tyr
                325                 330                 335
Leu Cys Phe Ser Ser Lys Asp Phe Thr Trp Val Gln Asn Ala Leu Leu
            340                 345                 350
Lys His Leu Asp Thr Gln Tyr Ser Asp Gln Asn Arg Phe Asn Leu Cys
        355                 360                 365
Phe Glu Glu Arg Asp Phe Val Pro Gly Glu Asn Arg Ile Ala Asn Ile
    370                 375                 380
Gln Asp Ala Ile Trp Asn Ser Arg Lys Ile Val Cys Leu Val Ser Arg
385                 390                 395                 400
His Phe Leu Arg Asp Gly Trp Cys Leu Glu Ala Phe Ser Tyr Ala Gln
                405                 410                 415
Gly Arg Cys Leu Ser Asp Leu Asn Ser Ala Leu Ile Met Val Val Val
            420                 425                 430
Gly Ser Leu Ser Gln Tyr Gln Leu Met Lys His Gln Ser Ile Arg Gly
        435                 440                 445
Phe Val Gln Lys Gln Gln Tyr Leu Arg Trp Pro Glu Asp Phe Gln Asp
    450                 455                 460
Val Gly Trp Phe Leu His Lys Leu Ser Gln Gln Ile Leu Lys Lys Glu
465                 470                 475                 480
Lys Glu Lys Lys Lys Asp Asn Asn Ile Pro Leu Gln Thr Val Ala Thr
                485                 490                 495
Ile Ser
```

```
<210> SEQ ID NO 96
<211> LENGTH: 493
<212> TYPE: PRT
<213> ORGANISM: Artificial Sequence
<220> FEATURE:
<223> OTHER INFORMATION: CER21, amino acids 1-22 are signal peptide

<400> SEQUENCE: 96

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
        35                  40                  45

Arg Asn Ser Met Cys Trp Gly Lys Gly Ser Cys Pro Asn Ser Lys Cys
50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Lys Lys Pro Thr Thr Thr Thr
130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Lys Ser His
            260                 265                 270

Gln Ile Asn Ser Arg Gln Thr Ile Leu Ile Ala Cys Cys Val Gly
        275                 280                 285

Phe Val Leu Met Val Leu Leu Phe Leu Ala Phe Leu His His Leu Phe
        290                 295                 300

Tyr Trp Asp Val Trp Phe Ile Tyr Asn Val Cys Leu Ala Lys Val Lys
305                 310                 315                 320

Gly Tyr Arg Ser Leu Ser Thr Ser Gln Thr Phe Tyr Asp Ala Tyr Ile
                325                 330                 335

Ser Tyr Asp Thr Lys Asp Ala Ser Val Thr Asp Trp Val Ile Asn Glu
            340                 345                 350

Leu Arg Tyr His Leu Glu Glu Ser Arg Asp Lys Asn Val Leu Leu Cys
        355                 360                 365
```

-continued

```
Leu Glu Glu Arg Asp Trp Asp Pro Gly Leu Ala Ile Ile Asp Asn Leu
            370                 375                 380

Met Gln Ser Ile Asn Gln Ser Lys Lys Thr Val Phe Val Leu Thr Lys
385                 390                 395                 400

Lys Tyr Ala Lys Ser Trp Asn Phe Lys Thr Ala Phe Tyr Leu Ala Leu
                405                 410                 415

Gln Arg Leu Met Asp Glu Asn Met Asp Val Ile Ile Phe Ile Leu Leu
                420                 425                 430

Glu Pro Val Leu Gln His Ser Gln Tyr Leu Arg Leu Arg Gln Arg Ile
            435                 440                 445

Cys Lys Ser Ser Ile Leu Gln Trp Pro Asp Asn Pro Lys Ala Glu Gly
    450                 455                 460

Leu Phe Trp Gln Thr Leu Arg Asn Val Val Leu Thr Glu Asn Asp Ser
465                 470                 475                 480

Arg Tyr Asn Asn Met Tyr Val Asp Ser Ile Lys Gln Tyr
                485                 490
```

<210> SEQ ID NO 97
<211> LENGTH: 386
<212> TYPE: PRT
<213> ORGANISM: Artificial Sequence
<220> FEATURE:
<223> OTHER INFORMATION: CER25, amino acids 1-22 are signal peptide

<400> SEQUENCE: 97

```
Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
                20                  25                  30

Gly Gln Pro Val Thr Leu Pro Cys His Tyr Leu Ser Trp Ser Gln Ser
            35                  40                  45

Arg Asn Ser Met Cys Trp Gly Lys Gly Ser Cys Pro Asn Ser Lys Cys
50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
                100                 105                 110

Arg Ile Glu Val Pro Gly Trp Phe Asn Asp Val Lys Lys Asn Val Arg
            115                 120                 125

Leu Glu Leu Arg Arg Ala Thr Thr Lys Lys Pro Thr Thr Thr Thr
130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
    210                 215                 220

Ser Met Met Thr Ile Ser Thr Asp Ile Ala Val Leu Arg Pro Thr Gly
225                 230                 235                 240
```

Ser Asn Pro Gly Ile Leu Pro Ser Thr Ser Gln Leu Thr Thr Gln Lys
            245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ala Cys Cys Val Gly
            275                 280                 285

Phe Val Leu Met Val Leu Leu Phe Leu Ala Phe Leu Leu Trp Asn Lys
290                     295                 300

Lys Arg Met Arg Gly Pro Gly Lys Asp Pro Thr Arg Lys Cys Pro Asp
305                 310                 315                 320

Pro Arg Ser Ala Ser Ser Pro Lys Gln His Pro Ser Glu Ser Val Tyr
                325                 330                 335

Thr Ala Leu Gln Arg Arg Glu Thr Glu Val Tyr Ala Cys Ile Glu Asn
            340                 345                 350

Glu Asp Gly Ser Ser Pro Thr Ala Lys Gln Ser Pro Leu Ser Gln Glu
            355                 360                 365

Arg Pro His Arg Phe Glu Asp Asp Gly Glu Leu Asn Leu Val Tyr Glu
370                 375                 380

Asn Leu
385

<210> SEQ ID NO 98
<211> LENGTH: 475
<212> TYPE: PRT
<213> ORGANISM: Artificial Sequence
<220> FEATURE:
<223> OTHER INFORMATION: CER27, amino acids 1-22 are signal peptide

<400> SEQUENCE: 98

Met Ser Lys Gly Leu Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
                20                  25                  30

Gly Gln Pro Val Thr Leu Pro Cys His Tyr Leu Ser Trp Ser Gln Ser
            35                  40                  45

Arg Asn Ser Met Cys Trp Gly Lys Gly Ser Cys Pro Asn Ser Lys Cys
50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Thr Lys Lys Pro Thr Thr Thr Thr
130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
        195                 200                 205

-continued

Phe Thr Thr Glu Ser Glu Thr Leu Pro Ala Ser Asn His Ser Gln Arg
    210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ala Cys Cys Val Gly
        275                 280                 285

Phe Val Leu Met Val Leu Leu Phe Leu Ala Phe Leu His Arg Phe His
    290                 295                 300

Gly Leu Trp Tyr Met Lys Met Met Trp Ala Trp Leu Gln Ala Lys Arg
305                 310                 315                 320

Lys Pro Arg Lys Ala Pro Ser Arg Asn Ile Cys Tyr Asp Ala Phe Val
                325                 330                 335

Ser Tyr Ser Glu Arg Asp Ala Tyr Trp Val Glu Asn Leu Met Val Gln
            340                 345                 350

Glu Leu Glu Asn Phe Asn Pro Pro Phe Lys Leu Cys Leu His Lys Arg
        355                 360                 365

Asp Phe Ile Pro Gly Lys Trp Ile Ile Asp Asn Ile Ile Asp Ser Ile
    370                 375                 380

Glu Lys Ser His Lys Thr Val Phe Val Leu Ser Glu Asn Phe Val Lys
385                 390                 395                 400

Ser Glu Trp Cys Lys Tyr Glu Leu Asp Phe Ser His Phe Arg Leu Phe
                405                 410                 415

Asp Glu Asn Asn Asp Ala Ala Ile Leu Ile Leu Leu Glu Pro Ile Glu
            420                 425                 430

Lys Lys Ala Ile Pro Gln Arg Phe Cys Lys Leu Arg Lys Ile Met Asn
        435                 440                 445

Thr Lys Thr Tyr Leu Glu Trp Pro Met Asp Glu Ala Gln Arg Glu Gly
    450                 455                 460

Phe Trp Val Asn Leu Arg Ala Ala Ile Lys Ser
465                 470                 475

<210> SEQ ID NO 99
<211> LENGTH: 574
<212> TYPE: PRT
<213> ORGANISM: Artificial Sequence
<220> FEATURE:
<223> OTHER INFORMATION: CER29, amino acids 1-22 are signal peptide

<400> SEQUENCE: 99

Met Ser Lys Gly Leu Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
        35                  40                  45

Arg Asn Ser Met Cys Trp Gly Lys Gly Ser Cys Pro Asn Ser Lys Cys
    50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

-continued

```
Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
            115                 120                 125

Leu Glu Leu Arg Arg Ala Thr Thr Thr Lys Lys Pro Thr Thr Thr Thr
            130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
            195                 200                 205

Phe Thr Thr Glu Ser Glu Thr Leu Pro Ala Ser Asn His Ser Gln Arg
            210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ala Cys Cys Val Gly
            275                 280                 285

Phe Val Leu Met Val Leu Leu Phe Leu Ala Phe Leu Met Ser Leu Leu
            290                 295                 300

Asn Cys Glu Asn Ser Cys Gly Ser Ser Gln Ser Glu Ser Asp Cys Cys
305                 310                 315                 320

Val Ala Met Ala Ser Ser Cys Ser Ala Val Thr Lys Asp Asp Ser Val
                325                 330                 335

Gly Gly Thr Ala Ser Thr Gly Asn Leu Ser Ser Ser Phe Met Glu Glu
            340                 345                 350

Ile Gln Gly Tyr Asp Val Glu Phe Asp Pro Pro Leu Glu Ser Lys Tyr
            355                 360                 365

Glu Cys Pro Ile Cys Leu Met Ala Leu Arg Glu Ala Val Gln Thr Pro
            370                 375                 380

Cys Gly His Arg Phe Cys Lys Ala Cys Ile Ile Lys Ser Ile Arg Asp
385                 390                 395                 400

Ala Gly His Lys Cys Pro Val Asp Asn Glu Ile Leu Leu Glu Asn Gln
                405                 410                 415

Leu Phe Pro Asp Asn Phe Ala Lys Arg Glu Ile Leu Ser Leu Met Val
            420                 425                 430

Lys Cys Pro Asn Glu Gly Cys Leu His Lys Met Glu Leu Arg His Leu
            435                 440                 445

Glu Asp His Gln Ala His Cys Glu Phe Ala Leu Met Asp Cys Pro Gln
            450                 455                 460

Cys Gln Arg Pro Phe Gln Lys Phe His Ile Asn Ile His Ile Leu Lys
465                 470                 475                 480

Asp Cys Pro Arg Arg Gln Val Ser Cys Asp Asn Cys Ala Ala Ser Met
                485                 490                 495

Ala Phe Glu Asp Lys Glu Ile His Asp Gln Asn Cys Pro Leu Ala Asn
            500                 505                 510
```

-continued

```
Val Ile Cys Glu Tyr Cys Asn Thr Ile Leu Ile Arg Glu Gln Met Pro
            515                 520                 525

Asn His Tyr Asp Leu Asp Cys Pro Thr Ala Pro Ile Pro Cys Thr Phe
            530                 535                 540

Ser Thr Phe Gly Cys His Glu Lys Met Gln Arg Asn His Leu Ala Arg
545                 550                 555                 560

His Leu Gln Glu Asn Thr Gln Ser His Met Arg Met Leu Ala
                565                 570

<210> SEQ ID NO 100
<211> LENGTH: 574
<212> TYPE: PRT
<213> ORGANISM: Artificial Sequence
<220> FEATURE:
<223> OTHER INFORMATION: CER31, amino acids 1-22 are signal peptide

<400> SEQUENCE: 100

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
        35                  40                  45

Arg Asn Ser Met Cys Trp Gly Lys Gly Ser Cys Pro Asn Ser Lys Cys
    50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Lys Lys Pro Thr Thr Thr Thr
130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
    210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ala Cys Cys Val Gly
        275                 280                 285

Phe Val Leu Met Val Leu Leu Phe Leu Ala Phe Leu Met Glu Ser Ser
    290                 295                 300
```

```
Lys Lys Met Asp Ser Pro Gly Ala Leu Gln Thr Asn Pro Pro Leu Lys
305                 310                 315                 320

Leu His Thr Asp Arg Ser Ala Gly Thr Pro Val Phe Val Pro Glu Gln
                325                 330                 335

Gly Gly Tyr Lys Glu Lys Phe Val Lys Thr Val Glu Asp Lys Tyr Lys
                340                 345                 350

Cys Glu Lys Cys His Leu Val Leu Cys Ser Pro Lys Gln Thr Glu Cys
                355                 360                 365

Gly His Arg Phe Cys Glu Ser Cys Met Ala Ala Leu Leu Ser Ser Ser
                370                 375                 380

Ser Pro Lys Cys Thr Ala Cys Gln Glu Ser Ile Val Lys Asp Lys Val
385                 390                 395                 400

Phe Lys Asp Asn Cys Cys Lys Arg Glu Ile Leu Ala Leu Gln Ile Tyr
                405                 410                 415

Cys Arg Asn Glu Ser Arg Gly Cys Ala Glu Gln Leu Met Leu Gly His
                420                 425                 430

Leu Leu Val His Leu Lys Asn Asp Cys His Phe Glu Glu Leu Pro Cys
                435                 440                 445

Val Arg Pro Asp Cys Lys Glu Lys Val Leu Arg Lys Asp Leu Arg Asp
                450                 455                 460

His Val Glu Lys Ala Cys Lys Tyr Arg Glu Ala Thr Cys Ser His Cys
465                 470                 475                 480

Lys Ser Gln Val Pro Met Ile Ala Leu Gln Lys His Glu Asp Thr Asp
                485                 490                 495

Cys Pro Cys Val Val Val Ser Cys Pro His Lys Cys Ser Val Gln Thr
                500                 505                 510

Leu Leu Arg Ser Glu Leu Ser Ala His Leu Ser Glu Cys Val Asn Ala
                515                 520                 525

Pro Ser Thr Cys Ser Phe Lys Arg Tyr Gly Cys Val Phe Gln Gly Thr
530                 535                 540

Asn Gln Gln Ile Lys Ala His Glu Ala Ser Ser Ala Val Gln His Val
545                 550                 555                 560

Asn Leu Leu Lys Glu Trp Ser Asn Ser Leu Glu Lys Lys Val
                565                 570

<210> SEQ ID NO 101
<211> LENGTH: 776
<212> TYPE: PRT
<213> ORGANISM: Artificial Sequence
<220> FEATURE:
<223> OTHER INFORMATION: CER1, amino acids 1-22 are signal peptide

<400> SEQUENCE: 101

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
                20                  25                  30

Gly Gln Pro Val Thr Leu Pro Cys His Tyr Leu Ser Trp Ser Gln Ser
                35                  40                  45

Arg Asn Ser Met Cys Trp Gly Lys Gly Ser Cys Pro Asn Ser Lys Cys
                50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95
```

```
Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Lys Lys Pro Thr Thr Thr Thr Thr
    130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
    210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ala Cys Cys Val Gly
            275                 280                 285

Phe Val Leu Met Val Leu Leu Phe Leu Ala Phe Leu Ala Leu Arg Arg
    290                 295                 300

Arg Val Gln Glu Thr Lys Phe Gly Gly Ala Phe Ser Glu Glu Asp Ser
305                 310                 315                 320

Gln Leu Val Val Asn Tyr Arg Ala Lys Lys Ser Phe Cys Arg Arg Ala
                325                 330                 335

Ile Glu Leu Thr Leu Gln Ser Leu Gly Val Ser Glu Glu Leu Gln Asn
            340                 345                 350

Lys Leu Glu Asp Val Val Ile Asp Arg Asn Leu Leu Val Leu Gly Lys
        355                 360                 365

Val Leu Gly Glu Gly Glu Phe Gly Ser Val Met Glu Gly Asn Leu Lys
    370                 375                 380

Gln Glu Asp Gly Thr Ser Gln Lys Val Ala Val Lys Thr Met Lys Leu
385                 390                 395                 400

Asp Asn Phe Ser Gln Arg Glu Ile Glu Glu Phe Leu Ser Glu Ala Ala
                405                 410                 415

Cys Met Lys Asp Phe Asn His Pro Asn Val Ile Arg Leu Leu Gly Val
            420                 425                 430

Cys Ile Glu Leu Ser Ser Gln Gly Ile Pro Lys Pro Met Val Ile Leu
        435                 440                 445

Pro Phe Met Lys Tyr Gly Asp Leu His Thr Phe Leu Leu Tyr Ser Arg
    450                 455                 460

Leu Asn Thr Gly Pro Lys Tyr Ile His Leu Gln Thr Leu Leu Lys Phe
465                 470                 475                 480

Met Met Asp Ile Ala Gln Gly Met Glu Tyr Leu Ser Asn Arg Asn Phe
                485                 490                 495

Leu His Arg Asp Leu Ala Ala Arg Asn Cys Met Leu Arg Asp Asp Met
            500                 505                 510

Thr Val Cys Val Ala Asp Phe Gly Leu Ser Lys Lys Ile Tyr Ser Gly
```

```
                    515                 520                 525
Asp Tyr Tyr Arg Gln Gly Arg Ile Ala Lys Met Pro Val Lys Trp Ile
    530                 535                 540

Ala Ile Glu Ser Leu Ala Asp Arg Val Tyr Thr Ser Lys Ser Asp Val
545                 550                 555                 560

Trp Ala Phe Gly Val Thr Met Trp Glu Ile Thr Thr Arg Gly Met Thr
                    565                 570                 575

Pro Tyr Pro Gly Val Gln Asn His Glu Met Tyr Asp Tyr Leu Leu His
            580                 585                 590

Gly His Arg Leu Lys Gln Pro Glu Asp Cys Leu Asp Glu Leu Tyr Asp
                595                 600                 605

Ile Met Tyr Ser Cys Trp Ser Ala Asp Pro Leu Asp Arg Pro Thr Phe
        610                 615                 620

Ser Val Leu Arg Leu Gln Leu Glu Lys Leu Ser Glu Ser Leu Pro Asp
625                 630                 635                 640

Ala Gln Asp Lys Glu Ser Ile Ile Tyr Ile Asn Thr Gln Leu Leu Glu
                    645                 650                 655

Ser Cys Glu Gly Ile Ala Asn Gly Pro Ser Leu Thr Gly Leu Asp Met
                660                 665                 670

Asn Ile Asp Pro Asp Ser Ile Ile Ala Ser Cys Thr Pro Gly Ala Ala
            675                 680                 685

Val Ser Val Val Thr Ala Glu Val His Glu Asn Asn Leu Arg Glu Glu
690                 695                 700

Arg Tyr Ile Leu Asn Gly Gly Asn Glu Glu Trp Glu Asp Val Ser Ser
705                 710                 715                 720

Thr Pro Phe Ala Ala Val Thr Pro Glu Lys Asp Gly Val Leu Pro Glu
                    725                 730                 735

Asp Arg Leu Thr Lys Asn Gly Val Ser Trp Ser His His Ser Thr Leu
                740                 745                 750

Pro Leu Gly Ser Pro Ser Pro Asp Glu Leu Leu Phe Val Asp Asp Ser
            755                 760                 765

Leu Glu Asp Ser Glu Val Leu Met
    770                 775

<210> SEQ ID NO 102
<211> LENGTH: 487
<212> TYPE: PRT
<213> ORGANISM: Artificial Sequence
<220> FEATURE:
<223> OTHER INFORMATION: CER6, amino acids 1-22 are signal peptide

<400> SEQUENCE: 102

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
                20                  25                  30

Gly Gln Pro Val Thr Leu Pro Cys His Tyr Leu Ser Trp Ser Gln Ser
            35                  40                  45

Arg Asn Ser Met Cys Trp Gly Lys Gly Ser Cys Pro Asn Ser Lys Cys
        50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                    85                  90                  95

Leu Thr Ile Ser Asn Thr Asn Arg Gly Asp Ser Gly Val Tyr Cys Cys
```

```
            100                 105                 110
Arg Ile Glu Val Pro Gly Trp Phe Asn Asp Val Lys Lys Asn Val Arg
            115                 120                 125

Leu Glu Leu Arg Arg Ala Thr Thr Thr Lys Lys Pro Thr Thr Thr Thr
130                 135                 140

Arg Pro Thr Thr Thr Pro Tyr Val Thr Thr Thr Thr Pro Glu Leu Leu
145                 150                 155                 160

Pro Thr Thr Val Met Thr Thr Ser Val Leu Pro Thr Thr Thr Pro Pro
                    165                 170                 175

Gln Thr Leu Ala Thr Thr Ala Phe Ser Thr Ala Val Thr Thr Cys Pro
                180                 185                 190

Ser Thr Thr Pro Gly Ser Phe Ser Gln Glu Thr Thr Lys Gly Ser Ala
            195                 200                 205

Phe Thr Thr Glu Ser Glu Thr Leu Pro Ala Ser Asn His Ser Gln Arg
            210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
                260                 265                 270

Gln Ile Asn Ser Arg Gln Thr Thr Ile Ile Gly Val Ser Val Leu Ser
            275                 280                 285

Val Leu Val Val Ser Val Val Ala Val Leu Val Tyr Lys Phe Tyr Phe
        290                 295                 300

His Leu Met Leu Leu Ala Gly Cys Ile Lys Tyr Gly Arg Gly Glu Asn
305                 310                 315                 320

Ile Tyr Asp Ala Phe Val Ile Tyr Ser Ser Gln Asp Glu Asp Trp Val
                325                 330                 335

Arg Asn Glu Leu Val Lys Asn Leu Glu Glu Gly Val Pro Pro Phe Gln
                340                 345                 350

Leu Cys Leu His Tyr Arg Asp Phe Ile Pro Gly Val Ala Ile Ala Ala
                355                 360                 365

Asn Ile Ile His Glu Gly Phe His Lys Ser Arg Lys Val Ile Val Val
            370                 375                 380

Val Ser Gln His Phe Ile Gln Ser Arg Trp Cys Ile Phe Glu Tyr Glu
385                 390                 395                 400

Ile Ala Gln Thr Trp Gln Phe Leu Ser Ser Arg Ala Gly Ile Ile Phe
                405                 410                 415

Ile Val Leu Gln Lys Val Glu Lys Thr Leu Leu Arg Gln Gln Val Glu
                420                 425                 430

Leu Tyr Arg Leu Leu Ser Arg Asn Thr Tyr Leu Glu Trp Glu Asp Ser
            435                 440                 445

Val Leu Gly Arg His Ile Phe Trp Arg Arg Leu Arg Lys Ala Leu Leu
        450                 455                 460

Asp Gly Lys Ser Trp Asn Pro Glu Gly Thr Val Gly Thr Gly Cys Asn
465                 470                 475                 480

Trp Gln Glu Ala Thr Ser Ile
                485

<210> SEQ ID NO 103
<211> LENGTH: 500
<212> TYPE: PRT
<213> ORGANISM: Artificial Sequence
```

<220> FEATURE:
<223> OTHER INFORMATION: CER7, amino acids 1-22 are signal peptide

<400> SEQUENCE: 103

```
Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
                20                  25                  30

Gly Gln Pro Val Thr Leu Pro Cys His Tyr Leu Ser Trp Ser Gln Ser
                35                  40                  45

Arg Asn Ser Met Cys Trp Gly Lys Gly Ser Cys Pro Asn Ser Lys Cys
50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
                100                 105                 110

Arg Ile Glu Val Pro Gly Trp Phe Asn Asp Val Lys Lys Asn Val Arg
                115                 120                 125

Leu Glu Leu Arg Arg Ala Thr Thr Lys Lys Pro Thr Thr Thr Thr Thr
            130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
                180                 185                 190

Ser Thr Thr Pro Gly Ser Phe Ser Gln Glu Thr Thr Lys Gly Ser Ala
                195                 200                 205

Phe Thr Thr Glu Ser Glu Thr Leu Pro Ala Ser Asn His Ser Gln Arg
            210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
                260                 265                 270

Gln Ile Asn Ser Arg Gln Thr Pro Val Leu Ser Leu Asn Ile Thr Cys
            275                 280                 285

Gln Met Asn Lys Thr Ile Ile Gly Val Ser Val Leu Ser Val Leu Val
            290                 295                 300

Val Ser Val Val Ala Val Leu Val Tyr Lys Phe Tyr Phe His Leu Met
305                 310                 315                 320

Leu Leu Ala Gly Cys Ile Lys Tyr Gly Arg Gly Glu Asn Ile Tyr Asp
                325                 330                 335

Ala Phe Val Ile Tyr Ser Ser Gln Asp Glu Asp Trp Val Arg Asn Glu
                340                 345                 350

Leu Val Lys Asn Leu Glu Glu Gly Val Pro Pro Phe Gln Leu Cys Leu
            355                 360                 365

His Tyr Arg Asp Phe Ile Pro Gly Val Ala Ile Ala Ala Asn Ile Ile
            370                 375                 380

His Glu Gly Phe His Lys Ser Arg Lys Val Ile Val Val Val Ser Gln
385                 390                 395                 400
```

```
His Phe Ile Gln Ser Arg Trp Cys Ile Phe Glu Tyr Glu Ile Ala Gln
            405                 410                 415

Thr Trp Gln Phe Leu Ser Ser Arg Ala Gly Ile Ile Phe Ile Val Leu
            420                 425                 430

Gln Lys Val Glu Lys Thr Leu Leu Arg Gln Val Glu Leu Tyr Arg
            435                 440                 445

Leu Leu Ser Arg Asn Thr Tyr Leu Glu Trp Glu Asp Ser Val Leu Gly
            450                 455                 460

Arg His Ile Phe Trp Arg Arg Leu Arg Lys Ala Leu Leu Asp Gly Lys
465                 470                 475                 480

Ser Trp Asn Pro Glu Gly Thr Val Gly Thr Gly Cys Asn Trp Gln Glu
            485                 490                 495

Ala Thr Ser Ile
            500

<210> SEQ ID NO 104
<211> LENGTH: 740
<212> TYPE: PRT
<213> ORGANISM: Artificial Sequence
<220> FEATURE:
<223> OTHER INFORMATION: CER8, amino acids 1-22 are signal peptide

<400> SEQUENCE: 104

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
            35                  40                  45

Arg Asn Ser Met Cys Trp Gly Lys Gly Ser Cys Pro Asn Ser Lys Cys
    50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
            85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
            115                 120                 125

Leu Glu Leu Arg Arg Ala Thr Thr Lys Lys Pro Thr Thr Thr Thr
    130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Pro Pro
            165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
            195                 200                 205

Phe Thr Thr Glu Ser Glu Thr Leu Pro Ala Ser Asn His Ser Gln Arg
            210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
            245                 250                 255
```

```
Thr Thr Leu Thr Thr Ser Glu Ser Leu Gln Lys Thr Thr Lys Ser His
            260             265             270
Gln Ile Asn Ser Arg Gln Thr Ile Leu Ile Ala Cys Cys Val Gly
            275             280             285
Phe Val Leu Met Val Leu Leu Phe Leu Ala Phe Leu Leu Arg Lys Arg
290             295             300
Arg Lys Glu Thr Arg Phe Gly Gln Ala Phe Asp Ser Val Met Ala Arg
305             310             315             320
Gly Glu Pro Ala Val His Phe Arg Ala Ala Arg Ser Phe Asn Arg Glu
                325             330             335
Arg Pro Glu Arg Ile Glu Ala Thr Leu Asp Ser Leu Gly Ile Ser Asp
            340             345             350
Glu Leu Lys Glu Lys Leu Glu Asp Val Leu Ile Pro Glu Gln Gln Phe
            355             360             365
Thr Leu Gly Arg Met Leu Gly Lys Gly Glu Phe Gly Ser Val Arg Glu
    370             375             380
Ala Gln Leu Lys Gln Glu Asp Gly Ser Phe Val Lys Val Ala Val Lys
385             390             395             400
Met Leu Lys Ala Asp Ile Ile Ala Ser Ser Asp Ile Glu Glu Phe Leu
            405             410             415
Arg Glu Ala Ala Cys Met Lys Glu Phe Asp His Pro His Val Ala Lys
            420             425             430
Leu Val Gly Val Ser Leu Arg Ser Arg Ala Lys Gly Arg Leu Pro Ile
            435             440             445
Pro Met Val Ile Leu Pro Phe Met Lys His Gly Asp Leu His Ala Phe
    450             455             460
Leu Leu Ala Ser Arg Ile Gly Glu Asn Pro Phe Asn Leu Pro Leu Gln
465             470             475             480
Thr Leu Ile Arg Phe Met Val Asp Ile Ala Cys Gly Met Glu Tyr Leu
            485             490             495
Ser Ser Arg Asn Phe Ile His Arg Asp Leu Ala Ala Arg Asn Cys Met
            500             505             510
Leu Ala Glu Asp Met Thr Val Cys Val Ala Asp Phe Gly Leu Ser Arg
            515             520             525
Lys Ile Tyr Ser Gly Asp Tyr Tyr Arg Gln Gly Cys Ala Ser Lys Leu
    530             535             540
Pro Val Lys Trp Leu Ala Leu Glu Ser Leu Ala Asp Asn Leu Tyr Thr
545             550             555             560
Val Gln Ser Asp Val Trp Ala Phe Gly Val Thr Met Trp Glu Ile Met
            565             570             575
Thr Arg Gly Gln Thr Pro Tyr Ala Gly Ile Glu Asn Ala Glu Ile Tyr
            580             585             590
Asn Tyr Leu Ile Gly Gly Asn Arg Leu Lys Gln Pro Pro Glu Cys Met
    595             600             605
Glu Asp Val Tyr Asp Leu Met Tyr Gln Cys Trp Ser Ala Asp Pro Lys
            610             615             620
Gln Arg Pro Ser Phe Thr Cys Leu Arg Met Glu Leu Glu Asn Ile Leu
625             630             635             640
Gly Gln Leu Ser Val Leu Ser Ala Ser Gln Asp Pro Leu Tyr Ile Asn
            645             650             655
Ile Glu Arg Ala Glu Glu Pro Thr Ala Gly Gly Ser Leu Glu Leu Pro
            660             665             670
```

```
Gly Arg Asp Gln Pro Tyr Ser Gly Ala Asp Gly Ser Gly Met Gly
            675                 680                 685

Ala Val Gly Gly Thr Pro Ser Asp Cys Arg Tyr Ile Leu Thr Pro Gly
690                 695                 700

Gly Leu Ala Glu Gln Pro Gly Gln Ala Glu His Gln Pro Glu Ser Pro
705                 710                 715                 720

Leu Asn Glu Thr Gln Arg Leu Leu Leu Gln Gln Gly Leu Leu Pro
            725                 730                 735

His Ser Ser Cys
            740

<210> SEQ ID NO 105
<211> LENGTH: 352
<212> TYPE: PRT
<213> ORGANISM: Artificial Sequence
<220> FEATURE:
<223> OTHER INFORMATION: CER9, amino acids 1-22 are signal peptide

<400> SEQUENCE: 105

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
                20                  25                  30

Gly Gln Pro Val Thr Leu Pro Cys His Tyr Leu Ser Trp Ser Gln Ser
            35                  40                  45

Arg Asn Ser Met Cys Trp Gly Lys Gly Ser Cys Pro Asn Ser Lys Cys
50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Thr Lys Lys Pro Thr Thr Thr Thr
130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Pro Pro
                165                 170                 175

Gln Thr Leu Ala Thr Thr Ala Phe Ser Thr Ala Val Thr Cys Pro
            180                 185                 190

Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ile Ala Cys Cys Val Gly
        275                 280                 285
```

Phe Val Leu Met Val Leu Leu Phe Leu Ala Phe Leu Tyr Phe Leu Gly
            290                 295                 300

Arg Leu Val Pro Arg Gly Arg Gly Ala Ala Glu Ala Ala Thr Arg Lys
305                 310                 315                 320

Gln Arg Ile Thr Glu Thr Glu Ser Pro Tyr Gln Glu Leu Gln Gly Gln
                325                 330                 335

Arg Ser Asp Val Tyr Ser Asp Leu Asn Thr Gln Arg Pro Tyr Tyr Lys
            340                 345                 350

<210> SEQ ID NO 106
<211> LENGTH: 352
<212> TYPE: PRT
<213> ORGANISM: Artificial Sequence
<220> FEATURE:
<223> OTHER INFORMATION: CER10, amino acids 1-22 are signal peptide

<400> SEQUENCE: 106

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
            35                  40                  45

Arg Asn Ser Met Cys Trp Gly Lys Gly Ser Cys Pro Asn Ser Lys Cys
50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
            115                 120                 125

Leu Glu Leu Arg Arg Ala Thr Thr Thr Lys Lys Pro Thr Thr Thr Thr
130                 135                 140

Arg Pro Thr Thr Thr Pro Tyr Val Thr Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
            195                 200                 205

Phe Thr Thr Glu Ser Glu Thr Leu Pro Ala Ser Asn His Ser Gln Arg
210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Gly Val Leu Ala Gly Ile Val Met Gly
            275                 280                 285

Asp Leu Val Leu Thr Val Leu Ile Ala Leu Ala Val Tyr Phe Leu Gly
            290                 295                 300

```
Arg Leu Val Pro Arg Gly Arg Gly Ala Ala Glu Ala Ala Thr Arg Lys
305                 310                 315                 320

Gln Arg Ile Thr Glu Thr Glu Ser Pro Tyr Gln Glu Leu Gln Gly Gln
                325                 330                 335

Arg Ser Asp Val Tyr Ser Asp Leu Asn Thr Gln Arg Pro Tyr Tyr Lys
            340                 345                 350

<210> SEQ ID NO 107
<211> LENGTH: 722
<212> TYPE: PRT
<213> ORGANISM: Artificial Sequence
<220> FEATURE:
<223> OTHER INFORMATION: CER11, amino acids 1-22 are signal peptide

<400> SEQUENCE: 107

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
                20                  25                  30

Gly Gln Pro Val Thr Leu Pro Cys His Tyr Leu Ser Trp Ser Gln Ser
            35                  40                  45

Arg Asn Ser Met Cys Trp Gly Lys Gly Ser Cys Pro Asn Ser Lys Cys
50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Thr Lys Lys Pro Thr Thr Thr Thr
130                 135                 140

Arg Pro Thr Thr Thr Pro Tyr Val Thr Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ala Cys Cys Val Gly
        275                 280                 285

Phe Val Leu Met Val Leu Leu Phe Leu Ala Phe Leu His Arg Arg Lys
290                 295                 300

Lys Glu Thr Arg Tyr Gly Glu Val Phe Glu Pro Thr Val Glu Arg Gly
305                 310                 315                 320
```

```
Glu Leu Val Val Arg Tyr Arg Val Arg Lys Ser Tyr Ser Arg Arg Thr
                325                 330                 335

Thr Glu Ala Thr Leu Asn Ser Leu Gly Ile Ser Glu Glu Leu Lys Glu
            340                 345                 350

Lys Leu Arg Asp Val Met Val Asp Arg His Lys Val Ala Leu Gly Lys
        355                 360                 365

Thr Leu Gly Glu Gly Glu Phe Gly Ala Val Met Glu Gly Gln Leu Asn
370                 375                 380

Gln Asp Asp Ser Ile Leu Lys Val Ala Val Lys Thr Met Lys Ile Ala
385                 390                 395                 400

Ile Cys Thr Arg Ser Glu Leu Glu Asp Phe Leu Ser Glu Ala Val Cys
                405                 410                 415

Met Lys Glu Phe Asp His Pro Asn Val Met Arg Leu Ile Gly Val Cys
            420                 425                 430

Phe Gln Gly Ser Glu Arg Glu Ser Phe Pro Ala Pro Val Val Ile Leu
        435                 440                 445

Pro Phe Met Lys His Gly Asp Leu His Ser Phe Leu Leu Tyr Ser Arg
    450                 455                 460

Leu Gly Asp Gln Pro Val Tyr Leu Pro Thr Gln Met Leu Val Lys Phe
465                 470                 475                 480

Met Ala Asp Ile Ala Ser Gly Met Glu Tyr Leu Ser Thr Lys Arg Phe
                485                 490                 495

Ile His Arg Asp Leu Ala Ala Arg Asn Cys Met Leu Asn Glu Asn Met
            500                 505                 510

Ser Val Cys Val Ala Asp Phe Gly Leu Ser Lys Lys Ile Tyr Asn Gly
        515                 520                 525

Asp Tyr Tyr Arg Gln Gly Arg Ile Ala Lys Met Pro Val Lys Trp Ile
    530                 535                 540

Ala Ile Glu Ser Leu Ala Asp Arg Val Tyr Thr Ser Lys Ser Asp Val
545                 550                 555                 560

Trp Ser Phe Gly Val Thr Met Trp Glu Ile Ala Thr Arg Gly Gln Thr
                565                 570                 575

Pro Tyr Pro Gly Val Glu Asn Ser Glu Ile Tyr Asp Tyr Leu Arg Gln
            580                 585                 590

Gly Asn Arg Leu Lys Gln Pro Ala Asp Cys Leu Asp Gly Leu Tyr Ala
        595                 600                 605

Leu Met Ser Arg Cys Trp Glu Leu Asn Pro Gln Asp Arg Pro Ser Phe
    610                 615                 620

Thr Glu Leu Arg Glu Asp Leu Glu Asn Thr Leu Lys Ala Leu Pro Pro
625                 630                 635                 640

Ala Gln Glu Pro Asp Glu Ile Leu Tyr Val Asn Met Asp Glu Gly Gly
                645                 650                 655

Gly Tyr Pro Glu Pro Pro Gly Ala Ala Gly Gly Ala Asp Pro Pro Thr
            660                 665                 670

Gln Pro Asp Pro Lys Asp Ser Cys Ser Cys Leu Thr Ala Ala Glu Val
        675                 680                 685

His Pro Ala Gly Arg Tyr Val Leu Cys Pro Ser Thr Thr Pro Ser Pro
    690                 695                 700

Ala Gln Pro Ala Asp Arg Gly Ser Pro Ala Ala Pro Gly Gln Glu Asp
705                 710                 715                 720

Gly Ala

<210> SEQ ID NO 108
```

<211> LENGTH: 342
<212> TYPE: PRT
<213> ORGANISM: Artificial Sequence
<220> FEATURE:
<223> OTHER INFORMATION: CER12, amino acids 1-22 are signal peptide

<400> SEQUENCE: 108

```
Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
                20                  25                  30

Gly Gln Pro Val Thr Leu Pro Cys His Tyr Leu Ser Trp Ser Gln Ser
            35                  40                  45

Arg Asn Ser Met Cys Trp Gly Lys Gly Ser Cys Pro Asn Ser Lys Cys
50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
                100                 105                 110

Arg Ile Glu Val Pro Gly Trp Phe Asn Asp Val Lys Lys Asn Val Arg
            115                 120                 125

Leu Glu Leu Arg Arg Ala Thr Thr Thr Lys Lys Pro Thr Thr Thr Thr
130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
            195                 200                 205

Phe Thr Thr Glu Ser Glu Thr Leu Pro Ala Ser Asn His Ser Gln Arg
210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ile Ala Cys Cys Val Gly
            275                 280                 285

Phe Val Leu Met Val Leu Leu Phe Leu Ala Phe Leu Arg Leu Lys Ile
290                 295                 300

Gln Val Arg Lys Ala Ala Ile Thr Ser Tyr Glu Lys Ser Asp Gly Val
305                 310                 315                 320

Tyr Thr Gly Leu Ser Thr Arg Asn Gln Glu Thr Tyr Glu Thr Leu Lys
                325                 330                 335

His Glu Lys Pro Pro Gln
            340
```

<210> SEQ ID NO 109
<211> LENGTH: 342
<212> TYPE: PRT
<213> ORGANISM: Artificial Sequence
<220> FEATURE:
<223> OTHER INFORMATION: CER13, amino acids 1-22 are signal peptide

<400> SEQUENCE: 109

```
Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
                20                  25                  30

Gly Gln Pro Val Thr Leu Pro Cys His Tyr Leu Ser Trp Ser Gln Ser
            35                  40                  45

Arg Asn Ser Met Cys Trp Gly Lys Gly Ser Cys Pro Asn Ser Lys Cys
        50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Lys Lys Pro Thr Thr Thr Thr
130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Leu Cys Tyr Ile Leu Asp Ala Ile Leu
        275                 280                 285

Phe Leu Tyr Gly Ile Val Leu Thr Leu Leu Tyr Cys Arg Leu Lys Ile
290                 295                 300

Gln Val Arg Lys Ala Ala Ile Thr Ser Tyr Glu Lys Ser Asp Gly Val
305                 310                 315                 320

Tyr Thr Gly Leu Ser Thr Arg Asn Gln Glu Thr Tyr Glu Thr Leu Lys
                325                 330                 335

His Glu Lys Pro Pro Gln
            340
```

<210> SEQ ID NO 110
<211> LENGTH: 455
<212> TYPE: PRT
<213> ORGANISM: Artificial Sequence
<220> FEATURE:
<223> OTHER INFORMATION: CER15, amino acids 1-22 are signal peptide -continued

```
<400> SEQUENCE: 110

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
        35                  40                  45

Arg Asn Ser Met Cys Trp Gly Lys Gly Ser Cys Pro Asn Ser Lys Cys
    50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Lys Lys Pro Thr Thr Thr Thr
130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
            165                 170                 175

Gln Thr Leu Ala Thr Thr Ala Phe Ser Thr Ala Val Thr Thr Cys Pro
        180                 185                 190

Ser Thr Thr Pro Gly Ser Phe Ser Gln Glu Thr Thr Lys Gly Ser Ala
    195                 200                 205

Phe Thr Thr Glu Ser Glu Thr Leu Pro Ala Ser Asn His Ser Gln Arg
210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ile Ala Cys Cys Val Gly
        275                 280                 285

Phe Val Leu Met Val Leu Leu Phe Leu Ala Phe Leu Met Ala Ala Gly
    290                 295                 300

Gly Pro Gly Ala Gly Ser Ala Ala Pro Val Ser Ser Thr Ser Ser Leu
305                 310                 315                 320

Pro Leu Ala Ala Leu Asn Met Arg Val Arg Arg Arg Leu Ser Leu Phe
                325                 330                 335

Leu Asn Val Arg Thr Gln Val Ala Ala Asp Trp Thr Ala Leu Ala Glu
            340                 345                 350

Glu Met Asp Phe Glu Tyr Leu Glu Ile Arg Gln Leu Glu Thr Gln Ala
        355                 360                 365

Asp Pro Thr Gly Arg Leu Leu Asp Ala Trp Gln Gly Arg Pro Gly Ala
    370                 375                 380

Ser Val Gly Arg Leu Leu Glu Leu Leu Thr Lys Leu Gly Arg Asp Asp
385                 390                 395                 400

Val Leu Leu Glu Leu Gly Pro Ser Ile Glu Glu Asp Cys Gln Lys Tyr
                405                 410                 415
```

-continued

Ile Leu Lys Gln Gln Gln Glu Glu Ala Glu Lys Pro Leu Gln Val Ala
            420                 425                 430

Ala Val Asp Ser Ser Val Pro Arg Thr Ala Glu Leu Ala Gly Ile Thr
            435                 440                 445

Thr Leu Asp Asp Pro Leu Gly
        450                 455

<210> SEQ ID NO 111
<211> LENGTH: 441
<212> TYPE: PRT
<213> ORGANISM: Artificial Sequence
<220> FEATURE:
<223> OTHER INFORMATION: CER16, amino acids 1-22 are signal peptide

<400> SEQUENCE: 111

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
        35                  40                  45

Arg Asn Ser Met Cys Trp Gly Lys Gly Ser Cys Pro Asn Ser Lys Cys
    50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Thr Lys Lys Pro Thr Thr Thr Thr
130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
    210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ala Cys Cys Val Gly
        275                 280                 285

Phe Val Leu Met Val Leu Leu Phe Leu Ala Phe Leu His Met Pro Glu
    290                 295                 300

Arg Phe Asp Ala Phe Ile Cys Tyr Cys Pro Ser Asp Ile Gln Phe Val
305                 310                 315                 320

Gln Glu Met Ile Arg Gln Leu Glu Gln Thr Asn Tyr Arg Leu Lys Leu
                325                 330                 335

Cys Val Ser Asp Arg Asp Val Leu Pro Gly Thr Cys Val Trp Ser Ile
            340                 345                 350

Ala Ser Glu Leu Ile Glu Lys Arg Cys Arg Arg Met Val Val Val
        355                 360                 365

Ser Asp Asp Tyr Leu Gln Ser Lys Glu Cys Asp Phe Gln Thr Lys Phe
370                 375                 380

Ala Leu Ser Leu Ser Pro Gly Ala His Gln Lys Arg Leu Ile Pro Ile
385                 390                 395                 400

Lys Tyr Lys Ala Met Lys Lys Glu Phe Pro Ser Ile Leu Arg Phe Ile
                405                 410                 415

Thr Val Cys Asp Tyr Thr Asn Pro Cys Thr Lys Ser Trp Phe Trp Thr
            420                 425                 430

Arg Leu Ala Lys Ala Leu Ser Leu Pro
                435                 440

<210> SEQ ID NO 112
<211> LENGTH: 479
<212> TYPE: PRT
<213> ORGANISM: Artificial Sequence
<220> FEATURE:
<223> OTHER INFORMATION: CER17, amino acids 1-22 are signal peptide

<400> SEQUENCE: 112

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
        35                  40                  45

Arg Asn Ser Met Cys Trp Gly Lys Gly Ser Cys Pro Asn Ser Lys Cys
50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Lys Lys Pro Thr Thr Thr Thr
130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Lys Gly Ser Ala
        195                 200                 205

Phe Thr Thr Glu Ser Glu Thr Leu Pro Ala Ser Asn His Ser Gln Arg
    210                 215                 220

Ser Met Met Thr Ile Ser Thr Asp Ile Ala Val Leu Arg Pro Thr Gly
225                 230                 235                 240

```
Ser Asn Pro Gly Ile Leu Pro Ser Thr Ser Gln Leu Thr Thr Gln Lys
            245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ala Cys Cys Val Gly
            275                 280                 285

Phe Val Leu Met Val Leu Leu Phe Leu Ala Phe Leu Glu Gly Trp Arg
            290                 295                 300

Ile Ser Phe Tyr Trp Asn Val Ser Val His Arg Val Leu Gly Phe Lys
305                 310                 315                 320

Glu Ile Asp Arg Gln Thr Glu Gln Phe Glu Tyr Ala Ala Tyr Ile Ile
            325                 330                 335

His Ala Tyr Lys Asp Lys Asp Trp Val Trp Glu His Phe Ser Ser Met
            340                 345                 350

Glu Lys Glu Asp Gln Ser Leu Lys Phe Cys Leu Glu Glu Arg Asp Phe
            355                 360                 365

Glu Ala Gly Val Phe Glu Leu Glu Ala Ile Val Asn Ser Ile Lys Arg
            370                 375                 380

Ser Arg Lys Ile Ile Phe Val Ile Thr His His Leu Leu Lys Asp Pro
385                 390                 395                 400

Leu Cys Lys Arg Phe Lys Val His His Ala Val Gln Gln Ala Ile Glu
            405                 410                 415

Gln Asn Leu Asp Ser Ile Ile Leu Val Phe Leu Glu Glu Ile Pro Asp
            420                 425                 430

Tyr Lys Leu Asn His Ala Leu Cys Leu Arg Arg Gly Met Phe Lys Ser
            435                 440                 445

His Cys Ile Leu Asn Trp Pro Val Gln Lys Glu Arg Ile Gly Ala Phe
            450                 455                 460

Arg His Lys Leu Gln Val Ala Leu Gly Ser Lys Asn Ser Val His
465                 470                 475

<210> SEQ ID NO 113
<211> LENGTH: 479
<212> TYPE: PRT
<213> ORGANISM: Artificial Sequence
<220> FEATURE:
<223> OTHER INFORMATION: CER18, amino acids 1-22 are signal peptide

<400> SEQUENCE: 113

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
            35                  40                  45

Arg Asn Ser Met Cys Trp Gly Lys Gly Ser Cys Pro Asn Ser Lys Cys
            50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
            85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
            115                 120                 125
```

Leu Glu Leu Arg Arg Ala Thr Thr Lys Lys Pro Thr Thr Thr
            130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
                180                 185                 190

Ser Thr Thr Pro Gly Ser Phe Ser Gln Glu Thr Thr Lys Gly Ser Ala
                195                 200                 205

Phe Thr Thr Glu Ser Glu Thr Leu Pro Ala Ser Asn His Ser Gln Arg
                210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
                260                 265                 270

Gln Ile Asn Ser Arg Gln Thr Phe Phe Met Ile Asn Thr Ser Ile Leu
                275                 280                 285

Leu Ile Phe Ile Phe Ile Val Leu Leu Ile His Phe Glu Gly Trp Arg
290                 295                 300

Ile Ser Phe Tyr Trp Asn Val Ser Val His Arg Val Leu Gly Phe Lys
305                 310                 315                 320

Glu Ile Asp Arg Gln Thr Glu Gln Phe Glu Tyr Ala Ala Tyr Ile Ile
                325                 330                 335

His Ala Tyr Lys Asp Lys Asp Trp Val Trp Glu His Phe Ser Ser Met
                340                 345                 350

Glu Lys Glu Asp Gln Ser Leu Lys Phe Cys Leu Glu Arg Asp Phe
                355                 360                 365

Glu Ala Gly Val Phe Glu Leu Glu Ala Ile Val Asn Ser Ile Lys Arg
                370                 375                 380

Ser Arg Lys Ile Ile Phe Val Ile Thr His His Leu Leu Lys Asp Pro
385                 390                 395                 400

Leu Cys Lys Arg Phe Lys Val His His Ala Val Gln Gln Ala Ile Glu
                405                 410                 415

Gln Asn Leu Asp Ser Ile Ile Leu Val Phe Leu Glu Glu Ile Pro Asp
                420                 425                 430

Tyr Lys Leu Asn His Ala Leu Cys Leu Arg Arg Gly Met Phe Lys Ser
                435                 440                 445

His Cys Ile Leu Asn Trp Pro Val Gln Lys Glu Arg Ile Gly Ala Phe
                450                 455                 460

Arg His Lys Leu Gln Val Ala Leu Gly Ser Lys Asn Ser Val His
465                 470                 475

<210> SEQ ID NO 114
<211> LENGTH: 498
<212> TYPE: PRT
<213> ORGANISM: Artificial Sequence
<220> FEATURE:
<223> OTHER INFORMATION: CER20, amino acids 1-22 are signal peptide

<400> SEQUENCE: 114

Met Ser Lys Gly Leu Leu Leu Leu Trp Leu Val Thr Glu Leu Trp Trp
1               5                   10                  15

-continued

```
Leu Tyr Leu Thr Pro Ala Ala Ser Glu Asp Thr Ile Ile Gly Phe Leu
             20                  25                  30

Gly Gln Pro Val Thr Leu Pro Cys His Tyr Leu Ser Trp Ser Gln Ser
             35                  40                  45

Arg Asn Ser Met Cys Trp Gly Lys Gly Ser Cys Pro Asn Ser Lys Cys
 50                  55                  60

Asn Ala Glu Leu Leu Arg Thr Asp Gly Thr Arg Ile Ile Ser Arg Lys
 65                  70                  75                  80

Ser Thr Lys Tyr Thr Leu Leu Gly Lys Val Gln Phe Gly Glu Val Ser
                 85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
            115                 120                 125

Leu Glu Leu Arg Arg Ala Thr Thr Thr Lys Lys Pro Thr Thr Thr Thr
130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
            165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
            195                 200                 205

Phe Thr Thr Glu Ser Glu Thr Leu Pro Ala Ser Asn His Ser Gln Arg
            210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Phe Ser Leu Phe Ile Val Cys Thr Val
            275                 280                 285

Thr Leu Thr Leu Phe Leu Met Thr Ile Leu Thr Val Thr Lys Phe Arg
            290                 295                 300

Gly Phe Cys Phe Ile Cys Tyr Lys Thr Ala Gln Arg Leu Val Phe Lys
305                 310                 315                 320

Asp His Pro Gln Gly Thr Glu Pro Asp Met Tyr Lys Tyr Asp Ala Tyr
                325                 330                 335

Leu Cys Phe Ser Ser Lys Asp Phe Thr Trp Val Gln Asn Ala Leu Leu
            340                 345                 350

Lys His Leu Asp Thr Gln Tyr Ser Asp Gln Asn Arg Phe Asn Leu Cys
            355                 360                 365

Phe Glu Glu Arg Asp Phe Val Pro Gly Glu Asn Arg Ile Ala Asn Ile
            370                 375                 380

Gln Asp Ala Ile Trp Asn Ser Arg Lys Ile Val Cys Leu Val Ser Arg
385                 390                 395                 400

His Phe Leu Arg Asp Gly Trp Cys Leu Glu Ala Phe Ser Tyr Ala Gln
                405                 410                 415

Gly Arg Cys Leu Ser Asp Leu Asn Ser Ala Leu Ile Met Val Val Val
            420                 425                 430
```

-continued

```
Gly Ser Leu Ser Gln Tyr Gln Leu Met Lys His Gln Ser Ile Arg Gly
            435                 440                 445

Phe Val Gln Lys Gln Gly Tyr Leu Arg Trp Pro Glu Asp Phe Gln Asp
450                 455                 460

Val Gly Trp Phe Leu His Lys Leu Ser Gln Gln Ile Leu Lys Lys Glu
465                 470                 475                 480

Lys Glu Lys Lys Lys Asp Asn Asn Ile Pro Leu Gln Thr Val Ala Thr
                485                 490                 495

Ile Ser
```

<210> SEQ ID NO 115
<211> LENGTH: 493
<212> TYPE: PRT
<213> ORGANISM: Artificial Sequence
<220> FEATURE:
<223> OTHER INFORMATION: CER22, amino acids 1-22 are signal peptide

<400> SEQUENCE: 115

```
Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
                20                  25                  30

Gly Gln Pro Val Thr Leu Pro Cys His Tyr Leu Ser Trp Ser Gln Ser
            35                  40                  45

Arg Asn Ser Met Cys Trp Gly Lys Gly Ser Cys Pro Asn Ser Lys Cys
50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Thr Lys Lys Pro Thr Thr Thr Thr
130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ala Val Ile Leu Phe Phe Thr Phe
        275                 280                 285

Phe Ile Thr Thr Met Val Met Leu Ala Ala Leu Ala His His Leu Phe
```

```
                290                 295                 300
Tyr Trp Asp Val Trp Phe Ile Tyr Asn Val Cys Leu Ala Lys Val Lys
305                 310                 315                 320

Gly Tyr Arg Ser Leu Ser Thr Ser Gln Thr Phe Tyr Asp Ala Tyr Ile
                325                 330                 335

Ser Tyr Asp Thr Lys Asp Ala Ser Val Thr Asp Trp Val Ile Asn Glu
            340                 345                 350

Leu Arg Tyr His Leu Glu Glu Ser Arg Asp Lys Asn Val Leu Leu Cys
            355                 360                 365

Leu Glu Glu Arg Asp Trp Asp Pro Gly Leu Ala Ile Ile Asp Asn Leu
        370                 375                 380

Met Gln Ser Ile Asn Gln Ser Lys Lys Thr Val Phe Val Leu Thr Lys
385                 390                 395                 400

Lys Tyr Ala Lys Ser Trp Asn Phe Lys Thr Ala Phe Tyr Leu Ala Leu
                405                 410                 415

Gln Arg Leu Met Asp Glu Asn Met Asp Val Ile Ile Phe Ile Leu Leu
            420                 425                 430

Glu Pro Val Leu Gln His Ser Gln Tyr Leu Arg Leu Arg Gln Arg Ile
        435                 440                 445

Cys Lys Ser Ser Ile Leu Gln Trp Pro Asp Asn Pro Lys Ala Glu Gly
    450                 455                 460

Leu Phe Trp Gln Thr Leu Arg Asn Val Val Leu Thr Glu Asn Asp Ser
465                 470                 475                 480

Arg Tyr Asn Asn Met Tyr Val Asp Ser Ile Lys Gln Tyr
                485                 490
```

<210> SEQ ID NO 116
<211> LENGTH: 493
<212> TYPE: PRT
<213> ORGANISM: Artificial Sequence
<220> FEATURE:
<223> OTHER INFORMATION: CER23, amino acids 1-22 are signal peptide

<400> SEQUENCE: 116

```
Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
                20                  25                  30

Gly Gln Pro Val Thr Leu Pro Cys His Tyr Leu Ser Trp Ser Gln Ser
            35                  40                  45

Arg Asn Ser Met Cys Trp Gly Lys Gly Ser Cys Pro Asn Ser Lys Cys
    50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Lys Lys Pro Thr Thr Thr
    130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
```

```
                165                 170                 175
Gln Thr Leu Ala Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
    210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
            245                 250                 255

Thr Thr Leu Thr Thr Ser Glu Ser Leu Gln Lys Thr Thr Lys Ser His
        260                 265                 270

Gln Ile Asn Ser Arg Gln Thr Ile Leu Ile Ala Cys Cys Val Gly
    275                 280                 285

Phe Val Leu Met Val Leu Leu Phe Leu Ala Phe Leu Gly Trp Asp Leu
290                 295                 300

Trp Tyr Cys Phe His Leu Cys Leu Ala Trp Leu Pro Trp Arg Gly Arg
305                 310                 315                 320

Gln Ser Gly Arg Asp Glu Asp Ala Leu Pro Tyr Asp Ala Phe Val Val
            325                 330                 335

Phe Asp Lys Thr Gln Ser Ala Val Ala Asp Trp Val Tyr Asn Glu Leu
        340                 345                 350

Arg Gly Gln Leu Glu Glu Cys Arg Gly Arg Trp Ala Leu Arg Leu Cys
    355                 360                 365

Leu Glu Glu Arg Asp Trp Leu Pro Gly Lys Thr Leu Phe Glu Asn Leu
370                 375                 380

Trp Ala Ser Val Tyr Gly Ser Arg Lys Thr Leu Phe Val Leu Ala His
385                 390                 395                 400

Thr Asp Arg Val Ser Gly Leu Leu Arg Ala Ser Phe Leu Leu Ala Gln
            405                 410                 415

Gln Arg Leu Leu Glu Asp Arg Lys Asp Val Val Val Leu Val Ile Leu
        420                 425                 430

Ser Pro Asp Gly Arg Arg Ser Arg Tyr Val Arg Leu Arg Gln Arg Leu
    435                 440                 445

Cys Arg Gln Ser Val Leu Leu Trp Pro His Gln Pro Ser Gly Gln Arg
450                 455                 460

Ser Phe Trp Ala Gln Leu Gly Met Ala Leu Thr Arg Asp Asn His His
465                 470                 475                 480

Phe Tyr Asn Arg Asn Phe Cys Gln Gly Pro Thr Ala Glu
            485                 490

<210> SEQ ID NO 117
<211> LENGTH: 493
<212> TYPE: PRT
<213> ORGANISM: Artificial Sequence
<220> FEATURE:
<223> OTHER INFORMATION: CER24, amino acids 1-22 are signal peptide

<400> SEQUENCE: 117

Met Ser Lys Gly Leu Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
```

```
             35                  40                  45
Arg Asn Ser Met Cys Trp Gly Lys Gly Ser Cys Pro Asn Ser Lys Cys
 50                  55                  60

Asn Ala Glu Leu Leu Arg Thr Asp Gly Thr Arg Ile Ile Ser Arg Lys
 65                  70                  75                  80

Ser Thr Lys Tyr Thr Leu Leu Gly Lys Val Gln Phe Gly Glu Val Ser
                 85                  90                  95

Leu Thr Ile Ser Asn Thr Asn Arg Gly Asp Ser Gly Val Tyr Cys Cys
                100                 105                 110

Arg Ile Glu Val Pro Gly Trp Phe Asn Asp Val Lys Lys Asn Val Arg
            115                 120                 125

Leu Glu Leu Arg Arg Ala Thr Thr Lys Lys Pro Thr Thr Thr Thr Thr
        130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
                180                 185                 190

Ser Thr Thr Pro Gly Ser Phe Ser Gln Glu Thr Thr Lys Gly Ser Ala
            195                 200                 205

Phe Thr Thr Glu Ser Glu Thr Leu Pro Ala Ser Asn His Ser Gln Arg
        210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
                260                 265                 270

Gln Ile Asn Ser Arg Gln Thr Phe Ala Leu Ser Leu Leu Ala Val Ala
            275                 280                 285

Leu Gly Leu Gly Val Pro Met Leu His His Leu Cys Gly Trp Asp Leu
        290                 295                 300

Trp Tyr Cys Phe His Leu Cys Leu Ala Trp Leu Pro Trp Arg Gly Arg
305                 310                 315                 320

Gln Ser Gly Arg Asp Glu Asp Ala Leu Pro Tyr Asp Ala Phe Val Val
                325                 330                 335

Phe Asp Lys Thr Gln Ser Ala Val Ala Asp Trp Val Tyr Asn Glu Leu
                340                 345                 350

Arg Gly Gln Leu Glu Glu Cys Arg Gly Arg Trp Ala Leu Arg Leu Cys
            355                 360                 365

Leu Glu Glu Arg Asp Trp Leu Pro Gly Lys Thr Leu Phe Glu Asn Leu
        370                 375                 380

Trp Ala Ser Val Tyr Gly Ser Arg Lys Thr Leu Phe Val Leu Ala His
385                 390                 395                 400

Thr Asp Arg Val Ser Gly Leu Leu Arg Ala Ser Phe Leu Leu Ala Gln
                405                 410                 415

Gln Arg Leu Leu Glu Asp Arg Lys Asp Val Val Val Leu Val Ile Leu
            420                 425                 430

Ser Pro Asp Gly Arg Arg Ser Arg Tyr Val Arg Leu Arg Gln Arg Leu
        435                 440                 445

Cys Arg Gln Ser Val Leu Leu Trp Pro His Gln Pro Ser Gly Gln Arg
450                 455                 460
```

Ser Phe Trp Ala Gln Leu Gly Met Ala Leu Thr Arg Asp Asn His His
465                 470                 475                 480

Phe Tyr Asn Arg Asn Phe Cys Gln Gly Pro Thr Ala Glu
                485                 490

<210> SEQ ID NO 118
<211> LENGTH: 485
<212> TYPE: PRT
<213> ORGANISM: Artificial Sequence
<220> FEATURE:
<223> OTHER INFORMATION: CER26, amino acids 1-22 are signal peptide

<400> SEQUENCE: 118

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
                20                  25                  30

Gly Gln Pro Val Thr Leu Pro Cys His Tyr Leu Ser Trp Ser Gln Ser
                35                  40                  45

Arg Asn Ser Met Cys Trp Gly Lys Gly Ser Cys Pro Asn Ser Lys Cys
50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
                100                 105                 110

Arg Ile Glu Val Pro Gly Trp Phe Asn Asp Val Lys Lys Asn Val Arg
                115                 120                 125

Leu Glu Leu Arg Arg Ala Thr Thr Thr Lys Lys Pro Thr Thr Thr Thr
130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
                180                 185                 190

Ser Thr Thr Pro Gly Ser Phe Ser Gln Glu Thr Thr Lys Gly Ser Ala
                195                 200                 205

Phe Thr Thr Glu Ser Glu Thr Leu Pro Ala Ser Asn His Ser Gln Arg
210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
                260                 265                 270

Gln Ile Asn Ser Arg Gln Thr Ile Leu Ile Ala Cys Cys Val Gly
                275                 280                 285

Phe Val Leu Met Val Leu Leu Phe Leu Ala Phe Leu Ser Tyr Leu Asp
                290                 295                 300

Leu Pro Trp Tyr Leu Arg Met Val Cys Gln Trp Thr Gln Thr Arg Arg
305                 310                 315                 320

Arg Ala Arg Asn Ile Pro Leu Glu Glu Leu Gln Arg Asn Leu Gln Phe
                325                 330                 335

His Ala Phe Ile Ser Tyr Ser Gly His Asp Ser Phe Trp Val Lys Asn
            340                 345                 350

Glu Leu Leu Pro Asn Leu Glu Lys Glu Gly Met Gln Ile Cys Leu His
        355                 360                 365

Glu Arg Asn Phe Val Pro Gly Lys Ser Ile Val Glu Asn Ile Ile Thr
    370                 375                 380

Cys Ile Glu Lys Ser Tyr Lys Ser Ile Phe Val Leu Ser Pro Asn Phe
385                 390                 395                 400

Val Gln Ser Glu Trp Cys His Tyr Glu Leu Tyr Phe Ala His His Asn
                405                 410                 415

Leu Phe His Glu Gly Ser Asn Ser Leu Ile Leu Ile Leu Leu Glu Pro
            420                 425                 430

Ile Pro Gln Tyr Ser Ile Pro Ser Ser Tyr His Lys Leu Lys Ser Leu
        435                 440                 445

Met Ala Arg Arg Thr Tyr Leu Glu Trp Pro Lys Glu Lys Ser Lys Arg
    450                 455                 460

Gly Leu Phe Trp Ala Asn Leu Arg Ala Ala Ile Asn Ile Lys Leu Thr
465                 470                 475                 480

Glu Gln Ala Lys Lys
            485

<210> SEQ ID NO 119
<211> LENGTH: 489
<212> TYPE: PRT
<213> ORGANISM: Artificial Sequence
<220> FEATURE:
<223> OTHER INFORMATION: CER28, amino acids 1-22 are signal peptide

<400> SEQUENCE: 119

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
        35                  40                  45

Arg Asn Ser Met Cys Trp Gly Lys Gly Ser Cys Pro Asn Ser Lys Cys
    50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Thr Lys Lys Pro Thr Thr Thr Thr
    130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Pro Pro
                165                 170                 175

Gln Thr Leu Ala Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
        195                 200                 205

```
Phe Thr Thr Glu Ser Glu Thr Leu Pro Ala Ser Asn His Ser Gln Arg
    210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ala Cys Cys Val Gly
            275                 280                 285

Phe Val Leu Met Val Leu Leu Phe Leu Ala Phe Leu His Leu Tyr Phe
    290                 295                 300

Trp Asp Val Trp Tyr Ile Tyr His Phe Cys Lys Ala Lys Ile Lys Gly
305                 310                 315                 320

Tyr Gln Arg Leu Ile Ser Pro Asp Cys Cys Tyr Asp Ala Phe Ile Val
                325                 330                 335

Tyr Asp Thr Lys Asp Pro Ala Val Thr Glu Trp Val Leu Ala Glu Leu
            340                 345                 350

Val Ala Lys Leu Glu Asp Pro Arg Glu Lys His Phe Asn Leu Cys Leu
    355                 360                 365

Glu Glu Arg Asp Trp Leu Pro Gly Gln Pro Val Leu Glu Asn Leu Ser
370                 375                 380

Gln Ser Ile Gln Leu Ser Lys Lys Thr Val Phe Val Met Thr Asp Lys
385                 390                 395                 400

Tyr Ala Lys Thr Glu Asn Phe Lys Ile Ala Phe Tyr Leu Ser His Gln
                405                 410                 415

Arg Leu Met Asp Glu Lys Val Asp Val Ile Ile Leu Ile Phe Leu Glu
            420                 425                 430

Lys Pro Phe Gln Lys Ser Lys Phe Leu Gln Leu Arg Lys Arg Leu Cys
    435                 440                 445

Gly Ser Ser Val Leu Glu Trp Pro Thr Asn Pro Gln Ala His Pro Tyr
450                 455                 460

Phe Trp Gln Cys Leu Lys Asn Ala Leu Ala Thr Asp Asn His Val Ala
465                 470                 475                 480

Tyr Ser Gln Val Phe Lys Glu Thr Val
                485

<210> SEQ ID NO 120
<211> LENGTH: 603
<212> TYPE: PRT
<213> ORGANISM: Artificial Sequence
<220> FEATURE:
<223> OTHER INFORMATION: CER30, amino acids 1-22 are signal peptide

<400> SEQUENCE: 120

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
                20                  25                  30

Gly Gln Pro Val Thr Leu Pro Cys His Tyr Leu Ser Trp Ser Gln Ser
            35                  40                  45

Arg Asn Ser Met Cys Trp Gly Lys Gly Ser Cys Pro Asn Ser Lys Cys
50                  55                  60

Asn Ala Glu Leu Leu Arg Thr Asp Gly Thr Arg Ile Ile Ser Arg Lys
65                  70                  75                  80
```

```
Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Lys Lys Pro Thr Thr Thr Thr Thr
    130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
    210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ala Cys Cys Val Gly
        275                 280                 285

Phe Val Leu Met Val Leu Leu Phe Leu Ala Phe Leu Met Ala Ala Ala
    290                 295                 300

Ser Val Thr Pro Pro Gly Ser Leu Glu Leu Leu Gln Pro Gly Phe Ser
305                 310                 315                 320

Lys Thr Leu Leu Gly Thr Lys Leu Glu Ala Lys Tyr Leu Cys Ser Ala
                325                 330                 335

Cys Arg Asn Val Leu Arg Arg Pro Phe Gln Ala Gln Cys Gly His Arg
            340                 345                 350

Tyr Cys Ser Phe Cys Leu Ala Ser Ile Leu Ser Ser Gly Pro Gln Asn
        355                 360                 365

Cys Ala Ala Cys Val His Glu Gly Ile Tyr Glu Glu Gly Ile Ser Ile
    370                 375                 380

Leu Glu Ser Ser Ser Ala Phe Pro Asp Asn Ala Ala Arg Arg Glu Val
385                 390                 395                 400

Glu Ser Leu Pro Ala Val Cys Pro Ser Asp Gly Cys Thr Trp Lys Gly
                405                 410                 415

Thr Leu Lys Glu Tyr Glu Ser Cys His Glu Gly Arg Cys Pro Leu Met
            420                 425                 430

Leu Thr Glu Cys Pro Ala Cys Lys Gly Leu Val Arg Leu Gly Glu Lys
        435                 440                 445

Glu Arg His Leu Glu His Glu Cys Pro Glu Arg Ser Leu Ser Cys Arg
    450                 455                 460

His Cys Arg Ala Pro Cys Cys Gly Ala Asp Val Lys Ala His His Glu
465                 470                 475                 480

Val Cys Pro Lys Phe Pro Leu Thr Cys Asp Gly Cys Gly Lys Lys Lys
                485                 490                 495
```

-continued

```
Ile Pro Arg Glu Lys Phe Gln Asp His Val Lys Thr Cys Gly Lys Cys
                500                 505                 510

Arg Val Pro Cys Arg Phe His Ala Ile Gly Cys Leu Glu Thr Val Glu
            515                 520                 525

Gly Glu Lys Gln Gln Glu His Glu Val Gln Trp Leu Arg Glu His Leu
        530                 535                 540

Ala Met Leu Leu Ser Ser Val Leu Glu Ala Lys Pro Leu Leu Gly Asp
545                 550                 555                 560

Gln Ser His Ala Gly Ser Glu Leu Leu Gln Arg Cys Glu Ser Leu Glu
                565                 570                 575

Lys Lys Thr Ala Thr Phe Glu Asn Ile Val Cys Val Leu Asn Arg Glu
            580                 585                 590

Val Glu Arg Val Ala Met Thr Ala Glu Ala Cys
        595                 600

<210> SEQ ID NO 121
<211> LENGTH: 540
<212> TYPE: PRT
<213> ORGANISM: Artificial Sequence
<220> FEATURE:
<223> OTHER INFORMATION: CER85,amino acids 1-22 are signal peptide

<400> SEQUENCE: 121

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
                20                  25                  30

Gly Gln Pro Val Thr Leu Pro Cys His Tyr Leu Ser Trp Ser Gln Ser
            35                  40                  45

Arg Asn Ser Met Cys Trp Gly Lys Gly Ser Cys Pro Asn Ser Lys Cys
        50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
                100                 105                 110

Arg Ile Glu Val Pro Gly Trp Phe Asn Asp Val Lys Lys Asn Val Arg
            115                 120                 125

Leu Glu Leu Arg Arg Ala Thr Thr Lys Lys Pro Thr Thr Thr Thr
        130                 135                 140

Arg Pro Thr Thr Thr Pro Tyr Val Thr Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
    210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255
```

```
Thr Thr Leu Thr Thr Ser Glu Ser Leu Gln Lys Thr Lys Ser His
            260             265             270

Gln Ile Asn Ser Arg Gln Thr Ile Leu Ile Ala Cys Cys Val Gly
        275             280             285

Phe Val Leu Met Val Leu Leu Phe Leu Ala Phe Leu Met Ala Ala Gly
    290             295             300

Gly Pro Gly Ala Gly Ser Ala Ala Pro Val Ser Ser Thr Ser Leu
305         310             315             320

Pro Leu Ala Ala Leu Asn Met Arg Val Arg Arg Leu Ser Leu Phe
            325             330             335

Leu Asn Val Arg Thr Gln Val Ala Ala Asp Trp Thr Ala Leu Ala Glu
        340             345             350

Glu Met Asp Phe Glu Tyr Leu Glu Ile Arg Gln Leu Glu Thr Gln Ala
            355             360             365

Asp Pro Thr Gly Arg Leu Leu Asp Ala Trp Gln Gly Arg Pro Gly Ala
        370             375             380

Ser Val Gly Arg Leu Leu Glu Leu Leu Thr Lys Leu Gly Arg Asp Asp
385         390             395             400

Val Leu Leu Glu Leu Gly Pro Ser Ile Glu Glu Asp Cys Gln Lys Tyr
            405             410             415

Ile Leu Lys Gln Gln Gln Glu Glu Ala Glu Lys Pro Leu Gln Val Ala
        420             425             430

Ala Val Asp Ser Ser Val Pro Arg Thr Ala Glu Leu Ala Gly Ile Thr
        435             440             445

Thr Leu Asp Asp Pro Leu Gly Ser Trp Arg Arg Arg Gln Arg Arg Leu
    450             455             460

Arg Gly Ala Ser Ser Ala Glu Ala Pro Asp Gly Asp Lys Asp Ala Pro
465         470             475             480

Glu Pro Leu Asp Lys Val Ile Ile Leu Ser Pro Gly Ile Ser Asp Ala
            485             490             495

Thr Ala Pro Ala Trp Pro Pro Gly Glu Asp Pro Gly Thr Thr Pro
        500             505             510

Pro Gly His Ser Val Pro Val Pro Ala Thr Glu Leu Gly Ser Thr Glu
        515             520             525

Leu Val Thr Thr Lys Thr Ala Gly Pro Glu Gln Gln
    530             535             540

<210> SEQ ID NO 122
<211> LENGTH: 507
<212> TYPE: PRT
<213> ORGANISM: Artificial Sequence
<220> FEATURE:
<223> OTHER INFORMATION: CER86,amino acids 1-22 are signal peptide

<400> SEQUENCE: 122

Met Ser Lys Gly Leu Leu Leu Trp Leu Val Thr Glu Leu Trp Trp
1           5               10              15

Leu Tyr Leu Thr Pro Ala Ala Ser Glu Asp Thr Ile Gly Phe Leu
            20              25              30

Gly Gln Pro Val Thr Leu Pro Cys His Tyr Leu Ser Trp Ser Gln Ser
        35              40              45

Arg Asn Ser Met Cys Trp Gly Lys Gly Ser Cys Pro Asn Ser Lys Cys
        50              55              60

Asn Ala Glu Leu Leu Arg Thr Asp Gly Thr Arg Ile Ile Ser Arg Lys
65              70              75              80
```

```
Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Lys Lys Pro Thr Thr Thr
130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
                180                 185                 190

Ser Thr Thr Pro Gly Ser Phe Ser Gln Glu Thr Thr Lys Gly Ser Ala
                195                 200                 205

Phe Thr Thr Glu Ser Glu Thr Leu Pro Ala Ser Asn His Ser Gln Arg
                210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
                260                 265                 270

Gln Ile Asn Ser Arg Gln Thr Ile Leu Ile Ala Cys Cys Val Gly
                275                 280                 285

Phe Val Leu Met Val Leu Leu Phe Leu Ala Phe Leu Met Ala Ala Gly
            290                 295                 300

Gly Pro Gly Ala Gly Ser Ala Ala Pro Val Ser Ser Thr Ser Ser Leu
305                 310                 315                 320

Pro Leu Ala Ala Leu Asn Met Arg Val Arg Arg Leu Ser Leu Phe
                325                 330                 335

Leu Asn Val Arg Thr Gln Val Ala Ala Asp Trp Thr Ala Leu Ala Glu
                340                 345                 350

Glu Met Asp Phe Glu Tyr Leu Glu Ile Arg Gln Leu Glu Thr Gln Ala
                355                 360                 365

Asp Pro Thr Gly Arg Leu Leu Asp Ala Trp Gln Gly Arg Pro Gly Ala
                370                 375                 380

Ser Val Gly Arg Leu Leu Glu Leu Leu Thr Lys Leu Gly Arg Asp Asp
385                 390                 395                 400

Val Leu Leu Glu Leu Gly Pro Ser Ile Glu Glu Asp Cys Gln Lys Tyr
                405                 410                 415

Ile Leu Lys Gln Gln Gln Glu Glu Ala Glu Lys Pro Leu Gln Val Ala
                420                 425                 430

Ala Val Asp Ser Ser Val Pro Arg Thr Ala Glu Leu Ala Gly Ile Thr
                435                 440                 445

Thr Leu Asp Asp Pro Leu Gly Tyr Phe Leu Gly Arg Leu Val Pro Arg
450                 455                 460

Gly Arg Gly Ala Ala Glu Ala Thr Arg Lys Gln Arg Ile Thr Glu
465                 470                 475                 480

Thr Glu Ser Pro Tyr Gln Glu Leu Gln Gly Gln Arg Ser Asp Val Tyr
                485                 490                 495

Ser Asp Leu Asn Thr Gln Arg Pro Tyr Tyr Lys
```

-continued

```
                500                 505
```

<210> SEQ ID NO 123
<211> LENGTH: 540
<212> TYPE: PRT
<213> ORGANISM: Artificial Sequence
<220> FEATURE:
<223> OTHER INFORMATION: CER87,amino acids 1-22 are signal peptide

<400> SEQUENCE: 123

```
Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
        35                  40                  45

Arg Asn Ser Met Cys Trp Gly Lys Gly Ser Cys Pro Asn Ser Lys Cys
    50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Thr Lys Lys Pro Thr Thr Thr Thr
    130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
    210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ala Cys Cys Val Gly
        275                 280                 285

Phe Val Leu Met Val Leu Leu Phe Leu Ala Phe Leu Ser Trp Arg Arg
    290                 295                 300

Arg Gln Arg Arg Leu Arg Gly Ala Ser Ala Glu Ala Pro Asp Gly
305                 310                 315                 320

Asp Lys Asp Ala Pro Glu Pro Leu Asp Lys Val Ile Ile Leu Ser Pro
                325                 330                 335

Gly Ile Ser Asp Ala Thr Ala Pro Ala Trp Pro Pro Gly Glu Asp
            340                 345                 350

Pro Gly Thr Thr Pro Pro Gly His Ser Val Pro Val Pro Ala Thr Glu
```

-continued 355                360                365
Leu Gly Ser Thr Glu Leu Val Thr Thr Lys Thr Ala Gly Pro Glu Gln
            370                375                380

Gln Met Ala Ala Gly Gly Pro Gly Ala Gly Ser Ala Ala Pro Val Ser
385                390                395                400

Ser Thr Ser Ser Leu Pro Leu Ala Ala Leu Asn Met Arg Val Arg Arg
                405                410                415

Arg Leu Ser Leu Phe Leu Asn Val Arg Thr Gln Val Ala Ala Asp Trp
            420                425                430

Thr Ala Leu Ala Glu Glu Met Asp Phe Glu Tyr Leu Glu Ile Arg Gln
            435                440                445

Leu Glu Thr Gln Ala Asp Pro Thr Gly Arg Leu Leu Asp Ala Trp Gln
            450                455                460

Gly Arg Pro Gly Ala Ser Val Gly Arg Leu Leu Glu Leu Leu Thr Lys
465                470                475                480

Leu Gly Arg Asp Asp Val Leu Leu Glu Leu Gly Pro Ser Ile Glu Glu
                485                490                495

Asp Cys Gln Lys Tyr Ile Leu Lys Gln Gln Gln Glu Glu Ala Glu Lys
            500                505                510

Pro Leu Gln Val Ala Ala Val Asp Ser Ser Val Pro Arg Thr Ala Glu
            515                520                525

Leu Ala Gly Ile Thr Thr Leu Asp Asp Pro Leu Gly
            530                535                540

<210> SEQ ID NO 124
<211> LENGTH: 507
<212> TYPE: PRT
<213> ORGANISM: Artificial Sequence
<220> FEATURE:
<223> OTHER INFORMATION: CER88, amino acids 1-22 are signal peptide

<400> SEQUENCE: 124

Met Ser Lys Gly Leu Leu Leu Trp Leu Val Thr Glu Leu Trp Trp
1                5                10                15

Leu Tyr Leu Thr Pro Ala Ala Ser Glu Asp Thr Ile Ile Gly Phe Leu
            20                25                30

Gly Gln Pro Val Thr Leu Pro Cys His Tyr Leu Ser Trp Ser Gln Ser
            35                40                45

Arg Asn Ser Met Cys Trp Gly Lys Gly Ser Cys Pro Asn Ser Lys Cys
        50                55                60

Asn Ala Glu Leu Leu Arg Thr Asp Gly Thr Arg Ile Ile Ser Arg Lys
65                70                75                80

Ser Thr Lys Tyr Thr Leu Leu Gly Lys Val Gln Phe Gly Glu Val Ser
                85                90                95

Leu Thr Ile Ser Asn Thr Asn Arg Gly Asp Ser Gly Val Tyr Cys Cys
            100                105                110

Arg Ile Glu Val Pro Gly Trp Phe Asn Asp Val Lys Lys Asn Val Arg
            115                120                125

Leu Glu Leu Arg Arg Ala Thr Thr Lys Lys Pro Thr Thr Thr Thr
130                135                140

Arg Pro Thr Thr Thr Pro Tyr Val Thr Thr Thr Pro Glu Leu Leu
145                150                155                160

Pro Thr Thr Val Met Thr Thr Ser Val Leu Pro Thr Thr Thr Pro Pro
                165                170                175

Gln Thr Leu Ala Thr Thr Ala Phe Ser Thr Ala Val Thr Thr Cys Pro

```
                    180                 185                 190
Ser Thr Thr Pro Gly Ser Phe Ser Gln Glu Thr Thr Lys Gly Ser Ala
                195                 200                 205

Phe Thr Thr Glu Ser Glu Thr Leu Pro Ala Ser Asn His Ser Gln Arg
        210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ala Cys Cys Val Gly
            275                 280                 285

Phe Val Leu Met Val Leu Leu Phe Leu Ala Phe Leu Tyr Phe Leu Gly
        290                 295                 300

Arg Leu Val Pro Arg Gly Arg Gly Ala Ala Glu Ala Ala Thr Arg Lys
305                 310                 315                 320

Gln Arg Ile Thr Glu Thr Glu Ser Pro Tyr Gln Glu Leu Gln Gly Gln
                325                 330                 335

Arg Ser Asp Val Tyr Ser Asp Leu Asn Thr Gln Arg Pro Tyr Tyr Lys
            340                 345                 350

Met Ala Ala Gly Gly Pro Gly Ala Gly Ser Ala Ala Pro Val Ser Ser
        355                 360                 365

Thr Ser Ser Leu Pro Leu Ala Ala Leu Asn Met Arg Val Arg Arg Arg
    370                 375                 380

Leu Ser Leu Phe Leu Asn Val Arg Thr Gln Val Ala Ala Asp Trp Thr
385                 390                 395                 400

Ala Leu Ala Glu Glu Met Asp Phe Glu Tyr Leu Glu Ile Arg Gln Leu
                405                 410                 415

Glu Thr Gln Ala Asp Pro Thr Gly Arg Leu Leu Asp Ala Trp Gln Gly
            420                 425                 430

Arg Pro Gly Ala Ser Val Gly Arg Leu Leu Glu Leu Leu Thr Lys Leu
        435                 440                 445

Gly Arg Asp Asp Val Leu Leu Glu Leu Gly Pro Ser Ile Glu Glu Asp
    450                 455                 460

Cys Gln Lys Tyr Ile Leu Lys Gln Gln Gln Glu Glu Ala Glu Lys Pro
465                 470                 475                 480

Leu Gln Val Ala Ala Val Asp Ser Ser Val Pro Arg Thr Ala Glu Leu
                485                 490                 495

Ala Gly Ile Thr Thr Leu Asp Asp Pro Leu Gly
            500                 505

<210> SEQ ID NO 125
<211> LENGTH: 500
<212> TYPE: PRT
<213> ORGANISM: Artificial Sequence
<220> FEATURE:
<223> OTHER INFORMATION: CER89, amino acids 1-22 are signal peptide

<400> SEQUENCE: 125

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
                20                  25                  30

Gly Gln Pro Val Thr Leu Pro Cys His Tyr Leu Ser Trp Ser Gln Ser
```

-continued

```
                35                  40                  45
Arg Asn Ser Met Cys Trp Gly Lys Gly Ser Cys Pro Asn Ser Lys Cys
 50                  55                  60
Asn Ala Glu Leu Leu Arg Thr Asp Gly Thr Arg Ile Ile Ser Arg Lys
 65                  70                  75                  80
Ser Thr Lys Tyr Thr Leu Leu Gly Lys Val Gln Phe Gly Glu Val Ser
                 85                  90                  95
Leu Thr Ile Ser Asn Thr Asn Arg Gly Asp Ser Gly Val Tyr Cys Cys
                100                 105                 110
Arg Ile Glu Val Pro Gly Trp Phe Asn Asp Val Lys Lys Asn Val Arg
                115                 120                 125
Leu Glu Leu Arg Arg Ala Thr Thr Lys Lys Pro Thr Thr Thr
130                 135                 140
Arg Pro Thr Thr Thr Pro Tyr Val Thr Thr Thr Pro Glu Leu Leu
145                 150                 155                 160
Pro Thr Thr Val Met Thr Thr Ser Val Leu Pro Thr Thr Thr Pro Pro
                165                 170                 175
Gln Thr Leu Ala Thr Thr Ala Phe Ser Thr Ala Val Thr Thr Cys Pro
                180                 185                 190
Ser Thr Thr Pro Gly Ser Phe Ser Gln Glu Thr Thr Lys Gly Ser Ala
                195                 200                 205
Phe Thr Thr Glu Ser Glu Thr Leu Pro Ala Ser Asn His Ser Gln Arg
                210                 215                 220
Ser Met Met Thr Ile Ser Thr Asp Ile Ala Val Leu Arg Pro Thr Gly
225                 230                 235                 240
Ser Asn Pro Gly Ile Leu Pro Ser Thr Ser Gln Leu Thr Thr Gln Lys
                245                 250                 255
Thr Thr Leu Thr Thr Ser Glu Ser Leu Gln Lys Thr Thr Lys Ser His
                260                 265                 270
Gln Ile Asn Ser Arg Gln Thr Ile Leu Ile Ile Ala Cys Cys Val Gly
                275                 280                 285
Phe Val Leu Met Val Leu Leu Phe Leu Ala Phe Leu Met Ala Ala Gly
                290                 295                 300
Gly Pro Gly Ala Gly Ser Ala Ala Pro Val Ser Ser Thr Ser Ser Leu
305                 310                 315                 320
Pro Leu Ala Ala Leu Asn Met Arg Val Arg Arg Arg Leu Ser Leu Phe
                325                 330                 335
Leu Asn Val Arg Thr Gln Val Ala Ala Asp Trp Thr Ala Leu Ala Glu
                340                 345                 350
Glu Met Asp Phe Glu Tyr Leu Glu Ile Arg Gln Leu Glu Thr Gln Ala
                355                 360                 365
Asp Pro Thr Gly Arg Leu Leu Asp Ala Trp Gln Gly Arg Pro Gly Ala
                370                 375                 380
Ser Val Gly Arg Leu Leu Glu Leu Leu Thr Lys Leu Gly Arg Asp Asp
385                 390                 395                 400
Val Leu Leu Glu Leu Gly Pro Ser Ile Glu Glu Asp Cys Gln Lys Tyr
                405                 410                 415
Ile Leu Lys Gln Gln Gln Glu Glu Ala Glu Lys Pro Leu Gln Val Ala
                420                 425                 430
Ala Val Asp Ser Ser Val Pro Arg Thr Ala Glu Leu Ala Gly Ile Thr
                435                 440                 445
Thr Leu Asp Asp Pro Leu Gly Asp Ser Lys Ala Gly Met Glu Glu Asp
450                 455                 460
```

```
His Thr Tyr Glu Gly Leu Asp Ile Asp Gln Thr Ala Thr Tyr Glu Asp
465                 470                 475                 480

Ile Val Thr Leu Arg Thr Gly Glu Val Lys Trp Ser Val Gly Glu His
                485                 490                 495

Pro Gly Gln Glu
            500

<210> SEQ ID NO 126
<211> LENGTH: 541
<212> TYPE: PRT
<213> ORGANISM: Artificial Sequence
<220> FEATURE:
<223> OTHER INFORMATION: CER90, amino acids 1-22 are signal peptide

<400> SEQUENCE: 126

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
                20                  25                  30

Gly Gln Pro Val Thr Leu Pro Cys His Tyr Leu Ser Trp Ser Gln Ser
            35                  40                  45

Arg Asn Ser Met Cys Trp Gly Lys Gly Ser Cys Pro Asn Ser Lys Cys
50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Lys Lys Pro Thr Thr Thr Thr
130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ala Cys Cys Val Gly
        275                 280                 285

Phe Val Leu Met Val Leu Leu Phe Leu Ala Phe Leu Met Ala Ala Gly
290                 295                 300

Gly Pro Gly Ala Gly Ser Ala Ala Pro Val Ser Ser Thr Ser Ser Leu
305                 310                 315                 320
```

-continued

```
Pro Leu Ala Ala Leu Asn Met Arg Val Arg Arg Leu Ser Leu Phe
            325                 330                 335

Leu Asn Val Arg Thr Gln Val Ala Ala Asp Trp Thr Ala Leu Ala Glu
            340                 345                 350

Glu Met Asp Phe Glu Tyr Leu Glu Ile Arg Gln Leu Glu Thr Gln Ala
            355                 360                 365

Asp Pro Thr Gly Arg Leu Leu Asp Ala Trp Gln Gly Arg Pro Gly Ala
            370                 375                 380

Ser Val Gly Arg Leu Leu Glu Leu Leu Thr Lys Leu Gly Arg Asp Asp
385                 390                 395                 400

Val Leu Leu Glu Leu Gly Pro Ser Ile Glu Asp Cys Gln Lys Tyr
            405                 410                 415

Ile Leu Lys Gln Gln Gln Glu Glu Ala Glu Lys Pro Leu Gln Val Ala
            420                 425                 430

Ala Val Asp Ser Ser Val Pro Arg Thr Ala Glu Leu Ala Gly Ile Thr
            435                 440                 445

Thr Leu Asp Asp Pro Leu Gly Leu Trp Asn Lys Lys Arg Met Arg Gly
            450                 455                 460

Pro Gly Lys Asp Pro Thr Arg Lys Cys Pro Asp Pro Arg Ser Ala Ser
465                 470                 475                 480

Ser Pro Lys Gln His Pro Ser Glu Ser Val Tyr Thr Ala Leu Gln Arg
            485                 490                 495

Arg Glu Thr Glu Val Tyr Ala Cys Ile Glu Asn Glu Asp Gly Ser Ser
            500                 505                 510

Pro Thr Ala Lys Gln Ser Pro Leu Ser Gln Glu Arg Pro His Arg Phe
            515                 520                 525

Glu Asp Asp Gly Glu Leu Asn Leu Val Tyr Glu Asn Leu
            530                 535                 540
```

<210> SEQ ID NO 127
<211> LENGTH: 692
<212> TYPE: PRT
<213> ORGANISM: Artificial Sequence
<220> FEATURE:
<223> OTHER INFORMATION: CER91, amino acids 1-22 are signal peptide

<400> SEQUENCE: 127

```
Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
            35                  40                  45

Arg Asn Ser Met Cys Trp Gly Lys Gly Ser Cys Pro Asn Ser Lys Cys
            50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
            85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
            115                 120                 125

Leu Glu Leu Arg Arg Ala Thr Thr Thr Lys Lys Pro Thr Thr Thr Thr
            130                 135                 140
```

```
Arg Pro Thr Thr Thr Pro Tyr Val Thr Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
    210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ile Ala Cys Cys Val Gly
        275                 280                 285

Phe Val Leu Met Val Leu Leu Phe Leu Ala Phe Leu Met Ala Ala Gly
    290                 295                 300

Gly Pro Gly Ala Gly Ser Ala Ala Pro Val Ser Ser Thr Ser Ser Leu
305                 310                 315                 320

Pro Leu Ala Ala Leu Asn Met Arg Val Arg Arg Leu Ser Leu Phe
                325                 330                 335

Leu Asn Val Arg Thr Gln Val Ala Ala Asp Trp Thr Ala Leu Ala Glu
            340                 345                 350

Glu Met Asp Phe Glu Tyr Leu Glu Ile Arg Gln Leu Glu Thr Gln Ala
        355                 360                 365

Asp Pro Thr Gly Arg Leu Leu Asp Ala Trp Gln Gly Arg Pro Gly Ala
    370                 375                 380

Ser Val Gly Arg Leu Leu Glu Leu Leu Thr Lys Leu Gly Arg Asp Asp
385                 390                 395                 400

Val Leu Leu Glu Leu Gly Pro Ser Ile Glu Asp Cys Gln Lys Tyr
                405                 410                 415

Ile Leu Lys Gln Gln Gln Glu Glu Ala Glu Lys Pro Leu Gln Val Ala
            420                 425                 430

Ala Val Asp Ser Ser Val Pro Arg Thr Ala Glu Leu Ala Gly Ile Thr
        435                 440                 445

Thr Leu Asp Asp Pro Leu Gly Gly Ser Gly Ala Thr Asn Phe Ser Leu
    450                 455                 460

Leu Lys Gln Ala Gly Asp Val Glu Glu Asn Pro Gly Pro Met Ala Ser
465                 470                 475                 480

Arg Gly Ala Thr Arg Pro Asn Gly Pro Asn Thr Gly Asn Lys Ile Cys
                485                 490                 495

Gln Phe Lys Leu Val Leu Leu Gly Glu Ser Ala Val Gly Lys Ser Ser
            500                 505                 510

Leu Val Leu Arg Phe Val Lys Gly Gln Phe His Glu Phe Gln Glu Ser
        515                 520                 525

Thr Ile Gly Ala Ala Phe Leu Thr Gln Thr Val Cys Leu Asp Asp Thr
    530                 535                 540

Thr Val Lys Phe Glu Ile Trp Asp Thr Ala Gly Gln Glu Arg Tyr His
545                 550                 555                 560
```

```
Ser Leu Ala Pro Met Tyr Tyr Arg Gly Ala Gln Ala Ile Val Val
            565                 570                 575

Tyr Asp Ile Thr Asn Glu Glu Ser Phe Ala Arg Ala Lys Asn Trp Val
        580                 585                 590

Lys Glu Leu Gln Arg Gln Ala Ser Pro Asn Ile Val Ile Ala Leu Ser
        595                 600                 605

Gly Asn Lys Ala Asp Leu Ala Asn Lys Arg Ala Val Asp Phe Gln Glu
        610                 615                 620

Ala Gln Ser Tyr Ala Asp Asp Asn Ser Leu Leu Phe Met Glu Thr Ser
625                 630                 635                 640

Ala Lys Thr Ser Met Asn Val Asn Glu Ile Phe Met Ala Ile Ala Lys
            645                 650                 655

Lys Leu Pro Lys Asn Glu Pro Gln Asn Pro Gly Ala Asn Ser Ala Arg
            660                 665                 670

Gly Arg Gly Val Asp Leu Thr Glu Pro Thr Gln Pro Thr Arg Asn Gln
            675                 680                 685

Cys Cys Ser Asn
            690

<210> SEQ ID NO 128
<211> LENGTH: 931
<212> TYPE: PRT
<213> ORGANISM: Artificial Sequence
<220> FEATURE:
<223> OTHER INFORMATION: CER92,amino acids 1-22 are signal peptide

<400> SEQUENCE: 128

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
        35                  40                  45

Arg Asn Ser Met Cys Trp Gly Lys Gly Ser Cys Pro Asn Ser Lys Cys
    50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Thr Lys Pro Thr Thr Thr Thr
130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
    210                 215                 220
```

```
Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ala Cys Cys Val Gly
        275                 280                 285

Phe Val Leu Met Val Leu Leu Phe Leu Ala Phe Leu Ala Leu Arg Arg
    290                 295                 300

Arg Val Gln Glu Thr Lys Phe Gly Gly Ala Phe Ser Glu Glu Asp Ser
305                 310                 315                 320

Gln Leu Val Val Asn Tyr Arg Ala Lys Lys Ser Phe Cys Arg Arg Ala
                325                 330                 335

Ile Glu Leu Thr Leu Gln Ser Leu Gly Val Ser Glu Glu Leu Gln Asn
            340                 345                 350

Lys Leu Glu Asp Val Val Ile Asp Arg Asn Leu Leu Val Leu Gly Lys
        355                 360                 365

Val Leu Gly Glu Gly Glu Phe Gly Ser Val Met Glu Gly Asn Leu Lys
    370                 375                 380

Gln Glu Asp Gly Thr Ser Gln Lys Val Ala Val Lys Thr Met Lys Leu
385                 390                 395                 400

Asp Asn Phe Ser Gln Arg Glu Ile Glu Glu Phe Leu Ser Glu Ala Ala
                405                 410                 415

Cys Met Lys Asp Phe Asn His Pro Asn Val Ile Arg Leu Leu Gly Val
            420                 425                 430

Cys Ile Glu Leu Ser Ser Gln Gly Ile Pro Lys Pro Met Val Ile Leu
        435                 440                 445

Pro Phe Met Lys Tyr Gly Asp Leu His Thr Phe Leu Leu Tyr Ser Arg
    450                 455                 460

Leu Asn Thr Gly Pro Lys Tyr Ile His Leu Gln Thr Leu Leu Lys Phe
465                 470                 475                 480

Met Met Asp Ile Ala Gln Gly Met Glu Tyr Leu Ser Asn Arg Asn Phe
                485                 490                 495

Leu His Arg Asp Leu Ala Ala Arg Asn Cys Met Leu Arg Asp Asp Met
            500                 505                 510

Thr Val Cys Val Ala Asp Phe Gly Leu Ser Lys Lys Ile Tyr Ser Gly
        515                 520                 525

Asp Tyr Tyr Arg Gln Gly Arg Ile Ala Lys Met Pro Val Lys Trp Ile
    530                 535                 540

Ala Ile Glu Ser Leu Ala Asp Arg Val Tyr Thr Ser Lys Ser Asp Val
545                 550                 555                 560

Trp Ala Phe Gly Val Thr Met Trp Glu Ile Thr Thr Arg Gly Met Thr
                565                 570                 575

Pro Tyr Pro Gly Val Gln Asn His Glu Met Tyr Asp Tyr Leu Leu His
            580                 585                 590

Gly His Arg Leu Lys Gln Pro Glu Asp Cys Leu Asp Glu Leu Tyr Asp
        595                 600                 605

Ile Met Tyr Ser Cys Trp Ser Ala Asp Pro Leu Asp Arg Pro Thr Phe
    610                 615                 620

Ser Val Leu Arg Leu Gln Leu Glu Lys Leu Ser Glu Ser Leu Pro Asp
625                 630                 635                 640

Ala Gln Asp Lys Glu Ser Ile Ile Tyr Ile Asn Thr Gln Leu Leu Glu
```

```
                    645                 650                 655
Ser Cys Glu Gly Ile Ala Asn Gly Pro Ser Leu Thr Gly Leu Asp Met
                660                 665                 670

Asn Ile Asp Pro Asp Ser Ile Ile Ala Ser Cys Thr Pro Gly Ala Ala
            675                 680                 685

Val Ser Val Val Thr Ala Glu Val His Glu Asn Asn Leu Arg Glu Glu
        690                 695                 700

Arg Tyr Ile Leu Asn Gly Gly Asn Glu Glu Trp Glu Asp Val Ser Ser
705                 710                 715                 720

Thr Pro Phe Ala Ala Val Thr Pro Glu Lys Asp Gly Val Leu Pro Glu
                725                 730                 735

Asp Arg Leu Thr Lys Asn Gly Val Ser Trp Ser His His Ser Thr Leu
            740                 745                 750

Pro Leu Gly Ser Pro Ser Pro Asp Glu Leu Leu Phe Val Asp Asp Ser
        755                 760                 765

Leu Glu Asp Ser Glu Val Leu Met Met Ala Ala Gly Pro Gly Ala
    770                 775                 780

Gly Ser Ala Ala Pro Val Ser Ser Thr Ser Ser Leu Pro Leu Ala Ala
785                 790                 795                 800

Leu Asn Met Arg Val Arg Arg Arg Leu Ser Leu Phe Leu Asn Val Arg
                805                 810                 815

Thr Gln Val Ala Ala Asp Trp Thr Ala Leu Ala Glu Glu Met Asp Phe
            820                 825                 830

Glu Tyr Leu Glu Ile Arg Gln Leu Glu Thr Gln Ala Asp Pro Thr Gly
        835                 840                 845

Arg Leu Leu Asp Ala Trp Gln Gly Arg Pro Gly Ala Ser Val Gly Arg
    850                 855                 860

Leu Leu Glu Leu Leu Thr Lys Leu Gly Arg Asp Asp Val Leu Leu Glu
865                 870                 875                 880

Leu Gly Pro Ser Ile Glu Glu Asp Cys Gln Lys Tyr Ile Leu Lys Gln
                885                 890                 895

Gln Gln Glu Glu Ala Glu Lys Pro Leu Gln Val Ala Ala Val Asp Ser
            900                 905                 910

Ser Val Pro Arg Thr Ala Glu Leu Ala Gly Ile Thr Thr Leu Asp Asp
        915                 920                 925

Pro Leu Gly
    930

<210> SEQ ID NO 129
<211> LENGTH: 861
<212> TYPE: PRT
<213> ORGANISM: Artificial Sequence
<220> FEATURE:
<223> OTHER INFORMATION: CER93, amino acids 1-22 are signal peptide

<400> SEQUENCE: 129

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
                20                  25                  30

Gly Gln Pro Val Thr Leu Pro Cys His Tyr Leu Ser Trp Ser Gln Ser
            35                  40                  45

Arg Asn Ser Met Cys Trp Gly Lys Gly Ser Cys Pro Asn Ser Lys Cys
        50                  55                  60

Asn Ala Glu Leu Leu Arg Thr Asp Gly Thr Arg Ile Ile Ser Arg Lys
```

-continued

```
                65                  70                  75                  80
        Ser Thr Lys Tyr Thr Leu Leu Gly Lys Val Gln Phe Gly Glu Val Ser
                        85                  90                  95

Leu Thr Ile Ser Asn Thr Asn Arg Gly Asp Ser Gly Val Tyr Cys Cys
                       100                 105                 110

Arg Ile Glu Val Pro Gly Trp Phe Asn Asp Val Lys Lys Asn Val Arg
                       115                 120                 125

Leu Glu Leu Arg Arg Ala Thr Thr Lys Lys Pro Thr Thr Thr
        130                     135                 140

Arg Pro Thr Thr Thr Pro Tyr Val Thr Thr Thr Pro Glu Leu Leu
        145                 150                 155                 160

Pro Thr Thr Val Met Thr Thr Ser Val Leu Pro Thr Thr Pro Pro
                        165                 170                 175

Gln Thr Leu Ala Thr Thr Ala Phe Ser Thr Ala Val Thr Cys Pro
                        180                 185                 190

Ser Thr Thr Pro Gly Ser Phe Ser Gln Glu Thr Thr Lys Gly Ser Ala
                       195                 200                 205

Phe Thr Thr Glu Ser Glu Thr Leu Pro Ala Ser Asn His Ser Gln Arg
                       210                 215                 220

Ser Met Met Thr Ile Ser Thr Asp Ile Ala Val Leu Arg Pro Thr Gly
        225                     230                 235                 240

Ser Asn Pro Gly Ile Leu Pro Ser Thr Ser Gln Leu Thr Thr Gln Lys
                        245                 250                 255

Thr Thr Leu Thr Thr Ser Glu Ser Leu Gln Lys Thr Thr Lys Ser His
                        260                 265                 270

Gln Ile Asn Ser Arg Gln Thr Ile Leu Ile Ala Cys Cys Val Gly
                        275                 280                 285

Phe Val Leu Met Val Leu Leu Phe Leu Ala Phe Ala Leu Arg Arg
                        290                 295                 300

Arg Val Gln Glu Thr Lys Phe Gly Gly Ala Phe Ser Glu Glu Asp Ser
        305                     310                 315                 320

Gln Leu Val Val Asn Tyr Arg Ala Lys Lys Ser Phe Cys Arg Arg Ala
                        325                 330                 335

Ile Glu Leu Thr Leu Gln Ser Leu Gly Val Ser Glu Glu Leu Gln Asn
                        340                 345                 350

Lys Leu Glu Asp Val Val Ile Asp Arg Asn Leu Leu Val Leu Gly Lys
                        355                 360                 365

Val Leu Gly Glu Gly Glu Phe Gly Ser Val Met Glu Gly Asn Leu Lys
                        370                 375                 380

Gln Glu Asp Gly Thr Ser Gln Lys Val Ala Val Lys Thr Met Lys Leu
        385                     390                 395                 400

Asp Asn Phe Ser Gln Arg Glu Ile Glu Glu Phe Leu Ser Glu Ala Ala
                        405                 410                 415

Cys Met Lys Asp Phe Asn His Pro Asn Val Ile Arg Leu Leu Gly Val
                        420                 425                 430

Cys Ile Glu Leu Ser Ser Gln Gly Ile Pro Lys Pro Met Val Ile Leu
                        435                 440                 445

Pro Phe Met Lys Tyr Gly Asp Leu His Thr Phe Leu Leu Tyr Ser Arg
                        450                 455                 460

Leu Asn Thr Gly Pro Lys Tyr Ile His Leu Gln Thr Leu Leu Lys Phe
        465                     470                 475                 480

Met Met Asp Ile Ala Gln Gly Met Glu Tyr Leu Ser Asn Arg Asn Phe
                        485                 490                 495
```

Leu His Arg Asp Leu Ala Ala Arg Asn Cys Met Leu Arg Asp Asp Met
            500                 505                 510

Thr Val Cys Val Ala Asp Phe Gly Leu Ser Lys Lys Ile Tyr Ser Gly
            515                 520                 525

Asp Tyr Tyr Arg Gln Gly Arg Ile Ala Lys Met Pro Val Lys Trp Ile
            530                 535                 540

Ala Ile Glu Ser Leu Ala Asp Arg Val Tyr Thr Ser Lys Ser Asp Val
545                 550                 555                 560

Trp Ala Phe Gly Val Thr Met Trp Glu Ile Thr Thr Arg Gly Met Thr
            565                 570                 575

Pro Tyr Pro Gly Val Gln Asn His Glu Met Tyr Asp Tyr Leu Leu His
            580                 585                 590

Gly His Arg Leu Lys Gln Pro Glu Asp Cys Leu Asp Glu Leu Tyr Asp
            595                 600                 605

Ile Met Tyr Ser Cys Trp Ser Ala Asp Pro Leu Asp Arg Pro Thr Phe
            610                 615                 620

Ser Val Leu Arg Leu Gln Leu Glu Lys Leu Ser Glu Ser Leu Pro Asp
625                 630                 635                 640

Ala Gln Asp Lys Glu Ser Ile Ile Tyr Ile Asn Thr Gln Leu Leu Glu
            645                 650                 655

Ser Cys Glu Gly Ile Ala Asn Gly Pro Ser Leu Thr Gly Leu Asp Met
            660                 665                 670

Asn Ile Asp Pro Asp Ser Ile Ile Ala Ser Cys Thr Pro Gly Ala Ala
            675                 680                 685

Val Ser Val Val Thr Ala Glu Val His Glu Asn Asn Leu Arg Glu Glu
690                 695                 700

Arg Tyr Ile Leu Asn Gly Gly Asn Glu Glu Trp Glu Asp Val Ser Ser
705                 710                 715                 720

Thr Pro Phe Ala Ala Val Thr Pro Glu Lys Asp Gly Val Leu Pro Glu
            725                 730                 735

Asp Arg Leu Thr Lys Asn Gly Val Ser Trp Ser His His Ser Thr Leu
            740                 745                 750

Pro Leu Gly Ser Pro Ser Pro Asp Glu Leu Leu Phe Val Asp Asp Ser
            755                 760                 765

Leu Glu Asp Ser Glu Val Leu Met Ser Trp Arg Arg Arg Gln Arg Arg
770                 775                 780

Leu Arg Gly Ala Ser Ser Ala Glu Ala Pro Asp Gly Asp Lys Asp Ala
785                 790                 795                 800

Pro Glu Pro Leu Asp Lys Val Ile Ile Leu Ser Pro Gly Ile Ser Asp
            805                 810                 815

Ala Thr Ala Pro Ala Trp Pro Pro Gly Glu Asp Pro Gly Thr Thr
            820                 825                 830

Pro Pro Gly His Ser Val Pro Val Pro Ala Thr Glu Leu Gly Ser Thr
            835                 840                 845

Glu Leu Val Thr Thr Lys Thr Ala Gly Pro Glu Gln Gln
    850                 855                 860

<210> SEQ ID NO 130
<211> LENGTH: 828
<212> TYPE: PRT
<213> ORGANISM: Artificial Sequence
<220> FEATURE:
<223> OTHER INFORMATION: CER94, amino acids 1-22 are signal peptide

<400> SEQUENCE: 130

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
        35                  40                  45

Arg Asn Ser Met Cys Trp Gly Lys Gly Ser Cys Pro Asn Ser Lys Cys
    50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
            85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
    115                 120                 125

Leu Glu Leu Arg Arg Ala Thr Thr Lys Lys Pro Thr Thr Thr Thr Thr
    130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
        180                 185                 190

Ser Thr Thr Pro Gly Ser Phe Ser Gln Glu Thr Thr Lys Gly Ser Ala
            195                 200                 205

Phe Thr Thr Glu Ser Glu Thr Leu Pro Ala Ser Asn His Ser Gln Arg
210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
            245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ala Cys Cys Val Gly
    275                 280                 285

Phe Val Leu Met Val Leu Leu Phe Leu Ala Phe Leu Ala Leu Arg Arg
    290                 295                 300

Arg Val Gln Glu Thr Lys Phe Gly Gly Ala Phe Ser Glu Glu Asp Ser
305                 310                 315                 320

Gln Leu Val Val Asn Tyr Arg Ala Lys Lys Ser Phe Cys Arg Arg Ala
            325                 330                 335

Ile Glu Leu Thr Leu Gln Ser Leu Gly Val Ser Glu Glu Leu Gln Asn
            340                 345                 350

Lys Leu Glu Asp Val Val Ile Asp Arg Asn Leu Leu Val Leu Gly Lys
            355                 360                 365

Val Leu Gly Glu Gly Glu Phe Gly Ser Val Met Glu Gly Asn Leu Lys
    370                 375                 380

Gln Glu Asp Gly Thr Ser Gln Lys Val Ala Val Lys Thr Met Lys Leu
385                 390                 395                 400

Asp Asn Phe Ser Gln Arg Glu Ile Glu Glu Phe Leu Ser Glu Ala Ala
                405                 410                 415

-continued

```
Cys Met Lys Asp Phe Asn His Pro Asn Val Ile Arg Leu Leu Gly Val
            420                 425                 430

Cys Ile Glu Leu Ser Ser Gln Gly Ile Pro Lys Pro Met Val Ile Leu
        435                 440                 445

Pro Phe Met Lys Tyr Gly Asp Leu His Thr Phe Leu Leu Tyr Ser Arg
    450                 455                 460

Leu Asn Thr Gly Pro Lys Tyr Ile His Leu Gln Thr Leu Leu Lys Phe
465                 470                 475                 480

Met Met Asp Ile Ala Gln Gly Met Glu Tyr Leu Ser Asn Arg Asn Phe
                485                 490                 495

Leu His Arg Asp Leu Ala Ala Arg Asn Cys Met Leu Arg Asp Asp Met
            500                 505                 510

Thr Val Cys Val Ala Asp Phe Gly Leu Ser Lys Lys Ile Tyr Ser Gly
        515                 520                 525

Asp Tyr Tyr Arg Gln Gly Arg Ile Ala Lys Met Pro Val Lys Trp Ile
    530                 535                 540

Ala Ile Glu Ser Leu Ala Asp Arg Val Tyr Thr Ser Lys Ser Asp Val
545                 550                 555                 560

Trp Ala Phe Gly Val Thr Met Trp Glu Ile Thr Thr Arg Gly Met Thr
                565                 570                 575

Pro Tyr Pro Gly Val Gln Asn His Glu Met Tyr Asp Tyr Leu Leu His
            580                 585                 590

Gly His Arg Leu Lys Gln Pro Glu Asp Cys Leu Asp Glu Leu Tyr Asp
        595                 600                 605

Ile Met Tyr Ser Cys Trp Ser Ala Asp Pro Leu Asp Arg Pro Thr Phe
    610                 615                 620

Ser Val Leu Arg Leu Gln Leu Glu Lys Leu Ser Glu Ser Leu Pro Asp
625                 630                 635                 640

Ala Gln Asp Lys Glu Ser Ile Ile Tyr Ile Asn Thr Gln Leu Leu Glu
                645                 650                 655

Ser Cys Glu Gly Ile Ala Asn Gly Pro Ser Leu Thr Gly Leu Asp Met
            660                 665                 670

Asn Ile Asp Pro Asp Ser Ile Ile Ala Ser Cys Thr Pro Gly Ala Ala
        675                 680                 685

Val Ser Val Val Thr Ala Glu Val His Glu Asn Asn Leu Arg Glu Glu
    690                 695                 700

Arg Tyr Ile Leu Asn Gly Gly Asn Glu Glu Trp Glu Asp Val Ser Ser
705                 710                 715                 720

Thr Pro Phe Ala Ala Val Thr Pro Glu Lys Asp Gly Val Leu Pro Glu
                725                 730                 735

Asp Arg Leu Thr Lys Asn Gly Val Ser Trp Ser His His Ser Thr Leu
            740                 745                 750

Pro Leu Gly Ser Pro Ser Pro Asp Glu Leu Leu Phe Val Asp Asp Ser
        755                 760                 765

Leu Glu Asp Ser Glu Val Leu Met Tyr Phe Leu Gly Arg Leu Val Pro
    770                 775                 780

Arg Gly Arg Gly Ala Ala Glu Ala Ala Thr Arg Lys Gln Arg Ile Thr
785                 790                 795                 800

Glu Thr Glu Ser Pro Tyr Gln Glu Leu Gln Gly Gln Arg Ser Asp Val
                805                 810                 815

Tyr Ser Asp Leu Asn Thr Gln Arg Pro Tyr Tyr Lys
            820                 825
```

-continued

```
<210> SEQ ID NO 131
<211> LENGTH: 821
<212> TYPE: PRT
<213> ORGANISM: Artificial Sequence
<220> FEATURE:
<223> OTHER INFORMATION: CER95, amino acids 1-22 are signal peptide

<400> SEQUENCE: 131

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
        35                  40                  45

Arg Asn Ser Met Cys Trp Gly Lys Gly Ser Cys Pro Asn Ser Lys Cys
50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Lys Lys Pro Thr Thr Thr Thr
130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ile Ala Cys Cys Val Gly
        275                 280                 285

Phe Val Leu Met Val Leu Leu Phe Leu Ala Phe Leu Ala Leu Arg Arg
290                 295                 300

Arg Val Gln Glu Thr Lys Phe Gly Gly Ala Phe Ser Glu Glu Asp Ser
305                 310                 315                 320

Gln Leu Val Val Asn Tyr Arg Ala Lys Lys Ser Phe Cys Arg Arg Ala
                325                 330                 335

Ile Glu Leu Thr Leu Gln Ser Leu Gly Val Ser Glu Glu Leu Gln Asn
            340                 345                 350

Lys Leu Glu Asp Val Val Ile Asp Arg Asn Leu Leu Val Leu Gly Lys
        355                 360                 365

Val Leu Gly Glu Gly Glu Phe Gly Ser Val Met Glu Gly Asn Leu Lys
```

```
              370                 375                 380
        Gln Glu Asp Gly Thr Ser Gln Lys Val Ala Val Lys Thr Met Lys Leu
        385                 390                 395                 400

Asp Asn Phe Ser Gln Arg Glu Ile Glu Phe Leu Ser Glu Ala Ala
                            405                 410                 415

Cys Met Lys Asp Phe Asn His Pro Asn Val Ile Arg Leu Leu Gly Val
                        420                 425                 430

Cys Ile Glu Leu Ser Ser Gln Gly Ile Pro Lys Pro Met Val Ile Leu
                        435                 440                 445

Pro Phe Met Lys Tyr Gly Asp Leu His Thr Phe Leu Leu Tyr Ser Arg
        450                 455                 460

Leu Asn Thr Gly Pro Lys Tyr Ile His Leu Gln Thr Leu Leu Lys Phe
        465                 470                 475                 480

Met Met Asp Ile Ala Gln Gly Met Glu Tyr Leu Ser Asn Arg Asn Phe
                        485                 490                 495

Leu His Arg Asp Leu Ala Ala Arg Asn Cys Met Leu Arg Asp Asp Met
                        500                 505                 510

Thr Val Cys Val Ala Asp Phe Gly Leu Ser Lys Lys Ile Tyr Ser Gly
                        515                 520                 525

Asp Tyr Tyr Arg Gln Gly Arg Ile Ala Lys Met Pro Val Lys Trp Ile
        530                 535                 540

Ala Ile Glu Ser Leu Ala Asp Arg Val Tyr Thr Ser Lys Ser Asp Val
        545                 550                 555                 560

Trp Ala Phe Gly Val Thr Met Trp Glu Ile Thr Thr Arg Gly Met Thr
                            565                 570                 575

Pro Tyr Pro Gly Val Gln Asn His Glu Met Tyr Asp Tyr Leu Leu His
                        580                 585                 590

Gly His Arg Leu Lys Gln Pro Glu Asp Cys Leu Asp Glu Leu Tyr Asp
                        595                 600                 605

Ile Met Tyr Ser Cys Trp Ser Ala Asp Pro Leu Asp Arg Pro Thr Phe
                        610                 615                 620

Ser Val Leu Arg Leu Gln Leu Glu Lys Leu Ser Glu Ser Leu Pro Asp
        625                 630                 635                 640

Ala Gln Asp Lys Glu Ser Ile Ile Tyr Ile Asn Thr Gln Leu Leu Glu
                            645                 650                 655

Ser Cys Glu Gly Ile Ala Asn Gly Pro Ser Leu Thr Gly Leu Asp Met
                        660                 665                 670

Asn Ile Asp Pro Asp Ser Ile Ile Ala Ser Cys Thr Pro Gly Ala Ala
                        675                 680                 685

Val Ser Val Val Thr Ala Glu Val His Glu Asn Asn Leu Arg Glu Glu
        690                 695                 700

Arg Tyr Ile Leu Asn Gly Gly Asn Glu Glu Trp Glu Asp Val Ser Ser
        705                 710                 715                 720

Thr Pro Phe Ala Ala Val Thr Pro Glu Lys Asp Gly Val Leu Pro Glu
                            725                 730                 735

Asp Arg Leu Thr Lys Asn Gly Val Ser Trp Ser His His Ser Thr Leu
                        740                 745                 750

Pro Leu Gly Ser Pro Ser Pro Asp Glu Leu Leu Phe Val Asp Asp Ser
                        755                 760                 765

Leu Glu Asp Ser Glu Val Leu Met Asp Ser Lys Ala Gly Met Glu Glu
                770                 775                 780

Asp His Thr Tyr Glu Gly Leu Asp Ile Asp Gln Thr Ala Thr Tyr Glu
        785                 790                 795                 800
```

```
Asp Ile Val Thr Leu Arg Thr Gly Glu Val Lys Trp Ser Val Gly Glu
            805                 810                 815

His Pro Gly Gln Glu
            820

<210> SEQ ID NO 132
<211> LENGTH: 862
<212> TYPE: PRT
<213> ORGANISM: Artificial Sequence
<220> FEATURE:
<223> OTHER INFORMATION: CER96, amino acids 1-22 are signal peptide

<400> SEQUENCE: 132

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
                20                  25                  30

Gly Gln Pro Val Thr Leu Pro Cys His Tyr Leu Ser Trp Ser Gln Ser
            35                  40                  45

Arg Asn Ser Met Cys Trp Gly Lys Gly Ser Cys Pro Asn Ser Lys Cys
    50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Thr Lys Lys Pro Thr Thr Thr Thr
    130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
    210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ile Ala Cys Cys Val Gly
        275                 280                 285

Phe Val Leu Met Val Leu Leu Phe Leu Ala Phe Leu Ala Leu Arg Arg
    290                 295                 300

Arg Val Gln Glu Thr Lys Phe Gly Gly Ala Phe Ser Glu Glu Asp Ser
305                 310                 315                 320

Gln Leu Val Val Asn Tyr Arg Ala Lys Lys Ser Phe Cys Arg Arg Ala
                325                 330                 335
```

Ile Glu Leu Thr Leu Gln Ser Leu Gly Val Ser Glu Leu Gln Asn
                340                 345                 350

Lys Leu Glu Asp Val Val Ile Asp Arg Asn Leu Leu Val Leu Gly Lys
            355                 360                 365

Val Leu Gly Glu Gly Glu Phe Gly Ser Val Met Glu Gly Asn Leu Lys
370                 375                 380

Gln Glu Asp Gly Thr Ser Gln Lys Val Ala Val Lys Thr Met Lys Leu
385                 390                 395                 400

Asp Asn Phe Ser Gln Arg Glu Ile Glu Phe Leu Ser Glu Ala Ala
                405                 410                 415

Cys Met Lys Asp Phe Asn His Pro Asn Val Ile Arg Leu Leu Gly Val
            420                 425                 430

Cys Ile Glu Leu Ser Ser Gln Gly Ile Pro Lys Pro Met Val Ile Leu
        435                 440                 445

Pro Phe Met Lys Tyr Gly Asp Leu His Thr Phe Leu Leu Tyr Ser Arg
    450                 455                 460

Leu Asn Thr Gly Pro Lys Tyr Ile His Leu Gln Thr Leu Leu Lys Phe
465                 470                 475                 480

Met Met Asp Ile Ala Gln Gly Met Glu Tyr Leu Ser Asn Arg Asn Phe
                485                 490                 495

Leu His Arg Asp Leu Ala Ala Arg Asn Cys Met Leu Arg Asp Asp Met
            500                 505                 510

Thr Val Cys Val Ala Asp Phe Gly Leu Ser Lys Lys Ile Tyr Ser Gly
        515                 520                 525

Asp Tyr Tyr Arg Gln Gly Arg Ile Ala Lys Met Pro Val Lys Trp Ile
    530                 535                 540

Ala Ile Glu Ser Leu Ala Asp Arg Val Tyr Thr Ser Lys Ser Asp Val
545                 550                 555                 560

Trp Ala Phe Gly Val Thr Met Trp Glu Ile Thr Thr Arg Gly Met Thr
                565                 570                 575

Pro Tyr Pro Gly Val Gln Asn His Glu Met Tyr Asp Tyr Leu Leu His
            580                 585                 590

Gly His Arg Leu Lys Gln Pro Glu Asp Cys Leu Asp Glu Leu Tyr Asp
        595                 600                 605

Ile Met Tyr Ser Cys Trp Ser Ala Asp Pro Leu Asp Arg Pro Thr Phe
    610                 615                 620

Ser Val Leu Arg Leu Gln Leu Glu Lys Leu Ser Glu Ser Leu Pro Asp
625                 630                 635                 640

Ala Gln Asp Lys Glu Ser Ile Ile Tyr Ile Asn Thr Gln Leu Leu Glu
                645                 650                 655

Ser Cys Glu Gly Ile Ala Asn Gly Pro Ser Leu Thr Gly Leu Asp Met
            660                 665                 670

Asn Ile Asp Pro Asp Ser Ile Ile Ala Ser Cys Thr Pro Gly Ala Ala
        675                 680                 685

Val Ser Val Val Thr Ala Glu Val His Glu Asn Asn Leu Arg Glu Glu
    690                 695                 700

Arg Tyr Ile Leu Asn Gly Gly Asn Glu Glu Trp Glu Asp Val Ser Ser
705                 710                 715                 720

Thr Pro Phe Ala Ala Val Thr Pro Glu Lys Asp Gly Val Leu Pro Glu
                725                 730                 735

Asp Arg Leu Thr Lys Asn Gly Val Ser Trp Ser His Ser Thr Leu
            740                 745                 750

-continued

```
Pro Leu Gly Ser Pro Ser Pro Asp Glu Leu Leu Phe Val Asp Asp Ser
        755                 760                 765
Leu Glu Asp Ser Glu Val Leu Met Leu Trp Asn Lys Lys Arg Met Arg
    770                 775                 780
Gly Pro Gly Lys Asp Pro Thr Arg Lys Cys Pro Asp Pro Arg Ser Ala
785             790                 795                 800
Ser Ser Pro Lys Gln His Pro Ser Glu Ser Val Tyr Thr Ala Leu Gln
                805                 810                 815
Arg Arg Glu Thr Glu Val Tyr Ala Cys Ile Glu Asn Glu Asp Gly Ser
            820                 825                 830
Ser Pro Thr Ala Lys Gln Ser Pro Leu Ser Gln Glu Arg Pro His Arg
        835                 840                 845
Phe Glu Asp Asp Gly Glu Leu Asn Leu Val Tyr Glu Asn Leu
    850                 855                 860

<210> SEQ ID NO 133
<211> LENGTH: 774
<212> TYPE: PRT
<213> ORGANISM: Artificial Sequence
<220> FEATURE:
<223> OTHER INFORMATION: CER97, amino acids 1-22 are signal peptide

<400> SEQUENCE: 133

Met Ser Lys Gly Leu Leu Leu Trp Leu Val Thr Glu Leu Trp Trp
1               5                   10                  15
Leu Tyr Leu Thr Pro Ala Ala Ser Glu Asp Thr Ile Ile Gly Phe Leu
            20                  25                  30
Gly Gln Pro Val Thr Leu Pro Cys His Tyr Leu Ser Trp Ser Gln Ser
        35                  40                  45
Arg Asn Ser Met Cys Trp Gly Lys Gly Ser Cys Pro Asn Ser Lys Cys
    50                  55                  60
Asn Ala Glu Leu Leu Arg Thr Asp Gly Thr Arg Ile Ile Ser Arg Lys
65                  70                  75                  80
Ser Thr Lys Tyr Thr Leu Leu Gly Lys Val Gln Phe Gly Glu Val Ser
                85                  90                  95
Leu Thr Ile Ser Asn Thr Asn Arg Gly Asp Ser Gly Val Tyr Cys Cys
            100                 105                 110
Arg Ile Glu Val Pro Gly Trp Phe Asn Asp Val Lys Lys Asn Val Arg
        115                 120                 125
Leu Glu Leu Arg Arg Ala Thr Thr Lys Lys Pro Thr Thr Thr Thr
    130                 135                 140
Arg Pro Thr Thr Thr Pro Tyr Val Thr Thr Thr Pro Glu Leu Leu
145                 150                 155                 160
Pro Thr Thr Val Met Thr Thr Ser Val Leu Pro Thr Thr Thr Pro Pro
                165                 170                 175
Gln Thr Leu Ala Thr Ala Phe Ser Thr Ala Val Thr Thr Cys Pro
            180                 185                 190
Ser Thr Thr Pro Gly Ser Phe Ser Gln Glu Thr Thr Lys Gly Ser Ala
        195                 200                 205
Phe Thr Thr Glu Ser Glu Thr Leu Pro Ala Ser Asn His Ser Gln Arg
    210                 215                 220
Ser Met Met Thr Ile Ser Thr Asp Ile Ala Val Leu Arg Pro Thr Gly
225                 230                 235                 240
Ser Asn Pro Gly Ile Leu Pro Ser Thr Ser Gln Leu Thr Thr Gln Lys
                245                 250                 255
```

```
Thr Thr Leu Thr Thr Ser Glu Ser Leu Gln Lys Thr Thr Lys Ser His
            260             265                 270

Gln Ile Asn Ser Arg Gln Thr Ile Leu Ile Ala Cys Cys Val Gly
        275                 280                 285

Phe Val Leu Met Val Leu Leu Phe Leu Ala Phe Leu His Arg Arg Lys
    290                 295                 300

Lys Glu Thr Arg Tyr Gly Glu Val Phe Glu Pro Thr Val Glu Arg Gly
305                 310                 315                 320

Glu Leu Val Val Arg Tyr Arg Val Arg Lys Ser Tyr Ser Arg Arg Thr
                325                 330                 335

Thr Glu Ala Thr Leu Asn Ser Leu Gly Ile Ser Glu Glu Leu Lys Glu
            340                 345                 350

Lys Leu Arg Asp Val Met Val Asp Arg His Lys Val Ala Leu Gly Lys
        355                 360                 365

Thr Leu Gly Glu Gly Glu Phe Gly Ala Val Met Glu Gly Gln Leu Asn
    370                 375                 380

Gln Asp Asp Ser Ile Leu Lys Val Ala Val Lys Thr Met Lys Ile Ala
385                 390                 395                 400

Ile Cys Thr Arg Ser Glu Leu Glu Asp Phe Leu Ser Glu Ala Val Cys
                405                 410                 415

Met Lys Glu Phe Asp His Pro Asn Val Met Arg Leu Ile Gly Val Cys
            420                 425                 430

Phe Gln Gly Ser Glu Arg Glu Ser Phe Pro Ala Pro Val Val Ile Leu
        435                 440                 445

Pro Phe Met Lys His Gly Asp Leu His Ser Phe Leu Leu Tyr Ser Arg
    450                 455                 460

Leu Gly Asp Gln Pro Val Tyr Leu Pro Thr Gln Met Leu Val Lys Phe
465                 470                 475                 480

Met Ala Asp Ile Ala Ser Gly Met Glu Tyr Leu Ser Thr Lys Arg Phe
                485                 490                 495

Ile His Arg Asp Leu Ala Ala Arg Asn Cys Met Leu Asn Glu Asn Met
            500                 505                 510

Ser Val Cys Val Ala Asp Phe Gly Leu Ser Lys Lys Ile Tyr Asn Gly
        515                 520                 525

Asp Tyr Tyr Arg Gln Gly Arg Ile Ala Lys Met Pro Val Lys Trp Ile
    530                 535                 540

Ala Ile Glu Ser Leu Ala Asp Arg Val Tyr Thr Ser Lys Ser Asp Val
545                 550                 555                 560

Trp Ser Phe Gly Val Thr Met Trp Glu Ile Ala Thr Arg Gly Gln Thr
                565                 570                 575

Pro Tyr Pro Gly Val Glu Asn Ser Glu Ile Tyr Asp Tyr Leu Arg Gln
            580                 585                 590

Gly Asn Arg Leu Lys Gln Pro Ala Asp Cys Leu Asp Gly Leu Tyr Ala
        595                 600                 605

Leu Met Ser Arg Cys Trp Glu Leu Asn Pro Gln Asp Arg Pro Ser Phe
    610                 615                 620

Thr Glu Leu Arg Glu Asp Leu Glu Asn Thr Leu Lys Ala Leu Pro Pro
625                 630                 635                 640

Ala Gln Glu Pro Asp Glu Ile Leu Tyr Val Asn Met Asp Glu Gly Gly
                645                 650                 655

Gly Tyr Pro Glu Pro Pro Gly Ala Ala Gly Gly Ala Asp Pro Pro Thr
            660                 665                 670

Gln Pro Asp Pro Lys Asp Ser Cys Ser Cys Leu Thr Ala Ala Glu Val
```

```
                675                 680                 685
His Pro Ala Gly Arg Tyr Val Leu Cys Pro Ser Thr Thr Pro Ser Pro
    690                 695                 700

Ala Gln Pro Ala Asp Arg Gly Ser Pro Ala Ala Pro Gly Gln Glu Asp
705                 710                 715                 720

Gly Ala Tyr Phe Leu Gly Arg Leu Val Pro Arg Gly Arg Gly Ala Ala
                725                 730                 735

Glu Ala Ala Thr Arg Lys Gln Arg Ile Thr Glu Thr Glu Ser Pro Tyr
                740                 745                 750

Gln Glu Leu Gln Gly Gln Arg Ser Asp Val Tyr Ser Asp Leu Asn Thr
            755                 760                 765

Gln Arg Pro Tyr Tyr Lys
        770
```

<210> SEQ ID NO 134
<211> LENGTH: 767
<212> TYPE: PRT
<213> ORGANISM: Artificial Sequence
<220> FEATURE:
<223> OTHER INFORMATION: CER98, amino acids 1-22 are signal peptide

<400> SEQUENCE: 134

```
Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
                20                  25                  30

Gly Gln Pro Val Thr Leu Pro Cys His Tyr Leu Ser Trp Ser Gln Ser
            35                  40                  45

Arg Asn Ser Met Cys Trp Gly Lys Gly Ser Cys Pro Asn Ser Lys Cys
    50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Lys Lys Pro Thr Thr Thr Thr Thr
    130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Ala Phe Ser Thr Ala Val Thr Thr Cys Pro
            180                 185                 190

Ser Thr Thr Pro Gly Ser Phe Ser Gln Glu Thr Lys Gly Ser Ala
        195                 200                 205

Phe Thr Thr Glu Ser Glu Thr Leu Pro Ala Ser Asn His Ser Gln Arg
    210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
```

```
                260                 265                 270
Gln Ile Asn Ser Arg Gln Thr Ile Leu Ile Ala Cys Cys Val Gly
            275                 280                 285

Phe Val Leu Met Val Leu Leu Phe Leu Ala Phe Leu His Arg Arg Lys
290                 295                 300

Lys Glu Thr Arg Tyr Gly Glu Val Phe Glu Pro Thr Val Glu Arg Gly
305                 310                 315                 320

Glu Leu Val Val Arg Tyr Arg Val Arg Lys Ser Tyr Ser Arg Arg Thr
                325                 330                 335

Thr Glu Ala Thr Leu Asn Ser Leu Gly Ile Ser Glu Glu Leu Lys Glu
            340                 345                 350

Lys Leu Arg Asp Val Met Val Asp Arg His Lys Val Ala Leu Gly Lys
        355                 360                 365

Thr Leu Gly Glu Gly Glu Phe Gly Ala Val Met Glu Gly Gln Leu Asn
    370                 375                 380

Gln Asp Asp Ser Ile Leu Lys Val Ala Val Lys Thr Met Lys Ile Ala
385                 390                 395                 400

Ile Cys Thr Arg Ser Glu Leu Glu Asp Phe Leu Ser Glu Ala Val Cys
                405                 410                 415

Met Lys Glu Phe Asp His Pro Asn Val Met Arg Leu Ile Gly Val Cys
            420                 425                 430

Phe Gln Gly Ser Glu Arg Glu Ser Phe Pro Ala Pro Val Val Ile Leu
        435                 440                 445

Pro Phe Met Lys His Gly Asp Leu His Ser Phe Leu Leu Tyr Ser Arg
    450                 455                 460

Leu Gly Asp Gln Pro Val Tyr Leu Pro Thr Gln Met Leu Val Lys Phe
465                 470                 475                 480

Met Ala Asp Ile Ala Ser Gly Met Glu Tyr Leu Ser Thr Lys Arg Phe
                485                 490                 495

Ile His Arg Asp Leu Ala Ala Arg Asn Cys Met Leu Asn Glu Asn Met
            500                 505                 510

Ser Val Cys Val Ala Asp Phe Gly Leu Ser Lys Lys Ile Tyr Asn Gly
        515                 520                 525

Asp Tyr Tyr Arg Gln Gly Arg Ile Ala Lys Met Pro Val Lys Trp Ile
    530                 535                 540

Ala Ile Glu Ser Leu Ala Asp Arg Val Tyr Thr Ser Lys Ser Asp Val
545                 550                 555                 560

Trp Ser Phe Gly Val Thr Met Trp Glu Ile Ala Thr Arg Gly Gln Thr
                565                 570                 575

Pro Tyr Pro Gly Val Glu Asn Ser Glu Ile Tyr Asp Tyr Leu Arg Gln
            580                 585                 590

Gly Asn Arg Leu Lys Gln Pro Ala Asp Cys Leu Asp Gly Leu Tyr Ala
        595                 600                 605

Leu Met Ser Arg Cys Trp Glu Leu Asn Pro Gln Asp Arg Pro Ser Phe
    610                 615                 620

Thr Glu Leu Arg Glu Asp Leu Glu Asn Thr Leu Lys Ala Leu Pro Pro
625                 630                 635                 640

Ala Gln Glu Pro Asp Glu Ile Leu Tyr Val Asn Met Asp Glu Gly Gly
                645                 650                 655

Gly Tyr Pro Glu Pro Pro Gly Ala Ala Gly Gly Ala Asp Pro Pro Thr
            660                 665                 670

Gln Pro Asp Pro Lys Asp Ser Cys Ser Cys Leu Thr Ala Ala Glu Val
        675                 680                 685
```

His Pro Ala Gly Arg Tyr Val Leu Cys Pro Ser Thr Pro Ser Pro
690                 695                 700

Ala Gln Pro Ala Asp Arg Gly Ser Pro Ala Ala Pro Gly Gln Glu Asp
705                 710                 715                 720

Gly Ala Asp Ser Lys Ala Gly Met Glu Glu Asp His Thr Tyr Glu Gly
            725                 730                 735

Leu Asp Ile Asp Gln Thr Ala Thr Tyr Glu Asp Ile Val Thr Leu Arg
            740                 745                 750

Thr Gly Glu Val Lys Trp Ser Val Gly Glu His Pro Gly Gln Glu
            755                 760                 765

<210> SEQ ID NO 135
<211> LENGTH: 808
<212> TYPE: PRT
<213> ORGANISM: Artificial Sequence
<220> FEATURE:
<223> OTHER INFORMATION: CER99, amino acids 1-22 are signal peptide

<400> SEQUENCE: 135

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
            35                  40                  45

Arg Asn Ser Met Cys Trp Gly Lys Gly Ser Cys Pro Asn Ser Lys Cys
    50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Lys Lys Pro Thr Thr Thr Thr
130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Cys Pro
            180                 185                 190

Ser Thr Thr Pro Gly Ser Phe Ser Gln Glu Thr Thr Lys Gly Ser Ala
            195                 200                 205

Phe Thr Thr Glu Ser Glu Thr Leu Pro Ala Ser Asn His Ser Gln Arg
    210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Gln Lys
            245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ile Ala Cys Cys Val Gly
        275                 280                 285

```
Phe Val Leu Met Val Leu Leu Phe Leu Ala Phe Leu His Arg Arg Lys
        290                 295                 300

Lys Glu Thr Arg Tyr Gly Glu Val Phe Glu Pro Thr Val Glu Arg Gly
305                 310                 315                 320

Glu Leu Val Val Arg Tyr Arg Val Arg Lys Ser Tyr Ser Arg Arg Thr
                325                 330                 335

Thr Glu Ala Thr Leu Asn Ser Leu Gly Ile Ser Glu Glu Leu Lys Glu
            340                 345                 350

Lys Leu Arg Asp Val Met Val Asp Arg His Lys Val Ala Leu Gly Lys
        355                 360                 365

Thr Leu Gly Glu Gly Glu Phe Gly Ala Val Met Glu Gly Gln Leu Asn
    370                 375                 380

Gln Asp Asp Ser Ile Leu Lys Val Ala Val Lys Thr Met Lys Ile Ala
385                 390                 395                 400

Ile Cys Thr Arg Ser Glu Leu Glu Asp Phe Leu Ser Glu Ala Val Cys
                405                 410                 415

Met Lys Glu Phe Asp His Pro Asn Val Met Arg Leu Ile Gly Val Cys
            420                 425                 430

Phe Gln Gly Ser Glu Arg Glu Ser Phe Pro Ala Pro Val Val Ile Leu
        435                 440                 445

Pro Phe Met Lys His Gly Asp Leu His Ser Phe Leu Leu Tyr Ser Arg
    450                 455                 460

Leu Gly Asp Gln Pro Val Tyr Leu Pro Thr Gln Met Leu Val Lys Phe
465                 470                 475                 480

Met Ala Asp Ile Ala Ser Gly Met Glu Tyr Leu Ser Thr Lys Arg Phe
                485                 490                 495

Ile His Arg Asp Leu Ala Ala Arg Asn Cys Met Leu Asn Glu Asn Met
            500                 505                 510

Ser Val Cys Val Ala Asp Phe Gly Leu Ser Lys Lys Ile Tyr Asn Gly
        515                 520                 525

Asp Tyr Tyr Arg Gln Gly Arg Ile Ala Lys Met Pro Val Lys Trp Ile
    530                 535                 540

Ala Ile Glu Ser Leu Ala Asp Arg Val Tyr Thr Ser Lys Ser Asp Val
545                 550                 555                 560

Trp Ser Phe Gly Val Thr Met Trp Glu Ile Ala Thr Arg Gly Gln Thr
                565                 570                 575

Pro Tyr Pro Gly Val Glu Asn Ser Glu Ile Tyr Asp Tyr Leu Arg Gln
            580                 585                 590

Gly Asn Arg Leu Lys Gln Pro Ala Asp Cys Leu Asp Gly Leu Tyr Ala
        595                 600                 605

Leu Met Ser Arg Cys Trp Glu Leu Asn Pro Gln Asp Arg Pro Ser Phe
    610                 615                 620

Thr Glu Leu Arg Glu Asp Leu Glu Asn Thr Leu Lys Ala Leu Pro Pro
625                 630                 635                 640

Ala Gln Glu Pro Asp Glu Ile Leu Tyr Val Asn Met Asp Glu Gly Gly
                645                 650                 655

Gly Tyr Pro Glu Pro Pro Gly Ala Ala Gly Gly Ala Asp Pro Pro Thr
            660                 665                 670

Gln Pro Asp Pro Lys Asp Ser Cys Ser Cys Leu Thr Ala Ala Glu Val
        675                 680                 685

His Pro Ala Gly Arg Tyr Val Leu Cys Pro Ser Thr Thr Pro Ser Pro
    690                 695                 700
```

```
Ala Gln Pro Ala Asp Arg Gly Ser Pro Ala Ala Pro Gly Gln Glu Asp
705                 710                 715                 720

Gly Ala Leu Trp Asn Lys Lys Arg Met Arg Gly Pro Gly Lys Asp Pro
            725                 730                 735

Thr Arg Lys Cys Pro Asp Pro Arg Ser Ala Ser Ser Pro Lys Gln His
            740                 745                 750

Pro Ser Glu Ser Val Tyr Thr Ala Leu Gln Arg Arg Glu Thr Glu Val
            755                 760                 765

Tyr Ala Cys Ile Glu Asn Glu Asp Gly Ser Ser Pro Thr Ala Lys Gln
            770                 775                 780

Ser Pro Leu Ser Gln Glu Arg Pro His Arg Phe Glu Asp Asp Gly Glu
785                 790                 795                 800

Leu Asn Leu Val Tyr Glu Asn Leu
                805

<210> SEQ ID NO 136
<211> LENGTH: 579
<212> TYPE: PRT
<213> ORGANISM: Artificial Sequence
<220> FEATURE:
<223> OTHER INFORMATION: CER102, amino acids 1-22 are signal peptide

<400> SEQUENCE: 136

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
            35                  40                  45

Arg Asn Ser Met Cys Trp Gly Lys Gly Ser Cys Pro Asn Ser Lys Cys
50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
            85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
            115                 120                 125

Leu Glu Leu Arg Arg Ala Thr Thr Thr Lys Lys Pro Thr Thr Thr Thr
130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
            165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
            195                 200                 205

Phe Thr Thr Glu Ser Glu Thr Leu Pro Ala Ser Asn His Ser Gln Arg
            210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
            245                 250                 255
```

```
Thr Thr Leu Thr Thr Ser Glu Ser Leu Gln Lys Thr Lys Ser His
            260                 265                 270

Gln Ile Asn Ser Arg Gln Thr Ile Leu Ile Ala Cys Cys Val Gly
            275                 280                 285

Phe Val Leu Met Val Leu Leu Phe Leu Ala Phe Leu His His Leu Phe
        290                 295                 300

Tyr Trp Asp Val Trp Phe Ile Tyr Asn Val Cys Leu Ala Lys Val Lys
305                 310                 315                 320

Gly Tyr Arg Ser Leu Ser Thr Ser Gln Thr Phe Tyr Asp Ala Tyr Ile
                325                 330                 335

Ser Tyr Asp Thr Lys Asp Ala Ser Val Thr Asp Trp Val Ile Asn Glu
            340                 345                 350

Leu Arg Tyr His Leu Glu Glu Ser Arg Asp Lys Asn Val Leu Leu Cys
            355                 360                 365

Leu Glu Glu Arg Asp Trp Asp Pro Gly Leu Ala Ile Ile Asp Asn Leu
            370                 375                 380

Met Gln Ser Ile Asn Gln Ser Lys Lys Thr Val Phe Val Leu Thr Lys
385                 390                 395                 400

Lys Tyr Ala Lys Ser Trp Asn Phe Lys Thr Ala Phe Tyr Leu Ala Leu
                405                 410                 415

Gln Arg Leu Met Asp Glu Asn Met Asp Val Ile Ile Phe Ile Leu Leu
            420                 425                 430

Glu Pro Val Leu Gln His Ser Gln Tyr Leu Arg Leu Arg Gln Arg Ile
            435                 440                 445

Cys Lys Ser Ser Ile Leu Gln Trp Pro Asp Asn Pro Lys Ala Glu Gly
450                 455                 460

Leu Phe Trp Gln Thr Leu Arg Asn Val Val Leu Thr Glu Asn Asp Ser
465                 470                 475                 480

Arg Tyr Asn Asn Met Tyr Val Asp Ser Ile Lys Gln Tyr Leu Trp Asn
                485                 490                 495

Lys Lys Arg Met Arg Gly Pro Gly Lys Asp Pro Thr Arg Lys Cys Pro
            500                 505                 510

Asp Pro Arg Ser Ala Ser Ser Pro Lys Gln His Pro Ser Glu Ser Val
            515                 520                 525

Tyr Thr Ala Leu Gln Arg Arg Glu Thr Glu Val Tyr Ala Cys Ile Glu
            530                 535                 540

Asn Glu Asp Gly Ser Ser Pro Thr Ala Lys Gln Ser Pro Leu Ser Gln
545                 550                 555                 560

Glu Arg Pro His Arg Phe Glu Asp Asp Gly Leu Asn Leu Val Tyr
                565                 570                 575

Glu Asn Leu

<210> SEQ ID NO 137
<211> LENGTH: 538
<212> TYPE: PRT
<213> ORGANISM: Artificial Sequence
<220> FEATURE:
<223> OTHER INFORMATION: CER103A, amino acids 1-22 are signal peptide

<400> SEQUENCE: 137

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
```

```
                35                  40                  45
Arg Asn Ser Met Cys Trp Gly Lys Gly Ser Cys Pro Asn Ser Lys Cys
 50                  55                  60
Asn Ala Glu Leu Leu Arg Thr Asp Gly Thr Arg Ile Ile Ser Arg Lys
 65                  70                  75                  80
Ser Thr Lys Tyr Thr Leu Leu Gly Lys Val Gln Phe Gly Glu Val Ser
                 85                  90                  95
Leu Thr Ile Ser Asn Thr Asn Arg Gly Asp Ser Gly Val Tyr Cys Cys
                100                 105                 110
Arg Ile Glu Val Pro Gly Trp Phe Asn Asp Val Lys Lys Asn Val Arg
                115                 120                 125
Leu Glu Leu Arg Arg Ala Thr Thr Lys Lys Pro Thr Thr Thr Thr Thr
                130                 135                 140
Arg Pro Thr Thr Thr Pro Tyr Val Thr Thr Thr Pro Glu Leu Leu
145                 150                 155                 160
Pro Thr Thr Val Met Thr Thr Ser Val Leu Pro Thr Thr Thr Pro Pro
                165                 170                 175
Gln Thr Leu Ala Thr Thr Ala Phe Ser Thr Ala Val Thr Thr Cys Pro
                180                 185                 190
Ser Thr Thr Pro Gly Ser Phe Ser Gln Glu Thr Thr Lys Gly Ser Ala
                195                 200                 205
Phe Thr Thr Glu Ser Gly Thr Leu Pro Ala Ser Asn His Ser Gln Arg
                210                 215                 220
Ser Met Met Thr Ile Ser Thr Asp Ile Ala Val Leu Arg Pro Thr Gly
225                 230                 235                 240
Ser Asn Pro Gly Ile Leu Pro Ser Thr Ser Gln Leu Thr Thr Gln Lys
                245                 250                 255
Thr Thr Leu Thr Thr Ser Glu Ser Leu Gln Lys Thr Thr Lys Ser His
                260                 265                 270
Gln Ile Asn Ser Arg Gln Thr Ile Leu Ile Ile Ala Cys Cys Val Gly
                275                 280                 285
Phe Val Leu Met Val Leu Leu Phe Leu Ala Phe Leu His His Leu Phe
                290                 295                 300
Tyr Trp Asp Val Trp Phe Ile Tyr Asn Val Cys Leu Ala Lys Val Lys
305                 310                 315                 320
Gly Tyr Arg Ser Leu Ser Thr Ser Gln Thr Phe Tyr Asp Ala Tyr Ile
                325                 330                 335
Ser Tyr Asp Thr Lys Asp Ala Ser Val Thr Asp Trp Val Ile Asn Glu
                340                 345                 350
Leu Arg Tyr His Leu Glu Glu Ser Arg Asp Lys Asn Val Leu Leu Cys
                355                 360                 365
Leu Glu Glu Arg Asp Trp Asp Pro Gly Leu Ala Ile Ile Asp Asn Leu
                370                 375                 380
Met Gln Ser Ile Asn Gln Ser Lys Lys Thr Val Phe Val Leu Thr Lys
385                 390                 395                 400
Lys Tyr Ala Lys Ser Trp Asn Phe Lys Thr Ala Phe Tyr Leu Ala Leu
                405                 410                 415
Gln Arg Leu Met Asp Glu Asn Met Asp Val Ile Ile Phe Ile Leu Leu
                420                 425                 430
Glu Pro Val Leu Gln His Ser Gln Tyr Leu Arg Leu Arg Gln Arg Ile
                435                 440                 445
Cys Lys Ser Ser Ile Leu Gln Trp Pro Asp Asn Pro Lys Ala Glu Gly
                450                 455                 460
```

```
Leu Phe Trp Gln Thr Leu Arg Asn Val Val Leu Thr Glu Asn Asp Ser
465                 470                 475                 480

Arg Tyr Asn Asn Met Tyr Val Asp Ser Ile Lys Gln Tyr Asp Ser Lys
            485                 490                 495

Ala Gly Met Glu Glu Asp His Thr Tyr Glu Gly Leu Asp Ile Asp Gln
        500                 505                 510

Thr Ala Thr Tyr Glu Asp Ile Val Thr Leu Arg Thr Gly Glu Val Lys
            515                 520                 525

Trp Ser Val Gly Glu His Pro Gly Gln Glu
        530                 535

<210> SEQ ID NO 138
<211> LENGTH: 522
<212> TYPE: PRT
<213> ORGANISM: Artificial Sequence
<220> FEATURE:
<223> OTHER INFORMATION: CER103B, amino acids 1-22 are signal peptide

<400> SEQUENCE: 138

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
        35                  40                  45

Arg Asn Ser Met Cys Trp Gly Lys Gly Ser Cys Pro Asn Ser Lys Cys
    50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Thr Lys Lys Pro Thr Thr Thr Thr
    130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Cys Pro
            180                 185                 190

Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
    210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ile Ala Cys Cys Val Gly
        275                 280                 285
```

```
Phe Val Leu Met Val Leu Leu Phe Leu Ala Phe Leu His Leu Phe
    290                 295                 300

Tyr Trp Asp Val Trp Phe Ile Tyr Asn Val Cys Leu Ala Lys Val Lys
305                 310                 315                 320

Gly Tyr Arg Ser Leu Ser Thr Ser Gln Thr Phe Tyr Asp Ala Tyr Ile
                325                 330                 335

Ser Tyr Asp Thr Lys Asp Ala Ser Val Thr Asp Trp Val Ile Asn Glu
            340                 345                 350

Leu Arg Tyr His Leu Glu Glu Ser Arg Asp Lys Asn Val Leu Leu Cys
        355                 360                 365

Leu Glu Glu Arg Asp Trp Asp Pro Gly Leu Ala Ile Ile Asp Asn Leu
    370                 375                 380

Met Gln Ser Ile Asn Gln Ser Lys Lys Thr Val Phe Val Leu Thr Lys
385                 390                 395                 400

Lys Tyr Ala Lys Ser Trp Asn Phe Lys Thr Ala Phe Tyr Leu Ala Leu
                405                 410                 415

Gln Arg Leu Met Asp Glu Asn Met Asp Val Ile Ile Phe Ile Leu Leu
            420                 425                 430

Glu Pro Val Leu Gln His Ser Gln Tyr Leu Arg Leu Arg Gln Arg Ile
        435                 440                 445

Cys Lys Ser Ser Ile Leu Gln Trp Pro Asp Asn Pro Lys Ala Glu Gly
    450                 455                 460

Leu Phe Trp Gln Thr Leu Arg Asn Val Val Leu Thr Glu Asn Asp Ser
465                 470                 475                 480

Arg Tyr Asn Asn Met Tyr Val Asp Ser Ile Lys Gln Tyr Asp Ser Lys
                485                 490                 495

Ala Gly Met Glu Glu Asp His Thr Tyr Glu Gly Leu Asp Ile Asp Gln
            500                 505                 510

Thr Ala Thr Tyr Glu Asp Ile Val Thr Leu
        515                 520

<210> SEQ ID NO 139
<211> LENGTH: 545
<212> TYPE: PRT
<213> ORGANISM: Artificial Sequence
<220> FEATURE:
<223> OTHER INFORMATION: CER104, amino acids 1-22 are signal peptide

<400> SEQUENCE: 139

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
        35                  40                  45

Arg Asn Ser Met Cys Trp Gly Lys Gly Ser Cys Pro Asn Ser Lys Cys
    50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125
```

Leu Glu Leu Arg Arg Ala Thr Thr Lys Lys Pro Thr Thr Thr
130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
                180                 185                 190

Ser Thr Thr Pro Gly Ser Phe Ser Gln Glu Thr Thr Lys Gly Ser Ala
            195                 200                 205

Phe Thr Thr Glu Ser Glu Thr Leu Pro Ala Ser Asn His Ser Gln Arg
            210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ile Ala Cys Cys Val Gly
            275                 280                 285

Phe Val Leu Met Val Leu Leu Phe Leu Ala Phe Leu His His Leu Phe
290                 295                 300

Tyr Trp Asp Val Trp Phe Ile Tyr Asn Val Cys Leu Ala Lys Val Lys
305                 310                 315                 320

Gly Tyr Arg Ser Leu Ser Thr Ser Gln Thr Phe Tyr Asp Ala Tyr Ile
                325                 330                 335

Ser Tyr Asp Thr Lys Asp Ala Ser Val Thr Asp Trp Val Ile Asn Glu
            340                 345                 350

Leu Arg Tyr His Leu Glu Glu Ser Arg Asp Lys Asn Val Leu Leu Cys
            355                 360                 365

Leu Glu Glu Arg Asp Trp Asp Pro Gly Leu Ala Ile Ile Asp Asn Leu
370                 375                 380

Met Gln Ser Ile Asn Gln Ser Lys Lys Thr Val Phe Val Leu Thr Lys
385                 390                 395                 400

Lys Tyr Ala Lys Ser Trp Asn Phe Lys Thr Ala Phe Tyr Leu Ala Leu
                405                 410                 415

Gln Arg Leu Met Asp Glu Asn Met Asp Val Ile Ile Phe Ile Leu Leu
            420                 425                 430

Glu Pro Val Leu Gln His Ser Gln Tyr Leu Arg Leu Arg Gln Arg Ile
            435                 440                 445

Cys Lys Ser Ser Ile Leu Gln Trp Pro Asp Asn Pro Lys Ala Glu Gly
450                 455                 460

Leu Phe Trp Gln Thr Leu Arg Asn Val Val Leu Thr Glu Asn Asp Ser
465                 470                 475                 480

Arg Tyr Asn Asn Met Tyr Val Asp Ser Ile Lys Gln Tyr Tyr Phe Leu
                485                 490                 495

Gly Arg Leu Val Pro Arg Gly Arg Gly Ala Ala Glu Ala Ala Thr Arg
            500                 505                 510

Lys Gln Arg Ile Thr Glu Thr Glu Ser Pro Tyr Gln Glu Leu Gln Gly
            515                 520                 525

Gln Arg Ser Asp Val Tyr Ser Asp Leu Asn Thr Gln Arg Pro Tyr Tyr
530                 535                 540

Lys
545

<210> SEQ ID NO 140
<211> LENGTH: 578
<212> TYPE: PRT
<213> ORGANISM: Artificial Sequence
<220> FEATURE:
<223> OTHER INFORMATION: CER105, amino acids 1-22 are signal peptide

<400> SEQUENCE: 140

```
Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
            35                  40                  45

Arg Asn Ser Met Cys Trp Gly Lys Gly Ser Cys Pro Asn Ser Lys Cys
50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Thr Lys Lys Pro Thr Thr Thr Thr
130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ala Cys Cys Val Gly
        275                 280                 285

Phe Val Leu Met Val Leu Leu Phe Leu Ala Phe Leu His His Leu Phe
290                 295                 300

Tyr Trp Asp Val Trp Phe Ile Tyr Asn Val Cys Leu Ala Lys Val Lys
305                 310                 315                 320

Gly Tyr Arg Ser Leu Ser Thr Ser Gln Thr Phe Tyr Asp Ala Tyr Ile
                325                 330                 335

Ser Tyr Asp Thr Lys Asp Ala Ser Val Thr Asp Trp Val Ile Asn Glu
            340                 345                 350
```

Leu Arg Tyr His Leu Glu Glu Ser Arg Asp Lys Asn Val Leu Leu Cys
            355                 360                 365

Leu Glu Glu Arg Asp Trp Asp Pro Gly Leu Ala Ile Ile Asp Asn Leu
    370                 375                 380

Met Gln Ser Ile Asn Gln Ser Lys Lys Thr Val Phe Val Leu Thr Lys
385                 390                 395                 400

Lys Tyr Ala Lys Ser Trp Asn Phe Lys Thr Ala Phe Tyr Leu Ala Leu
                405                 410                 415

Gln Arg Leu Met Asp Glu Asn Met Asp Val Ile Ile Phe Ile Leu Leu
            420                 425                 430

Glu Pro Val Leu Gln His Ser Gln Tyr Leu Arg Leu Arg Gln Arg Ile
            435                 440                 445

Cys Lys Ser Ser Ile Leu Gln Trp Pro Asp Asn Pro Lys Ala Glu Gly
        450                 455                 460

Leu Phe Trp Gln Thr Leu Arg Asn Val Val Leu Thr Glu Asn Asp Ser
465                 470                 475                 480

Arg Tyr Asn Asn Met Tyr Val Asp Ser Ile Lys Gln Tyr Ser Trp Arg
                485                 490                 495

Arg Arg Gln Arg Arg Leu Arg Gly Ala Ser Ser Ala Glu Ala Pro Asp
            500                 505                 510

Gly Asp Lys Asp Ala Pro Glu Pro Leu Asp Lys Val Ile Ile Leu Ser
        515                 520                 525

Pro Gly Ile Ser Asp Ala Thr Ala Pro Ala Trp Pro Pro Gly Glu
        530                 535                 540

Asp Pro Gly Thr Thr Pro Pro Gly His Ser Val Pro Val Pro Ala Thr
545                 550                 555                 560

Glu Leu Gly Ser Thr Glu Leu Val Thr Thr Lys Thr Ala Gly Pro Glu
                565                 570                 575

Gln Gln

<210> SEQ ID NO 141
<211> LENGTH: 579
<212> TYPE: PRT
<213> ORGANISM: Artificial Sequence
<220> FEATURE:
<223> OTHER INFORMATION: CER106, amino acids 1-22 are signal peptide

<400> SEQUENCE: 141

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
        35                  40                  45

Arg Asn Ser Met Cys Trp Gly Lys Gly Ser Cys Pro Asn Ser Lys Cys
    50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Thr Lys Lys Pro Thr Thr Thr Thr

```
                130                 135                 140
Arg Pro Thr Thr Thr Pro Tyr Val Thr Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
                180                 185                 190

Ser Thr Thr Pro Gly Ser Phe Ser Gln Glu Thr Thr Lys Gly Ser Ala
                195                 200                 205

Phe Thr Thr Glu Ser Glu Thr Leu Pro Ala Ser Asn His Ser Gln Arg
                210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
                260                 265                 270

Gln Ile Asn Ser Arg Gln Thr Ile Leu Ile Ile Ala Cys Cys Val Gly
                275                 280                 285

Phe Val Leu Met Val Leu Leu Phe Leu Ala Phe Leu Leu Trp Asn Lys
                290                 295                 300

Lys Arg Met Arg Gly Pro Gly Lys Asp Pro Thr Arg Lys Cys Pro Asp
305                 310                 315                 320

Pro Arg Ser Ala Ser Ser Pro Lys Gln His Pro Ser Glu Ser Val Tyr
                325                 330                 335

Thr Ala Leu Gln Arg Arg Glu Thr Glu Val Tyr Ala Cys Ile Glu Asn
                340                 345                 350

Glu Asp Gly Ser Ser Pro Thr Ala Lys Gln Ser Pro Leu Ser Gln Glu
                355                 360                 365

Arg Pro His Arg Phe Glu Asp Asp Gly Glu Leu Asn Leu Val Tyr Glu
                370                 375                 380

Asn Leu His His Leu Phe Tyr Trp Asp Val Trp Phe Ile Tyr Asn Val
385                 390                 395                 400

Cys Leu Ala Lys Val Lys Gly Tyr Arg Ser Leu Ser Thr Ser Gln Thr
                405                 410                 415

Phe Tyr Asp Ala Tyr Ile Ser Tyr Asp Thr Lys Asp Ala Ser Val Thr
                420                 425                 430

Asp Trp Val Ile Asn Glu Leu Arg Tyr His Leu Glu Glu Ser Arg Asp
                435                 440                 445

Lys Asn Val Leu Leu Cys Leu Glu Glu Arg Asp Trp Asp Pro Gly Leu
450                 455                 460

Ala Ile Ile Asp Asn Leu Met Gln Ser Ile Asn Gln Ser Lys Lys Thr
465                 470                 475                 480

Val Phe Val Leu Thr Lys Lys Tyr Ala Lys Ser Trp Asn Phe Lys Thr
                485                 490                 495

Ala Phe Tyr Leu Ala Leu Gln Arg Leu Met Asp Glu Asn Met Asp Val
                500                 505                 510

Ile Ile Phe Ile Leu Leu Glu Pro Val Leu Gln His Ser Gln Tyr Leu
                515                 520                 525

Arg Leu Arg Gln Arg Ile Cys Lys Ser Ser Ile Leu Gln Trp Pro Asp
                530                 535                 540

Asn Pro Lys Ala Glu Gly Leu Phe Trp Gln Thr Leu Arg Asn Val Val
545                 550                 555                 560
```

-continued

```
Leu Thr Glu Asn Asp Ser Arg Tyr Asn Asn Met Tyr Val Asp Ser Ile
                565                 570                 575
Lys Gln Tyr

<210> SEQ ID NO 142
<211> LENGTH: 522
<212> TYPE: PRT
<213> ORGANISM: Artificial Sequence
<220> FEATURE:
<223> OTHER INFORMATION: CER107, amino acids 1-22 are signal peptide

<400> SEQUENCE: 142

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
                20                  25                  30

Gly Gln Pro Val Thr Leu Pro Cys His Tyr Leu Ser Trp Ser Gln Ser
                35                  40                  45

Arg Asn Ser Met Cys Trp Gly Lys Gly Ser Cys Pro Asn Ser Lys Cys
        50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
                100                 105                 110

Arg Ile Glu Val Pro Gly Trp Phe Asn Asp Val Lys Lys Asn Val Arg
                115                 120                 125

Leu Glu Leu Arg Arg Ala Thr Thr Thr Lys Lys Pro Thr Thr Thr Thr
        130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Pro Pro
                165                 170                 175

Gln Thr Leu Ala Thr Thr Ala Phe Ser Thr Ala Val Thr Cys Pro
                180                 185                 190

Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
                260                 265                 270

Gln Ile Asn Ser Arg Gln Thr Ile Leu Ile Ile Ala Cys Cys Val Gly
        275                 280                 285

Phe Val Leu Met Val Leu Leu Phe Leu Ala Phe Leu Asp Ser Lys Ala
290                 295                 300

Gly Met Glu Glu Asp His Thr Tyr Glu Gly Leu Asp Ile Asp Gln Thr
305                 310                 315                 320

Ala Thr Tyr Glu Asp Ile Val Thr Leu His His Leu Phe Tyr Trp Asp
                325                 330                 335
```

```
Val Trp Phe Ile Tyr Asn Val Cys Leu Ala Lys Val Lys Gly Tyr Arg
            340                 345                 350

Ser Leu Ser Thr Ser Gln Thr Phe Tyr Asp Ala Tyr Ile Ser Tyr Asp
            355                 360                 365

Thr Lys Asp Ala Ser Val Thr Asp Trp Val Ile Asn Glu Leu Arg Tyr
370                 375                 380

His Leu Glu Glu Ser Arg Asp Lys Asn Val Leu Leu Cys Leu Glu Glu
385                 390                 395                 400

Arg Asp Trp Asp Pro Gly Leu Ala Ile Ile Asp Asn Leu Met Gln Ser
                405                 410                 415

Ile Asn Gln Ser Lys Lys Thr Val Phe Val Leu Thr Lys Lys Tyr Ala
            420                 425                 430

Lys Ser Trp Asn Phe Lys Thr Ala Phe Tyr Leu Ala Leu Gln Arg Leu
            435                 440                 445

Met Asp Glu Asn Met Asp Val Ile Ile Phe Ile Leu Leu Glu Pro Val
            450                 455                 460

Leu Gln His Ser Gln Tyr Leu Arg Leu Arg Arg Ile Cys Lys Ser
465                 470                 475                 480

Ser Ile Leu Gln Trp Pro Asp Asn Pro Lys Ala Glu Gly Leu Phe Trp
            485                 490                 495

Gln Thr Leu Arg Asn Val Val Leu Thr Glu Asn Asp Ser Arg Tyr Asn
            500                 505                 510

Asn Met Tyr Val Asp Ser Ile Lys Gln Tyr
            515                 520

<210> SEQ ID NO 143
<211> LENGTH: 545
<212> TYPE: PRT
<213> ORGANISM: Artificial Sequence
<220> FEATURE:
<223> OTHER INFORMATION: CER108, amino acids 1-22 are signal peptide

<400> SEQUENCE: 143

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
            35                  40                  45

Arg Asn Ser Met Cys Trp Gly Lys Gly Ser Cys Pro Asn Ser Lys Cys
        50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Thr Lys Lys Pro Thr Thr Thr Thr
130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Pro Pro
                165                 170                 175
```

```
Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
    210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ala Cys Cys Val Gly
            275                 280                 285

Phe Val Leu Met Val Leu Leu Phe Leu Ala Phe Leu Tyr Phe Leu Gly
    290                 295                 300

Arg Leu Val Pro Arg Gly Arg Gly Ala Ala Glu Ala Ala Thr Arg Lys
305                 310                 315                 320

Gln Arg Ile Thr Glu Thr Glu Ser Pro Tyr Gln Glu Leu Gln Gly Gln
                325                 330                 335

Arg Ser Asp Val Tyr Ser Asp Leu Asn Thr Gln Arg Pro Tyr Tyr Lys
                340                 345                 350

His His Leu Phe Tyr Trp Asp Val Trp Phe Ile Tyr Asn Val Cys Leu
            355                 360                 365

Ala Lys Val Lys Gly Tyr Arg Ser Leu Ser Thr Ser Gln Thr Phe Tyr
    370                 375                 380

Asp Ala Tyr Ile Ser Tyr Asp Thr Lys Asp Ala Ser Val Thr Asp Trp
385                 390                 395                 400

Val Ile Asn Glu Leu Arg Tyr His Leu Glu Glu Ser Arg Asp Lys Asn
                405                 410                 415

Val Leu Leu Cys Leu Glu Glu Arg Asp Trp Asp Pro Gly Leu Ala Ile
            420                 425                 430

Ile Asp Asn Leu Met Gln Ser Ile Asn Gln Ser Lys Lys Thr Val Phe
            435                 440                 445

Val Leu Thr Lys Lys Tyr Ala Lys Ser Trp Asn Phe Lys Thr Ala Phe
450                 455                 460

Tyr Leu Ala Leu Gln Arg Leu Met Asp Glu Asn Met Asp Val Ile Ile
465                 470                 475                 480

Phe Ile Leu Leu Glu Pro Val Leu Gln His Ser Gln Tyr Leu Arg Leu
                485                 490                 495

Arg Gln Arg Ile Cys Lys Ser Ser Ile Leu Gln Trp Pro Asp Asn Pro
            500                 505                 510

Lys Ala Glu Gly Leu Phe Trp Gln Thr Leu Arg Asn Val Val Leu Thr
        515                 520                 525

Glu Asn Asp Ser Arg Tyr Asn Asn Met Tyr Val Asp Ser Ile Lys Gln
    530                 535                 540

Tyr
545

<210> SEQ ID NO 144
<211> LENGTH: 578
<212> TYPE: PRT
<213> ORGANISM: Artificial Sequence
<220> FEATURE:
<223> OTHER INFORMATION: CER109, amino acids 1-22 are signal peptide
```

<400> SEQUENCE: 144

```
Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
        35                  40                  45

Arg Asn Ser Met Cys Trp Gly Lys Gly Ser Cys Pro Asn Ser Lys Cys
    50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Thr Lys Lys Pro Thr Thr Thr Thr
    130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
    210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ala Cys Cys Val Gly
        275                 280                 285

Phe Val Leu Met Val Leu Leu Phe Leu Ala Phe Leu Ser Trp Arg Arg
    290                 295                 300

Arg Gln Arg Arg Leu Arg Gly Ala Ser Ser Ala Glu Ala Pro Asp Gly
305                 310                 315                 320

Asp Lys Asp Ala Pro Glu Pro Leu Asp Lys Val Ile Ile Leu Ser Pro
                325                 330                 335

Gly Ile Ser Asp Ala Thr Ala Pro Ala Trp Pro Pro Gly Glu Asp
            340                 345                 350

Pro Gly Thr Thr Pro Pro Gly His Ser Val Pro Val Pro Ala Thr Glu
        355                 360                 365

Leu Gly Ser Thr Glu Leu Val Thr Thr Lys Thr Ala Gly Pro Glu Gln
    370                 375                 380

Gln His His Leu Phe Tyr Trp Asp Val Trp Phe Ile Tyr Asn Val Cys
385                 390                 395                 400

Leu Ala Lys Val Lys Gly Tyr Arg Ser Leu Ser Thr Ser Gln Thr Phe
```

```
            405                 410                 415
Tyr Asp Ala Tyr Ile Ser Tyr Asp Thr Lys Asp Ala Ser Val Thr Asp
        420                 425                 430

Trp Val Ile Asn Glu Leu Arg Tyr His Leu Glu Glu Ser Arg Asp Lys
        435                 440                 445

Asn Val Leu Leu Cys Leu Glu Arg Asp Trp Asp Pro Gly Leu Ala
        450                 455                 460

Ile Ile Asp Asn Leu Met Gln Ser Ile Asn Gln Ser Lys Lys Thr Val
465                 470                 475                 480

Phe Val Leu Thr Lys Lys Tyr Ala Lys Ser Trp Asn Phe Lys Thr Ala
                485                 490                 495

Phe Tyr Leu Ala Leu Gln Arg Leu Met Asp Glu Asn Met Asp Val Ile
                500                 505                 510

Ile Phe Ile Leu Leu Glu Pro Val Leu Gln His Ser Gln Tyr Leu Arg
                515                 520                 525

Leu Arg Gln Arg Ile Cys Lys Ser Ser Ile Leu Gln Trp Pro Asp Asn
530                 535                 540

Pro Lys Ala Glu Gly Leu Phe Trp Gln Thr Leu Arg Asn Val Val Leu
545                 550                 555                 560

Thr Glu Asn Asp Ser Arg Tyr Asn Asn Met Tyr Val Asp Ser Ile Lys
                565                 570                 575

Gln Tyr

<210> SEQ ID NO 145
<211> LENGTH: 626
<212> TYPE: PRT
<213> ORGANISM: Artificial Sequence
<220> FEATURE:
<223> OTHER INFORMATION: CER110, amino acids 1-22 are signal peptide

<400> SEQUENCE: 145

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
                20                  25                  30

Gly Gln Pro Val Thr Leu Pro Cys His Tyr Leu Ser Trp Ser Gln Ser
                35                  40                  45

Arg Asn Ser Met Cys Trp Gly Lys Gly Ser Cys Pro Asn Ser Lys Cys
            50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
                100                 105                 110

Arg Ile Glu Val Pro Gly Trp Phe Asn Asp Val Lys Lys Asn Val Arg
                115                 120                 125

Leu Glu Leu Arg Arg Ala Thr Thr Lys Lys Pro Thr Thr Thr Thr
            130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Pro Pro
                165                 170                 175

Gln Thr Leu Ala Thr Thr Ala Phe Ser Thr Ala Val Thr Thr Cys Pro
                180                 185                 190
```

```
Ser Thr Thr Pro Gly Ser Phe Ser Gln Glu Thr Thr Lys Gly Ser Ala
            195                 200                 205

Phe Thr Thr Glu Ser Glu Thr Leu Pro Ala Ser Asn His Ser Gln Arg
    210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ala Cys Cys Val Gly
            275                 280                 285

Phe Val Leu Met Val Leu Leu Phe Leu Ala Phe Leu Met Ser Leu Leu
    290                 295                 300

Asn Cys Glu Asn Ser Cys Gly Ser Ser Gln Ser Glu Ser Asp Cys Cys
305                 310                 315                 320

Val Ala Met Ala Ser Ser Cys Ser Ala Val Thr Lys Asp Asp Ser Val
                325                 330                 335

Gly Gly Thr Ala Ser Thr Gly Asn Leu Ser Ser Ser Phe Met Glu Glu
            340                 345                 350

Ile Gln Gly Tyr Asp Val Glu Phe Asp Pro Pro Leu Glu Ser Lys Tyr
            355                 360                 365

Glu Cys Pro Ile Cys Leu Met Ala Leu Arg Glu Ala Val Gln Thr Pro
    370                 375                 380

Cys Gly His Arg Phe Cys Lys Ala Cys Ile Ile Lys Ser Ile Arg Asp
385                 390                 395                 400

Ala Gly His Lys Cys Pro Val Asp Asn Glu Ile Leu Leu Glu Asn Gln
                405                 410                 415

Leu Phe Pro Asp Asn Phe Ala Lys Arg Glu Ile Leu Ser Leu Met Val
            420                 425                 430

Lys Cys Pro Asn Glu Gly Cys Leu His Lys Met Glu Leu Arg His Leu
    435                 440                 445

Glu Asp His Gln Ala His Cys Glu Phe Ala Leu Met Asp Cys Pro Gln
    450                 455                 460

Cys Gln Arg Pro Phe Gln Lys Phe His Ile Asn Ile His Ile Leu Lys
465                 470                 475                 480

Asp Cys Pro Arg Arg Gln Val Ser Cys Asp Asn Cys Ala Ala Ser Met
                485                 490                 495

Ala Phe Glu Asp Lys Glu Ile His Asp Gln Asn Cys Pro Leu Ala Asn
            500                 505                 510

Val Ile Cys Glu Tyr Cys Asn Thr Ile Leu Ile Arg Glu Gln Met Pro
    515                 520                 525

Asn His Tyr Asp Leu Asp Cys Pro Thr Ala Pro Ile Pro Cys Thr Phe
    530                 535                 540

Ser Thr Phe Gly Cys His Glu Lys Met Gln Arg Asn His Leu Ala Arg
545                 550                 555                 560

His Leu Gln Glu Asn Thr Gln Ser His Met Arg Met Leu Ala Tyr Phe
                565                 570                 575

Leu Gly Arg Leu Val Pro Arg Gly Arg Gly Ala Ala Glu Ala Ala Thr
            580                 585                 590

Arg Lys Gln Arg Ile Thr Glu Thr Glu Ser Pro Tyr Gln Glu Leu Gln
    595                 600                 605
```

Gly Gln Arg Ser Asp Val Tyr Ser Asp Leu Asn Thr Gln Arg Pro Tyr
610                 615                 620

Tyr Lys
625

<210> SEQ ID NO 146
<211> LENGTH: 619
<212> TYPE: PRT
<213> ORGANISM: Artificial Sequence
<220> FEATURE:
<223> OTHER INFORMATION: CER111A, amino acids 1-22 are signal peptide

<400> SEQUENCE: 146

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
                20                  25                  30

Gly Gln Pro Val Thr Leu Pro Cys His Tyr Leu Ser Trp Ser Gln Ser
                35                  40                  45

Arg Asn Ser Met Cys Trp Gly Lys Gly Ser Cys Pro Asn Ser Lys Cys
        50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
                100                 105                 110

Arg Ile Glu Val Pro Gly Trp Phe Asn Asp Val Lys Lys Asn Val Arg
                115                 120                 125

Leu Glu Leu Arg Arg Ala Thr Thr Thr Lys Lys Pro Thr Thr Thr Thr
130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Pro Pro
                165                 170                 175

Gln Thr Leu Ala Thr Thr Ala Phe Ser Thr Ala Val Thr Thr Cys Pro
                180                 185                 190

Ser Thr Thr Pro Gly Ser Phe Ser Gln Glu Thr Thr Lys Gly Ser Ala
                195                 200                 205

Phe Thr Thr Glu Ser Glu Thr Leu Pro Ala Ser Asn His Ser Gln Arg
        210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
                260                 265                 270

Gln Ile Asn Ser Arg Gln Thr Ile Leu Ile Ala Cys Cys Val Gly
        275                 280                 285

Phe Val Leu Met Val Leu Leu Phe Leu Ala Phe Leu Met Ser Leu Leu
                290                 295                 300

Asn Cys Glu Asn Ser Cys Gly Ser Ser Gln Ser Glu Ser Asp Cys Cys
305                 310                 315                 320

Val Ala Met Ala Ser Ser Cys Ser Ala Val Thr Lys Asp Asp Ser Val
                325                 330                 335

```
Gly Gly Thr Ala Ser Thr Gly Asn Leu Ser Ser Ser Phe Met Glu Glu
                340                 345                 350

Ile Gln Gly Tyr Asp Val Glu Phe Asp Pro Pro Leu Glu Ser Lys Tyr
                355                 360                 365

Glu Cys Pro Ile Cys Leu Met Ala Leu Arg Glu Ala Val Gln Thr Pro
                370                 375                 380

Cys Gly His Arg Phe Cys Lys Ala Cys Ile Ile Lys Ser Ile Arg Asp
385                 390                 395                 400

Ala Gly His Lys Cys Pro Val Asp Asn Glu Ile Leu Leu Glu Asn Gln
                405                 410                 415

Leu Phe Pro Asp Asn Phe Ala Lys Arg Glu Ile Leu Ser Leu Met Val
                420                 425                 430

Lys Cys Pro Asn Glu Gly Cys Leu His Lys Met Glu Leu Arg His Leu
                435                 440                 445

Glu Asp His Gln Ala His Cys Glu Phe Ala Leu Met Asp Cys Pro Gln
                450                 455                 460

Cys Gln Arg Pro Phe Gln Lys Phe His Ile Asn Ile His Ile Leu Lys
465                 470                 475                 480

Asp Cys Pro Arg Arg Gln Val Ser Cys Asp Asn Cys Ala Ala Ser Met
                485                 490                 495

Ala Phe Glu Asp Lys Glu Ile His Asp Gln Asn Cys Pro Leu Ala Asn
                500                 505                 510

Val Ile Cys Glu Tyr Cys Asn Thr Ile Leu Ile Arg Glu Gln Met Pro
                515                 520                 525

Asn His Tyr Asp Leu Asp Cys Pro Thr Ala Pro Ile Pro Cys Thr Phe
                530                 535                 540

Ser Thr Phe Gly Cys His Glu Lys Met Gln Arg Asn His Leu Ala Arg
545                 550                 555                 560

His Leu Gln Glu Asn Thr Gln Ser His Met Arg Met Leu Ala Asp Ser
                565                 570                 575

Lys Ala Gly Met Glu Glu Asp His Thr Tyr Glu Gly Leu Asp Ile Asp
                580                 585                 590

Gln Thr Ala Thr Tyr Glu Asp Ile Val Thr Leu Arg Thr Gly Glu Val
                595                 600                 605

Lys Trp Ser Val Gly Glu His Pro Gly Gln Glu
610                 615

<210> SEQ ID NO 147
<211> LENGTH: 603
<212> TYPE: PRT
<213> ORGANISM: Artificial Sequence
<220> FEATURE:
<223> OTHER INFORMATION: CER111B, amino acids 1-22 are signal peptide

<400> SEQUENCE: 147

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
                20                  25                  30

Gly Gln Pro Val Thr Leu Pro Cys His Tyr Leu Ser Trp Ser Gln Ser
                35                  40                  45

Arg Asn Ser Met Cys Trp Gly Lys Gly Ser Cys Pro Asn Ser Lys Cys
                50                  55                  60

Asn Ala Glu Leu Leu Arg Thr Asp Gly Thr Arg Ile Ile Ser Arg Lys
65                  70                  75                  80
```

-continued

Ser Thr Lys Tyr Thr Leu Leu Gly Lys Val Gln Phe Gly Glu Val Ser
            85                  90                  95

Leu Thr Ile Ser Asn Thr Asn Arg Gly Asp Ser Gly Val Tyr Cys Cys
        100                 105                 110

Arg Ile Glu Val Pro Gly Trp Phe Asn Asp Val Lys Lys Asn Val Arg
        115                 120                 125

Leu Glu Leu Arg Arg Ala Thr Thr Lys Lys Pro Thr Thr Thr Thr Thr
130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
    210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ile Ala Cys Cys Val Gly
        275                 280                 285

Phe Val Leu Met Val Leu Leu Phe Leu Ala Phe Leu Met Ser Leu Leu
    290                 295                 300

Asn Cys Glu Asn Ser Cys Gly Ser Ser Gln Ser Glu Ser Asp Cys Cys
305                 310                 315                 320

Val Ala Met Ala Ser Ser Cys Ser Ala Val Thr Lys Asp Asp Ser Val
                325                 330                 335

Gly Gly Thr Ala Ser Thr Gly Asn Leu Ser Ser Ser Phe Met Glu Glu
            340                 345                 350

Ile Gln Gly Tyr Asp Val Glu Phe Asp Pro Pro Leu Glu Ser Lys Tyr
        355                 360                 365

Glu Cys Pro Ile Cys Leu Met Ala Leu Arg Glu Ala Val Gln Thr Pro
    370                 375                 380

Cys Gly His Arg Phe Cys Lys Ala Cys Ile Ile Lys Ser Ile Arg Asp
385                 390                 395                 400

Ala Gly His Lys Cys Pro Val Asp Asn Glu Ile Leu Leu Glu Asn Gln
                405                 410                 415

Leu Phe Pro Asp Asn Phe Ala Lys Arg Glu Ile Leu Ser Leu Met Val
            420                 425                 430

Lys Cys Pro Asn Glu Gly Cys Leu His Lys Met Glu Leu Arg His Leu
        435                 440                 445

Glu Asp His Gln Ala His Cys Glu Phe Ala Leu Met Asp Cys Pro Gln
    450                 455                 460

Cys Gln Arg Pro Phe Gln Lys Phe His Ile Asn Ile His Ile Leu Lys
465                 470                 475                 480

Asp Cys Pro Arg Arg Gln Val Ser Cys Asp Asn Cys Ala Ala Ser Met
                485                 490                 495

Ala Phe Glu Asp Lys Glu Ile His Asp Gln Asn Cys Pro Leu Ala Asn

```
                500              505              510
Val Ile Cys Glu Tyr Cys Asn Thr Ile Leu Ile Arg Glu Gln Met Pro
            515              520              525

Asn His Tyr Asp Leu Asp Cys Pro Thr Ala Pro Ile Pro Cys Thr Phe
            530              535              540

Ser Thr Phe Gly Cys His Glu Lys Met Gln Arg Asn His Leu Ala Arg
545              550              555              560

His Leu Gln Glu Asn Thr Gln Ser His Met Arg Met Leu Ala Asp Ser
                565              570              575

Lys Ala Gly Met Glu Glu Asp His Thr Tyr Glu Gly Leu Asp Ile Asp
            580              585              590

Gln Thr Ala Thr Tyr Glu Asp Ile Val Thr Leu
            595              600
```

<210> SEQ ID NO 148
<211> LENGTH: 660
<212> TYPE: PRT
<213> ORGANISM: Artificial Sequence
<220> FEATURE:
<223> OTHER INFORMATION: CER112, amino acids 1-22 are signal peptide

<400> SEQUENCE: 148

```
Met Ser Lys Gly Leu Leu Leu Trp Leu Val Thr Glu Leu Trp Trp
1               5               10              15

Leu Tyr Leu Thr Pro Ala Ala Ser Glu Asp Thr Ile Gly Phe Leu
            20              25              30

Gly Gln Pro Val Thr Leu Pro Cys His Tyr Leu Ser Trp Ser Gln Ser
            35              40              45

Arg Asn Ser Met Cys Trp Gly Lys Gly Ser Cys Pro Asn Ser Lys Cys
50              55              60

Asn Ala Glu Leu Leu Arg Thr Asp Gly Thr Arg Ile Ile Ser Arg Lys
65              70              75              80

Ser Thr Lys Tyr Thr Leu Leu Gly Lys Val Gln Phe Gly Glu Val Ser
                85              90              95

Leu Thr Ile Ser Asn Thr Asn Arg Gly Asp Ser Gly Val Tyr Cys Cys
            100             105             110

Arg Ile Glu Val Pro Gly Trp Phe Asn Asp Val Lys Lys Asn Val Arg
            115             120             125

Leu Glu Leu Arg Arg Ala Thr Thr Lys Lys Pro Thr Thr Thr Thr
            130             135             140

Arg Pro Thr Thr Thr Pro Tyr Val Thr Thr Thr Pro Glu Leu Leu
145             150             155             160

Pro Thr Thr Val Met Thr Thr Ser Val Leu Pro Thr Thr Thr Pro Pro
                165             170             175

Gln Thr Leu Ala Thr Ala Phe Ser Thr Ala Val Thr Thr Cys Pro
            180             185             190

Ser Thr Thr Pro Gly Ser Phe Ser Gln Glu Thr Thr Lys Gly Ser Ala
            195             200             205

Phe Thr Thr Glu Ser Glu Thr Leu Pro Ala Ser Asn His Ser Gln Arg
210             215             220

Ser Met Met Thr Ile Ser Thr Asp Ile Ala Val Leu Arg Pro Thr Gly
225             230             235             240

Ser Asn Pro Gly Ile Leu Pro Ser Thr Ser Gln Leu Thr Thr Gln Lys
                245             250             255

Thr Thr Leu Thr Thr Ser Glu Ser Leu Gln Lys Thr Thr Lys Ser His
```

```
              260                 265                 270
Gln Ile Asn Ser Arg Gln Thr Ile Leu Ile Ala Cys Cys Val Gly
            275                 280                 285

Phe Val Leu Met Val Leu Leu Phe Leu Ala Phe Leu Met Ser Leu Leu
            290                 295                 300

Asn Cys Glu Asn Ser Cys Gly Ser Ser Gln Ser Glu Ser Asp Cys Cys
305                 310                 315                 320

Val Ala Met Ala Ser Ser Cys Ser Ala Val Thr Lys Asp Asp Ser Val
                325                 330                 335

Gly Gly Thr Ala Ser Thr Gly Asn Leu Ser Ser Phe Met Glu Glu
                340                 345                 350

Ile Gln Gly Tyr Asp Val Glu Phe Asp Pro Pro Leu Glu Ser Lys Tyr
            355                 360                 365

Glu Cys Pro Ile Cys Leu Met Ala Leu Arg Glu Ala Val Gln Thr Pro
            370                 375                 380

Cys Gly His Arg Phe Cys Lys Ala Cys Ile Ile Lys Ser Ile Arg Asp
385                 390                 395                 400

Ala Gly His Lys Cys Pro Val Asp Asn Glu Ile Leu Leu Glu Asn Gln
                405                 410                 415

Leu Phe Pro Asp Asn Phe Ala Lys Arg Glu Ile Leu Ser Leu Met Val
                420                 425                 430

Lys Cys Pro Asn Glu Gly Cys Leu His Lys Met Glu Leu Arg His Leu
            435                 440                 445

Glu Asp His Gln Ala His Cys Glu Phe Ala Leu Met Asp Cys Pro Gln
            450                 455                 460

Cys Gln Arg Pro Phe Gln Lys Phe His Ile Asn Ile His Ile Leu Lys
465                 470                 475                 480

Asp Cys Pro Arg Arg Gln Val Ser Cys Asp Asn Cys Ala Ala Ser Met
                485                 490                 495

Ala Phe Glu Asp Lys Glu Ile His Asp Gln Asn Cys Pro Leu Ala Asn
                500                 505                 510

Val Ile Cys Glu Tyr Cys Asn Thr Ile Leu Ile Arg Glu Gln Met Pro
            515                 520                 525

Asn His Tyr Asp Leu Asp Cys Pro Thr Ala Pro Ile Pro Cys Thr Phe
            530                 535                 540

Ser Thr Phe Gly Cys His Glu Lys Met Gln Arg Asn His Leu Ala Arg
545                 550                 555                 560

His Leu Gln Glu Asn Thr Gln Ser His Met Arg Met Leu Ala Leu Trp
                565                 570                 575

Asn Lys Lys Arg Met Arg Gly Pro Gly Lys Asp Pro Thr Arg Lys Cys
            580                 585                 590

Pro Asp Pro Arg Ser Ala Ser Ser Pro Lys Gln His Pro Ser Glu Ser
            595                 600                 605

Val Tyr Thr Ala Leu Gln Arg Arg Glu Thr Glu Val Tyr Ala Cys Ile
            610                 615                 620

Glu Asn Glu Asp Gly Ser Ser Pro Thr Ala Lys Gln Ser Pro Leu Ser
625                 630                 635                 640

Gln Glu Arg Pro His Arg Phe Glu Asp Asp Gly Glu Leu Asn Leu Val
                645                 650                 655

Tyr Glu Asn Leu
            660

<210> SEQ ID NO 149
```

```
<211> LENGTH: 659
<212> TYPE: PRT
<213> ORGANISM: Artificial Sequence
<220> FEATURE:
<223> OTHER INFORMATION: CER113, amino acids 1-22 are signal peptide

<400> SEQUENCE: 149
```

| | | | | | | | | | | | | | | | |
|---|---|---|---|---|---|---|---|---|---|---|---|---|---|---|---|
| Met | Ser | Lys | Gly | Leu | Leu | Leu | Trp | Leu | Val | Thr | Glu | Leu | Trp | Trp | |
| 1 | | | | 5 | | | | | 10 | | | | | 15 | |
| Leu | Tyr | Leu | Thr | Pro | Ala | Ala | Ser | Glu | Asp | Thr | Ile | Ile | Gly | Phe | Leu |
| | | | 20 | | | | | 25 | | | | | 30 | | |
| Gly | Gln | Pro | Val | Thr | Leu | Pro | Cys | His | Tyr | Leu | Ser | Trp | Ser | Gln | Ser |
| | | | 35 | | | | | 40 | | | | | 45 | | |
| Arg | Asn | Ser | Met | Cys | Trp | Gly | Lys | Gly | Ser | Cys | Pro | Asn | Ser | Lys | Cys |
| | 50 | | | | | 55 | | | | | 60 | | | | |
| Asn | Ala | Glu | Leu | Leu | Arg | Thr | Asp | Gly | Thr | Arg | Ile | Ile | Ser | Arg | Lys |
| 65 | | | | | 70 | | | | | 75 | | | | | 80 |
| Ser | Thr | Lys | Tyr | Thr | Leu | Leu | Gly | Lys | Val | Gln | Phe | Gly | Glu | Val | Ser |
| | | | | 85 | | | | | 90 | | | | | 95 | |
| Leu | Thr | Ile | Ser | Asn | Thr | Asn | Arg | Gly | Asp | Ser | Gly | Val | Tyr | Cys | Cys |
| | | | | 100 | | | | | 105 | | | | | 110 | |
| Arg | Ile | Glu | Val | Pro | Gly | Trp | Phe | Asn | Asp | Val | Lys | Lys | Asn | Val | Arg |
| | | | | 115 | | | | | 120 | | | | | 125 | |
| Leu | Glu | Leu | Arg | Arg | Ala | Thr | Thr | Thr | Lys | Lys | Pro | Thr | Thr | Thr | Thr |
| | 130 | | | | | 135 | | | | | 140 | | | | |
| Arg | Pro | Thr | Thr | Thr | Pro | Tyr | Val | Thr | Thr | Thr | Pro | Glu | Leu | Leu | |
| 145 | | | | | 150 | | | | | 155 | | | | | 160 |
| Pro | Thr | Thr | Val | Met | Thr | Thr | Ser | Val | Leu | Pro | Thr | Thr | Pro | Pro | |
| | | | | 165 | | | | | 170 | | | | | 175 | |
| Gln | Thr | Leu | Ala | Thr | Thr | Ala | Phe | Ser | Thr | Ala | Val | Thr | Thr | Cys | Pro |
| | | | | 180 | | | | | 185 | | | | | 190 | |
| Ser | Thr | Thr | Pro | Gly | Ser | Phe | Ser | Gln | Glu | Thr | Thr | Lys | Gly | Ser | Ala |
| | | | | 195 | | | | | 200 | | | | | 205 | |
| Phe | Thr | Thr | Glu | Ser | Glu | Thr | Leu | Pro | Ala | Ser | Asn | His | Ser | Gln | Arg |
| | 210 | | | | | 215 | | | | | 220 | | | | |
| Ser | Met | Met | Thr | Ile | Ser | Thr | Asp | Ile | Ala | Val | Leu | Arg | Pro | Thr | Gly |
| 225 | | | | | 230 | | | | | 235 | | | | | 240 |
| Ser | Asn | Pro | Gly | Ile | Leu | Pro | Ser | Thr | Ser | Gln | Leu | Thr | Thr | Gln | Lys |
| | | | | 245 | | | | | 250 | | | | | 255 | |
| Thr | Thr | Leu | Thr | Thr | Ser | Glu | Ser | Leu | Gln | Lys | Thr | Thr | Lys | Ser | His |
| | | | | 260 | | | | | 265 | | | | | 270 | |
| Gln | Ile | Asn | Ser | Arg | Gln | Thr | Ile | Leu | Ile | Ile | Ala | Cys | Cys | Val | Gly |
| | | | | 275 | | | | | 280 | | | | | 285 | |
| Phe | Val | Leu | Met | Val | Leu | Leu | Phe | Leu | Ala | Phe | Leu | Met | Ser | Leu | Leu |
| | | 290 | | | | | 295 | | | | | 300 | | | |
| Asn | Cys | Glu | Asn | Ser | Cys | Gly | Ser | Ser | Gln | Ser | Glu | Ser | Asp | Cys | Cys |
| 305 | | | | | 310 | | | | | 315 | | | | | 320 |
| Val | Ala | Met | Ala | Ser | Ser | Cys | Ser | Ala | Val | Thr | Lys | Asp | Asp | Ser | Val |
| | | | | 325 | | | | | 330 | | | | | 335 | |
| Gly | Gly | Thr | Ala | Ser | Thr | Gly | Asn | Leu | Ser | Ser | Ser | Phe | Met | Glu | Glu |
| | | | | 340 | | | | | 345 | | | | | 350 | |
| Ile | Gln | Gly | Tyr | Asp | Val | Glu | Phe | Asp | Pro | Pro | Leu | Glu | Ser | Lys | Tyr |
| | | | | 355 | | | | | 360 | | | | | 365 | |
| Glu | Cys | Pro | Ile | Cys | Leu | Met | Ala | Leu | Arg | Glu | Ala | Val | Gln | Thr | Pro |
| | 370 | | | | | 375 | | | | | 380 | | | | |

```
Cys Gly His Arg Phe Cys Lys Ala Cys Ile Ile Lys Ser Ile Arg Asp
385                 390                 395                 400

Ala Gly His Lys Cys Pro Val Asp Asn Glu Ile Leu Leu Glu Asn Gln
            405                 410                 415

Leu Phe Pro Asp Asn Phe Ala Lys Arg Glu Ile Leu Ser Leu Met Val
        420                 425                 430

Lys Cys Pro Asn Glu Gly Cys Leu His Lys Met Glu Leu Arg His Leu
    435                 440                 445

Glu Asp His Gln Ala His Cys Glu Phe Ala Leu Met Asp Cys Pro Gln
450                 455                 460

Cys Gln Arg Pro Phe Gln Lys Phe His Ile Asn Ile His Ile Leu Lys
465                 470                 475                 480

Asp Cys Pro Arg Arg Gln Val Ser Cys Asp Asn Cys Ala Ala Ser Met
                485                 490                 495

Ala Phe Glu Asp Lys Glu Ile His Asp Gln Asn Cys Pro Leu Ala Asn
            500                 505                 510

Val Ile Cys Glu Tyr Cys Asn Thr Ile Leu Ile Arg Glu Gln Met Pro
        515                 520                 525

Asn His Tyr Asp Leu Asp Cys Pro Thr Ala Pro Ile Pro Cys Thr Phe
    530                 535                 540

Ser Thr Phe Gly Cys His Glu Lys Met Gln Arg Asn His Leu Ala Arg
545                 550                 555                 560

His Leu Gln Glu Asn Thr Gln Ser His Met Arg Met Leu Ala Ser Trp
                565                 570                 575

Arg Arg Arg Gln Arg Arg Leu Arg Gly Ala Ser Ser Ala Glu Ala Pro
            580                 585                 590

Asp Gly Asp Lys Asp Ala Pro Glu Pro Leu Asp Lys Val Ile Ile Leu
        595                 600                 605

Ser Pro Gly Ile Ser Asp Ala Thr Ala Pro Ala Trp Pro Pro Pro Gly
    610                 615                 620

Glu Asp Pro Gly Thr Thr Pro Pro Gly His Ser Val Pro Val Pro Ala
625                 630                 635                 640

Thr Glu Leu Gly Ser Thr Glu Leu Val Thr Thr Lys Thr Ala Gly Pro
                645                 650                 655

Glu Gln Gln

<210> SEQ ID NO 150
<211> LENGTH: 1050
<212> TYPE: PRT
<213> ORGANISM: Artificial Sequence
<220> FEATURE:
<223> OTHER INFORMATION: CER114, amino acids 1-22 are signal peptide

<400> SEQUENCE: 150

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Gly Phe Leu
            20                  25                  30

Gly Gln Pro Val Thr Leu Pro Cys His Tyr Leu Ser Trp Ser Gln Ser
        35                  40                  45

Arg Asn Ser Met Cys Trp Gly Lys Gly Ser Cys Pro Asn Ser Lys Cys
    50                  55                  60

Asn Ala Glu Leu Leu Arg Thr Asp Gly Thr Arg Ile Ile Ser Arg Lys
65                  70                  75                  80
```

```
Ser Thr Lys Tyr Thr Leu Leu Gly Lys Val Gln Phe Gly Glu Val Ser
                 85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Lys Lys Pro Thr Thr Thr Thr Thr
    130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
    210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ala Cys Cys Val Gly
        275                 280                 285

Phe Val Leu Met Val Leu Leu Phe Leu Ala Phe Leu Met Ser Leu Leu
    290                 295                 300

Asn Cys Glu Asn Ser Cys Gly Ser Ser Gln Ser Glu Ser Asp Cys Cys
305                 310                 315                 320

Val Ala Met Ala Ser Ser Cys Ser Ala Val Thr Lys Asp Asp Ser Val
                325                 330                 335

Gly Gly Thr Ala Ser Thr Gly Asn Leu Ser Ser Ser Phe Met Glu Glu
            340                 345                 350

Ile Gln Gly Tyr Asp Val Glu Phe Asp Pro Pro Leu Glu Ser Lys Tyr
        355                 360                 365

Glu Cys Pro Ile Cys Leu Met Ala Leu Arg Glu Ala Val Gln Thr Pro
    370                 375                 380

Cys Gly His Arg Phe Cys Lys Ala Cys Ile Ile Lys Ser Ile Arg Asp
385                 390                 395                 400

Ala Gly His Lys Cys Pro Val Asp Asn Glu Ile Leu Leu Glu Asn Gln
                405                 410                 415

Leu Phe Pro Asp Asn Phe Ala Lys Arg Glu Ile Leu Ser Leu Met Val
            420                 425                 430

Lys Cys Pro Asn Glu Gly Cys Leu His Lys Met Glu Leu Arg His Leu
        435                 440                 445

Glu Asp His Gln Ala His Cys Glu Phe Ala Leu Met Asp Cys Pro Gln
    450                 455                 460

Cys Gln Arg Pro Phe Gln Lys Phe His Ile Asn Ile His Ile Leu Lys
465                 470                 475                 480

Asp Cys Pro Arg Arg Gln Val Ser Cys Asp Asn Cys Ala Ala Ser Met
                485                 490                 495

Ala Phe Glu Asp Lys Glu Ile His Asp Gln Asn Cys Pro Leu Ala Asn
```

```
                500                 505                 510
Val Ile Cys Glu Tyr Cys Asn Thr Ile Leu Ile Arg Glu Gln Met Pro
            515                 520                 525

Asn His Tyr Asp Leu Asp Cys Pro Thr Ala Pro Ile Pro Cys Thr Phe
            530                 535                 540

Ser Thr Phe Gly Cys His Glu Lys Met Gln Arg Asn His Leu Ala Arg
545                 550                 555                 560

His Leu Gln Glu Asn Thr Gln Ser His Met Arg Met Leu Ala Ala Leu
                565                 570                 575

Arg Arg Arg Val Gln Glu Thr Lys Phe Gly Ala Phe Ser Glu Glu
            580                 585                 590

Asp Ser Gln Leu Val Val Asn Tyr Arg Ala Lys Lys Ser Phe Cys Arg
            595                 600                 605

Arg Ala Ile Glu Leu Thr Leu Gln Ser Leu Gly Val Ser Glu Glu Leu
            610                 615                 620

Gln Asn Lys Leu Glu Asp Val Val Ile Asp Arg Asn Leu Leu Val Leu
625                 630                 635                 640

Gly Lys Val Leu Gly Glu Gly Glu Phe Gly Ser Val Met Glu Gly Asn
                645                 650                 655

Leu Lys Gln Glu Asp Gly Thr Ser Gln Lys Val Ala Val Lys Thr Met
                660                 665                 670

Lys Leu Asp Asn Phe Ser Gln Arg Glu Ile Glu Glu Phe Leu Ser Glu
            675                 680                 685

Ala Ala Cys Met Lys Asp Phe Asn His Pro Asn Val Ile Arg Leu Leu
            690                 695                 700

Gly Val Cys Ile Glu Leu Ser Ser Gln Gly Ile Pro Lys Pro Met Val
705                 710                 715                 720

Ile Leu Pro Phe Met Lys Tyr Gly Asp Leu His Thr Phe Leu Leu Tyr
                725                 730                 735

Ser Arg Leu Asn Thr Gly Pro Lys Tyr Ile His Leu Gln Thr Leu Leu
                740                 745                 750

Lys Phe Met Met Asp Ile Ala Gln Gly Met Glu Tyr Leu Ser Asn Arg
            755                 760                 765

Asn Phe Leu His Arg Asp Leu Ala Ala Arg Asn Cys Met Leu Arg Asp
            770                 775                 780

Asp Met Thr Val Cys Val Ala Asp Phe Gly Leu Ser Lys Lys Ile Tyr
785                 790                 795                 800

Ser Gly Asp Tyr Tyr Arg Gln Gly Arg Ile Ala Lys Met Pro Val Lys
                805                 810                 815

Trp Ile Ala Ile Glu Ser Leu Ala Asp Arg Val Tyr Thr Ser Lys Ser
            820                 825                 830

Asp Val Trp Ala Phe Gly Val Thr Met Trp Glu Ile Thr Thr Arg Gly
            835                 840                 845

Met Thr Pro Tyr Pro Gly Val Gln Asn His Glu Met Tyr Asp Tyr Leu
            850                 855                 860

Leu His Gly His Arg Leu Lys Gln Pro Glu Asp Cys Leu Asp Glu Leu
865                 870                 875                 880

Tyr Asp Ile Met Tyr Ser Cys Trp Ser Ala Asp Pro Leu Asp Arg Pro
                885                 890                 895

Thr Phe Ser Val Leu Arg Leu Gln Leu Glu Lys Leu Ser Glu Ser Leu
                900                 905                 910

Pro Asp Ala Gln Asp Lys Glu Ser Ile Ile Tyr Ile Asn Thr Gln Leu
            915                 920                 925
```

-continued

```
Leu Glu Ser Cys Glu Gly Ile Ala Asn Gly Pro Ser Leu Thr Gly Leu
            930                 935                 940

Asp Met Asn Ile Asp Pro Asp Ser Ile Ile Ala Ser Cys Thr Pro Gly
945                 950                 955                 960

Ala Ala Val Ser Val Val Thr Ala Glu Val His Glu Asn Asn Leu Arg
                965                 970                 975

Glu Glu Arg Tyr Ile Leu Asn Gly Gly Asn Glu Glu Trp Glu Asp Val
            980                 985                 990

Ser Ser Thr Pro Phe Ala Ala Val Thr Pro Glu Lys Asp Gly Val Leu
            995                 1000                1005

Pro Glu Asp Arg Leu Thr Lys Asn Gly Val Ser Trp Ser His His Ser
        1010                1015                1020

Thr Leu Pro Leu Gly Ser Pro Ser Pro Asp Glu Leu Leu Phe Val Asp
1025                1030                1035                1040

Asp Ser Leu Glu Asp Ser Glu Val Leu Met
            1045                1050

<210> SEQ ID NO 151
<211> LENGTH: 1050
<212> TYPE: PRT
<213> ORGANISM: Artificial Sequence
<220> FEATURE:
<223> OTHER INFORMATION: CER115, amino acids 1-22 are signal peptide

<400> SEQUENCE: 151

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
                20                  25                  30

Gly Gln Pro Val Thr Leu Pro Cys His Tyr Leu Ser Trp Ser Gln Ser
            35                  40                  45

Arg Asn Ser Met Cys Trp Gly Lys Gly Ser Cys Pro Asn Ser Lys Cys
50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Lys Lys Pro Thr Thr Thr Thr
130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
    210                 215                 220

Ser Met Met Thr Ile Ser Thr Asp Ile Ala Val Leu Arg Pro Thr Gly
225                 230                 235                 240
```

```
Ser Asn Pro Gly Ile Leu Pro Ser Thr Ser Gln Leu Thr Thr Gln Lys
            245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ala Cys Cys Val Gly
            275                 280                 285

Phe Val Leu Met Val Leu Leu Phe Leu Ala Phe Leu Ala Leu Arg Arg
            290                 295                 300

Arg Val Gln Glu Thr Lys Phe Gly Gly Ala Phe Ser Glu Glu Asp Ser
305                 310                 315                 320

Gln Leu Val Val Asn Tyr Arg Ala Lys Lys Ser Phe Cys Arg Arg Ala
            325                 330                 335

Ile Glu Leu Thr Leu Gln Ser Leu Gly Val Ser Glu Glu Leu Gln Asn
            340                 345                 350

Lys Leu Glu Asp Val Val Ile Asp Arg Asn Leu Leu Val Leu Gly Lys
            355                 360                 365

Val Leu Gly Glu Gly Glu Phe Gly Ser Val Met Glu Gly Asn Leu Lys
            370                 375                 380

Gln Glu Asp Gly Thr Ser Gln Lys Val Ala Val Lys Thr Met Lys Leu
385                 390                 395                 400

Asp Asn Phe Ser Gln Arg Glu Ile Glu Glu Phe Leu Ser Glu Ala Ala
            405                 410                 415

Cys Met Lys Asp Phe Asn His Pro Asn Val Ile Arg Leu Leu Gly Val
            420                 425                 430

Cys Ile Glu Leu Ser Ser Gln Gly Ile Pro Lys Pro Met Val Ile Leu
            435                 440                 445

Pro Phe Met Lys Tyr Gly Asp Leu His Thr Phe Leu Leu Tyr Ser Arg
            450                 455                 460

Leu Asn Thr Gly Pro Lys Tyr Ile His Leu Gln Thr Leu Leu Lys Phe
465                 470                 475                 480

Met Met Asp Ile Ala Gln Gly Met Glu Tyr Leu Ser Asn Arg Asn Phe
            485                 490                 495

Leu His Arg Asp Leu Ala Ala Arg Asn Cys Met Leu Arg Asp Asp Met
            500                 505                 510

Thr Val Cys Val Ala Asp Phe Gly Leu Ser Lys Lys Ile Tyr Ser Gly
            515                 520                 525

Asp Tyr Tyr Arg Gln Gly Arg Ile Ala Lys Met Pro Val Lys Trp Ile
530                 535                 540

Ala Ile Glu Ser Leu Ala Asp Arg Val Tyr Thr Ser Lys Ser Asp Val
545                 550                 555                 560

Trp Ala Phe Gly Val Thr Met Trp Glu Ile Thr Thr Arg Gly Met Thr
            565                 570                 575

Pro Tyr Pro Gly Val Gln Asn His Glu Met Tyr Asp Tyr Leu Leu His
            580                 585                 590

Gly His Arg Leu Lys Gln Pro Glu Asp Cys Leu Asp Glu Leu Tyr Asp
            595                 600                 605

Ile Met Tyr Ser Cys Trp Ser Ala Asp Pro Leu Asp Arg Pro Thr Phe
            610                 615                 620

Ser Val Leu Arg Leu Gln Leu Glu Lys Leu Ser Glu Ser Leu Pro Asp
625                 630                 635                 640

Ala Gln Asp Lys Glu Ser Ile Ile Tyr Ile Asn Thr Gln Leu Leu Glu
            645                 650                 655
```

```
Ser Cys Glu Gly Ile Ala Asn Gly Pro Ser Leu Thr Gly Leu Asp Met
            660                 665                 670

Asn Ile Asp Pro Asp Ser Ile Ile Ala Ser Cys Thr Pro Gly Ala Ala
        675                 680                 685

Val Ser Val Thr Ala Glu Val His Glu Asn Asn Leu Arg Glu Glu
    690                 695                 700

Arg Tyr Ile Leu Asn Gly Gly Asn Glu Glu Trp Glu Asp Val Ser Ser
705                 710                 715                 720

Thr Pro Phe Ala Ala Val Thr Pro Glu Lys Asp Gly Val Leu Pro Glu
                725                 730                 735

Asp Arg Leu Thr Lys Asn Gly Val Ser Trp Ser His His Ser Thr Leu
            740                 745                 750

Pro Leu Gly Ser Pro Ser Pro Asp Glu Leu Leu Phe Val Asp Asp Ser
        755                 760                 765

Leu Glu Asp Ser Glu Val Leu Met Met Ser Leu Leu Asn Cys Glu Asn
    770                 775                 780

Ser Cys Gly Ser Ser Gln Ser Glu Ser Asp Cys Cys Val Ala Met Ala
785                 790                 795                 800

Ser Ser Cys Ser Ala Val Thr Lys Asp Asp Ser Val Gly Gly Thr Ala
                805                 810                 815

Ser Thr Gly Asn Leu Ser Ser Ser Phe Met Glu Glu Ile Gln Gly Tyr
            820                 825                 830

Asp Val Glu Phe Asp Pro Pro Leu Glu Ser Lys Tyr Glu Cys Pro Ile
        835                 840                 845

Cys Leu Met Ala Leu Arg Glu Ala Val Gln Thr Pro Cys Gly His Arg
    850                 855                 860

Phe Cys Lys Ala Cys Ile Ile Lys Ser Ile Arg Asp Ala Gly His Lys
865                 870                 875                 880

Cys Pro Val Asp Asn Glu Ile Leu Leu Glu Asn Gln Leu Phe Pro Asp
                885                 890                 895

Asn Phe Ala Lys Arg Glu Ile Leu Ser Leu Met Val Lys Cys Pro Asn
            900                 905                 910

Glu Gly Cys Leu His Lys Met Glu Leu Arg His Leu Glu Asp His Gln
        915                 920                 925

Ala His Cys Glu Phe Ala Leu Met Asp Cys Pro Gln Cys Gln Arg Pro
    930                 935                 940

Phe Gln Lys Phe His Ile Asn Ile His Ile Leu Lys Asp Cys Pro Arg
945                 950                 955                 960

Arg Gln Val Ser Cys Asp Asn Cys Ala Ala Ser Met Ala Phe Glu Asp
                965                 970                 975

Lys Glu Ile His Asp Gln Asn Cys Pro Leu Ala Asn Val Ile Cys Glu
            980                 985                 990

Tyr Cys Asn Thr Ile Leu Ile Arg Glu Gln Met Pro Asn His Tyr Asp
        995                 1000                1005

Leu Asp Cys Pro Thr Ala Pro Ile Pro Cys Thr Phe Ser Thr Phe Gly
    1010                1015                1020

Cys His Glu Lys Met Gln Arg Asn His Leu Ala Arg His Leu Gln Glu
1025                1030                1035                1040

Asn Thr Gln Ser His Met Arg Met Leu Ala
                1045                1050

<210> SEQ ID NO 152
<211> LENGTH: 767
<212> TYPE: PRT
```

<213> ORGANISM: Artificial Sequence
<220> FEATURE:
<223> OTHER INFORMATION: CER116, amino acids 1-22 are signal peptide

<400> SEQUENCE: 152

```
Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
            35                  40                  45

Arg Asn Ser Met Cys Trp Gly Lys Gly Ser Cys Pro Asn Ser Lys Cys
50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
            115                 120                 125

Leu Glu Leu Arg Arg Ala Thr Thr Thr Lys Lys Pro Thr Thr Thr Thr
130                 135                 140

Arg Pro Thr Thr Thr Pro Tyr Val Thr Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
            195                 200                 205

Phe Thr Thr Glu Ser Glu Thr Leu Pro Ala Ser Asn His Ser Gln Arg
210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
            245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ala Cys Cys Val Gly
            275                 280                 285

Phe Val Leu Met Val Leu Leu Phe Leu Ala Phe Leu Met Ser Leu Leu
            290                 295                 300

Asn Cys Glu Asn Ser Cys Gly Ser Ser Gln Ser Glu Ser Asp Cys Cys
305                 310                 315                 320

Val Ala Met Ala Ser Ser Cys Ser Ala Val Thr Lys Asp Asp Ser Val
            325                 330                 335

Gly Gly Thr Ala Ser Thr Gly Asn Leu Ser Ser Ser Phe Met Glu Glu
            340                 345                 350

Ile Gln Gly Tyr Asp Val Glu Phe Asp Pro Pro Leu Glu Ser Lys Tyr
            355                 360                 365

Glu Cys Pro Ile Cys Leu Met Ala Leu Arg Glu Ala Val Gln Thr Pro
370                 375                 380

Cys Gly His Arg Phe Cys Lys Ala Cys Ile Ile Lys Ser Ile Arg Asp
```

```
            385                 390                 395                 400
Ala Gly His Lys Cys Pro Val Asp Asn Glu Ile Leu Leu Glu Asn Gln
                405                 410                 415

Leu Phe Pro Asp Asn Phe Ala Lys Arg Glu Ile Leu Ser Leu Met Val
                420                 425                 430

Lys Cys Pro Asn Glu Gly Cys Leu His Lys Met Glu Leu Arg His Leu
                435                 440                 445

Glu Asp His Gln Ala His Cys Glu Phe Ala Leu Met Asp Cys Pro Gln
        450                 455                 460

Cys Gln Arg Pro Phe Gln Lys Phe His Ile Asn Ile His Ile Leu Lys
465                 470                 475                 480

Asp Cys Pro Arg Arg Gln Val Ser Cys Asp Asn Cys Ala Ala Ser Met
                485                 490                 495

Ala Phe Glu Asp Lys Glu Ile His Asp Gln Asn Cys Pro Leu Ala Asn
                500                 505                 510

Val Ile Cys Glu Tyr Cys Asn Thr Ile Leu Ile Arg Glu Gln Met Pro
                515                 520                 525

Asn His Tyr Asp Leu Asp Cys Pro Thr Ala Pro Ile Pro Cys Thr Phe
            530                 535                 540

Ser Thr Phe Gly Cys His Glu Lys Met Gln Arg Asn His Leu Ala Arg
545                 550                 555                 560

His Leu Gln Glu Asn Thr Gln Ser His Met Arg Met Leu Ala His His
                565                 570                 575

Leu Phe Tyr Trp Asp Val Trp Phe Ile Tyr Asn Val Cys Leu Ala Lys
                580                 585                 590

Val Lys Gly Tyr Arg Ser Leu Ser Thr Ser Gln Thr Phe Tyr Asp Ala
            595                 600                 605

Tyr Ile Ser Tyr Asp Thr Lys Asp Ala Ser Val Thr Asp Trp Val Ile
            610                 615                 620

Asn Glu Leu Arg Tyr His Leu Glu Gly Ser Arg Asp Lys Asn Val Leu
625                 630                 635                 640

Leu Cys Leu Glu Glu Arg Asp Trp Asp Pro Gly Leu Ala Ile Ile Asp
                645                 650                 655

Asn Leu Met Gln Ser Ile Asn Gln Ser Lys Lys Thr Val Phe Val Leu
            660                 665                 670

Thr Lys Lys Tyr Ala Lys Ser Trp Asn Phe Lys Thr Ala Phe Tyr Leu
            675                 680                 685

Ala Leu Gln Arg Leu Met Asp Glu Asn Met Asp Val Ile Ile Phe Ile
        690                 695                 700

Leu Leu Glu Pro Val Leu Gln His Ser Gln Tyr Leu Arg Leu Arg Gln
705                 710                 715                 720

Arg Ile Cys Lys Ser Ser Ile Leu Gln Trp Pro Asp Asn Pro Lys Ala
                725                 730                 735

Glu Gly Leu Phe Trp Gln Thr Leu Arg Asn Val Val Leu Thr Glu Asn
                740                 745                 750

Asp Ser Arg Tyr Asn Asn Met Tyr Val Asp Ser Ile Lys Gln Tyr
            755                 760                 765

<210> SEQ ID NO 153
<211> LENGTH: 767
<212> TYPE: PRT
<213> ORGANISM: Artificial Sequence
<220> FEATURE:
<223> OTHER INFORMATION: CER117, amino acids 1-22 are signal peptide
```

```
<400> SEQUENCE: 153

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
        35                  40                  45

Arg Asn Ser Met Cys Trp Gly Lys Gly Ser Cys Pro Asn Ser Lys Cys
    50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Lys Lys Pro Thr Thr Thr Thr
130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
            195                 200                 205

Phe Thr Thr Glu Ser Glu Thr Leu Pro Ala Ser Asn His Ser Gln Arg
            210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ala Cys Cys Val Gly
            275                 280                 285

Phe Val Leu Met Val Leu Leu Phe Leu Ala Phe Leu His His Leu Phe
290                 295                 300

Tyr Trp Asp Val Trp Phe Ile Tyr Asn Val Cys Leu Ala Lys Val Lys
305                 310                 315                 320

Gly Tyr Arg Ser Leu Ser Thr Ser Gln Thr Phe Tyr Asp Ala Tyr Ile
            325                 330                 335

Ser Tyr Asp Thr Lys Asp Ala Ser Val Thr Asp Trp Val Ile Asn Glu
            340                 345                 350

Leu Arg Tyr His Leu Glu Glu Ser Arg Asp Lys Asn Val Leu Leu Cys
            355                 360                 365

Leu Glu Glu Arg Asp Trp Asp Pro Gly Leu Ala Ile Ile Asp Asn Leu
370                 375                 380

Met Gln Ser Ile Asn Gln Ser Lys Lys Thr Val Phe Val Leu Thr Lys
385                 390                 395                 400

Lys Tyr Ala Lys Ser Trp Asn Phe Lys Thr Ala Phe Tyr Leu Ala Leu
            405                 410                 415
```

```
Gln Arg Leu Met Asp Glu Asn Met Asp Val Ile Ile Phe Ile Leu Leu
            420                 425                 430

Glu Pro Val Leu Gln His Ser Gln Tyr Leu Arg Leu Arg Gln Arg Ile
        435                 440                 445

Cys Lys Ser Ser Ile Leu Gln Trp Pro Asp Asn Pro Lys Ala Glu Gly
    450                 455                 460

Leu Phe Trp Gln Thr Leu Arg Asn Val Val Leu Thr Glu Asn Asp Ser
465                 470                 475                 480

Arg Tyr Asn Asn Met Tyr Val Asp Ser Ile Lys Gln Tyr Met Ser Leu
                485                 490                 495

Leu Asn Cys Glu Asn Ser Cys Gly Ser Ser Gln Ser Glu Ser Asp Cys
            500                 505                 510

Cys Val Ala Met Ala Ser Ser Cys Ser Ala Val Thr Lys Asp Asp Ser
        515                 520                 525

Val Gly Gly Thr Ala Ser Thr Gly Asn Leu Ser Ser Ser Phe Met Glu
530                 535                 540

Glu Ile Gln Gly Tyr Asp Val Glu Phe Asp Pro Pro Leu Glu Ser Lys
545                 550                 555                 560

Tyr Glu Cys Pro Ile Cys Leu Met Ala Leu Arg Glu Ala Val Gln Thr
                565                 570                 575

Pro Cys Gly His Arg Phe Cys Lys Ala Cys Ile Ile Lys Ser Ile Arg
            580                 585                 590

Asp Ala Gly His Lys Cys Pro Val Asp Asn Glu Ile Leu Leu Glu Asn
        595                 600                 605

Gln Leu Phe Pro Asp Asn Phe Ala Lys Arg Glu Ile Leu Ser Leu Met
    610                 615                 620

Val Lys Cys Pro Asn Glu Gly Cys Leu His Lys Met Glu Leu Arg His
625                 630                 635                 640

Leu Glu Asp His Gln Ala His Cys Glu Phe Ala Leu Met Asp Cys Pro
                645                 650                 655

Gln Cys Gln Arg Pro Phe Gln Lys Phe His Ile Asn Ile His Ile Leu
            660                 665                 670

Lys Asp Cys Pro Arg Arg Gln Val Ser Cys Asp Asn Cys Ala Ala Ser
        675                 680                 685

Met Ala Phe Glu Asp Lys Glu Ile His Asp Gln Asn Cys Pro Leu Ala
    690                 695                 700

Asn Val Ile Cys Glu Tyr Cys Asn Thr Ile Leu Ile Arg Glu Gln Met
705                 710                 715                 720

Pro Asn His Tyr Asp Leu Asp Cys Pro Thr Ala Pro Ile Pro Cys Thr
                725                 730                 735

Phe Ser Thr Phe Gly Cys His Glu Lys Met Gln Arg Asn His Leu Ala
            740                 745                 750

Arg His Leu Gln Glu Asn Thr Gln Ser His Met Arg Met Leu Ala
        755                 760                 765

<210> SEQ ID NO 154
<211> LENGTH: 571
<212> TYPE: PRT
<213> ORGANISM: Artificial Sequence
<220> FEATURE:
<223> OTHER INFORMATION: CER118, amino acids 1-22 are signal peptide

<400> SEQUENCE: 154

Met Ser Lys Gly Leu Leu Leu Leu Trp Leu Val Thr Glu Leu Trp Trp
1               5                   10                  15
```

```
Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
        35                  40                  45

Arg Asn Ser Met Cys Trp Gly Lys Gly Ser Cys Pro Asn Ser Lys Cys
50                      55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
                100                 105                 110

Arg Ile Glu Val Pro Gly Trp Phe Asn Asp Val Lys Lys Asn Val Arg
        115                 120                 125

Leu Glu Leu Arg Arg Ala Thr Thr Lys Lys Pro Thr Thr Thr Thr Thr
130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
    210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ile Ala Cys Cys Val Gly
        275                 280                 285

Phe Val Leu Met Val Leu Leu Phe Leu Ala Phe Leu Ser Tyr Leu Asp
    290                 295                 300

Leu Pro Trp Tyr Leu Arg Met Val Cys Gln Trp Thr Gln Thr Arg Arg
305                 310                 315                 320

Arg Ala Arg Asn Ile Pro Leu Glu Glu Leu Gln Arg Asn Leu Gln Phe
                325                 330                 335

His Ala Phe Ile Ser Tyr Ser Gly His Asp Ser Phe Trp Val Lys Asn
            340                 345                 350

Glu Leu Leu Pro Asn Leu Glu Lys Glu Gly Met Gln Ile Cys Leu His
        355                 360                 365

Glu Arg Asn Phe Val Pro Gly Lys Ser Ile Val Glu Asn Ile Ile Thr
    370                 375                 380

Cys Ile Glu Lys Ser Tyr Lys Ser Ile Phe Val Leu Ser Pro Asn Phe
385                 390                 395                 400

Val Gln Ser Glu Trp Cys His Tyr Glu Leu Tyr Phe Ala His His Asn
                405                 410                 415

Leu Phe His Glu Gly Ser Asn Ser Leu Ile Leu Ile Leu Leu Glu Pro
            420                 425                 430
```

```
Ile Pro Gln Tyr Ser Ile Pro Ser Tyr His Lys Leu Lys Ser Leu
            435                 440                 445

Met Ala Arg Arg Thr Tyr Leu Glu Trp Pro Lys Glu Lys Ser Lys Arg
450                 455                 460

Gly Leu Phe Trp Ala Asn Leu Arg Ala Ala Ile Asn Ile Lys Leu Thr
465                 470                 475                 480

Glu Gln Ala Lys Lys Leu Trp Asn Lys Lys Arg Met Arg Gly Pro Gly
                485                 490                 495

Lys Asp Pro Thr Arg Lys Cys Pro Asp Pro Arg Ser Ala Ser Ser Pro
                500                 505                 510

Lys Gln His Pro Ser Glu Ser Val Tyr Thr Ala Leu Gln Arg Arg Glu
                515                 520                 525

Thr Glu Val Tyr Ala Cys Ile Glu Asn Glu Asp Gly Ser Ser Pro Thr
530                 535                 540

Ala Lys Gln Ser Pro Leu Ser Gln Glu Arg Pro His Arg Phe Glu Asp
545                 550                 555                 560

Asp Gly Glu Leu Asn Leu Val Tyr Glu Asn Leu
                565                 570

<210> SEQ ID NO 155
<211> LENGTH: 514
<212> TYPE: PRT
<213> ORGANISM: Artificial Sequence
<220> FEATURE:
<223> OTHER INFORMATION: CER119, amino acids 1-22 are signal peptide

<400> SEQUENCE: 155

Met Ser Lys Gly Leu Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
                20                  25                  30

Gly Gln Pro Val Thr Leu Pro Cys His Tyr Leu Ser Trp Ser Gln Ser
            35                  40                  45

Arg Asn Ser Met Cys Trp Gly Lys Gly Ser Cys Pro Asn Ser Lys Cys
        50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Lys Lys Pro Thr Thr Thr Thr
130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
    210                 215                 220
```

```
Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
            245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ile Ala Cys Cys Val Gly
            275                 280                 285

Phe Val Leu Met Val Leu Leu Phe Leu Ala Phe Leu Ser Tyr Leu Asp
            290                 295                 300

Leu Pro Trp Tyr Leu Arg Met Val Cys Gln Trp Thr Gln Thr Arg Arg
305                 310                 315                 320

Arg Ala Arg Asn Ile Pro Leu Glu Glu Leu Gln Arg Asn Leu Gln Phe
                325                 330                 335

His Ala Phe Ile Ser Tyr Ser Gly His Asp Ser Phe Trp Val Lys Asn
                340                 345                 350

Glu Leu Leu Pro Asn Leu Glu Lys Glu Gly Met Gln Ile Cys Leu His
            355                 360                 365

Glu Arg Asn Phe Val Pro Gly Lys Ser Ile Val Glu Asn Ile Ile Thr
370                 375                 380

Cys Ile Glu Lys Ser Tyr Lys Ser Ile Phe Val Leu Ser Pro Asn Phe
385                 390                 395                 400

Val Gln Ser Glu Trp Cys His Tyr Glu Leu Tyr Phe Ala His His Asn
                405                 410                 415

Leu Phe His Glu Gly Ser Asn Ser Leu Ile Leu Ile Leu Leu Glu Pro
            420                 425                 430

Ile Pro Gln Tyr Ser Ile Pro Ser Ser Tyr His Lys Leu Lys Ser Leu
            435                 440                 445

Met Ala Arg Arg Thr Tyr Leu Glu Trp Pro Lys Glu Lys Ser Lys Arg
    450                 455                 460

Gly Leu Phe Trp Ala Asn Leu Arg Ala Ala Ile Asn Ile Lys Leu Thr
465                 470                 475                 480

Glu Gln Ala Lys Lys Asp Ser Lys Ala Gly Met Glu Glu Asp His Thr
                485                 490                 495

Tyr Glu Gly Leu Asp Ile Asp Gln Thr Ala Thr Tyr Glu Asp Ile Val
            500                 505                 510

Thr Leu

<210> SEQ ID NO 156
<211> LENGTH: 537
<212> TYPE: PRT
<213> ORGANISM: Artificial Sequence
<220> FEATURE:
<223> OTHER INFORMATION: CER120, amino acids 1-22 are signal peptide

<400> SEQUENCE: 156

Met Ser Lys Gly Leu Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
            35                  40                  45

Arg Asn Ser Met Cys Trp Gly Lys Gly Ser Cys Pro Asn Ser Lys Cys
        50                  55                  60

Asn Ala Glu Leu Leu Arg Thr Asp Gly Thr Arg Ile Ile Ser Arg Lys
```

-continued

```
                65                  70                  75                  80
Ser Thr Lys Tyr Thr Leu Leu Gly Lys Val Gln Phe Gly Glu Val Ser
                        85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Lys Lys Pro Thr Thr Thr
    130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Pro Pro
                    165                 170                 175

Gln Thr Leu Ala Thr Thr Ala Phe Ser Thr Ala Val Thr Thr Cys Pro
                180                 185                 190

Ser Thr Thr Pro Gly Ser Phe Ser Gln Glu Thr Thr Lys Gly Ser Ala
            195                 200                 205

Phe Thr Thr Glu Ser Glu Thr Leu Pro Ala Ser Asn His Ser Gln Arg
        210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                    245                 250                 255

Thr Thr Leu Thr Thr Ser Glu Ser Leu Gln Lys Thr Thr Lys Ser His
                260                 265                 270

Gln Ile Asn Ser Arg Gln Thr Ile Leu Ile Ala Cys Cys Val Gly
            275                 280                 285

Phe Val Leu Met Val Leu Leu Phe Leu Ala Phe Leu Ser Tyr Leu Asp
        290                 295                 300

Leu Pro Trp Tyr Leu Arg Met Val Cys Gln Trp Thr Gln Thr Arg Arg
305                 310                 315                 320

Arg Ala Arg Asn Ile Pro Leu Glu Glu Leu Gln Arg Asn Leu Gln Phe
                    325                 330                 335

His Ala Phe Ile Ser Tyr Ser Gly His Asp Ser Phe Trp Val Lys Asn
                340                 345                 350

Glu Leu Leu Pro Asn Leu Glu Lys Glu Gly Met Gln Ile Cys Leu His
            355                 360                 365

Glu Arg Asn Phe Val Pro Gly Lys Ser Ile Val Glu Asn Ile Ile Thr
        370                 375                 380

Cys Ile Glu Lys Ser Tyr Lys Ser Ile Phe Val Leu Ser Pro Asn Phe
385                 390                 395                 400

Val Gln Ser Glu Trp Cys His Tyr Glu Leu Tyr Phe Ala His His Asn
                    405                 410                 415

Leu Phe His Glu Gly Ser Asn Ser Leu Ile Leu Ile Leu Leu Glu Pro
                420                 425                 430

Ile Pro Gln Tyr Ser Ile Pro Ser Ser Tyr His Lys Leu Lys Ser Leu
            435                 440                 445

Met Ala Arg Arg Thr Tyr Leu Glu Trp Pro Lys Glu Lys Ser Lys Arg
        450                 455                 460

Gly Leu Phe Trp Ala Asn Leu Arg Ala Ala Ile Asn Ile Lys Leu Thr
465                 470                 475                 480

Glu Gln Ala Lys Lys Tyr Phe Leu Gly Arg Leu Val Pro Arg Gly Arg
                    485                 490                 495
```

Gly Ala Ala Glu Ala Ala Thr Arg Lys Gln Arg Ile Thr Glu Thr Glu
            500                 505                 510

Ser Pro Tyr Gln Glu Leu Gln Gly Gln Arg Ser Asp Val Tyr Ser Asp
        515                 520                 525

Leu Asn Thr Gln Arg Pro Tyr Tyr Lys
    530                 535

<210> SEQ ID NO 157
<211> LENGTH: 759
<212> TYPE: PRT
<213> ORGANISM: Artificial Sequence
<220> FEATURE:
<223> OTHER INFORMATION: CER121, amino acids 1-22 are signal peptide

<400> SEQUENCE: 157

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
        35                  40                  45

Arg Asn Ser Met Cys Trp Gly Lys Gly Ser Cys Pro Asn Ser Lys Cys
    50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Lys Lys Pro Thr Thr Thr Thr
    130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
    210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ala Cys Cys Val Gly
        275                 280                 285

Phe Val Leu Met Val Leu Leu Phe Leu Ala Phe Leu Ser Tyr Leu Asp
    290                 295                 300

Leu Pro Trp Tyr Leu Arg Met Val Cys Gln Trp Thr Gln Thr Arg Arg
305                 310                 315                 320

```
Arg Ala Arg Asn Ile Pro Leu Glu Glu Leu Gln Arg Asn Leu Gln Phe
                325                 330                 335

His Ala Phe Ile Ser Tyr Ser Gly His Asp Ser Phe Trp Val Lys Asn
                340                 345                 350

Glu Leu Leu Pro Asn Leu Glu Lys Gly Met Gln Ile Cys Leu His
            355                 360                 365

Glu Arg Asn Phe Val Pro Gly Lys Ser Ile Val Glu Asn Ile Ile Thr
            370                 375                 380

Cys Ile Glu Lys Ser Tyr Lys Ser Ile Phe Val Leu Ser Pro Asn Phe
385                 390                 395                 400

Val Gln Ser Glu Trp Cys His Tyr Glu Leu Tyr Phe Ala His His Asn
                405                 410                 415

Leu Phe His Glu Gly Ser Asn Ser Leu Ile Leu Ile Leu Leu Glu Pro
            420                 425                 430

Ile Pro Gln Tyr Ser Ile Pro Ser Ser Tyr His Lys Leu Lys Ser Leu
            435                 440                 445

Met Ala Arg Arg Thr Tyr Leu Glu Trp Pro Lys Glu Lys Ser Lys Arg
    450                 455                 460

Gly Leu Phe Trp Ala Asn Leu Arg Ala Ala Ile Asn Ile Lys Leu Thr
465                 470                 475                 480

Glu Gln Ala Lys Lys Met Ser Leu Leu Asn Cys Glu Asn Ser Cys Gly
                485                 490                 495

Ser Ser Gln Ser Glu Ser Asp Cys Cys Val Ala Met Ala Ser Ser Cys
            500                 505                 510

Ser Ala Val Thr Lys Asp Asp Ser Val Gly Thr Ala Ser Thr Gly
            515                 520                 525

Asn Leu Ser Ser Ser Phe Met Glu Glu Ile Gln Gly Tyr Asp Val Glu
            530                 535                 540

Phe Asp Pro Pro Leu Glu Ser Lys Tyr Glu Cys Pro Ile Cys Leu Met
545                 550                 555                 560

Ala Leu Arg Glu Ala Val Gln Thr Pro Cys Gly His Arg Phe Cys Lys
                565                 570                 575

Ala Cys Ile Ile Lys Ser Ile Arg Asp Ala Gly His Lys Cys Pro Val
            580                 585                 590

Asp Asn Glu Ile Leu Leu Glu Asn Gln Leu Phe Pro Asp Asn Phe Ala
            595                 600                 605

Lys Arg Glu Ile Leu Ser Leu Met Val Lys Cys Pro Asn Glu Gly Cys
    610                 615                 620

Leu His Lys Met Glu Leu Arg His Leu Glu Asp His Gln Ala His Cys
625                 630                 635                 640

Glu Phe Ala Leu Met Asp Cys Pro Gln Cys Gln Arg Pro Phe Gln Lys
                645                 650                 655

Phe His Ile Asn Ile His Ile Leu Lys Asp Cys Pro Arg Arg Gln Val
            660                 665                 670

Ser Cys Asp Asn Cys Ala Ala Ser Met Ala Phe Glu Asp Lys Glu Ile
            675                 680                 685

His Asp Gln Asn Cys Pro Leu Ala Asn Val Ile Cys Glu Tyr Cys Asn
    690                 695                 700

Thr Ile Leu Ile Arg Glu Gln Met Pro Asn His Tyr Asp Leu Asp Cys
705                 710                 715                 720

Pro Thr Ala Pro Ile Pro Cys Thr Phe Ser Thr Phe Gly Cys His Glu
                725                 730                 735
```

```
Lys Met Gln Arg Asn His Leu Ala Arg His Leu Gln Glu Asn Thr Gln
                740                 745                 750

Ser His Met Arg Met Leu Ala
            755

<210> SEQ ID NO 158
<211> LENGTH: 113
<212> TYPE: PRT
<213> ORGANISM: Homo sapiens
<220> FEATURE:
<223> OTHER INFORMATION: wildtype CD3zeta signaling domain

<400> SEQUENCE: 158

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg

<210> SEQ ID NO 159
<211> LENGTH: 112
<212> TYPE: PRT
<213> ORGANISM: Homo sapiens
<220> FEATURE:
<223> OTHER INFORMATION: variant CD3zeta signaling domain

<400> SEQUENCE: 159

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 160
<211> LENGTH: 42
<212> TYPE: PRT
<213> ORGANISM: Homo sapiens
<220> FEATURE:
<223> OTHER INFORMATION: 4-1BB costimulatory signaling domain

<400> SEQUENCE: 160
```

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 161
<211> LENGTH: 41
<212> TYPE: PRT
<213> ORGANISM: Homo sapiens
<220> FEATURE:
<223> OTHER INFORMATION: CD28 costimulatory signaling domain variant,
      L186G/L187G substitutions with positions in
      reference to full length protein

<400> SEQUENCE: 161

Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 162
<211> LENGTH: 41
<212> TYPE: PRT
<213> ORGANISM: Homo sapiens
<220> FEATURE:
<223> OTHER INFORMATION: wildtype CD28 costimulatory signaling domain

<400> SEQUENCE: 162

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 163
<211> LENGTH: 527
<212> TYPE: PRT
<213> ORGANISM: Artificial Sequence
<220> FEATURE:
<223> OTHER INFORMATION: CER122, amino acids 1-22 are signal peptide

<400> SEQUENCE: 163

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
        35                  40                  45

Arg Asn Ser Met Cys Trp Gly Lys Gly Ser Cys Pro Asn Ser Lys Cys
    50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
```

```
              100                 105                 110
Arg Ile Glu Val Pro Gly Trp Phe Asn Asp Val Lys Lys Asn Val Arg
            115                 120                 125
Leu Glu Leu Arg Arg Ala Thr Thr Lys Lys Pro Thr Thr Thr Thr Thr
130                 135                 140
Arg Pro Thr Thr Thr Pro Tyr Val Thr Thr Thr Pro Glu Leu Leu
145                 150                 155                 160
Pro Thr Thr Val Met Thr Thr Ser Val Leu Pro Thr Thr Thr Pro Pro
                165                 170                 175
Gln Thr Leu Ala Thr Thr Ala Phe Ser Thr Ala Val Thr Thr Cys Pro
            180                 185                 190
Ser Thr Thr Pro Gly Ser Phe Ser Gln Glu Thr Thr Lys Gly Ser Ala
        195                 200                 205
Phe Thr Thr Glu Ser Glu Thr Leu Pro Ala Ser Asn His Ser Gln Arg
            210                 215                 220
Ser Met Met Thr Ile Ser Thr Asp Ile Ala Val Leu Arg Pro Thr Gly
225                 230                 235                 240
Ser Asn Pro Gly Ile Leu Pro Ser Thr Ser Gln Leu Thr Thr Gln Lys
                245                 250                 255
Thr Thr Leu Thr Thr Ser Glu Ser Leu Gln Lys Thr Thr Lys Ser His
            260                 265                 270
Gln Ile Asn Ser Arg Gln Thr Ile Leu Ile Ile Ala Cys Cys Val Gly
        275                 280                 285
Phe Val Leu Met Val Leu Leu Phe Leu Ala Phe Leu His Arg Phe His
            290                 295                 300
Gly Leu Trp Tyr Met Lys Met Met Trp Ala Trp Leu Gln Ala Lys Arg
305                 310                 315                 320
Lys Pro Arg Lys Ala Pro Ser Arg Asn Ile Cys Tyr Asp Ala Phe Val
                325                 330                 335
Ser Tyr Ser Glu Arg Asp Ala Tyr Trp Val Glu Asn Leu Met Val Gln
            340                 345                 350
Glu Leu Glu Asn Phe Asn Pro Pro Phe Lys Leu Cys Leu His Lys Arg
        355                 360                 365
Asp Phe Ile Pro Gly Lys Trp Ile Ile Asp Asn Ile Ile Asp Ser Ile
            370                 375                 380
Glu Lys Ser His Lys Thr Val Phe Val Leu Ser Glu Asn Phe Val Lys
385                 390                 395                 400
Ser Glu Trp Cys Lys Tyr Glu Leu Asp Phe Ser His Phe Arg Leu Phe
                405                 410                 415
Asp Glu Asn Asn Asp Ala Ala Ile Leu Ile Leu Leu Glu Pro Ile Glu
            420                 425                 430
Lys Lys Ala Ile Pro Gln Arg Phe Cys Lys Leu Arg Lys Ile Met Asn
        435                 440                 445
Thr Lys Thr Tyr Leu Glu Trp Pro Met Asp Glu Ala Gln Arg Glu Gly
            450                 455                 460
Phe Trp Val Asn Leu Arg Ala Ala Ile Lys Ser Tyr Phe Leu Gly Arg
465                 470                 475                 480
Leu Val Pro Arg Gly Arg Gly Ala Ala Glu Ala Ala Thr Arg Lys Gln
                485                 490                 495
Arg Ile Thr Glu Thr Glu Ser Pro Tyr Gln Glu Leu Gln Gly Gln Arg
            500                 505                 510
Ser Asp Val Tyr Ser Asp Leu Asn Thr Gln Arg Pro Tyr Tyr Lys
        515                 520                 525
```

<210> SEQ ID NO 164
<211> LENGTH: 749
<212> TYPE: PRT
<213> ORGANISM: Artificial Sequence
<220> FEATURE:
<223> OTHER INFORMATION: CER123, amino acids 1-22 are signal peptide

<400> SEQUENCE: 164

| Met | Ser | Lys | Gly | Leu | Leu | Leu | Trp | Leu | Val | Thr | Glu | Leu | Trp | Trp |
|---|---|---|---|---|---|---|---|---|---|---|---|---|---|---|
| 1 | | | | 5 | | | | | 10 | | | | | 15 |

| Leu | Tyr | Leu | Thr | Pro | Ala | Ala | Ser | Glu | Asp | Thr | Ile | Ile | Gly | Phe | Leu |
|---|---|---|---|---|---|---|---|---|---|---|---|---|---|---|---|
| | | | 20 | | | | | 25 | | | | | 30 | | |

| Gly | Gln | Pro | Val | Thr | Leu | Pro | Cys | His | Tyr | Leu | Ser | Trp | Ser | Gln | Ser |
|---|---|---|---|---|---|---|---|---|---|---|---|---|---|---|---|
| | | 35 | | | | | 40 | | | | | 45 | | | |

| Arg | Asn | Ser | Met | Cys | Trp | Gly | Lys | Gly | Ser | Cys | Pro | Asn | Ser | Lys | Cys |
|---|---|---|---|---|---|---|---|---|---|---|---|---|---|---|---|
| | 50 | | | | | 55 | | | | | 60 | | | | |

| Asn | Ala | Glu | Leu | Leu | Arg | Thr | Asp | Gly | Thr | Arg | Ile | Ile | Ser | Arg | Lys |
|---|---|---|---|---|---|---|---|---|---|---|---|---|---|---|---|
| 65 | | | | | 70 | | | | | 75 | | | | | 80 |

| Ser | Thr | Lys | Tyr | Thr | Leu | Leu | Gly | Lys | Val | Gln | Phe | Gly | Glu | Val | Ser |
|---|---|---|---|---|---|---|---|---|---|---|---|---|---|---|---|
| | | | | 85 | | | | | 90 | | | | | 95 | |

| Leu | Thr | Ile | Ser | Asn | Thr | Asn | Arg | Gly | Asp | Ser | Gly | Val | Tyr | Cys | Cys |
|---|---|---|---|---|---|---|---|---|---|---|---|---|---|---|---|
| | | | 100 | | | | | 105 | | | | | 110 | | |

| Arg | Ile | Glu | Val | Pro | Gly | Trp | Phe | Asn | Asp | Val | Lys | Lys | Asn | Val | Arg |
|---|---|---|---|---|---|---|---|---|---|---|---|---|---|---|---|
| | | 115 | | | | | 120 | | | | | 125 | | | |

| Leu | Glu | Leu | Arg | Arg | Ala | Thr | Thr | Thr | Lys | Lys | Pro | Thr | Thr | Thr | Thr |
|---|---|---|---|---|---|---|---|---|---|---|---|---|---|---|---|
| | 130 | | | | | 135 | | | | | 140 | | | | |

| Arg | Pro | Thr | Thr | Thr | Pro | Tyr | Val | Thr | Thr | Thr | Pro | Glu | Leu | Leu |
|---|---|---|---|---|---|---|---|---|---|---|---|---|---|---|
| 145 | | | | | 150 | | | | | 155 | | | | 160 |

| Pro | Thr | Thr | Val | Met | Thr | Thr | Ser | Val | Leu | Pro | Thr | Thr | Thr | Pro | Pro |
|---|---|---|---|---|---|---|---|---|---|---|---|---|---|---|---|
| | | | | 165 | | | | | 170 | | | | | 175 | |

| Gln | Thr | Leu | Ala | Thr | Thr | Ala | Phe | Ser | Thr | Ala | Val | Thr | Thr | Cys | Pro |
|---|---|---|---|---|---|---|---|---|---|---|---|---|---|---|---|
| | | | 180 | | | | | 185 | | | | | 190 | | |

| Ser | Thr | Thr | Pro | Gly | Ser | Phe | Ser | Gln | Glu | Thr | Thr | Lys | Gly | Ser | Ala |
|---|---|---|---|---|---|---|---|---|---|---|---|---|---|---|---|
| | | | 195 | | | | | 200 | | | | | 205 | | |

| Phe | Thr | Thr | Glu | Ser | Glu | Thr | Leu | Pro | Ala | Ser | Asn | His | Ser | Gln | Arg |
|---|---|---|---|---|---|---|---|---|---|---|---|---|---|---|---|
| | 210 | | | | | 215 | | | | | 220 | | | | |

| Ser | Met | Met | Thr | Ile | Ser | Thr | Asp | Ile | Ala | Val | Leu | Arg | Pro | Thr | Gly |
|---|---|---|---|---|---|---|---|---|---|---|---|---|---|---|---|
| 225 | | | | | 230 | | | | | 235 | | | | | 240 |

| Ser | Asn | Pro | Gly | Ile | Leu | Pro | Ser | Thr | Ser | Gln | Leu | Thr | Thr | Gln | Lys |
|---|---|---|---|---|---|---|---|---|---|---|---|---|---|---|---|
| | | | | 245 | | | | | 250 | | | | | 255 | |

| Thr | Thr | Leu | Thr | Thr | Ser | Glu | Ser | Leu | Gln | Lys | Thr | Thr | Lys | Ser | His |
|---|---|---|---|---|---|---|---|---|---|---|---|---|---|---|---|
| | | | 260 | | | | | 265 | | | | | 270 | | |

| Gln | Ile | Asn | Ser | Arg | Gln | Thr | Ile | Leu | Ile | Ala | Cys | Cys | Val | Gly |
|---|---|---|---|---|---|---|---|---|---|---|---|---|---|---|
| | | 275 | | | | | 280 | | | | | 285 | | |

| Phe | Val | Leu | Met | Val | Leu | Leu | Phe | Leu | Ala | Phe | Leu | His | Arg | Phe | His |
|---|---|---|---|---|---|---|---|---|---|---|---|---|---|---|---|
| | 290 | | | | | 295 | | | | | 300 | | | | |

| Gly | Leu | Trp | Tyr | Met | Lys | Met | Met | Trp | Ala | Trp | Leu | Gln | Ala | Lys | Arg |
|---|---|---|---|---|---|---|---|---|---|---|---|---|---|---|---|
| 305 | | | | | 310 | | | | | 315 | | | | | 320 |

| Lys | Pro | Arg | Lys | Ala | Pro | Ser | Arg | Asn | Ile | Cys | Tyr | Asp | Ala | Phe | Val |
|---|---|---|---|---|---|---|---|---|---|---|---|---|---|---|---|
| | | | | 325 | | | | | 330 | | | | | 335 | |

| Ser | Tyr | Ser | Glu | Arg | Asp | Ala | Tyr | Trp | Val | Glu | Asn | Leu | Met | Val | Gln |
|---|---|---|---|---|---|---|---|---|---|---|---|---|---|---|---|
| | | | 340 | | | | | 345 | | | | | 350 | | |

| Glu | Leu | Glu | Asn | Phe | Asn | Pro | Pro | Phe | Lys | Leu | Cys | Leu | His | Lys | Arg |
|---|---|---|---|---|---|---|---|---|---|---|---|---|---|---|---|
| | | | 355 | | | | | 360 | | | | | 365 | | |

Asp Phe Ile Pro Gly Lys Trp Ile Ile Asp Asn Ile Ile Asp Ser Ile
                370                 375                 380

Glu Lys Ser His Lys Thr Val Phe Val Leu Ser Glu Asn Phe Val Lys
385                 390                 395                 400

Ser Glu Trp Cys Lys Tyr Glu Leu Asp Phe Ser His Phe Arg Leu Phe
                405                 410                 415

Asp Glu Asn Asn Asp Ala Ala Ile Leu Ile Leu Leu Glu Pro Ile Glu
                420                 425                 430

Lys Lys Ala Ile Pro Gln Arg Phe Cys Lys Leu Arg Lys Ile Met Asn
                435                 440                 445

Thr Lys Thr Tyr Leu Glu Trp Pro Met Asp Glu Ala Gln Arg Glu Gly
                450                 455                 460

Phe Trp Val Asn Leu Arg Ala Ala Ile Lys Ser Met Ser Leu Leu Asn
465                 470                 475                 480

Cys Glu Asn Ser Cys Gly Ser Ser Gln Ser Glu Ser Asp Cys Cys Val
                485                 490                 495

Ala Met Ala Ser Ser Cys Ser Ala Val Thr Lys Asp Asp Ser Val Gly
                500                 505                 510

Gly Thr Ala Ser Thr Gly Asn Leu Ser Ser Ser Phe Met Glu Glu Ile
                515                 520                 525

Gln Gly Tyr Asp Val Glu Phe Asp Pro Pro Leu Glu Ser Lys Tyr Glu
                530                 535                 540

Cys Pro Ile Cys Leu Met Ala Leu Arg Glu Ala Val Gln Thr Pro Cys
545                 550                 555                 560

Gly His Arg Phe Cys Lys Ala Cys Ile Ile Lys Ser Ile Arg Asp Ala
                565                 570                 575

Gly His Lys Cys Pro Val Asp Asn Glu Ile Leu Leu Glu Asn Gln Leu
                580                 585                 590

Phe Pro Asp Asn Phe Ala Lys Arg Glu Ile Leu Ser Leu Met Val Lys
                595                 600                 605

Cys Pro Asn Glu Gly Cys Leu His Lys Met Glu Leu Arg His Leu Glu
                610                 615                 620

Asp His Gln Ala His Cys Glu Phe Ala Leu Met Asp Cys Pro Gln Cys
625                 630                 635                 640

Gln Arg Pro Phe Gln Lys Phe His Ile Asn Ile His Ile Leu Lys Asp
                645                 650                 655

Cys Pro Arg Arg Gln Val Ser Cys Asp Asn Cys Ala Ala Ser Met Ala
                660                 665                 670

Phe Glu Asp Lys Glu Ile His Asp Gln Asn Cys Pro Leu Ala Asn Val
                675                 680                 685

Ile Cys Glu Tyr Cys Asn Thr Ile Leu Ile Arg Glu Gln Met Pro Asn
690                 695                 700

His Tyr Asp Leu Asp Cys Pro Thr Ala Pro Ile Pro Cys Thr Phe Ser
705                 710                 715                 720

Thr Phe Gly Cys His Glu Lys Met Gln Arg Asn His Leu Ala Arg His
                725                 730                 735

Leu Gln Glu Asn Thr Gln Ser His Met Arg Met Leu Ala
                740                 745

<210> SEQ ID NO 165
<211> LENGTH: 561
<212> TYPE: PRT
<213> ORGANISM: Artificial Sequence
<220> FEATURE:

<223> OTHER INFORMATION: CER124, amino acids 1-22 are signal peptide

<400> SEQUENCE: 165

```
Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
                20                  25                  30

Gly Gln Pro Val Thr Leu Pro Cys His Tyr Leu Ser Trp Ser Gln Ser
                35                  40                  45

Arg Asn Ser Met Cys Trp Gly Lys Gly Ser Cys Pro Asn Ser Lys Cys
50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
                100                 105                 110

Arg Ile Glu Val Pro Gly Trp Phe Asn Asp Val Lys Lys Asn Val Arg
                115                 120                 125

Leu Glu Leu Arg Arg Ala Thr Thr Thr Lys Lys Pro Thr Thr Thr Thr
130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
                180                 185                 190

Ser Thr Thr Pro Gly Ser Phe Ser Gln Glu Thr Thr Lys Gly Ser Ala
                195                 200                 205

Phe Thr Thr Glu Ser Glu Thr Leu Pro Ala Ser Asn His Ser Gln Arg
210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
                260                 265                 270

Gln Ile Asn Ser Arg Gln Thr Ile Leu Ile Ala Cys Cys Val Gly
                275                 280                 285

Phe Val Leu Met Val Leu Leu Phe Leu Ala Phe Leu His Arg Phe His
                290                 295                 300

Gly Leu Trp Tyr Met Lys Met Met Trp Ala Trp Leu Gln Ala Lys Arg
305                 310                 315                 320

Lys Pro Arg Lys Ala Pro Ser Arg Asn Ile Cys Tyr Asp Ala Phe Val
                325                 330                 335

Ser Tyr Ser Glu Arg Asp Ala Tyr Trp Val Glu Asn Leu Met Val Gln
                340                 345                 350

Glu Leu Glu Asn Phe Asn Pro Pro Phe Lys Leu Cys Leu His Lys Arg
                355                 360                 365

Asp Phe Ile Pro Gly Lys Trp Ile Ile Asp Asn Ile Ile Asp Ser Ile
                370                 375                 380

Glu Lys Ser His Lys Thr Val Phe Val Leu Ser Glu Asn Phe Val Lys
385                 390                 395                 400
```

```
Ser Glu Trp Cys Lys Tyr Glu Leu Asp Phe Ser His Phe Arg Leu Phe
                405                 410                 415
Asp Glu Asn Asn Asp Ala Ala Ile Leu Ile Leu Leu Glu Pro Ile Glu
            420                 425                 430
Lys Lys Ala Ile Pro Gln Arg Phe Cys Lys Leu Arg Lys Ile Met Asn
        435                 440                 445
Thr Lys Thr Tyr Leu Glu Trp Pro Met Asp Glu Ala Gln Arg Glu Gly
    450                 455                 460
Phe Trp Val Asn Leu Arg Ala Ala Ile Lys Ser Leu Trp Asn Lys Lys
465                 470                 475                 480
Arg Met Arg Gly Pro Gly Lys Asp Pro Thr Arg Lys Cys Pro Asp Pro
                485                 490                 495
Arg Ser Ala Ser Ser Pro Lys Gln His Pro Ser Glu Ser Val Tyr Thr
            500                 505                 510
Ala Leu Gln Arg Arg Glu Thr Glu Val Tyr Ala Cys Ile Glu Asn Glu
        515                 520                 525
Asp Gly Ser Ser Pro Thr Ala Lys Gln Ser Pro Leu Ser Gln Glu Arg
    530                 535                 540
Pro His Arg Phe Glu Asp Asp Gly Glu Leu Asn Leu Val Tyr Glu Asn
545                 550                 555                 560
Leu

<210> SEQ ID NO 166
<211> LENGTH: 520
<212> TYPE: PRT
<213> ORGANISM: Artificial Sequence
<220> FEATURE:
<223> OTHER INFORMATION: CER125A, amino acids 1-22 are signal peptide

<400> SEQUENCE: 166

Met Ser Lys Gly Leu Leu Leu Trp Leu Val Thr Glu Leu Trp Trp
1               5                   10                  15
Leu Tyr Leu Thr Pro Ala Ala Ser Glu Asp Thr Ile Ile Gly Phe Leu
                20                  25                  30
Gly Gln Pro Val Thr Leu Pro Cys His Tyr Leu Ser Trp Ser Gln Ser
            35                  40                  45
Arg Asn Ser Met Cys Trp Gly Lys Gly Ser Cys Pro Asn Ser Lys Cys
        50                  55                  60
Asn Ala Glu Leu Leu Arg Thr Asp Gly Thr Arg Ile Ile Ser Arg Lys
65                  70                  75                  80
Ser Thr Lys Tyr Thr Leu Leu Gly Lys Val Gln Phe Gly Glu Val Ser
                85                  90                  95
Leu Thr Ile Ser Asn Thr Asn Arg Gly Asp Ser Gly Val Tyr Cys Cys
            100                 105                 110
Arg Ile Glu Val Pro Gly Trp Phe Asn Asp Val Lys Lys Asn Val Arg
        115                 120                 125
Leu Glu Leu Arg Arg Ala Thr Thr Thr Lys Lys Pro Thr Thr Thr Thr
    130                 135                 140
Arg Pro Thr Thr Thr Pro Tyr Val Thr Thr Thr Pro Glu Leu Leu
145                 150                 155                 160
Pro Thr Thr Val Met Thr Thr Ser Val Leu Pro Thr Thr Pro Pro
                165                 170                 175
Gln Thr Leu Ala Thr Ala Phe Ser Thr Ala Val Thr Thr Cys Pro
            180                 185                 190
Ser Thr Thr Pro Gly Ser Phe Ser Gln Glu Thr Thr Lys Gly Ser Ala
```

```
                195                 200                 205
Phe Thr Thr Glu Ser Glu Thr Leu Pro Ala Ser Asn His Ser Gln Arg
210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ala Cys Cys Val Gly
            275                 280                 285

Phe Val Leu Met Val Leu Leu Phe Leu Ala Phe Leu His Arg Phe His
290                 295                 300

Gly Leu Trp Tyr Met Lys Met Met Trp Ala Trp Leu Gln Ala Lys Arg
305                 310                 315                 320

Lys Pro Arg Lys Ala Pro Ser Arg Asn Ile Cys Tyr Asp Ala Phe Val
                325                 330                 335

Ser Tyr Ser Glu Arg Asp Ala Tyr Trp Val Glu Asn Leu Met Val Gln
            340                 345                 350

Glu Leu Glu Asn Phe Asn Pro Pro Phe Lys Leu Cys Leu His Lys Arg
            355                 360                 365

Asp Phe Ile Pro Gly Lys Trp Ile Ile Asp Asn Ile Ile Asp Ser Ile
370                 375                 380

Glu Lys Ser His Lys Thr Val Phe Val Leu Ser Glu Asn Phe Val Lys
385                 390                 395                 400

Ser Glu Trp Cys Lys Tyr Glu Leu Asp Phe Ser His Phe Arg Leu Phe
                405                 410                 415

Asp Glu Asn Asn Asp Ala Ala Ile Leu Ile Leu Leu Glu Pro Ile Glu
            420                 425                 430

Lys Lys Ala Ile Pro Gln Arg Phe Cys Lys Leu Arg Lys Ile Met Asn
            435                 440                 445

Thr Lys Thr Tyr Leu Glu Trp Pro Met Asp Glu Ala Gln Arg Glu Gly
450                 455                 460

Phe Trp Val Asn Leu Arg Ala Ala Ile Lys Ser Asp Ser Lys Ala Gly
465                 470                 475                 480

Met Glu Glu Asp His Thr Tyr Glu Gly Leu Asp Ile Asp Gln Thr Ala
                485                 490                 495

Thr Tyr Glu Asp Ile Val Thr Leu Arg Thr Gly Glu Val Lys Trp Ser
            500                 505                 510

Val Gly Glu His Pro Gly Gln Glu
            515                 520

<210> SEQ ID NO 167
<211> LENGTH: 504
<212> TYPE: PRT
<213> ORGANISM: Artificial Sequence
<220> FEATURE:
<223> OTHER INFORMATION: CER125B,amino acids 1-22 are signal peptide

<400> SEQUENCE: 167

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
                20                  25                  30

Gly Gln Pro Val Thr Leu Pro Cys His Tyr Leu Ser Trp Ser Gln Ser
```

-continued

```
                35                  40                  45
Arg Asn Ser Met Cys Trp Gly Lys Gly Ser Cys Pro Asn Ser Lys Cys
 50                  55                  60
Asn Ala Glu Leu Leu Arg Thr Asp Gly Thr Arg Ile Ile Ser Arg Lys
 65                  70                  75                  80
Ser Thr Lys Tyr Thr Leu Leu Gly Lys Val Gln Phe Gly Glu Val Ser
                 85                  90                  95
Leu Thr Ile Ser Asn Thr Asn Arg Gly Asp Ser Gly Val Tyr Cys Cys
                100                 105                 110
Arg Ile Glu Val Pro Gly Trp Phe Asn Asp Val Lys Lys Asn Val Arg
                115                 120                 125
Leu Glu Leu Arg Arg Ala Thr Thr Lys Lys Pro Thr Thr Thr Thr Thr
                130                 135                 140
Arg Pro Thr Thr Thr Pro Tyr Val Thr Thr Thr Pro Glu Leu Leu
145                 150                 155                 160
Pro Thr Thr Val Met Thr Thr Ser Val Leu Pro Thr Thr Thr Pro Pro
                165                 170                 175
Gln Thr Leu Ala Thr Thr Ala Phe Ser Thr Ala Val Thr Thr Cys Pro
                180                 185                 190
Ser Thr Thr Pro Gly Ser Phe Ser Gln Glu Thr Thr Lys Gly Ser Ala
                195                 200                 205
Phe Thr Thr Glu Ser Glu Thr Leu Pro Ala Ser Asn His Ser Gln Arg
                210                 215                 220
Ser Met Met Thr Ile Ser Thr Asp Ile Ala Val Leu Arg Pro Thr Gly
225                 230                 235                 240
Ser Asn Pro Gly Ile Leu Pro Ser Thr Ser Gln Leu Thr Thr Gln Lys
                245                 250                 255
Thr Thr Leu Thr Thr Ser Glu Ser Leu Gln Lys Thr Thr Lys Ser His
                260                 265                 270
Gln Ile Asn Ser Arg Gln Thr Ile Leu Ile Ile Ala Cys Cys Val Gly
                275                 280                 285
Phe Val Leu Met Val Leu Leu Phe Leu Ala Phe Leu His Arg Phe His
                290                 295                 300
Gly Leu Trp Tyr Met Lys Met Met Trp Ala Trp Leu Gln Ala Lys Arg
305                 310                 315                 320
Lys Pro Arg Lys Ala Pro Ser Arg Asn Ile Cys Tyr Asp Ala Phe Val
                325                 330                 335
Ser Tyr Ser Glu Arg Asp Ala Tyr Trp Val Glu Asn Leu Met Val Gln
                340                 345                 350
Glu Leu Glu Asn Phe Asn Pro Pro Phe Lys Leu Cys Leu His Lys Arg
                355                 360                 365
Asp Phe Ile Pro Gly Lys Trp Ile Ile Asp Asn Ile Ile Asp Ser Ile
                370                 375                 380
Glu Lys Ser His Lys Thr Val Phe Val Leu Ser Glu Asn Phe Val Lys
385                 390                 395                 400
Ser Glu Trp Cys Lys Tyr Glu Leu Asp Phe Ser His Phe Arg Leu Phe
                405                 410                 415
Asp Glu Asn Asn Asp Ala Ala Ile Leu Ile Leu Leu Glu Pro Ile Glu
                420                 425                 430
Lys Lys Ala Ile Pro Gln Arg Phe Cys Lys Leu Arg Lys Ile Met Asn
                435                 440                 445
Thr Lys Thr Tyr Leu Glu Trp Pro Met Asp Glu Ala Gln Arg Glu Gly
                450                 455                 460
```

```
Phe Trp Val Asn Leu Arg Ala Ala Ile Lys Ser Asp Ser Lys Ala Gly
465                 470                 475                 480

Met Glu Glu Asp His Thr Tyr Glu Gly Leu Asp Ile Asp Gln Thr Ala
                485                 490                 495

Thr Tyr Glu Asp Ile Val Thr Leu
            500

<210> SEQ ID NO 168
<211> LENGTH: 24
<212> TYPE: PRT
<213> ORGANISM: Artificial Sequence
<220> FEATURE:
<223> OTHER INFORMATION: T2A self-cleaving peptide variant

<400> SEQUENCE: 168

Leu Glu Gly Gly Gly Glu Gly Arg Gly Ser Leu Leu Thr Cys Gly Asp
1               5                   10                  15

Val Glu Glu Asn Pro Gly Pro Arg
            20

<210> SEQ ID NO 169
<211> LENGTH: 778
<212> TYPE: PRT
<213> ORGANISM: Artificial Sequence
<220> FEATURE:
<223> OTHER INFORMATION: CER126, amino acids 1-22 are signal peptide

<400> SEQUENCE: 169

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
                20                  25                  30

Gly Gln Pro Val Thr Leu Pro Cys His Tyr Leu Ser Trp Ser Gln Ser
            35                  40                  45

Arg Asn Ser Met Cys Trp Gly Lys Gly Ser Cys Pro Asn Ser Lys Cys
        50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Thr Lys Lys Pro Thr Thr Thr Thr
130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
    210                 215                 220

Ser Met Met Thr Ile Ser Thr Asp Ile Ala Val Leu Arg Pro Thr Gly
```

```
                225                 230                 235                 240
        Ser Asn Pro Gly Ile Leu Pro Ser Thr Ser Gln Leu Thr Thr Gln Lys
                        245                 250                 255

Thr Thr Leu Thr Thr Ser Glu Ser Leu Gln Lys Thr Thr Lys Ser His
                        260                 265                 270

Gln Ile Asn Ser Arg Gln Thr Ile Leu Ile Ala Cys Cys Val Gly
                        275                 280                 285

Phe Val Leu Met Val Leu Leu Phe Leu Ala Phe Leu His Arg Phe His
                290                 295                 300

Gly Leu Trp Tyr Met Lys Met Met Trp Ala Trp Leu Gln Ala Lys Arg
        305                 310                 315                 320

Lys Pro Arg Lys Ala Pro Ser Arg Asn Ile Cys Tyr Asp Ala Phe Val
                        325                 330                 335

Ser Tyr Ser Glu Arg Asp Ala Tyr Trp Val Glu Asn Leu Met Val Gln
                        340                 345                 350

Glu Leu Glu Asn Phe Asn Pro Pro Phe Lys Leu Cys Leu His Lys Arg
                        355                 360                 365

Asp Phe Ile Pro Gly Lys Trp Ile Ile Asp Asn Ile Ile Asp Ser Ile
                370                 375                 380

Glu Lys Ser His Lys Thr Val Phe Val Leu Ser Glu Asn Phe Val Lys
        385                 390                 395                 400

Ser Glu Trp Cys Lys Tyr Glu Leu Asp Phe Ser His Phe Arg Leu Phe
                        405                 410                 415

Asp Glu Asn Asn Asp Ala Ala Ile Leu Ile Leu Leu Glu Pro Ile Glu
                        420                 425                 430

Lys Lys Ala Ile Pro Gln Arg Phe Cys Lys Leu Arg Lys Ile Met Asn
                        435                 440                 445

Thr Lys Thr Tyr Leu Glu Trp Pro Met Asp Glu Ala Gln Arg Glu Gly
                450                 455                 460

Phe Trp Val Asn Leu Arg Ala Ala Ile Lys Ser Met Ala Ala Ala Ser
        465                 470                 475                 480

Val Thr Pro Pro Gly Ser Leu Glu Leu Leu Gln Pro Gly Phe Ser Lys
                        485                 490                 495

Thr Leu Leu Gly Thr Lys Leu Glu Ala Lys Tyr Leu Cys Ser Ala Cys
                        500                 505                 510

Arg Asn Val Leu Arg Arg Pro Phe Gln Ala Gln Cys Gly His Arg Tyr
                        515                 520                 525

Cys Ser Phe Cys Leu Ala Ser Ile Leu Ser Ser Gly Pro Gln Asn Cys
                530                 535                 540

Ala Ala Cys Val His Glu Gly Ile Tyr Glu Glu Gly Ile Ser Ile Leu
        545                 550                 555                 560

Glu Ser Ser Ser Ala Phe Pro Asp Asn Ala Ala Arg Arg Glu Val Glu
                        565                 570                 575

Ser Leu Pro Ala Val Cys Pro Ser Asp Gly Cys Thr Trp Lys Gly Thr
                        580                 585                 590

Leu Lys Glu Tyr Glu Ser Cys His Glu Gly Arg Cys Pro Leu Met Leu
                        595                 600                 605

Thr Glu Cys Pro Ala Cys Lys Gly Leu Val Arg Leu Gly Glu Lys Glu
                        610                 615                 620

Arg His Leu Glu His Glu Cys Pro Glu Arg Ser Leu Ser Cys Arg His
        625                 630                 635                 640

Cys Arg Ala Pro Cys Cys Gly Ala Asp Val Lys Ala His His Glu Val
                        645                 650                 655
```

```
Cys Pro Lys Phe Pro Leu Thr Cys Asp Gly Cys Gly Lys Lys Ile
            660                 665                 670

Pro Arg Glu Lys Phe Gln Asp His Val Lys Thr Cys Gly Lys Cys Arg
        675                 680                 685

Val Pro Cys Arg Phe His Ala Ile Gly Cys Leu Glu Thr Val Glu Gly
    690                 695                 700

Glu Lys Gln Gln Glu His Glu Val Gln Trp Leu Arg Glu His Leu Ala
705                 710                 715                 720

Met Leu Leu Ser Ser Val Leu Glu Ala Lys Pro Leu Leu Gly Asp Gln
                725                 730                 735

Ser His Ala Gly Ser Glu Leu Leu Gln Arg Cys Glu Ser Leu Glu Lys
            740                 745                 750

Lys Thr Ala Thr Phe Glu Asn Ile Val Cys Val Leu Asn Arg Glu Val
        755                 760                 765

Glu Arg Val Ala Met Thr Ala Glu Ala Cys
    770                 775
```

<210> SEQ ID NO 170
<211> LENGTH: 778
<212> TYPE: PRT
<213> ORGANISM: Artificial Sequence
<220> FEATURE:
<223> OTHER INFORMATION: CER127, amino acids 1-22 are signal peptide

<400> SEQUENCE: 170

```
Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
        35                  40                  45

Arg Asn Ser Met Cys Trp Gly Lys Gly Ser Cys Pro Asn Ser Lys Cys
    50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Lys Lys Pro Thr Thr Thr Thr
    130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Ala Phe Ser Thr Ala Val Thr Thr Cys Pro
            180                 185                 190

Ser Thr Thr Pro Gly Ser Phe Ser Gln Glu Thr Lys Gly Ser Ala
        195                 200                 205

Phe Thr Thr Glu Ser Glu Thr Leu Pro Ala Ser Asn His Ser Gln Arg
    210                 215                 220

Ser Met Met Thr Ile Ser Thr Asp Ile Ala Val Leu Arg Pro Thr Gly
225                 230                 235                 240
```

```
Ser Asn Pro Gly Ile Leu Pro Ser Thr Ser Gln Leu Thr Thr Gln Lys
            245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ala Cys Cys Val Gly
            275                 280                 285

Phe Val Leu Met Val Leu Leu Phe Leu Ala Phe Leu Met Ala Ala Ala
            290                 295                 300

Ser Val Thr Pro Pro Gly Ser Leu Glu Leu Leu Gln Pro Gly Phe Ser
305                 310                 315                 320

Lys Thr Leu Leu Gly Thr Lys Leu Glu Ala Lys Tyr Leu Cys Ser Ala
            325                 330                 335

Cys Arg Asn Val Leu Arg Arg Pro Phe Gln Ala Gln Cys Gly His Arg
            340                 345                 350

Tyr Cys Ser Phe Cys Leu Ala Ser Ile Leu Ser Ser Gly Pro Gln Asn
            355                 360                 365

Cys Ala Ala Cys Val His Glu Gly Ile Tyr Glu Glu Gly Ile Ser Ile
            370                 375                 380

Leu Glu Ser Ser Ser Ala Phe Pro Asp Asn Ala Ala Arg Arg Glu Val
385                 390                 395                 400

Glu Ser Leu Pro Ala Val Cys Pro Ser Asp Gly Cys Thr Trp Lys Gly
            405                 410                 415

Thr Leu Lys Glu Tyr Glu Ser Cys His Glu Gly Arg Cys Pro Leu Met
            420                 425                 430

Leu Thr Glu Cys Pro Ala Cys Lys Gly Leu Val Arg Leu Gly Glu Lys
            435                 440                 445

Glu Arg His Leu Glu His Glu Cys Pro Glu Arg Ser Leu Ser Cys Arg
            450                 455                 460

His Cys Arg Ala Pro Cys Cys Gly Ala Asp Val Lys Ala His His Glu
465                 470                 475                 480

Val Cys Pro Lys Phe Pro Leu Thr Cys Asp Gly Cys Gly Lys Lys Lys
            485                 490                 495

Ile Pro Arg Glu Lys Phe Gln Asp His Val Lys Thr Cys Gly Lys Cys
            500                 505                 510

Arg Val Pro Cys Arg Phe His Ala Ile Gly Cys Leu Glu Thr Val Glu
            515                 520                 525

Gly Glu Lys Gln Gln Glu His Glu Val Gln Trp Leu Arg Glu His Leu
            530                 535                 540

Ala Met Leu Leu Ser Ser Val Leu Glu Ala Lys Pro Leu Leu Gly Asp
545                 550                 555                 560

Gln Ser His Ala Gly Ser Glu Leu Leu Gln Arg Cys Glu Ser Leu Glu
            565                 570                 575

Lys Lys Thr Ala Thr Phe Glu Asn Ile Val Cys Val Leu Asn Arg Glu
            580                 585                 590

Val Glu Arg Val Ala Met Thr Ala Glu Ala Cys His Arg Phe His Gly
            595                 600                 605

Leu Trp Tyr Met Lys Met Met Trp Ala Trp Leu Gln Ala Lys Arg Lys
            610                 615                 620

Pro Arg Lys Ala Pro Ser Arg Asn Ile Cys Tyr Asp Ala Phe Val Ser
625                 630                 635                 640

Tyr Ser Glu Arg Asp Ala Tyr Trp Val Glu Asn Leu Met Val Gln Glu
            645                 650                 655
```

-continued

```
Leu Glu Asn Phe Asn Pro Pro Phe Lys Leu Cys Leu His Lys Arg Asp
            660                 665                 670

Phe Ile Pro Gly Lys Trp Ile Ile Asp Asn Ile Asp Ser Ile Glu
        675                 680                 685

Lys Ser His Lys Thr Val Phe Val Leu Ser Glu Asn Phe Val Lys Ser
    690                 695                 700

Glu Trp Cys Lys Tyr Glu Leu Asp Phe Ser His Phe Arg Leu Phe Asp
705                 710                 715                 720

Glu Asn Asn Asp Ala Ala Ile Leu Ile Leu Glu Pro Ile Glu Lys
                725                 730                 735

Lys Ala Ile Pro Gln Arg Phe Cys Lys Leu Arg Lys Ile Met Asn Thr
            740                 745                 750

Lys Thr Tyr Leu Glu Trp Pro Met Asp Glu Ala Gln Arg Glu Gly Phe
        755                 760                 765

Trp Val Asn Leu Arg Ala Ala Ile Lys Ser
        770                 775

<210> SEQ ID NO 171
<211> LENGTH: 796
<212> TYPE: PRT
<213> ORGANISM: Artificial Sequence
<220> FEATURE:
<223> OTHER INFORMATION: CER128, amino acids 1-22 are signal peptide

<400> SEQUENCE: 171

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
        35                  40                  45

Arg Asn Ser Met Cys Trp Gly Lys Gly Ser Cys Pro Asn Ser Lys Cys
    50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Lys Lys Pro Thr Thr Thr
    130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
    210                 215                 220

Ser Met Met Thr Ile Ser Thr Asp Ile Ala Val Leu Arg Pro Thr Gly
225                 230                 235                 240
```

```
Ser Asn Pro Gly Ile Leu Pro Ser Thr Ser Gln Leu Thr Thr Gln Lys
            245                 250                 255

Thr Thr Leu Thr Thr Ser Glu Ser Leu Gln Lys Thr Thr Lys Ser His
        260                 265                 270

Gln Ile Asn Ser Arg Gln Thr Ile Leu Ile Ala Cys Cys Val Gly
    275                 280                 285

Phe Val Leu Met Val Leu Leu Phe Leu Ala Phe Leu Met Ala Ala Ala
290                 295                 300

Ser Val Thr Pro Pro Gly Ser Leu Glu Leu Leu Gln Pro Gly Phe Ser
305                 310                 315                 320

Lys Thr Leu Leu Gly Thr Lys Leu Glu Ala Lys Tyr Leu Cys Ser Ala
                325                 330                 335

Cys Arg Asn Val Leu Arg Arg Pro Phe Gln Ala Gln Cys Gly His Arg
            340                 345                 350

Tyr Cys Ser Phe Cys Leu Ala Ser Ile Leu Ser Ser Gly Pro Gln Asn
        355                 360                 365

Cys Ala Ala Cys Val His Glu Gly Ile Tyr Glu Glu Gly Ile Ser Ile
    370                 375                 380

Leu Glu Ser Ser Ser Ala Phe Pro Asp Asn Ala Ala Arg Arg Glu Val
385                 390                 395                 400

Glu Ser Leu Pro Ala Val Cys Pro Ser Asp Gly Cys Thr Trp Lys Gly
                405                 410                 415

Thr Leu Lys Glu Tyr Glu Ser Cys His Glu Gly Arg Cys Pro Leu Met
            420                 425                 430

Leu Thr Glu Cys Pro Ala Cys Lys Gly Leu Val Arg Leu Gly Glu Lys
        435                 440                 445

Glu Arg His Leu Glu His Glu Cys Pro Glu Arg Ser Leu Ser Cys Arg
    450                 455                 460

His Cys Arg Ala Pro Cys Cys Gly Ala Asp Val Lys Ala His His Glu
465                 470                 475                 480

Val Cys Pro Lys Phe Pro Leu Thr Cys Asp Gly Cys Gly Lys Lys Lys
                485                 490                 495

Ile Pro Arg Glu Lys Phe Gln Asp His Val Lys Thr Cys Gly Lys Cys
            500                 505                 510

Arg Val Pro Cys Arg Phe His Ala Ile Gly Cys Leu Glu Thr Val Glu
        515                 520                 525

Gly Glu Lys Gln Gln Glu His Glu Val Gln Trp Leu Arg Glu His Leu
    530                 535                 540

Ala Met Leu Leu Ser Ser Val Leu Glu Ala Lys Pro Leu Leu Gly Asp
545                 550                 555                 560

Gln Ser His Ala Gly Ser Glu Leu Leu Gln Arg Cys Glu Ser Leu Glu
                565                 570                 575

Lys Lys Thr Ala Thr Phe Glu Asn Ile Val Cys Val Leu Asn Arg Glu
            580                 585                 590

Val Glu Arg Val Ala Met Thr Ala Glu Ala Cys His His Leu Phe Tyr
        595                 600                 605

Trp Asp Val Trp Phe Ile Tyr Asn Val Cys Leu Ala Lys Val Lys Gly
    610                 615                 620

Tyr Arg Ser Leu Ser Thr Ser Gln Thr Phe Tyr Asp Ala Tyr Ile Ser
625                 630                 635                 640

Tyr Asp Thr Lys Asp Ala Ser Val Thr Asp Trp Val Ile Asn Glu Leu
                645                 650                 655

Arg Tyr His Leu Glu Glu Ser Arg Asp Lys Asn Val Leu Leu Cys Leu
```

```
                  660                 665                 670
Glu Glu Arg Asp Trp Asp Pro Gly Leu Ala Ile Ile Asp Asn Leu Met
            675                 680                 685

Gln Ser Ile Asn Gln Ser Lys Lys Thr Val Phe Val Leu Thr Lys Lys
        690                 695                 700

Tyr Ala Lys Ser Trp Asn Phe Lys Thr Ala Phe Tyr Leu Ala Leu Gln
705                 710                 715                 720

Arg Leu Met Asp Glu Asn Met Asp Val Ile Ile Phe Ile Leu Leu Glu
                725                 730                 735

Pro Val Leu Gln His Ser Gln Tyr Leu Arg Leu Arg Gln Arg Ile Cys
                740                 745                 750

Lys Ser Ser Ile Leu Gln Trp Pro Asp Asn Pro Lys Ala Glu Gly Leu
            755                 760                 765

Phe Trp Gln Thr Leu Arg Asn Val Val Leu Thr Glu Asn Asp Ser Arg
        770                 775                 780

Tyr Asn Asn Met Tyr Val Asp Ser Ile Lys Gln Tyr
785                 790                 795

<210> SEQ ID NO 172
<211> LENGTH: 796
<212> TYPE: PRT
<213> ORGANISM: Artificial Sequence
<220> FEATURE:
<223> OTHER INFORMATION: CER129, amino acids 1-22 are signal peptide

<400> SEQUENCE: 172

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
        35                  40                  45

Arg Asn Ser Met Cys Trp Gly Lys Gly Ser Cys Pro Asn Ser Lys Cys
    50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Thr Lys Lys Pro Thr Thr Thr Thr
    130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Pro Pro
                165                 170                 175

Gln Thr Leu Ala Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
    210                 215                 220

Ser Met Met Thr Ile Ser Thr Asp Ile Ala Val Leu Arg Pro Thr Gly
```

-continued

```
                225                 230                 235                 240
Ser Asn Pro Gly Ile Leu Pro Ser Thr Ser Gln Leu Thr Thr Gln Lys
                    245                 250                 255

Thr Thr Leu Thr Thr Ser Glu Ser Leu Gln Lys Thr Thr Lys Ser His
                260                 265                 270

Gln Ile Asn Ser Arg Gln Thr Ile Leu Ile Ala Cys Cys Val Gly
                275                 280                 285

Phe Val Leu Met Val Leu Leu Phe Leu Ala Phe Leu His His Leu Phe
        290                 295                 300

Tyr Trp Asp Val Trp Phe Ile Tyr Asn Val Cys Leu Ala Lys Val Lys
305                 310                 315                 320

Gly Tyr Arg Ser Leu Ser Thr Ser Gln Thr Phe Tyr Asp Ala Tyr Ile
                325                 330                 335

Ser Tyr Asp Thr Lys Asp Ala Ser Val Thr Asp Trp Val Ile Asn Glu
                340                 345                 350

Leu Arg Tyr His Leu Glu Glu Ser Arg Asp Lys Asn Val Leu Leu Cys
                355                 360                 365

Leu Glu Glu Arg Asp Trp Asp Pro Gly Leu Ala Ile Ile Asp Asn Leu
        370                 375                 380

Met Gln Ser Ile Asn Gln Ser Lys Lys Thr Val Phe Val Leu Thr Lys
385                 390                 395                 400

Lys Tyr Ala Lys Ser Trp Asn Phe Lys Thr Ala Phe Tyr Leu Ala Leu
                405                 410                 415

Gln Arg Leu Met Asp Glu Asn Met Asp Val Ile Ile Phe Ile Leu Leu
                420                 425                 430

Glu Pro Val Leu Gln His Ser Gln Tyr Leu Arg Leu Arg Gln Arg Ile
        435                 440                 445

Cys Lys Ser Ser Ile Leu Gln Trp Pro Asp Asn Pro Lys Ala Glu Gly
        450                 455                 460

Leu Phe Trp Gln Thr Leu Arg Asn Val Val Leu Thr Glu Asn Asp Ser
465                 470                 475                 480

Arg Tyr Asn Asn Met Tyr Val Asp Ser Ile Lys Gln Tyr Met Ala Ala
                485                 490                 495

Ala Ser Val Thr Pro Pro Gly Ser Leu Glu Leu Leu Gln Pro Gly Phe
                500                 505                 510

Ser Lys Thr Leu Leu Gly Thr Lys Leu Glu Ala Lys Tyr Leu Cys Ser
        515                 520                 525

Ala Cys Arg Asn Val Leu Arg Arg Pro Phe Gln Ala Gln Cys Gly His
        530                 535                 540

Arg Tyr Cys Ser Phe Cys Leu Ala Ser Ile Leu Ser Ser Gly Pro Gln
545                 550                 555                 560

Asn Cys Ala Ala Cys Val His Glu Gly Ile Tyr Glu Glu Gly Ile Ser
                565                 570                 575

Ile Leu Glu Ser Ser Ser Ala Phe Pro Asp Asn Ala Ala Arg Arg Glu
        580                 585                 590

Val Glu Ser Leu Pro Ala Val Cys Pro Ser Asp Gly Cys Thr Trp Lys
        595                 600                 605

Gly Thr Leu Lys Glu Tyr Glu Ser Cys His Glu Gly Arg Cys Pro Leu
        610                 615                 620

Met Leu Thr Glu Cys Pro Ala Cys Lys Gly Leu Val Arg Leu Gly Glu
625                 630                 635                 640

Lys Glu Arg His Leu Glu His Glu Cys Pro Glu Arg Ser Leu Ser Cys
                645                 650                 655
```

```
Arg His Cys Arg Ala Pro Cys Cys Gly Ala Asp Val Lys Ala His His
                660                 665                 670

Glu Val Cys Pro Lys Phe Pro Leu Thr Cys Asp Gly Cys Gly Lys Lys
            675                 680                 685

Lys Ile Pro Arg Glu Lys Phe Gln Asp His Val Lys Thr Cys Gly Lys
690                 695                 700

Cys Arg Val Pro Cys Arg Phe His Ala Ile Gly Cys Leu Glu Thr Val
705                 710                 715                 720

Glu Gly Glu Lys Gln Gln Glu His Glu Val Gln Trp Leu Arg Glu His
                725                 730                 735

Leu Ala Met Leu Leu Ser Ser Val Leu Glu Ala Lys Pro Leu Leu Gly
            740                 745                 750

Asp Gln Ser His Ala Gly Ser Glu Leu Leu Gln Arg Cys Glu Ser Leu
        755                 760                 765

Glu Lys Lys Thr Ala Thr Phe Glu Asn Ile Val Cys Val Leu Asn Arg
770                 775                 780

Glu Val Glu Arg Val Ala Met Thr Ala Glu Ala Cys
785                 790                 795

<210> SEQ ID NO 173
<211> LENGTH: 530
<212> TYPE: PRT
<213> ORGANISM: Artificial Sequence
<220> FEATURE:
<223> OTHER INFORMATION: CER119A, amino acids 1-22 are signal peptide

<400> SEQUENCE: 173

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
                20                  25                  30

Gly Gln Pro Val Thr Leu Pro Cys His Tyr Leu Ser Trp Ser Gln Ser
            35                  40                  45

Arg Asn Ser Met Cys Trp Gly Lys Gly Ser Cys Pro Asn Ser Lys Cys
50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Thr Lys Lys Pro Thr Thr Thr Thr
    130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Lys Gly Ser Ala
        195                 200                 205

Phe Thr Thr Glu Ser Glu Thr Leu Pro Ala Ser Asn His Ser Gln Arg
    210                 215                 220
```

```
Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ala Cys Cys Val Gly
            275                 280                 285

Phe Val Leu Met Val Leu Leu Phe Leu Ala Phe Leu Ser Tyr Leu Asp
        290                 295                 300

Leu Pro Trp Tyr Leu Arg Met Val Cys Gln Trp Thr Gln Thr Arg Arg
305                 310                 315                 320

Arg Ala Arg Asn Ile Pro Leu Glu Glu Leu Gln Arg Asn Leu Gln Phe
                325                 330                 335

His Ala Phe Ile Ser Tyr Ser Gly His Asp Ser Phe Trp Val Lys Asn
                340                 345                 350

Glu Leu Leu Pro Asn Leu Glu Lys Glu Gly Met Gln Ile Cys Leu His
            355                 360                 365

Glu Arg Asn Phe Val Pro Gly Lys Ser Ile Val Glu Asn Ile Ile Thr
        370                 375                 380

Cys Ile Glu Lys Ser Tyr Lys Ser Ile Phe Val Leu Ser Pro Asn Phe
385                 390                 395                 400

Val Gln Ser Glu Trp Cys His Tyr Glu Leu Tyr Phe Ala His His Asn
                405                 410                 415

Leu Phe His Glu Gly Ser Asn Ser Leu Ile Leu Ile Leu Leu Glu Pro
            420                 425                 430

Ile Pro Gln Tyr Ser Ile Pro Ser Ser Tyr His Lys Leu Lys Ser Leu
        435                 440                 445

Met Ala Arg Arg Thr Tyr Leu Glu Trp Pro Lys Glu Lys Ser Lys Arg
450                 455                 460

Gly Leu Phe Trp Ala Asn Leu Arg Ala Ala Ile Asn Ile Lys Leu Thr
465                 470                 475                 480

Glu Gln Ala Lys Lys Asp Ser Lys Ala Gly Met Glu Glu Asp His Thr
                485                 490                 495

Tyr Glu Gly Leu Asp Ile Asp Gln Thr Ala Thr Tyr Glu Asp Ile Val
            500                 505                 510

Thr Leu Arg Thr Gly Glu Val Lys Trp Ser Val Gly Glu His Pro Gly
            515                 520                 525

Gln Glu
530

<210> SEQ ID NO 174
<211> LENGTH: 504
<212> TYPE: PRT
<213> ORGANISM: Artificial Sequence
<220> FEATURE:
<223> OTHER INFORMATION: hCER21

<400> SEQUENCE: 174

Glu Thr Val Val Thr Glu Val Leu Gly His Arg Val Thr Leu Pro Cys
1               5                   10                  15

Leu Tyr Ser Ser Trp Ser His Asn Ser Asn Ser Met Cys Trp Gly Lys
            20                  25                  30

Asp Gln Cys Pro Tyr Ser Gly Cys Lys Glu Ala Leu Ile Arg Thr Asp
        35                  40                  45
```

```
Gly Met Arg Val Thr Ser Arg Lys Ser Ala Lys Tyr Arg Leu Gln Gly
     50                  55                  60

Thr Ile Pro Arg Gly Asp Val Ser Leu Thr Ile Leu Asn Pro Ser Glu
 65              70                  75                  80

Ser Asp Ser Gly Val Tyr Cys Cys Arg Ile Glu Val Pro Gly Trp Phe
                 85                  90                  95

Asn Asp Val Lys Ile Asn Val Arg Leu Asn Leu Gln Arg Ala Ser Thr
            100                 105                 110

Thr Thr His Arg Thr Ala Thr Thr Thr Arg Arg Thr Thr Thr
            115                 120                 125

Ser Pro Thr Thr Thr Arg Gln Met Thr Thr Thr Pro Ala Ala Leu Pro
            130                 135                 140

Thr Thr Val Val Thr Thr Pro Asp Leu Thr Thr Gly Thr Pro Leu Gln
145                 150                 155                 160

Met Thr Thr Ile Ala Val Phe Thr Thr Ala Asn Thr Cys Leu Ser Leu
                165                 170                 175

Thr Pro Ser Thr Leu Pro Glu Glu Ala Thr Gly Leu Leu Thr Pro Glu
            180                 185                 190

Pro Ser Lys Glu Gly Pro Ile Leu Thr Ala Glu Ser Glu Thr Val Leu
            195                 200                 205

Pro Ser Asp Ser Trp Ser Ser Val Glu Ser Thr Ser Ala Asp Thr Val
210                 215                 220

Leu Leu Thr Ser Lys Glu Ser Lys Val Trp Asp Leu Pro Ser Thr Ser
225                 230                 235                 240

His Val Ser Met Trp Lys Thr Ser Asp Ser Val Ser Ser Pro Gln Pro
                245                 250                 255

Gly Ala Ser Asp Thr Ala Val Pro Glu Gln Asn Lys Thr Thr Lys Thr
            260                 265                 270

Gly Gln Met Asp Gly Ile Pro Met Ser Met Lys Asn Glu Met Pro Ile
            275                 280                 285

Ser Gln Leu Leu Met Ile Ile Ala Pro Ser Leu Gly Phe Val Leu Phe
            290                 295                 300

Ala Leu Phe Val Ala Phe Leu His His Leu Phe Tyr Trp Asp Val Trp
305                 310                 315                 320

Phe Ile Tyr Asn Val Cys Leu Ala Lys Val Lys Gly Tyr Arg Ser Leu
                325                 330                 335

Ser Thr Ser Gln Thr Phe Tyr Asp Ala Tyr Ile Ser Tyr Asp Thr Lys
            340                 345                 350

Asp Ala Ser Val Thr Asp Trp Val Ile Asn Glu Leu Arg Tyr His Leu
            355                 360                 365

Glu Glu Ser Arg Asp Lys Asn Val Leu Leu Cys Leu Glu Glu Arg Asp
            370                 375                 380

Trp Asp Pro Gly Leu Ala Ile Ile Asp Asn Leu Met Gln Ser Ile Asn
385                 390                 395                 400

Gln Ser Lys Lys Thr Val Phe Val Leu Thr Lys Lys Tyr Ala Lys Ser
            405                 410                 415

Trp Asn Phe Lys Thr Ala Phe Tyr Leu Ala Leu Gln Arg Leu Met Asp
            420                 425                 430

Glu Asn Met Asp Val Ile Ile Phe Ile Leu Leu Glu Pro Val Leu Gln
            435                 440                 445

His Ser Gln Tyr Leu Arg Leu Arg Gln Arg Ile Cys Lys Ser Ser Ile
            450                 455                 460
```

```
Leu Gln Trp Pro Asp Asn Pro Lys Ala Glu Gly Leu Phe Trp Gln Thr
465                 470                 475                 480

Leu Arg Asn Val Val Leu Thr Glu Asn Asp Ser Arg Tyr Asn Asn Met
                485                 490                 495

Tyr Val Asp Ser Ile Lys Gln Tyr
            500

<210> SEQ ID NO 175
<211> LENGTH: 585
<212> TYPE: PRT
<213> ORGANISM: Artificial Sequence
<220> FEATURE:
<223> OTHER INFORMATION: hCER29

<400> SEQUENCE: 175

Glu Thr Val Val Thr Glu Val Leu Gly His Arg Val Thr Leu Pro Cys
1               5                   10                  15

Leu Tyr Ser Ser Trp Ser His Asn Ser Asn Ser Met Cys Trp Gly Lys
                20                  25                  30

Asp Gln Cys Pro Tyr Ser Gly Cys Lys Glu Ala Leu Ile Arg Thr Asp
            35                  40                  45

Gly Met Arg Val Thr Ser Arg Lys Ser Ala Lys Tyr Arg Leu Gln Gly
50                  55                  60

Thr Ile Pro Arg Gly Asp Val Ser Leu Thr Ile Leu Asn Pro Ser Glu
65                  70                  75                  80

Ser Asp Ser Gly Val Tyr Cys Cys Arg Ile Glu Val Pro Gly Trp Phe
                85                  90                  95

Asn Asp Val Lys Ile Asn Val Arg Leu Asn Leu Gln Arg Ala Ser Thr
            100                 105                 110

Thr Thr His Arg Thr Ala Thr Thr Thr Arg Arg Thr Thr Thr Thr
            115                 120                 125

Ser Pro Thr Thr Thr Arg Gln Met Thr Thr Thr Pro Ala Ala Leu Pro
130                 135                 140

Thr Thr Val Val Thr Thr Pro Asp Leu Thr Thr Gly Thr Pro Leu Gln
145                 150                 155                 160

Met Thr Thr Ile Ala Val Phe Thr Thr Ala Asn Thr Cys Leu Ser Leu
                165                 170                 175

Thr Pro Ser Thr Leu Pro Glu Glu Ala Thr Gly Leu Leu Thr Pro Glu
            180                 185                 190

Pro Ser Lys Glu Gly Pro Ile Leu Thr Ala Glu Ser Glu Thr Val Leu
        195                 200                 205

Pro Ser Asp Ser Trp Ser Ser Val Glu Ser Thr Ser Ala Asp Thr Val
210                 215                 220

Leu Leu Thr Ser Lys Glu Ser Lys Val Trp Asp Leu Pro Ser Thr Ser
225                 230                 235                 240

His Val Ser Met Trp Lys Thr Ser Asp Ser Val Ser Ser Pro Gln Pro
                245                 250                 255

Gly Ala Ser Asp Thr Ala Val Pro Glu Gln Asn Lys Thr Thr Lys Thr
            260                 265                 270

Gly Gln Met Asp Gly Ile Pro Met Ser Met Lys Asn Glu Met Pro Ile
        275                 280                 285

Ser Gln Leu Leu Met Ile Ile Ala Pro Ser Leu Gly Phe Val Leu Phe
290                 295                 300

Ala Leu Phe Val Ala Phe Leu Met Ser Leu Leu Asn Cys Glu Asn Ser
305                 310                 315                 320
```

Cys Gly Ser Ser Gln Ser Glu Ser Asp Cys Val Ala Met Ala Ser
                325                 330                 335

Ser Cys Ser Ala Val Thr Lys Asp Asp Ser Val Gly Gly Thr Ala Ser
            340                 345                 350

Thr Gly Asn Leu Ser Ser Ser Phe Met Glu Glu Ile Gln Gly Tyr Asp
        355                 360                 365

Val Glu Phe Asp Pro Pro Leu Glu Ser Lys Tyr Glu Cys Pro Ile Cys
370                 375                 380

Leu Met Ala Leu Arg Glu Ala Val Gln Thr Pro Cys Gly His Arg Phe
385                 390                 395                 400

Cys Lys Ala Cys Ile Ile Lys Ser Ile Arg Asp Ala Gly His Lys Cys
                405                 410                 415

Pro Val Asp Asn Glu Ile Leu Leu Glu Asn Gln Leu Phe Pro Asp Asn
            420                 425                 430

Phe Ala Lys Arg Glu Ile Leu Ser Leu Met Val Lys Cys Pro Asn Glu
        435                 440                 445

Gly Cys Leu His Lys Met Glu Leu Arg His Leu Glu Asp His Gln Ala
450                 455                 460

His Cys Glu Phe Ala Leu Met Asp Cys Pro Gln Cys Gln Arg Pro Phe
465                 470                 475                 480

Gln Lys Phe His Ile Asn Ile His Ile Leu Lys Asp Cys Pro Arg Arg
                485                 490                 495

Gln Val Ser Cys Asp Asn Cys Ala Ala Ser Met Ala Phe Glu Asp Lys
            500                 505                 510

Glu Ile His Asp Gln Asn Cys Pro Leu Ala Asn Val Ile Cys Glu Tyr
        515                 520                 525

Cys Asn Thr Ile Leu Ile Arg Glu Gln Met Pro Asn His Tyr Asp Leu
530                 535                 540

Asp Cys Pro Thr Ala Pro Ile Pro Cys Thr Phe Ser Thr Phe Gly Cys
545                 550                 555                 560

His Glu Lys Met Gln Arg Asn His Leu Ala Arg His Leu Gln Glu Asn
                565                 570                 575

Thr Gln Ser His Met Arg Met Leu Ala
            580                 585

<210> SEQ ID NO 176
<211> LENGTH: 556
<212> TYPE: PRT
<213> ORGANISM: Artificial Sequence
<220> FEATURE:
<223> OTHER INFORMATION: hCER104

<400> SEQUENCE: 176

Glu Thr Val Val Thr Glu Val Leu Gly His Arg Val Thr Leu Pro Cys
1               5                   10                  15

Leu Tyr Ser Ser Trp Ser His Asn Ser Asn Ser Met Cys Trp Gly Lys
            20                  25                  30

Asp Gln Cys Pro Tyr Ser Gly Cys Lys Glu Ala Leu Ile Arg Thr Asp
        35                  40                  45

Gly Met Arg Val Thr Ser Arg Lys Ser Ala Lys Tyr Arg Leu Gln Gly
    50                  55                  60

Thr Ile Pro Arg Gly Asp Val Ser Leu Thr Ile Leu Asn Pro Ser Glu
65                  70                  75                  80

Ser Asp Ser Gly Val Tyr Cys Cys Arg Ile Glu Val Pro Gly Trp Phe
                85                  90                  95

-continued

Asn Asp Val Lys Ile Asn Val Arg Leu Asn Leu Gln Arg Ala Ser Thr
            100                 105                 110

Thr Thr His Arg Thr Ala Thr Thr Thr Arg Arg Thr Thr Thr Thr
        115                 120                 125

Ser Pro Thr Thr Thr Arg Gln Met Thr Thr Thr Pro Ala Ala Leu Pro
    130                 135                 140

Thr Thr Val Val Thr Thr Pro Asp Leu Thr Thr Gly Thr Pro Leu Gln
145                 150                 155                 160

Met Thr Thr Ile Ala Val Phe Thr Thr Ala Asn Thr Cys Leu Ser Leu
                165                 170                 175

Thr Pro Ser Thr Leu Pro Glu Glu Ala Thr Gly Leu Leu Thr Pro Glu
            180                 185                 190

Pro Ser Lys Glu Gly Pro Ile Leu Thr Ala Glu Ser Glu Thr Val Leu
        195                 200                 205

Pro Ser Asp Ser Trp Ser Ser Val Glu Ser Thr Ser Ala Asp Thr Val
    210                 215                 220

Leu Leu Thr Ser Lys Glu Ser Lys Val Trp Asp Leu Pro Ser Thr Ser
225                 230                 235                 240

His Val Ser Met Trp Lys Thr Ser Asp Ser Val Ser Ser Pro Gln Pro
                245                 250                 255

Gly Ala Ser Asp Thr Ala Val Pro Glu Gln Asn Lys Thr Thr Lys Thr
            260                 265                 270

Gly Gln Met Asp Gly Ile Pro Met Ser Met Lys Asn Glu Met Pro Ile
        275                 280                 285

Ser Gln Leu Leu Met Ile Ile Ala Pro Ser Leu Gly Phe Val Leu Phe
    290                 295                 300

Ala Leu Phe Val Ala Phe Leu His His Leu Phe Tyr Trp Asp Val Trp
305                 310                 315                 320

Phe Ile Tyr Asn Val Cys Leu Ala Lys Val Lys Gly Tyr Arg Ser Leu
                325                 330                 335

Ser Thr Ser Gln Thr Phe Tyr Asp Ala Tyr Ile Ser Tyr Asp Thr Lys
            340                 345                 350

Asp Ala Ser Val Thr Asp Trp Val Ile Asn Glu Leu Arg Tyr His Leu
        355                 360                 365

Glu Glu Ser Arg Asp Lys Asn Val Leu Leu Cys Leu Glu Glu Arg Asp
    370                 375                 380

Trp Asp Pro Gly Leu Ala Ile Ile Asp Asn Leu Met Gln Ser Ile Asn
385                 390                 395                 400

Gln Ser Lys Lys Thr Val Phe Val Leu Thr Lys Lys Tyr Ala Lys Ser
                405                 410                 415

Trp Asn Phe Lys Thr Ala Phe Tyr Leu Ala Leu Gln Arg Leu Met Asp
            420                 425                 430

Glu Asn Met Asp Val Ile Ile Phe Ile Leu Leu Glu Pro Val Leu Gln
        435                 440                 445

His Ser Gln Tyr Leu Arg Leu Arg Gln Arg Ile Cys Lys Ser Ser Ile
    450                 455                 460

Leu Gln Trp Pro Asp Asn Pro Lys Ala Glu Gly Leu Phe Trp Gln Thr
465                 470                 475                 480

Leu Arg Asn Val Val Leu Thr Glu Asn Asp Ser Arg Tyr Asn Asn Met
                485                 490                 495

Tyr Val Asp Ser Ile Lys Gln Tyr Tyr Phe Leu Gly Arg Leu Val Pro
            500                 505                 510

Arg Gly Arg Gly Ala Ala Glu Ala Ala Thr Arg Lys Gln Arg Ile Thr

-continued

```
            515                 520                 525
Glu Thr Glu Ser Pro Tyr Gln Glu Leu Gln Gly Gln Arg Ser Asp Val
            530                 535                 540
Tyr Ser Asp Leu Asn Thr Gln Arg Pro Tyr Tyr Lys
545                 550                 555

<210> SEQ ID NO 177
<211> LENGTH: 778
<212> TYPE: PRT
<213> ORGANISM: Artificial Sequence
<220> FEATURE:
<223> OTHER INFORMATION: hCER116

<400> SEQUENCE: 177

Glu Thr Val Val Thr Glu Val Leu Gly His Arg Val Thr Leu Pro Cys
1               5                   10                  15

Leu Tyr Ser Ser Trp Ser His Asn Ser Asn Ser Met Cys Trp Gly Lys
                20                  25                  30

Asp Gln Cys Pro Tyr Ser Gly Cys Lys Glu Ala Leu Ile Arg Thr Asp
            35                  40                  45

Gly Met Arg Val Thr Ser Arg Lys Ser Ala Lys Tyr Arg Leu Gln Gly
        50                  55                  60

Thr Ile Pro Arg Gly Asp Val Ser Leu Thr Ile Leu Asn Pro Ser Glu
65                  70                  75                  80

Ser Asp Ser Gly Val Tyr Cys Cys Arg Ile Glu Val Pro Gly Trp Phe
                85                  90                  95

Asn Asp Val Lys Ile Asn Val Arg Leu Asn Leu Gln Arg Ala Ser Thr
                100                 105                 110

Thr Thr His Arg Thr Ala Thr Thr Thr Thr Arg Arg Thr Thr Thr Thr
            115                 120                 125

Ser Pro Thr Thr Thr Arg Gln Met Thr Thr Thr Pro Ala Ala Leu Pro
        130                 135                 140

Thr Thr Val Val Thr Thr Pro Asp Leu Thr Thr Gly Thr Pro Leu Gln
145                 150                 155                 160

Met Thr Thr Ile Ala Val Phe Thr Thr Ala Asn Thr Cys Leu Ser Leu
                165                 170                 175

Thr Pro Ser Thr Leu Pro Glu Glu Ala Thr Gly Leu Leu Thr Pro Glu
                180                 185                 190

Pro Ser Lys Glu Gly Pro Ile Leu Thr Ala Glu Ser Glu Thr Val Leu
            195                 200                 205

Pro Ser Asp Ser Trp Ser Val Glu Ser Thr Ser Ala Asp Thr Val
        210                 215                 220

Leu Leu Thr Ser Lys Glu Ser Lys Val Trp Asp Leu Pro Ser Thr Ser
225                 230                 235                 240

His Val Ser Met Trp Lys Thr Ser Asp Ser Val Ser Ser Pro Gln Pro
                245                 250                 255

Gly Ala Ser Asp Thr Ala Val Pro Glu Gln Asn Lys Thr Thr Lys Thr
                260                 265                 270

Gly Gln Met Asp Gly Ile Pro Met Ser Met Lys Asn Glu Met Pro Ile
            275                 280                 285

Ser Gln Leu Leu Met Ile Ile Ala Pro Ser Leu Gly Phe Val Leu Phe
        290                 295                 300

Ala Leu Phe Val Ala Phe Leu Met Ser Leu Leu Asn Cys Glu Asn Ser
305                 310                 315                 320

Cys Gly Ser Ser Gln Ser Glu Ser Asp Cys Cys Val Ala Met Ala Ser
```

```
                325                 330                 335
Ser Cys Ser Ala Val Thr Lys Asp Asp Ser Val Gly Gly Thr Ala Ser
            340                 345                 350

Thr Gly Asn Leu Ser Ser Phe Met Glu Glu Ile Gln Gly Tyr Asp
        355                 360                 365

Val Glu Phe Asp Pro Pro Leu Glu Ser Lys Tyr Glu Cys Pro Ile Cys
    370                 375                 380

Leu Met Ala Leu Arg Glu Ala Val Gln Thr Pro Cys Gly His Arg Phe
385                 390                 395                 400

Cys Lys Ala Cys Ile Ile Lys Ser Ile Arg Asp Ala Gly His Lys Cys
                405                 410                 415

Pro Val Asp Asn Glu Ile Leu Leu Glu Asn Gln Leu Phe Pro Asp Asn
            420                 425                 430

Phe Ala Lys Arg Glu Ile Leu Ser Leu Met Val Lys Cys Pro Asn Glu
        435                 440                 445

Gly Cys Leu His Lys Met Glu Leu Arg His Leu Glu Asp His Gln Ala
    450                 455                 460

His Cys Glu Phe Ala Leu Met Asp Cys Pro Gln Cys Gln Arg Pro Phe
465                 470                 475                 480

Gln Lys Phe His Ile Asn Ile His Ile Leu Lys Asp Cys Pro Arg Arg
                485                 490                 495

Gln Val Ser Cys Asp Asn Cys Ala Ala Ser Met Ala Phe Glu Asp Lys
            500                 505                 510

Glu Ile His Asp Gln Asn Cys Pro Leu Ala Asn Val Ile Cys Glu Tyr
        515                 520                 525

Cys Asn Thr Ile Leu Ile Arg Glu Gln Met Pro Asn His Tyr Asp Leu
    530                 535                 540

Asp Cys Pro Thr Ala Pro Ile Pro Cys Thr Phe Ser Thr Phe Gly Cys
545                 550                 555                 560

His Glu Lys Met Gln Arg Asn His Leu Ala Arg His Leu Gln Glu Asn
                565                 570                 575

Thr Gln Ser His Met Arg Met Leu Ala His His Leu Phe Tyr Trp Asp
            580                 585                 590

Val Trp Phe Ile Tyr Asn Val Cys Leu Ala Lys Val Lys Gly Tyr Arg
        595                 600                 605

Ser Leu Ser Thr Ser Gln Thr Phe Tyr Asp Ala Tyr Ile Ser Tyr Asp
    610                 615                 620

Thr Lys Asp Ala Ser Val Thr Asp Trp Val Ile Asn Glu Leu Arg Tyr
625                 630                 635                 640

His Leu Glu Glu Ser Arg Asp Lys Asn Val Leu Leu Cys Leu Glu Glu
                645                 650                 655

Arg Asp Trp Asp Pro Gly Leu Ala Ile Ile Asp Asn Leu Met Gln Ser
            660                 665                 670

Ile Asn Gln Ser Lys Lys Thr Val Phe Val Leu Thr Lys Lys Tyr Ala
        675                 680                 685

Lys Ser Trp Asn Phe Lys Thr Ala Phe Tyr Leu Ala Leu Gln Arg Leu
    690                 695                 700

Met Asp Glu Asn Met Asp Val Ile Ile Phe Ile Leu Leu Glu Pro Val
705                 710                 715                 720

Leu Gln His Ser Gln Tyr Leu Arg Leu Arg Gln Arg Ile Cys Lys Ser
                725                 730                 735

Ser Ile Leu Gln Trp Pro Asp Asn Pro Lys Ala Glu Gly Leu Phe Trp
            740                 745                 750
```

Gln Thr Leu Arg Asn Val Val Leu Thr Glu Asn Asp Ser Arg Tyr Asn
        755                 760                 765

Asn Met Tyr Val Asp Ser Ile Lys Gln Tyr
        770                 775

<210> SEQ ID NO 178
<211> LENGTH: 778
<212> TYPE: PRT
<213> ORGANISM: Artificial Sequence
<220> FEATURE:
<223> OTHER INFORMATION: hCER117

<400> SEQUENCE: 178

Glu Thr Val Val Thr Glu Val Leu Gly His Arg Val Thr Leu Pro Cys
1               5                   10                  15

Leu Tyr Ser Ser Trp Ser His Asn Ser Asn Ser Met Cys Trp Gly Lys
            20                  25                  30

Asp Gln Cys Pro Tyr Ser Gly Cys Lys Glu Ala Leu Ile Arg Thr Asp
        35                  40                  45

Gly Met Arg Val Thr Ser Arg Lys Ser Ala Lys Tyr Arg Leu Gln Gly
    50                  55                  60

Thr Ile Pro Arg Gly Asp Val Ser Leu Thr Ile Leu Asn Pro Ser Glu
65                  70                  75                  80

Ser Asp Ser Gly Val Tyr Cys Cys Arg Ile Glu Val Pro Gly Trp Phe
                85                  90                  95

Asn Asp Val Lys Ile Asn Val Arg Leu Asn Leu Gln Arg Ala Ser Thr
            100                 105                 110

Thr Thr His Arg Thr Ala Thr Thr Thr Arg Arg Thr Thr Thr Thr
        115                 120                 125

Ser Pro Thr Thr Thr Arg Gln Met Thr Thr Pro Ala Ala Leu Pro
    130                 135                 140

Thr Thr Val Val Thr Thr Pro Asp Leu Thr Thr Gly Thr Pro Leu Gln
145                 150                 155                 160

Met Thr Thr Ile Ala Val Phe Thr Thr Ala Asn Thr Cys Leu Ser Leu
                165                 170                 175

Thr Pro Ser Thr Leu Pro Glu Glu Ala Thr Gly Leu Leu Thr Pro Glu
            180                 185                 190

Pro Ser Lys Glu Gly Pro Ile Leu Thr Ala Glu Ser Glu Thr Val Leu
        195                 200                 205

Pro Ser Asp Ser Trp Ser Ser Val Glu Ser Thr Ser Ala Asp Thr Val
    210                 215                 220

Leu Leu Thr Ser Lys Glu Ser Lys Val Trp Asp Leu Pro Ser Thr Ser
225                 230                 235                 240

His Val Ser Met Trp Lys Thr Ser Asp Ser Val Ser Ser Pro Gln Pro
                245                 250                 255

Gly Ala Ser Asp Thr Ala Val Pro Glu Gln Asn Lys Thr Thr Lys Thr
            260                 265                 270

Gly Gln Met Asp Gly Ile Pro Met Ser Met Lys Asn Glu Met Pro Ile
        275                 280                 285

Ser Gln Leu Leu Met Ile Ile Ala Pro Ser Leu Gly Phe Val Leu Phe
    290                 295                 300

Ala Leu Phe Val Ala Phe Leu His His Leu Phe Tyr Trp Asp Val Trp
305                 310                 315                 320

Phe Ile Tyr Asn Val Cys Leu Ala Lys Val Lys Gly Tyr Arg Ser Leu
                325                 330                 335

```
Ser Thr Ser Gln Thr Phe Tyr Asp Ala Tyr Ile Ser Tyr Asp Thr Lys
            340                 345                 350

Asp Ala Ser Val Thr Asp Trp Val Ile Asn Glu Leu Arg Tyr His Leu
            355                 360                 365

Glu Glu Ser Arg Asp Lys Asn Val Leu Leu Cys Leu Glu Glu Arg Asp
370                 375                 380

Trp Asp Pro Gly Leu Ala Ile Ile Asp Asn Leu Met Gln Ser Ile Asn
385                 390                 395                 400

Gln Ser Lys Lys Thr Val Phe Val Leu Thr Lys Lys Tyr Ala Lys Ser
                405                 410                 415

Trp Asn Phe Lys Thr Ala Phe Tyr Leu Ala Leu Gln Arg Leu Met Asp
                420                 425                 430

Glu Asn Met Asp Val Ile Ile Phe Ile Leu Leu Glu Pro Val Leu Gln
            435                 440                 445

His Ser Gln Tyr Leu Arg Leu Arg Gln Arg Ile Cys Lys Ser Ser Ile
450                 455                 460

Leu Gln Trp Pro Asp Asn Pro Lys Ala Glu Gly Leu Phe Trp Gln Thr
465                 470                 475                 480

Leu Arg Asn Val Val Leu Thr Glu Asn Asp Ser Arg Tyr Asn Asn Met
                485                 490                 495

Tyr Val Asp Ser Ile Lys Gln Tyr Met Ser Leu Leu Asn Cys Glu Asn
            500                 505                 510

Ser Cys Gly Ser Ser Gln Ser Glu Ser Asp Cys Cys Val Ala Met Ala
            515                 520                 525

Ser Ser Cys Ser Ala Val Thr Lys Asp Asp Ser Val Gly Gly Thr Ala
530                 535                 540

Ser Thr Gly Asn Leu Ser Ser Ser Phe Met Glu Glu Ile Gln Gly Tyr
545                 550                 555                 560

Asp Val Glu Phe Asp Pro Pro Leu Glu Ser Lys Tyr Glu Cys Pro Ile
                565                 570                 575

Cys Leu Met Ala Leu Arg Glu Ala Val Gln Thr Pro Cys Gly His Arg
            580                 585                 590

Phe Cys Lys Ala Cys Ile Ile Lys Ser Ile Arg Asp Ala Gly His Lys
            595                 600                 605

Cys Pro Val Asp Asn Glu Ile Leu Leu Glu Asn Gln Leu Phe Pro Asp
610                 615                 620

Asn Phe Ala Lys Arg Glu Ile Leu Ser Leu Met Val Lys Cys Pro Asn
625                 630                 635                 640

Glu Gly Cys Leu His Lys Met Glu Leu Arg His Leu Glu Asp His Gln
                645                 650                 655

Ala His Cys Glu Phe Ala Leu Met Asp Cys Pro Gln Cys Gln Arg Pro
            660                 665                 670

Phe Gln Lys Phe His Ile Asn Ile His Ile Leu Lys Asp Cys Pro Arg
            675                 680                 685

Arg Gln Val Ser Cys Asp Asn Cys Ala Ala Ser Met Ala Phe Glu Asp
            690                 695                 700

Lys Glu Ile His Asp Gln Asn Cys Pro Leu Ala Asn Val Ile Cys Glu
705                 710                 715                 720

Tyr Cys Asn Thr Ile Leu Ile Arg Glu Gln Met Pro Asn His Tyr Asp
                725                 730                 735

Leu Asp Cys Pro Thr Ala Pro Ile Pro Cys Thr Phe Ser Thr Phe Gly
                740                 745                 750
```

Cys His Glu Lys Met Gln Arg Asn His Leu Ala Arg His Leu Gln Glu
              755                 760                 765

Asn Thr Gln Ser His Met Arg Met Leu Ala
              770                 775

<210> SEQ ID NO 179
<211> LENGTH: 538
<212> TYPE: PRT
<213> ORGANISM: Artificial Sequence
<220> FEATURE:
<223> OTHER INFORMATION: hCER122

<400> SEQUENCE: 179

Glu Thr Val Val Thr Glu Val Leu Gly His Arg Val Thr Leu Pro Cys
1               5                   10                  15

Leu Tyr Ser Ser Trp Ser His Asn Ser Asn Ser Met Cys Trp Gly Lys
              20                  25                  30

Asp Gln Cys Pro Tyr Ser Gly Cys Lys Glu Ala Leu Ile Arg Thr Asp
              35                  40                  45

Gly Met Arg Val Thr Ser Arg Lys Ser Ala Lys Tyr Arg Leu Gln Gly
    50                  55                  60

Thr Ile Pro Arg Gly Asp Val Ser Leu Thr Ile Leu Asn Pro Ser Glu
65                  70                  75                  80

Ser Asp Ser Gly Val Tyr Cys Cys Arg Ile Glu Val Pro Gly Trp Phe
                85                  90                  95

Asn Asp Val Lys Ile Asn Val Arg Leu Asn Leu Gln Arg Ala Ser Thr
              100                 105                 110

Thr Thr His Arg Thr Ala Thr Thr Thr Arg Arg Thr Thr Thr Thr
              115                 120                 125

Ser Pro Thr Thr Thr Arg Gln Met Thr Thr Thr Pro Ala Ala Leu Pro
    130                 135                 140

Thr Thr Val Val Thr Thr Pro Asp Leu Thr Thr Gly Thr Pro Leu Gln
145                 150                 155                 160

Met Thr Thr Ile Ala Val Phe Thr Thr Ala Asn Thr Cys Leu Ser Leu
                165                 170                 175

Thr Pro Ser Thr Leu Pro Glu Glu Ala Thr Gly Leu Leu Thr Pro Glu
              180                 185                 190

Pro Ser Lys Glu Gly Pro Ile Leu Thr Ala Glu Ser Glu Thr Val Leu
              195                 200                 205

Pro Ser Asp Ser Trp Ser Ser Val Glu Ser Thr Ser Ala Asp Thr Val
    210                 215                 220

Leu Leu Thr Ser Lys Glu Ser Lys Val Trp Asp Leu Pro Ser Thr Ser
225                 230                 235                 240

His Val Ser Met Trp Lys Thr Ser Asp Ser Val Ser Ser Pro Gln Pro
                245                 250                 255

Gly Ala Ser Asp Thr Ala Val Pro Glu Gln Asn Lys Thr Thr Lys Thr
              260                 265                 270

Gly Gln Met Asp Gly Ile Pro Met Ser Met Lys Asn Glu Met Pro Ile
              275                 280                 285

Ser Gln Leu Leu Met Ile Ile Ala Pro Ser Leu Gly Phe Val Leu Phe
    290                 295                 300

Ala Leu Phe Val Ala Phe Leu His Arg Phe His Gly Leu Trp Tyr Met
305                 310                 315                 320

Lys Met Met Trp Ala Trp Leu Gln Ala Lys Arg Lys Pro Arg Lys Ala
                325                 330                 335

```
Pro Ser Arg Asn Ile Cys Tyr Asp Ala Phe Val Ser Tyr Ser Glu Arg
            340                 345                 350

Asp Ala Tyr Trp Val Glu Asn Leu Met Val Gln Glu Leu Glu Asn Phe
            355                 360                 365

Asn Pro Pro Phe Lys Leu Cys Leu His Lys Arg Asp Phe Ile Pro Gly
            370                 375                 380

Lys Trp Ile Ile Asp Asn Ile Ile Asp Ser Ile Glu Lys Ser His Lys
385                 390                 395                 400

Thr Val Phe Val Leu Ser Glu Asn Phe Lys Ser Glu Trp Cys Lys
                405                 410                 415

Tyr Glu Leu Asp Phe Ser His Phe Arg Leu Phe Asp Glu Asn Asn Asp
            420                 425                 430

Ala Ala Ile Leu Ile Leu Leu Glu Pro Ile Glu Lys Lys Ala Ile Pro
            435                 440                 445

Gln Arg Phe Cys Lys Leu Arg Lys Ile Met Asn Thr Lys Thr Tyr Leu
            450                 455                 460

Glu Trp Pro Met Asp Glu Ala Gln Arg Glu Gly Phe Trp Val Asn Leu
465                 470                 475                 480

Arg Ala Ala Ile Lys Ser Tyr Phe Leu Gly Arg Leu Val Pro Arg Gly
                485                 490                 495

Arg Gly Ala Ala Glu Ala Ala Thr Arg Lys Gln Arg Ile Thr Glu Thr
            500                 505                 510

Glu Ser Pro Tyr Gln Glu Leu Gln Gly Gln Arg Ser Asp Val Tyr Ser
            515                 520                 525

Asp Leu Asn Thr Gln Arg Pro Tyr Tyr Lys
            530                 535

<210> SEQ ID NO 180
<211> LENGTH: 760
<212> TYPE: PRT
<213> ORGANISM: Artificial Sequence
<220> FEATURE:
<223> OTHER INFORMATION: hCER123

<400> SEQUENCE: 180

Glu Thr Val Val Thr Glu Val Leu Gly His Arg Val Thr Leu Pro Cys
1               5                   10                  15

Leu Tyr Ser Ser Trp Ser His Asn Ser Asn Ser Met Cys Trp Gly Lys
                20                  25                  30

Asp Gln Cys Pro Tyr Ser Gly Cys Lys Glu Ala Leu Ile Arg Thr Asp
            35                  40                  45

Gly Met Arg Val Thr Ser Arg Lys Ser Ala Lys Tyr Arg Leu Gln Gly
        50                  55                  60

Thr Ile Pro Arg Gly Asp Val Ser Leu Thr Ile Leu Asn Pro Ser Glu
65                  70                  75                  80

Ser Asp Ser Gly Val Tyr Cys Cys Arg Ile Glu Val Pro Gly Trp Phe
                85                  90                  95

Asn Asp Val Lys Ile Asn Val Arg Leu Asn Leu Gln Arg Ala Ser Thr
            100                 105                 110

Thr Thr His Arg Thr Ala Thr Thr Thr Thr Arg Arg Thr Thr Thr Thr
            115                 120                 125

Ser Pro Thr Thr Thr Arg Gln Met Thr Thr Pro Ala Ala Leu Pro
            130                 135                 140

Thr Thr Val Val Thr Thr Pro Asp Leu Thr Thr Gly Thr Pro Leu Gln
145                 150                 155                 160
```

```
Met Thr Thr Ile Ala Val Phe Thr Thr Ala Asn Thr Cys Leu Ser Leu
                165                 170                 175
Thr Pro Ser Thr Leu Pro Glu Glu Ala Thr Gly Leu Leu Thr Pro Glu
            180                 185                 190
Pro Ser Lys Glu Gly Pro Ile Leu Thr Ala Glu Ser Glu Thr Val Leu
            195                 200                 205
Pro Ser Asp Ser Trp Ser Ser Val Glu Ser Thr Ser Ala Asp Thr Val
            210                 215                 220
Leu Leu Thr Ser Lys Glu Ser Lys Val Trp Asp Leu Pro Ser Thr Ser
225                 230                 235                 240
His Val Ser Met Trp Lys Thr Ser Asp Ser Val Ser Ser Pro Gln Pro
                245                 250                 255
Gly Ala Ser Asp Thr Ala Val Pro Glu Gln Asn Lys Thr Thr Lys Thr
            260                 265                 270
Gly Gln Met Asp Gly Ile Pro Met Ser Met Lys Asn Glu Met Pro Ile
            275                 280                 285
Ser Gln Leu Leu Met Ile Ile Ala Pro Ser Leu Gly Phe Val Leu Phe
            290                 295                 300
Ala Leu Phe Val Ala Phe Leu His Arg Phe His Gly Leu Trp Tyr Met
305                 310                 315                 320
Lys Met Met Trp Ala Trp Leu Gln Ala Lys Arg Lys Pro Arg Lys Ala
                325                 330                 335
Pro Ser Arg Asn Ile Cys Tyr Asp Ala Phe Val Ser Tyr Ser Glu Arg
            340                 345                 350
Asp Ala Tyr Trp Val Glu Asn Leu Met Val Gln Glu Leu Glu Asn Phe
            355                 360                 365
Asn Pro Pro Phe Lys Leu Cys Leu His Lys Arg Asp Phe Ile Pro Gly
370                 375                 380
Lys Trp Ile Ile Asp Asn Ile Ile Asp Ser Ile Glu Lys Ser His Lys
385                 390                 395                 400
Thr Val Phe Val Leu Ser Glu Asn Phe Val Lys Ser Glu Trp Cys Lys
                405                 410                 415
Tyr Glu Leu Asp Phe Ser His Phe Arg Leu Phe Asp Glu Asn Asn Asp
            420                 425                 430
Ala Ala Ile Leu Ile Leu Leu Glu Pro Ile Glu Lys Lys Ala Ile Pro
            435                 440                 445
Gln Arg Phe Cys Lys Leu Arg Lys Ile Met Asn Thr Lys Thr Tyr Leu
            450                 455                 460
Glu Trp Pro Met Asp Glu Ala Gln Arg Glu Gly Phe Trp Val Asn Leu
465                 470                 475                 480
Arg Ala Ala Ile Lys Ser Met Ser Leu Leu Asn Cys Glu Asn Ser Cys
                485                 490                 495
Gly Ser Ser Gln Ser Glu Ser Asp Cys Cys Val Ala Met Ala Ser Ser
            500                 505                 510
Cys Ser Ala Val Thr Lys Asp Asp Ser Val Gly Gly Thr Ala Ser Thr
            515                 520                 525
Gly Asn Leu Ser Ser Ser Phe Met Glu Glu Ile Gln Gly Tyr Asp Val
530                 535                 540
Glu Phe Asp Pro Pro Leu Glu Ser Lys Tyr Glu Cys Pro Ile Cys Leu
545                 550                 555                 560
Met Ala Leu Arg Glu Ala Val Gln Thr Pro Cys Gly His Arg Phe Cys
                565                 570                 575
Lys Ala Cys Ile Ile Lys Ser Ile Arg Asp Ala Gly His Lys Cys Pro
```

```
                580             585             590
Val Asp Asn Glu Ile Leu Leu Glu Asn Gln Leu Phe Pro Asp Asn Phe
            595                 600                 605

Ala Lys Arg Glu Ile Leu Ser Leu Met Val Lys Cys Pro Asn Glu Gly
        610                 615                 620

Cys Leu His Lys Met Glu Leu Arg His Leu Glu Asp His Gln Ala His
625                 630                 635                 640

Cys Glu Phe Ala Leu Met Asp Cys Pro Gln Cys Gln Arg Pro Phe Gln
                645                 650                 655

Lys Phe His Ile Asn Ile His Ile Leu Lys Asp Cys Pro Arg Arg Gln
            660                 665                 670

Val Ser Cys Asp Asn Cys Ala Ala Ser Met Ala Phe Glu Asp Lys Glu
        675                 680                 685

Ile His Asp Gln Asn Cys Pro Leu Ala Asn Val Ile Cys Glu Tyr Cys
            690                 695                 700

Asn Thr Ile Leu Ile Arg Glu Gln Met Pro Asn His Tyr Asp Leu Asp
705                 710                 715                 720

Cys Pro Thr Ala Pro Ile Pro Cys Thr Phe Ser Thr Phe Gly Cys His
                725                 730                 735

Glu Lys Met Gln Arg Asn His Leu Ala Arg His Leu Gln Glu Asn Thr
            740                 745                 750

Gln Ser His Met Arg Met Leu Ala
        755                 760

<210> SEQ ID NO 181
<211> LENGTH: 789
<212> TYPE: PRT
<213> ORGANISM: Artificial Sequence
<220> FEATURE:
<223> OTHER INFORMATION: hCER126

<400> SEQUENCE: 181

Glu Thr Val Val Thr Glu Val Leu Gly His Arg Val Thr Leu Pro Cys
1               5                   10                  15

Leu Tyr Ser Ser Trp Ser His Asn Ser Asn Ser Met Cys Trp Gly Lys
            20                  25                  30

Asp Gln Cys Pro Tyr Ser Gly Cys Lys Glu Ala Leu Ile Arg Thr Asp
        35                  40                  45

Gly Met Arg Val Thr Ser Arg Lys Ser Ala Lys Tyr Arg Leu Gln Gly
    50                  55                  60

Thr Ile Pro Arg Gly Asp Val Ser Leu Thr Ile Leu Asn Pro Ser Glu
65                  70                  75                  80

Ser Asp Ser Gly Val Tyr Cys Cys Arg Ile Glu Val Pro Gly Trp Phe
                85                  90                  95

Asn Asp Val Lys Ile Asn Val Arg Leu Asn Leu Gln Arg Ala Ser Thr
            100                 105                 110

Thr Thr His Arg Thr Ala Thr Thr Thr Arg Arg Thr Thr Thr Thr Thr
        115                 120                 125

Ser Pro Thr Thr Thr Arg Gln Met Thr Thr Thr Pro Ala Ala Leu Pro
    130                 135                 140

Thr Thr Val Val Thr Thr Pro Asp Leu Thr Thr Gly Thr Pro Leu Gln
145                 150                 155                 160

Met Thr Thr Ile Ala Val Phe Thr Thr Ala Asn Thr Cys Leu Ser Leu
                165                 170                 175

Thr Pro Ser Thr Leu Pro Glu Glu Ala Thr Gly Leu Leu Thr Pro Glu
```

```
                180                 185                 190
Pro Ser Lys Glu Gly Pro Ile Leu Thr Ala Glu Ser Glu Thr Val Leu
        195                 200                 205
Pro Ser Asp Ser Trp Ser Ser Val Glu Ser Thr Ser Ala Asp Thr Val
        210                 215                 220
Leu Leu Thr Ser Lys Glu Ser Lys Val Trp Asp Leu Pro Ser Thr Ser
225                 230                 235                 240
His Val Ser Met Trp Lys Thr Ser Asp Ser Val Ser Ser Pro Gln Pro
                245                 250                 255
Gly Ala Ser Asp Thr Ala Val Pro Glu Gln Asn Lys Thr Thr Lys Thr
                260                 265                 270
Gly Gln Met Asp Gly Ile Pro Met Ser Met Lys Asn Glu Met Pro Ile
            275                 280                 285
Ser Gln Leu Leu Met Ile Ile Ala Pro Ser Leu Gly Phe Val Leu Phe
            290                 295                 300
Ala Leu Phe Val Ala Phe Leu His Arg Phe His Gly Leu Trp Tyr Met
305                 310                 315                 320
Lys Met Met Trp Ala Trp Leu Gln Ala Lys Arg Lys Pro Arg Lys Ala
                325                 330                 335
Pro Ser Arg Asn Ile Cys Tyr Asp Ala Phe Val Ser Tyr Ser Glu Arg
                340                 345                 350
Asp Ala Tyr Trp Val Glu Asn Leu Met Val Gln Glu Leu Glu Asn Phe
            355                 360                 365
Asn Pro Pro Phe Lys Leu Cys Leu His Lys Arg Asp Phe Ile Pro Gly
        370                 375                 380
Lys Trp Ile Ile Asp Asn Ile Ile Asp Ser Ile Glu Lys Ser His Lys
385                 390                 395                 400
Thr Val Phe Val Leu Ser Glu Asn Phe Val Lys Ser Glu Trp Cys Lys
                405                 410                 415
Tyr Glu Leu Asp Phe Ser His Phe Arg Leu Phe Asp Glu Asn Asn Asp
                420                 425                 430
Ala Ala Ile Leu Ile Leu Leu Glu Pro Ile Glu Lys Lys Ala Ile Pro
            435                 440                 445
Gln Arg Phe Cys Lys Leu Arg Lys Ile Met Asn Thr Lys Thr Tyr Leu
        450                 455                 460
Glu Trp Pro Met Asp Glu Ala Gln Arg Glu Gly Phe Trp Val Asn Leu
465                 470                 475                 480
Arg Ala Ala Ile Lys Ser Met Ala Ala Ala Ser Val Thr Pro Pro Gly
                485                 490                 495
Ser Leu Glu Leu Leu Gln Pro Gly Phe Ser Lys Thr Leu Leu Gly Thr
            500                 505                 510
Lys Leu Glu Ala Lys Tyr Leu Cys Ser Ala Cys Arg Asn Val Leu Arg
            515                 520                 525
Arg Pro Phe Gln Ala Gln Cys Gly His Arg Tyr Cys Ser Phe Cys Leu
        530                 535                 540
Ala Ser Ile Leu Ser Ser Gly Pro Gln Asn Cys Ala Ala Cys Val His
545                 550                 555                 560
Glu Gly Ile Tyr Glu Glu Gly Ile Ser Ile Leu Glu Ser Ser Ser Ala
                565                 570                 575
Phe Pro Asp Asn Ala Ala Arg Arg Glu Val Glu Ser Leu Pro Ala Val
            580                 585                 590
Cys Pro Ser Asp Gly Cys Thr Trp Lys Gly Thr Leu Lys Glu Tyr Glu
            595                 600                 605
```

-continued

```
Ser Cys His Glu Gly Arg Cys Pro Leu Met Leu Thr Glu Cys Pro Ala
    610             615                 620

Cys Lys Gly Leu Val Arg Leu Gly Glu Lys Glu Arg His Leu Glu His
625             630                 635                 640

Glu Cys Pro Glu Arg Ser Leu Ser Cys Arg His Cys Arg Ala Pro Cys
            645                 650                 655

Cys Gly Ala Asp Val Lys Ala His His Glu Val Cys Pro Lys Phe Pro
            660                 665             670

Leu Thr Cys Asp Gly Cys Gly Lys Lys Lys Ile Pro Arg Glu Lys Phe
        675             680                 685

Gln Asp His Val Lys Thr Cys Gly Lys Cys Arg Val Pro Cys Arg Phe
    690             695                 700

His Ala Ile Gly Cys Leu Glu Thr Val Glu Gly Glu Lys Gln Gln Glu
705             710                 715                 720

His Glu Val Gln Trp Leu Arg Glu His Leu Ala Met Leu Leu Ser Ser
                725                 730                 735

Val Leu Glu Ala Lys Pro Leu Leu Gly Asp Gln Ser His Ala Gly Ser
            740                 745             750

Glu Leu Leu Gln Arg Cys Glu Ser Leu Glu Lys Lys Thr Ala Thr Phe
        755                 760                 765

Glu Asn Ile Val Cys Val Leu Asn Arg Glu Val Glu Arg Val Ala Met
    770                 775                 780

Thr Ala Glu Ala Cys
785
```